(12) United States Patent
Hoge et al.

(10) Patent No.: US 10,258,698 B2
(45) Date of Patent: Apr. 16, 2019

(54) FORMULATION AND DELIVERY OF MODIFIED NUCLEOSIDE, NUCLEOTIDE, AND NUCLEIC ACID COMPOSITIONS

(71) Applicant: ModernaTX, Inc., Cambridge, MA (US)

(72) Inventors: Stephen G. Hoge, Brookline, MA (US); Örn Almarsson, Shrewsbury, MA (US); David D. Hile, Westborough, MA (US); Ciarán Lawlor, Cambridge, MA (US); John Podobinski, Boston, MA (US); Staci Sabnis, Somerville, MA (US); Antonin de Fougerolles, Waterloo (BE); Divakar Ramakrishnan, Lexington, MA (US); Kristy M. Wood, Wellesley, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 14/775,773

(22) PCT Filed: Mar. 14, 2014

(86) PCT No.: PCT/US2014/027077
§ 371 (c)(1),
(2) Date: Sep. 14, 2015

(87) PCT Pub. No.: WO2014/152211
PCT Pub. Date: Sep. 25, 2014

(65) Prior Publication Data
US 2016/0038612 A1    Feb. 11, 2016

Related U.S. Application Data

(60) Provisional application No. 61/782,716, filed on Mar. 14, 2013, provisional application No. 61/821,406, filed on May 9, 2013, provisional application No. 61/840,510, filed on Jun. 28, 2013, provisional application No. 61/877,485, filed on Sep. 13, 2013, provisional application No. 61/942,894, filed on Feb. 21, 2014.

(51) Int. Cl.
| A61K 48/00 | (2006.01) |
| A61K 31/7105 | (2006.01) |
| C12Q 1/68 | (2018.01) |
| C12N 15/87 | (2006.01) |
| C12N 15/88 | (2006.01) |
| A61K 47/52 | (2017.01) |

(52) U.S. Cl.
CPC .......... *A61K 48/0066* (2013.01); *A61K 47/52* (2017.08); *A61K 48/005* (2013.01); *A61K 48/0075* (2013.01); *C12N 15/87* (2013.01); *C12N 15/88* (2013.01)

(58) Field of Classification Search
None
See application file for complete search history.

(56) References Cited

U.S. PATENT DOCUMENTS

| 5,489,677 | A | 2/1996 | Sanghvi et al. |
| 8,039,214 | B2 | 10/2011 | Dahl et al. |
| 8,058,069 | B2 | 11/2011 | Yaworski et al. |
| 8,158,601 | B2 | 4/2012 | Chen et al. |
| 8,217,016 | B2 | 7/2012 | Hoerr et al. |
| 8,278,036 | B2 | 10/2012 | Kariko et al. |
| 8,329,887 | B2 | 12/2012 | Dahl et al. |
| 8,664,194 | B2 | 3/2014 | de Fougerolles et al. |
| 8,680,069 | B2 | 3/2014 | de Fougerolles et al. |
| 8,691,750 | B2 | 4/2014 | Constien et al. |
| 8,691,966 | B2 | 4/2014 | Kariko et al. |
| 8,710,200 | B2 | 4/2014 | Schrum et al. |
| 8,716,465 | B2 | 5/2014 | Rossi et al. |
| 8,748,089 | B2 | 6/2014 | Kariko et al. |
| 8,754,062 | B2 | 6/2014 | de Fougerolles et al. |
| 8,802,438 | B2 | 8/2014 | Rossi et al. |
| 8,808,982 | B2 | 8/2014 | Dahl et al. |
| 8,822,663 | B2 | 9/2014 | Schrum et al. |
| 8,835,108 | B2 | 9/2014 | Kariko et al. |
| 8,846,348 | B2 | 9/2014 | Jendrisak et al. |
| 8,853,179 | B2 | 10/2014 | Mauro et al. |

(Continued)

FOREIGN PATENT DOCUMENTS

| EP | 1 270 732 A1 | 1/2003 |
| WO | 199116024 A1 | 10/1991 |

(Continued)

OTHER PUBLICATIONS

Piggotts, Electroporation of RNA stimulates immunity to an encoded reporter gene in mice, Molecular Medicine REPORTS 2: 753-756, 2009.*

(Continued)

*Primary Examiner* — Maria Marvich
(74) *Attorney, Agent, or Firm* — Clark & Elbing LLP

(57) ABSTRACT

The present disclosure provides, inter alia, formulation compositions comprising modified nucleic acid molecules which may encode a protein, a protein precursor, or a partially or fully processed form of the protein or a protein precursor. The formulation composition may further include a modified nucleic acid molecule and a delivery agent. The present invention further provides nucleic acids useful for encoding polypeptides capable of modulating a cell's function and/or activity.

6 Claims, 6 Drawing Sheets
Specification includes a Sequence Listing.

(56) References Cited

U.S. PATENT DOCUMENTS

| | | |
|---|---|---|
| 8,853,377 B2 | 10/2014 | Guild et al. |
| 8,871,230 B2 | 10/2014 | Rudolph et al. |
| 8,883,506 B2 | 11/2014 | Rossi et al. |
| 8,980,864 B2 | 3/2015 | Hoge et al. |
| 8,999,380 B2 | 4/2015 | Bancel et al. |
| 9,050,297 B2 | 6/2015 | Chakraborty et al. |
| 9,061,059 B2 | 6/2015 | Chakraborty et al. |
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,149,506 B2 | 10/2015 | Chakraborty et al. |
| 9,428,535 B2 | 8/2016 | de Fougerolles et al. |
| 9,533,047 B2 | 1/2017 | de Fougerolles et al. |
| 9,675,668 B2 | 6/2017 | Bancel et al. |
| 2005/0032730 A1 | 2/2005 | Von Der Mulbe et al. |
| 2006/0247195 A1 | 11/2006 | Ray |
| 2007/0105799 A1 | 5/2007 | Hermanson |
| 2007/0143878 A1 | 6/2007 | Bhat et al. |
| 2008/0267873 A1 | 10/2008 | Hoerr et al. |
| 2009/0099078 A1 | 4/2009 | Lee et al. |
| 2009/0264511 A1 | 10/2009 | de Fougerolles et al. |
| 2010/0028943 A1 | 2/2010 | Thomas et al. |
| 2010/0047261 A1 | 2/2010 | Hoerr et al. |
| 2010/0129877 A1 | 5/2010 | Sahin et al. |
| 2010/0168206 A1 | 7/2010 | Gollob et al. |
| 2010/0189729 A1 | 7/2010 | Hoerr et al. |
| 2010/0239608 A1 | 9/2010 | Von Der Mulbe et al. |
| 2010/0258135 A1 | 10/2010 | Persson |
| 2011/0045022 A1 | 2/2011 | Tsai |
| 2011/0065103 A1 | 3/2011 | Sahin et al. |
| 2011/0077287 A1 | 3/2011 | Von Der Mulbe et al. |
| 2011/0086904 A1 | 4/2011 | Russell |
| 2011/0143397 A1 | 6/2011 | Kariko et al. |
| 2011/0244026 A1 | 10/2011 | Guild et al. |
| 2011/0250237 A1 | 10/2011 | O'Hagan |
| 2011/0300205 A1 | 12/2011 | Geall et al. |
| 2011/0311472 A1 | 12/2011 | Hoerr et al. |
| 2012/0027813 A1 | 2/2012 | Podda et al. |
| 2012/0046346 A1 | 2/2012 | Rossi et al. |
| 2012/0053333 A1 | 3/2012 | Mauro et al. |
| 2012/0065252 A1 | 3/2012 | Schrum et al. |
| 2012/0156251 A1 | 6/2012 | Brito et al. |
| 2012/0195917 A1 | 8/2012 | Sahin et al. |
| 2012/0195936 A1 | 8/2012 | Rudolph et al. |
| 2012/0237975 A1 | 9/2012 | Schrum et al. |
| 2012/0251618 A1 | 10/2012 | Schrum et al. |
| 2012/0301955 A1 | 11/2012 | Thomas et al. |
| 2012/0322864 A1 | 12/2012 | Rossi et al. |
| 2012/0322865 A1 | 12/2012 | Rossi et al. |
| 2013/0102034 A1 | 4/2013 | Schrum |
| 2013/0115272 A1 | 5/2013 | de Fougerolles et al. |
| 2013/0123481 A1 | 5/2013 | de Fougerolles et al. |
| 2013/0149375 A1 | 6/2013 | Geall |
| 2013/0156849 A1 | 6/2013 | de Fougerolles et al. |
| 2013/0165504 A1 | 6/2013 | Bancel et al. |
| 2013/0171241 A1 | 7/2013 | Geall |
| 2013/0177639 A1 | 7/2013 | Geall et al. |
| 2013/0177640 A1 | 7/2013 | Geall et al. |
| 2013/0183355 A1 | 7/2013 | Jain et al. |
| 2013/0189295 A1 | 7/2013 | Aric et al. |
| 2013/0189351 A1 | 7/2013 | Geall |
| 2013/0189741 A1 | 7/2013 | Meis et al. |
| 2013/0195967 A1 | 8/2013 | Guild et al. |
| 2013/0195968 A1 | 8/2013 | Geall et al. |
| 2013/0195969 A1 | 8/2013 | Geall et al. |
| 2013/0202684 A1 | 8/2013 | Geall et al. |
| 2013/0203115 A1 | 8/2013 | Schrum et al. |
| 2013/0236974 A1 | 9/2013 | de Fougerolles et al. |
| 2013/0237592 A1 | 9/2013 | de Fougerolles et al. |
| 2013/0237593 A1 | 9/2013 | de Fougerolles et al. |
| 2013/0237594 A1 | 9/2013 | de Fougerolles et al. |
| 2013/0244278 A1 | 9/2013 | de Fougerolles et al. |
| 2013/0244279 A1 | 9/2013 | de Fougerolles et al. |
| 2013/0244282 A1 | 9/2013 | Schrum et al. |
| 2013/0245103 A1 | 9/2013 | de Fougerolles et al. |
| 2013/0245106 A1 | 9/2013 | de Fougerolles et al. |
| 2013/0245107 A1 | 9/2013 | de Fougerolles et al. |
| 2013/0252281 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2013/0273104 A1 | 10/2013 | Podda et al. |
| 2013/0273109 A1 | 10/2013 | Settembre et al. |
| 2014/0004593 A1 | 1/2014 | Boldog et al. |
| 2014/0010861 A1 | 1/2014 | Bancel et al. |
| 2014/0030292 A1 | 1/2014 | Franti et al. |
| 2014/0073687 A1 | 3/2014 | Chien et al. |
| 2014/0105930 A1 | 4/2014 | Springer |
| 2014/0105964 A1 | 4/2014 | Bancel et al. |
| 2014/0105965 A1 | 4/2014 | Bancel et al. |
| 2014/0105966 A1 | 4/2014 | Bancel et al. |
| 2014/0107189 A1 | 4/2014 | Bancel et al. |
| 2014/0113959 A1 | 4/2014 | Bancel et al. |
| 2014/0113960 A1 | 4/2014 | Bancel et al. |
| 2014/0141037 A1 | 5/2014 | Swanson et al. |
| 2014/0141067 A1 | 5/2014 | Bancel et al. |
| 2014/0141068 A1 | 5/2014 | Bancel et al. |
| 2014/0141070 A1 | 5/2014 | Geall et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0161873 A1 | 6/2014 | Bancel et al. |
| 2014/0162934 A1 | 6/2014 | Constien et al. |
| 2014/0162962 A1 | 6/2014 | Constien et al. |
| 2014/0170175 A1 | 6/2014 | Constien et al. |
| 2014/0171485 A1 | 6/2014 | Bancel et al. |
| 2014/0178429 A1 | 6/2014 | Tsai |
| 2014/0178438 A1 | 6/2014 | Ugur et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0193484 A1 | 7/2014 | Bertholet Girardin et al. |
| 2014/0194494 A1 | 7/2014 | Bancel et al. |
| 2014/0199371 A1 | 7/2014 | Bancel et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0212498 A1 | 7/2014 | Brito et al. |
| 2014/0212504 A1 | 7/2014 | Weers et al. |
| 2014/0220083 A1 | 8/2014 | Brito et al. |
| 2014/0221465 A1 | 8/2014 | Bancel et al. |
| 2014/0227237 A1 | 8/2014 | June et al. |
| 2014/0227300 A1 | 8/2014 | Chin et al. |
| 2014/0227346 A1 | 8/2014 | Geall et al. |
| 2014/0242152 A1 | 8/2014 | Geall et al. |
| 2014/0243399 A1 | 8/2014 | Schrum et al. |
| 2014/0248312 A1 | 9/2014 | Rappuoli et al. |
| 2014/0248314 A1 | 9/2014 | Swanson et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0255472 A1 | 9/2014 | Geall et al. |
| 2014/0271829 A1 | 9/2014 | Lilja et al. |
| 2014/0275227 A1 | 9/2014 | Hoge et al. |
| 2014/0275229 A1 | 9/2014 | Bancel et al. |
| 2014/0288160 A1 | 9/2014 | Guild et al. |
| 2014/0294938 A1 | 10/2014 | Guild et al. |
| 2014/0294939 A1 | 10/2014 | Guild et al. |
| 2014/0294940 A1 | 10/2014 | Guild et al. |
| 2014/0308746 A1 | 10/2014 | Rossi et al. |
| 2014/0309277 A1 | 10/2014 | Baryza et al. |
| 2014/0315988 A1 | 10/2014 | Dahl et al. |
| 2014/0328825 A1 | 11/2014 | Meis et al. |
| 2014/0341995 A1 | 11/2014 | Rudolph et al. |
| 2014/0343129 A1 | 11/2014 | de Fougerolles et al. |

(56) References Cited

U.S. PATENT DOCUMENTS

| | | |
|---|---|---|
| 2014/0363876 A1 | 12/2014 | Jendrisak et al. |
| 2014/0370545 A1 | 12/2014 | Mauro et al. |
| 2014/0371302 A1 | 12/2014 | Afeyan et al. |
| 2014/0378538 A1 | 12/2014 | Bancel et al. |
| 2015/0004217 A1 | 1/2015 | Guild et al. |
| 2015/0005372 A1 | 1/2015 | Hoge et al. |
| 2015/0017206 A1 | 1/2015 | Rueckl et al. |
| 2015/0017211 A1 | 1/2015 | de Fougerolles et al. |
| 2015/0030576 A1 | 1/2015 | Bancel et al. |
| 2015/0038558 A1 | 2/2015 | Kariko et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0141498 A1 | 5/2015 | Mutzke |
| 2015/0141499 A1 | 5/2015 | Bancel et al. |
| 2015/0166616 A1 | 6/2015 | Bancel et al. |
| 2015/0167017 A1 | 6/2015 | Roy et al. |
| 2015/0246139 A1 | 9/2015 | Bancel et al. |
| 2015/0307542 A1 | 10/2015 | Roy et al. |
| 2016/0024547 A1 | 1/2016 | Bancel et al. |
| 2016/0038612 A1 | 2/2016 | Hoge et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2017/0136131 A1 | 5/2017 | Roy et al. |
| 2017/0136132 A1 | 5/2017 | Roy et al. |
| 2017/0175129 A1 | 6/2017 | Roy et al. |

FOREIGN PATENT DOCUMENTS

| | | |
|---|---|---|
| WO | 1999014346 | 3/1999 |
| WO | 2005005622 | 1/2005 |
| WO | 2007024708 | 3/2007 |
| WO | 2007064952 | 3/2007 |
| WO | 2008052770 | 5/2008 |
| WO | 2008083949 | 7/2008 |
| WO | 2008140615 | 11/2008 |
| WO | 2009077134 | 6/2009 |
| WO | 2009127230 | 10/2009 |
| WO | 2010042877 | 4/2010 |
| WO | 2010054406 | 5/2010 |
| WO | 2010061996 A1 | 6/2010 |
| WO | 2010088537 | 8/2010 |
| WO | 2010098861 | 9/2010 |
| WO | 2010129709 | 11/2010 |
| WO | 2011068810 | 6/2011 |
| WO | 2011071931 | 6/2011 |
| WO | 2011071936 | 6/2011 |
| WO | 2011130624 A2 | 10/2011 |
| WO | 2012019168 | 2/2012 |
| WO | 2012045075 | 4/2012 |
| WO | 2012045082 | 4/2012 |
| WO | 2012089338 | 7/2012 |
| WO | 2012135805 | 10/2012 |
| WO | WO-2012/158736 A1 | 11/2012 |
| WO | 2012170889 | 12/2012 |
| WO | 2012170930 | 12/2012 |
| WO | 2013039857 | 3/2013 |
| WO | WO-2013/039861 A2 | 3/2013 |
| WO | WO-2013/052523 A1 | 4/2013 |
| WO | WO-2013/090648 A1 | 6/2013 |
| WO | WO-2013/096709 A2 | 6/2013 |
| WO | 2013100869 | 7/2013 |
| WO | WO-2013/101690 A1 | 7/2013 |
| WO | 2013126776 | 8/2013 |
| WO | 2013129935 | 9/2013 |
| WO | 2013129936 | 9/2013 |
| WO | 2013134349 | 9/2013 |
| WO | WO-2013/130161 A1 | 9/2013 |
| WO | 2013/151666 A2 | 10/2013 |
| WO | 2013151663 A1 | 10/2013 |
| WO | 2013151664 A1 | 10/2013 |
| WO | 2013151665 A2 | 10/2013 |
| WO | 2013151667 A1 | 10/2013 |
| WO | 2013151668 A2 | 10/2013 |
| WO | 2013151669 A1 | 10/2013 |
| WO | 2013151670 A2 | 10/2013 |
| WO | 2013151671 A1 | 10/2013 |
| WO | 2013151672 A2 | 10/2013 |
| WO | 2013151736 A2 | 10/2013 |
| WO | 2014028429 A2 | 2/2014 |
| WO | WO-2014/081507 A1 | 5/2014 |
| WO | 2014093574 A1 | 6/2014 |
| WO | 2014093924 A1 | 6/2014 |
| WO | WO-2014/113089 A2 | 7/2014 |
| WO | 2014144039 A1 | 9/2014 |
| WO | 2014144711 A1 | 9/2014 |
| WO | 2014144767 A1 | 9/2014 |
| WO | 2014152027 A1 | 9/2014 |
| WO | 2014152030 A1 | 9/2014 |
| WO | 2014152031 A1 | 9/2014 |
| WO | 2014152211 A1 | 9/2014 |
| WO | 2014152540 A1 | 9/2014 |
| WO | 2014158795 A1 | 10/2014 |
| WO | 2014159813 A1 | 10/2014 |
| WO | 2014164253 A1 | 10/2014 |
| WO | 2015006747 A2 | 1/2015 |
| WO | 2015034925 A1 | 3/2015 |
| WO | 2015034928 A1 | 3/2015 |
| WO | 2015038892 A1 | 3/2015 |
| WO | 2015048744 A2 | 4/2015 |
| WO | 2015051173 A2 | 4/2015 |
| WO | 2015051214 A1 | 4/2015 |
| WO | 2015058069 A1 | 4/2015 |
| WO | WO-2015/051169 A2 | 4/2015 |
| WO | WO-2015/085318 A2 | 6/2015 |
| WO | WO-2015/089511 A2 | 6/2015 |
| WO | 2015105926 A1 | 7/2015 |
| WO | WO-2015/196118 A1 | 12/2015 |
| WO | WO-2015/196128 A2 | 12/2015 |
| WO | WO-2015/196130 A2 | 12/2015 |
| WO | WO-2016/011222 A2 | 1/2016 |
| WO | WO-2016/011226 A1 | 1/2016 |
| WO | WO-2016/036902 A1 | 3/2016 |
| WO | WO-2016/118724 A1 | 7/2016 |
| WO | WO-2016/118725 A1 | 7/2016 |

OTHER PUBLICATIONS

Johansson et al, Intradermal Electroporation of Naked Replicon RNA Elicits Strong Immune Responses, PLoS ONE, 2012, pp. 1-7.*

Kariko et al, Incorporation of Pseudouridine Into mRNA Yields Superior Nonimmunogenic Vector With Increased Translational Capacity and Biological Stability, Mol Ther. Nov. 2008 ; 16(11): 1833-1840.*

Matsuda, Daiki, et al. Determinants of Initiation Codon Selection during Translation in Mammalian Cells, PLos ONE, Nov. 2010, vol. 5, Issue 11, pp. 1-13.

Ray, Debashish, et al. A compendium of RNA-binding motifs for decoding gene regulaton, Nature, vol. 499, Jul. 11, 2013, pp. 172-177.

Mieszawska, Aneta J., et al. Synthesis of Polymer—Lipid Nanoparticles for Image-Guided Delivery of Dual Modality Therapy. Bioconjugate Chemistry, American Chemical Society, ACS Publications received Apr. 2, 2013, dx. doi.org/10.1021/bc400166j, A-F.

Chang et al., Synthesis and Solution Conformation Studies of 3-Substituted Uridine and Pseudouridine Derivatives. Bioorg Med Chem. Mar. 1, 2008; 16(5): 2676-2686.

Department of Chemistry, University of Maine. 2008, Structure and Properties of Nucleosides and Nucleotides, p. 1-5.

Le et al., Safety, tolerability and humoral immune responses after intramuscular administration of a malaria DNA vaccine to healthy adult volunteers. Vaccine. Mar. 17, 2000;18(18):1893-901.

Fattori et al., Gene electro-transfer of an improved erythropoietin plasmid in mice and non-human primates. Gene Med 2005; 7: 228-236.

(56) References Cited

OTHER PUBLICATIONS

Lorenz, C., et al., Protein expression from exogenous mRNA: Uptake by receptor-mediated endocytosis and trafficking via the lysosomal pathway. RNA Biology, vol. 8, No. 4, Jul. 1, 2011, pp. 627-636.

Lonez, C., et al. "Cationic liposomal lipids: From gene carriers to cell singalling," Progress in Lipid Research, Pergamon Press, Paris, FR. 47(5): 340-347 (2008).

Warren, L. et al. Highly efficient reprogramming to pluripotency and directed differentiation of human cells with synthetic modified mRNA. Cell Stem Cell. Nov. 5, 2010;7(5):618-30.

Kormann, M. et al. Expression of therapeutic proteins after delivery of chemically modified mRNA in mice. Nat Biotechnol. Feb. 2011;29(2):154-7.

Helm, M., "Post-transcriptional nucleotide modification and alternative folding of RNA," Nucleic Acids Research, 2006, vol. 34, No. 2, pp. 721-733.

Limbach, P.A., et al., "Summary: the modified nucleosides of RNA," Nucleic Acids Research, 1994, vol. 22, No. 12, pp. 2183-2196.

Rozenski, J., "The RNA Modification Database: 1999 update," Nucleic Acids Research, 1999, vol. 27, No. 1, pp. 196-197.

Kore, Anilkumar R., et al. Synthesis and biological validation of N7—(4-chlorophenoxyethyl) substituted dinucleotide cap analogs for mRNA translation. Bioorganic & Medicinal Chemistry 21 (2013), pp. 4570-4574.

Bolukbasi, Mehmet Fatih, et al. miR-1289 and "Zipcode"-like Sequence Enrich mRNAs in Microvesicles. Molecular Therapy-Nucleic Acids (2012) 1, e10: doi:10.1038/mtna.2011.2, pp. 1-10.

Kate E. Broderick et al: "Optimized in vivo transfer of small interfering RNA targeting dermal tissue using in vivo surface electroporation", Molecular therapy. Nucleic acids, Jan. 1, 2012 (Jan. 1, 2012), p. e11.

Tendeloo Van V F I et al: "Highly Efficient Gene Delivery by MRNA Electroporation in Human Hematopoietic Cells: Superiority to Lipofection and Passive Pusling of MRNA and to Electroporation of Plasmid CDNA for Tumor Antigen Loading of Dendritic Cells", Blood, American Society of Hematology, US, vol. 98, No. 1, Jul. 1, 2001 (Jul. 1, 2001), pp. 49-56.

Karikó et al., "mRNA is an endogenous ligand for Toll-like receptor 3," J Biol Chem. 279(13):12542-50 (2004).

Karikó et al., "Suppression of RNA recognition by Toll-like receptors: the impact of nucleoside modification and the evolutionary origin of RNA," Immunity. 23(2):165-75 (2005).

\* cited by examiner

98N12-5 (TETA5-LAP)

DLIN-DMA

DLIN-K-DMA (2,2-DILINOLEYL-4-DIMETHYLAMINOMETHYL-[1,3]-DIOXOLANE)

DLIN-KC2-DMA

PRIOR ART

DLIN-MC3-DMA

C12-200

PRIOR ART

PRIOR ART

FORMULATION AND DELIVERY OF MODIFIED NUCLEOSIDE, NUCLEOTIDE, AND NUCLEIC ACID COMPOSITIONS

REFERENCE TO RELATED APPLICATIONS

This application is a 35 U.S.C. § 371 U.S. National Stage Entry of International Application No. PCT/US2014/027077 filed Mar. 14, 2014 which claims priority to U.S. Provisional Patent Application No. 61/782,716, filed Mar. 14, 2013, entitled Formulation and Delivery of Modified Nucleoside, Nucleotide, and Nucleic Acid Compositions, U.S. Provisional Patent Application No. 61/821,406, filed May 9, 2013, entitled Formulation and Delivery of Modified Nucleoside, Nucleotide, and Nucleic Acid Compositions, U.S. Provisional Patent Application No. 61/840,510, filed Jun. 28, 2013, entitled Formulation and Delivery of Modified Nucleoside, Nucleotide, and Nucleic Acid Compositions, U.S. Provisional Patent Application No. 61/877,485, filed Sep. 13, 2013, entitled Formulation and Delivery of Modified Nucleoside, Nucleotide, and Nucleic Acid Composition, and U.S. Provisional Patent Application No. 61/942,894, filed Feb. 21, 2014, entitled Formulation and Delivery of Modified Nucleoside, Nucleotide, and Nucleic Acid Compositions, the contents of each of which are incorporated herein by reference in their entirety.

REFERENCE TO THE SEQUENCE LISTING

The present application is being filed along with a Sequence Listing in electronic format. The Sequence Listing file, entitled M30US371SEQLST.txt, was created on Aug. 20, 2015 and is 34,969 bytes in size. The information in electronic format of the Sequence Listing is incorporated herein by reference in its entirety.

BACKGROUND OF THE INVENTION

In general, exogenous unmodified nucleic acid molecules, particularly viral nucleic acids, introduced into the cell induce an innate immune response which results in cytokine and interferon (IFN) production and ultimately cell death. It is of great interest for therapeutics, diagnostics, reagents and for biological assays to be able to deliver a nucleic acid, e.g., a ribonucleic acid (RNA), into a cell, such as to cause intracellular translation of the nucleic acid and production of the encoded protein instead of generating an innate immune response. Thus, there is a need to develop formulation compositions comprising a delivery agent that can effectively facilitate the in vivo delivery of nucleic acids to targeted cells without generating an innate immune response.

SUMMARY OF THE INVENTION

The present disclosure provides a method of increasing the duration of protein expression from an mRNA in a mammalian cell or tissue of a mammal comprising administering the mRNA via electroporation. In one aspect the injection is an intramuscular injection or an intradermal injection. The mRNA may comprise at least one chemical modification such as, but not limited to, pseudouridine, 1-methylpseudouridine and 5-methylcytosine. As a non-limiting example, the mRNA may be administered at a dose such as 025 mg/kg, 0.25 mg/kg, 2.5 mg/kg and 5 mg/kg.

In one aspect, one or more electric pulses are delivered in a first stage, second stage and a third stage. As a non-limiting example, the first stage is a single pulse at an amplitude of approximately 450V for a pulse duration of approximately 0.05 ms and a pause interval of approximately 0.2 ms, the second stage is a single pulse at an amplitude of approximately 450V for a pulse duration of approximately 0.05 ms and a pause interval of approximately 50 ms and the third stage is a pulse repeated eight times at an amplitude of approximately 110V for a pulse duration of approximately 10 ms and a pause interval of approximately 20 ms.

In one aspect, administration comprising the steps of injecting the mammal with mRNA and delivering one or more electric pulses at or near the site of injection.

In one aspect, the duration is increased for at least 2 hours, at least 8 hours, at least 24 hours, at least 1 week, at least 2 weeks or at least 3 weeks as compared to the administration of mRNA without electroporation.

The present disclosure provides, inter alia, formulation compositions comprising nucleic acid molecules which may be modified and which may encode a protein, a protein precursor, or a partially or fully processed form of the protein or a protein precursor. The formulation compositions may further include a modified nucleic acid molecule and a delivery agent. The present invention further provides nucleic acids useful for encoding polypeptides capable of modulating a cell's function and/or activity.

In one aspect a method of producing a polypeptide of interest in a mammalian cell or tissue is described. The method comprises contacting the mammalian cell or tissue with a formulation comprising a modified mRNA encoding a polypeptide of interest. The formulation may be, but is not limited to, nanoparticles, poly(lactic-co-glycolic acid) (PLGA) microspheres, lipidoids, lipoplex, liposome, polymers, carbohydrates (including simple sugars), cationic lipids, fibrin gel, fibrin hydrogel, fibrin glue, fibrin sealant, fibrinogen, thrombin, rapidly eliminated lipid nanoparticles (reLNPs) and combinations thereof. The modified mRNA may comprise a purified IVT transcript.

In one embodiment, the formulation comprising the modified mRNA is a nanoparticle which may comprise at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG and PEGylated lipids. In another aspect, the lipid may be a cationic lipid such as, but not limited to, DLin-DMA, DLin-D-DMA, DLin-MC3-DMA, DLin-KC2-DMA and DODMA.

The lipid to modified mRNA ratio in the formulation may be between 10:1 and 50:1. The mean size of the nanoparticle formulation may comprise the modified mRNA is less than 60 nm or between 60 and 225 nm. The PDI of the nanoparticle formulation comprising the modified mRNA is between 0.03 and 0.15. The zeta potential of the lipid may be from −10 to +10 at a pH of 7.4

The formulations of modified mRNA may comprise a fusogenic lipid, cholesterol and a PEG lipid. The formulation may have a molar ratio 50:10:38.5:1.5-3.0 (cationic lipid:fusogenic lipid: cholesterol: PEG lipid). The PEG lipid may be selected from, but is not limited to PEG-c-DOMG, PEG-DMG. The fusogenic lipid may be DSPC.

The mammalian cell or tissue may be contacted using a device such as, but not limited to, a syringe pump, internal osmotic pump and external osmotic pump.

The mammalian cell or tissue may be contacted with an electroporation device after the cell or tissue is contacted with the formulation of mRNA or modified mRNA.

The formulation of modified mRNA may be a PLGA microsphere which may be between 4 and 20 μm in size. The modified mRNA may be released from the formulation at less than 50% in a 48 hour time period. The PLGA microsphere formulation may be stable in serum. Stability may be determined relative to unformulated modified mRNA in 90%.

The loading weight percent of the modified mRNA PLGA microsphere may be at least 0.05%, at least 0.1%, at least 0.2%, at least 0.3%, at least 0.4% or at least 0.5%. The encapsulation efficiency of the modified mRNA in the PLGA microsphere may be at least 50%, at least 70%, at least 90% or at least 97%.

A lipid nanoparticle of the present invention may be formulated in a sealant such as, but not limited to, a fibrin sealant.

The mammalian cells or tissues may be contacted by a route of administration such as, but not limited to, intravenous, intramuscular, intravitreal, intrathecal, intratumoral, pulmonary, subcutaneous and intradermally. The mammalian cells or tissues may be contacted using a split dosing schedule. The mammalian cell or tissue may be contacted by injection. The injection may be made to tissue selected from the group consisting of intradermal space, epidermis, subcutaneous tissue and muscle. The polypeptide of interest may be produced in the cell or tissue in a location systemic from the location of contacting.

The polypeptide of interest may be detectable in serum for up to 72 hours after contacting. The level of the polypeptide of interest can be higher than the levels prior to dosing. The level of the polypeptide of interest may be greater in the serum of female subjects than in the serum of male subjects.

The formulation of modified mRNA may comprise more than one modified mRNA. The formulation may have two or three modified mRNA.

The formulation comprising the modified mRNA may comprise a rapidly eliminated lipid nanoparticle (reLNP) which may comprise a reLNP lipid, fusogenic lipid, cholesterol and a PEG lipid at a molar ratio of 50:10:38.5:1.5 (reLNP lipid:fusogenic lipid: cholesterol: PEG lipid). The fusogenic lipid may be DSPC and the PEG lipid may be PEG-c-DOMG. The reLNP lipid may be DLin-DMA with an internal or terminal ester or DLin-MC3-DMA with an internal or terminal ester. The total lipid to modified mRNA weight ration may be between 10:1 and 30:1.

The formulation comprising modified mRNA may comprise a fibrin sealant.

The formulation comprising modified mRNA may comprise a lipidoid where the lipid is selected from the group consisting of C12-200 and 98N12-5.

The formulation comprising modified mRNA may include a polymer. The polymer may be coated, covered, surrounded, enclosed or comprise a layer of a hydrogel or surgical sealant. The polymer may be selected from the group consisting of PLGA, ethylene vinyl acetate, poloxamer and GELSITE®.

A polypeptide of interest may be produced in a mammalian cell or tissue by contacting the mammalian cell or tissue with a buffer formulation comprising a modified mRNA encoding the polypeptide of interest. The buffer formulation may be selected from, but is not limited to, saline, phosphate buffered saline and Ringer's lactate. The buffer formulation may comprise a calcium concentration of between 1 to 10 mM. The modified mRNA in the buffer formulation may comprise a purified IVT transcript.

A pharmacologic effect in a primate may be produced by contacting the primate with a composition comprising a formulated modified mRNA encoding a polypeptide of interest. The modified mRNA may comprise a purified IVT transcript and/or may be formulated in nanoparticles, poly(lactic-co-glycolic acid)(PLGA) microspheres, lipidoids, lipoplex, liposome, polymers, carbohydrates (including simple sugars), cationic lipids, fibrin gel, fibrin hydrogel, fibrin glue, fibrin sealant, fibrinogen, thrombin, rapidly eliminated lipid nanoparticles (reLNPs) and combinations thereof. The pharmacological effect may be greater than the pharmacologic effect associated with a therapeutic agent and/or composition known to produce said pharmacologic effect. The composition may comprise a formulated or unformulated modified mRNA. The pharmacologic effect may result in a therapeutically effective outcome of a disease, disorder, condition or infection. Such therapeutically effective outcome may include, but is not limited to, treatment, improvement of one or more symptoms, diagnosis, prevention, and delay of onset. The pharmacologic effect may include, but is not limited to, change in cell count, alteration in serum chemistry, alteration of enzyme activity, increase in hemoglobin, and increase in hematocrit.

In one embodiment, the present disclosure provides a formulation composition which comprises a modified nucleic acid molecule and a delivery agent. The modified nucleic acid molecule may be selected from the group consisting of DNA, complimentary DNA (cDNA), RNA, messenger RNA (mRNA), RNAi-inducing agents, RNAi agents, siRNA, shRNA, miRNA, antisense RNA, ribozymes, catalytic DNA, RNA that induce triple helix formation, aptamers, vectors and combinations thereof. If the modified nucleic acid molecule is mRNA the mRNA may be derived from cDNA.

In one embodiment, the modified nucleic acid molecule may comprise at least one modification and a translatable region. In some instances, the modified nucleic acid comprises at least two modifications and a translatable region. The modification may be located on the backbone and/or a nucleoside of the nucleic acid molecule. The modification may be located on both a nucleoside and a backbone linkage.

In one embodiment, a modification may be located on the backbone linkage of the modified nucleic acid molecule. The backbone linkage may be modified by replacing of one or more oxygen atoms. The modification of the backbone linkage may comprise replacing at least one phosphodiester linkage with a phosphorothioate linkage.

In one embodiment, a modification may be located on a nucleoside of the modified nucleic acid molecule. The modification on the nucleoside may be located on the sugar of said nucleoside. The modification of the nucleoside may occur at the 2' position on the nucleoside.

The nucleoside modification may include a compound selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine. In another embodiment, the modifications are independently selected from the group consisting of 5-methylcytosine, pseudouridine and 1-methylpseudouridine In one embodiment, a modification may be located on a nucleobase of the modified nucleic acid molecule. The modification on the nucleobase may be selected from the group consisting of cytosine, guanine, adenine, thymine and uracil. The modification on the nucleobase may be selected from the group consisting of deaza-adenosine and deaza-guanosine, and the linker may be attached at a C-7 or C-8 position of said deaza-adenosine or deaza-guanosine. The modified nucleobase may be selected from the group consisting of cytosine and uracil, and the linker may be attached to the modified nucleobase at an N-3 or C-5 position. The linker attached to the nucleobase may be selected from the group consisting of diethylene glycol, dipropylene glycol, triethylene glycol, tripropylene glycol, tetraethylene glycol, tetraethylene glycol, divalent alkyl, alkenyl, alkynyl moiety, ester, amide, and ether moiety.

In one embodiment, two modifications of the nucleic acid molecule may be located on nucleosides of the modified nucleic acid molecule. The modified nucleosides may be selected from 5-methylcytosine and pseudouridine.

In one embodiment, two modifications of the modified nucleic acid molecule may be located on a nucleotide or a nucleoside. In one embodiment, the present disclosure provides a formulation comprising a nucleic acid molecule such as, but not limited to, SEQ ID NO: 4, SEQ ID NO: 5, SEQ ID NO: 7 and SEQ ID NO: 8 and a delivery agent. The nucleic acid molecule may comprise a polyA tail about 160 nucleotides in length. Further, the nucleic acid molecule may comprise at least one 5' terminal cap such as, but not limited to, Cap0, Cap1, ARCA, inosine, N1-methyl-guanosine, 2'fluoro-guanosine, 7-deaza-guanosine, 8-oxo-guanosine, 2-amino-guanosine, LNA-guanosine, and 2-azido-guanosine.

In one embodiment, the present disclosure provides a nucleic acid of SEQ ID NO: 4, a 5' terminal cap which is Cap1, a poly A tail of approximately 160 nucleotides in length and a delivery agent.

In one embodiment, the present disclosure provides a nucleic acid of SEQ ID NO: 5, a 5' terminal cap which is Cap1, a poly A tail of approximately 160 nucleotides in length and a delivery agent.

In one embodiment, the present disclosure provides a nucleic acid of SEQ ID NO: 7, a 5' terminal cap which is Cap1, a poly A tail of approximately 160 nucleotides in length and a delivery agent.

In one embodiment, the present disclosure provides a nucleic acid of SEQ ID NO: 8, a 5' terminal cap which is Cap1, a poly A tail of approximately 160 nucleotides in length and a delivery agent.

In one embodiment, the delivery agent comprises at least one method to improve delivery selected from the group consisting of lipidoids, liposomes, lipid nanoparticles, rapidly eliminated lipid nanoparticles (reLNPs), polymers, lipoplexes, peptides, proteins, hydrogels, sealants, chemical modifications, conjugation, cells and enhancers. The lipidoid, lipid nanoparticle and rapidly eliminated lipid nanoparticles which may be used as a delivery agent may include a lipid which may be selected from the group consisting of C12-200, MD1, 98N12-5, DLin-DMA, DLin-K-DMA, DLin-KC2-DMA, DLin-MC3-DMA, PLGA, PEG, PEG-DMG, PEGylated lipids and analogs thereof. The rapidly eliminated lipid nanoparticle may have an ester linkage at the terminal end of the lipid chain, or an ester linkage may be an internal linkage located to the right or left of a saturated carbon in the lipid chain. The rapidly eliminated lipid nanoparticle which may be used as a delivery agent may be, but is not limited to, DLin-MC3-DMA and DLin-DMA.

In one embodiment, the lipid nanoparticle may comprise PEG and at least one component such as, but not limited to, cholesterol, cationic lipid and fusogenic lipid.

In one embodiment, the lipid nanoparticle may comprise at least one of a PEG, cholesterol, cationic lipid and fusogenic lipid.

In one embodiment, the fusogenic lipid is disteroylphophatidyl choline (DSPC). In another embodiment, the PEG lipid is PEG-DMG. In yet another embodiment, the cationic lipid may be, but not limited to, DLin-DMA, DLin-MC3-DMA, C12-200, 98N12-5 and DLin-KC2-DMA.

In one embodiment, the lipid nanoparticle composition may comprise 50 mol % cationic lipid, 10 mol % DSPC, 1.5-3.0 mol % PEG and 37-38.5 mol % cholesterol.

In one embodiment, a modified nucleic acid may be formulated with PLGA to form a sustained release formulation. In another embodiment, a modified nucleic acid may be formulated with PLGA and other active and/or inactive components to form a sustained release formulation. In one embodiment, the modified nucleic acid molecule may include, but is not limited to, SEQ ID NO: 7 and SEQ ID NO: 8.

In one embodiment, a sustained release formulation may comprise a sustained release microsphere. The sustained release microsphere may be about 10 to about 50 um in diameter. In another embodiment, the sustained release microsphere may contain about 0.001 to about 1.0 weight percent of at least one modified nucleic acid molecule.

In one embodiment, the modified nucleic acids of the present invention may include at least one stop codon before the 3' untranslated region (UTR). The stop codon may be selected from TGA, TAA and TAG. In one embodiment, the modified nucleic acids of the present invention include the stop codon TGA and one additional stop codon. In a further embodiment the addition stop codon may be TAA. In another embodiment, the modified nucleic acid of the present invention includes three stop codons.

In one embodiment, the present disclosure provides a controlled release formulation comprising a modified nucleic acid which may encode a polypeptide of interest. The modified nucleic acid may be encapsulated or substantially encapsulated in a delivery agent. The delivery agent may be coated, covered, surrounded, enclosed or comprise a layer of polymer, hydrogel and/or surgical sealant. In a further embodiment, the controlled release formulation may comprise a second layer of polymer, hydrogel and/or surgical sealant.

In one embodiment, the delivery agent of the controlled release formulation may include, but is not limited to, lipidoids, liposomes, lipid nanoparticles, rapidly eliminated lipid nanoparticles, lipoplexes and self-assembled lipid nanoparticles.

The polymer which may be used in the controlled release formulation may include, but is not limited to, PLGA, ethylene vinyl acetate, poloxamer and GELSITE®. The surgical sealant which may be used in the controlled release formulation may include, but is not limited to, fibrinogen polymers, TISSEELL®, PEG-based sealants and COSEAL®.

In one embodiment, the delivery agent of the controlled release formulation comprises a lipid nanoparticle or a rapidly eliminated lipid nanoparticle delivery agent. In one aspect, the lipid nanoparticle or rapidly eliminated lipid nanoparticle may be coated, substantially coated, covered, substantially covered, surrounded, substantially surrounded, enclosed, substantially enclosed or comprises a layer of polymer, hydrogel and/or surgical sealant. In another aspect, the delivery agent may be a lipid nanoparticle which may be coated, substantially coated, covered, substantially covered, surrounded, substantially surrounded, enclosed, substantially enclosed or comprises a layer of PLGA.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

DETAILED DESCRIPTION

Figure 1:
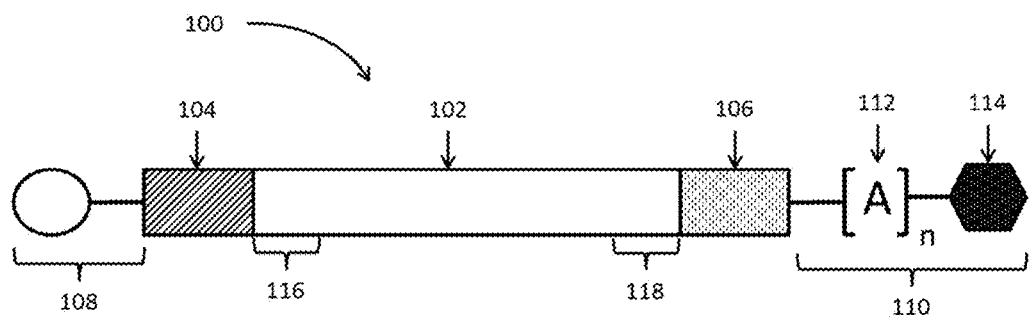
FIG. 1 is a schematic of a nucleic acid molecule, modified nucleic acid molecule and/or mmRNA.

The delivery of nucleic acids into cells has many undesired complications including the integration of the nucleic acid into the target cell genome which may result in imprecise expression levels, the deleterious transfer of the nucleic acid to progeny and neighbor cells and a substantial risk of causing mutations. The nucleic acid molecules of the present disclosure may be modified and may be capable of reducing the innate immune activity of a population of cells into which they are introduced, thus increasing the efficiency of protein production in that cell population. Further, one or more additional advantageous activities and/or properties of the nucleic acids and proteins of the present disclosure are described herein.

In addition, provided herein are methods of treating a subject having or being suspected of having a disease, disorder and/or condition the methods comprising administering to a subject in need of such treatment a composition described herein in an amount sufficient to treat the disease, disorder and/or condition.

Unless otherwise defined, all technical and scientific terms used herein have the same meaning as commonly understood by one of ordinary skill in the art to which this invention belongs. Although methods and materials similar or equivalent to those described herein can be used in the practice or testing of methods featured in the invention, suitable methods and materials are described below.

Nucleic Acid Molecules and Modified Nucleic Acid Molecules

The present disclosure provides nucleic acids, including RNA such as mRNA, which may contain one or more modified nucleosides or nucleotides (termed "modified nucleic acid molecules," "modified mRNA," "modified mRNA molecules" or "mmRNA") as described herein. The modification of the nucleic acid molecules of the present invention may have useful properties including, but not limited to, a significant decrease in or a lack of a substantial induction of the innate immune response of a cell into which the modified mRNA is introduced. The modified nucleic acid molecules may also exhibit enhanced efficiency of protein production, intracellular retention of nucleic acids, and viability of contacted cells, as well as having reduced immunogenicity as compared to unmodified nucleic acid molecules.

Provided are nucleic acid molecules containing a translatable region. The terms "nucleic acid" and "nucleic acid molecules" include any compound and/or substance that is or can be incorporated into an oligonucleotide chain. Exemplary nucleic acids for use in accordance with the present disclosure include, but are not limited to, one or more of DNA, cDNA, RNA including messenger RNA (mRNA), hybrids thereof, RNAi-inducing agents, RNAi agents, siRNA, shRNA, miRNA, antisense RNA, ribozymes, catalytic DNA, RNA that induce triple helix formation, aptamers, vectors and the like. As a non-limiting example, a nucleic acid molecule may be an mRNA.

Provided are modified nucleic acid molecules containing a translatable region and one, two, or more than two different nucleoside modifications Exemplary nucleic acids for use in this disclosure include ribonucleic acids (RNA), deoxyribonucleic acids (DNAs), threose nucleic acids (TNAs), glycol nucleic acids (GNAs), locked nucleic acids (LNAs) or a hybrid thereof. In preferred embodiments, the modified nucleic acid molecules include messenger RNA (mRNA). As described herein, the modified nucleic acid molecules of the present disclosure may not substantially induce an innate immune response of a cell into which the modified mRNA is introduced. In another embodiment, the modified nucleic acid molecule may exhibit reduced degradation, as compared to a nucleic acid that has not been modified, in a cell where the modified nucleic acid molecule is introduced.

In certain embodiments, it is desirable to intracellularly degrade a nucleic acid molecule or a modified nucleic acid molecule introduced into the cell. For example it would be desirable to degrade a nucleic acid molecule or a modified nucleic acid molecule if precise timing of protein production was desired. Thus, the present disclosure provides a nucleic acid molecule or a modified nucleic acid molecule containing a degradation domain, which is capable of being acted on in a directed manner within a cell.

Traditionally, the basic components of an mRNA molecule include at least a coding region, a 5'UTR, a 3'UTR, a 5' cap and a poly-A tail. Building on this wild type modular structure, the present invention expands the scope of functionality of traditional mRNA molecules by providing nucleic acid molecules, modified nucleic acid molecules and/or mmRNA which maintain a modular organization, but which may comprise one or more structural and/or chemical modifications or alterations which impart useful properties to the polynucleotide including, in some embodiments, the lack of a substantial induction of the innate immune response of a cell into which the nucleic acid molecules, modified nucleic acid molecules and/or mmRNA are introduced. As used herein, a "structural" feature or modification is one in which two or more linked nucleotides are inserted, deleted, duplicated, inverted or randomized in a nucleic acid molecule, a modified nucleic acid molecule or mmRNA without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" may be chemically modified to "AT-5meC-G". The same polynucleotide may be structurally modified from "ATCG" to "ATCCG". Here, the dinucleotide "CC" has been inserted, resulting in a structural modification to the polynucleotide.

In some embodiments, the modified nucleic acid molecules may be chemically modified on the sugar, nucleobase (e.g., in the 5' position of the nucleobase), or phosphate backbone (e.g., replacing the phosphate with another moiety such as a thiophospate). In some embodiments, the modification may result in a disruption of a major groove binding partner interaction, which may contribute to an innate immune response. In some embodiments, the formulation composition, when administered to a subject, can result in improved bioavailability, therapeutic window, or volume of distribution of the modified nucleic acid molecule relative to administration of the modified nucleic acid molecule without the incorporation of the delivery agent. In some embodiments, the modified nucleosides and nucleotides of the modified nucleic acid molecules of the present invention may be synthesized using the O-protected compounds described in International Pub. No. WO2012138530, the contents of which is herein incorporated by reference in its entirety.

In certain embodiments, the nucleic acid molecule or modified nucleic acid molecule may comprise mRNA. In particular embodiments, the modified mRNA (mmRNA) may be derived from cDNA. In certain embodiments, mmRNA may comprise at least two nucleoside modifications. In one embodiment, the nucleoside modifications may be selected from 5-methylcytosine and pseudouridine. In another embodiment, at least one of the nucleoside modifications is not 5-methylcytosine and/or pseudouridine. In certain embodiments the delivery agent may comprise formulations allowing for localized and systemic delivery of mmRNA. The formulations of the nucleic acid molecules, modified nucleic acids molecules and/or mmRNA may be selected from, but are not limited to, lipidoids, liposomes and lipid nanoparticles, rapidly eliminated lipid nanoparticles, polymers, lipoplexes, peptides and proteins, at least one chemical modification and conjugation, enhancers, and/or cells.

In one embodiment, the nucleic acid molecules, modified nucleic acid molecules of the present invention may include at least two stop codons before the 3' untranslated region (UTR). The stop codon may be selected from TGA, TAA and TAG. In one embodiment, the nucleic acids of the present invention include the stop codon TGA and one additional stop codon. In a further embodiment the addition stop codon may be TAA. In another embodiment, the nucleic acid molecules, modified nucleic acid molecules may comprise three stop codons.

Other components of a nucleic acid are optional in a nucleic acid molecule or a modified nucleic acid molecule but these components may be beneficial in some embodiments.

mmRNA Architecture

The mmRNA of the present invention are distinguished from wild type mRNA in their functional and/or structural design features which serve to, as evidenced herein, overcome existing problems of effective polypeptide production using nucleic acid-based therapeutics.

FIG. 1 shows a representative mmRNA 100 of the present invention. mmRNA refers to a polynucleotide transcript which encodes one or more polypeptides of interest and which retains sufficient structural and/or chemical features to allow the polypeptide of interest encoded therein to be translated. Non-limiting examples of polypeptides of interest and polynucleotides encoding polypeptide of interest are described in Table 6 of U.S. Provisional Patent Application No. 61/618,862, filed Apr. 2, 2012, entitled Modified Polynucleotides for the Production of Biologics; U.S. Provisional Patent Application No. 61/681,645, filed Aug. 10, 2012, entitled Modified Polynucleotides for the Production of Biologics; U.S. Provisional Patent Application No. 61/737,130, filed Dec. 14, 2012, entitled Modified Polynucleotides for the Production of Biologics; International Application No PCT/US2013/030062, filed Mar. 9, 2013, entitled Modified Polynucleotides for the Production of Biologics and Proteins Associated with Human Disease; U.S. Provisional Patent Application No. 61/618,866, filed Apr. 2, 2012, entitled Modified Polynucleotides for the Production of Antibodies; U.S. Provisional Patent Application No. 61/681,647, filed Aug. 10, 2012, entitled Modified Polynucleotides for the Production of Antibodies; U.S. Provisional Patent Application No. 61/737,134, filed Dec. 14, 2012, entitled Modified Polynucleotides for the Production of Antibodies; International Application No PCT/US2013/030063, filed Mar. 9, 2013, entitled Modified Polynucleotides; U.S. Provisional Patent Application No. 61/618,868, filed Apr. 2, 2012, entitled Modified Polynucleotides for the Production of Vaccines; U.S. Provisional Patent Application No. 61/681,648, filed Aug. 10, 2012, entitled Modified Polynucleotides for the Production of Vaccines; U.S. Provisional Patent Application No. 61/737,135, filed Dec. 14, 2012, entitled Modified Polynucleotides for the Production of Vaccines; U.S. Provisional Patent Application No. 61/618,870, filed Apr. 2, 2012, entitled Modified Polynucleotides for the Production of Therapeutic Proteins and Peptides; U.S. Provisional Patent Application No. 61/681,649, filed Aug. 10, 2012, entitled Modified Polynucleotides for the Production of Therapeutic Proteins and Peptides; U.S.

Provisional Patent Application No. 61/737,139, filed Dec. 14, 2012, Modified Polynucleotides for the Production of Therapeutic Proteins and Peptides; U.S. Provisional Patent Application No. 61/618,873, filed Apr. 2, 2012, entitled Modified Polynucleotides for the Production of Secreted Proteins; U.S. Provisional Patent Application No. 61/681,650, filed Aug. 10, 2012, entitled Modified Polynucleotides for the Production of Secreted Proteins; U.S. Provisional Patent Application No. 61/737,147, filed Dec. 14, 2012, entitled Modified Polynucleotides for the Production of Secreted Proteins; International Application No. PCT/US2013/030064, entitled Modified Polynucleotides for the Production of Secreted Proteins; U.S. Provisional Patent Application No. 61/618,878, filed Apr. 2, 2012, entitled Modified Polynucleotides for the Production of Plasma Membrane Proteins; U.S. Provisional Patent Application No. 61/681,654, filed Aug. 10, 2012, entitled Modified Polynucleotides for the Production of Plasma Membrane Proteins; U.S. Provisional Patent Application No. 61/737,152, filed Dec. 14, 2012, entitled Modified Polynucleotides for the Production of Plasma Membrane Proteins; International Application No PCT/US2013/030059, filed Mar. 9, 2013, entitled Modified Polynucleotides for the Production of Membrane Proteins; U.S. Provisional Patent Application No. 61/618,885, filed Apr. 2, 2012, entitled Modified Polynucleotides for the Production of Cytoplasmic and Cytoskeletal Proteins; U.S. Provisional Patent Application No. 61/681,658, filed Aug. 10, 2012, entitled Modified Polynucleotides for the Production of Cytoplasmic and Cytoskeletal Proteins; U.S. Provisional Patent Application No. 61/737,155, filed Dec. 14, 2012, entitled Modified Polynucleotides for the Production of Cytoplasmic and Cytoskeletal Proteins; International Application No. PCT/US2013/030066, filed Mar. 9, 2013, entitled Modified Polynucleotides for the Production of Cytoplasmic and Cytoskeletal Proteins; U.S. Provisional Patent Application No. 61/618,896, filed Apr. 2, 2012, entitled Modified Polynucleotides for the Production of Intracellular Membrane Bound Proteins; U.S. Provisional Patent Application No. 61/668,157, filed Jul. 5, 2012, entitled Modified Polynucleotides for the Production of Intracellular Membrane Bound Proteins; U.S. Provisional Patent Application No. 61/681,661, filed Aug. 10, 2012, entitled Modified Polynucleotides for the Production of Intracellular Membrane Bound Proteins; U.S. Provisional Patent Application No. 61/737,160, filed Dec. 14, 2012, entitled Modified Polynucleotides for the Production of Intracellular Membrane Bound Proteins; U.S. Provisional Patent Application No. 61/618,911, filed Apr. 2, 2012, entitled Modified Polynucleotides for the Production of Nuclear Proteins; U.S. Provisional Patent Application No. 61/681,667, filed Aug. 10, 2012, entitled Modified Polynucleotides for the Production of Nuclear Proteins; U.S. Provisional Patent Application No. 61/737,168, filed Dec. 14, 2012, entitled Modified Polynucleotides for the Production of Nuclear Proteins; International Application No. PCT/US2013/030067, filed Mar. 9, 2013, entitled Modified Polynucleotides for the Production of Nuclear Proteins; U.S. Provisional Patent Application No. 61/618,922, filed Apr. 2, 2012, entitled Modified Polynucleotides for the Production of Proteins; U.S. Provisional Patent Application No. 61/681,675, filed Aug. 10, 2012, entitled Modified Polynucleotides for the Production of Proteins; U.S. Provisional Patent Application No. 61/737,174, filed Dec. 14, 2012, entitled Modified Polynucleotides for the Production of Proteins; International Application No. PCT/US2013/030060, filed Mar. 9, 2013, entitled Modified Polynucleotides for the Production of Proteins; U.S. Provisional Patent Application No. 61/618,935, filed Apr. 2, 2012, entitled Modified Polynucleotides for the Production of Proteins Associated with Human Disease; U.S. Provisional Patent Application No. 61/681,687, filed Aug. 10, 2012, entitled Modified Polynucleotides for the Production of Proteins Associated with Human Disease; U.S. Provisional Patent Application No. 61/737,184, filed Dec. 14, 2012, entitled Modified Polynucleotides for the Production of Proteins Associated with Human Disease; International Application No. PCT/US2013/030061, filed Mar. 9, 2013, entitled Modified Polynucleotides for the Production of Proteins Associated with Human Disease; U.S. Provisional Patent Application No. 61/618,945, filed Apr. 2, 2012, entitled Modified Polynucleotides for the Production of Proteins Associated with Human Disease; U.S. Provisional Patent Application No. 61/681,696, filed Aug. 10, 2012, entitled Modified Polynucleotides for the Production of Proteins Associated with Human Disease; U.S. Provisional Patent Application No. 61/737,191, filed Dec. 14, 2012, entitled Modified Polynucleotides for the Production of Proteins Associated with Human Disease; U.S. Provisional Patent Application No. 61/618,953, filed Apr. 2, 2012, entitled Modified Polynucleotides for the Production of Proteins Associated with Human Disease; U.S. Provisional Patent Application No. 61/681,704, filed Aug. 10, 2012, entitled Modified Polynucleotides for the Production of Proteins Associated with Human Disease; U.S. Provisional Patent Application No. 61/737,203, filed Dec. 14, 2012, entitled Modified Polynucleotides for the Production of Proteins Associated with Human Disease; International Application No. PCT/US2013/031821, filed Mar. 15, 2013, entitled In Vivo Production of Proteins; U.S. Provisional Patent Application No. 61/681,720, filed Aug. 10, 2012, entitled Modified Polynucleotides for the Production of Cosmetic Proteins and Peptides; U.S. Provisional Patent Application No. 61/737,213, filed Dec. 14, 2012, entitled Modified Polynucleotides for the Production of Cosmetic Proteins and Peptides; International Application No. PCT/US2013/030068, filed Mar. 9, 2013, entitled Modified Polynucleotides for the Production of Cosmetic Proteins and Peptides; U.S. Provisional Patent Application No. 61/681,742, filed Aug. 10, 2012, entitled Modified Polynucleotides for the Production of Oncology-Related Proteins and Peptides and International Application No. PCT/US2013/030070, filed Mar. 9, 2013, entitled Modified Polynucleotides for the Production of Oncology-Related Proteins and Peptides, and, the contents of each of which are incorporated herein by reference in their entirety.

Returning to FIG. 1, the mmRNA 100 here contains a first region of linked nucleotides 102 that is flanked by a first flanking region 104 and a second flaking region 106. As used herein, the "first region" may be referred to as a "coding region" or "region encoding" or simply the "first region." This first region may include, but is not limited to, the encoded polypeptide of interest. In one aspect, the first region 102 may include, but is not limited to, the open reading frame encoding at least one polypeptide of interest. The open reading frame may be codon optimized in whole or in part. The flanking region 104 may comprise a region of linked nucleotides comprising one or more complete or incomplete 5' UTRs sequences which may be completely codon optimized or partially codon optimized. The flanking region 104 may include at least one nucleic acid sequence including, but not limited to, miR sequences, TERZAK™ sequences and translation control sequences. The flanking region 104 may also comprise a 5' terminal cap 108. The 5' terminal capping region 108 may include a naturally occurring cap, a synthetic cap or an optimized cap. Non-limiting examples of optimized caps include the caps taught by Rhoads in U.S. Pat. No. 7,074,596 and International Patent Publication No. WO2008157668, WO2009149253 and WO2013103659. The second flanking region 106 may comprise a region of linked nucleotides comprising one or more complete or incomplete 3' UTRs. The second flanking region 106 may be completely codon optimized or partially codon optimized. The flanking region 104 may include at least one nucleic acid sequence including, but not limited to, miR sequences and translation control sequences. After the second flanking region 106 the mmRNA may comprise a 3' tailing sequence 110. The 3' tailing sequence 110 may include a synthetic tailing region 112 and/or a chain terminating nucleoside 114. Non-liming examples of a synthetic tailing region include a polyA sequence, a polyC sequence, a polyA-G quartet. Non-limiting examples of chain terminating nucleosides include 2'-O methyl, F and locked nucleic acids (LNA).

Bridging the 5' terminus of the first region 102 and the first flanking region 104 is a first operational region 114. Traditionally this operational region comprises a Start codon. The operational region may alternatively comprise any translation initiation sequence or signal including a Start codon.

Bridging the 3' terminus of the first region 102 and the second flanking region 106 is a second operational region 116. Traditionally this operational region comprises a Stop codon. The operational region may alternatively comprise any translation initiation sequence or signal including a Stop codon. According to the present invention, multiple serial stop codons may also be used.

Generally, the shortest length of the first region of the mmRNA can be the length of a nucleic acid sequence that is sufficient to encode for a dipeptide, a tripeptide, a tetrapeptide, a pentapeptide, a hexapeptide, a heptapeptide, an octapeptide, a nonapeptide, or a decapeptide. In another embodiment, the length may be sufficient to encode a peptide of 2-30 amino acids, e.g. 5-30, 10-30, 2-25, 5-25, 10-25, or 10-20 amino acids. The length may be sufficient to encode for a peptide of at least 11, 12, 13, 14, 15, 17, 20, 25 or 30 amino acids, or a peptide that is no longer than 40 amino acids, e.g. no longer than 35, 30, 25, 20, 17, 15, 14, 13, 12, 11 or 10 amino acids. Examples of dipeptides that the polynucleotide sequences can encode or include, but are not limited to, carnosine and anserine.

Generally, the length of the first region encoding the polypeptide of interest is greater than about 30 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000, 4,000, 5,000, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the nucleic acid molecules, modified nucleic acid molecules and/or mmRNA includes from about 30 to about 100,000 nucleotides (e.g., from 30 to 50, from 30 to 100, from 30 to 250, from 30 to 500, from 30 to 1,000, from 30 to 1,500, from 30 to 3,000, from 30 to 5,000, from 30 to 7,000, from 30 to 10,000, from 30 to 25,000, from 30 to 50,000, from 30 to 70,000, from 100 to 250, from 100 to 500, from 100 to 1,000, from 100 to 1,500, from 100 to 3,000, from 100 to 5,000, from 100 to 7,000, from 100 to 10,000, from 100 to 25,000, from 100 to 50,000, from 100 to 70,000, from 100 to 100,000, from 500 to 1,000, from 500 to 1,500, from 500 to 2,000, from 500 to 3,000, from 500 to 5,000, from 500 to 7,000, from 500 to 10,000, from 500 to 25,000, from 500 to 50,000, from 500 to 70,000, from 500 to 100,000, from 1,000 to 1,500, from 1,000 to 2,000, from 1,000 to 3,000, from 1,000 to 5,000, from 1,000 to 7,000, from 1,000 to 10,000, from 1,000 to 25,000, from 1,000 to 50,000, from 1,000 to 70,000, from 1,000 to 100,000, from 1,500 to 3,000, from 1,500 to 5,000, from 1,500 to 7,000, from 1,500 to 10,000, from 1,500 to 25,000, from 1,500 to 50,000, from 1,500 to 70,000, from 1,500 to 100,000, from 2,000 to 3,000, from 2,000 to 5,000, from 2,000 to 7,000, from 2,000 to 10,000, from 2,000 to 25,000, from 2,000 to 50,000, from 2,000 to 70,000, and from 2,000 to 100,000).

According to the present invention, the first and second flanking regions may range independently from 15-1,000 nucleotides in length (e.g., greater than 30, 40, 45, 50, 55, 60, 70, 80, 90, 100, 120, 140, 160, 180, 200, 250, 300, 350, 400, 450, 500, 600, 700, 800, and 900 nucleotides or at least 30, 40, 45, 50, 55, 60, 70, 80, 90, 100, 120, 140, 160, 180, 200, 250, 300, 350, 400, 450, 500, 600, 700, 800, 900, and 1,000 nucleotides).

According to the present invention, the synthetic tailing region may range from absent to 500 nucleotides in length (e.g., at least 60, 70, 80, 90, 120, 140, 160, 180, 200, 250, 300, 350, 400, 450, or 500 nucleotides). Where the synthetic tailing region is a polyA tail, the length may be determined in units of or as a function of polyA Binding Protein binding. In this embodiment, the polyA tail is long enough to bind at least 4 monomers of PolyA Binding Protein. PolyA Binding Protein monomers bind to stretches of approximately 38 nucleotides. As such, it has been observed that polyA tails of about 80 nucleotides and 160 nucleotides are functional.

According to the present invention, the 5' terminal capping region may comprise a single cap or a series of nucleotides forming the cap. In this embodiment the capping region may be from 1 to 10, e.g. 2-9, 3-8, 4-7, 1-5, 5-10, or at least 2, or 10 or fewer nucleotides in length. In some embodiments, the cap is absent.

According to the present invention, the first and second operational regions may range from 3 to 40, e.g., 5-30, 10-20, 15, or at least 4, or 30 or fewer nucleotides in length and may comprise, in addition to a Start and/or Stop codon, one or more signal and/or restriction sequences.

In one embodiment, the nucleic acid molecules, modified nucleic acid and/or mmRNA may include modified nucleosides such as, but not limited to, the modified nucleosides described in US Patent Publication No. US20130115272 including pseudouridine, 1-methylpseudouridine, 5-methoxyuridine and 5-methylcytosine. As a non-limiting example, the modified nucleic acid and/or mmRNA may include 1-methylpseudouridine and 5-methylcytosine. As another non-limiting example, the modified nucleic acid and/or mmRNA may include 1-methylpseudouridine. As yet another non-limiting example, the modified nucleic acid and/or mmRNA may include 5-methoxyuridine and 5-methylcytosine. As a non-limiting example, the modified nucleic acid and/or mmRNA may include 5-methoxyuridine.

Untranslated Regions (UTRs)

Untranslated regions (UTRs) of a gene are transcribed but not translated. The 5' UTR starts at the transcription start site and continues to the start codon but does not include the start codon; whereas, the 3' UTR starts immediately following a stop codon and continues until the transcriptional termination signal. There is growing body of evidence about the regulatory roles played by the UTRs in terms of stability of the nucleic acid molecule and translation. The regulatory features of a UTR can be incorporated into the modified mRNA molecules of the present invention to enhance the stability of the molecule. The specific features can also be incorporated to ensure controlled down-regulation of the transcript in case they are misdirected to undesired organs sites.

5' UTR and Translation Initiation

Natural 5' UTRs bear features which play roles in for translation initiation. They harbor signatures like Kozak sequences which are commonly known to be involved in the process by which the ribosome initiates translation of many genes. Kozak sequences have the consensus CCR(A/G)CCAUGG, where R is a purine (adenine or guanine) three bases upstream of the start codon (AUG), which is followed by another 'G'. 5' UTR also have been known to form secondary structures which are involved in elongation factor binding.

By engineering the features typically found in abundantly expressed genes of specific target organs, one can enhance the stability and protein production of the modified mRNA molecules of the invention. For example, introduction of 5' UTR of liver-expressed mRNA, such as albumin, serum amyloid A, Apolipoprotein A/B/E, transferrin, alpha fetoprotein, erythropoietin, or Factor VIII, could be used to enhance expression of a nucleic acid molecule or a modified nucleic acid molecule, such as a mRNA or a mmRNA, in hepatic cell lines or liver. Likewise, use of 5' UTR from other tissue-specific mRNA to improve expression in that tissue is possible for muscle (MyoD, Myosin, Myoglobin, Myogenin, Herculin), for endothelial cells (Tie-1, CD36), for myeloid cells (C/EBP, AML1, G-CSF, GM-CSF, CD11b, MSR, Fr-1, i-NOS), for leukocytes (CD45, CD18), for adipose tissue (CD36, GLUT4, ACRP30, adiponectin) and for lung epithelial cells (SP-A/B/C/D).

Other non-UTR sequences may be incorporated into the 5' (or 3' UTR) UTRs of the nucleic acid molecules or modified nucleic acid molecules of the present invention. For example, introns or portions of introns sequences may be incorporated into the flanking regions of the nucleic acid molecule or modified nucleic acid molecules of the invention. Incorporation of intronic sequences may increase protein production as well as mRNA levels.

The 5'UTR may selected for use in the present invention may be a structured UTR such as, but not limited to, 5'UTRs to control translation. As a non-limiting example, a structured 5'UTR may be beneficial when using any of the terminal modifications described in U.S. Provisional Application No. 61/758,921 filed Jan. 31, 2013, entitled Differential Targeting Using RNA Constructs; U.S. Provisional Application No. 61/781,139 filed Mar. 14, 2013, entitled Differential Targeting Using RNA Constructs; U.S. Provisional Application No. 61/729,933, filed Nov. 26, 2012 entitled Terminally Optimized RNAs; U.S. Provisional Application No. 61/737,224 filed Dec. 14, 2012 entitled Terminally Optimized RNAs and U.S. Provisional Application No. 61/829,359 filed May 31, 2013 entitled Terminally Optimized RNAs; each of which is herein incorporated by reference in their entirety.

5'UTR and Histone Stem Loops

In one embodiment, the nucleic acid molecules, modified nucleic acid molecules and/or mmRNA may include a nucleic acid sequence which is derived from the 5'UTR of a 5'-terminal oligopyrimidine (TOP) gene and at least one histone stem loop. Non-limiting examples of nucleic acid sequences which are derived from the 5'UTR of a TOP gene are taught in International Patent Publication No. WO2013143699, the contents of which are herein incorporated by reference in its entirety.

3' UTR and the AU Rich Elements

3' UTRs are known to have stretches of Adenosines and Uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) nonamers. Molecules containing this type of AREs include GM-CSF and TNF-a. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of modified mRNA of the invention. When engineering specific modified mRNA, one or more copies of an ARE can be introduced to make modified mRNA of the invention less stable and thereby curtail translation and decrease production of the resultant protein.

Likewise, AREs can be identified and removed or mutated to increase the intracellular stability and thus increase translation and production of the resultant protein. Transfection experiments can be conducted in relevant cell lines, using modified mRNA of the invention and protein production can be assayed at various time points post-transfection. For example, cells can be transfected with different ARE-engineering molecules and by using an ELISA kit to the relevant protein and assaying protein produced at 6 hours, 12 hours, 24 hours, 48 hours, and 7 days post-transfection.

Incorporating microRNA Binding Sites microRNAs (or miRNA) are 19-25 nucleotide long non-coding RNAs that bind to the 3' UTR of nucleic acid molecules and down-regulate gene expression either by reducing nucleic acid molecule stability or by inhibiting translation. The modified mRNA of the invention may comprise one or more microRNA target sequences, microRNA sequences, or microRNA seeds. Such sequences may correspond to any known microRNA such as those taught in US Publication US2005/0261218 and US Publication US2005/0059005, the contents of which are incorporated herein by reference in their entirety.

A microRNA sequence comprises a "seed" region, i.e., a sequence in the region of positions 2-8 of the mature microRNA, which sequence has perfect Watson-Crick complementarity to the miRNA target sequence. A microRNA seed may comprise positions 2-8 or 2-7 of the mature microRNA. In some embodiments, a microRNA seed may comprise 7 nucleotides (e.g., nucleotides 2-8 of the mature microRNA), wherein the seed-complementary site in the corresponding miRNA target is flanked by an adenine (A) opposed to microRNA position 1. In some embodiments, a microRNA seed may comprise 6 nucleotides (e.g., nucleotides 2-7 of the mature microRNA), wherein the seed-complementary site in the corresponding miRNA target is flanked by an adenine (A) opposed to microRNA position 1. See for example, Grimson A, Farh K K, Johnston W K, Garrett-Engele P, Lim L P, Bartel D P; Mol Cell. 2007 Jul. 6; 27(1):91-105; each of which is herein incorporated by reference in their entirety. The bases of the microRNA seed have complete complementarity with the target sequence. By engineering microRNA target sequences into the 3'UTR of modified mRNA of the invention one can target the molecule for degradation or reduced translation, provided the microRNA in question is available. This process will reduce the hazard of off target effects upon nucleic acid molecule delivery. Identification of microRNA, microRNA target regions, and their expression patterns and role in biology have been reported (Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/1eu.2011.356); Bartel Cell 2009 136:215-233; Landgraf et al, Cell, 2007 129:1401-1414; each of which is herein incorporated by reference in its entirety).

For example, if the nucleic acid molecule or modified nucleic acid molecule is a mRNA or a modified mRNA and is not intended to be delivered to the liver but ends up there, then miR-122, a microRNA abundant in liver, can inhibit the expression of the gene of interest if one or multiple target sites of miR-122 are engineered into the 3' UTR of the mRNA or modified mRNA. Introduction of one or multiple binding sites for different microRNA can be engineered to further decrease the longevity, stability, and protein translation of a nucleic acid molecule, a modified nucleic acid molecule and/or modified mRNA.

As used herein, the term "microRNA site" refers to a microRNA target site or a microRNA recognition site, or any nucleotide sequence to which a microRNA binds or associates. It should be understood that "binding" may follow traditional Watson-Crick hybridization rules or may reflect any stable association of the microRNA with the target sequence at or adjacent to the microRNA site.

Conversely, for the purposes of the modified mRNA of the present invention, microRNA binding sites can be engineered out of (i.e. removed from) sequences in which they naturally occur in order to increase protein expression in specific tissues. For example, miR-122 binding sites may be removed to improve protein expression in the liver. Regulation of expression in multiple tissues can be accomplished through introduction or removal or one or several microRNA binding sites.

Examples of tissues where microRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-id, miR-149), kidney (miR-192, miR-194, miR-204), and lung epithelial cells (let-7, miR-133, miR-126). MicroRNA can also regulate complex biological processes such as angiogenesis (miR-132) (Anand and Cheresh Curr Opin Hematol 2011 18:171-176; herein incorporated by reference in its entirety). In the modified mRNA of the present invention, binding sites for microRNAs that are involved in such processes may be removed or introduced, in order to tailor the expression of the modified mRNA expression to biologically relevant cell types or to the context of relevant biological processes.

Lastly, through an understanding of the expression patterns of microRNA in different cell types, modified mRNA can be engineered for more targeted expression in specific cell types or only under specific biological conditions. Through introduction of tissue-specific microRNA binding sites, modified mRNA could be designed that would be optimal for protein expression in a tissue or in the context of a biological condition.

Transfection experiments can be conducted in relevant cell lines, using engineered modified mRNA and protein production can be assayed at various time points post-transfection. For example, cells can be transfected with different microRNA binding site-engineering modified mRNA and by using an ELISA kit to the relevant protein and assaying protein produced at 6 hour, 12 hour, 24 hour, 48 hour, 72 hour and 7 days post-transfection. In vivo experiments can also be conducted using microRNA-binding site-engineered molecules to examine changes in tissue-specific expression of formulated modified mRNA.

3'UTR and Albumin Variants

3' UTRs of the nucleic acid molecules, modified nucleic acid molecules and/or mmRNA may comprise a nucleic acid sequence which is derived from the 3' UTR of an albumin gene or from a variant of the 3'UTR of the albumin gene. The incorporation of a nucleic acid sequence from the 3' UTR of an albumin gene or an albumin gene variant may increase the stabilization of the nucleic acid and/or prolong the protein expression from the nucleic acid sequence. Non-limiting examples of nucleic acid sequence which are derived from the 3' UTR of an albumin gene or from a variant of the 3'UTR of the albumin gene are taught in International Patent Publication No. WO2013143698, the contents of which are herein incorporated by reference in its entirety. As a non-limiting example, the 3'UTR element may include a nucleic acid sequence which has an identity of at least about 40%, at least about 50%, at least about 60%, at least about 70%, at least about 80%, at least about 90%, at least about 95%, at least about 99% to the nucleic acid sequence according to SEQ ID No. 1, SEQ ID No. 2, SEQ ID No. 32, SEQ ID NO. 33, SEQ ID No. 34, or SEQ ID No. 35 of International Patent Publication No. WO2013143698, the contents of which are herein incorporated by reference in its entirety.

In one embodiment, the nucleic acid molecules, modified nucleic acid molecules and/or mmRNA may include a nucleic acid sequence which is derived from the 5'UTR of a 5'-terminal oligopyrimidine (TOP) gene and a nucleic acid sequence which is derived from the 3' UTR of an albumin gene or from a variant of the 3'UTR of the albumin gene. Non-limiting examples of nucleic acid sequences which are derived from the 5'UTR of a TOP gene and nucleic acid sequences which are derived from the 3' UTR of an albumin gene or from a variant of the 3'UTR of the albumin gene are taught in International Patent Publication No. WO2013143700, the contents of which are herein incorporated by reference in its entirety.

5' Capping

The 5' cap structure of an mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns removal during mRNA splicing.

Endogenous mRNA molecules may be 5'-end capped generating a 5'-ppp-5'-triphosphate linkage between a terminal guanosine cap residue and the 5'-terminal transcribed sense nucleotide of the mRNA molecule. This 5'-guanylate cap may then be methylated to generate an N7-methyl-guanylate residue. The ribose sugars of the terminal and/or anteterminal transcribed nucleotides of the 5' end of the mRNA may optionally also be 2'-O-methylated. 5'-decapping through hydrolysis and cleavage of the guanylate cap structure may target a nucleic acid molecule, such as an mRNA molecule, for degradation.

Modifications to the modified mRNA of the present invention may generate a non-hydrolyzable cap structure preventing decapping and thus increasing mRNA half-life. Because cap structure hydrolysis requires cleavage of 5'-ppp-5' phosphorodiester linkages, modified nucleotides may be used during the capping reaction. For example, a Vaccinia Capping Enzyme from New England Biolabs (Ipswich, Mass.) may be used with α-thio-guanosine nucleotides according to the manufacturer's instructions to create a phosphorothioate linkage in the 5'-ppp-5' cap. Additional modified guanosine nucleotides may be used such as α-methyl-phosphonate and seleno-phosphate nucleotides.

Additional modifications include, but are not limited to, 2'-O-methylation of the ribose sugars of 5'-terminal and/or 5'-anteterminal nucleotides of the mRNA (as mentioned above) on the 2'-hydroxyl group of the sugar ring. Multiple distinct 5'-cap structures can be used to generate the 5'-cap of a nucleic acid molecule, such as an mRNA molecule.

Cap analogs, which herein are also referred to as synthetic cap analogs, chemical caps, chemical cap analogs, or structural or functional cap analogs, differ from natural (i.e. endogenous, wild-type or physiological) 5'-caps in their chemical structure, while retaining cap function. Cap analogs may be chemically (i.e. non-enzymatically) or enzymatically synthesized and/or linked to a nucleic acid molecule.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine ($m^7$G-3'mppp-G; which may equivalently be designated 3'-O-Me-m7G(5')ppp(5')G). The 3'-O atom of the other, unmodified, guanine becomes linked to the 5'-terminal nucleotide of the capped nucleic acid molecule (e.g. an mRNA or mmRNA). The N7- and 3'-O-methlyated guanine provides the terminal moiety of the capped nucleic acid molecule (e.g. mRNA or mmRNA).

Another exemplary cap is mCAP, which is similar to ARCA but has a 2'-O-methyl group on guanosine (i.e., N7,2'-O-dimethyl-guanosine-5'-triphosphate-5'-guanosine, $m^7$Gm-ppp-G).

While cap analogs allow for the concomitant capping of a nucleic acid molecule in an in vitro transcription reaction, up to 20% of transcripts can remain uncapped. This, as well as the structural differences of a cap analog from an endogenous 5'-cap structures of nucleic acids produced by the endogenous, cellular transcription machinery, may lead to reduced translational competency and reduced cellular stability.

Modified mRNA of the present invention may also be capped post-transcriptionally, using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures of the present invention are those which, among other things, have enhanced binding of cap binding proteins, increased half life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of an mRNA and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include, but are not limited to, 7 mG(5')ppp(5')N,pN2p (cap 0), 7 mG(5')ppp(5')N1mpNp (cap 1), and 7 mG(5')-ppp(5')N1mpN2mp (cap 2).

Because the modified mRNA may be capped post-transcriptionally, and because this process is more efficient, nearly 100% of the modified mRNA may be capped. This is in contrast to ~80% when a cap analog is linked to an mRNA in the course of an in vitro transcription reaction.

According to the present invention, 5' terminal caps may include endogenous caps or cap analogs. According to the present invention, a 5' terminal cap may comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

Viral Sequences

Additional viral sequences such as, but not limited to, the translation enhancer sequence of the barley yellow dwarf virus (BYDV-PAV) can be engineered and inserted in the 3' UTR of the modified mRNA of the invention and can stimulate the translation of the mRNA in vitro and in vivo. Transfection experiments can be conducted in relevant cell lines at and protein production can be assayed by ELISA at 12 hour, 24 hour, 48 hour, 72 hour and day 7 post-transfection.

IRES Sequences

Further, provided are modified mRNA which may contain an internal ribosome entry site (IRES). First identified as a feature Picorna virus RNA, IRES plays an important role in initiating protein synthesis in absence of the 5' cap structure. An IRES may act as the sole ribosome binding site, or may serve as one of multiple ribosome binding sites of an mRNA. Modified mRNA containing more than one functional ribosome binding site may encode several peptides or polypeptides that are translated independently by the ribosomes ("multicistronic nucleic acid molecules"). When modified mRNA are provided with an IRES, further optionally provided is a second translatable region. Examples of IRES sequences that can be used according to the invention include without limitation, those from picornaviruses (e.g. FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

Poly-A Tails

During RNA processing, a long chain of adenine nucleotides (poly-A tail) may be added to a nucleic acid molecule or a modified nucleic acid molecule such as a mRNA or a modified mRNA molecules in order to increase stability. Immediately after transcription, the 3' end of the transcript may be cleaved to free a 3' hydroxyl. Then poly-A polymerase adds a chain of adenine nucleotides to the RNA. The process, called polyadenylation, adds a poly-A tail that can be between, for example, approximately 100 and 250 residues long.

It has been discovered that unique poly-A tail lengths provide certain advantages to the modified mRNA of the present invention.

Generally, the length of a poly-A tail of the present invention is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides). In some embodiments, the modified mRNA includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In one embodiment, the poly-A tail is designed relative to the length of the overall modified mRNA. This design may be based on the length of the coding region, the length of a particular feature or region (such as the flanking regions), or based on the length of the ultimate product expressed from the modified mRNA.

In this context the poly-A tail may be 10, 20, 30, 40, 50, 60, 70, 80, 90, or 100% greater in length than the modified mRNA, region or feature thereof. The poly-A tail may also be designed as a fraction of modified mRNA to which it belongs. In this context, the poly-A tail may be 10, 20, 30, 40, 50, 60, 70, 80, or 90% or more of the total length of the molecule or the total length of the molecule minus the poly-A tail. Further, engineered binding sites and conjugation of modified mRNA for Poly-A binding protein may enhance expression.

Additionally, multiple distinct modified mRNA may be linked together to the PABP (Poly-A binding protein) through the 3'-end using modified nucleotides at the 3'-terminus of the poly-A tail. Transfection experiments can be conducted in relevant cell lines at and protein production can be assayed by ELISA at 12 hour, 24 hour, 48 hour, 72 hour and day 7 post-transfection.

In one embodiment, the modified mRNA of the present invention are designed to include a polyA-G Quartet. The G-quartet is a cyclic hydrogen bonded array of four guanine nucleotides that can be formed by G-rich sequences in both DNA and RNA. In this embodiment, the G-quartet is incorporated at the end of the poly-A tail. The resultant mmRNA molecule is assayed for stability, protein production and other parameters including half-life at various time points. It has been discovered that the polyA-G quartet results in protein production equivalent to at least 75% of that seen using a poly-A tail of 120 nucleotides alone.

Modifications

The modified nucleic acids and modified mRNA (mmRNA) of the invention may contain one, two, or more different modifications. In some embodiments, modified nucleic acids and mmRNA may contain one, two, or more different nucleoside or nucleotide modifications. In some embodiments, a modified nucleic acid or mmRNA (e.g., having one or more mmRNA molecules) introduced to a cell may exhibit reduced degradation in the cell, as compared to an unmodified nucleic acid or mmRNA. Non-limiting examples of modified nucleosides and nucleotides which may be included in the modified nucleic acid molecules and/or mmRNA are taught in International Patent Publication No. WO2013052523, the contents of which are herein incorporated by reference in its entirety.

The modified nucleic acids and mmRNA can include any useful modification, such as to the sugar, the nucleobase (e.g., one or more modifications of a nucleobase, such as by replacing or substituting an atom of a pyrimidine nucleobase with optionally substituted amino, optionally substituted thiol, optionally substituted alkyl (e.g., methyl or ethyl), or halo (e.g., chloro or fluoro), or the internucleoside linkage (e.g., one or more modification to the phosphodiester backbone). In certain embodiments, modifications are present in both the sugar and the internucleoside linkage (e.g., one or modifications, such as those present in ribonucleic acids (RNA), deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

As described herein, the modified nucleic acids and mmRNA of the invention do not substantially induce an innate immune response of a cell into which the mRNA is introduced. In certain embodiments, it may desirable to intracellularly degrade a modified nucleic acid molecule or modified nucleic acid molecule introduced into the cell. For example, degradation of a modified nucleic acid molecule or modified mRNA may be preferable if precise timing of protein production is desired. Thus, in some embodiments, the invention provides a modified nucleic acid molecule containing a degradation domain, which is capable of being acted on in a directed manner within a cell. In another aspect, the present disclosure provides nucleic acids comprising a nucleoside or nucleotide that can disrupt the binding of a major groove interacting, e.g. binding, partner with the nucleic acid (e.g., where the modified nucleotide has decreased binding affinity to major groove interacting partner, as compared to an unmodified nucleotide).

The modified nucleic acid and mmRNA can optionally include other agents (e.g., RNAi-inducing agents, RNAi agents, siRNA, shRNA, miRNA, antisense RNA, ribozymes, catalytic DNA, tRNA, RNA that induce triple helix formation, aptamers, vectors, etc.). In some embodiments, the modified nucleic acids or mmRNA may include one or more messenger RNA (mRNA) and one or more modified nucleoside or nucleotides (e.g., mmRNA molecules). Details for these modified nucleic acids and mmRNA follow.

Modified Nucleic Acids

The modified nucleic acids or mmRNA of the invention may include a first region of linked nucleosides encoding a polypeptide of interest, a first flanking region located at the 5' terminus of the first region, and a second flanking region located at the 3' terminus of the first region.

In some embodiments, the modified nucleic acids or mmRNA includes n number of linked nucleosides having Formula (Ia) or Formula (Ia-1):

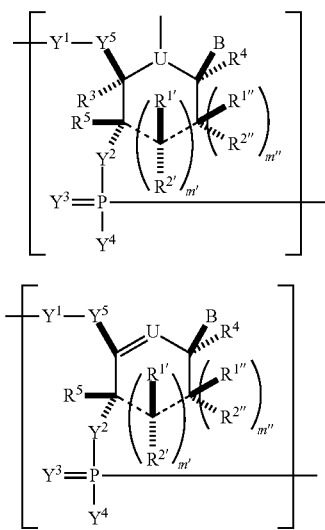

(Ia)

(Ia-1)

or a pharmaceutically acceptable salt or stereoisomer thereof, wherein

U is O, S, N(RU)nu, or C(RU)nu, wherein nu is an integer from 0 to 2 and each RU is, independently, H, halo, or optionally substituted alkyl;

- - - is a single bond or absent;

each of R1', R2', R1", R2", R1, R2, R3, R4, and R5 is, if present, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent; wherein the combination of R3 with one or more of R1', R1", R2', R2", or R5 (e.g., the combination of R1' and R3, the combination of R1" and R3, the combination of R2' and R3, the combination of R2" and R3, or the combination of R5 and R3) can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); wherein the combination of R5 with one or more of R1', R1", R2', or R2" (e.g., the combination of R1' and R5, the combination of R1" and R5, the combination of R2' and R5, or the combination of R2" and R5) can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); and wherein the combination of R4 and one or more of R1', R1", R2', R2", R3, or R5 can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl);

each of m' and m" is, independently, an integer from 0 to 3 (e.g., from 0 to 2, from 0 to 1, from 1 to 3, or from 1 to 2);

each of Y1, Y2, and Y3, is, independently, O, S, Se, —NRN1-, optionally substituted alkylene, or optionally substituted heteroalkylene, wherein RN1 is H, optionally substituted alkyl, optionally substituted alkenyl, optionally substituted alkynyl, optionally substituted aryl, or absent;

each Y4 is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino;

each Y5 is, independently, O, S, Se, optionally substituted alkylene (e.g., methylene), or optionally substituted heteroalkylene;

n is an integer from 1 to 100,000; and

B is a nucleobase (e.g., a purine, a pyrimidine, or derivatives thereof), wherein the combination of B and R1', the combination of B and R2', the combination of B and R1", or the combination of B and R2" can, taken together with the carbons to which they are attached, optionally form a bicyclic group (e.g., a bicyclic heterocyclyl) or wherein the combination of B, R1", and R3 or the combination of B, R2", and R3 can optionally form a tricyclic or tetracyclic group (e.g., a tricyclic or tetracyclic heterocyclyl, such as in Formula (IIo)-(IIp) herein). In some embodiments, the modified nucleic acid or mmRNA includes a modified ribose.

In some embodiments, the modified nucleic acid or mmRNA includes n number of linked nucleosides having Formula (Ia-2)-(Ia-5) or a pharmaceutically acceptable salt or stereoisomer thereof.

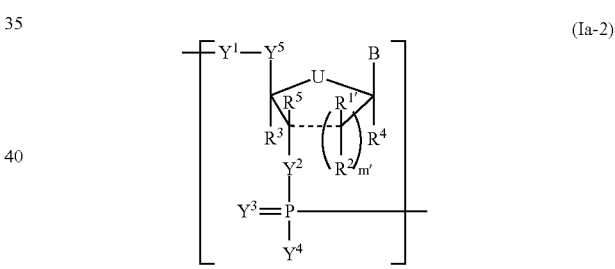

(Ia-2)

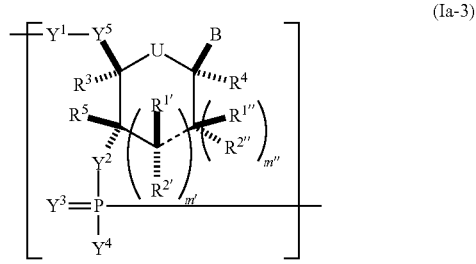

(Ia-3)

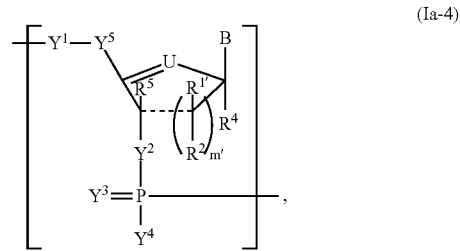

(Ia-4)

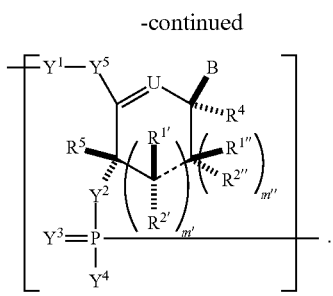
(Ia-5)

In some embodiments, the modified nucleic acid or mmRNA includes n number of linked nucleosides having Formula (Ib) or Formula (Ib-1):

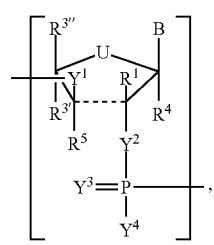
(Ib)

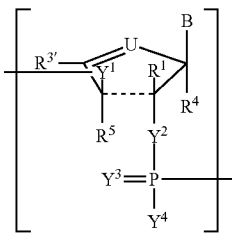
(Ib-1)

or a pharmaceutically acceptable salt or stereoisomer thereof, wherein

U is O, S, N(R$^U$)$_{nu}$, or C(R$^U$)$_{nu}$, wherein nu is an integer from 0 to 2 and each R$^U$ is, independently, H, halo, or optionally substituted alkyl;

- - - is a single bond or absent;

each of R$^1$, R$^{3'}$, R$^{3''}$, and R$^4$ is, independently, H, halo, hydroxy, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent; and wherein the combination of R$^1$ and R$^{3'}$ or the combination of R$^1$ and R$^{3''}$ can be taken together to form optionally substituted alkylene or optionally substituted heteroalkylene (e.g., to produce a locked nucleic acid);

each R$^5$ is, independently, H, halo, hydroxy, optionally substituted alkyl, optionally substituted alkoxy, optionally substituted alkenyloxy, optionally substituted alkynyloxy, optionally substituted aminoalkoxy, optionally substituted alkoxyalkoxy, or absent;

each of Y$^1$, Y$^2$, and Y$^3$ is, independently, O, S, Se, —NR$^{N1}$—, optionally substituted alkylene, or optionally substituted heteroalkylene, wherein R$^{N1}$ is H, optionally substituted alkyl, optionally substituted alkenyl, optionally substituted alkynyl, or optionally substituted aryl;

each Y$^4$ is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted alkoxyalkoxy, or optionally substituted amino;

n is an integer from 1 to 100,000; and

B is a nucleobase.

In some embodiments, the modified nucleic acid or mmRNA includes n number of linked nucleosides having Formula (Ic):

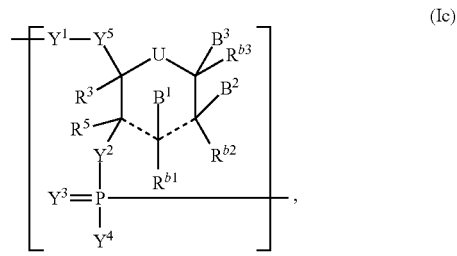
(Ic)

or a pharmaceutically acceptable salt or stereoisomer thereof, wherein

U is O, S, N(RU)nu, or C(RU)nu, wherein nu is an integer from 0 to 2 and each RU is, independently, H, halo, or optionally substituted alkyl;

- - - is a single bond or absent;

each of B1, B2, and B3 is, independently, a nucleobase (e.g., a purine, a pyrimidine, or derivatives thereof, as described herein), H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, or optionally substituted aminoalkynyl, wherein one and only one of B1, B2, and B3 is a nucleobase;

each of Rb1, Rb2, Rb3, R3, and R5 is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl or optionally substituted aminoalkynyl;

each of Y1, Y2, and Y3, is, independently, O, S, Se, —NRN1-, optionally substituted alkylene, or optionally substituted heteroalkylene, wherein RN1 is H, optionally substituted alkyl, optionally substituted alkenyl, optionally substituted alkynyl, or optionally substituted aryl;

each Y4 is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino;

each Y5 is, independently, O, S, Se, optionally substituted alkylene (e.g., methylene), or optionally substituted heteroalkylene;

n is an integer from 1 to 100,000; and wherein the ring including U can include one or more double bonds.

In particular embodiments, the ring including U does not have a double bond between U—CB3Rb3 or between CB3Rb3-CB2Rb2.

In some embodiments, the modified nucleic acid or mmRNA includes n number of linked nucleosides having Formula (Id):

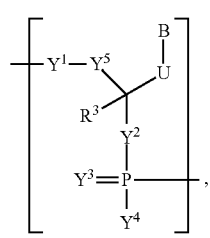

or a pharmaceutically acceptable salt or stereoisomer thereof, wherein

U is O, S, N(R$^U$)$_{nu}$, or C(R$^U$)$_{nu}$, wherein nu is an integer from 0 to 2 and each R$^U$ is, independently, H, halo, or optionally substituted alkyl;

each R$^3$ is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, or optionally substituted aminoalkynyl;

each of Y$^1$, Y$^2$, and Y$^3$, is, independently, O, S, Se, —NR$^{N1}$—, optionally substituted alkylene, or optionally substituted heteroalkylene, wherein R$^{N1}$ is H, optionally substituted alkyl, optionally substituted alkenyl, optionally substituted alkynyl, or optionally substituted aryl;

each Y$^4$ is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino;

each Y$^5$ is, independently, O, S, optionally substituted alkylene (e.g., methylene), or optionally substituted heteroalkylene;

n is an integer from 1 to 100,000; and

B is a nucleobase (e.g., a purine, a pyrimidine, or derivatives thereof).

In some embodiments, the modified nucleic acid molecules or modified mRNA includes n number of linked nucleosides having Formula (Ie):

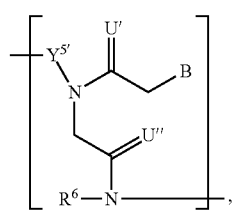

or a pharmaceutically acceptable salt or stereoisomer thereof, wherein each of U' and U" is, independently, O, S, N(R$^U$)$_{nu}$, or C(R$^U$)$_{nu}$, wherein nu is an integer from 0 to 2 and each R$^U$ is, independently, H, halo, or optionally substituted alkyl;

each R$^6$ is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, or optionally substituted aminoalkynyl;

each Y$^{5'}$ is, independently, O, S, optionally substituted alkylene (e.g., methylene or ethylene), or optionally substituted heteroalkylene;

n is an integer from 1 to 100,000; and

B is a nucleobase (e.g., a purine, a pyrimidine, or derivatives thereof).

In some embodiments, the modified nucleic acid or mmRNA includes n number of linked nucleosides having Formula (If) or (If-1):

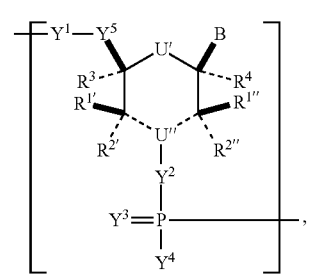

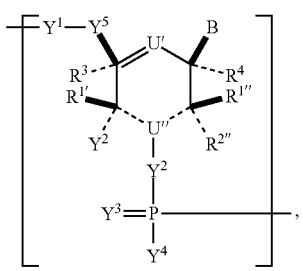

or a pharmaceutically acceptable salt or stereoisomer thereof, wherein each of U' and U" is, independently, O, S, N, N(RU)nu, or C(RU)nu, wherein nu is an integer from 0 to 2 and each RU is, independently, H, halo, or optionally substituted alkyl (e.g., U' is O and U" is N);

- - - is a single bond or absent;

each of R1', R2', R1", R2", R3, and R4 is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent; and wherein the combination of R1' and R3, the combination of R1" and R3, the combination of R2' and R3, or the combination of R2" and R3 can be taken together to form optionally substituted alkylene or optionally substituted heteroalkylene (e.g., to produce a locked nucleic acid); each of m' and m"

is, independently, an integer from 0 to 3 (e.g., from 0 to 2, from 0 to 1, from 1 to 3, or from 1 to 2);

each of Y1, Y2, and Y3, is, independently, O, S, Se, —NRN1-, optionally substituted alkylene, or optionally substituted heteroalkylene, wherein RN1 is H, optionally substituted alkyl, optionally substituted alkenyl, optionally substituted alkynyl, optionally substituted aryl, or absent;

each Y4 is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino;

each Y5 is, independently, O, S, Se, optionally substituted alkylene (e.g., methylene), or optionally substituted heteroalkylene;

n is an integer from 1 to 100,000; and

B is a nucleobase (e.g., a purine, a pyrimidine, or derivatives thereof).

In some embodiments of the modified nucleic acid or mmRNA (e.g., (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), the ring including U has one or two double bonds.

In some embodiments of the modified nucleic acid or mmRNA (e.g., Formulas (Ia)-Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), each of R1, R1', and R1", if present, is H. In further embodiments, each of R2, R2', and R2", if present, is, independently, H, halo (e.g., fluoro), hydroxy, optionally substituted alkoxy (e.g., methoxy or ethoxy), or optionally substituted alkoxyalkoxy. In particular embodiments, alkoxyalkoxy is —(CH2)s2(OCH2CH2)s1(CH2)s3OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C1-20 alkyl). In some embodiments, s2 is 0, s1 is 1 or 2, s3 is 0 or 1, and R' is C1-6 alkyl.

In some embodiments of the modified nucleic acid or mmRNA (e.g., Formulas (Ia)-Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), each of R2, R2', and R2", if present, is H. In further embodiments, each of R1, R1', and R1", if present, is, independently, H, halo (e.g., fluoro), hydroxy, optionally substituted alkoxy (e.g., methoxy or ethoxy), or optionally substituted alkoxyalkoxy. In particular embodiments, alkoxyalkoxy is —(CH2)s2(OCH2CH2)s1(CH2)s3OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C1-20 alkyl). In some embodiments, s2 is 0, s1 is 1 or 2, s3 is 0 or 1, and R' is C1-6 alkyl.

In some embodiments of the modified nucleic acid or mmRNA (e.g., Formulas (Ia)-Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), each of R3, R4, and R5 is, independently, H, halo (e.g., fluoro), hydroxy, optionally substituted alkyl, optionally substituted alkoxy (e.g., methoxy or ethoxy), or optionally substituted alkoxyalkoxy. In particular embodiments, R3 is H, R4 is H, R5 is H, or R3, R4, and R5 are all H. In particular embodiments, R3 is C1-6 alkyl, R4 is C1-6 alkyl, R5 is C1-6 alkyl, or R3, R4, and R5 are all C1-6 alkyl. In particular embodiments, R3 and R4 are both H, and R5 is C1-6 alkyl.

In some embodiments of the modified nucleic acids or mmRNA (e.g., Formulas (Ia)-Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), R3 and R5 join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl, such as trans-3',4' analogs, wherein R3 and R5 join together to form heteroalkylene (e.g., —(CH2)b1O(CH2)b2O(CH2)b3-, wherein each of b1, b2, and b3 are, independently, an integer from 0 to 3).

In some embodiments of the modified nucleic acids or mmRNA (e.g., Formulas (Ia)-Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), R3 and one or more of R1', R1", R2', R2", or R5 join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl, R3 and one or more of R1', R1", R2', R2", or R5 join together to form heteroalkylene (e.g., —(CH2)b1O(CH2)b2O(CH2)b3-, wherein each of b1, b2, and b3 are, independently, an integer from 0 to 3).

In some embodiments of the modified nucleic acids or mmRNA (e.g., Formulas (Ia)-Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), R5 and one or more of R1', R1", R2', or R2" join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl, R5 and one or more of R1', R1", R2', or R2" join together to form heteroalkylene (e.g., —(CH2)b1O(CH2)b2O(CH2)b3-, wherein each of b1, b2, and b3 are, independently, an integer from 0 to 3).

In some embodiments of the modified nucleic acids or mmRNA (e.g., Formulas (Ia)-Ia-5), (Ib)-(If-1), (IIa)-(IIp), (IIb-1), (IIb-2), (IIc-1)-(11c-2), (IIn-1), (IIn-2), (IVa)-(IV1), and (IXa)-(IXr)), each Y2 is, independently, O, S, or —NRN1-, wherein RN1 is H, optionally substituted alkyl, optionally substituted alkenyl, optionally substituted alkynyl, or optionally substituted aryl. In particular embodiments, Y2 is NRN1-, wherein RN1 is H or optionally substituted alkyl (e.g., C1-6 alkyl, such as methyl, ethyl, isopropyl, or n-propyl).

In some embodiments of the modified nucleic acids or mmRNA (e.g., Formulas (Ia)-Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), each Y3 is, independently, O or S.

In some embodiments of the modified nucleic acids or mmRNA (e.g., Formulas (Ia)-Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), R1 is H; each R2 is, independently, H, halo (e.g., fluoro), hydroxy, optionally substituted alkoxy (e.g., methoxy or ethoxy), or optionally substituted alkoxyalkoxy (e.g., —(CH2)s2(OCH2CH2)s1(CH2)s3OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C1-20 alkyl, such as wherein s2 is 0, s1 is 1 or 2, s3 is 0 or 1, and R' is C1-6 alkyl); each Y2 is, independently, O or —NRN1-, wherein RN1 is H, optionally substituted alkyl, optionally substituted alkenyl, optionally substituted alkynyl, or optionally substituted aryl (e.g., wherein RN1 is H or optionally substituted alkyl (e.g., C1-6 alkyl, such as methyl, ethyl, isopropyl, or n-propyl));

and each Y3 is, independently, O or S (e.g., S). In further embodiments, R3 is H, halo (e.g., fluoro), hydroxy, optionally substituted alkyl, optionally substituted alkoxy (e.g., methoxy or ethoxy), or optionally substituted alkoxyalkoxy. In yet further embodiments, each Y1 is, independently, O or —NRN1-, wherein RN1 is H, optionally substituted alkyl, optionally substituted alkenyl, optionally substituted alkynyl, or optionally substituted aryl (e.g., wherein RN1 is H or optionally substituted alkyl (e.g., C1-6 alkyl, such as methyl, ethyl, isopropyl, or n-propyl)); and each Y4 is, independently, H, hydroxy, thiol, optionally substituted alkyl, optionally substituted alkoxy, optionally substituted thioalkoxy, optionally substituted alkoxyalkoxy, or optionally substituted amino.

In some embodiments of the modified nucleic acids or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), each R1 is, independently, H, halo (e.g., fluoro), hydroxy, optionally substituted alkoxy (e.g., methoxy or ethoxy), or optionally substituted alkoxyalkoxy (e.g., —(CH2)s2(OCH2CH2)s1(CH2)s3OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C1-20 alkyl, such as wherein s2 is 0, s1 is 1 or 2, s3 is 0 or 1, and R' is C1-6 alkyl); R2 is H; each Y2 is, independently, O or —NRN1-, wherein RN1 is H, optionally substituted alkyl, optionally substituted alkenyl, optionally substituted alkynyl, or optionally substituted aryl (e.g., wherein RN1 is H or optionally substituted alkyl (e.g., C1-6 alkyl, such as methyl, ethyl, isopropyl, or n-propyl)); and each Y3 is, independently, O or S (e.g., S). In further embodiments, R3 is H, halo (e.g., fluoro), hydroxy, optionally substituted alkyl, optionally substituted alkoxy (e.g., methoxy or ethoxy), or optionally substituted alkoxyalkoxy. In yet further embodiments, each Y1 is, independently, O or —NRN1-, wherein RN1 is H, optionally substituted alkyl, optionally substituted alkenyl, optionally substituted alkynyl, or optionally substituted aryl (e.g., wherein RN1 is H or optionally substituted alkyl (e.g., C1-6 alkyl, such as methyl, ethyl, isopropyl, or n-propyl)); and each Y4 is, independently, H, hydroxy, thiol, optionally substituted alkyl, optionally substituted alkoxy, optionally substituted thioalkoxy, optionally substituted alkoxyalkoxy, or optionally substituted amino.

In some embodiments of the modified nucleic acids or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), the ring including U is in the β-D (e.g., β-D-ribo) configuration.

In some embodiments of the modified nucleic acids or mmRNA (e.g Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), the ring including U is in the α-L (e.g., α-L-ribo) configuration.

In some embodiments of the modified nucleic acids or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), one or more B is not pseudouridine (ψ) or 5-methyl-cytidine (m5C). In some embodiments, about 10% to about 100% of B nucleobases is not ψ or m5C (e.g., from 10% to 20%, from 10% to 35%, from 10% to 50%, from 10% to 60%, from 10% to 75%, from 10% to 90%, from 10% to 95%, from 10% to 98%, from 10% to 99%, from 20% to 35%, from 20% to 50%, from 20% to 60%, from 20% to 75%, from 20% to 90%, from 20% to 95%, from 20% to 98%, from 20% to 99%, from 20% to 100%, from 50% to 60%, from 50% to 75%, from 50% to 90%, from 50% to 95%, from 50% to 98%, from 50% to 99%, from 50% to 100%, from 75% to 90%, from 75% to 95%, from 75% to 98%, from 75% to 99%, and from 75% to 100% of n number of B is not ψ or m5C). In some embodiments, B is not ψ or m5C.

In some embodiments of the modified nucleic acids or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), when B is an unmodified nucleobase selected from cytosine, guanine, uracil and adenine, then at least one of Y1, Y2, or Y3 is not O.

In some embodiments, the modified nucleic acids or mmRNA includes a modified ribose. In some embodiments, modified nucleic acids or mmRNA includes n number of linked nucleosides having Formula (IIa)-(IIc):

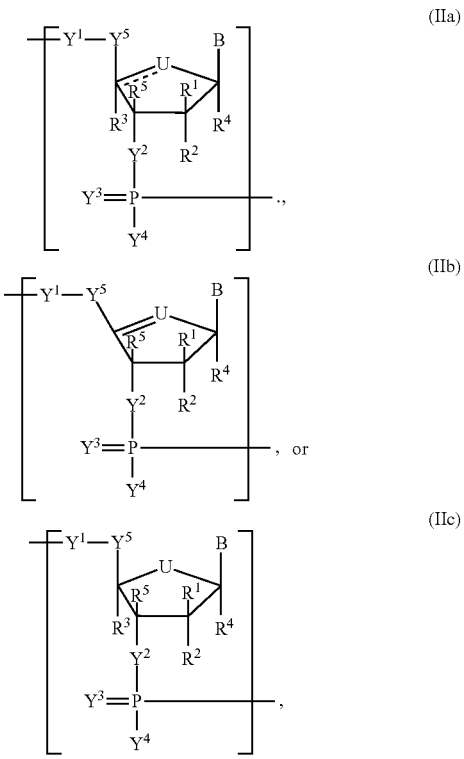

or a pharmaceutically acceptable salt or stereoisomer thereof. In particular embodiments, U is O or $C(R^U)_{nu}$, wherein nu is an integer from 0 to 2 and each $R^U$ is, independently, H, halo, or optionally substituted alkyl (e.g., U is —CH2— or —CH—). In other embodiments, each of $R^1$, $R^2$, $R^3$, $R^4$, and $R^5$ is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent (e.g., each $R^1$ and $R^2$ is, independently, H, halo, hydroxy, optionally substituted alkyl, or optionally substituted alkoxy; each $R^3$ and $R^4$ is, independently, H or optionally substituted alkyl; and $R^5$ is H or hydroxy), and ---is a single bond or double bond.

In particular embodiments, the modified nucleic acid or mmRNA includes n number of linked nucleosides having Formula (IIb-1)-(IIb-2):

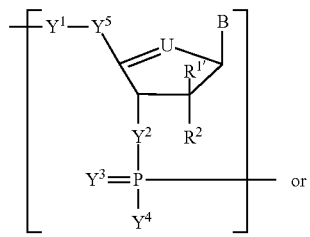

(IIb-1)

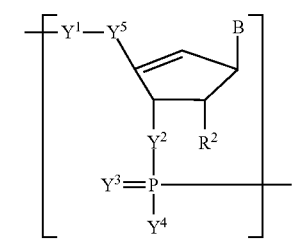

(IIb-2)

or a pharmaceutically acceptable salt or stereoisomer thereof. In some embodiments, U is O or $C(R^U)_{nu}$, wherein nu is an integer from 0 to 2 and each $R^U$ is, independently, H, halo, or optionally substituted alkyl (e.g., U is —CH$_2$— or —CH—). In other embodiments, each of $R^1$ and $R^2$ is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent (e.g., each $R^1$ and $R^2$ is, independently, H, halo, hydroxy, optionally substituted alkyl, or optionally substituted alkoxy, e.g., H, halo, hydroxy, alkyl, or alkoxy). In particular embodiments, $R^2$ is hydroxy or optionally substituted alkoxy (e.g., methoxy, ethoxy, or any described herein).

In particular embodiments, the modified nucleic acid or mmRNA includes n number of linked nucleosides having Formula (IIc-1)-(IIc-4):

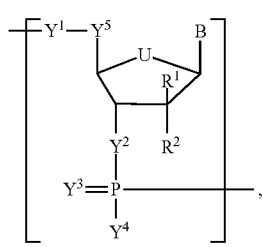

(IIc-1)

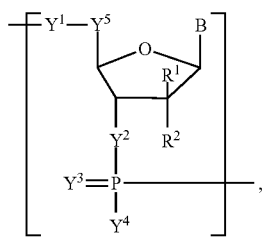

(IIc-2)

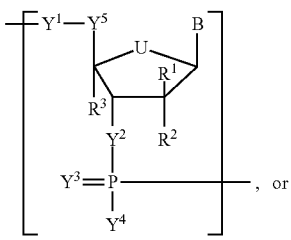

(IIc-3)

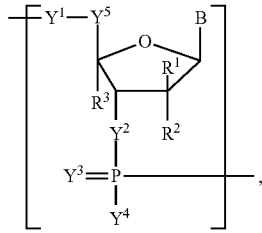

(IIc-4)

or a pharmaceutically acceptable salt or stereoisomer thereof. In some embodiments, U is O or $C(R^U)_{nu}$, wherein nu is an integer from 0 to 2 and each $R^U$ is, independently, H, halo, or optionally substituted alkyl (e.g., U is —CH$_2$— or —CH—). In some embodiments, each of $R^1$, $R^2$, and $R^3$ is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent (e.g., each $R^1$ and $R^2$ is, independently, H, halo, hydroxy, optionally substituted alkyl, or optionally substituted alkoxy, e.g., H, halo, hydroxy, alkyl, or alkoxy; and each $R^3$ is, independently, H or optionally substituted alkyl)). In particular embodiments, $R^2$ is optionally substituted alkoxy (e.g., methoxy or ethoxy, or any described herein). In particular embodiments, $R^1$ is optionally substituted alkyl, and $R^2$ is hydroxy. In other embodiments, $R^1$ is hydroxy, and $R^2$ is optionally substituted alkyl. In further embodiments, $R^3$ is optionally substituted alkyl.

In some embodiments, the modified nucleic acids or mmRNA includes an acyclic modified ribose. In some embodiments, the modified nucleic acids or mmRNA includes n number of linked nucleosides having Formula (IId)-(IIf):

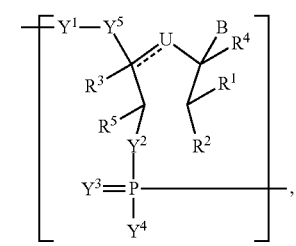

(IId)

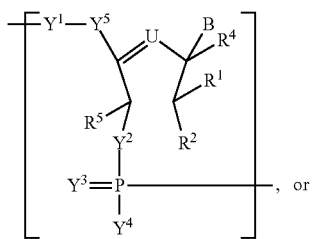

(IIe), or

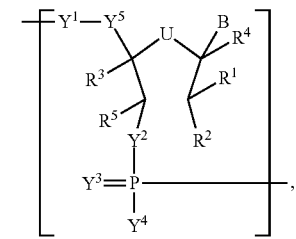

(IIf)

or a pharmaceutically acceptable salt or stereoisomer thereof.

In some embodiments, the modified nucleic acids or mmRNA includes an acyclic modified hexitol. In some embodiments, the modified nucleic acids or mmRNA includes n number of linked nucleosides having Formula (IIg)-(IIj):

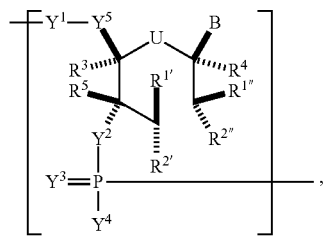

(IIg)

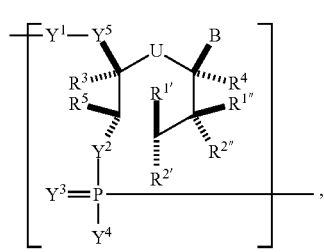

(IIh)

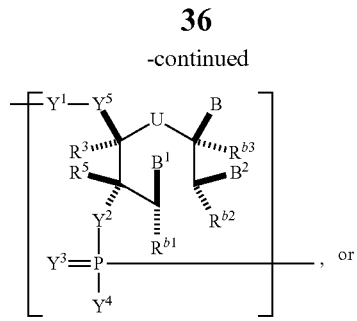

(IIi), or

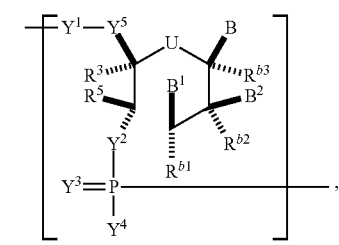

(IIj)

or a pharmaceutically acceptable salt or stereoisomer thereof.

In some embodiments, the modified nucleic acids or mmRNA includes a sugar moiety having a contracted or an expanded ribose ring. In some embodiments, the modified nucleic acids or mmRNA includes n number of linked nucleosides having Formula (IIk)-(IIm):

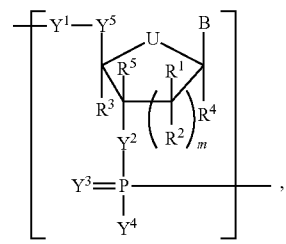

(IIk)

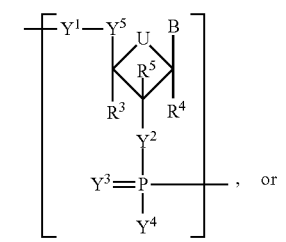

(IIl), or

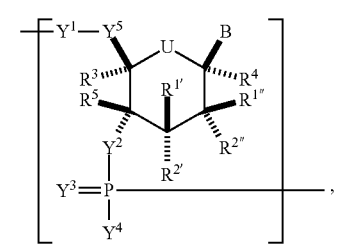

(IIm)

or a pharmaceutically acceptable salt or stereoisomer thereof, wherein each of $R^{1'}$, $R^{1''}$, $R^{2'}$, and $R^{2''}$ is, independently, H, halo, hydroxy, optionally substituted alkyl, optionally substituted alkoxy, optionally substituted alkenyloxy, optionally substituted alkynyloxy, optionally substituted aminoalkoxy, optionally substituted alkoxyalkoxy, or absent; and wherein the combination of $R^{2'}$ and $R^3$ or the combination of $R^{2''}$ and $R^3$ can be taken together to form optionally substituted alkylene or optionally substituted heteroalkylene.

In some embodiments, the modified nucleic acids or mmRNA includes a locked modified ribose. In some embodiments, the modified nucleic acids or mmRNA includes n number of linked nucleosides having Formula (IIn):

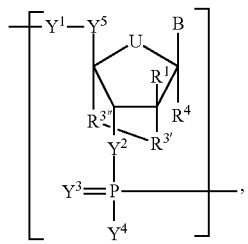

or a pharmaceutically acceptable salt or stereoisomer thereof, wherein $R^{3'}$ is O, S, or —$NR^{N1}$—, wherein $R^{N1}$ is H, optionally substituted alkyl, optionally substituted alkenyl, optionally substituted alkynyl, or optionally substituted aryl and $R^{3''}$ is optionally substituted alkylene (e.g., —$CH_2$—, —$CH_2CH_2$—, or —$CH_2CH_2CH_2$—) or optionally substituted heteroalkylene (e.g., —$CH_2NH$—, —$CH_2CH_2NH$—, —$CH_2OCH_2$—, or —$CH_2CH_2OCH_2$—) (e.g., $R^{3'}$ is O and $R^{3''}$ is optionally substituted alkylene (e.g., —$CH_2$—, —$CH_2CH_2$—, or —$CH_2CH_2CH_2$—)).

In some embodiments, the modified nucleic acid or mmRNA includes n number of linked nucleosides having Formula (IIn-1)-(II-n2):

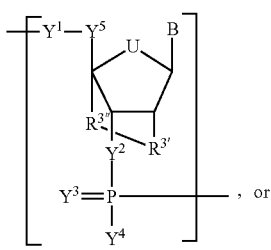

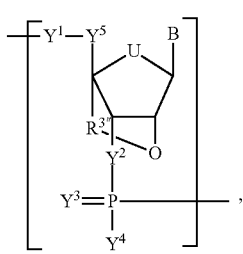

or a pharmaceutically acceptable salt or stereoisomer thereof, wherein $R^{3'}$ is O, S, or —$NR^{N1}$—, wherein $R^{N1}$ is H, optionally substituted alkyl, optionally substituted alkenyl, optionally substituted alkynyl, or optionally substituted aryl and $R^{3''}$ is optionally substituted alkylene (e.g., —$CH_2$—, —$CH_2CH_2$—, or —$CH_2CH_2CH_2$—) or optionally substituted heteroalkylene (e.g., —$CH_2NH$—, —$CH_2CH_2NH$—, —$CH_2OCH_2$—, or —$CH_2CH_2OCH_2$—) (e.g., $R^{3'}$ is O and $R^{3''}$ is optionally substituted alkylene (e.g., —$CH_2$—, —$CH_2CH_2$—, or —$CH_2CH_2CH_2$—)).

In some embodiments, the modified nucleic acids or mmRNA includes a locked modified ribose that forms a tetracyclic heterocyclyl. In some embodiments, the modified nucleic acids or mmRNA includes n number of linked nucleosides having Formula (IIo):

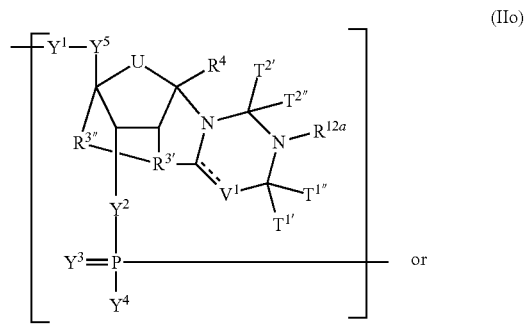

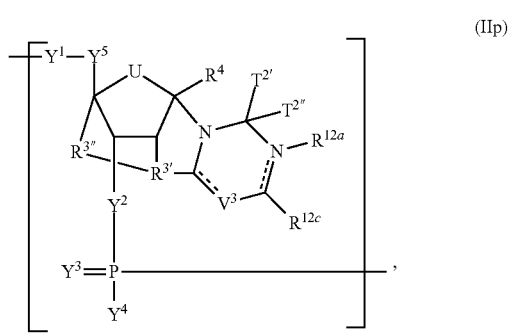

or a pharmaceutically acceptable salt or stereoisomer thereof, wherein $R^{12a}$, $R^{12c}$, $T^{1'}$, $T^{1''}$, $T^{2'}$, $T^{2''}$, $V^1$, and $V^3$ are as described herein.

Any of the formulas for the modified nucleic acids or mmRNA can include one or more nucleobases described herein (e.g., Formulas (b1)-(b43)).

In one embodiment, the present invention provides methods of preparing a modified nucleic acids or mmRNA comprising at least one nucleotide (e.g., mmRNA molecule), wherein the modified nucleic acid comprises n number of nucleosides having Formula (Ia), as defined herein:

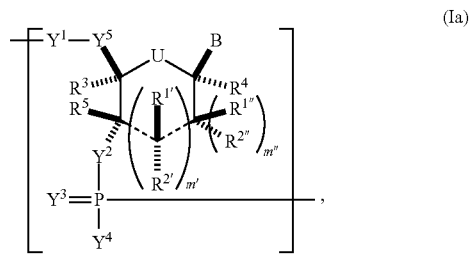

the method comprising reacting a compound of Formula (IIIa), as defined herein:

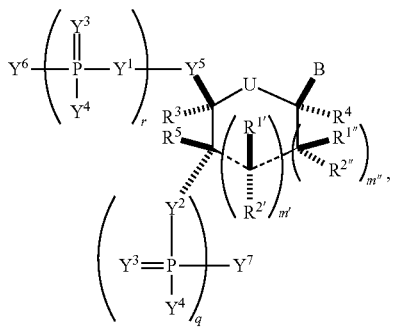

(IIIa)

with an RNA polymerase, and a cDNA template.

In a further embodiment, the present invention provides methods of amplifying a modified nucleic acids or mmRNA comprising at least one nucleotide (e.g., mmRNA molecule), the method comprising: reacting a compound of Formula (IIIa), as defined herein, with a primer, a cDNA template, and an RNA polymerase.

In one embodiment, the present invention provides methods of preparing a modified nucleic acids or mmRNA comprising at least one nucleotide (e.g., mmRNA molecule), wherein the modified nucleic acid comprises n number of nucleosides having Formula (Ia-1), as defined herein:

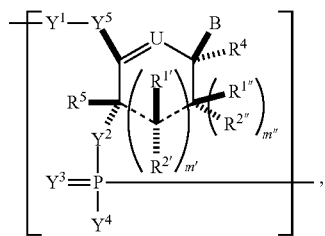

(Ia-1)

the method comprising reacting a compound of Formula (IIIa-1), as defined herein:

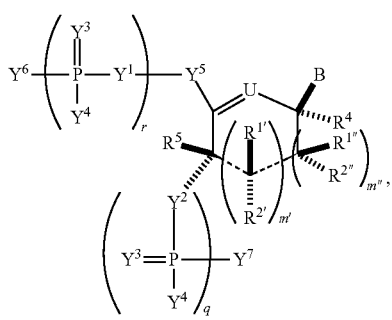

(IIIa-1)

with an RNA polymerase, and a cDNA template.

In a further embodiment, the present invention provides methods of amplifying a modified nucleic acids or mmRNA comprising at least one nucleotide (e.g., mmRNA molecule), the method comprising reacting a compound of Formula (IIIa-1), as defined herein, with a primer, a cDNA template, and an RNA polymerase.

In one embodiment, the present invention provides methods of preparing a modified mRNA comprising at least one nucleotide (e.g., mmRNA molecule), wherein the polynucleotide comprises n number of nucleosides having Formula (Ia-2), as defined herein:

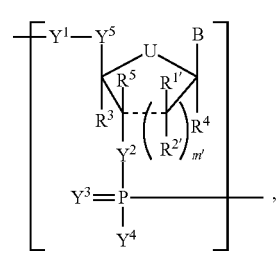

(Ia-2)

the method comprising reacting a compound of Formula (IIIa-2), as defined herein:

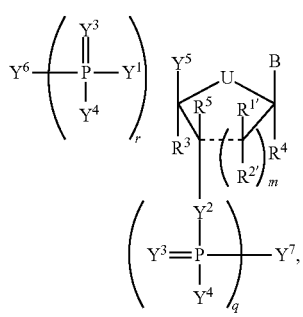

(IIIa-2)

with an RNA polymerase, and a cDNA template.

In a further embodiment, the present invention provides methods of amplifying a modified mRNA comprising at least one nucleotide (e.g., mmRNA molecule), the method comprising:

reacting a compound of Formula (IIIa-2), as defined herein, with a primer, a cDNA template, and an RNA polymerase.

In some embodiments, the reaction may be repeated from 1 to about 7,000 times. In any of the embodiments herein, B may be a nucleobase of Formula (b1)-(b43).

The modified nucleic acids and mmRNA can optionally include 5' and/or 3' flanking regions, which are described herein.

Modified RNA (e.g. mmRNA) Molecules

The present invention also includes building blocks, e.g., modified ribonucleosides, modified ribonucleotides, of modified RNA (mmRNA) molecules. For example, these mmRNA can be useful for preparing the modified nucleic acids or mmRNA of the invention.

In some embodiments, the building block molecule has Formula (IIIa) or (IIIa-1):

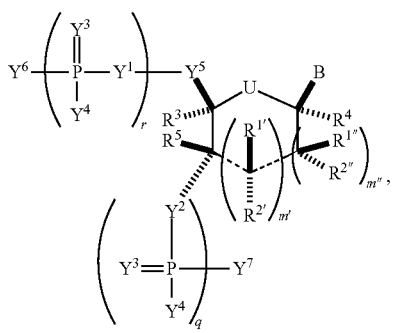

(IIIa)

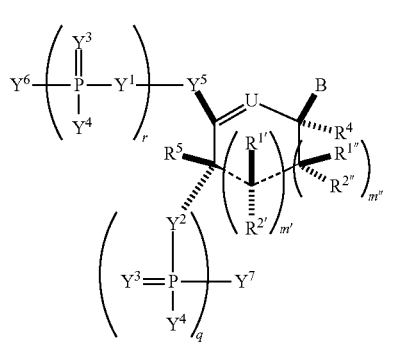

(IIIa-1)

or a pharmaceutically acceptable salt or stereoisomer thereof, wherein the substituents are as described herein (e.g., for Formula (Ia) and (Ia-1)), and wherein when B is an unmodified nucleobase selected from cytosine, guanine, uracil and adenine, then at least one of $Y^1$, $Y^2$, or $Y^3$ is not O.

In some embodiments, the building block molecule, which may be incorporated into a modified nucleic acid or mmRNA, has Formula (IVa)-(IVb):

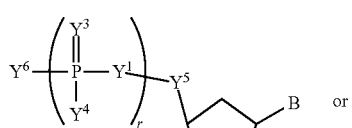

(IVa)

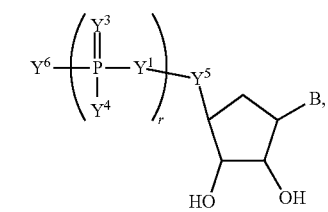

(IVb)

or a pharmaceutically acceptable salt or stereoisomer thereof, wherein B is as described herein (e.g., any one of (b1)-(b43)). In particular embodiments, Formula (IVa) or (IVb) is combined with a modified uracil (e.g., any one of formulas (b1)-(b9), (b21)-(b23), and (b28)-(b31), such as formula (b1), (b8), (b28), (b29), or (b30)). In particular embodiments, Formula (IVa) or (IVb) is combined with a modified cytosine (e.g., any one of formulas (b10)-(b14), (b24), (b25), and (b32)-(b36), such as formula (b10) or (b32)). In particular embodiments, Formula (IVa) or (IVb) is combined with a modified guanine (e.g., any one of formulas (b15)-(b17) and (b37)-(b40)). In particular embodiments, Formula (IVa) or (IVb) is combined with a modified adenine (e.g., any one of formulas (b18)-(b20) and (b41)-(b43)).

In some embodiments, the building block molecule, which may be incorporated into a modified nucleic acid molecule or mmRNA, has Formula (IVc)-(IVk):

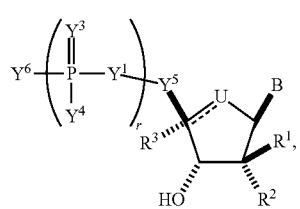

(IVc)

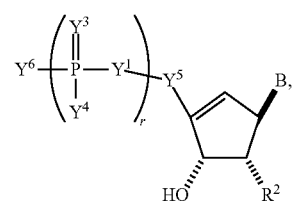

(IVd)

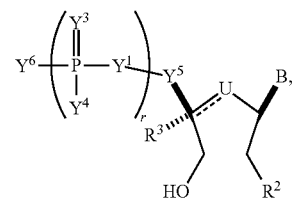

(IVe)

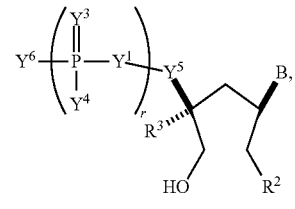

(IVf)

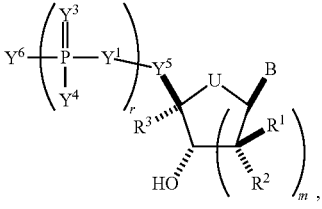

(IVg)

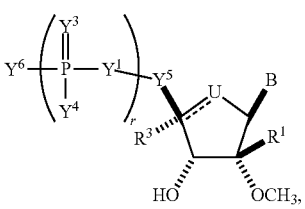

(IVh)

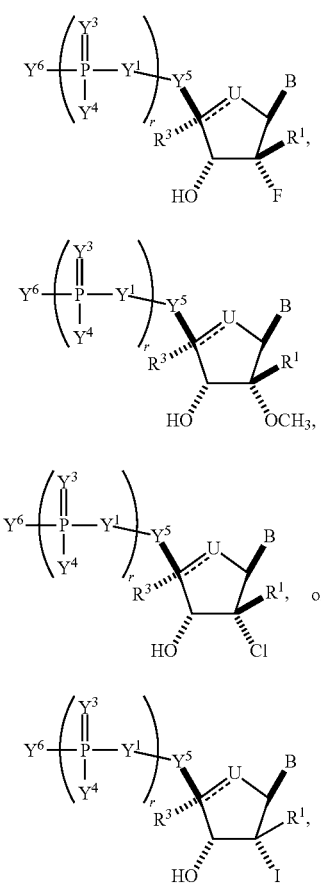

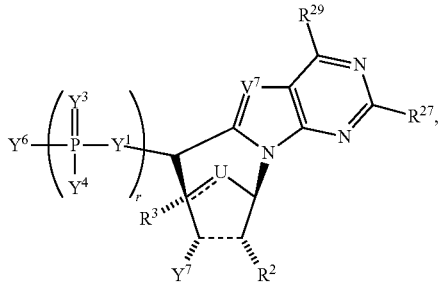

or a pharmaceutically acceptable salt or stereoisomer thereof, wherein B is as described herein (e.g., any one of (b1)-(b43)). In particular embodiments, one of Formulas (IVc)-(IVk) is combined with a modified uracil (e.g., any one of formulas (b1)-(b9), (b21)-(b23), and (b28)-(b31), such as formula (b1), (b8), (b28), (b29), or (b30)). In particular embodiments, one of Formulas (IVc)-(IVk) is combined with a modified cytosine (e.g., any one of formulas (b10)-(b14), (b24), (b25), and (b32)-(b36), such as formula (b10) or (b32)). In particular embodiments, one of Formulas (IVc)-(IVk) is combined with a modified guanine (e.g., any one of formulas (b15)-(b17) and (b37)-(b40)). In particular embodiments, one of Formulas (IVc)-(IVk) is combined with a modified adenine (e.g., any one of formulas (b18)-(b20) and (b41)-(b43)).

In other embodiments, the building block molecule, which may be incorporated into a modified nucleic acid molecule or mmRNA, has Formula (Va) or (Vb):

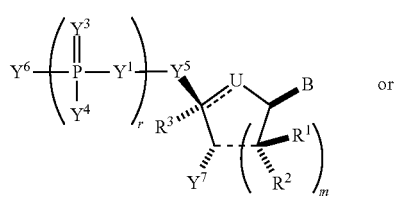

or a pharmaceutically acceptable salt or stereoisomer thereof, wherein B is as described herein (e.g., any one of (b1)-(b43)).

In other embodiments, the building block molecule, which may be incorporated into a modified nucleic acid molecule or mmRNA, has Formula (IXa)-(IXd):

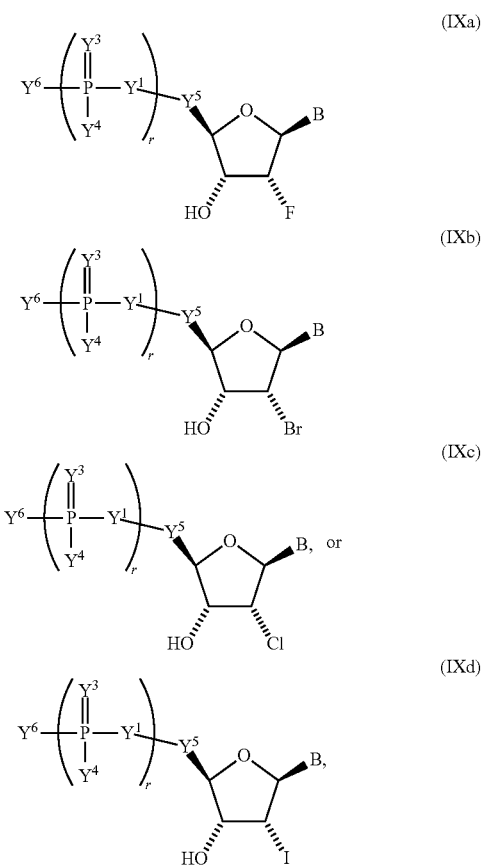

or a pharmaceutically acceptable salt or stereoisomer thereof, wherein B is as described herein (e.g., any one of (b1)-(b43)). In particular embodiments, one of Formulas (IXa)-(IXd) is combined with a modified uracil (e.g., any one of formulas (b1)-(b9), (b21)-(b23), and (b28)-(b31), such as formula (b1), (b8), (b28), (b29), or (b30)). In particular embodiments, one of Formulas (IXa)-(IXd) is combined with a modified cytosine (e.g., any one of formulas (b10)-(b14), (b24), (b25), and (b32)-(b36), such as formula (b10) or (b32)). In particular embodiments, one of Formulas (IXa)-(IXd) is combined with a modified guanine (e.g., any one of formulas (b15)-(b17) and (b37)-(b40)). In particular embodiments, one of Formulas (IXa)-(IXd) is combined with a modified adenine (e.g., any one of formulas (b18)-(b20) and (b41)-(b43)).

In other embodiments, the building block molecule, which may be incorporated into a modified nucleic acid molecule or mmRNA, has Formula (IXe)-(IXg):

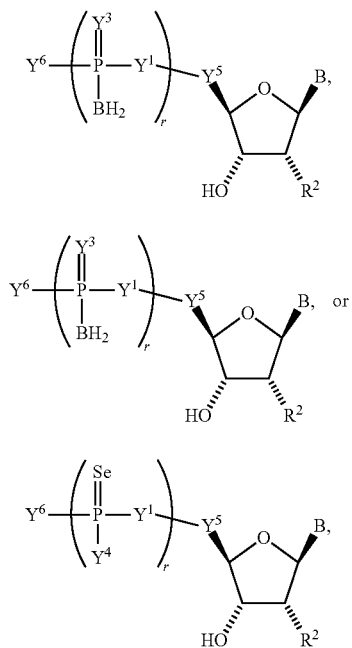

(IXe)

(IXf)

(IXg)

or a pharmaceutically acceptable salt or stereoisomer thereof, wherein B is as described herein (e.g., any one of (b1)-(b43)). In particular embodiments, one of Formulas (IXe)-(IXg) is combined with a modified uracil (e.g., any one of formulas (b1)-(b9), (b21)-(b23), and (b28)-(b31), such as formula (b1), (b8), (b28), (b29), or (b30)). In particular embodiments, one of Formulas (IXe)-(IXg) is combined with a modified cytosine (e.g., any one of formulas (b10)-(b14), (b24), (b25), and (b32)-(b36), such as formula (b10) or (b32)). In particular embodiments, one of Formulas (IXe)-(IXg) is combined with a modified guanine (e.g., any one of formulas (b15)-(b17) and (b37)-(b40)). In particular embodiments, one of Formulas (IXe)-(IXg) is combined with a modified adenine (e.g., any one of formulas (b18)-(b20) and (b41)-(b43)).

In other embodiments, the building block molecule, which may be incorporated into a modified nucleic acid molecule or mmRNA, has Formula (IXh)-(IXk):

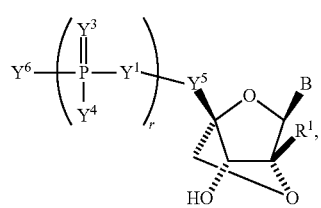

(IXh)

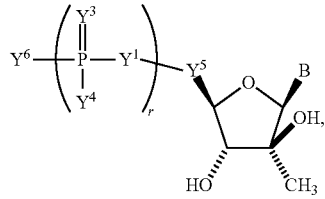

(IXi)

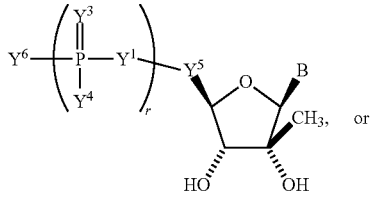

(IXj)

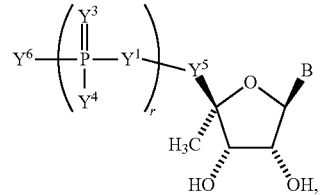

(IXk)

or a pharmaceutically acceptable salt or stereoisomer thereof, wherein B is as described herein (e.g., any one of (b1)-(b43)). In particular embodiments, one of Formulas (IXh)-(IXk) is combined with a modified uracil (e.g., any one of formulas (b1)-(b9), (b21)-(b23), and (b28)-(b31), such as formula (b1), (b8), (b28), (b29), or (b30)). In particular embodiments, one of Formulas (IXh)-(IXk) is combined with a modified cytosine (e.g., any one of formulas (b10)-(b14), (b24), (b25), and (b32)-(b36), such as formula (b10) or (b32)). In particular embodiments, one of Formulas (IXh)-(IXk) is combined with a modified guanine (e.g., any one of formulas (b15)-(b17) and (b37)-(b40)). In particular embodiments, one of Formulas (IXh)-(IXk) is combined with a modified adenine (e.g., any one of formulas (b18)-(b20) and (b41)-(b43)).

In other embodiments, the building block molecule, which may be incorporated into a modified nucleic acid molecule or mmRNA, has Formula (IXl)-(IXr):

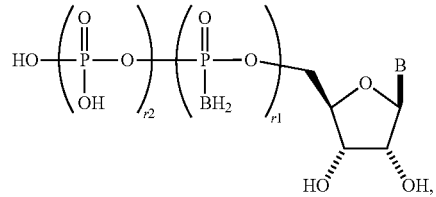

(IXl)

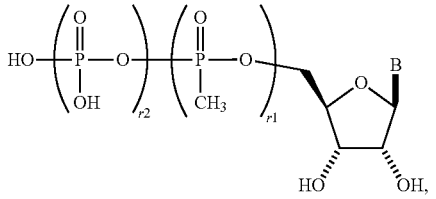

(IXm)

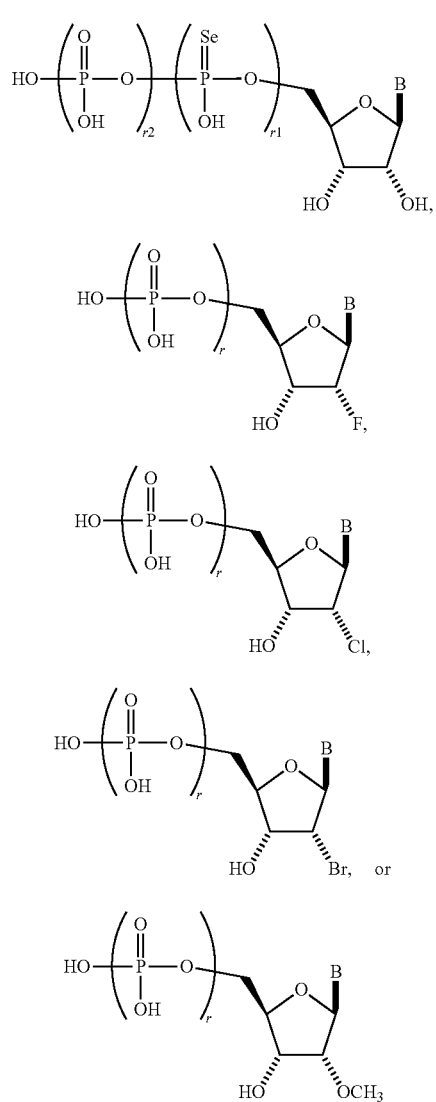

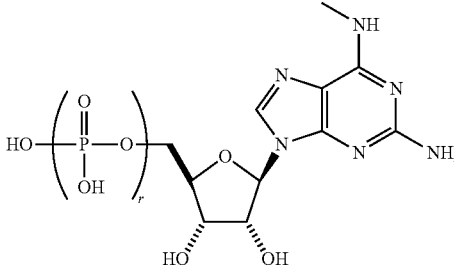

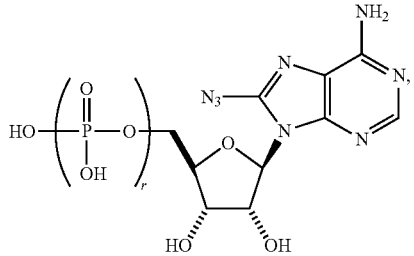

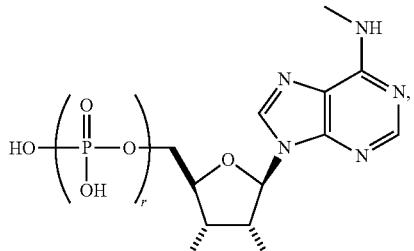

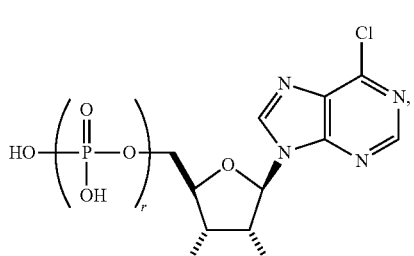

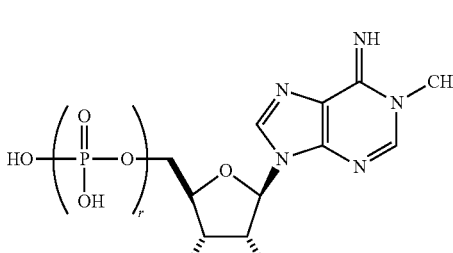

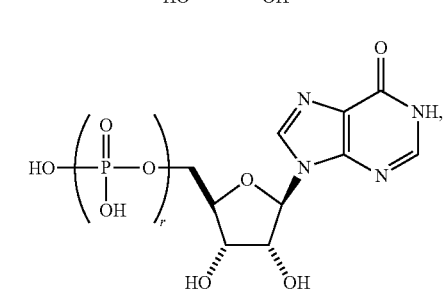

or a pharmaceutically acceptable salt or stereoisomer thereof, wherein each r1 and r2 is, independently, an integer from 0 to 5 (e.g., from 0 to 3, from 1 to 3, or from 1 to 5) and B is as described herein (e.g., any one of (b1)-(b43)). In particular embodiments, one of Formulas (IXl)-(IXr) is combined with a modified uracil (e.g., any one of formulas (b1)-(b9), (b21)-(b23), and (b28)-(b31), such as formula (b1), (b8), (b28), (b29), or (b30)). In particular embodiments, one of Formulas (IXl)-(IXr) is combined with a modified cytosine (e.g., any one of formulas (b10)-(b14), (b24), (b25), and (b32)-(b36), such as formula (b10) or (b32)). In particular embodiments, one of Formulas (IXl)-(IXr) is combined with a modified guanine (e.g., any one of formulas (b15)-(b17) and (b37)-(b40)). In particular embodiments, one of Formulas (IXl)-(IXr) is combined with a modified adenine (e.g., any one of formulas (b18)-(b20) and (b41)-(b43)).

In some embodiments, the building block molecule, which may be incorporated into a modified nucleic acid molecules or mmRNA, can be selected from the group consisting of:

-continued
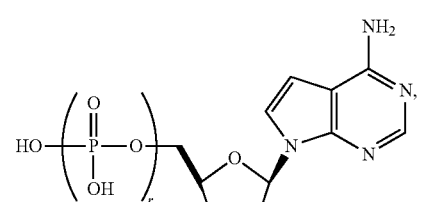
(BB-7)
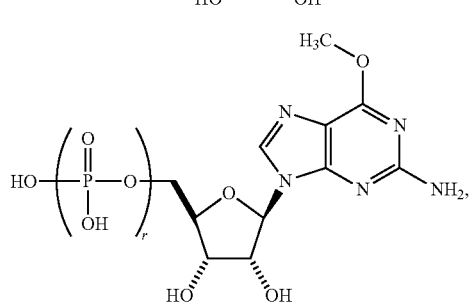
(BB-8)
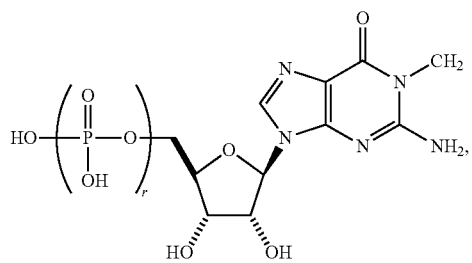
(BB-9)
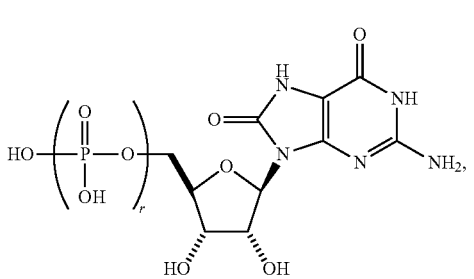
(BB-10)
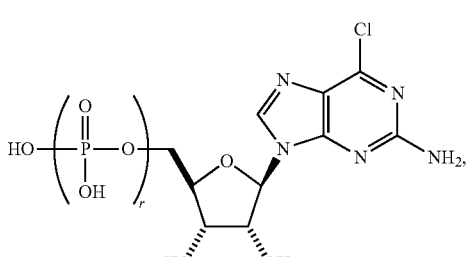
(BB-11)
and
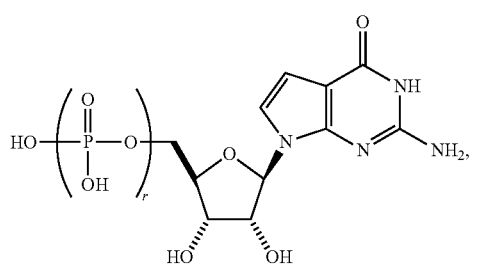
(BB-12)
or a pharmaceutically acceptable salt or stereoisomer thereof, wherein each r is, independently, an integer from 0 to 5 (e.g., from 0 to 3, from 1 to 3, or from 1 to 5).
In some embodiments, the building block molecule, which may be incorporated into a modified nucleic acid molecule or mmRNA, can be selected from the group consisting of:
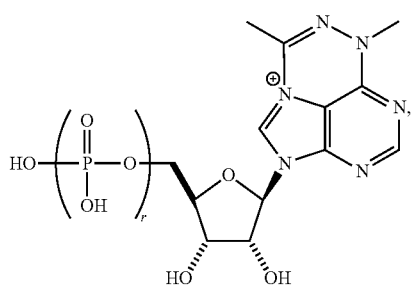
(BB-13)
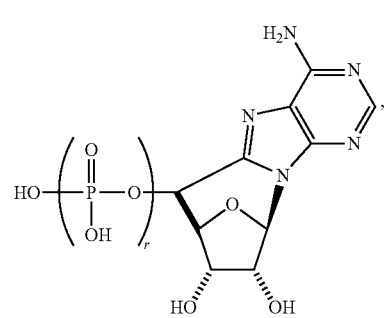
(BB-14)
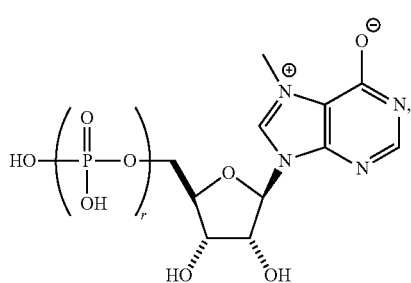
(BB-15)
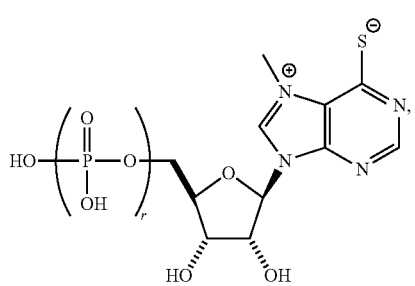
(BB-16)
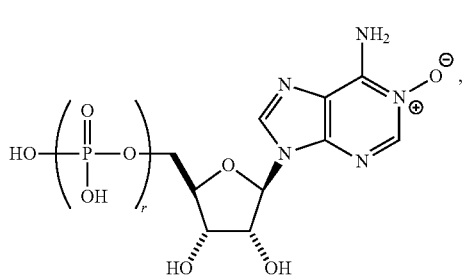
(BB-17)

(BB-18)
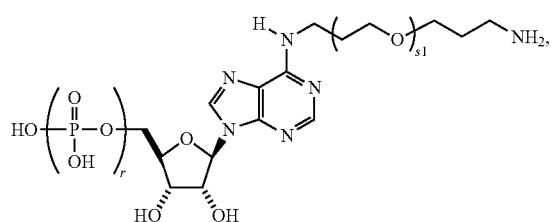

(BB-22)
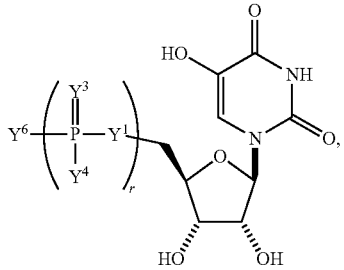

(BB-19)
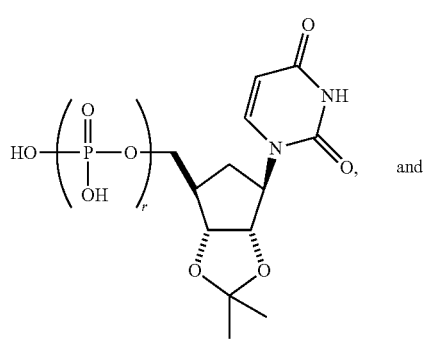
and (BB-23)
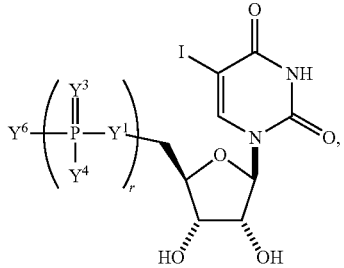

(BB-24)
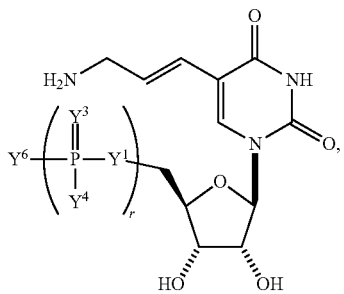

(BB-20)
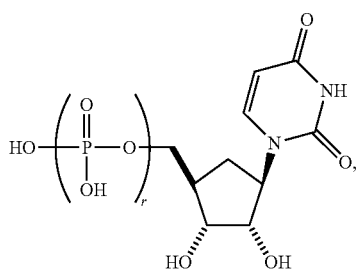

or a pharmaceutically acceptable salt or stereoisomer thereof, wherein each r is, independently, an integer from 0 to 5 (e.g., from 0 to 3, from 1 to 3, or from 1 to 5) and s1 is as described herein.

In some embodiments, the building block molecule, which may be incorporated into a nucleic acid (e.g., RNA, mRNA, or mmRNA), is a modified uridine (e.g., selected from the group consisting of:

(BB-25)
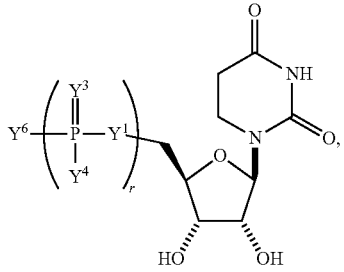

(BB-21)
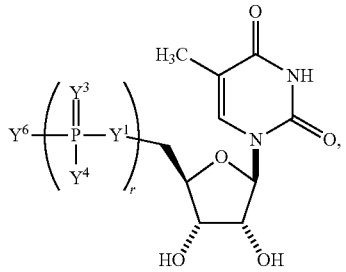

(BB-26)
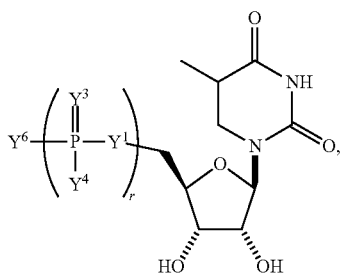

(BB-27)
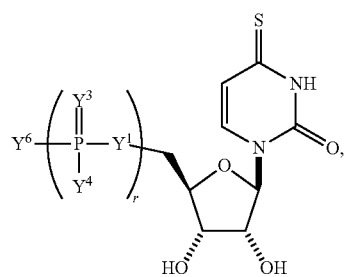
(BB-28)
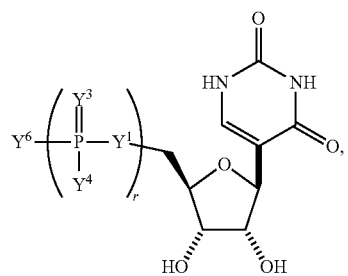
(BB-29)
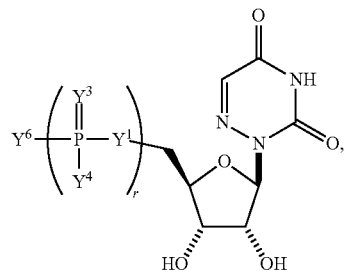
(BB-30)
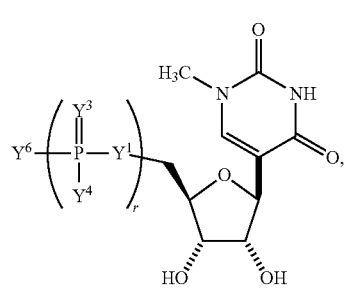
(BB-31)
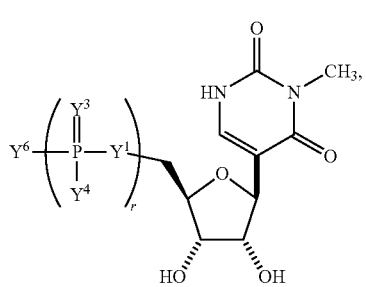
(BB-32)
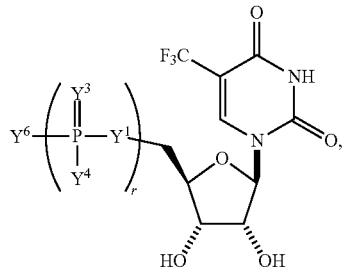
(BB-33)
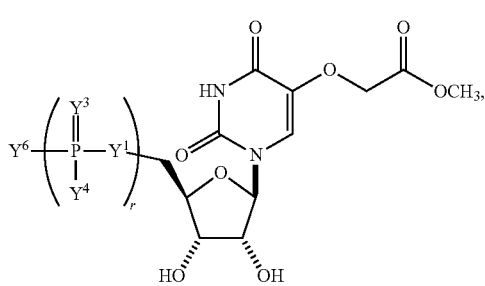
(BB-34)
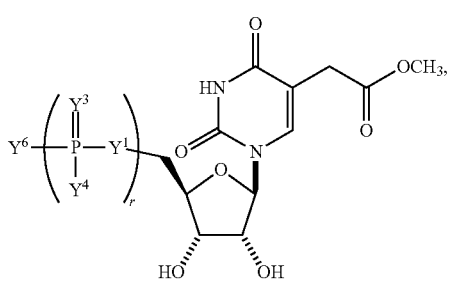
(BB-35)
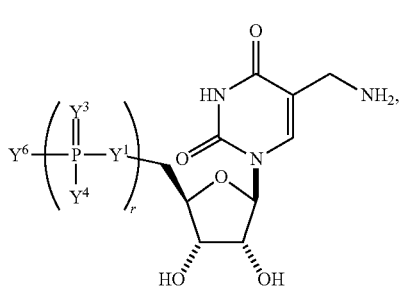
(BB-36)
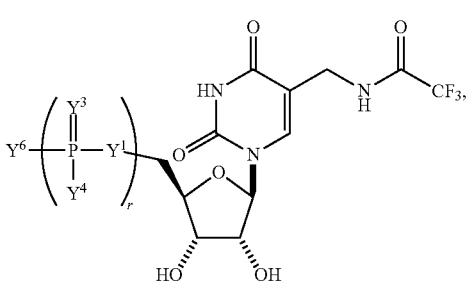

(BB-37)
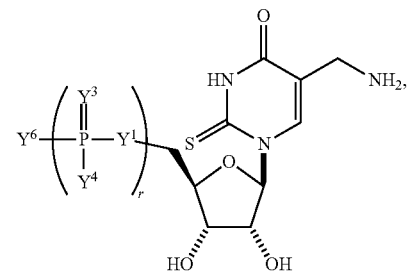
(BB-38)
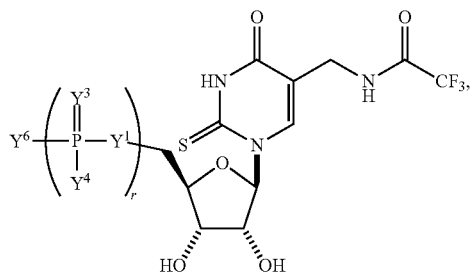
(BB-39)
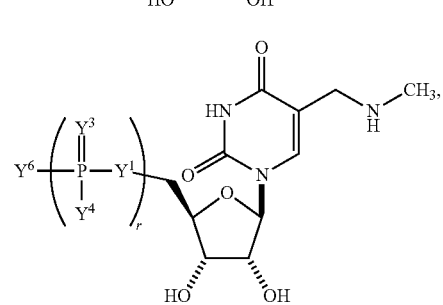
(BB-40)
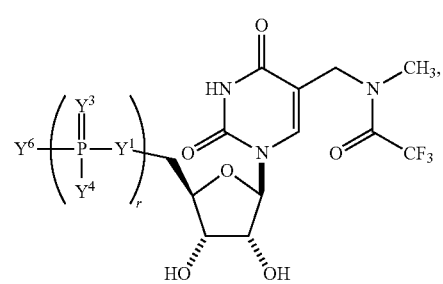
(BB-41)
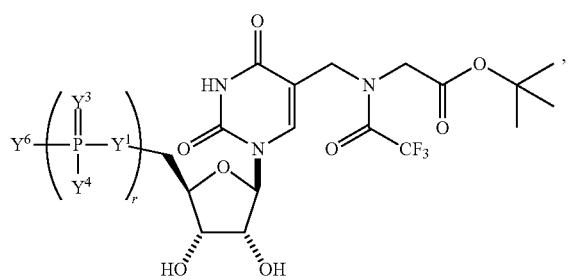
(BB-42)
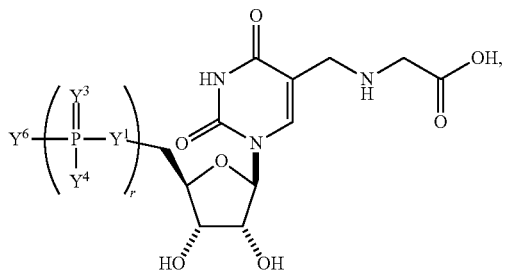
(BB-43)
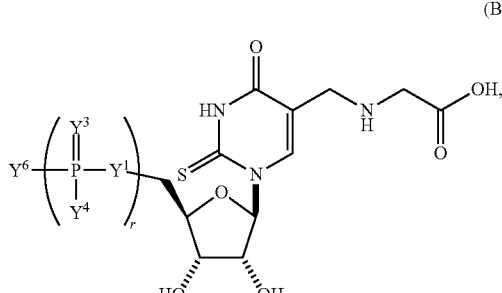
(BB-44)
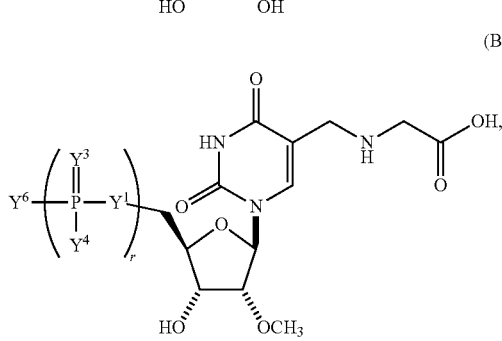
(BB-45)
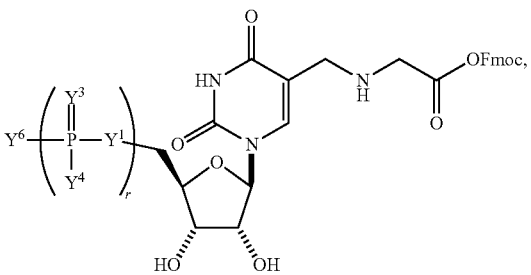
(BB-46)
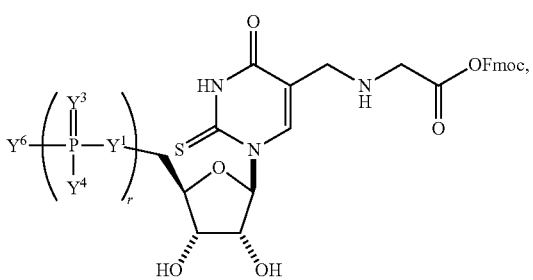

(BB-47)
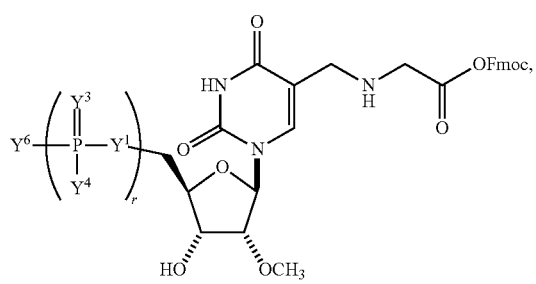
(BB-48)
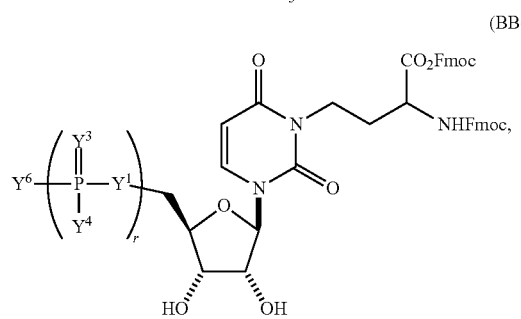
(BB-49)
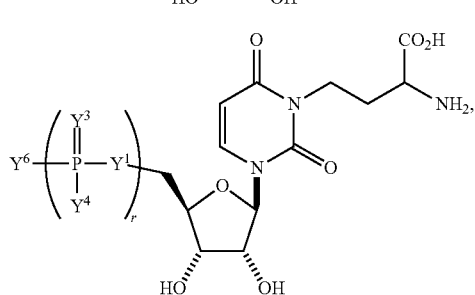
(BB-50)
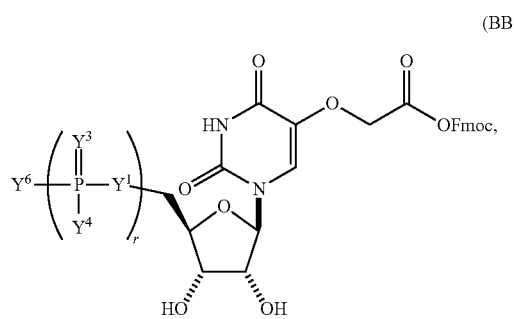
(BB-51)
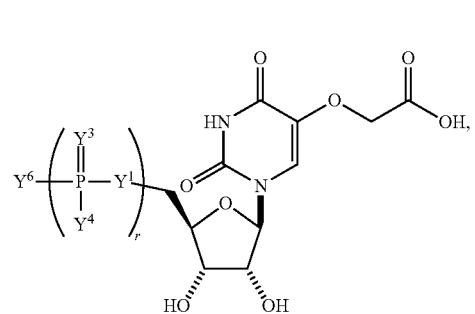
(BB-52)
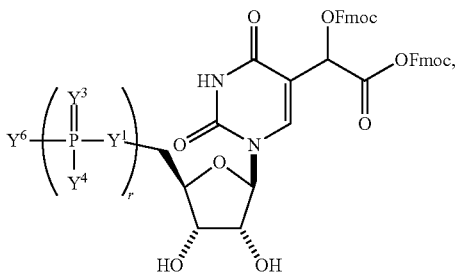
(BB-53)
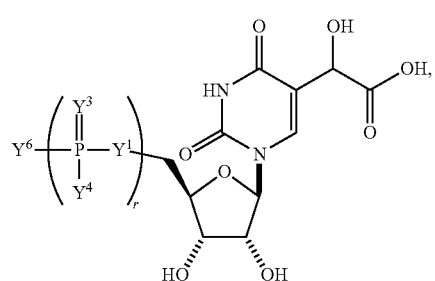
(BB-54)
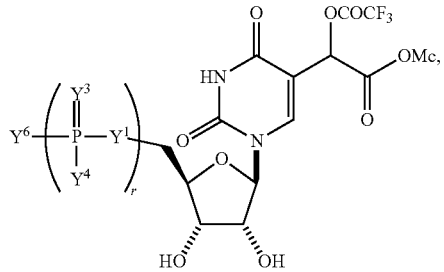
(BB-55)
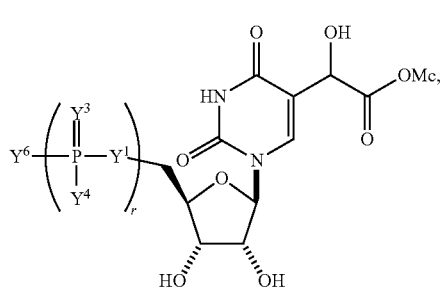
(BB-56)
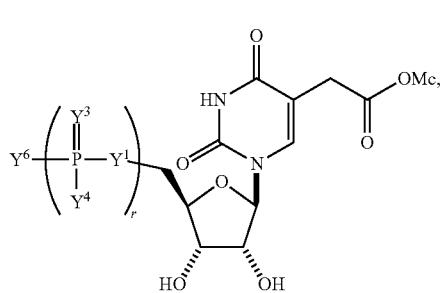

(BB-57)
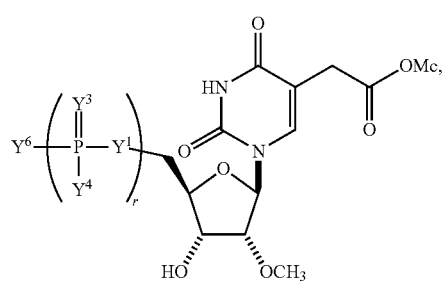
(BB-58)
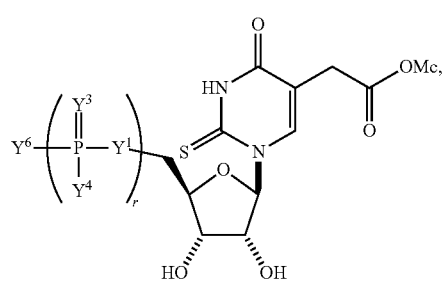
(BB-59)
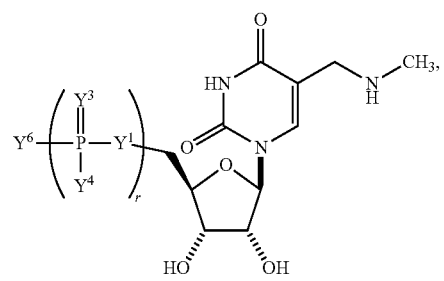
(BB-60)
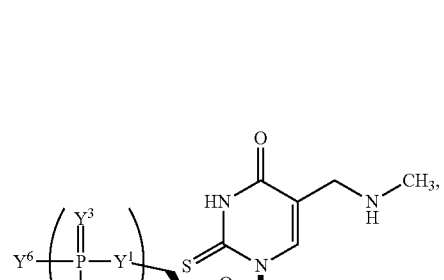
(BB-61)
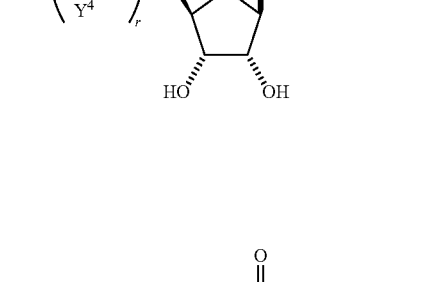
(BB-62)
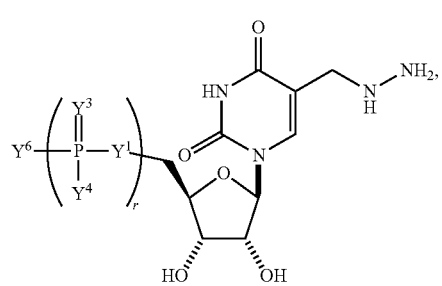
(BB-63)
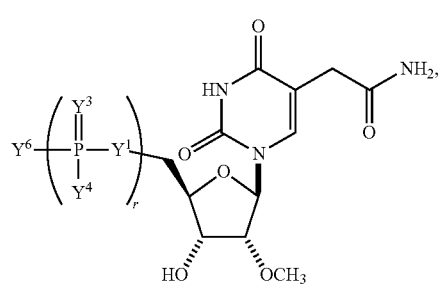
(BB-64)
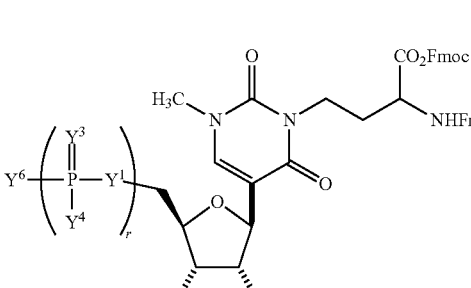
(BB-65)
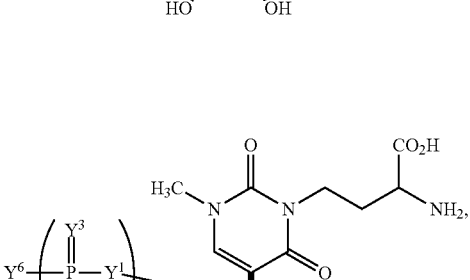
(BB-66)
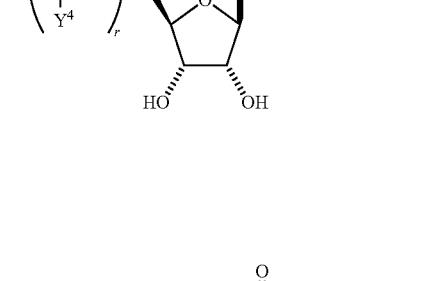

(BB-67)
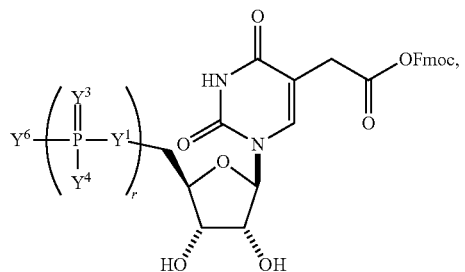
(BB-68)
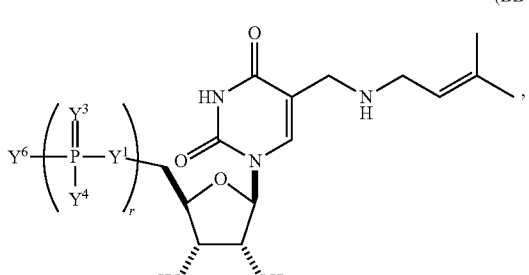
(BB-69)
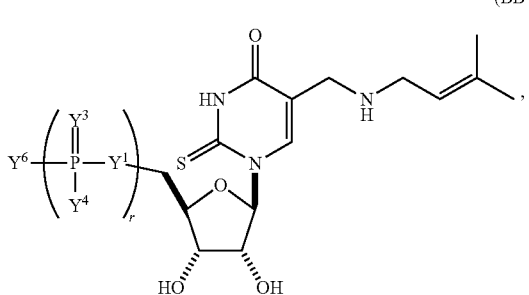
(BB-70)
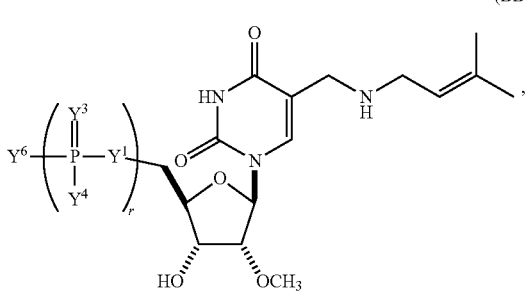
(BB-71)
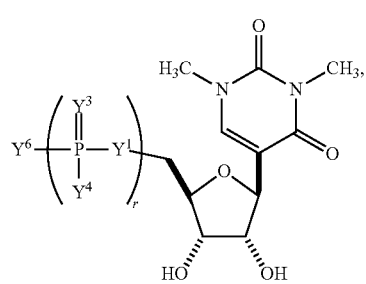
(BB-72)
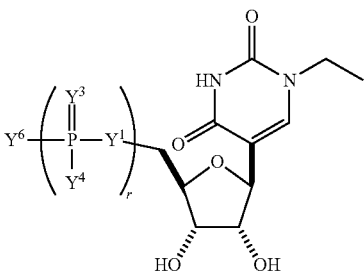
(BB-73)
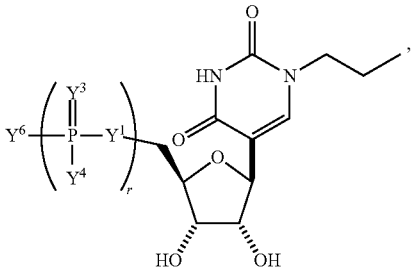
(BB-74)
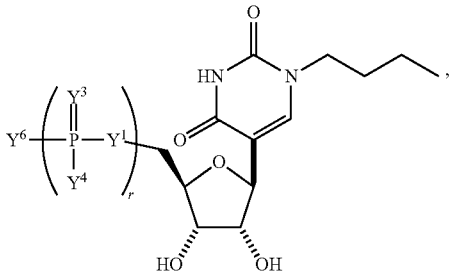
(BB-75)
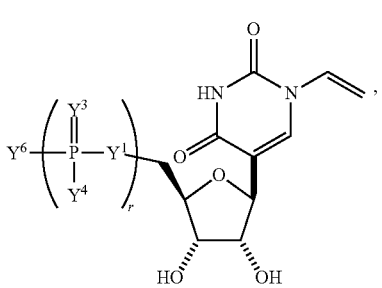
(BB-76)
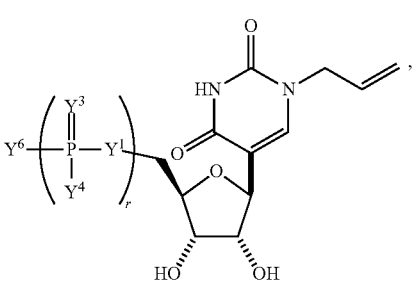

(BB-77)
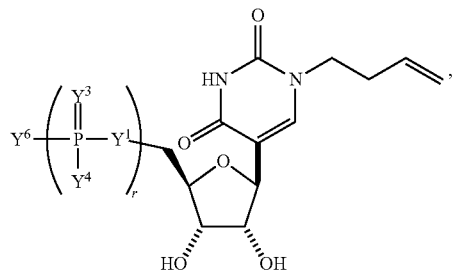
(BB-78)
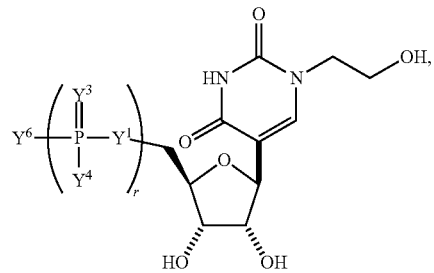
(BB-79)
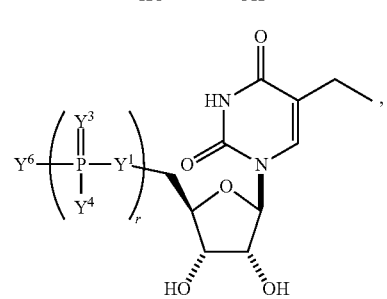
(BB-80)
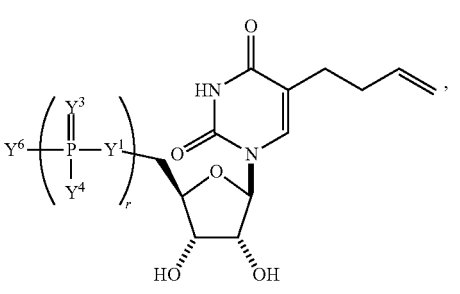
(BB-81)
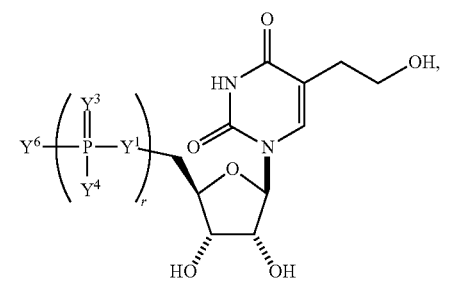
(BB-82)
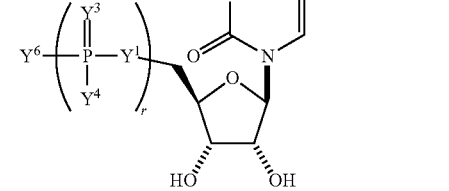
(BB-83)
(BB-84)
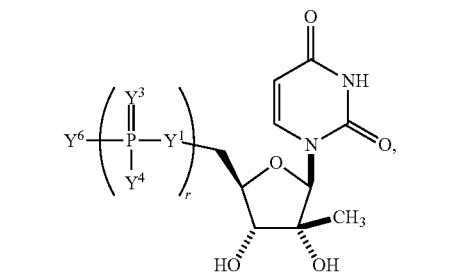
(BB-85)
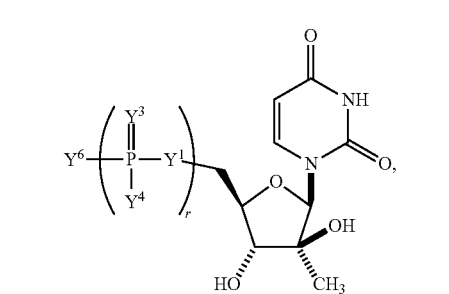
(BB-86)
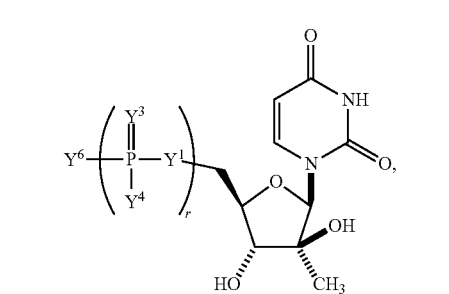

(BB-87)
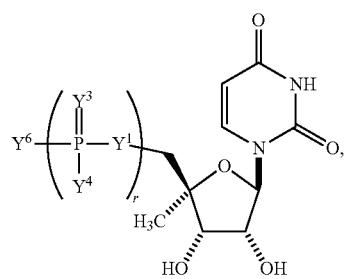
(BB-88)
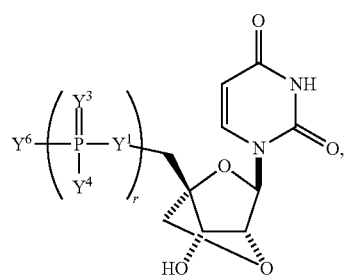
(BB-89)
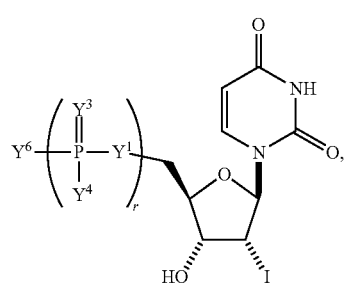
(BB-90)
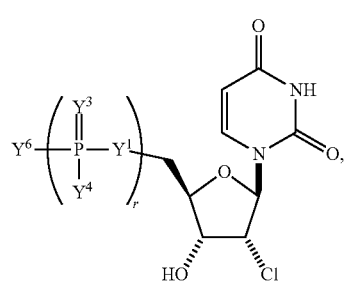
(BB-91)
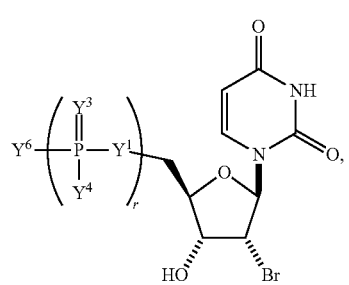
(BB-92)
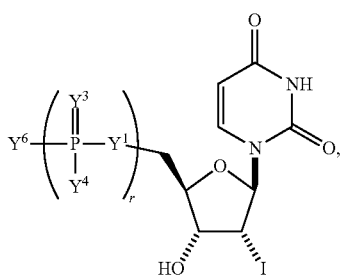
(BB-93)
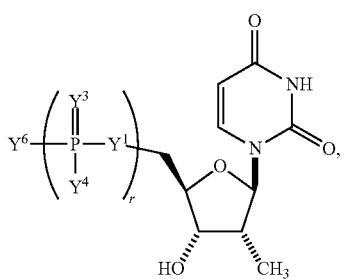
(BB-94)
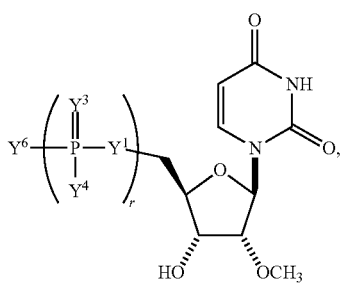
(BB-95)
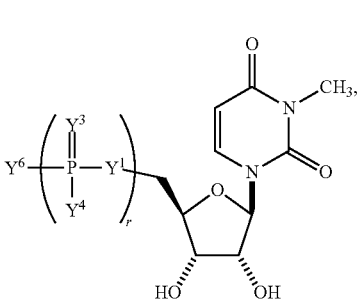
(BB-96)
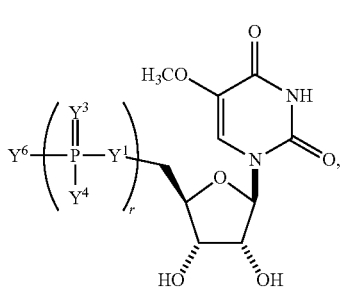

(BB-97)
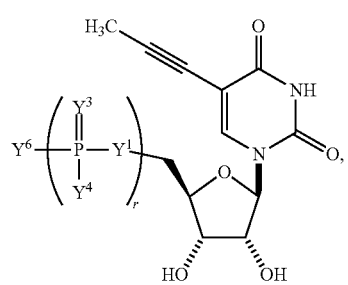
(BB-98)
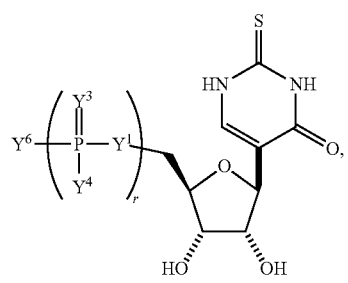
(BB-99)
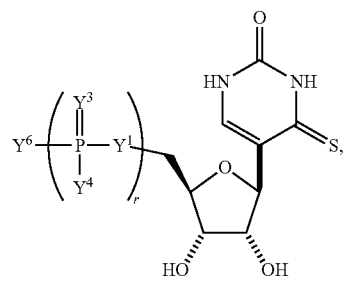
(BB-100)
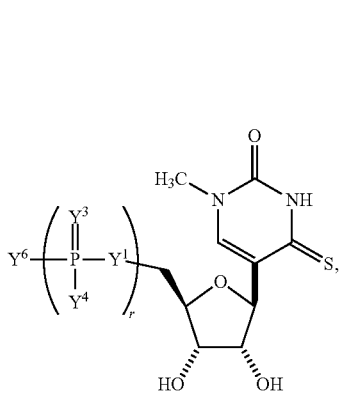
(BB-101)
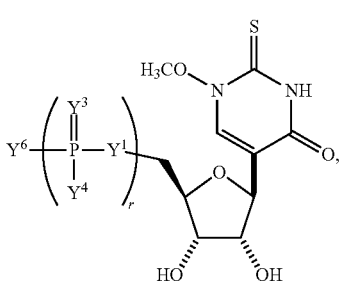
(BB-102)
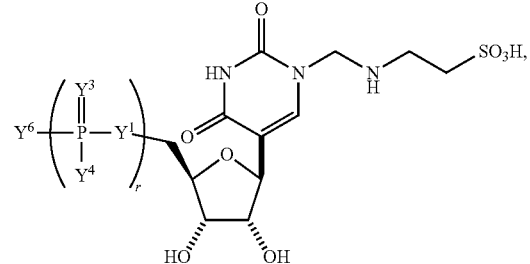
(BB-103)
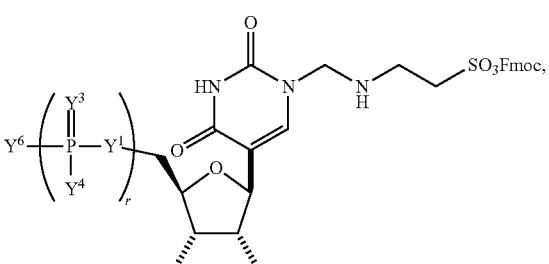
(BB-104)
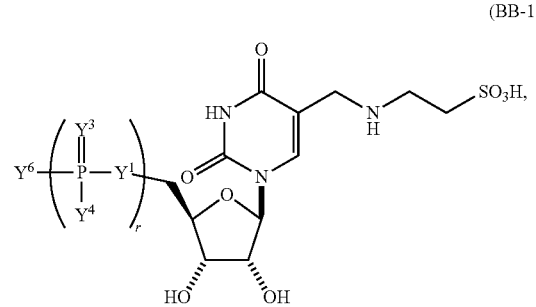
(BB-105)
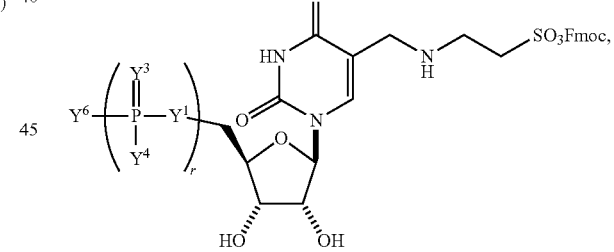
(BB-106)
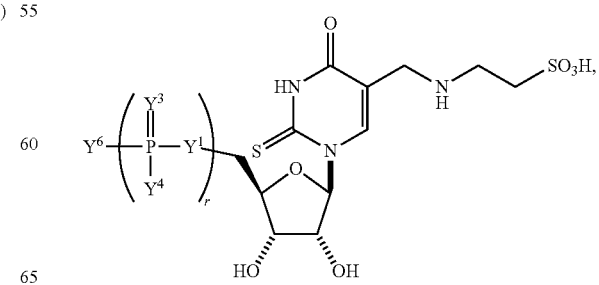

-continued
(BB-107)
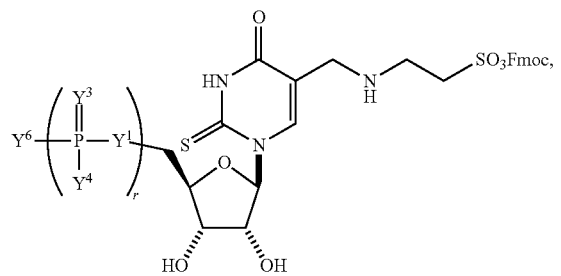
(BB-108)
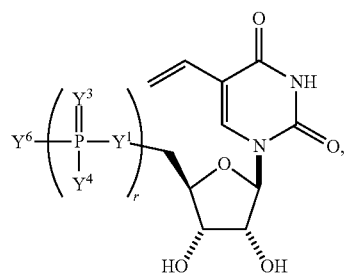
(BB-109)
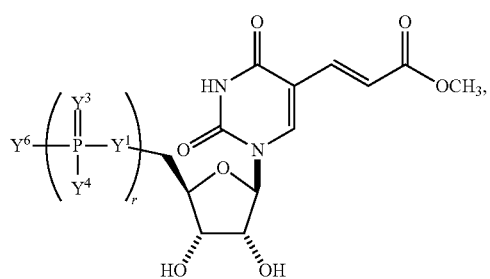
(BB-110)
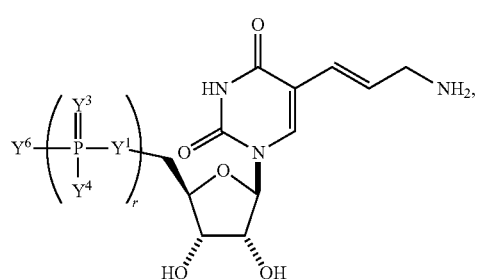
(BB-111)
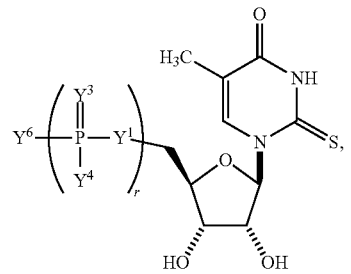
-continued
(BB-112)
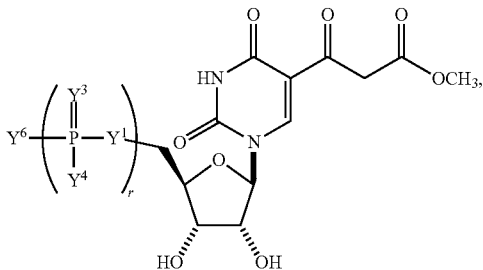
(BB-113)
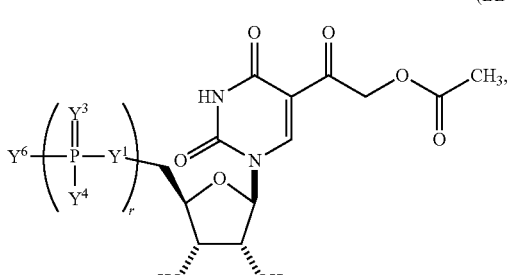
(BB-114)
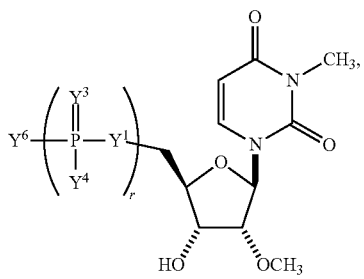
(BB-115)
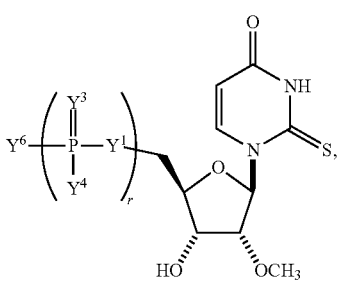
(BB-116)
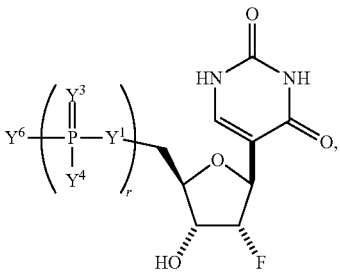

(BB-117)
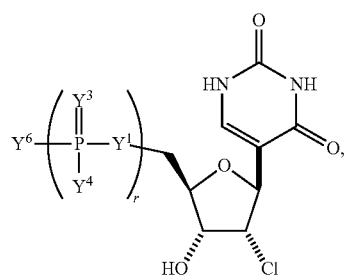

(BB-118)
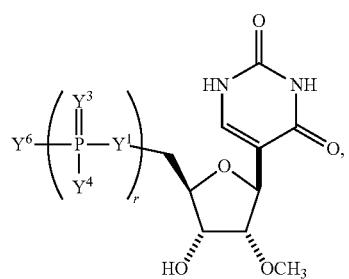

(BB-119)
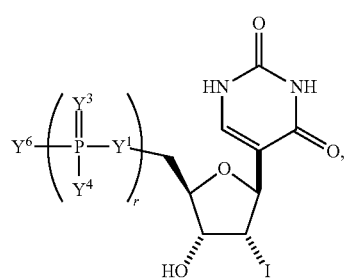

(BB-120)
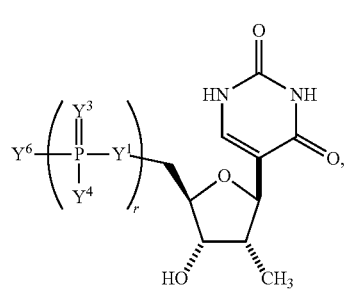

(BB-121)
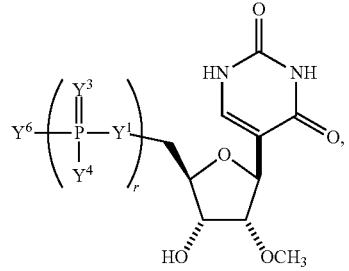

(BB-122)
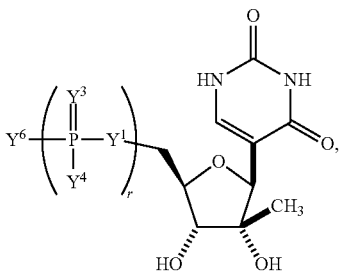

(BB-123)
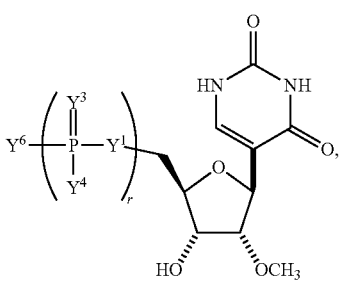

(BB-124)
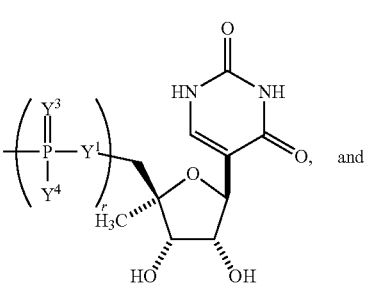

and (BB-125)
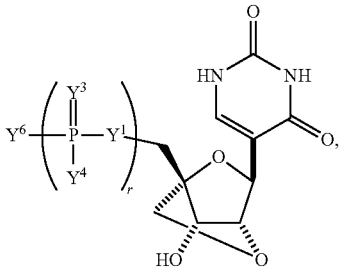

or a pharmaceutically acceptable salt or stereoisomer thereof, wherein $Y^1$, $Y^3$, $Y^4$, $Y^6$, and r are as described herein (e.g., each r is, independently, an integer from 0 to 5, such as from 0 to 3, from 1 to 3, or from 1 to 5)).

In some embodiments, the building block molecule, which may be incorporated into a modified nucleic acid molecule or mmRNA, is a modified cytidine (e.g., selected from the group consisting of:

(BB-126)
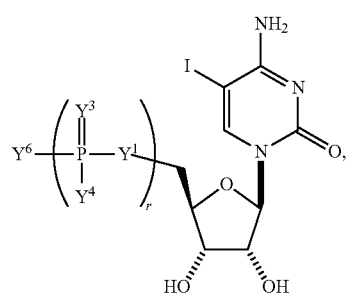
(BB-127)
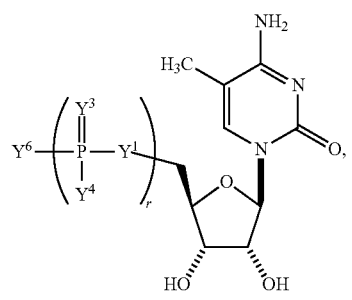
(BB-128)
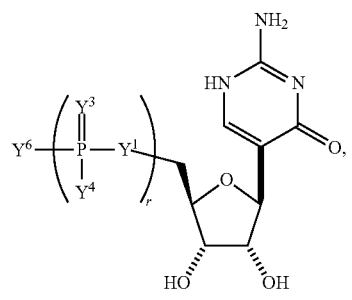
(BB-129)
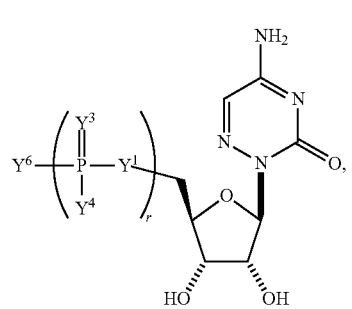
(BB-130)
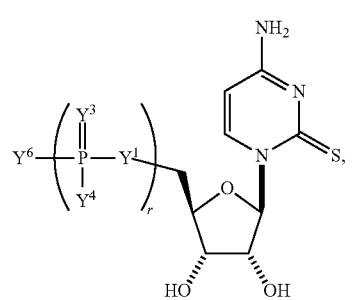
-continued
(BB-131)
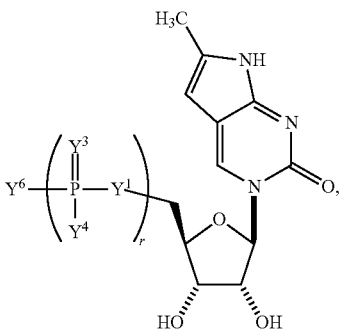
(BB-132)
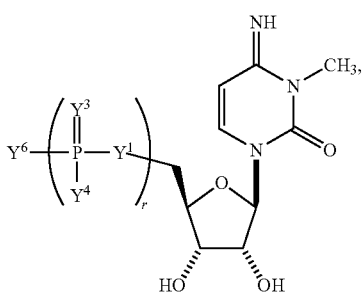
(BB-133)
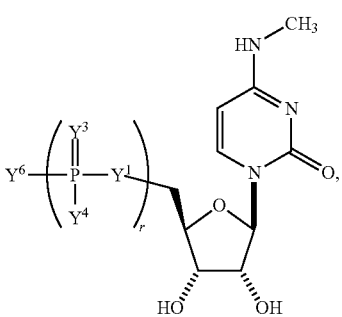
(BB-134)
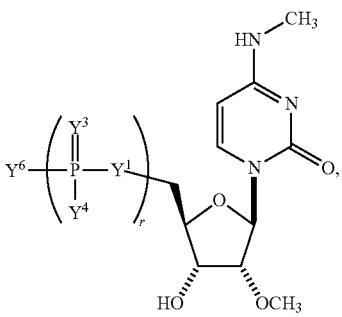
(BB-135)
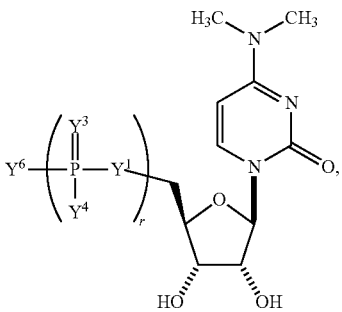

(BB-136)
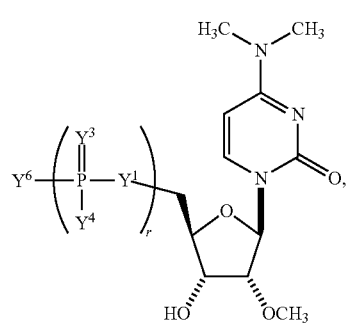
(BB-137)
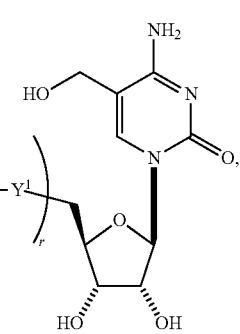
(BB-138)
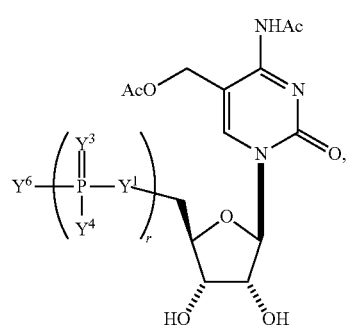
(BB-139)
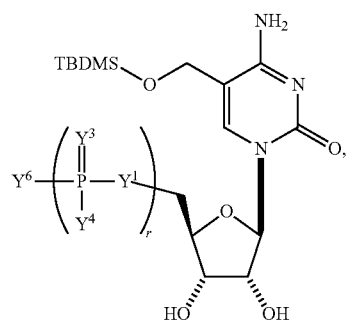
(BB-140)
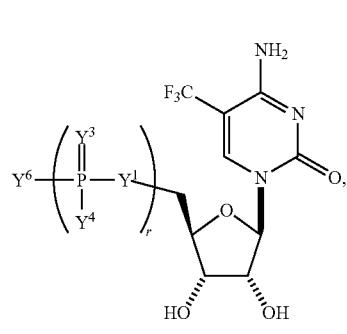
(BB-141)
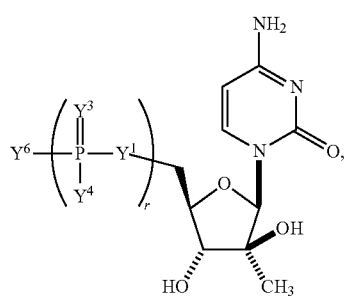
(BB-142)
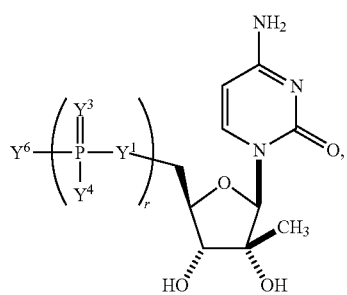
(BB-143)
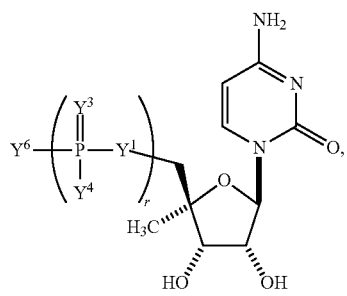
(BB-144)
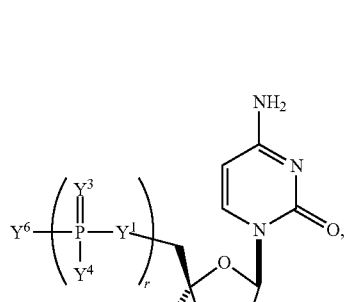
(BB-145)
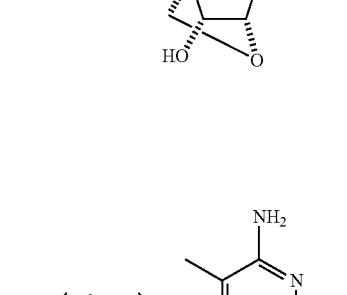

-continued
(BB-146)
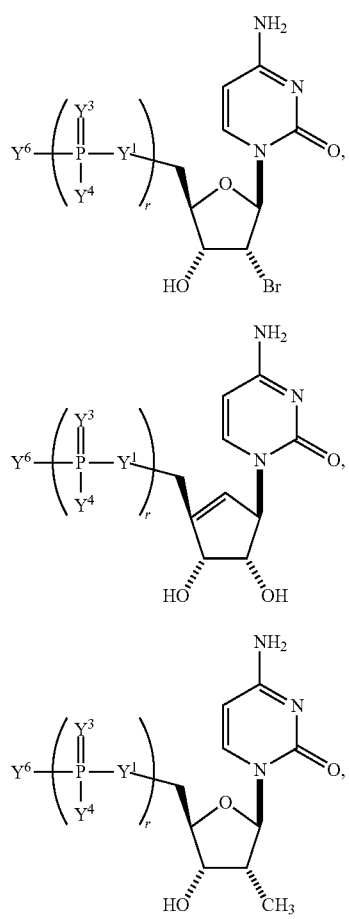
(BB-147)
(BB-148)
(BB-149)
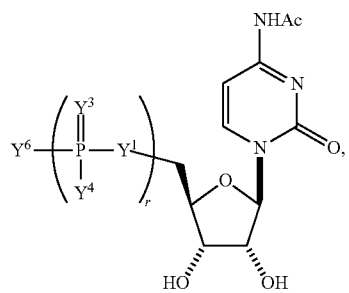
(BB-150)
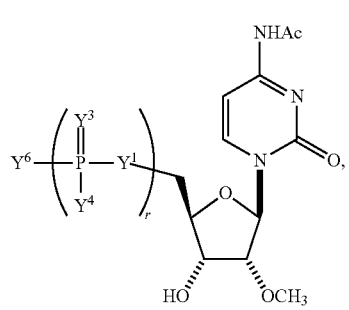
-continued
(BB-151)
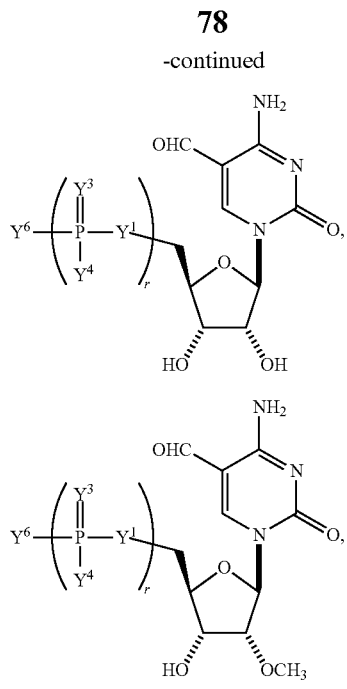
(BB-152)
(BB-153)
(BB-154)
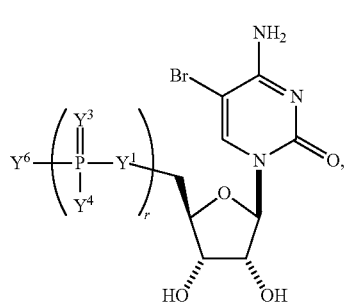
(BB-155)
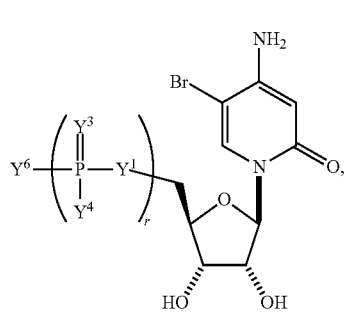

(BB-156)

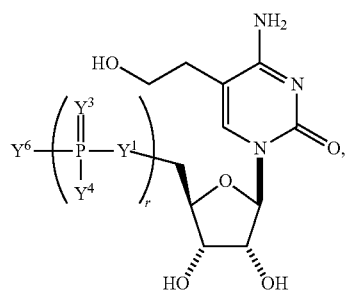

(BB-157)

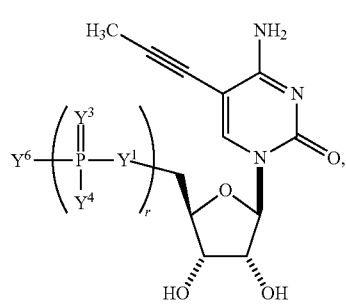

(BB-158)

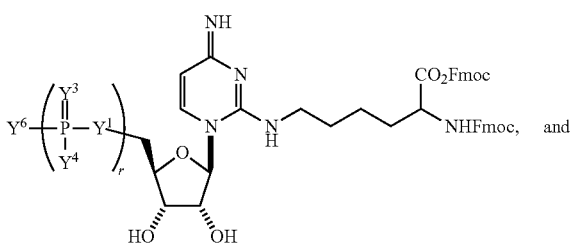

(BB-159)

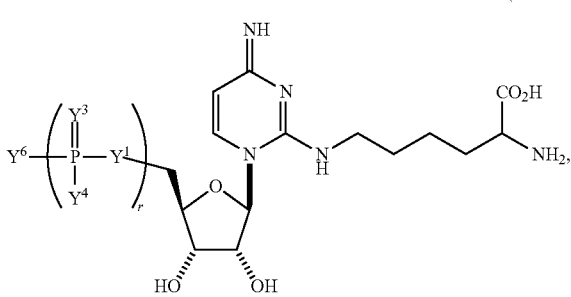

or a pharmaceutically acceptable salt or stereoisomer thereof, wherein $Y^1$, $Y^3$, $Y^4$, $Y^6$, and r are as described herein (e.g., each r is, independently, an integer from 0 to 5, such as from 0 to 3, from 1 to 3, or from 1 to 5)). For example, the building block molecule, which may be incorporated into a modified nucleic acid molecule or mmRNA, can be:

(BB-160)

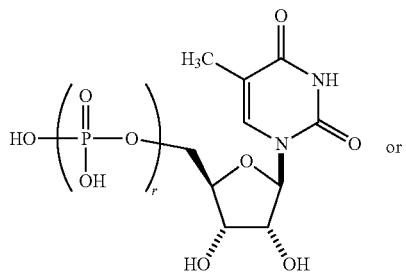

or (BB-161)

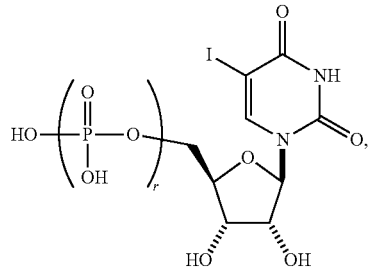

or a pharmaceutically acceptable salt or stereoisomer thereof, wherein each r is, independently, an integer from 0 to 5 (e.g., from 0 to 3, from 1 to 3, or from 1 to 5).

In some embodiments, the building block molecule, which may be incorporated into a modified nucleic acid molecule or mmRNA, is a modified adenosine (e.g., selected from the group consisting of:

(BB-162)

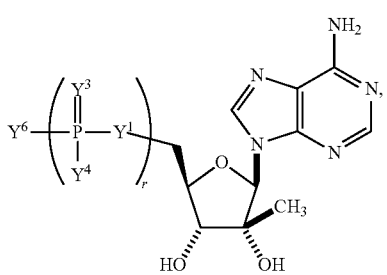

(BB-163)

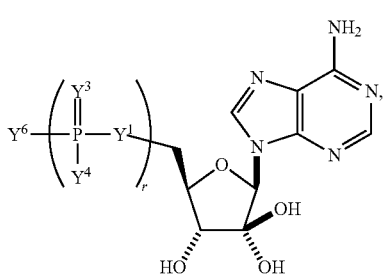

(BB-164)

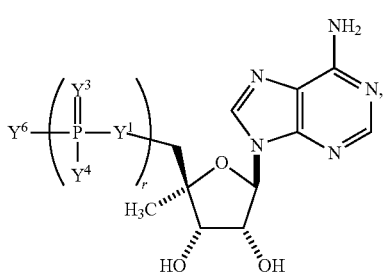

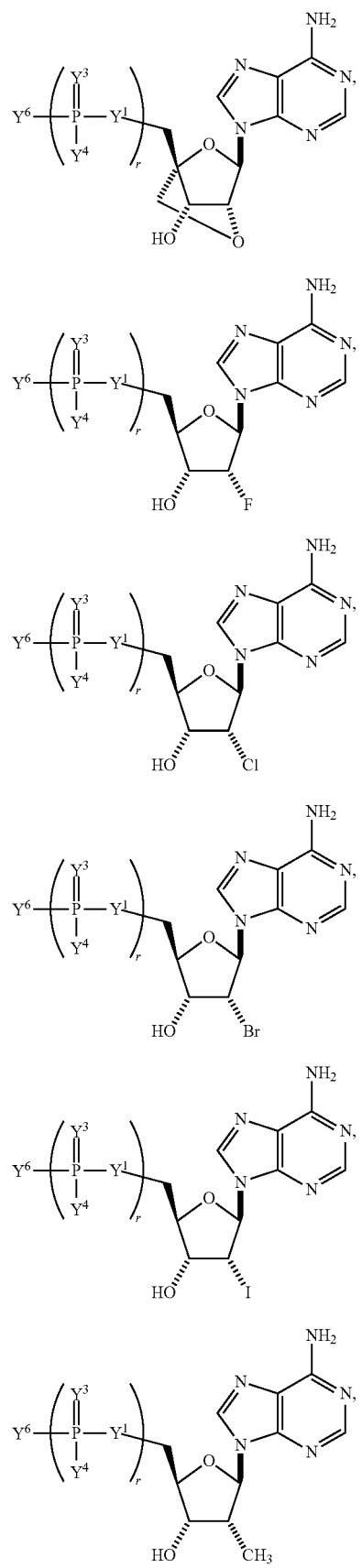
(BB-165)
(BB-166)
(BB-167)
(BB-168)
(BB-169)
(BB-170)
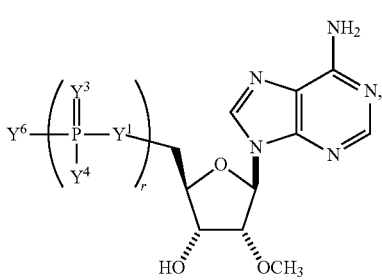
(BB-171)
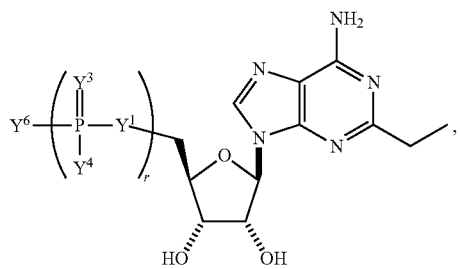
(BB-172)
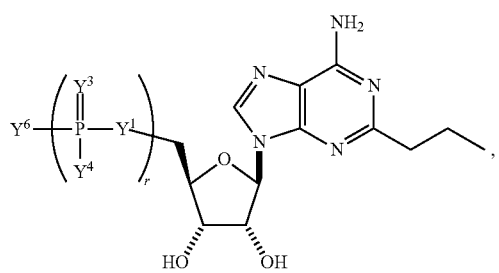
(BB-173)
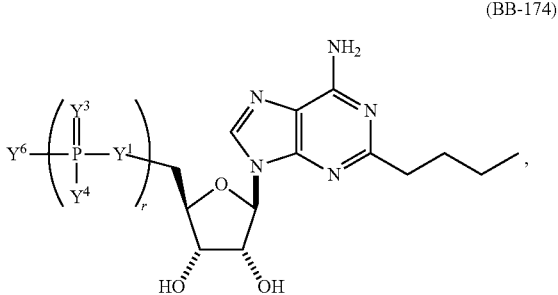
(BB-174)
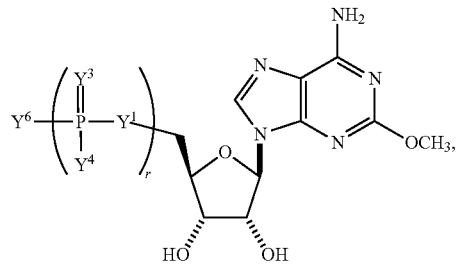
(BB-175)

(BB-176)
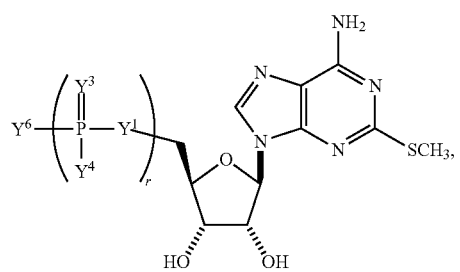
(BB-177)
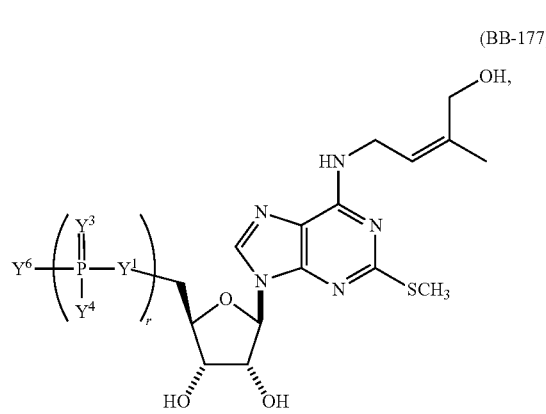
(BB-178)
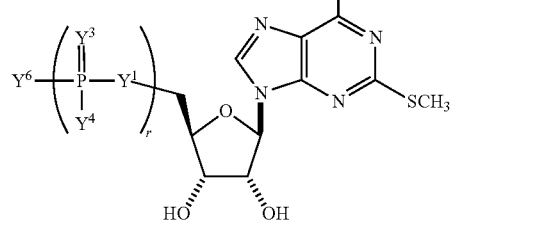
(BB-179)
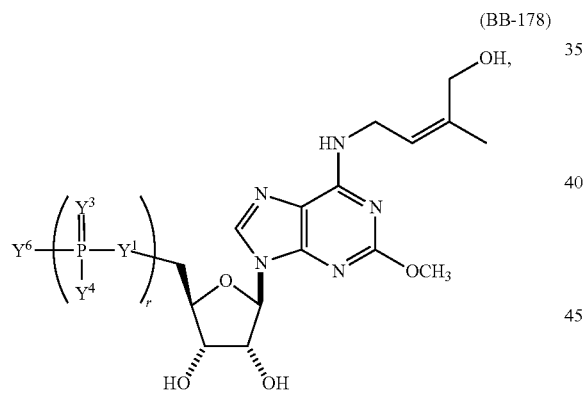
(BB-180)
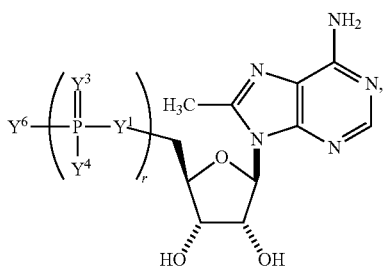
(BB-181)
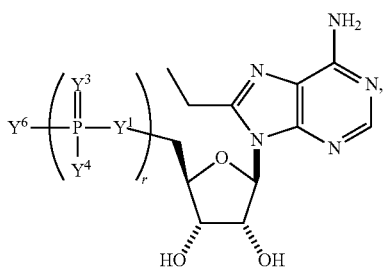
(BB-182)
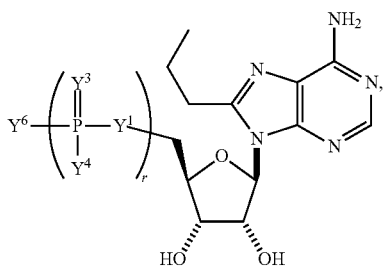
(BB-183)
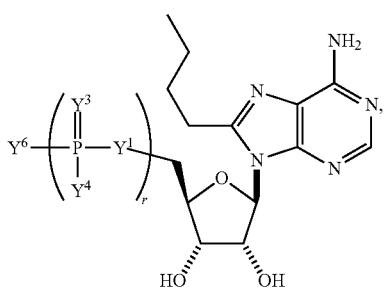
(BB-184)
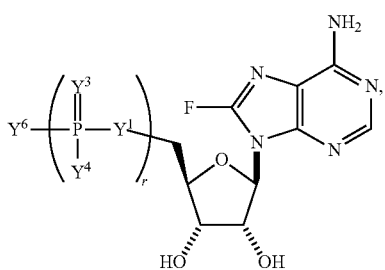
(BB-185)
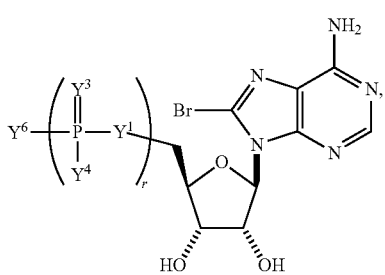

(BB-186)
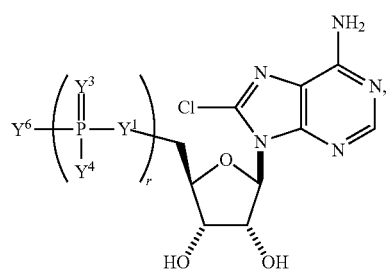
(BB-187)
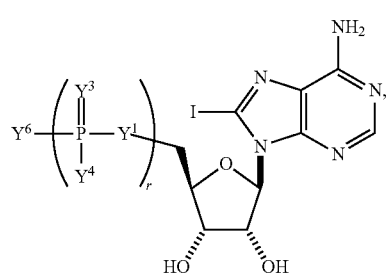
(BB-188)
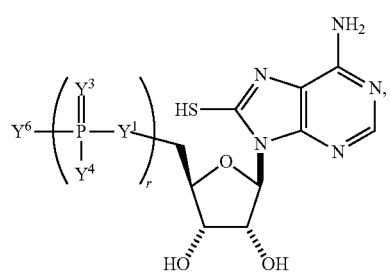
(BB-189)
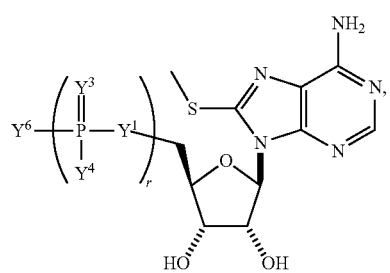
(BB-190)
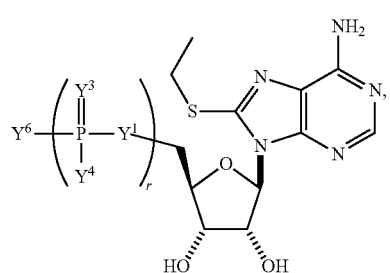
(BB-191)
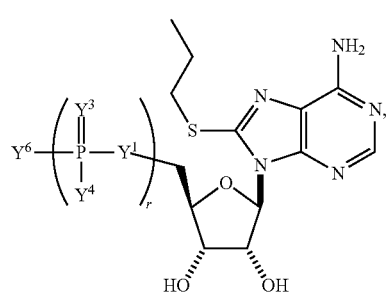
(BB-192)
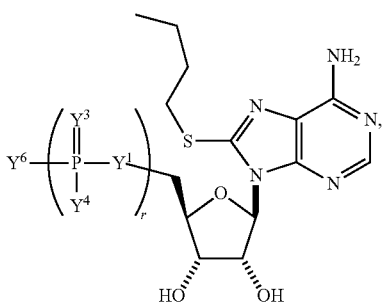
(B-193)
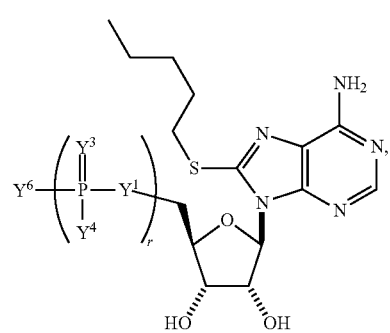
(BB-194)
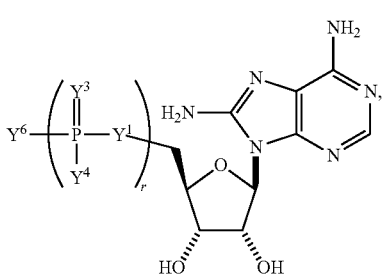
(BB-195)
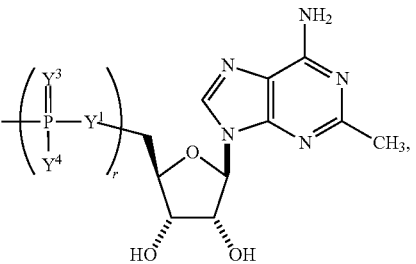
(BB-196)
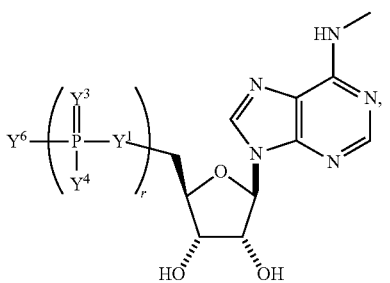

(BB-197)
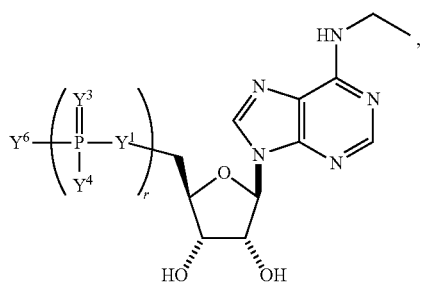

(BB-198)
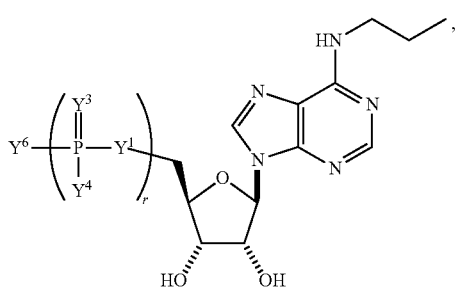

(BB-199)
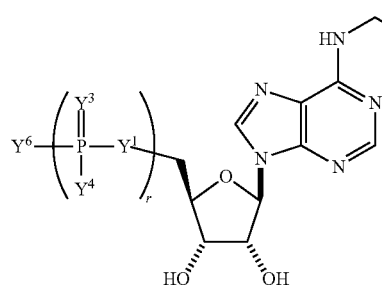, and (BB-200)
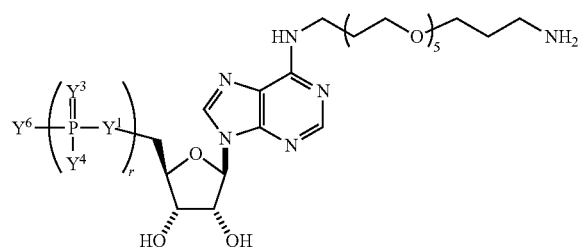

or a pharmaceutically acceptable salt or stereoisomer thereof, wherein $Y^1$, $Y^3$, $Y^4$, $Y^6$, and r are as described herein (e.g., each r is, independently, an integer from 0 to 5, such as from 0 to 3, from 1 to 3, or from 1 to 5)).

In some embodiments, the building block molecule, which may be incorporated into a modified nucleic acid molecule or mmRNA, is a modified guanosine (e.g., selected from the group consisting of:

(BB-201)
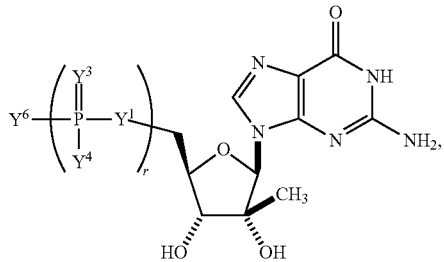

(BB-202)
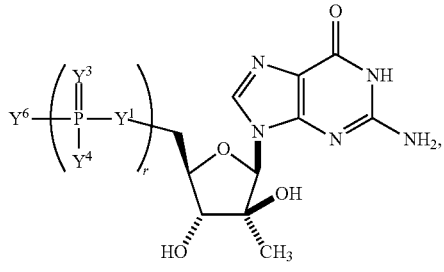

(BB-203)
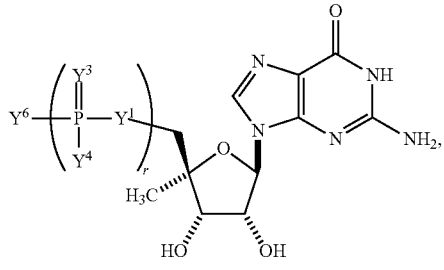

(BB-204)
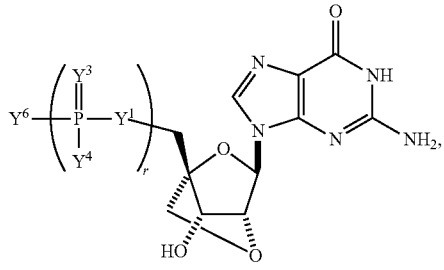

(BB-205)
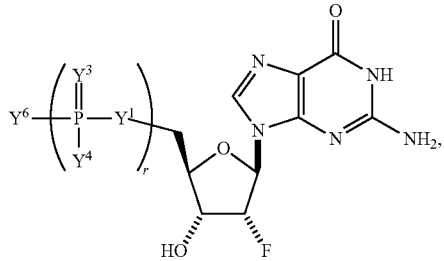

(BB-206)
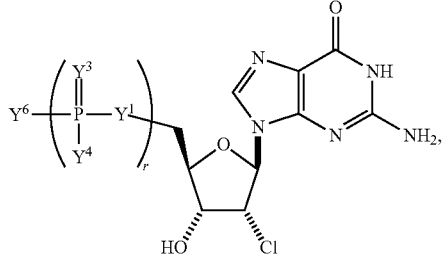

(BB-207)
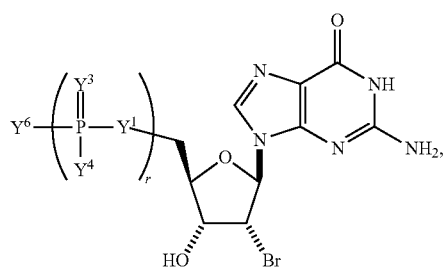
(BB-208)
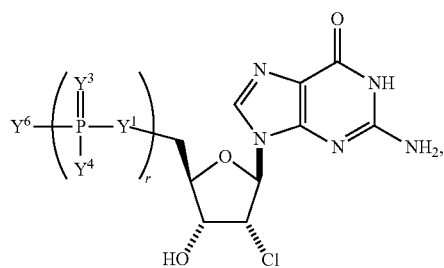
(BB-209)
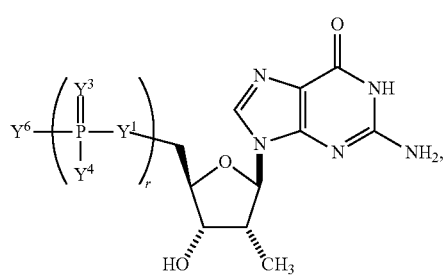
(BB-210)
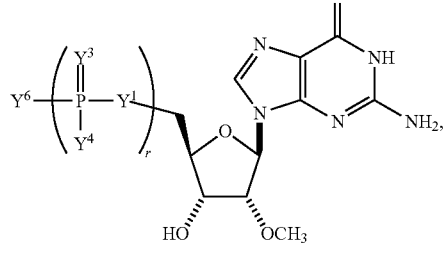
(BB-211)
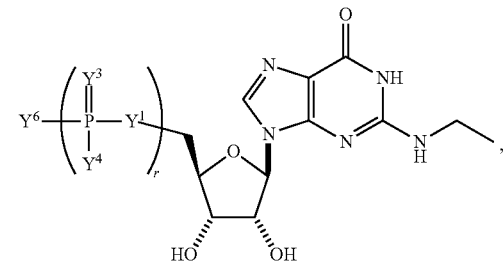
(BB-212)
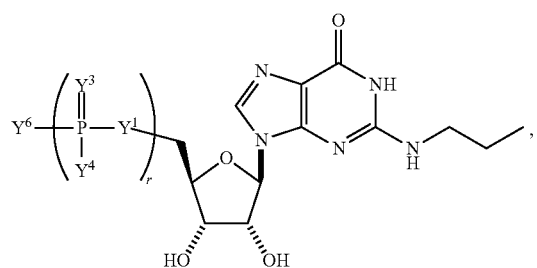
(BB-213)
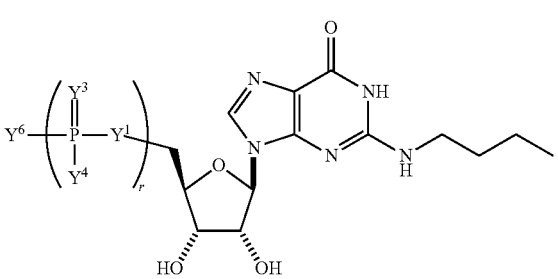
(BB-214)
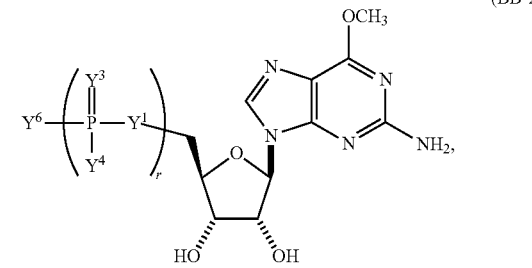
(BB-215)
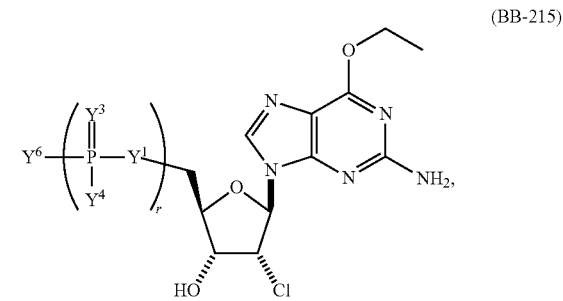
(BB-216)
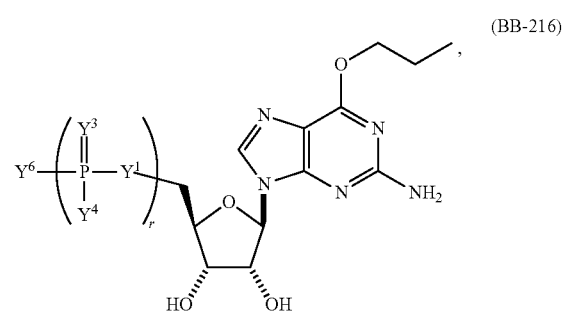

(BB-217)
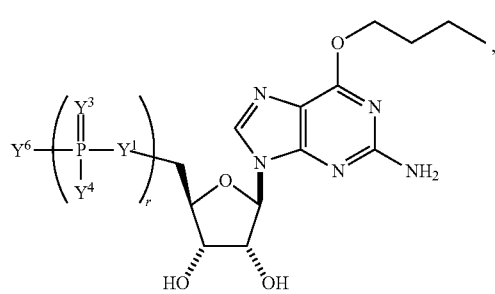
(BB-218)
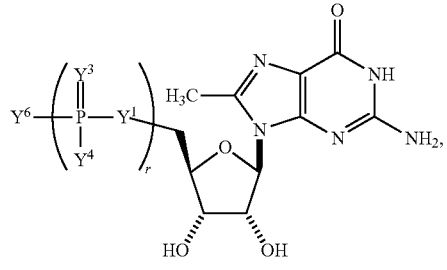
(BB-219)
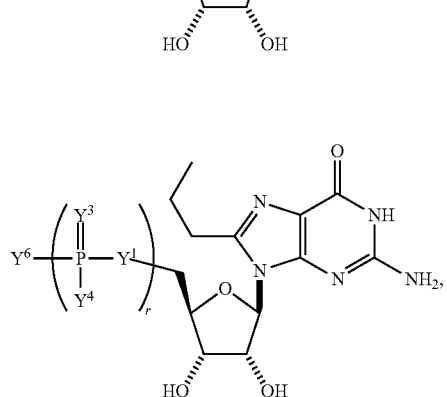
(BB-220)
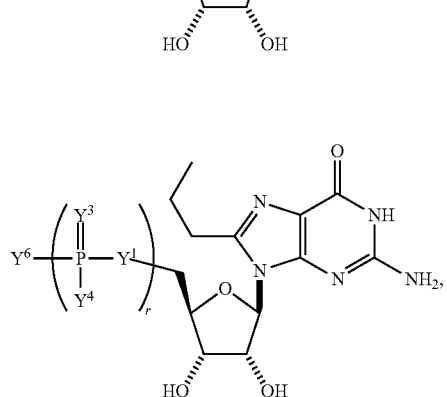
(BB-221)
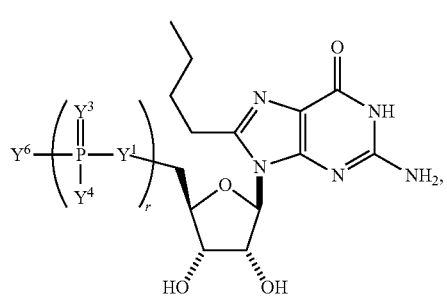
(BB-222)
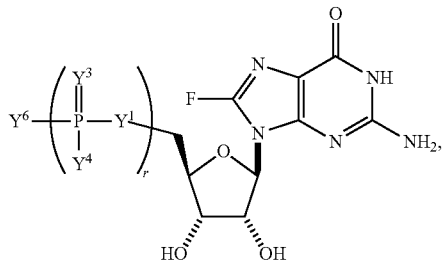
(B-223)
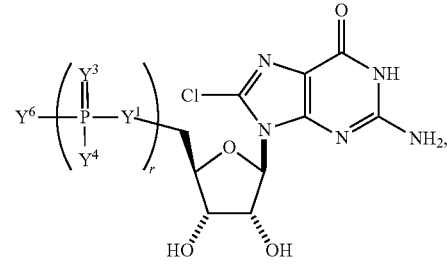
(B-224)
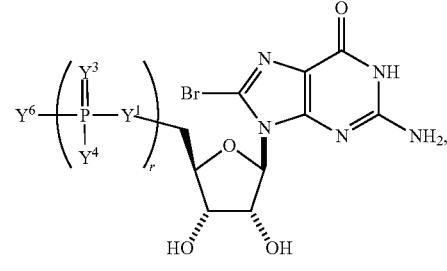
(B-225)
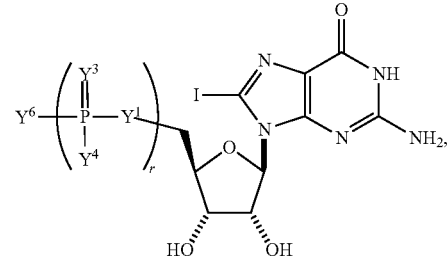
(BB-226)
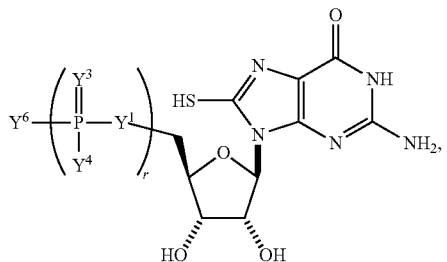

(BB-227)
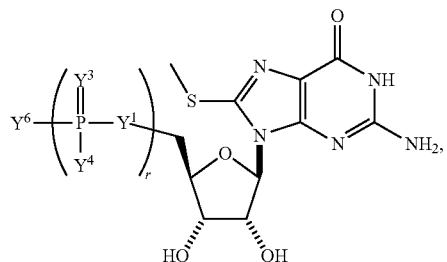
(BB-228)
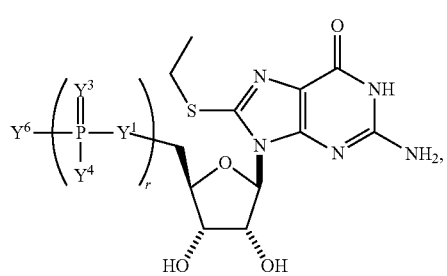
(BB-229)
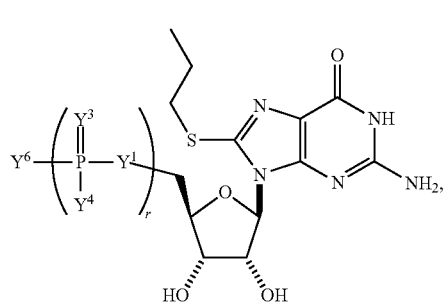
(BB-230)
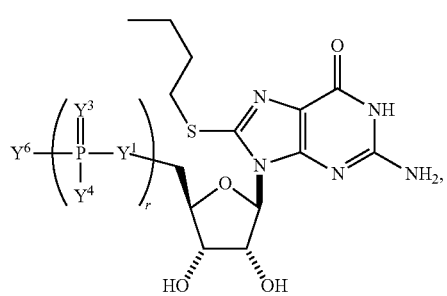
(BB-231)
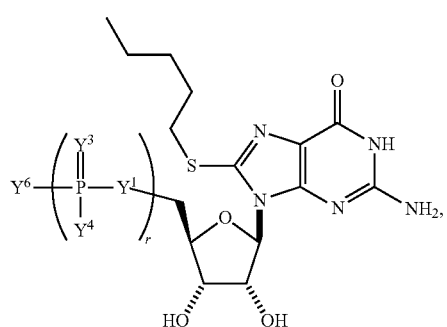
(BB-232)
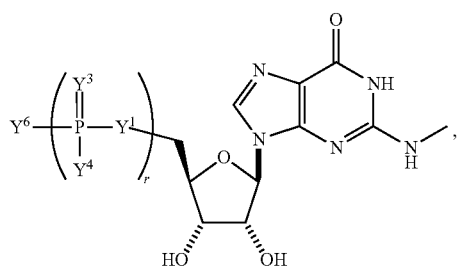
(BB-233)
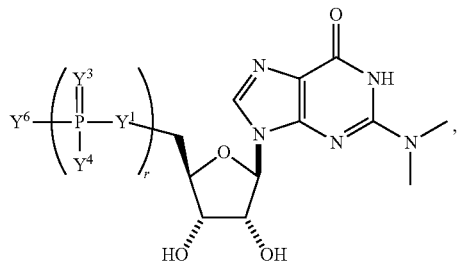
(BB-234)
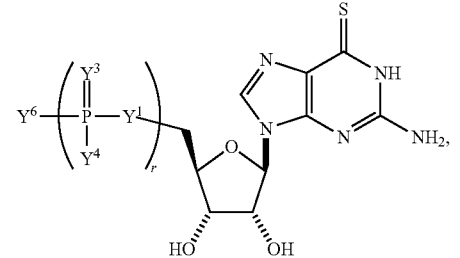
(BB-235)
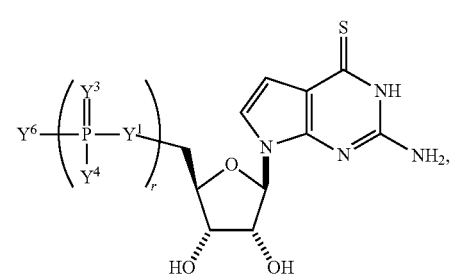
(BB-236)
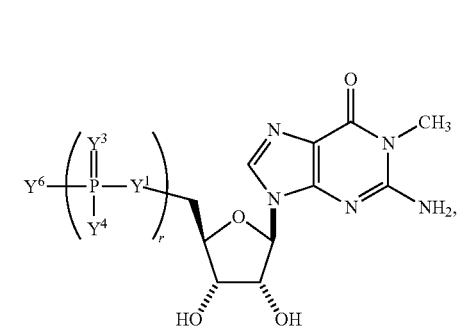
and -continued

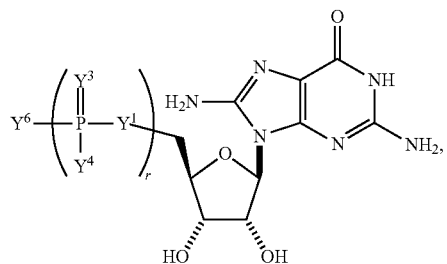
(BB-237)

or a pharmaceutically acceptable salt or stereoisomer thereof, wherein $Y^1$, $Y^3$, $Y^4$, $Y^6$, and r are as described herein (e.g., each r is, independently, an integer from 0 to 5, such as from 0 to 3, from 1 to 3, or from 1 to 5)).

In some embodiments, the chemical modification can include replacement of C group at C-5 of the ring (e.g., for a pyrimidine nucleoside, such as cytosine or uracil) with N (e.g., replacement of the >CH group at C-5 with >NR$^{N1}$ group, wherein R$^{N1}$ is H or optionally substituted alkyl). For example, the mmRNA molecule, which may be incorporated into a modified nucleic acid molecule or mmRNA, can be:

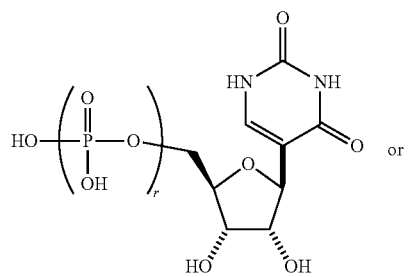
(BB-238)

or

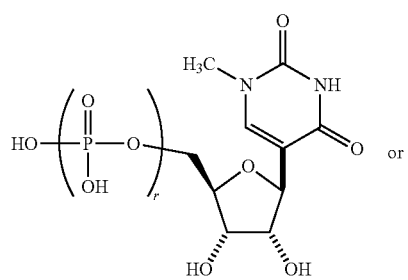
(BB-239)

or

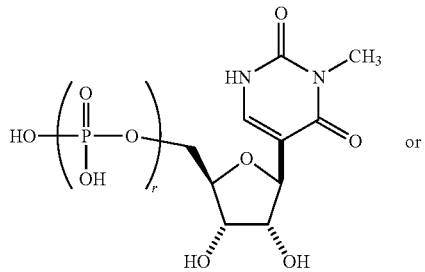
(BB-240)

or

-continued

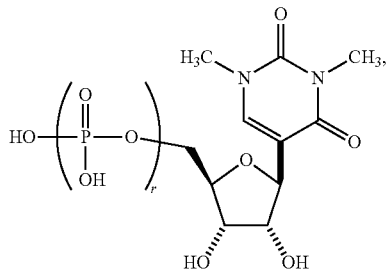
(BB-241)

or a pharmaceutically acceptable salt or stereoisomer thereof, wherein each r is, independently, an integer from 0 to 5 (e.g., from 0 to 3, from 1 to 3, or from 1 to 5).

In another embodiment, the chemical modification can include replacement of the hydrogen at C-5 of cytosine with halo (e.g., Br, Cl, F, or I) or optionally substituted alkyl (e.g., methyl). For example, the mmRNA molecule, which may be incorporated into a modified nucleic acid or mmRNA, can be:

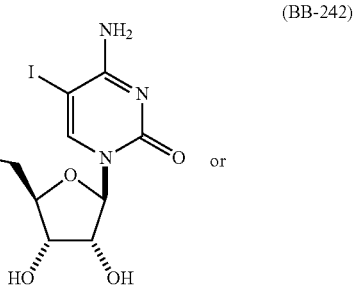
(BB-242)

or

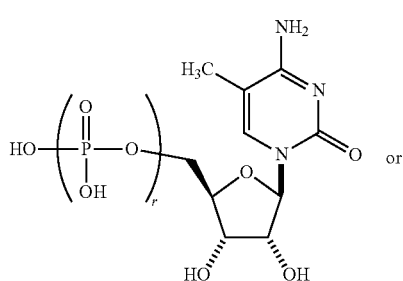
(BB-243)

or

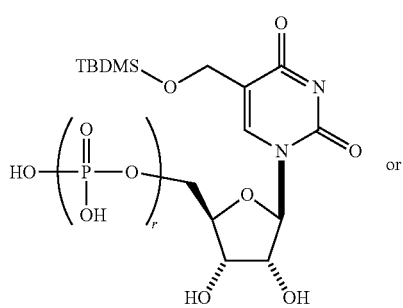
(BB-244)

or

-continued

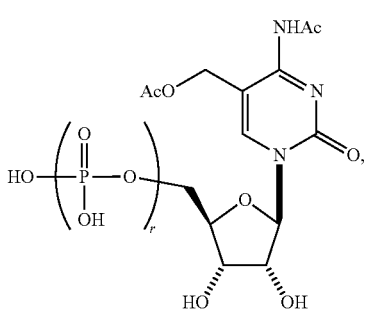

(BB-245)

or a pharmaceutically acceptable salt or stereoisomer thereof, wherein each r is, independently, an integer from 0 to 5 (e.g., from 0 to 3, from 1 to 3, or from 1 to 5).

In yet a further embodiment, the chemical modification can include a fused ring that is formed by the NH$_2$ at the C-4 position and the carbon atom at the C-5 position. For example, the building block molecule, which may be incorporated into a modified nucleic acid molecule or mmRNA, can be:

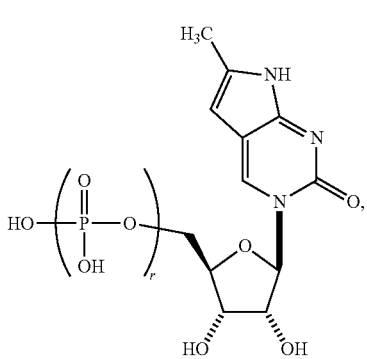

(BB-246)

or a pharmaceutically acceptable salt or stereoisomer thereof, wherein each r is, independently, an integer from 0 to 5 (e.g., from 0 to 3, from 1 to 3, or from 1 to 5).

Modifications on the Sugar

The modified nucleosides and nucleotides (e.g., building block molecules), which may be incorporated into a modified nucleic acid or mmRNA (e.g., RNA or mRNA, as described herein), can be modified on the sugar of the ribonucleic acid. For example, the 2' hydroxyl group (OH) can be modified or replaced with a number of different substituents. Exemplary substitutions at the 2'-position include, but are not limited to, H, halo, optionally substituted C1-6 alkyl; optionally substituted C1-6 alkoxy; optionally substituted C6-10 aryloxy; optionally substituted C3-8 cycloalkyl; optionally substituted C3-8 cycloalkoxy; optionally substituted C6-10 aryloxy; optionally substituted C6-10 aryl-C1-6 alkoxy, optionally substituted C1-12 (heterocyclyl)oxy; a sugar (e.g., ribose, pentose, or any described herein); a polyethyleneglycol (PEG), —O(CH2CH2O) nCH2CH2OR, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxyl is connected by a C1-6 alkylene or C1-6 heteroalkylene bridge to the 4'-carbon of the same ribose sugar, where exemplary bridges included methylene, propylene, ether, or amino bridges; aminoalkyl, as defined herein; aminoalkoxy, as defined herein; amino as defined herein; and amino acid, as defined herein.

Generally, RNA includes the sugar group ribose, which is a 5-membered ring having an oxygen. Exemplary, non-limiting modified nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone); multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a modified nucleic acid molecule or mmRNA can include nucleotides containing, e.g., arabinose, as the sugar.

Modifications on the Nucleobase

The present disclosure provides for modified nucleosides and nucleotides. As described herein "nucleoside" is defined as a compound containing a sugar molecule (e.g., a pentose or ribose) or a derivative thereof in combination with an organic base (e.g., a purine or pyrimidine) or a derivative thereof. As described herein, "nucleotide" is defined as a nucleoside including a phosphate group. The modified nucleotides (e.g., modified mRNA) may by synthesized by any useful method, as described herein (e.g., chemically, enzymatically, or recombinantly to include one or more modified or non-natural nucleosides).

The modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil.

The modified nucleosides and nucleotides can include a modified nucleobase. Examples of nucleobases found in RNA include, but are not limited to, adenine, guanine, cytosine, and uracil. Examples of nucleobase found in DNA include, but are not limited to, adenine, guanine, cytosine, and thymine. These nucleobases can be modified or wholly replaced to provide modified nucleic acids or mmRNA molecules having enhanced properties, e.g., resistance to nucleases through disruption of the binding of a major groove binding partner. Table 1 below identifies the chemical faces of each canonical nucleotide. Circles identify the atoms comprising the respective chemical regions.

TABLE 1

| Major Groove Face | Minor Groove Face |
|---|---|
| Pyrimidines | |

Cytidine:

Uridine:

| Purines | |

Adenosine:

Guanosine:

TABLE 1-continued
|  |
|---|
| Watson-Crick Base-pairing Face |
| Pyrimidines |
|---|
Cytidine:
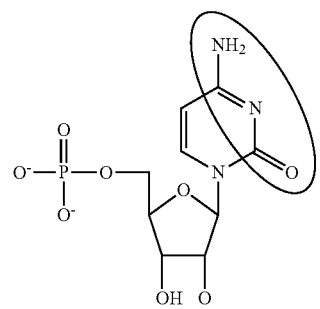 [SMILES: Nc1ccn(C2OC(COP(=O)([O-])[O-])C(O)C2O)c(=O)n1]
Uridine:
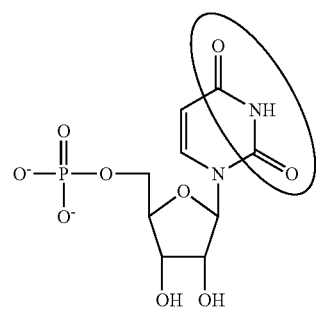 [SMILES: O=c1ccn(C2OC(COP(=O)([O-])[O-])C(O)C2O)c(=O)[nH]1]
| Purines |
|---|
Adenosine:
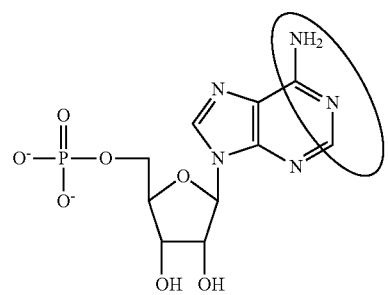 [SMILES: Nc1ncnc2c1ncn2C1OC(COP(=O)([O-])[O-])C(O)C1O]
Guanosine:
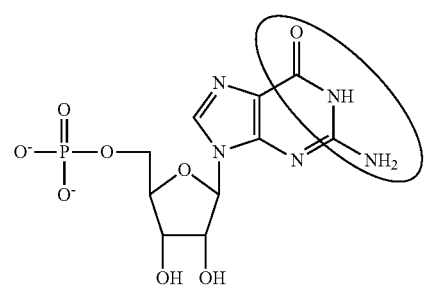 [SMILES: Nc1nc2c(ncn2C2OC(COP(=O)([O-])[O-])C(O)C2O)c(=O)[nH]1]

In some embodiments, B is a modified uracil. Exemplary modified uracils include those having Formula (b1)-(b5):

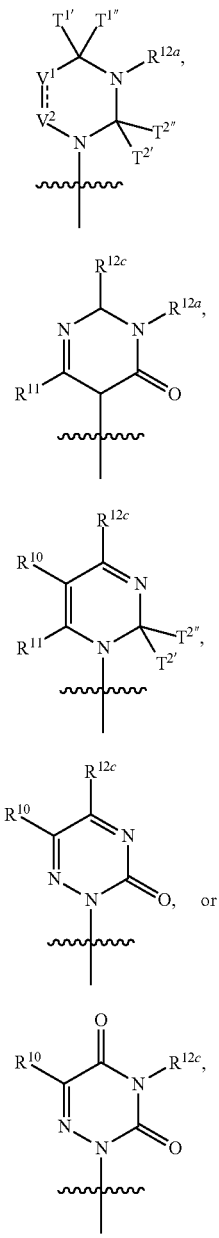

(b1)

(b2)

(b3)

(b4)

(b5)

or a pharmaceutically acceptable salt or stereoisomer thereof, wherein

⇌ is a single or double bond;

each of $T^{1'}$, $T^{1''}$, $T^{2'}$, and $T^{2''}$ is, independently, H, optionally substituted alkyl, optionally substituted alkoxy, or optionally substituted thioalkoxy, or the combination of $T^{1'}$ and $T^{1''}$ or the combination of $T^{2'}$ and $T^{2''}$ join together (e.g., as in $T^2$) to form O (oxo), S (thio), or Se (seleno);

each of $V^1$ and $V^2$ is, independently, O, S, N($R^{Vb}$)$_{nv}$, or C($R^{Vb}$)$_{nv}$, wherein nv is an integer from 0 to 2 and each $R^{Vb}$ is, independently, H, halo, optionally substituted amino acid, optionally substituted alkyl, optionally substituted haloalkyl, optionally substituted alkenyl, optionally substituted alkynyl, optionally substituted alkoxy, optionally substituted alkenyloxy, optionally substituted alkynyloxy, optionally substituted hydroxyalkyl, optionally substituted hydroxyalkenyl, optionally substituted hydroxyalkynyl, optionally substituted aminoalkyl (e.g., substituted with an N-protecting group, such as any described herein, e.g., trifluoroacetyl), optionally substituted aminoalkenyl, optionally substituted aminoalkynyl, optionally substituted acylaminoalkyl (e.g., substituted with an N-protecting group, such as any described herein, e.g., trifluoroacetyl), optionally substituted alkoxycarbonylalkyl, optionally substituted alkoxycarbonylalkenyl, optionally substituted alkoxycarbonylalkynyl, or optionally substituted alkoxycarbonylalkoxy (e.g., optionally substituted with any substituent described herein, such as those selected from (1)-(21) for alkyl);

$R^{10}$ is H, halo, optionally substituted amino acid, hydroxy, optionally substituted alkyl, optionally substituted alkenyl, optionally substituted alkynyl, optionally substituted aminoalkyl, optionally substituted hydroxyalkyl, optionally substituted hydroxyalkenyl, optionally substituted hydroxyalkynyl, optionally substituted aminoalkenyl, optionally substituted aminoalkynyl, optionally substituted alkoxy, optionally substituted alkoxycarbonylalkyl, optionally substituted alkoxycarbonylalkenyl, optionally substituted alkoxycarbonylalkynyl, optionally substituted alkoxycarbonylalkoxy, optionally substituted carboxyalkoxy, optionally substituted carboxyalkyl, or optionally substituted carbamoylalkyl;

$R^{11}$ is H or optionally substituted alkyl;

$R^{12a}$ is H, optionally substituted alkyl, optionally substituted hydroxyalkyl, optionally substituted hydroxyalkenyl, optionally substituted hydroxyalkynyl, optionally substituted aminoalkyl, optionally substituted aminoalkenyl, or optionally substituted aminoalkynyl, optionally substituted carboxyalkyl (e.g., optionally substituted with hydroxy), optionally substituted carboxyalkoxy, optionally substituted carboxyaminoalkyl, or optionally substituted carbamoylalkyl; and $R^{12c}$ is H, halo, optionally substituted alkyl, optionally substituted alkoxy, optionally substituted thioalkoxy, optionally substituted amino, optionally substituted hydroxyalkyl, optionally substituted hydroxyalkenyl, optionally substituted hydroxyalkynyl, optionally substituted aminoalkyl, optionally substituted aminoalkenyl, or optionally substituted aminoalkynyl.

Other exemplary modified uracils include those having Formula (b6)-(b9):

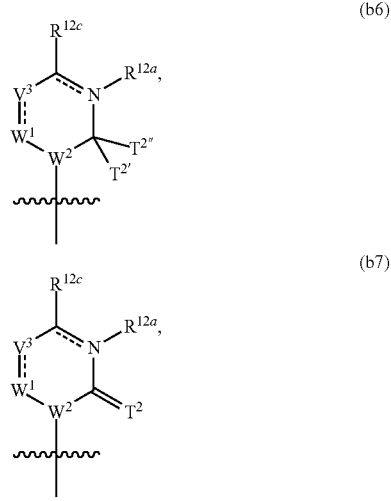

(b6)

(b7)

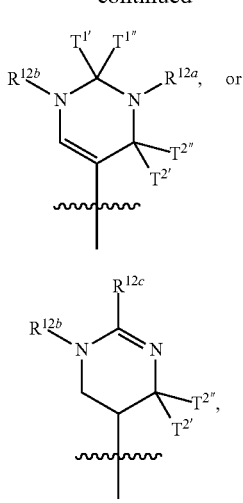

(b8)

(b9)

or a pharmaceutically acceptable salt or stereoisomer thereof, wherein

⁓ is a single or double bond;

each of T$^{1'}$, T$^{1''}$, T$^{2'}$, and T$^{2''}$ is, independently, H, optionally substituted alkyl, optionally substituted alkoxy, or optionally substituted thioalkoxy, or the combination of T$^{1'}$ and T$^{1''}$ join together (e.g., as in T$^1$) or the combination of T$^{2'}$ and T$^{2''}$ join together (e.g., as in T$^2$) to form O (oxo), S (thio), or Se (seleno), or each T$^1$ and T$^2$ is, independently, O (oxo), S (thio), or Se (seleno);

each of W$^1$ and W$^2$ is, independently, N(R$^{Wa}$)$_{nw}$ or C(R$^{Wa}$)$_{nw}$, wherein nw is an integer from 0 to 2 and each R$^{Wa}$ is, independently, H, optionally substituted alkyl, or optionally substituted alkoxy;

each V$^3$ is, independently, O, S, N(R$^{Va}$)$_{nv}$, or C(R$^{Va}$)$_{nv}$, wherein nv is an integer from 0 to 2 and each R$^{wa}$ is, independently, H, halo, optionally substituted amino acid, optionally substituted alkyl, optionally substituted hydroxyalkyl, optionally substituted hydroxyalkenyl, optionally substituted hydroxyalkynyl, optionally substituted alkenyl, optionally substituted alkynyl, optionally substituted heterocyclyl, optionally substituted alkheterocyclyl, optionally substituted alkoxy, optionally substituted alkenyloxy, or optionally substituted alkynyloxy, optionally substituted aminoalkyl (e.g., substituted with an N-protecting group, such as any described herein, e.g., trifluoroacetyl, or sulfoalkyl), optionally substituted aminoalkenyl, optionally substituted aminoalkynyl, optionally substituted acylaminoalkyl (e.g., substituted with an N-protecting group, such as any described herein, e.g., trifluoroacetyl), optionally substituted alkoxycarbonylalkyl, optionally substituted alkoxycarbonylalkenyl, optionally substituted alkoxycarbonylalkynyl, optionally substituted alkoxycarbonylacyl, optionally substituted alkoxycarbonylalkoxy, optionally substituted carboxyalkyl (e.g., optionally substituted with hydroxy and/or an O-protecting group), optionally substituted carboxyalkoxy, optionally substituted carboxyaminoalkyl, or optionally substituted carbamoylalkyl (e.g., optionally substituted with any substituent described herein, such as those selected from (1)-(21) for alkyl), and wherein R$^{Va}$ and R$^{12c}$ taken together with the carbon atoms to which they are attached can form optionally substituted cycloalkyl, optionally substituted aryl, or optionally substituted heterocyclyl (e.g., a 5- or 6-membered ring);

R$^{12a}$ is H, optionally substituted alkyl, optionally substituted hydroxyalkyl, optionally substituted hydroxyalkenyl, optionally substituted hydroxyalkynyl, optionally substituted aminoalkyl, optionally substituted aminoalkenyl, optionally substituted aminoalkynyl, optionally substituted carboxyalkyl (e.g., optionally substituted with hydroxy and/or an O-protecting group), optionally substituted carboxyalkoxy, optionally substituted carboxyaminoalkyl, optionally substituted carbamoylalkyl, or absent;

R$^{12b}$ is H, optionally substituted alkyl, optionally substituted alkenyl, optionally substituted alkynyl, optionally substituted hydroxyalkyl, optionally substituted hydroxyalkenyl, optionally substituted hydroxyalkynyl, optionally substituted aminoalkyl, optionally substituted aminoalkenyl, optionally substituted aminoalkynyl, optionally substituted alkaryl, optionally substituted heterocyclyl, optionally substituted alkheterocyclyl, optionally substituted amino acid, optionally substituted alkoxycarbonylacyl, optionally substituted alkoxycarbonylalkoxy, optionally substituted alkoxycarbonylalkyl, optionally substituted alkoxycarbonylalkenyl, optionally substituted alkoxycarbonylalkynyl, optionally substituted alkoxycarbonylalkoxy, optionally substituted carboxyalkyl (e.g., optionally substituted with hydroxy and/or an O-protecting group), optionally substituted carboxyalkoxy, optionally substituted carboxyaminoalkyl, or optionally substituted carbamoylalkyl, wherein the combination of R$^{12b}$ and T$^{1'}$ or the combination of R$^{12b}$ and R$^{12c}$ can join together to form optionally substituted heterocyclyl; and R$^{12c}$ is H, halo, optionally substituted alkyl, optionally substituted alkoxy, optionally substituted thioalkoxy, optionally substituted amino, optionally substituted aminoalkyl, optionally substituted aminoalkenyl, or optionally substituted aminoalkynyl.

Further exemplary modified uracils include those having Formula (b28)-(b31):

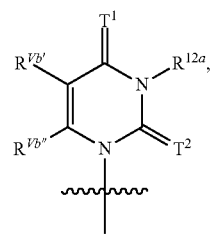

(b28)

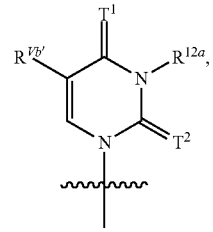

(b29)

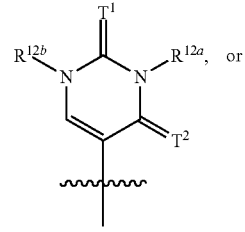

(b30)

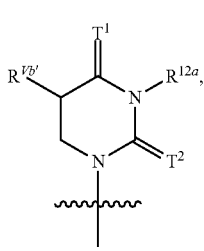

(b31)

or a pharmaceutically acceptable salt or stereoisomer thereof, wherein each of $T^1$ and $T^2$ is, independently, O (oxo), S (thio), or Se (seleno);

each $R^{Vb'}$ and $R^{Vb''}$ is, independently, H, halo, optionally substituted amino acid, optionally substituted alkyl, optionally substituted haloalkyl, optionally substituted hydroxyalkyl, optionally substituted hydroxyalkenyl, optionally substituted hydroxyalkynyl, optionally substituted alkenyl, optionally substituted alkynyl, optionally substituted alkoxy, optionally substituted alkenyloxy, optionally substituted alkynyloxy, optionally substituted aminoalkyl (e.g., substituted with an N-protecting group, such as any described herein, e.g., trifluoroacetyl, or sulfoalkyl), optionally substituted aminoalkenyl, optionally substituted aminoalkynyl, optionally substituted acylaminoalkyl (e.g., substituted with an N-protecting group, such as any described herein, e.g., trifluoroacetyl), optionally substituted alkoxycarbonylalkyl, optionally substituted alkoxycarbonylalkenyl, optionally substituted alkoxycarbonylalkynyl, optionally substituted alkoxycarbonylacyl, optionally substituted alkoxycarbonylalkoxy, optionally substituted carboxyalkyl (e.g., optionally substituted with hydroxy and/or an O-protecting group), optionally substituted carboxyalkoxy, optionally substituted carboxyaminoalkyl, or optionally substituted carbamoylalkyl (e.g., optionally substituted with any substituent described herein, such as those selected from (1)-(21) for alkyl) (e.g., $R^{Vb'}$ is optionally substituted alkyl, optionally substituted alkenyl, or optionally substituted aminoalkyl, e.g., substituted with an N-protecting group, such as any described herein, e.g., trifluoroacetyl, or sulfoalkyl);

$R^{12a}$ is H, optionally substituted alkyl, optionally substituted carboxyaminoalkyl, optionally substituted aminoalkyl (e.g., e.g., substituted with an N-protecting group, such as any described herein, e.g., trifluoroacetyl, or sulfoalkyl), optionally substituted aminoalkenyl, or optionally substituted aminoalkynyl; and $R^{12b}$ is H, optionally substituted alkyl, optionally substituted alkenyl, optionally substituted alkynyl, optionally substituted hydroxyalkyl, optionally substituted hydroxyalkenyl, optionally substituted hydroxyalkynyl, optionally substituted aminoalkyl, optionally substituted aminoalkenyl, optionally substituted aminoalkynyl (e.g., e.g., substituted with an N-protecting group, such as any described herein, e.g., trifluoroacetyl, or sulfoalkyl), optionally substituted alkoxycarbonylacyl, optionally substituted alkoxycarbonylalkoxy, optionally substituted alkoxycarbonylalkyl, optionally substituted alkoxycarbonylalkenyl, optionally substituted alkoxycarbonylalkynyl, optionally substituted alkoxycarbonylalkoxy, optionally substituted carboxyalkyl, optionally substituted carboxyalkyl, or optionally substituted carbamoylalkyl.

In particular embodiments, $T^1$ is O (oxo), and $T^2$ is S (thio) or Se (seleno). In other embodiments, $T^1$ is S (thio), and $T^2$ is O (oxo) or Se (seleno). In some embodiments, $R^{Vb'}$ is H, optionally substituted alkyl, or optionally substituted alkoxy.

In other embodiments, each $R^{12a}$ and $R^{12b}$ is, independently, H, optionally substituted alkyl, optionally substituted alkenyl, optionally substituted alkynyl, or optionally substituted hydroxyalkyl. In particular embodiments, $R^{12a}$ is H. In other embodiments, both $R^{12a}$ and $R^{12b}$ are H.

In some embodiments, each $R^{Vb'}$ of $R^{12b}$ is, independently, optionally substituted aminoalkyl (e.g., substituted with an N-protecting group, such as any described herein, e.g., trifluoroacetyl, or sulfoalkyl), optionally substituted aminoalkenyl, optionally substituted aminoalkynyl, or optionally substituted acylaminoalkyl (e.g., substituted with an N-protecting group, such as any described herein, e.g., trifluoroacetyl). In some embodiments, the amino and/or alkyl of the optionally substituted aminoalkyl is substituted with one or more of optionally substituted alkyl, optionally substituted alkenyl, optionally substituted sulfoalkyl, optionally substituted carboxy (e.g., substituted with an O-protecting group), optionally substituted hydroxy (e.g., substituted with an O-protecting group), optionally substituted carboxyalkyl (e.g., substituted with an O-protecting group), optionally substituted alkoxycarbonylalkyl (e.g., substituted with an O-protecting group), or N-protecting group. In some embodiments, optionally substituted aminoalkyl is substituted with an optionally substituted sulfoalkyl or optionally substituted alkenyl. In particular embodiments, $R^{12a}$ and $R^{Vb''}$ are both H. In particular embodiments, $T^1$ is O (oxo), and $T^2$ is S (thio) or Se (seleno).

In some embodiments, $R^{Vb'}$ is optionally substituted alkoxycarbonylalkyl or optionally substituted carbamoylalkyl.

In particular embodiments, the optional substituent for $R^{12a}$, $R^{12b}$, $R^{12c}$, or $R^{Va}$ is a polyethylene glycol group (e.g., —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C1-20 alkyl); or an aminopolyethylene glycol group (e.g., —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted C1-6 alkyl).

In some embodiments, B is a modified cytosine. Exemplary modified cytosines include compounds (b10)-(b14):

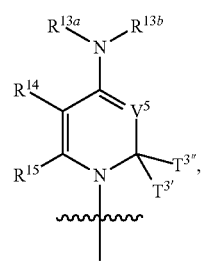

(b10)

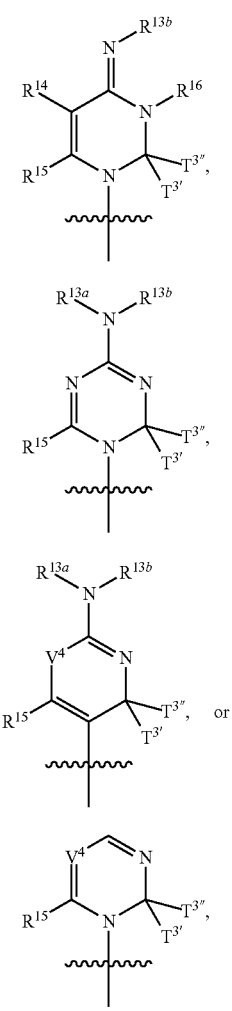

(b11)

(b12)

(b13)

(b14)

or a pharmaceutically acceptable salt or stereoisomer thereof, wherein each of $T^{3'}$ and $T^{3'''}$ is, independently, H, optionally substituted alkyl, optionally substituted alkoxy, or optionally substituted thioalkoxy, or the combination of $T^{3'}$ and $T^{3'''}$ join together (e.g., as in $T^3$) to form O (oxo), S (thio), or Se (seleno);

each $V^4$ is, independently, O, S, $N(R^{Vc})_{nv}$, or $C(R^{Vc})_{nv}$, wherein nv is an integer from 0 to 2 and each $R^{Vc}$ is, independently, H, halo, optionally substituted amino acid, optionally substituted alkyl, optionally substituted alkenyl, optionally substituted alkynyl, optionally substituted alkoxy, optionally substituted alkenyloxy, optionally substituted heterocyclyl, optionally substituted alkheterocyclyl, or optionally substituted alkynyloxy (e.g., optionally substituted with any substituent described herein, such as those selected from (1)-(21) for alkyl), wherein the combination of $R^{13b}$ and $R^{Vc}$ can be taken together to form optionally substituted heterocyclyl;

each $V^5$ is, independently, $N(R^{Vd})_{nv}$, or $C(R^{Vd})_{nv}$, wherein nv is an integer from 0 to 2 and each $R^{Vd}$ is, independently, H, halo, optionally substituted amino acid, optionally substituted alkyl, optionally substituted alkenyl, optionally substituted alkynyl, optionally substituted alkoxy, optionally substituted alkenyloxy, optionally substituted heterocyclyl, optionally substituted alkheterocyclyl, or optionally substituted alkynyloxy (e.g., optionally substituted with any substituent described herein, such as those selected from (1)-(21) for alkyl) (e.g., $V^5$ is —CH or N);

each of $R^{13a}$ and $R^{13b}$ is, independently, H, optionally substituted acyl, optionally substituted acyloxyalkyl, optionally substituted alkyl, or optionally substituted alkoxy, wherein the combination of $R^{13b}$ and $R^{14}$ can be taken together to form optionally substituted heterocyclyl;

each $R^{14}$ is, independently, H, halo, hydroxy, thiol, optionally substituted acyl, optionally substituted amino acid, optionally substituted alkyl, optionally substituted haloalkyl, optionally substituted alkenyl, optionally substituted alkynyl, optionally substituted hydroxyalkyl (e.g., substituted with an O-protecting group), optionally substituted hydroxyalkenyl, optionally substituted hydroxyalkynyl, optionally substituted alkoxy, optionally substituted alkenyloxy, optionally substituted alkynyloxy, optionally substituted aminoalkoxy, optionally substituted alkoxyalkoxy, optionally substituted acyloxyalkyl, optionally substituted amino (e.g., —NHR, wherein R is H, alkyl, aryl, or phosphoryl), azido, optionally substituted aryl, optionally substituted heterocyclyl, optionally substituted alkheterocyclyl, optionally substituted aminoalkyl, optionally substituted aminoalkenyl, or optionally substituted aminoalkyl; and each of $R^{15}$ and $R^{16}$ is, independently, H, optionally substituted alkyl, optionally substituted alkenyl, or optionally substituted alkynyl.

Further exemplary modified cytosines include those having Formula (b32)-(b35):

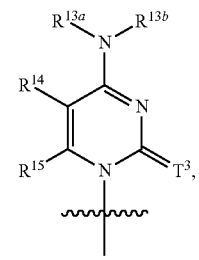

(b32)

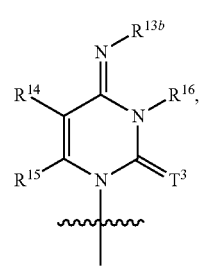

(b33)

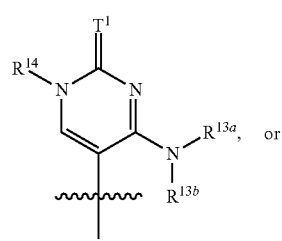

(b34)

(b35)

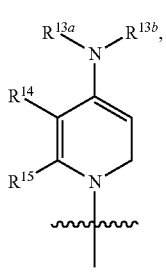

or a pharmaceutically acceptable salt or stereoisomer thereof, wherein each of $T^1$ and $T^3$ is, independently, O (oxo), S (thio), or Se (seleno);

each of $R^{13a}$ and $R^{13b}$ is, independently, H, optionally substituted acyl, optionally substituted acyloxyalkyl, optionally substituted alkyl, or optionally substituted alkoxy, wherein the combination of $R^{13b}$ and $R^{14}$ can be taken together to form optionally substituted heterocyclyl;

each $R^{14}$ is, independently, H, halo, hydroxy, thiol, optionally substituted acyl, optionally substituted amino acid, optionally substituted alkyl, optionally substituted haloalkyl, optionally substituted alkenyl, optionally substituted alkynyl, optionally substituted hydroxyalkyl (e.g., substituted with an O-protecting group), optionally substituted hydroxyalkenyl, optionally substituted hydroxyalkynyl, optionally substituted alkoxy, optionally substituted alkenyloxy, optionally substituted alkynyloxy, optionally substituted aminoalkoxy, optionally substituted alkoxyalkoxy, optionally substituted acyloxyalkyl, optionally substituted amino (e.g., —NHR, wherein R is H, alkyl, aryl, or phosphoryl), azido, optionally substituted aryl, optionally substituted heterocyclyl, optionally substituted alkheterocyclyl, optionally substituted aminoalkyl (e.g., hydroxyalkyl, alkyl, alkenyl, or alkynyl), optionally substituted aminoalkenyl, or optionally substituted aminoalkynyl; and each of $R^{15}$ and $R^{16}$ is, independently, H, optionally substituted alkyl, optionally substituted alkenyl, or optionally substituted alkynyl (e.g., $R^{15}$ is H, and $R^{16}$ is H or optionally substituted alkyl).

In some embodiments, $R^{15}$ is H, and $R^{16}$ is H or optionally substituted alkyl. In particular embodiments, $R^{14}$ is H, acyl, or hydroxyalkyl. In some embodiments, $R^{14}$ is halo. In some embodiments, both $R^{14}$ and $R^{15}$ are H. In some embodiments, both $R^{15}$ and $R^{16}$ are H. In some embodiments, each of $R^{14}$ and $R^{15}$ and $R^{16}$ is H. In further embodiments, each of $R^{13a}$ and $R^{13b}$ is independently, H or optionally substituted alkyl.

Further non-limiting examples of modified cytosines include compounds of Formula (b36):

(b36)

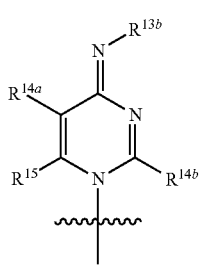

or a pharmaceutically acceptable salt or stereoisomer thereof, wherein each R13b is, independently, H, optionally substituted acyl, optionally substituted acyloxyalkyl, optionally substituted alkyl, or optionally substituted alkoxy, wherein the combination of R13b and R14b can be taken together to form optionally substituted heterocyclyl;

each R14a and R14b is, independently, H, halo, hydroxy, thiol, optionally substituted acyl, optionally substituted amino acid, optionally substituted alkyl, optionally substituted haloalkyl, optionally substituted alkenyl, optionally substituted alkynyl, optionally substituted hydroxyalkyl (e.g., substituted with an O-protecting group), optionally substituted hydroxyalkenyl, optionally substituted alkoxy, optionally substituted alkenyloxy, optionally substituted alkynyloxy, optionally substituted aminoalkoxy, optionally substituted alkoxyalkoxy, optionally substituted acyloxyalkyl, optionally substituted amino (e.g., —NHR, wherein R is H, alkyl, aryl, phosphoryl, optionally substituted aminoalkyl, or optionally substituted carboxyaminoalkyl), azido, optionally substituted aryl, optionally substituted heterocyclyl, optionally substituted alkheterocyclyl, optionally substituted aminoalkyl, optionally substituted aminoalkenyl, or optionally substituted aminoalkynyl; and each of R15 is, independently, H, optionally substituted alkyl, optionally substituted alkenyl, or optionally substituted alkynyl.

In particular embodiments, R14b is an optionally substituted amino acid (e.g., optionally substituted lysine). In some embodiments, R14a is H.

In some embodiments, B is a modified guanine. Exemplary modified guanines include compounds of Formula (b15)-(b17):

(b15)

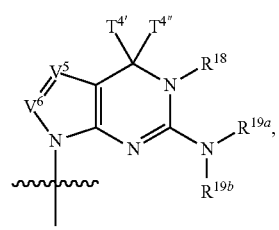

(b16)

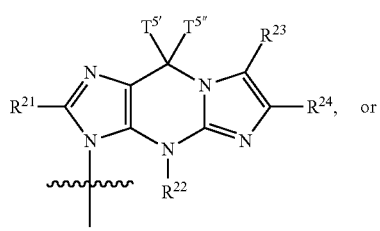

or (b17)

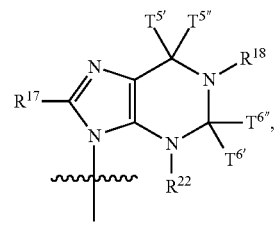

or a pharmaceutically acceptable salt or stereoisomer thereof, wherein each of T4', T4", T5', T5", T6', and T6" is, independently, H, optionally substituted alkyl, or optionally substituted alkoxy, and wherein the combination of T4' and T4" (e.g., as in T4) or the combination of T5' and T5" (e.g., as in T5) or the combination of T6' and T6" join together (e.g., as in T6) form O (oxo), S (thio), or Se (seleno);

each of V5 and V6 is, independently, O, S, N(RVd)nv, or C(RVd)nv, wherein nv is an integer from 0 to 2 and each RVd is, independently, H, halo, thiol, optionally substituted amino acid, cyano, amidine, optionally substituted aminoalkyl, optionally substituted aminoalkenyl, optionally substituted aminoalkynyl, optionally substituted alkyl, optionally substituted alkenyl, optionally substituted alkynyl, optionally substituted alkoxy, optionally substituted alkenyloxy, optionally substituted alkynyloxy (e.g., optionally substituted with any substituent described herein, such as those selected from (1)-(21) for alkyl), optionally substituted thioalkoxy, or optionally substituted amino; and each of R17, R18, R19a, R19b, R21, R22, R23, and R24 is, independently, H, halo, thiol, optionally substituted alkyl, optionally substituted alkenyl, optionally substituted alkynyl, optionally substituted thioalkoxy, optionally substituted amino, or optionally substituted amino acid.

Exemplary modified guanosines include compounds of Formula (b37)-(b40):

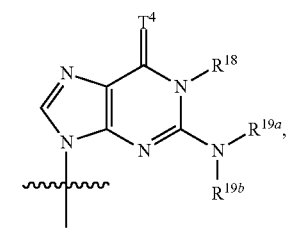

(b37)

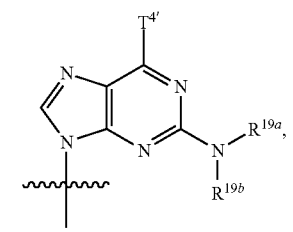

(b38)

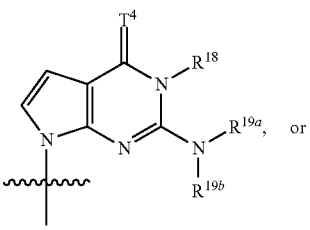

(b39)

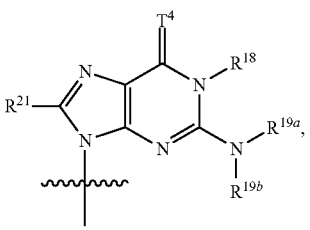

(b40)

or a pharmaceutically acceptable salt or stereoisomer thereof, wherein each of T4' is, independently, H, optionally substituted alkyl, or optionally substituted alkoxy, and each T4 is, independently, O (oxo), S (thio), or Se (seleno);

each of $R^{18}$, $R^{19a}$, $R^{19b}$, and $R^{21}$ is, independently, H, halo, thiol, optionally substituted alkyl, optionally substituted alkenyl, optionally substituted alkynyl, optionally substituted thioalkoxy, optionally substituted amino, or optionally substituted amino acid.

In some embodiments, $R^{18}$ is H or optionally substituted alkyl. In further embodiments, $T^4$ is oxo. In some embodiments, each of $R^{19a}$ and $R^{19b}$ is, independently, H or optionally substituted alkyl.

In some embodiments, B is a modified adenine. Exemplary modified adenines include compounds of Formula (b18)-(b20):

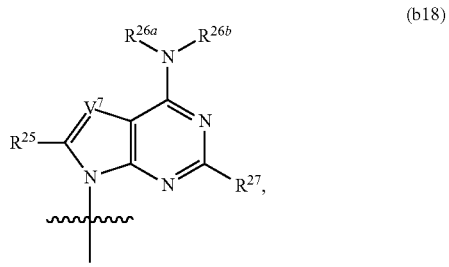

(b18)

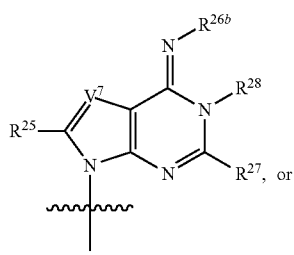

(b19)

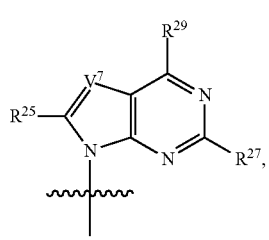

(b20)

or a pharmaceutically acceptable salt or stereoisomer thereof, wherein each V7 is, independently, O, S, N(RVe)nv, or C(RVe)nv, wherein nv is an integer from 0 to 2 and each RVe is, independently, H, halo, optionally substituted amino acid, optionally substituted alkyl, optionally substituted alkenyl, optionally substituted alkynyl, optionally substituted alkoxy, optionally substituted alkenyloxy, or optionally substituted alkynyloxy (e.g., optionally substituted with any substituent described herein, such as those selected from (1)-(21) for alkyl);

each R25 is, independently, H, halo, thiol, optionally substituted alkyl, optionally substituted alkenyl, optionally substituted alkynyl, optionally substituted thioalkoxy, or optionally substituted amino;

each of R26a and R26b is, independently, H, optionally substituted acyl, optionally substituted amino acid, optionally substituted carbamoylalkyl, optionally substituted alkyl, optionally substituted alkenyl, optionally substituted alkynyl, optionally substituted hydroxyalkyl, optionally substituted hydroxyalkenyl, optionally substituted hydroxyalkynyl, optionally substituted alkoxy, or polyethylene glycol group (e.g., —(CH2)s2(OCH2CH2)s1(CH2)s3OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C1-20 alkyl); or an amino-polyethylene glycol group (e.g., —NRN1(CH2)s2(CH2CH2O)s1(CH2)s3NRN1, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each RN1 is, independently, hydrogen or optionally substituted C1-6 alkyl);

each R27 is, independently, H, optionally substituted alkyl, optionally substituted alkenyl, optionally substituted alkynyl, optionally substituted alkoxy, optionally substituted thioalkoxy or optionally substituted amino;

each R28 is, independently, H, optionally substituted alkyl, optionally substituted alkenyl, or optionally substituted alkynyl; and each R29 is, independently, H, optionally substituted acyl, optionally substituted amino acid, optionally substituted carbamoylalkyl, optionally substituted alkyl, optionally substituted alkenyl, optionally substituted alkynyl, optionally substituted hydroxyalkyl, optionally substituted hydroxyalkenyl, optionally substituted alkoxy, or optionally substituted amino.

Exemplary modified adenines include compounds of Formula (b41)-(b43):

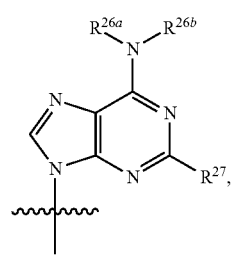
(b41)

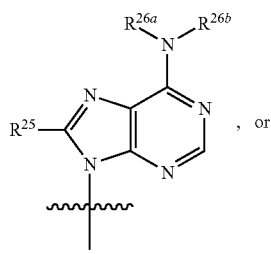
(b42)

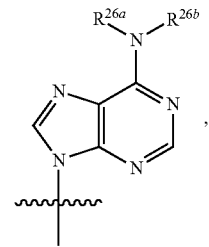
(b43)

or a pharmaceutically acceptable salt or stereoisomer thereof, wherein each $R^{25}$ is, independently, H, halo, thiol, optionally substituted alkyl, optionally substituted alkenyl, optionally substituted alkynyl, optionally substituted thioalkoxy, or optionally substituted amino;

each of $R^{26a}$ and $R^{26b}$ is, independently, H, optionally substituted acyl, optionally substituted amino acid, optionally substituted carbamoylalkyl, optionally substituted alkyl, optionally substituted alkenyl, optionally substituted alkynyl, optionally substituted hydroxyalkyl, optionally substituted hydroxyalkenyl, optionally substituted hydroxyalkynyl, optionally substituted alkoxy, or polyethylene glycol group (e.g., —(CH2)s2(OCH2CH2)s1(CH2)s3OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C120 alkyl); or an amino-polyethylene glycol group (e.g., —$NR^{N1}$(CH2)s2(CH2CH2O)s1(CH2)s3$NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl); and each $R^{27}$ is, independently, H, optionally substituted alkyl, optionally substituted alkenyl, optionally substituted alkynyl, optionally substituted alkoxy, optionally substituted thioalkoxy, or optionally substituted amino.

In some embodiments, $R^{26a}$ is H, and $R^{26b}$ is optionally substituted alkyl. In some embodiments, each of $R^{26a}$ and $R^{26b}$ is, independently, optionally substituted alkyl. In particular embodiments, $R^{27}$ is optionally substituted alkyl, optionally substituted alkoxy, or optionally substituted thioalkoxy. In other embodiments, $R^{25}$ is optionally substituted alkyl, optionally substituted alkoxy, or optionally substituted thioalkoxy.

In particular embodiments, the optional substituent for $R^{26a}$, $R^{26b}$, or $R^{29}$ is a polyethylene glycol group (e.g., —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C1-20 alkyl); or an amino-polyethylene glycol group (e.g., —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted C1-6 alkyl).

In some embodiments, B may have Formula (b21):

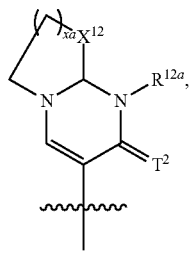
(b21)

wherein $X^{12}$ is, independently, O, S, optionally substituted alkylene (e.g., methylene), or optionally substituted heteroalkylene, xa is an integer from 0 to 3, and $R^{12a}$ and $T^2$ are as described herein.

In some embodiments, B may have Formula (b22):

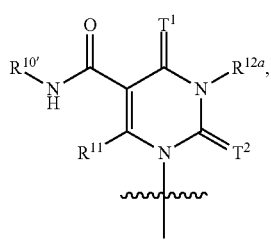
(b22)

wherein $R^{10'}$ is, independently, optionally substituted alkyl, optionally substituted alkenyl, optionally substituted alkynyl, optionally substituted aryl, optionally substituted heterocyclyl, optionally substituted aminoalkyl, optionally substituted aminoalkenyl, optionally substituted aminoalkynyl, optionally substituted alkoxy, optionally substituted alkoxycarbonylalkyl, optionally substituted alkoxycarbonylalkenyl, optionally substituted alkoxycarbonylalkynyl, optionally substituted alkoxycarbonylalkoxy, optionally substituted carboxyalkoxy, optionally substituted carboxyalkyl, or optionally substituted carbamoylalkyl, and $R^{11}$, $R^{12a}$, $T^1$, and $T^2$ are as described herein.

In some embodiments, B may have Formula (b23):

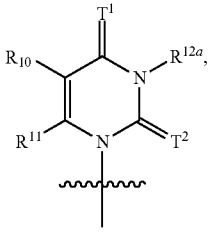
(b23)

wherein $R^{10}$ is optionally substituted heterocyclyl (e.g., optionally substituted furyl, optionally substituted thienyl, or optionally substituted pyrrolyl), optionally substituted aryl (e.g., optionally substituted phenyl or optionally substituted naphthyl), or any substituent described herein (e.g., for)$R^{10}$; and wherein $R^{11}$ (e.g., H or any substituent described herein), $R^{12a}$ (e.g., H or any substituent described herein), $T^1$ (e.g., oxo or any substituent described herein), and $T^2$ (e.g., oxo or any substituent described herein) are as described herein.

In some embodiments, B may have Formula (b24):

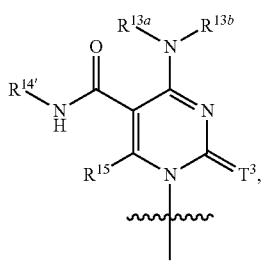
(b24)

wherein $R^{14'}$ is, independently, optionally substituted alkyl, optionally substituted alkenyl, optionally substituted alkynyl, optionally substituted aryl, optionally substituted heterocyclyl, optionally substituted alkaryl, optionally substituted alkheterocyclyl, optionally substituted aminoalkyl, optionally substituted aminoalkenyl, optionally substituted aminoalkynyl, optionally substituted alkoxy, optionally substituted alkoxycarbonylalkyl, optionally substituted alkoxycarbonylalkenyl, optionally substituted alkoxycarbonylalkynyl, optionally substituted alkoxycarbonylalkoxy, optionally substituted carboxyalkoxy, optionally substituted carboxyalkyl, or optionally substituted carbamoylalkyl, and $R^{13a}$, $R^{13b}$, $R^{15}$, and $T^3$ are as described herein.

In some embodiments, B may have Formula (b25):

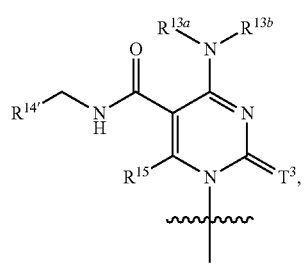
(b25)

wherein $R^{14'}$ is optionally substituted heterocyclyl (e.g., optionally substituted furyl, optionally substituted thienyl, or optionally substituted pyrrolyl), optionally substituted aryl (e.g., optionally substituted phenyl or optionally substituted naphthyl), or any substituent described herein (e.g., for $R^{14}$ or $R^{14'}$); and wherein $R^{13a}$ (e.g., H or any substituent described herein), $R^{13b}$ (e.g., H or any substituent described herein), $R^{15}$ (e.g., H or any substituent described herein), and $T^3$ (e.g., oxo or any substituent described herein) are as described herein.

In some embodiments, B is a nucleobase selected from the group consisting of cytosine, guanine, adenine, and uracil. In some embodiments, B may be:

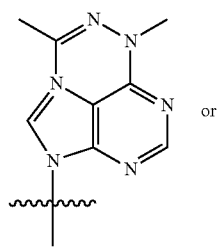
(b26)

or

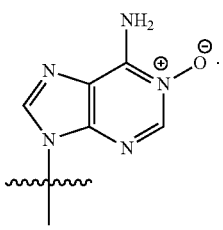
(b27)

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine (ho$^5$U), 5-aminoallyl-uridine, 5-halo-uridine (e.g., 5-iodo-uridine or 5-bromo-uridine), 3-methyl-uridine (m$^3$U), 5-methoxy-uridine (mo$^5$U), uridine 5-oxyacetic acid (cmo$^5$U), uridine 5-oxyacetic acid methyl ester (mcmo$^5$U), 5-carboxymethyl-uridine (cm$^5$U), 1-carboxymethyl-pseudouridine, 5-carboxyhydroxymethyl-uridine (chm$^5$U), 5-carboxyhydroxymethyl-uridine methyl ester (mchm$^5$U), 5-methoxycarbonylmethyl-uridine (mcm$^5$U), 5-methoxycarbonylmethyl-2-thio-uridine (mcm$^5$s$^2$U), 5-aminomethyl-2-thio-uridine (nm$^5$s$^2$U), 5-methylaminomethyl-uridine (mnm$^5$U), 5-methylaminomethyl-2-thio-uridine (mnm$^5$s$^2$U), 5-methylaminomethyl-2-seleno-uridine (mnm$^5$se$^2$U), 5-carbamoylmethyl-uridine (ncm$^5$U), 5-carboxymethylaminomethyl-uridine (cmnm$^5$U), 5-carboxymethylaminomethyl-2-thio-uridine (cmnm$^5$s$^2$U), 5-propynyl-uridine, 1-propynyl-pseudouridine, 5-taurinomethyl-uridine (τm5U), 1-taurinomethyl-pseudouridine, 5-taurinomethyl-2-thio-uridine(τrm5s2U), 1-taurinomethyl-4-thio-pseudouridine, 5-methyl-uridine (m5U, i.e., having the nucleobase deoxythymine), 1-methyl-pseudouridine (m1ψ), 5-methyl-2-thio-uridine (m5s2U), 1-methyl-4-thio-pseudouridine (m1s4ψ), 4-thio-1-methyl-pseudouridine, 3-methyl-pseudouridine (m3ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine (acp3U), 1-methyl-3-(3-amino-3-carboxypropyl)pseudouridine (acp3 ψ), 5-(isopentenylaminomethyl)uridine (inm5U), 5-(isopentenylaminomethyl)-2-thio-uridine (inm5s2U), α-thio-uridine, 2'-O-methyl-uridine (Um), 5,2'-O-dimethyl-uridine (m5Um), 2'-O-methyl-pseudouridine (ψm), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethylaminomethyl-2'-O-methyl-uridine (cmnm5Um), 3,2'-O-dimethyl-uridine (m3Um), 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine (m3C), N4-acetyl-cytidine (ac4C), 5-formyl-cytidine (f5C), N4-methyl-cytidine (m4C), 5-methyl-cytidine (m5C), 5-halo-cytidine (e.g., 5-iodo-cytidine), 5-hydroxymethyl-cytidine (hm5C), 1-methyl-pseudoisocytidine, pyrrolo-cytidine, pyrrolo-pseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k2C), α-thio-cytidine, 2'-O-methyl-cytidine (Cm), 5,2'-O-dimethyl-cytidine (m5Cm), N4-acetyl-2'-O-methyl-cytidine (ac4Cm), N4,2'-O-dimethyl-cytidine (m4Cm), 5-formyl-2'-O-methyl-cytidine (f5Cm), N4,N4,2'-O-trimethyl-cytidine (m42Cm), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m1A), 2-methyl-adenine (m2A), N6-methyl-adenosine (m6A), 2-methylthio-N6-methyl-adenosine (ms2m6A), N6-isopentenyl-adenosine (i6A), 2-methylthio-N6-isopentenyl-adenosine (ms2i6A), N6-(cis-hydroxyisopentenyl)adenosine (io6A), 2-methylthio-N6-(cis-hydroxyisopentenyl) adenosine (ms2io6A), N6-glycinylcarbamoyladenosine (g6A), N6-threonylcarbamoyl-adenosine (t6A), N6-methyl-N6-threonylcarbamoyl-adenosine (m6t6A), 2-methylthio-N6-threonylcarbamoyl-adenosine (ms2g6A), N6,N6-dimethyl-adenosine (m62A), N6-hydroxynorvalylcarbamoyl-adenosine (hn6A), 2-methylthio-N6-hydroxynorvalylcarbamoyl-adenosine (ms2hn6A), N6-acetyl-adenosine (ac6A), 7-methyl-adenine, 2-methylthio-adenine, 2-methoxy-adenine, α-thio-adenosine, 2'-O-methyl-adenosine (Am), N6,2'-O-dimethyl-adenosine (m6Am), N6,N6,2'-O-trimethyl-adenosine (m62Am), 1,2'-O-dimethyl-adenosine (m1Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine Exemplary nucleobases and nucleosides having a modified guanine include inosine (I), 1-methyl-inosine (mil), wyosine (imG), methylwyosine (mimG), 4-demethyl-wyosine (imG-14), isowyosine (imG2), wybutosine (yW), peroxywybutosine (o2yW), hydroxywybutosine (OHyW), undermodified hydroxywybutosine (OHyW*), 7-deaza-guanosine, queuosine (Q), epoxyqueuosine (oQ), galactosyl-queuosine (galQ), mannosyl-queuosine (manQ), 7-cyano-7-deaza-guanosine (preQ0), 7-aminomethyl-7-deaza-guanosine (preQ1), archaeosine (G+), 7-deaza-8-aza-guanosine, 6-thio-guanosine, 6-thio-7-deaza-guanosine, 6-thio-7-deaza-8-aza-guanosine, 7-methyl-guanosine (m7G), 6-thio-7-methyl-guanosine, 7-methyl-inosine, 6-methoxy-guanosine, 1-methyl-guanosine (m1G), N2-methyl-guanosine (m2G), N2,N2-dimethyl-guanosine (m22G), N2,7-dimethyl-guanosine (m2,7G), N2,N2,7-dimethyl-guanosine (m2,2,7G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m2Gm), N2,N2-dimethyl-2'-O-methyl-guanosine (m22Gm), 1-methyl-2'-O-methyl-guanosine (m1Gm), N2,7-dimethyl-2'-O-methyl-guanosine (m2,7Gm), 2'-O-methyl-inosine (Im), 1,2'-O-dimethyl-inosine (m1Im), 2'-O-ribosylguanosine (phosphate) (Gr(p)), 1-thio-guanosine, 06-methyl-guanosine, 2'-F-ara-guanosine, and 2'-F-guanosine.

The nucleobase of the nucleotide can be independently selected from a purine, a pyrimidine, a purine or pyrimidine analog. For example, the nucleobase can each be independently selected from adenine, cytosine, guanine, uracil, or hypoxanthine. In another embodiment, the nucleobase can also include, for example, naturally-occurring and synthetic derivatives of a base, including pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d] pyrimidines, pyrazin-2-ones, 1,2,4-triazine, pyridazine; and 1,3,5 triazine. When the nucleotides are depicted using the shorthand A, G, C, T or U, each letter refers to the representative base and/or derivatives thereof, e.g., A includes adenine or adenine analogs, e.g., 7-deaza adenine).

Modifications on the Internucleoside Linkage

The modified nucleosides and nucleotides, which may be incorporated into a modified nucleic acid or mmRNA molecule, can be modified on the internucleoside linkage (e.g., phosphate backbone). The phosphate groups of the backbone can be modified by replacing one or more of the oxygen atoms with a different substituent. Further, the modified nucleosides and nucleotides can include the wholesale replacement of an unmodified phosphate moiety with a modified phosphate as described herein. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The α-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment. Phosphorothioate linked modified nucleic acids or mmRNA molecules are expected to also reduce the innate immune response through weaker binding/activation of cellular innate immune molecules.

In specific embodiments, a modified nucleoside includes an alpha-thio-nucleoside (e.g., 5'-O-(1-thiophosphate)-adenosine, 5'-O-(1-thiophosphate)-cytidine (α-thio-cytidine), 5'-O-(1-thiophosphate)-guanosine, 5'-O-(1-thiophosphate)-uridine, or 5'-O-(1-thiophosphate)-pseudouridine).

Combinations of Modified Sugars, Nucleobases, and Internucleoside Linkages

The modified nucleic acids and mmRNA of the invention can include a combination of modifications to the sugar, the nucleobase, and/or the internucleoside linkage. These combinations can include any one or more modifications described herein. For examples, any of the nucleotides described herein in Formulas (Ia), (Ia-1)-(Ia-3), (Ib)-(If), (IIa)-(IIp), (IIb-1), (IIb-2), (IIc-1)-(IIc-2), (IIn-1), (IIn-2), (IVa)-(IV1), and (IXa)-(IXr) can be combined with any of the nucleobases described herein (e.g., in Formulas (b1)-(b43) or any other described herein).

Synthesis of Nucleic Acid Molecules, Modified Nucleic Acid Molecules and mmRNA Molecules The nucleic acid molecules, modified nucleic acid molecules and mmRNA molecules for use in accordance with the invention may be prepared according to any useful technique, as described herein. The modified nucleosides and nucleotides used in the synthesis of modified nucleic acid molecules and mmRNA molecules disclosed herein can be prepared from readily available starting materials using the following general methods and procedures. Where typical or preferred process conditions (e.g., reaction temperatures, times, mole ratios of reactants, solvents, pressures, etc.) are provided, a skilled artisan would be able to optimize and develop additional process conditions. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., 1H or 13C) infrared spectroscopy, spectrophotometry (e.g., UV-visible), or mass spectrometry, or by chromatography such as high performance liquid chromatography (HPLC) or thin layer chromatography.

Preparation of nucleic acid molecules, modified nucleic acid molecules and mmRNA molecules of the present invention can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

The reactions of the processes described herein can be carried out in suitable solvents, which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of modified nucleosides and nucleotides can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

Modified nucleosides and nucleotides (e.g., binding block molecules) can be prepared according to the synthetic methods described in Ogata et al., J. Org. Chem. 74:2585-2588 (2009); Purmal et al., Nucl. Acids Res. 22(1): 72-78, (1994); Fukuhara et al., Biochemistry, 1(4): 563-568 (1962); and Xu et al., Tetrahedron, 48(9): 1729-1740 (1992), each of which are incorporated by reference in their entirety.

The modified nucleic acid molecules and mmRNA of the invention need not be uniformly modified along the entire length of the molecule. For example, one or more or all types of nucleotide (e.g., purine or pyrimidine, or any one or more or all of A, G, U, C) may or may not be uniformly modified in a polynucleotide of the invention, or in a given predetermined sequence region thereof. In some embodiments, all nucleotides X in a polynucleotide of the invention (or in a given sequence region thereof) are modified, wherein X may any one of nucleotides A, G, U, C, or any one of the combinations A+G, A+U, A+C, G+U, G+C, U+C, A+G+U, A+G+C, G+U+C or A+G+C Different sugar modifications, nucleotide modifications, and/or internucleoside linkages (e.g., backbone structures) may exist at various positions in the modified nucleic acid molecules or mmRNA. One of ordinary skill in the art will appreciate that the nucleotide analogs or other modification(s) may be located at any position(s) of a modified nucleic acid molecule or mmRNA such that the function of the modified nucleic acid molecule or mmRNA is not substantially decreased. A modification may also be a 5' or 3' terminal modification. The modified nucleic acid molecule or mmRNA may contain from about 1% to about 100% modified nucleotides, or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, the modified nucleic acid molecule or mmRNA includes a modified pyrimidine (e.g., a modified uracil/uridine or modified cytosine/cytidine). In some embodiments, the uracil or uridine in the modified nucleic acid molecule or mmRNA molecule may be replaced with from about 1% to about 100% of a modified uracil or modified uridine (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100% of a modified uracil or modified uridine). The modified uracil or uridine can be replaced by a compound having a single unique structure or by a plurality of compounds having different structures (e.g., 2, 3, 4 or more unique structures, as described herein). In some embodiments, the cytosine or cytidine in the modified nucleic acid molecule or mmRNA molecule may be replaced with from about 1% to about 100% of a modified cytosine or modified cytidine (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100% of a modified cytosine or modified cytidine). The modified cytosine or cytidine can be replaced by a compound having a single unique structure or by a plurality of compounds having different structures (e.g., 2, 3, 4 or more unique structures, as described herein).

In some embodiments, the present disclosure provides methods of synthesizing a modified nucleic acid molecule or mmRNA including n number of linked nucleosides having Formula (Ia-1):

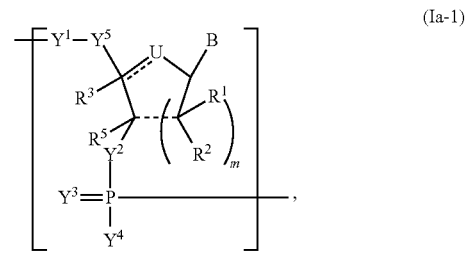

comprising:
a) reacting a nucleotide of Formula (IV-1):

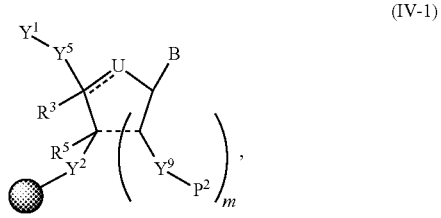

with a phosphoramidite compound of Formula (V-1):

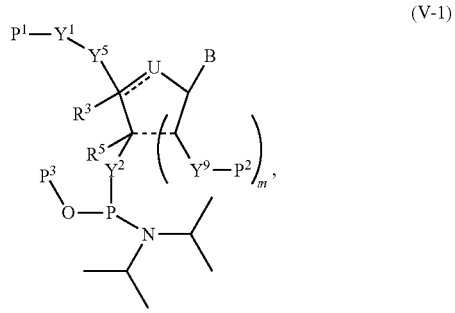

wherein Y9 is H, hydroxy, phosphoryl, pyrophosphate, sulfate, amino, thiol, optionally substituted amino acid, or a peptide (e.g., including from 2 to 12 amino acids); and each P1, P2, and P3 is, independently, a suitable protecting group; and ◯ denotes a solid support;

to provide a modified nucleic acid molecule or mmRNA of Formula (VI-1):

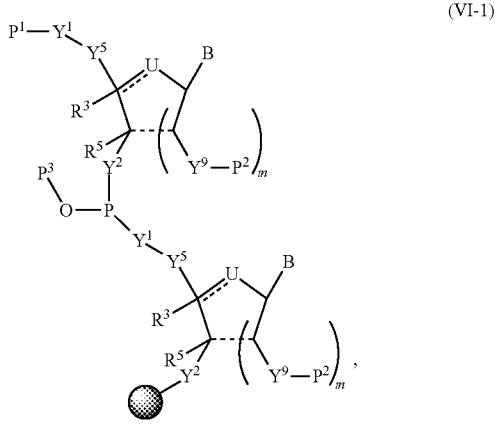

(VI-1)

and b) oxidizing or sulfurizing the modified nucleic acid molecule or mmRNA of Formula (V) to yield a modified nucleic acid molecule or mmRNA of Formula (VII-1):

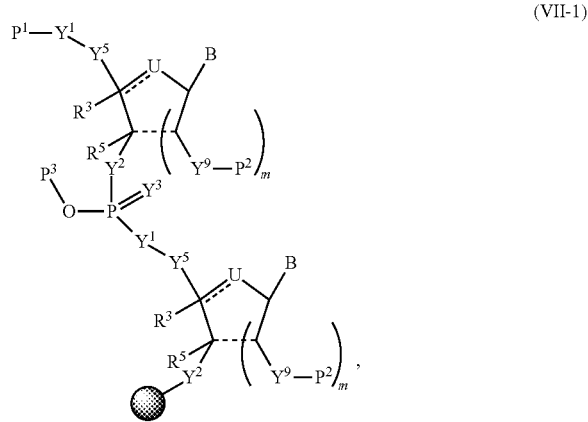

(VII-1)

and c) removing the protecting groups to yield the modified nucleic acid molecule or mmRNA of Formula (Ia).

In some embodiments, steps a) and b) are repeated from 1 to about 10,000 times. In some embodiments, the methods further comprise a nucleotide (e.g., building block molecule) selected from the group consisting of adenosine, cytosine, guanosine, and uracil. In some embodiments, the nucleobase may be a pyrimidine or derivative thereof. In some embodiments, the modified nucleic acid molecule or mmRNA is translatable.

Other components of modified nucleic acid molecules and mmRNA are optional, and are beneficial in some embodiments. For example, a 5' untranslated region (UTR) and/or a 3'UTR are provided, wherein either or both may independently contain one or more different nucleoside modifications. In such embodiments, nucleoside modifications may also be present in the translatable region. Also provided are modified nucleic acid molecules and mmRNA containing a Kozak sequence.

Exemplary syntheses of modified nucleotides, which are incorporated into a modified nucleic acid molecules or mmRNA, e.g., RNA or mRNA, are provided below in Scheme 1 through Scheme 11. Scheme 1 provides a general method for phosphorylation of nucleosides, including modified nucleosides.

Scheme 1

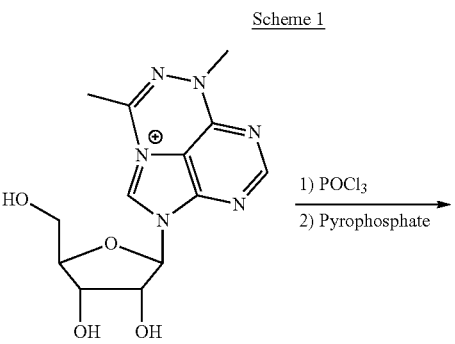

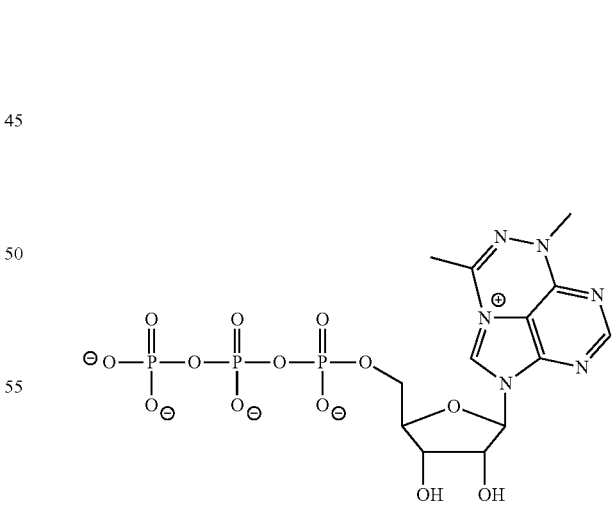

Various protecting groups may be used to control the reaction. For example, Scheme 2 provides the use of multiple protecting and deprotecting steps to promote phosphorylation at the 5' position of the sugar, rather than the 2' and 3' hydroxyl groups.

Scheme 2
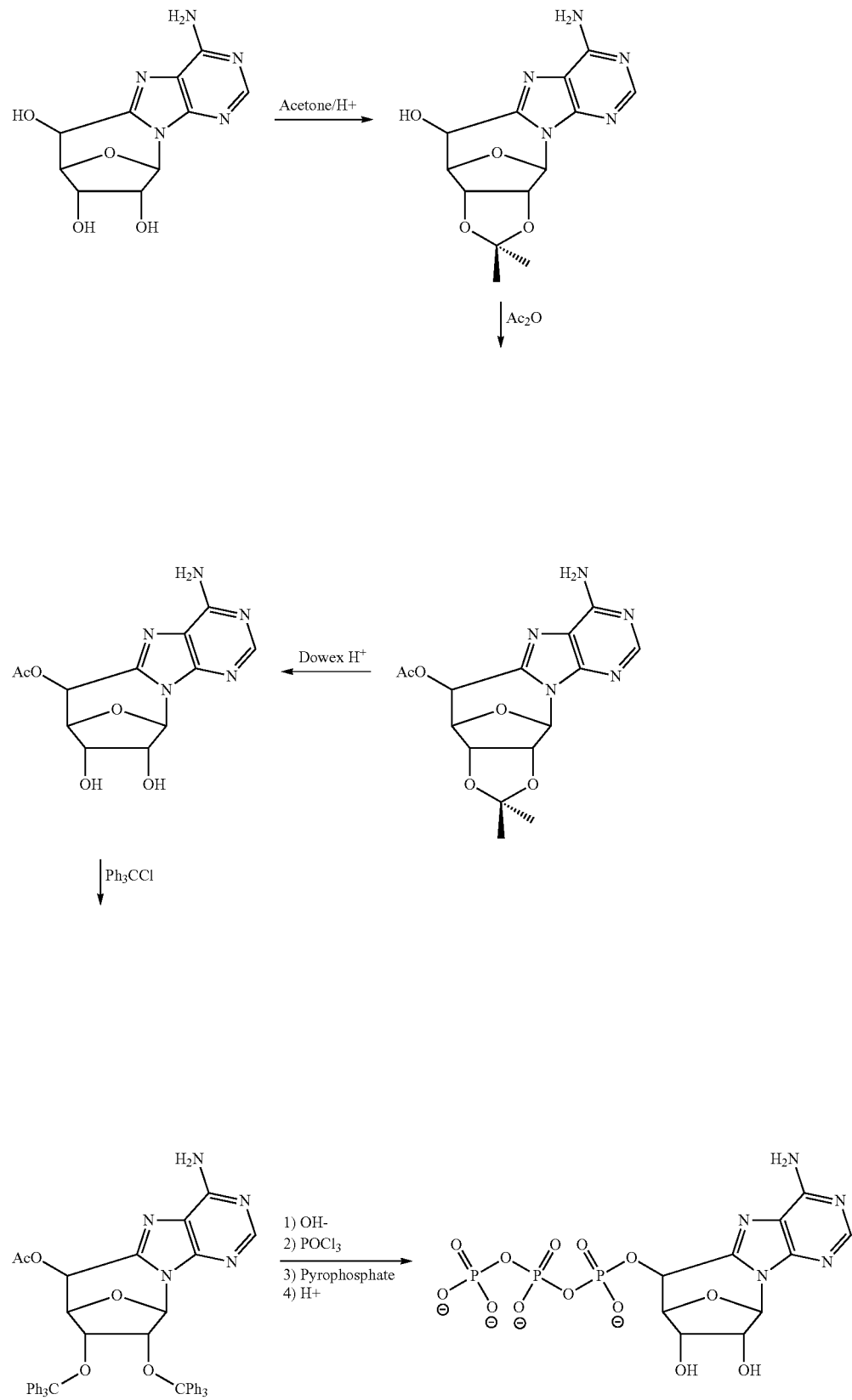

Modified nucleotides can be synthesized in any useful manner. Schemes 3, 4, and 7 provide exemplary methods for synthesizing modified nucleotides having a modified purine nucleobase; and Schemes 5 and 6 provide exemplary methods for synthesizing modified nucleotides having a modified pseudouridine or pseudoisocytidine, respectively.
Scheme 3
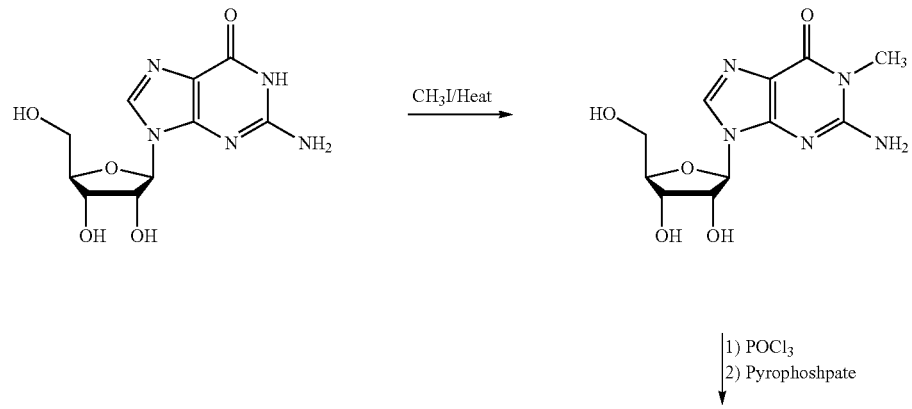
Scheme 4
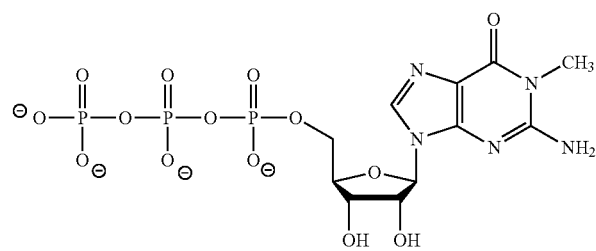
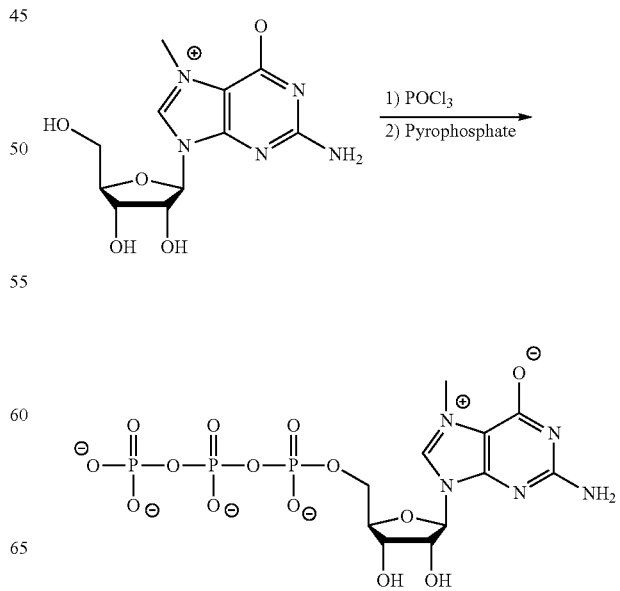

Scheme 5
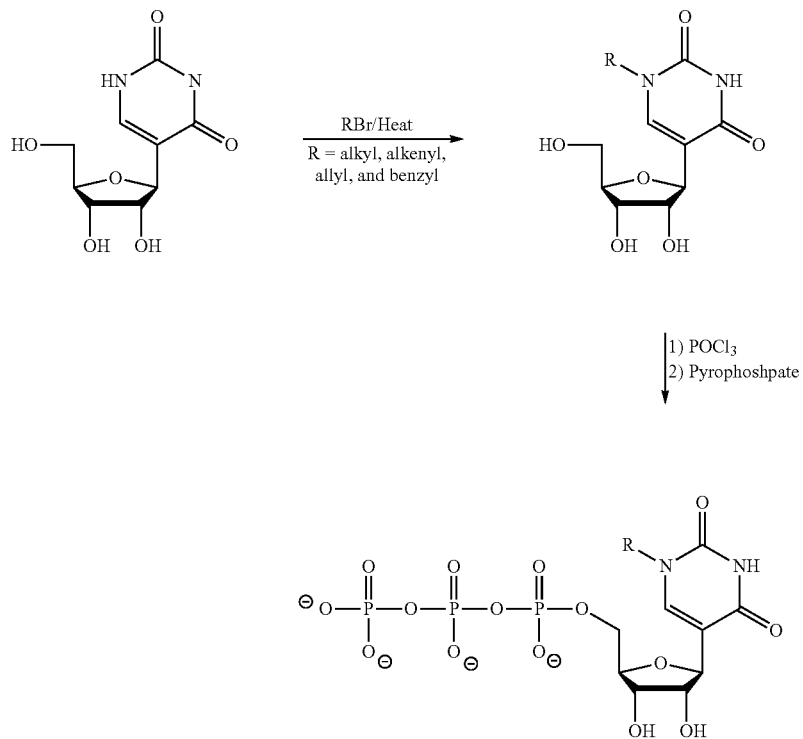
Scheme 6
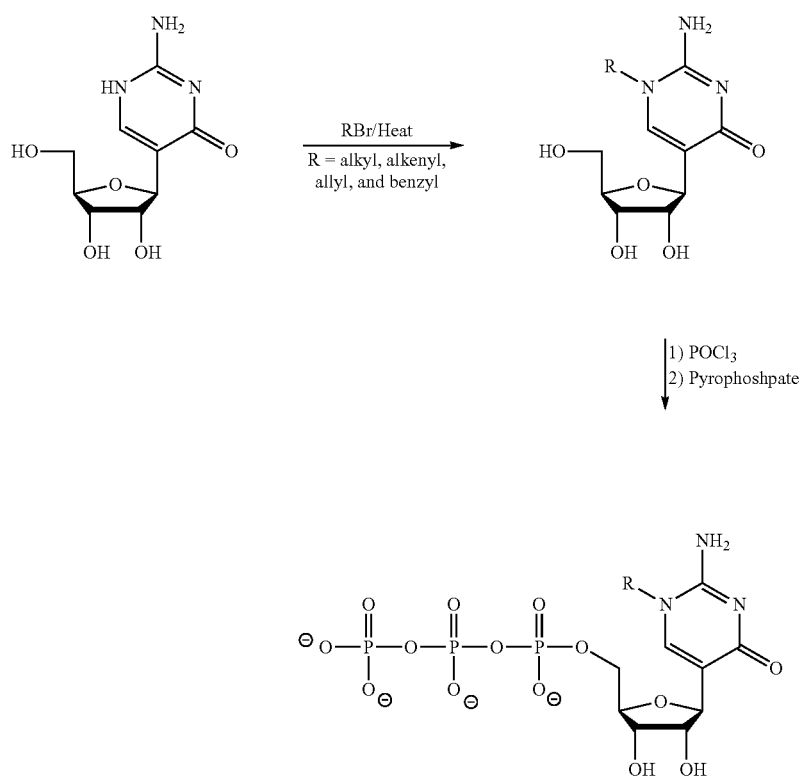

Scheme 7
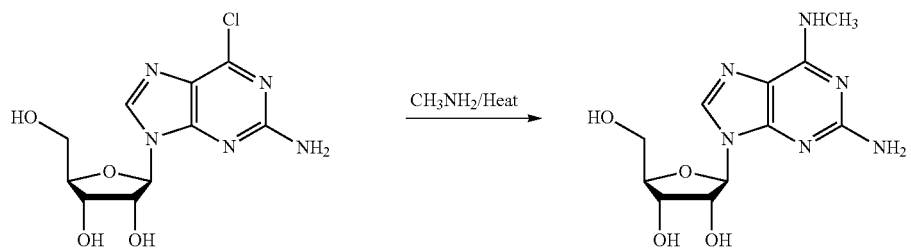
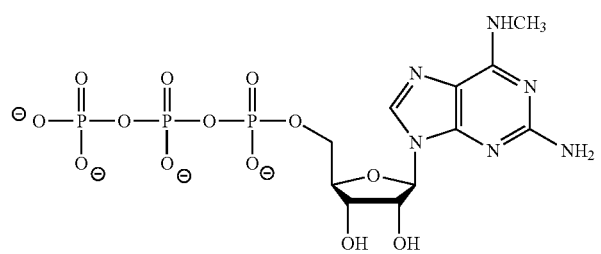
Schemes 8 and 9 provide exemplary syntheses of modified nucleotides. Scheme 10 provides a non-limiting biocatalytic method for producing nucleotides.
Scheme 8
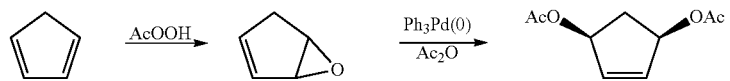
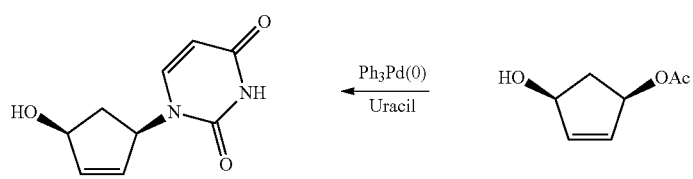

135 136
-continued
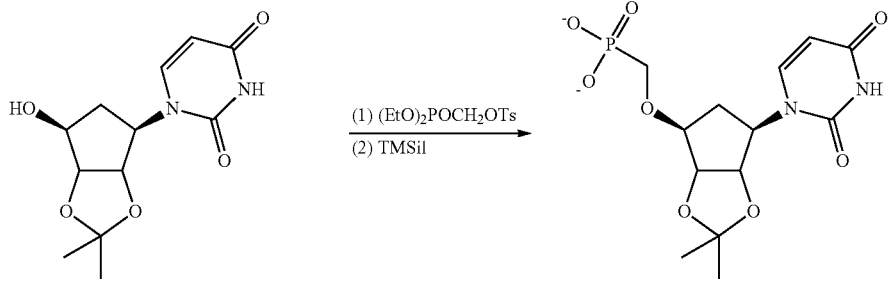
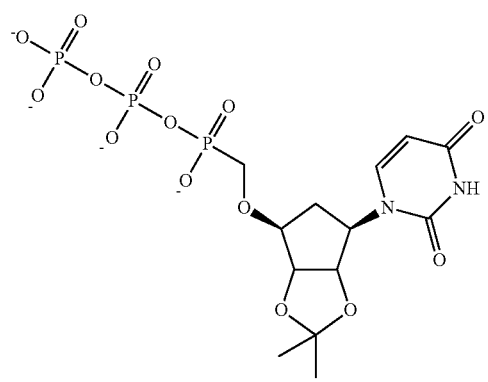
Scheme 9
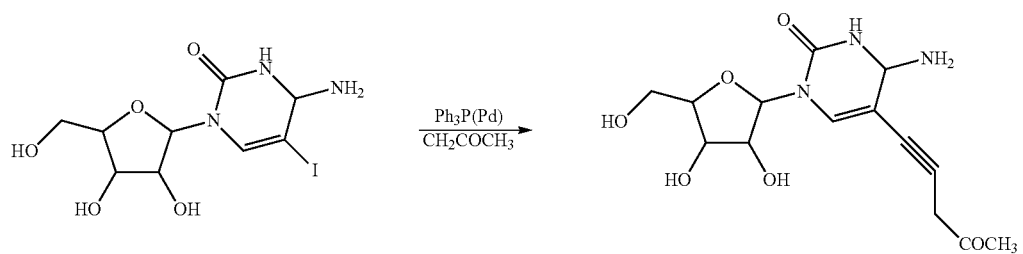

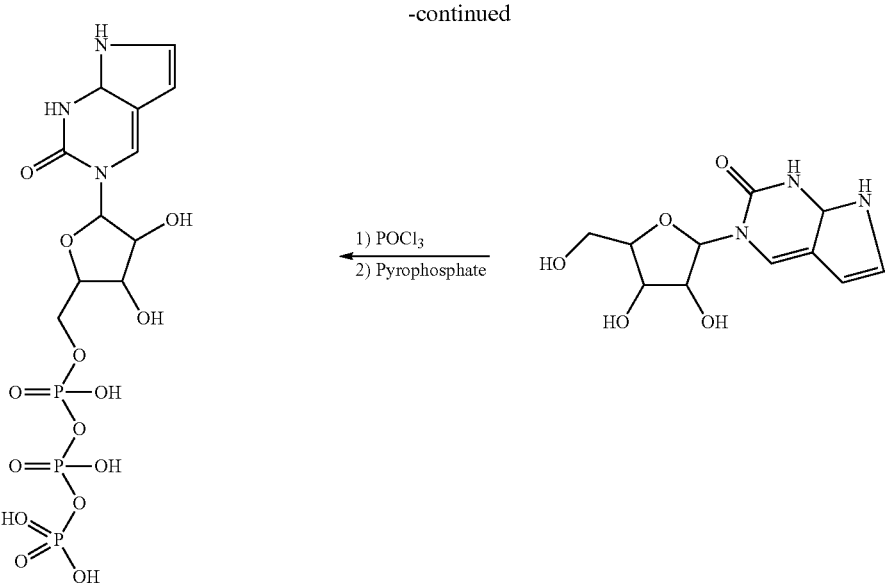

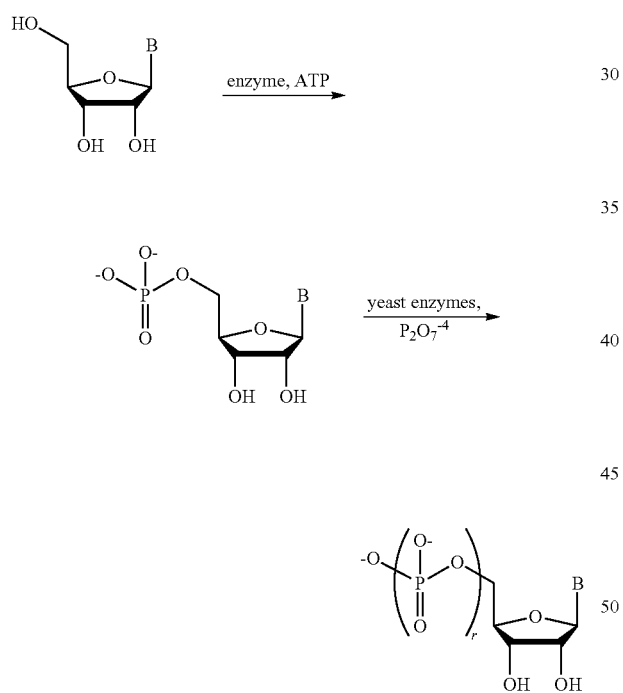

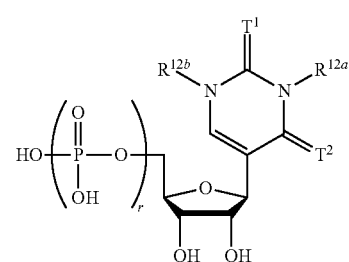

Scheme 11 provides an exemplary synthesis of a modified uracil, where the N1 position is modified with $R^{12b}$, as provided elsewhere, and the 5'-position of ribose is phosphorylated. $T^1$, $T^2$, $R^{12a}$, $R^{12b}$, and r are as provided herein. This synthesis, as well as optimized versions thereof, can be used to modify other pyrimidine nucleobases and purine nucleobases (see e.g., Formulas (b1)-(b43)) and/or to install one or more phosphate groups (e.g., at the 5' position of the sugar). This alkylating reaction can also be used to include one or more optionally substituted alkyl group at any reactive group (e.g., amino group) in any nucleobase described herein (e.g., the amino groups in the Watson-Crick base-pairing face for cytosine, uracil, adenine, and guanine)

Combinations of Nucleotides in mmRNA

Further examples of modified nucleotides and modified nucleotide combinations are provided below in Table 2. These combinations of modified nucleotides can be used to form the modified nucleic acid molecules or mmRNA of the invention. Unless otherwise noted, the modified nucleotides may be completely substituted for the natural nucleotides of the modified nucleic acid molecules or mmRNA of the invention. As a non-limiting example, the natural nucleotide uridine may be substituted with a modified nucleoside described herein. In another non-limiting example, the natural nucleotide uridine may be partially substituted (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9%) with at least one of the modified nucleoside disclosed herein.

TABLE 2

| Modified Nucleotide | Modified Nucleotide Combination |
|---|---|
| α-thio-cytidine | α-thio-cytidine/5-iodo-uridine |
| | α-thio-cytidine/N1-methyl-pseudo-uridine |
| | α-thio-cytidine/α-thio-uridine |
| | α-thio-cytidine/5-methyl-uridine |
| | α-thio-cytidine/pseudo-uridine |
| | about 50% of the cytosines are α-thio-cytidine |
| pseudoisocytidine | pseudoisocytidine/5-iodo-uridine |
| | pseudoisocytidine/N1-methyl-pseudouridine |
| | pseudoisocytidine/α-thio-uridine |
| | pseudoisocytidine/5-methyl-uridine |
| | pseudoisocytidine/pseudouridine |
| | about 25% of cytosines are pseudoisocytidine |
| | pseudoisocytidine/about 50% of uridines are N1-methyl-pseudouridine and about 50% of uridines are pseudouridine |
| | pseudoisocytidine/about 25% of uridines are N1-methyl-pseudouridine and about 25% of uridines are pseudouridine |
| pyrrolo-cytidine | pyrrolo-cytidine/5-iodo-uridine |
| | pyrrolo-cytidine/N1-methyl-pseudouridine |
| | pyrrolo-cytidine/α-thio-uridine |
| | pyrrolo-cytidine/5-methyl-uridine |
| | pyrrolo-cytidine/pseudouridine |
| | about 50% of the cytosines are pyrrolo-cytidine |
| 5-methyl-cytidine | 5-methyl-cytidine/5-iodo-uridine |
| | 5-methyl-cytidine/N1-methyl-pseudouridine |
| | 5-methyl-cytidine/α-thio-uridine |
| | 5-methyl-cytidine/5-methyl-uridine |
| | 5-methyl-cytidine/pseudouridine |
| | about 25% of cytosines are 5-methyl-cytidine |
| | about 50% of cytosines are 5-methyl-cytidine |
| | 5-methyl-cytidine/5-methoxy-uridine |
| | 5-methyl-cytidine/5-bromo-uridine |
| | 5-methyl-cytidine/2-thio-uridine |
| | 5-methyl-cytidine/about 50% of uridines are 2-thio-uridine |
| | about 50% of cytidines are 5-methyl-cytidine/about 50% of uridines are 2-thio-uridine |
| | about 50% of cytidines are 5-methyl-cytidine/about 50% of uridines are 2-thio-uridine |
| N4-acetyl-cytidine | N4-acetyl-cytidine/5-iodo-uridine |
| | N4-acetyl-cytidine/N1-methyl-pseudouridine |
| | N4-acetyl-cytidine/α-thio-uridine |
| | N4-acetyl-cytidine/5-methyl-uridine |
| | N4-acetyl-cytidine/pseudouridine |
| | about 50% of cytosines are N4-acetyl-cytidine |
| | about 25% of cytosines are N4-acetyl-cytidine |
| | N4-acetyl-cytidine/5-methoxy-uridine |
| | N4-acetyl-cytidine/5-bromo-uridine |
| | N4-acetyl-cytidine/2-thio-uridine |
| | about 50% of cytosines are N4-acetyl-cytidine/about 50% of uridines are 2-thio-uridine |

Further examples of modified nucleotide combinations are provided below in Table 3. These combinations of modified nucleotides can be used to form the modified nucleic acid molecules or mmRNA of the invention.

TABLE 3

| Modified Nucleotide | Modified Nucleotide Combination |
| --- | --- |
| modified cytidine having one or more nucleobases of Formula (b10) | modified cytidine with (b10)/pseudouridine<br>modified cytidine with (b10)/N1-methyl-pseudouridine<br>modified cytidine with (b10)/5-methoxy-uridine<br>modified cytidine with (b10)/5-methyl-uridine<br>modified cytidine with (b10)/5-bromo-uridine<br>modified cytidine with (b10)/2-thio-uridine<br>about 50% of cytidine substituted with modified cytidine (b10)/about 50% of uridines are 2-thio-uridine |
| modified cytidine having one or more nucleobases of Formula (b32) | modified cytidine with (b32)/pseudouridine<br>modified cytidine with (b32)/N1-methyl-pseudouridine<br>modified cytidine with (b32)/5-methoxy-uridine<br>modified cytidine with (b32)/5-methyl-uridine<br>modified cytidine with (b32)/5-bromo-uridine<br>modified cytidine with (b32)/2-thio-uridine<br>about 50% of cytidine substituted with modified cytidine (b32)/about 50% of uridines are 2-thio-uridine |
| modified uridine having one or more nucleobases of Formula (b1) | modified uridine with (b1)/N4-acetyl-cytidine<br>modified uridine with (b1)/5-methyl-cytidine |
| modified uridine having one or more nucleobases of Formula (b8) | modified uridine with (b8)/N4-acetyl-cytidine<br>modified uridine with (b8)/5-methyl-cytidine |
| modified uridine having one or more nucleobases of Formula (b28) | modified uridine with (b28)/N4-acetyl-cytidine<br>modified uridine with (b28)/5-methyl-cytidine |
| modified uridine having one or more nucleobases of Formula (b29) | modified uridine with (b29)/N4-acetyl-cytidine<br>modified uridine with (b29)/5-methyl-cytidine |
| modified uridine having one or more nucleobases of Formula (b30) | modified uridine with (b30)/N4-acetyl-cytidine<br>modified uridine with (b30)/5-methyl-cytidine |

In some embodiments, at least 25% of the cytosines are replaced by a compound of Formula (b10)-(b14) (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, at least 25% of the uracils are replaced by a compound of Formula (b1)-(b9) (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, at least 25% of the cytosines are replaced by a compound of Formula (b10)-(b14), and at least 25% of the uracils are replaced by a compound of Formula (b1)-(b9) (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

Synthesis of Nucleic Acid Molecules and Modified Nucleic Acid Molecules

Nucleic acid molecules and modified nucleic acid molecules for use in accordance with the present disclosure may be prepared according to any available technique including, but not limited to, in vitro transcription such as chemical synthesis and enzymatic synthesis, or enzymatic and chemical cleavage of a longer precursor, etc. Methods of synthesizing RNA are known in the art (see, e.g., Gait, M. J. (ed.) *Oligonucleotide synthesis: a practical approach*, Oxford [Oxfordshire], Washington, D.C.: IRL Press, 1984; and Herdewijn, P. (ed.) *Oligonucleotide synthesis: methods and applications*, Methods in Molecular Biology, v. 288 (Clifton, N.J.) Totowa, N.J.: Humana Press, 2005; both of which are incorporated herein by reference in their entirety).

The nucleic acid molecules and modified nucleic acid molecules disclosed herein can be prepared from readily available starting materials using the following general methods and procedures. It is understood that where typical or preferred process conditions (i.e., reaction temperatures, times, mole ratios of reactants, solvents, pressures, etc.) are given other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), mass spectrometry, or by chromatography such as high performance liquid chromatography (HPLC) or thin layer chromatography.

Preparation of nucleic acid molecules and modified nucleic acid molecules can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents, which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of nucleic acid molecules or modified nucleic acid molecules can be carried out by any of numerous methods known in the art. An example method includes, but is not limited to, fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

Modified nucleic acid molecules need not be uniformly modified along the entire length of the molecule. Different nucleic acid modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially decreased. A modification may also be a 5' or 3' terminal modification. The nucleic acids may contain at a minimum one modified nucleotide and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as uracil or cytosine. In some embodiments, at least 5%, at least 10%, at least 25%, at least 50%, at least 80%, at least 90% or 100% of the uracil in the nucleic acid may be replaced with a modified uracil. The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid may be replaced with a modified cytosine. The modified cytosine can be replaced by a compound having a single unique structure, or can be replaced by a plurality of compounds having different structures (e.g., 2, 3, 4 or more unique structures).

Generally, the shortest length of a modified mRNA, herein "mmRNA," of the present disclosure can be the length of an mRNA sequence that may be sufficient to encode for a dipeptide. In another embodiment, the length of the mRNA sequence may be sufficient to encode for a tripeptide. In another embodiment, the length of an mRNA sequence may be sufficient to encode for a tetrapeptide. In another embodiment, the length of an mRNA sequence may be sufficient to encode for a pentapeptide. In another embodiment, the length of an mRNA sequence may be sufficient to encode for a hexapeptide. In another embodiment, the length of an mRNA sequence may be sufficient to encode for a heptapeptide. In another embodiment, the length of an mRNA sequence may be sufficient to encode for an octapeptide. In another embodiment, the length of an mRNA sequence may be sufficient to encode for a nonapeptide. In another embodiment, the length of an mRNA sequence may be sufficient to encode for a decapeptide.

Examples of dipeptides that the nucleic acid molecules or modified nucleic acid molecule sequences can encode for include, but are not limited to, carnosine and anserine.

In a further embodiment, the nucleic acid molecules, modified nucleic acid molecules, mmRNA or mRNA may be greater than 30 nucleotides in length. In another embodiment, the nucleic acid molecules, modified nucleic acid molecules, mmRNA or RNA molecule may be greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, 3,000, 4,000 and 5,000 nucleotides).

In one embodiment, at least a portion of the nucleic acid molecule, modified nucleic acid molecule, mRNA or modified mRNA nucleotide sequence may be codon optimized by methods known in the art and/or described herein. After a sequence has been codon optimized it may be further evaluated for regions containing restriction sites. At least one nucleotide within the restriction site regions may be replaced with another nucleotide in order to remove the restriction site from the sequence but the replacement of nucleotides does alter the amino acid sequence which is encoded by the codon optimized nucleotide sequence.

Exemplary Properties of Modified Nucleic Acid Molecules
Major Groove Interacting Partners The modified nucleic acid molecules, e.g., modified mRNA (mmRNA), described herein can disrupt interactions with recognition receptors that detect and respond to RNA ligands through interactions, e.g. binding, with the major groove face of a nucleotide or nucleic acid. As such, RNA ligands comprising modified nucleotides or modified nucleic acid molecules, as described herein, decrease interactions with major groove binding partners, and therefore decrease an innate immune response, or expression and secretion of pro-inflammatory cytokines, or both.

Example major groove interacting, e.g. binding, partners include, but are not limited to, the following nucleases and helicases. Within membranes, TLRs (Toll-like Receptors) 3, 7, and 8 can respond to single- and double-stranded RNA. Within the cytoplasm, members of the superfamily 2 class of DEX(D/H) helicases and ATPases can sense RNA to initiate antiviral responses. These helicases include the RIG-I (retinoic acid-inducible gene I) and MDA5 (melanoma differentiation-associated gene 5). Other examples include laboratory of genetics and physiology 2 (LGP2), HIN-200 domain containing proteins, or Helicase-domain containing proteins.

Prevention or Reduction of Innate Cellular Immune Response Activation Using Modified Nucleic Acid Molecules The modified nucleic acid molecules, e.g., mmRNA, described herein, decrease the innate immune response in a cell. The term "innate immune response" includes a cellular response to exogenous nucleic acids, including, but not limited to, single stranded nucleic acids, generally of viral or bacterial origin, which involve the induction of cytokine expression and release, particularly the interferons, and cell death. Protein synthesis may also be reduced during the innate cellular immune response. While it is advantageous to eliminate the innate immune response in a cell, the present disclosure provides modified mRNA that substantially reduce the immune response, including interferon signaling, without entirely eliminating such a response. In some embodiments, the immune response may be reduced by 10%, 20%, 30%, 40%, 50%, 60%, 70%, 80%, 90%, 95%, 99%, 99.9%, or greater than 99.9% as compared to the immune response induced by a corresponding unmodified nucleic acid molecule. Such a reduction can be measured by the expression or activity level of Type 1 interferons or the expression of interferon-regulated genes such as the toll-like receptors (e.g., TLR7 and TLR8). Reduction of the innate immune response can also be measured by decreased cell death following one or more administrations of modified RNA to a cell population; e.g., cell death is 10%, 25%, 50%, 75%, 85%, 90%, 95%, or over 95% less than the cell death frequency observed with a corresponding unmodified nucleic acid molecule. Moreover, cell death may affect fewer than 50%, 40%, 30%, 20%, 10%, 5%, 1%, 0.1%, 0.01% or fewer than 0.01% of cells contacted with the modified nucleic acid molecules.

The present disclosure provides for the repeated introduction (e.g., transfection) of modified nucleic acid molecules into a target cell population, e.g., in vitro, ex vivo, or in vivo. The step of contacting the cell population may be repeated one or more times (such as two, three, four, five or more than five times). In some embodiments, the step of contacting the cell population with the modified nucleic acid molecules may be repeated a number of times sufficient such that a predetermined efficiency of protein translation in the cell population is achieved. Given the reduced cytotoxicity of the target cell population by the nucleic acid modifications, such repeated transfections are achievable in a variety of cell types.

The modified nucleic acids of the invention, including the combination of modifications taught herein may have superior properties making them more suitable as therapeutic modalities.

It has been determined that the "all or none" model in the art is sorely insufficient to describe the biological phenomena associated with the therapeutic utility of modified mRNA. The present inventors have determined that to improve protein production, one may consider the nature of the modification, or combination of modifications, the percent modification and survey more than one cytokine or metric to determine the efficacy and risk profile of a particular modified mRNA.

In one aspect of the invention, methods of determining the effectiveness of a modified mRNA as compared to unmodified involves the measure and analysis of one or more cytokines whose expression is triggered by the administration of the exogenous nucleic acid of the invention. These values are compared to administration of an unmodified nucleic acid or to a standard metric such as cytokine response, PolyIC, R-848 or other standard known in the art.

One example of a standard metric developed herein is the measure of the ratio of the level or amount of encoded polypeptide (protein) produced in the cell, tissue or organism to the level or amount of one or more (or a panel) of cytokines whose expression is triggered in the cell, tissue or organism as a result of administration or contact with the modified nucleic acid. Such ratios are referred to herein as the Protein:Cytokine Ratio or "PC" Ratio. The higher the PC ratio, the more efficacioius the modified nucleic acid (polynucleotide encoding the protein measured). Preferred PC Ratios, by cytokine, of the present invention may be greater than 1, greater than 10, greater than 100, greater than 1000, greater than 10,000 or more. Modified nucleic acids having higher PC Ratios than a modified nucleic acid of a different or unmodified construct are preferred.

The PC ratio may be further qualified by the percent modification present in the polynucleotide. For example, normalized to a 100% modified nucleic acid, the protein production as a function of cytokine (or risk) or cytokine profile can be determined.

In one embodiment, the present invention provides a method for determining, across chemistries, cytokines or percent modification, the relative efficacy of any particular modified polynucleotide by comparing the PC Ratio of the modified nucleic acid (polynucleotide).

Activation of the Immune Response: Vaccines

In one embodiment of the present invention, mRNA molecules may be used to elicit or provoke an immune response in an organism. The mRNA molecules to be delivered may encode an immunogenic peptide or polypeptide and may encode more than one such peptide or polypeptide.

Additionally, certain modified nucleosides, or combinations thereof, when introduced into the modified nucleic acid molecules or mmRNA of the invention will activate the innate immune response. Such activating molecules are useful as adjuvants when combined with polypeptides and/or other vaccines. In certain embodiments, the activating molecules contain a translatable region which encodes for a polypeptide sequence useful as a vaccine, thus providing the ability to be a self-adjuvant.

In one embodiment, the nucleic acid molecules, modified nucleic acid molecules and/or mmRNA of the invention may encode an immunogen. The delivery of nucleic acid molecules, modified nucleic acid molecules and/or mmRNA encoding an immunogen may activate the immune response. As a non-limiting example, the nucleic acid molecules, modified nucleic acid molecules and/or mmRNA encoding an immunogen may be delivered to cells to trigger multiple innate response pathways (see International Pub. No. WO2012006377 and WO2013087083 and US Patent Publication No. US20130177639; each of which is herein incorporated by reference in its entirety). As another non-limiting example, the nucleic acid molecules, modified nucleic acid molecules and mmRNA of the present invention encoding an immunogen may be delivered to a vertebrate in a dose amount large enough to be immunogenic to the vertebrate (see International Pub. No. WO2012006372 and WO2012006369 and US Publication No. US20130149375 and US20130177640; the contents of each of which are herein incorporated by reference in their entirety).

The nucleic acid molecules, modified nucleic acid molecules or mmRNA of invention may encode a polypeptide sequence for a vaccine and may further comprise an inhibitor. The inhibitor may impair antigen presentation and/or inhibit various pathways known in the art. As a non-limiting example, the nucleic acid molecules, modified nucleic acid molecules or mmRNA of the invention may be used for a vaccine in combination with an inhibitor which can impair antigen presentation (see International Pub. No. WO2012089225 and WO2012089338; each of which is herein incorporated by reference in their entirety).

In one embodiment, the nucleic acid molecules, modified nucleic acid molecules or mmRNA of the invention may be self-replicating RNA. Self-replicating RNA molecules can enhance efficiency of RNA delivery and expression of the enclosed gene product. In one embodiment, the modified nucleic acid molecules or mmRNA may comprise at least one modification described herein and/or known in the art. In one embodiment, the self-replicating RNA can be designed so that the self-replicating RNA does not induce production of infectious viral particles. As a non-limiting example the self-replicating RNA may be designed by the methods described in US Pub. No. US20110300205 and International Pub. Nos. WO2011005799 and WO2013055905, each of which is herein incorporated by reference in their entirety.

In one embodiment, the self-replicating nucleic acid molecules, modified nucleic acid molecules or mmRNA of the invention may encode a protein which may raise the immune response. As a non-limiting example, the nucleic acid molecules, modified nucleic acid molecules and/or mmRNA may be self-replicating mRNA and may encode at least one antigen (see US Pub. No. US20110300205, US20130171241, US20130177640 and US20130177639 and International Pub. Nos. WO2011005799, WO2012006372, WO2012006377, WO2012006378, WO2012006369 and WO2013055905; the contents of each of which is herein incorporated by reference in their entirety). In one aspect, the self-replicating RNA may be administered to mammals at a large enough dose to raise the immune response in a large mammal (see e.g., International Publication No. WO2012006369, herein incorporated by reference in its entirety).

In one embodiment, the self-replicating nucleic acid molecules, modified nucleic acids or mmRNA of the invention may be formulated using methods described herein or known in the art. As a non-limiting example, the self-replicating RNA may be formulated for delivery by the methods described in Geall et al (Nonviral delivery of self-amplifying RNA vaccines, PNAS 2012; PMID: 22908294; herein incorporated by reference in its entirety). As another non-limiting example, the nucleic acid molecules, modified nucleic acid molecules or mmRNA of the present invention (e.g., nucleic acid molecules encoding an immunogen) may be substantially encapsulated within a PEGylated liposome (see International Patent Application No. WO2013033563; herein incorporated by reference in its entirety). In yet another non-limiting example, the self-replicating RNA may be formulated as described in International Application No. WO2013055905, herein incorporated by reference in its entirety. In one non-limiting example, the self-replicating RNA may be formulated using biodegradable polymer particles as described in International Publication No WO2012006359 or US Patent Publication No. US20130183355, the contents of each of which are herein incorporated by reference in its entirety.

In one embodiment, the self-replicating RNA may be formulated in virion-like particles. As a non-limiting example, the self-replicating RNA is formulated in virion-like particles as described in International Publication No WO2012006376, herein incorporated by reference in its entirety.

In another embodiment, the self-replicating RNA may be formulated in a liposome. As a non-limiting example, the self-replicating RNA may be formulated in liposomes as described in International Publication No. WO20120067378, herein incorporated by reference in its entirety. In one aspect, the liposomes may comprise lipids which have a pKa value which may be advantageous for delivery of mRNA. In another aspect, the liposomes may have an essentially neutral surface charge at physiological pH and may therefore be effective for immunization (see e.g., the liposomes described in International Publication No. WO20120067378, herein incorporated by reference in its entirety).

In yet another embodiment, the self-replicating RNA may be formulated in a cationic oil-in-water emulsion. As a non-limiting example, the self-replicating RNA may be formulated in the cationic oil-in-water emulsion described in International Publication No. WO2012006380, herein incorporated by reference in its entirety. The cationic oil-in-water emulsions which may be used with the self replicating RNA described herein (e.g., nucleic acid molecules, modified nucleic acid molecules and/or mmRNA) may be made by the methods described in International Publication No. WO2012006380, herein incorporated by reference in its entirety.

In one embodiment, the nucleic acid molecules, modified nucleic acid molecules or mmRNA of the present invention may encode amphipathic and/or immunogenic amphipathic peptides.

In on embodiment, a formulation of the nucleic acid molecules, modified nucleic acid molecules or mmRNA of the present invention may further comprise an amphipathic and/or immunogenic amphipathic peptide. As a non-limiting example, the nucleic acid molecules, modified nucleic acid molecule or mmRNA comprising an amphipathic and/or immunogenic amphipathic peptide may be formulated as described in US. Pub. No. US20110250237 and International Pub. Nos. WO2010009277 and WO2010009065; each of which is herein incorporated by reference in their entirety.

In one embodiment, the nucleic acid molecules, modified nucleic acid molecules and mmRNA of the present invention may be immunostimultory. As a non-limiting example, the nucleic acid molecules, modified nucleic acid molecules and mmRNA may encode all or a part of a positive-sense or a negative-sense stranded RNA virus genome (see International Pub No. WO2012092569 and US Pub No. US20120177701, each of which is herein incorporated by reference in their entirety). In another non-limiting example, the immunostimultory nucleic acid molecules, modified nucleic acid molecules or mmRNA of the present invention may be formulated with an excipient for administration as described herein and/or known in the art (see International Pub No. WO2012068295 and US Pub No. US20120213812, each of which is herein incorporated by reference in their entirety).

In one embodiment, the response of the vaccine formulated by the methods described herein may be enhanced by the addition of various compounds to induce the therapeutic effect. As a non-limiting example, the vaccine formulation may include a MHC II binding peptide or a peptide having a similar sequence to a MHC II binding peptide (see International Pub Nos. WO2012027365, WO2011031298 and US Pub No. US20120070493, US20110110965, each of which is herein incorporated by reference in their entirety). As another example, the vaccine formulations may comprise modified nicotinic compounds which may generate an antibody response to nicotine residue in a subject (see International Pub No. WO2012061717 and US Pub No. US20120114677, each of which is herein incorporated by reference in their entirety).

Polypeptide Variants

The nucleic acid molecules and modified nucleic acid molecules encode polypeptides, e.g., a variant polypeptides, which have a certain identity to a reference polypeptide sequence. The term "identity," as known in the art, refers to a relationship between the sequences of two or more peptides, determined by comparing the sequences. In the art, "identity" also refers to the degree of sequence relatedness between peptides, as determined by the number of matches between strings of two or more amino acid residues. Identity measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988); all of which are herein incorporated by reference in their entirety.

In some embodiments, the polypeptide variant may have the same or a similar activity as the reference polypeptide. Alternatively, the variant may have an altered activity (e.g., increased or decreased) relative to a reference polypeptide. Generally, variants of a particular polynucleotide or polypeptide of the present disclosure will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular reference polynucleotide or polypeptide as determined by sequence alignment programs and parameters described herein and known to those skilled in the art.

As recognized by those skilled in the art, protein fragments, functional protein domains, and homologous proteins are also considered to be within the scope of this present disclosure. For example, provided herein is any protein fragment of a reference protein (meaning a polypeptide sequence which is at least one amino acid residue shorter than a reference polypeptide sequence but otherwise identical) 10, 20, 30, 40, 50, 60, 70, 80, 90, 100 or greater than 100 amino acids in length. In another example, any protein that includes a stretch of about 20, about 30, about 40, about 50, or about 100 amino acids which are about 40%, about 50%, about 60%, about 70%, about 80%, about 90%, about 95%, or about 100% identical to any of the sequences described herein can be utilized in accordance with the present disclosure. In certain embodiments, a protein sequence to be utilized in accordance with the present disclosure includes 2, 3, 4, 5, 6, 7, 8, 9, 10, or more mutations as shown in any of the sequences provided or referenced herein.

Polypeptide-Nucleic Acid Complexes

Proper protein translation involves the physical aggregation of a number of polypeptides and nucleic acids associated with the mRNA. Provided by the present disclosure are protein-nucleic acid complexes, containing a translatable mRNA having one or more nucleoside modifications (e.g., at least two different nucleoside modifications) and one or more polypeptides bound to the mRNA. Generally, the proteins are provided in an amount effective to prevent or to reduce an innate immune response of a cell into which the complex is introduced.

Untranslatable Nucleic Acid Molecules and Modified Nucleic Acid Molecules

As described herein, provided are mRNA having sequences that are substantially not translatable. Such mRNA may be effective as a vaccine when administered to a subject. It is further provided that the subject administered the vaccine may be a mammal, more preferably a human and most preferably a patient.

Also provided are nucleic acid molecules or modified nucleic acid molecules that contain one or more noncoding regions. Such nucleic acid molecules or modified nucleic acid molecules are generally not translated, but are capable of binding to and sequestering one or more translational machinery component such as a ribosomal protein or a transfer RNA (tRNA), thereby effectively reducing the protein expression in the cell. The nucleic acid molecules or modified nucleic acid molecule may contain a small nucleolar RNA (sno-RNA), micro RNA (miRNA), small interfering RNA (siRNA) or Piwi-interacting RNA (piRNA).

Pharmaceutical Compositions

Formulation, Administration, Delivery and Dosing

The present invention provides nucleic acid molecules, modified nucleic acid molecules and mmRNA compositions and complexes in combination with one or more pharmaceutically acceptable excipients. Pharmaceutical compositions may optionally comprise one or more additional active substances, e.g. therapeutically and/or prophylactically active substances. Pharmaceutical compositions of the present invention may be sterile and/or pyrogen-free. General considerations in the formulation and/or manufacture of pharmaceutical agents may be found, for example, in Remington: The Science and Practice of Pharmacy 21st ed., Lippincott Williams & Wilkins, 2005 (incorporated herein by reference in its entirety).

In some embodiments, compositions are administered to humans, human patients or subjects. For the purposes of the present disclosure, the phrase "active ingredient" generally refers to nucleic acid molecules, modified nucleic acid molecules and mmRNA to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

Formulations

The nucleic acid molecules, modified nucleic acid molecules, and mmRNA of the invention can be formulated using one or more excipients to: (1) increase stability; (2) increase cell transfection; (3) permit the sustained or delayed release (e.g., from a depot formulation of the nucleic acid molecules, modified nucleic acid molecules, or mmRNA); (4) alter the biodistribution (e.g., target the nucleic acid molecules, modified nucleic acid molecules, or mmRNA to specific tissues or cell types); (5) increase the translation of encoded protein in vivo; and/or (6) alter the release profile of encoded protein in vivo. In addition to traditional excipients such as any and all solvents, dispersion media, diluents, or other liquid vehicles, dispersion or suspension aids, surface active agents, isotonic agents, thickening or emulsifying agents, preservatives, excipients of the present invention can include, without limitation, lipidoids, liposomes, lipid nanoparticles, polymers, lipoplexes, core-shell nanoparticles, peptides, proteins, cells transfected with nucleic acid molecules, modified nucleic acid molecules, or mmRNA (e.g., for transplantation into a subject), hyaluronidase, nanoparticle mimics and combinations thereof. Accordingly, the formulations of the invention can include one or more excipients, each in an amount that together increases the stability of the nucleic acid molecules, modified nucleic acid molecules, or mmRNA, increases cell transfection by the nucleic acid molecules, modified nucleic acid molecules, or mmRNA, increases the expression of modified nucleic acid, or mmRNA encoded protein, and/or alters the release profile of nucleic acid molecules, modified nucleic acid molecules, or mmRNA encoded proteins. Further, the nucleic acid molecules, modified nucleic acids and mmRNA of the present invention may be formulated using self-assembled nucleic acid nanoparticles.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient may generally be equal to the dosage of the active ingredient which would be administered to a subject and/or a convenient fraction of such a dosage including, but not limited to, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient.

In some embodiments, the nucleic acid molecules, modified nucleic acids and/or modified mRNA formulations described herein may contain at least one nucleic acid molecules, modified nucleic acid and/or modified mRNA. As a non-limiting example, the formulations may contain 1, 2, 3, 4 or 5 nucleic acid molecules, modified nucleic acid and/or modified mRNA. In one embodiment, the formulation contains at least three nucleic acid molecules, modified nucleic acids and/or modified mRNA encoding proteins. In one embodiment, the formulation contains at least five nucleic acid molecules, modified nucleic acids and/or modified mRNA encoding proteins.

Pharmaceutical formulations may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

In some embodiments, the particle size of the lipid nanoparticle may be increased and/or decreased. The change in particle size may be able to help counter biological reaction such as, but not limited to, inflammation or may increase the biological effect of the nucleic acid molecules, modified nucleic acid and/or modified mRNA delivered to mammals.

Pharmaceutically acceptable excipients used in the manufacture of pharmaceutical compositions include, but are not limited to, inert diluents, surface active agents and/or emulsifiers, preservatives, buffering agents, lubricating agents, and/or oils. Such excipients may optionally be included in the pharmaceutical formulations of the invention.

Non-limiting examples of formulations and methods of delivery of nucleic acid molecules, modified nucleic acid molecules and/or mmRNA are taught in U.S. Provisional Patent Application No. 61/576,705, filed Dec. 16, 2011, entitled Modified Nucleoside, Nucleotide, and Nucleic Acid Compositions, U.S. Provisional Patent Application No. 61/618,957, filed Apr. 2, 2012, entitled Modified Nucleoside, Nucleotide, and Nucleic Acid Compositions, U.S. Provisional Patent Application No. 61/648,244, filed May 17, 2012, entitled Modified Nucleoside, Nucleotide, and Nucleic Acid Compositions, U.S. Provisional Patent Application No. 61/681,712, filed Aug. 10, 2012, entitled Modified Nucleoside, Nucleotide, Nucleic Acid Compositions and U.S. Provisional Patent Application No. 61/696,381 filed Sep. 4, 2012, entitled Modified Nucleoside, Nucleotide and Nucleic Acid Compositions, and Nucleic Acid Compositions, U.S. Provisional Patent Application No. 61/709,303 filed Oct. 3, 2012, entitled Modified Nucleoside, Nucleotide and Nucleic Acid Compositions, U.S. Provisional Patent Application No. 61/712,490 filed Oct. 11, 2012, entitled Modified Nucleoside, Nucleotide and Nucleic Acid Compositions, and International Pub. No. PCT/US2012/069610 filed Dec. 14, 2012 entitled Modified Nucleoside, Nucleotide, and Nucleic Acid Compositions, the contents of each of which are herein incorporated by reference in its entirety.

In one embodiment, the nucleic acid molecules, modified nucleic acid molecules and/or mmRNA are administered intramuscularly.

In one embodiment, the nucleic acid molecules, modified nucleic acid molecules and/or mmRNA are formulated for administration intramuscularly.

In one embodiment, the nucleic acid molecules, modified nucleic acid molecules and/or mmRNA are administered intradermally.

In one embodiment, the nucleic acid molecules, modified nucleic acid molecules and/or mmRNA are formulated for administration intradermally.

Lipidoids

The synthesis of lipidoids has been extensively described and formulations containing these compounds are particularly suited for delivery of modified nucleic acid molecules or mmRNA (see Mahon et al., Bioconjug Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

While these lipidoids have been used to effectively deliver double stranded small interfering RNA molecules in rodents and non-human primates (see Akinc et al., Nat Biotechnol. 2008 26:561-569; Frank-Kamenetsky et al., Proc Natl Acad Sci USA. 2008 105:11915-11920; Akinc et al., Mol Ther. 2009 17:872-879; Love et al., Proc Natl Acad Sci USA. 2010 107:1864-1869; Leuschner et al., Nat Biotechnol. 2011 29:1005-1010; all of which is incorporated herein in their entirety), the present disclosure describes their formulation and use in delivering single stranded nucleic acid molecules, modified nucleic acid molecules or mmRNA. Complexes, micelles, liposomes or particles can be prepared containing these lipidoids and therefore, can result in an effective delivery of the nucleic acid molecules, modified nucleic acid molecules or mmRNA, as judged by the production of an encoded protein, following the injection of a lipidoid formulation via localized and/or systemic routes of administration. Lipidoid complexes of nucleic acid molecules, modified nucleic acid molecules or mmRNA can be administered by various means including, but not limited to, intravenous, intramuscular, intradermal or subcutaneous routes. As a non-limiting example, formulations of lipidoids and nucleic acid molecules, modified nucleic acid molecules and/or mmRNA may be administered intramuscularly. As another non-limiting example, formulations of lipidoids nucleic acid molecules, modified nucleic acid molecules and/or mmRNA may be administered intradermally.

In vivo delivery of nucleic acids may be affected by many parameters, including, but not limited to, the formulation composition, nature of particle PEGylation, degree of loading, oligonucleotide to lipid ratio, and biophysical parameters such as, but not limited to, particle size (Akinc et al., Mol Ther. 2009 17:872-879; herein incorporated by reference in its entirety). As an example, small changes in the anchor chain length of poly(ethylene glycol) (PEG) lipids may result in significant effects on in vivo efficacy. Formulations with the different lipidoids, including, but not limited to penta[3-(1-laurylaminopropionyl)]-triethylenetetramine hydrochloride (TETA-5LAP; aka 98N12-5, see Murugaiah et al., Analytical Biochemistry, 401:61 (2010); the contents of which are herein incorporated by reference in its entirety), C12-200 (including derivatives and variants), and MD1, can be tested for in vivo activity.

Figure 2:
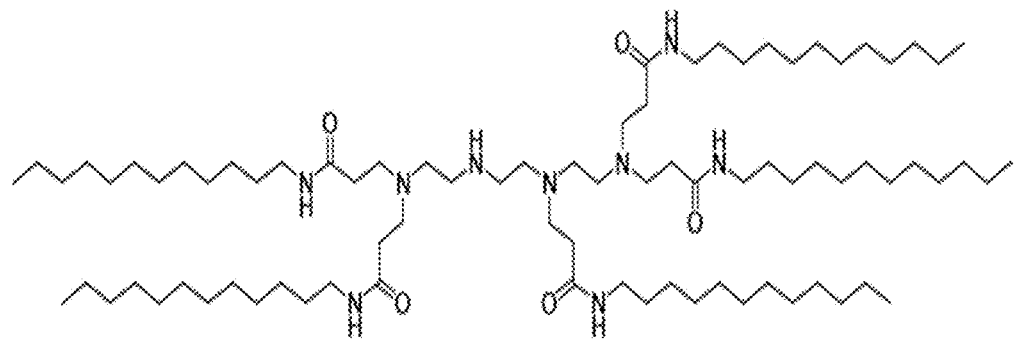
FIG. 2 illustrates lipid structures in the prior art useful in the present invention. Shown are the structures for 98N12-5 (TETA5-LAP), DLin-DMA, DLin-K-DMA (2,2-Dilinoleyl-4-dimethylaminomethyl-[1,3]-dioxolane), DLin-KC2-DMA, DLin-MC3-DMA and C12-200.
Figure 2:
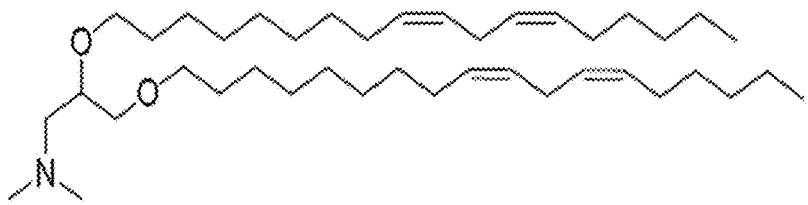
Figure 2:
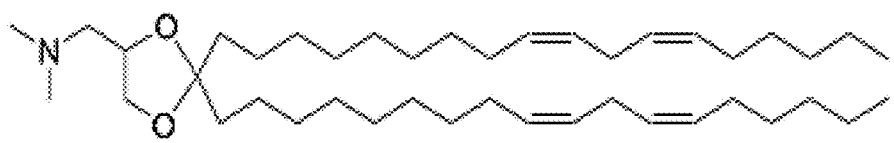
Figure 2:
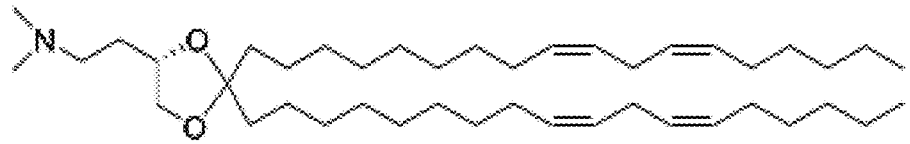
Figure 2:
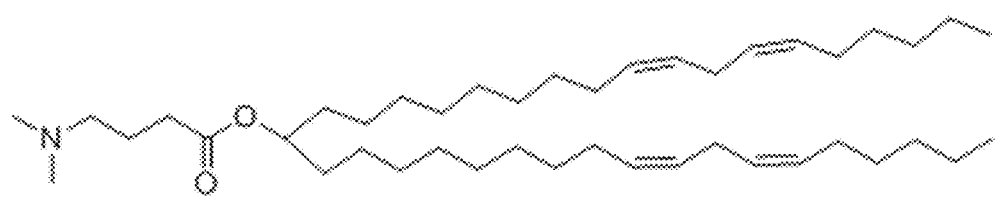
Figure 2:
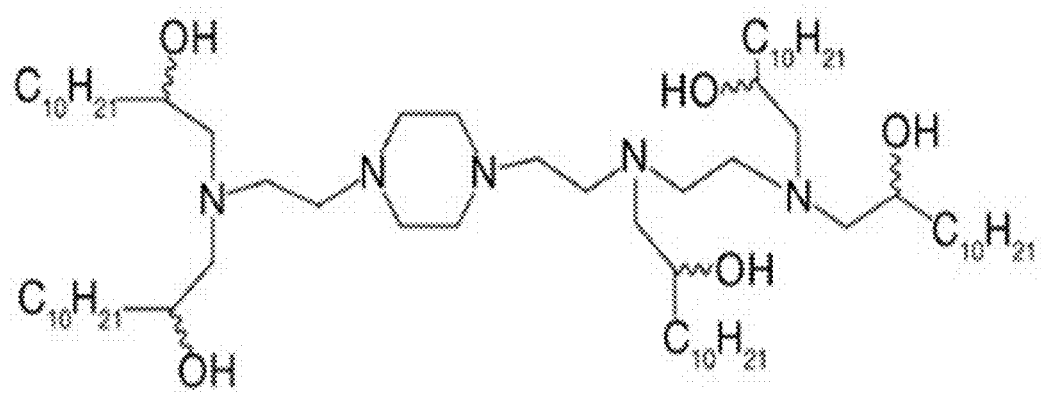

The lipidoid referred to herein as "98N12-5" is disclosed by Akinc et al., Mol Ther. 2009 17:872-879 and is incorporated by reference in its entirety (See FIG. 2).

The lipidoid referred to herein as "C12-200" is disclosed by Love et al., Proc Natl Acad Sci USA. 2010 107:1864-1869 and Liu and Huang, Molecular Therapy. 2010 669-670 (see FIG. 2); both of which are herein incorporated by reference in their entirety. The lipidoid formulations can include particles comprising either 3 or 4 or more components in addition to nucleic acid molecules, modified nucleic acid molecules or mmRNA. As an example, formulations with certain lipidoids, include, but are not limited to, 98N12-5 and may contain 42% lipidoid, 48% cholesterol and 10% PEG (C14 alkyl chain length). As another example, formulations with certain lipidoids, include, but are not limited to, C12-200 and may contain 50% lipidoid, 10% disteroylphosphatidyl choline, 38.5% cholesterol, and 1.5% PEG-DMG. In one embodiment, formulations of nucleic acid molecules, modified nucleic acid molecules or mmRNA comprising C12-200 may be administered intramuscularly. In another embodiment, formulations of nucleic acid molecules, modified nucleic acid molecules or mmRNA comprising C12-200 may be administered intradermally.

In one embodiment, a nucleic acid molecule, modified nucleic acid molecule or mmRNA formulated with a lipidoid for systemic intravenous administration can target the liver. For example, a final optimized intravenous formulation using nucleic acid molecule, modified nucleic acid molecule or mmRNA, and comprising a lipid molar composition of 42% 98N12-5, 48% cholesterol, and 10% PEG-lipid with a final weight ratio of about 7.5 to 1 total lipid to nucleic acid molecule, modified nucleic acid, or mmRNA, and a C14 alkyl chain length on the PEG lipid, with a mean particle size of roughly 50-60 nm, can result in the distribution of the formulation to be greater than 90% to the liver. (see, Akinc et al., Mol Ther. 2009 17:872-879; the contents of which is herein incorporated by reference in its entirety). In another example, an intravenous formulation using a C12-200 (see U.S. provisional application 61/175,770 and published international application WO2010129709, each of which is herein incorporated by reference in their entirety) lipidoid may have a molar ratio of 50/10/38.5/1.5 of C12-200/ disteroylphosphatidyl choline/cholesterol/PEG-DMG, with a weight ratio of 7 to 1 total lipid to nucleic acid molecule, modified nucleic acid molecule or mmRNA, and a mean particle size of 80 nm may be effective to deliver modified nucleic acid molecule or mmRNA to hepatocytes (see, Love et al., Proc Natl Acad Sci USA. 2010 107:1864-1869; the contents of which are herein incorporated by reference in its entirety). In another embodiment, an MD1 lipidoid-containing formulation may be used to effectively deliver nucleic acid molecule, modified nucleic acid molecule or mmRNA to hepatocytes in vivo. The characteristics of optimized lipidoid formulations for intramuscular or subcutaneous routes may vary significantly depending on the target cell type and the ability of formulations to diffuse through the extracellular matrix into the blood stream. While a particle size of less than 150 nm may be desired for effective hepatocyte delivery due to the size of the endothelial fenestrae (see, Akinc et al., Mol Ther. 2009 17:872-879; the contents of which are herein incorporated by reference in its entirety), use of a lipidoid-formulated nucleic acid molecules, modified nucleic acid molecules or mmRNA to deliver the formulation to other cells types including, but not limited to, endothelial cells, myeloid cells, and muscle cells may not be similarly size-limited. Use of lipidoid formulations to deliver siRNA in vivo to other non-hepatocyte cells such as myeloid cells and endothelium has been reported (see Akinc et al., Nat Biotechnol. 2008 26:561-569; Leuschner et al., Nat Biotechnol. 2011 29:1005-1010; Cho et al. Adv. Funct. Mater. 2009 19:3112-3118; 8th International Judah Folkman Conference, Cambridge, Mass. Oct. 8-9, 2010; the contents of each of which are herein incorporated by reference in its entirety). Effective delivery to myeloid cells, such as monocytes, lipidoid formulations may have a similar component molar ratio. Different ratios of lipidoids and other components including, but not limited to, disteroylphosphatidyl choline, cholesterol and PEG-DMG, may be used to optimize the formulation of the nucleic acid molecule, modified nucleic acid, or mmRNA for delivery to different cell types including, but not limited to, hepatocytes, myeloid cells, muscle cells, etc. For example, the component molar ratio may include, but is not limited to, 50% C12-200, 10% disteroylphosphatidyl choline, 38.5% cholesterol, and 1.5% PEG-DMG (see Leuschner et al., Nat Biotechnol 2011 29:1005-1010; the contents of which are herein incorporated by reference in its entirety). The use of lipidoid formulations for the localized delivery of nucleic acids to cells (such as, but not limited to, adipose cells and muscle cells) via either subcutaneous, intradermal or intramuscular delivery, may not require all of the formulation components desired for systemic delivery, and as such may comprise only the lipidoid and the nucleic acid molecule, modified nucleic acid molecule or mmRNA.

Combinations of different lipidoids may be used to improve the efficacy of nucleic acid molecule, modified nucleic acid molecule or mmRNA directed protein production as the lipidoids may be able to increase cell transfection by the nucleic acid molecule, modified nucleic acid molecule or mmRNA; and/or increase the translation of encoded protein (see Whitehead et al., Mol. Ther. 2011, 19:1688-1694, the contents of which are herein incorporated by reference in its entirety).

In one embodiment, the lipidoid may be prepared from the conjugate addition of alklamines to acrylates. As a non-limiting example, the lipidoid may be prepared by the methods described in International Patent Publication No. WO2014028487, the contents of which are herein incorporated by reference in its entirety. In one embodiment, the lipidoid may comprise a compound having formula (I), formula (II), formula (III), formula (IV) or formula (V) as described in International Patent Publication No. WO2014028487, the contents of which are herein incorporated by reference in its entirety. In one embodiment, the lipidoid may be biodegradable.

Liposomes, Lipoplexes, and Lipid Nanoparticles

The nucleic acid molecules, modified nucleic acid molecules and mmRNA of the invention can be formulated using one or more liposomes, lipoplexes, or lipid nanoparticles. In one embodiment, pharmaceutical compositions of nucleic acid molecule, modified nucleic acid molecule or mmRNA include liposomes. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physico-chemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

As a non-limiting example, liposomes such as synthetic membrane vesicles may be prepared by the methods, apparatus and devices described in US Patent Publication No. US20130177638, US20130177637, US20130177636, US20130177635, US20130177634, US20130177633, US20130183375, US20130183373 and US20130183372 and International Patent Publication No WO2008042973, the contents of each of which are herein incorporated by reference in its entirety.

In one embodiment, pharmaceutical compositions described herein may include, without limitation, liposomes such as those formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (US20100324120; herein incorporated by reference in its entirety) and liposomes which may deliver small molecule drugs such as, but not limited to, DOXIL® from Janssen Biotech, Inc. (Horsham, Pa.). In one embodiment, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles Hum Gene Ther. 2008 19:125-132; U.S. Patent Publication Nos US20130122104 and US20130303587; the contents of each of which are incorporated herein in their entireties). The original manufacture method by Wheeler et al. was a detergent dialysis method, which was later improved by Jeffs et al. and is referred to as the spontaneous vesicle formation method. The liposome formulations may be composed of 3 to 4 lipid components in addition to the nucleic acid molecule, modified nucleic acid molecule or mmRNA. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations may contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethyl-aminopropane (DLenDMA), as described by Heyes et al. In some embodiments, liposome formulations may comprise from about about 25.0% cholesterol to about 40.0% cholesterol, from about 30.0% cholesterol to about 45.0% cholesterol, from about 35.0% cholesterol to about 50.0% cholesterol and/or from about 48.5% cholesterol to about 60% cholesterol. In a preferred embodiment, formulations may comprise a percentage of cholesterol selected from the group consisting of 28.5%, 31.5%, 33.5%, 36.5%, 37.0%, 38.5%, 39.0% and 43.5%. In some embodiments, formulations may comprise from about 5.0% to about 10.0% DSPC and/or from about 7.0% to about 15.0% DSPC.

In one embodiment, pharmaceutical compositions may include liposomes which may be formed to deliver nucleic acid molecules, modified nucleic acid molecules or mmRNA which may encode at least one immunogen. The nucleic acid molecules, modified nucleic acid molecules or mmRNA may be encapsulated by the liposome and/or it may be contained in an aqueous core which may then be encapsulated by the liposome (see International Pub. Nos. WO2012031046, WO2012031043, WO2012030901 and WO2012006378 and US Patent Publication No. US20130189351, US20130195969 and US20130202684; the contents of each of which are herein incorporated by reference in their entirety).

In another embodiment, liposomes may be formulated for targeted delivery. As a non-limiting example, the liposome may be formulated for targeted delivery to the liver. The liposome used for targeted delivery may include, but is not limited to, the liposomes described in and methods of making liposomes described in US Patent Publication No. US20130195967, the contents of which are herein incorporated by reference in its entirety.

In another embodiment, the nucleic acid molecules, modified nucleic acid molecules or mmRNA, which may encode an immunogen or any other polypeptide of interest described herein, may be formulated in a cationic oil-in-water emulsion where the emulsion particle comprises an oil core and a cationic lipid which can interact with the mmRNA anchoring the molecule to the emulsion particle (see International Pub. No. WO2012006380; the contents of which are herein incorporated by reference in its entirety).

In one embodiment, formulations comprising liposomes and nucleic acid molecules, modified nucleic acid molecules or mmRNA may be administered intramuscularly.

In one embodiment, formulations comprising liposomes and nucleic acid molecules, modified nucleic acid molecules or mmRNA may be administered intradermally.

In one embodiment, the nucleic acid molecules, modified nucleic acid molecules or mmRNA may be formulated in a water-in-oil emulsion comprising a continuous hydrophobic phase in which the hydrophilic phase is dispersed. As a non-limiting example, the emulsion may be made by the methods described in International Publication No. WO201087791, herein incorporated by reference in its entirety.

In another embodiment, the lipid formulation may include at least cationic lipid, a lipid which may enhance transfection and a least one lipid which contains a hydrophilic head group linked to a lipid moiety (International Pub. No. WO2011076807 and U.S. Pub. No. 20110200582; each of which is herein incorporated by reference in their entirety). In another embodiment, the nucleic acid molecules, modified nucleic acid molecules or modified mRNA encoding an immunogen may be formulated in a lipid vesicle which may have crosslinks between functionalized lipid bilayers (see U.S. Pub. No. 20120177724, the contents of which are herein incorporated by reference in its entirety).

In one embodiment, the nucleic acid molecules, modified nucleic acids and/or mmRNA may be formulated in a lipsome as described in International Patent Publication No. WO2013086526, herein incorporated by reference in its entirety. The nucleic acid molecules, modified nucleic acids and/or mmRNA may be encapsulated in a liposome using reverse pH gradients and/or optimized internal buffer compositions as described in International Patent Publication No. WO2013086526, the contents of which are herein incorporated by reference in its entirety.

In one embodiment, the nucleic acid molecules, modified nucleic acids and/or mmRNA may be delivered in a liposome comprising an ionizable lipid. As a non-limiting example, the ionizable lipid may be any of the formulas of ionizable lipids described in International Patent Publication No. WO2013149140 and US Patent Publication No. US20130330401, the contents of each of which are herein incorporated by reference in their entirety.

In one embodiment, the nucleic acid molecules, modified nucleic acids and/or mmRNA may be administered using the nucleic acid based therapy methods described in International Publication No. WO2008042973 and U.S. Pat. No. 8,642,076, the contents of each of which are herein incorporated by reference in its entirety. As a non-limiting example, the nucleic acid molecules, modified nucleic acids and/or mmRNA may be administered by association complexes such as liposomes and lipoplexes as described in International Publication No. WO2008042973, the contents of which are herein incorporated by reference in its entirety. As another non-limiting example, the liposomes or lipoplexes may include a polyamine compound or a lipid moiety described in International Publication No. WO2008042973 and U.S. Pat. No. 8,642,076, the contents of each of which are herein incorporated by reference in its entirety. As yet another non-limiting example, the liposomes or lipoplexes may include a polyamine compound or a lipid moiety described by formula (XV) in U.S. Pat. No. 8,642,076, the contents of which are herein incorporated by reference in its entirety.

In one embodiment, the pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); herein incorporated by reference in its entirety) and hyaluronan-coated liposomes (Quiet Therapeutics, Israel).

In one embodiment, the nucleic acid molecules, modified nucleic acid molecules and/or mmRNA may be formulated in a liposome which can target the $\alpha_v\beta_3$ integrin receptor such as, but not limited to, the liposomes described in European Patent No. EP 1404860, the contents of which are herein incorporated by reference in its entirety.

In one embodiment, the nucleic acid molecules, modified nucleic acid molecules and/or mmRNA may be formulated in amphoteric liposomes such as, but not limited to, the liposomes comprising amphoteric lipids described in U.S. Pat. No. 8,580,297, the contents of which are herein incorporated by reference in its entirety.

In one embodiment, the liposomes for formulation and/or delivery of the nucleic acid molecules, modified nucleic acid molecules and/or mmRNA may be made using the apparatus and/or methods described in US Patent Publication No. US20140044772, the contents of which are herein incorporated by reference in its entirety. As a non-limiting example, the method may include providing a buffer solution in a first reservoir and a lipid solution in a second reservoir and continuously diluting the lipid solution with the buffer solution in a mixing chamber until a liposome is produced. The lipid solution may also comprise an organic solvent such as, but not limited to, a lower alkanol (see e.g., the method described by Maclachlan et al. in US Patent Publication No. US20140044772, the contents of which are herein incorporated by reference in its entirety).

In one embodiment, the liposomes for formulation and/or delivery of the nucleic acid molecules, modified nucleic acid molecules and/or mmRNA may be internal structured self assembled liposomes (ISSALs). As a non-limiting example, the ISSAL may be any of the ISSALs described in International Patent Publication No. WO2014026284, the contents of which are herein incorporated by reference in its entirety. In one embodiment, the ISSAL comprises a nuclear core molecule or complex comprising a first affinity enhance molecule and a liposome encompassing the nuclear core molecule or complex (see e.g., International Patent Publication No. WO2014026284, the contents of which are herein incorporated by reference in its entirety).

In one embodiment, the cationic lipid may be a low molecular weight cationic lipid such as those described in US Patent Application Nos. 20130090372, 20130274504 and 20130274523, the contents of each of which are herein incorporated by reference in its entirety.

In one embodiment, the nucleic acid molecules, modified nucleic acid molecules or modified mRNA may be formulated in a lipid vesicle which may have crosslinks between functionalized lipid bilayers.

In one embodiment, the nucleic acid molecules, modified nucleic acid molecules or modified mRNA may be formulated in a lipid-polycation complex. The formation of the lipid-polycation complex may be accomplished by methods known in the art and/or as described in U.S. Pub. No. 20120178702, the contents of which are herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012013326 or US Patent Pub. No. US20130142818; each of which is herein incorporated by reference in its entirety. In another embodiment, the nucleic acid molecules, modified nucleic acid molecules or modified mRNA may be formulated in a lipid-polycation complex which may further include a neutral lipid such as, but not limited to, cholesterol or dioleoyl phosphatidylethanolamine (DOPE).

In one embodiment, the nucleic acid molecules, modified nucleic acid molecules, modified mRNA may be formulated in an aminoalcohol lipidoid. Aminoalcohol lipidoids which may be used in the present invention may be prepared by the methods described in U.S. Pat. No. 8,450,298, herein incorporated by reference in its entirety.

The liposome formulation may be influenced by, but not limited to, the selection of the cationic lipid component, the degree of cationic lipid saturation, the nature of the PEGylation, ratio of all components and biophysical parameters such as size. In one example by Semple et al. (Semple et al. Nature Biotech. 2010 28:172-176; herein incorporated by reference in its entirety), the liposome formulation was composed of 57.1% cationic lipid, 7.1% dipalmitoylphosphatidylcholine, 34.3% cholesterol, and 1.4% PEG-c-DMA. As another example, changing the composition of the cationic lipid could more effectively deliver siRNA to various antigen presenting cells (Basha et al. Mol Ther. 2011 19:2186-2200; the content of which are herein incorporated by reference in its entirety). In some embodiments, liposome formulations may comprise from about 35 to about 45% cationic lipid, from about 40% to about 50% cationic lipid, from about 50% to about 60% cationic lipid and/or from about 55% to about 65% cationic lipid. In some embodiments, the ratio of lipid to nucleic acid molecule, modified nucleic acid molecule, mRNA or mmRNA in liposomes may be from about 5:1 to about 20:1, from about 10:1 to about 25:1, from about 15:1 to about 30:1, from about 20:1 to about 21:1 and/or at least 30:1.

In some embodiments, the ratio of PEG in the lipid nanoparticle (LNP) formulations may be increased or decreased and/or the carbon chain length of the PEG lipid may be modified from C14 to C18 to alter the pharmacokinetics and/or biodistribution of the LNP formulations. As a non-limiting example, LNP formulations may contain from about 0.5% to about 3.0%, from about 1.0% to about 3.5%, from about 1.5% to about 4.0%, from about 2.0% to about 4.5%, from about 2.5% to about 5.0% and/or from about 3.0% to about 6.0% of the lipid molar ratio of PEG-c-DOMG as compared to the cationic lipid, DSPC and cholesterol. In another embodiment the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In one embodiment, the formulation comprising the modified mRNA is a nanoparticle which may comprise at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In another aspect, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in US Patent Publication No. US20130150625, the contents of which is herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

In one embodiment, the cationic lipid may be selected from, but not limited to, a cationic lipid described in International Publication Nos. WO2012040184, WO2011153120, WO2011149733, WO2011090965, WO2011043913, WO2011022460, WO2012061259, WO2012054365, WO2012044638, WO2010080724, WO201021865, WO2008103276, WO2013086373 and WO2013086354, U.S. Pat. Nos. 7,893,302, 7,404,969, 8,283,333, 8,466,122 and 8,569,256 and US Patent Publication No. US20100036115, US20120202871, US 20130064894, US20130129785, US20130150625, US20130178541, US20130225836 and US20140039032; the contents of each of which are herein incorporated by reference in their entirety. In another embodiment, the cationic lipid may be selected from, but not limited to, formula A described in International Publication Nos. WO2012040184, WO2011153120, WO2011149733, WO2011090965, WO2011043913, WO2011022460, WO2012061259, WO2012054365, WO2012044638 and WO2013116126 or US Patent Publication No. US20130178541 and US20130225836; the contents of each of which is herein incorporated by reference in their entirety. In yet another embodiment, the cationic lipid may be selected from, but not limited to, formula CLI-CLXXIX of International Publication No. WO2008103276, formula CLI-CLXXIX of U.S. Pat. No. 7,893,302, formula CLI-CLXXXII of U.S. Pat. No. 7,404,969 and formula I-VI of US Patent Publication No. US20100036115, formula I of US Patent Publication No US20130123338; each of which is herein incorporated by reference in their entirety. As a non-limiting example, the cationic lipid may be selected from (20Z,23Z)—N,N-dimethylnonacosa-20,23-dien-10-amine, (17Z,20Z)—N,N-dimemylhexacosa-17,20-dien-9-amine, (1Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimethyloctacosa-19,22-dien-9-amine, (18Z,21 Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethyl-heptacosan-10-amine, (20Z,23Z)—N-ethyl-N-methylnona-cosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1S,2R)-2-octylcyclopropyl]eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine,N,N-dimethyl-1-[(1S,2S)-2-{[(1R,2R)-2-pentylcyclopropyl]methyl}cyclopropyl]nonadecan-10-amine,N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11 Z,14Z)-icosa-11,14-dien-1-yloxy]-N,N-dimethylpro-pan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy) propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentyl-cyclopropyl]methyl}cyclopropyl]octyl}oxy)propan-2-amine, N,N-dimethyl-1-{[8-(2-oclylcyclopropyl)octyl]oxy}-3-(octyloxy)propan-2-amine and (11E,20Z,23Z)—N,N-dimethylnonacosa-11,20,2-trien-10-amine or a pharmaceutically acceptable salt or stereoisomer thereof. In another embodiment, the cationic lipid may selected from, but not limited to, Formula (I) of U.S. Patent Application No. 20130064894, the contents of which are herein incorporated by reference in its entirety.

In one embodiment, the cationic lipid may be synthesized by methods known in the art and/or as described in International Publication Nos. WO2012040184, WO2011153120, WO2011149733, WO2011090965, WO2011043913, WO2011022460, WO2012061259, WO2012054365, WO2012044638, WO2010080724, WO201021865, WO2013086373, WO2013086354; the contents of each of which are herein incorporated by reference in their entirety.

In another embodiment, the cationic lipid may be a trialkyl cationic lipid. Non-limiting examples of trialkyl cationic lipids and methods of making and using the trialkyl cationic lipids are described in International Patent Publication No. WO2013126803, the contents of which are herein incorporated by reference in its entirety.

In one embodiment, the cationic lipid may have a positively charged hydrophilic head and a hydrophobic tail that are connected via a linker structure. As a non-limiting example, the hydrophilic head group may be primary, secondary, tertiary amines or quaternary ammonium salts. As another non-limiting example, the lipids may have guanidino, imidazole, pyridinium, phosphorus, and arsenic groups.

In one embodiment, the lipid or lipids which may be used in the formulation and/or delivery of nucleic acid molecules, modified nucleic acid molecules and/or mmRNA described herein may be, but is not limited to, 1,2-Dioleoyl-sn-glycero-3-phosphatidylcholine (DOPC), 1,2-Dioleoyl-sn-glycero-3-phosphatidylethanolamine (DOPE), cholesterol, N-[1-(2,3-Dioleyloxy)propyl]N,N,N-trimethylammonium chloride (DOTMA), 1,2-Dioleoyloxy-3-trimethylammonium-propane (DOTAP), Dioctadecylamidoglycylspermine (DOGS), N-(3-Aminopropyl)-N,N-dimethyl-2,3-bis(dodecyloxy)-1-propanaminium bromide (GAP-DLRIE), cetyltrimethylammonium bromide (CTAB), 6-lauroxyhexyl ornithinate (LHON), 1-)2,3-Dioleoloxypropyl)2,4,6-trimethylpyridinium (2Oc), 2,3-Dioleyloxy-N-[2(sperminecarboxamido)-ehtyl]-N,N-dimethyl-1-propanaminium trifluoroacetate (DOSPA), 1,2-Dioleyl-3-trimethylammonium-propane (DOPA), N-(2-Hydroxyethyl)-N,N-dimethyl-2,3-bis(tetradecyloxy)-1-propanaminium bromide (MDRIE), Dimyristooxypropyl dimethyl hydroxyethyl ammonium bromide (DMRI), 3β-[N—(N',N'-Dimethylaminoethane)-carbamoyl]cholesterol (DC-Chol), Bis-guanidium-tren-cholesterol (BGTC), 1,3-Dioleoxy-2-(6-carboxy-spermyl)-propylamide (DOSPER), Dimethyloctadecylammonium bromide (DDAB), Dioctadecylamidoglicylspermidin (DSL), rac-[(2,3-Dioctadecyloxypropyl)(2-hydroxyethyl)]-dimethylammonium chloride (CLIP-1), rac-[2(2,3-Dihexadecyloxypropyl-oxymethyloxy)ehtyl]trimethylammonium chloride (CLIP-6), Ethyldimyrisotylphosphatidylcholine (EDMPC), 1,2-Distearyloxy-N,N-dimethyl-3-aminopropane (DSDMA), 1,2-Dimyristoyl-trimethylammoniumpropane (DMTAP), O,O'-Dimyristyl-N-lysyl asparate (DMKE), 1,2-Distearoyl-sn-glycero-3-ethylphosphocholine (DSEPC), N-Palmitoyl-D-erythro-spingosyl carbamoyl-spermine (CCS), N-t-Butyl-No-tetradecyl-3-tetradecylaminopropionamidine (diC14-amidine), Octadecenolyoxy[ethyl-2-heptadecenyl-3 hydroxyethyl]imidazolinium chloride (DOTIM), N1-Cholesteryloxycarbonyl-3,7-diazanonane-1,9-diamine (CDAN) and 2-(3-[Bis-(3-amino-propyl)-amino]propylamino)-N-ditetradecylcarbamoylme-ethyl-acetamide (RPR2091290).

In one embodiment, the cationic lipid which may be used in the formulations and delivery agents described herein may be represented by formula (I) in US Patent Publication No. US20140039032, the contents of which are herein incorporated by reference in its entirety. As a non-limiting example, the cationic lipid having formula (I) in US Patent Publication No. US20140039032 may be used in a lipid nanoparticle to deliver nucleic acid molecules (e.g., nucleic acid molecules, modified nucleic acid molecules and/or mmRNA described herein).

In one embodiment, the lipids which may be used in the formulations and/or delivery of the nucleic acid molecules, modified nucleic acid molecules and/or mmRNA described herein may be a cleavable lipid. As a non-limiting example, the cleavable lipid and/or pharmaceutical compositions comprising cleavable lipids may be those described in International Patent Publication No. WO2012170889, the contents of which are herein incorporated by reference in its entirety. As another non-limiting example, the cleavable lipid may be HGT4001, HGT4002, HGT4003, HGT4004 and/or HGT4005 as described in International Patent Publication No. WO2012170889, the contents of which are herein incorporated by reference in its entirety.

In one embodiment, the polymers which may be used in the formulation and/or delivery of nucleic acid molecules, modified nucleic acid molecules and/or mmRNA described herein may be, but is not limited to, poly(ethylene)glycol (PEG), polyethylenimine (PEI), dithiobis(succinimidylpropionate) (DSP), Dimethyl-3,3'-dithiobispropionimidate (DTBP), poly(ethylene imine) biscarbamate (PEIC), poly (L-lysine) (PLL), histidine modified PLL, poly(N-vinylpyrrolidone) (PVP), poly(propylenimine (PPI), poly(amidoamine) (PAMAM), poly(amido ethylenimine) (SS-PAEI), triehtylenetetramine (TETA), poly(β-aminoester), poly(4-hydroxy-L-proine ester) (PHP), poly(allylamine), poly(α-[4-aminobutyl]-L-glycolic acid (PAGA), Poly(D,L-lactic-co-glycolid acid (PLGA), Poly(N-ethyl-4-vinylpyridinium bromide), poly(phosphazene)s (PPZ), poly(phosphoester)s (PPE), poly(phosphoramidate)s (PPA), poly(N-2-hydroxypropylmethacrylamide) (pHPMA), poly(2-(dimethylamino) ethyl methacrylate) (pDMAEMA), poly(2-aminoethyl propylene phosphate) PPE_EA), Chitsoan, galactosylated chitosan, N-dodecylated chitosan, histone, collagen and dextran-spermine. In one embodiment, the polymer may be an inert polymer such as, but not limited to, PEG. In one embodiment, the polymer may be a cationic polymer such as, but not limited to, PEI, PLL, TETA, poly(allylamine), Poly(N-ethyl-4-vinylpyridinium bromide), pHPMA and pDMAEMA. In one embodiment, the polymer may be a biodegradable PEI such as, but not limited to, DSP, DTBP and PEIC. In one embodiment, the polymer may be biodegradable such as, but not limited to, histine modified PLL, SS-PAEI, poly(β-aminoester), PHP, PAGA, PLGA, PPZ, PPE, PPA and PPE-EA.

In one embodiment, the LNP formulation may contain PEG-c-DOMG at 3% lipid molar ratio. In another embodiment, the LNP formulation may contain PEG-c-DOMG at 1.5% lipid molar ratio.

In one embodiment, the LNP formulation may contain PEG-DMG 2000 (1,2-dimyristoyl-sn-glycero-3-phophoethanolamine-N-[methoxy(polyethylene glycol)-2000). In one embodiment, the LNP formulation may contain PEG-DMG 2000, a cationic lipid known in the art and at least one other component. In another embodiment, the LNP formulation may contain PEG-DMG 2000, a cationic lipid known in the art, DSPC and cholesterol. As a non-limiting example, the LNP formulation may contain PEG-DMG 2000, DLin-DMA, DSPC and cholesterol. As another non-limiting example the LNP formulation may contain PEG-DMG 2000, DLin-DMA, DSPC and cholesterol in a molar ratio of 2:40:10:48 (see e.g. Geall et al., Nonviral delivery of self-amplifying RNA vaccines, PNAS 2012; PMID: 22908294; herein incorporated by reference in its entirety).

In one embodiment, the LNP formulation may be formulated by the methods described in International Publication Nos. WO2011127255 or WO2008103276, the contents of each of which is herein incorporated by reference in their entirety. As a non-limiting example, nucleic acid molecules, modified nucleic acid molecules or modified RNA described herein may be encapsulated in LNP formulations as described in WO2011127255 and/or WO2008103276; each of which is herein incorporated by reference in their entirety. As another non-limiting example, nucleic acid molecules, modified nucleic acid molecules or modified RNA described herein may be formulated in a nanoparticle to be delivered by a parenteral route as described in U.S. Pub. No. 20120207845 and International Publication No. WO2014008334; the contents of each of which are herein incorporated by reference in its entirety.

In one embodiment, LNP formulations described herein comprising nucleic acid molecules, modified nucleic acid molecules or mmRNA may be administered intramusculary. The LNP formulation may comprise a cationic lipid described herein, such as, but not limited to, DLin-DMA, DLin-KC2-DMA, DLin-MC3-DMA, DODMA and C12-200.

In one embodiment, LNP formulations described herein comprising nucleic acid molecules, modified nucleic acid molecules or mmRNA may be administered intradermally. The LNP formulation may comprise a cationic lipid described herein, such as, but not limited to, DLin-DMA, DLin-KC2-DMA, DLin-MC3-DMA, DODMA and C12-200.

In one embodiment, the nucleic acid molecules, modified nucleic acid molecules and/or mmRNA may be formulated in a lipid nanoparticle made by the methods described in US Patent Publication No US20130156845 or International Publication No WO2013093648 or WO2012024526, the contents of each of which is herein incorporated by reference in its entirety.

The lipid nanoparticles described herein may be made in a sterile environment by the system and/or methods described in US Patent Publication No. US20130164400, the contents of which are herein incorporated by reference in its entirety.

In one embodiment, the lipid nanoparticles which may be used to deliver the nucleic acid molecules, modified nucleic acids and/or mmRNA may be Particle Replication in Non-wetting Templates (PRINT) nanoparticles as described by Morton et al. (Scalable Manufacture of Built-to-Order Nanomedicine: Spray Assisted Layer-by-layer Functionalization of PRINT nanoparticles, *Adv. Mat.* 2013, 25, 4707-4713; the contents of which is herein incorporated by reference in its entirety). The PRINT nanoparticles may be manufactured by the methods outlined by Morton et al. in order to generate uniform nanoparticles which may have a desired composition, size, shape and surface functionality. As a non-limiting example, the modified nucleic acid molecules and/or mmRNA may be formulated in PRINT nanoparticles. As another non-limiting example, the modified nucleic acid molecules and/or mmRNA may be formulated in PRINT nanoparticles for targeted interaction with cancer cells.

In one embodiment, LNP formulations described herein made by the PRINT methods and comprising nucleic acid molecules, modified nucleic acid molecules or mmRNA may be administered intramuscularly.

In one embodiment, LNP formulations described herein made by the PRINT methods and comprising nucleic acid molecules, modified nucleic acid molecules or mmRNA may be administered intradermally.

In one embodiment, the LNP formulation may be formulated in a nanoparticle such as a nucleic acid-lipid particle described in U.S. Pat. No. 8,492,359, the contents of which are herein incorporated by reference in its entirety. As a non-limiting example, the lipid particle may comprise one or more active agents or therapeutic agents; one or more cationic lipids comprising from about 50 mol % to about 85 mol % of the total lipid present in the particle; one or more non-cationic lipids comprising from about 13 mol % to about 49.5 mol % of the total lipid present in the particle; and one or more conjugated lipids that inhibit aggregation of particles comprising from about 0.5 mol % to about 2 mol % of the total lipid present in the particle. The nucleic acid in the nanoparticle may be the nucleic acid molecules, modified nucleic acids or mmRNA described herein and/or are known in the art.

In one embodiment, the lipid nanoparticle may comprise a lipidoid prepared by conjugate addition of alkamines to acrylates as described in International Patent Publication No. WO2014028487, the contents of which are herein incorporated by reference in its entirety.

In one embodiment, LNP formulations described herein may comprise a polycationic composition. As a non-limiting example, the polycationic composition may be selected from formula 1-60 of US Patent Publication No. US20050222064; herein incorporated by reference in its entirety. In another embodiment, the LNP formulations comprising a polycationic composition may be used for the delivery of the nucleic acid molecules, modified nucleic acid molecules or modified RNA described herein in vivo and/or in vitro.

In one embodiment, the LNP formulations described herein may additionally comprise a permeability enhancer molecule. Non-limiting permeability enhancer molecules are described in US Patent Publication No. US20050222064; the contents of which are herein incorporated by reference in its entirety.

In one embodiment, the nucleic acid molecules, modified nucleic acids or mmRNA may be formulated in a lyophilized gel-phase liposomal composition as described in US Publication No. US2012060293, the contents of which are herein incorporated by reference in its entirety.

The nanoparticle formulations may comprise a phosphate conjugate. The phosphate conjugate may increase in vivo circulation times and/or increase the targeted delivery of the nanoparticle. Phosphate conjugates for use with the present invention may be made by the methods described in International Application No. WO2013033438 or US Patent Publication No. US20130196948, the contents of each of which are herein incorporated by reference in its entirety. As a non-limiting example, the phosphate conjugates may include a compound of any one of the formulas described in International Application No. WO2013033438, herein incorporated by reference in its entirety.

The nanoparticle formulation may comprise a polymer conjugate. The polymer conjugate may be a water soluble conjugate. The polymer conjugate may have a structure as described in U.S. Patent Application No. 20130059360, the contents of which are herein incorporated by reference in its entirety. In one aspect, polymer conjugates with the nucleic acid molecules, modified nucleic acids or mmRNA of the present invention may be made using the methods and/or segmented polymeric reagents described in U.S. Patent Application No. 20130072709, herein incorporated by reference in its entirety. In another aspect, the polymer conjugate may have pendant side groups comprising ring moieties such as, but not limited to, the polymer conjugates described in US Patent Publication No. US20130196948, the contents of which are herein incorporated by reference in its entirety.

The nanoparticle formulations may comprise a conjugate to enhance the delivery of nanoparticles of the present invention in a subject. Further, the conjugate may inhibit phagocytic clearance of the nanoparticles in a subject. In one aspect, the conjugate may be a "self" peptide designed from the human membrane protein CD47 (e.g., the "self" particles described by Rodriguez et al (Science 2013 339, 971-975), herein incorporated by reference in its entirety). As shown by Rodriguez et al. the self peptides delayed macrophage-mediated clearance of nanoparticles which enhanced delivery of the nanoparticles. In another aspect, the conjugate may be the membrane protein CD47 (e.g., see Rodriguez et al. Science 2013 339, 971-975, herein incorporated by reference in its entirety). Rodriguez et al. showed that, similarly to "self" peptides, CD47 can increase the circulating particle ratio in a subject as compared to scrambled peptides and PEG coated nanoparticles.

In one embodiment, the nucleic acid molecules, modified nucleic acids and mmRNA of the present invention are formulated in nanoparticles which comprise a conjugate to enhance the delivery of the nanoparticles of the present invention in a subject. The conjugate may be the CD47 membrane or the conjugate may be derived from the CD47 membrane protein, such as the "self" peptide described previously. In another aspect the nanoparticle may comprise PEG and a conjugate of CD47 or a derivative thereof. In yet another aspect, the nanoparticle may comprise both the "self" peptide described above and the membrane protein CD47.

In another aspect, a "self" peptide and/or CD47 protein may be conjugated to a virus-like particle or pseudovirion, as described herein for delivery of the nucleic acid molecules, modified nucleic acid molecules and/or mmRNA of the present invention.

In one embodiment, the conjugate may be for conjugated delivery of the nucleic acid molecules, modified nucleic acids and/or mmRNA to the liver. As a non-limiting example, the conjugate delivery system described in US Patent Publication No. US20130245091, the contents of which are herein incorporated by reference in its entirety, may be used to deliver the nucleic acid molecules, modified nucleic acids and/or mmRNA described herein.

In one embodiment, a non-linear multi-block copolymer-drug conjugate may be used to deliver active agents such as the polymer-drug conjugates and the formulas described in International Publication No. WO2013138346, incorporated by reference in its entirety. As a non-limiting example, a non-linear multi-block copolymer may be conjugated to a nucleic acid such as the nucleic acid molecules, modified nucleic acids and/or mmRNA described herein. As another non-limiting example, a non-linear multi-block copolymer may be conjugated to a nucleic acid such as the modified nucleic acids and/or mmRNA described herein to treat intraocular neovascular diseases.

In another embodiment, HIF-1 inhibitors may be conjugated to or dispersed in controlled release formulations such as a polymer-conjugate as described in International Publication No. WO2013138343, the contents of which are herein incorporated by reference in its entirety. Nucleic acid molecules, modified nucleic acids or mmRNA described herein may encode HIF-1 inhibitors and may be delivered using the controlled release formulations of polymer-conjugates. The polymer-conjugates comprising HIF-1 inhibitors may be used to treat a disease and/or disorder that is associated with vascularization such as, but not limited to, cancer, obesity, and ocular diseases such as wet AMD.

In one embodiment, albumin-binding lipids may be conjugated to cargo (e.g., the nucleic acid molecules, modified nucleic acid molecules, mmRNA and formulations thereof) for targeted delivery to the lymph nodes. Non-limiting examples of albumin-binding lipids and conjugates thereof are described in International Patent Publication No. WO2013151771, the contents of which are herein incorporated by reference in its entirety.

In another embodiment, pharmaceutical compositions comprising the nucleic acid molecules, modified nucleic acids and/or mmRNA of the present invention and a conjugate which may have a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in US Patent Publication No. US20130184443, the contents of which are herein incorporated by reference in its entirety.

The nanoparticle formulations may be a carbohydrate nanoparticle comprising a carbohydrate carrier and a nucleic acid molecule (e.g., mRNA) or modified nucleic acid molecule (e.g., mmRNA). As a non-limiting example, the carbohydrate carrier may include, but is not limited to, an anhydride-modified phytoglycogen or glycogen-type material, phtoglycogen octenyl succinate, phytoglycogen beta-dextrin, anhydride-modified phytoglycogen beta-dextrin. (See e.g., International Publication No. WO2012109121; the contents of which are herein incorporated by reference in its entirety).

Nanoparticle formulations of the present invention may be coated with a surfactant or polymer in order to improve the delivery of the particle. In one embodiment, the nanoparticle may be coated with a hydrophilic coating such as, but not limited to, PEG coatings and/or coatings that have a neutral surface charge. The hydrophilic coatings may help to deliver nanoparticles with larger payloads such as, but not limited to, nucleic acid molecules, modified nucleic acid molecules or modified mRNA within the central nervous system. As a non-limiting example nanoparticles comprising a hydrophilic coating and methods of making such nanoparticles are described in US Patent Publication No. US20130183244, the contents of which are herein incorporated by reference in its entirety.

In one embodiment, the lipid nanoparticles of the present invention may be hydrophilic polymer particles. Non-limiting examples of hydrophilic polymer particles and methods of making hydrophilic polymer particles are described in US Patent Publication No. US20130210991, the contents of which are herein incorporated by reference in its entirety.

In another embodiment, the lipid nanoparticles of the present invention may be hydrophobic polymer particles.

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In one embodiment, the internal ester linkage may be located on either side of the saturated carbon. Non-limiting examples of reLNPs include,

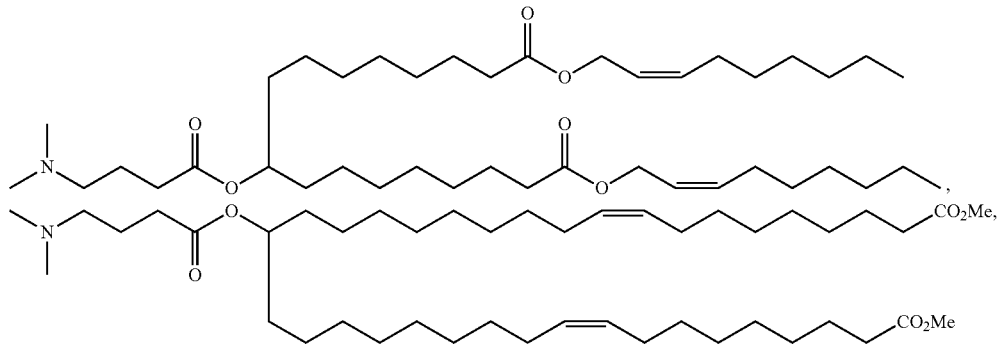

-continued

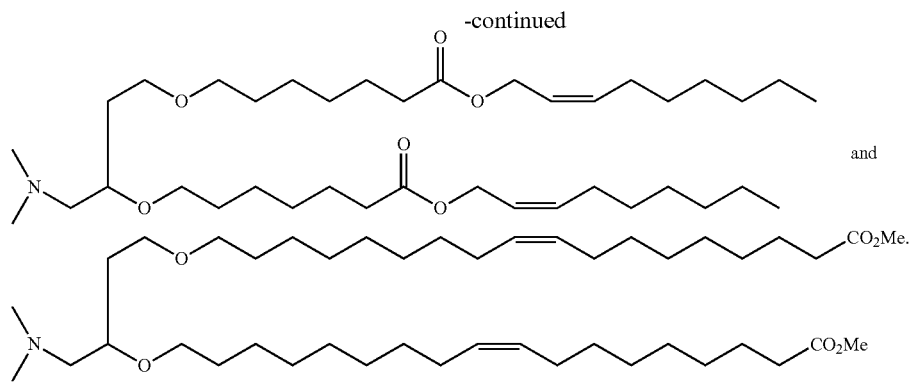

and

In one embodiment, formulations comprising reLNPs and nucleic acid molecules, modified nucleic acid molecules or mmRNA may be administered intramuscularly.

In one embodiment, formulations comprising reLNPs and nucleic acid molecules, modified nucleic acid molecules or mmRNA may be administered intradermally.

In one embodiment, an immune response may be elicited by delivering a lipid nanoparticle which may include a nanospecies, a polymer and an immunogen. (U.S. Publication No. 20120189700 and International Publication No. WO2012099805; each of which is herein incorporated by reference in their entirety). The polymer may encapsulate the nanospecies or partially encapsulate the nanospecies. The immunogen may be a recombinant protein encoded by a nucleic acid molecule, modified nucleic acid molecule or a modified RNA described herein. In one embodiment, the lipid nanoparticle may be formulated for use in a vaccine such as, but not limited to, against a pathogen.

Lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles may be removed from the mucosla tissue within seconds or within a few hours. Large polymeric nanoparticles (200 nm-500 nm in diameter) which have been coated densely with a low molecular weight polyethylene glycol (PEG) diffused through mucus only 4 to 6-fold lower than the same particles diffusing in water (Lai et al. PNAS 2007 104(5):1482-487; Lai et al. Adv Drug Deliv Rev. 2009 61(2): 158-171; each of which is herein incorporated by reference in their entirety). The transport of nanoparticles may be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier may be made as described in U.S. Pat. No. 8,241,670 or International Patent Publication No. WO2013110028, the contents of each of which are herein incorporated by reference in its entirety.

The lipid nanoparticle engineered to penetrate mucus may comprise a polymeric material (i.e. a polymeric core) and/or a polymer-vitamin conjugate and/or a tri-block co-polymer. The polymeric material may include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material may be biodegradable and/or biocompatible. Non-limiting examples of biocompatible polymers are described in International Patent Publication No. WO2013116804, the contents of which are herein incorporated by reference in its entirety. The polymeric material may additionally be irradiated. As a non-limiting example, the polymeric material may be gamma irradiated (See e.g., International App. No. WO201282165, herein incorporated by reference in its entirety). Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly (lactic acid-co-glycolic acid) (PLGA), poly(L-lactic acid-co-glycolic acid) (PLLGA), poly(D,L-lactide) (PDLA), poly (L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly (ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth) acrylate) (PMMA), poly(ethyl(meth)acrylate), poly(butyl (meth)acrylate), poly(isobutyl(meth)acrylate), poly(hexyl (meth)acrylate), poly(isodecyl(meth)acrylate), poly(lauryl (meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxalkanoates, polypropylene fumarate, polyoxymethylene, poloxamers, poly(ortho)esters, poly(butyric acid), poly(valeric acid), poly(lactide-co-caprolactone), PEG-PLGA-PEG and trimethylene carbonate, polyvinylpyrrolidone. The lipid nanoparticle may be coated or associated with a co-polymer such as, but not limited to, a block co-polymer, and (poly(ethylene glycol))-(poly(propylene oxide))-(poly(ethylene glycol)) triblock copolymer (see e.g., US Publication 20120121718 and US Publication 20100003337 and U.S. Pat. No. 8,263,665; each of which is herein incorporated by reference in their entirety). The co-polymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. Angew. Chem. Int. Ed. 2011 50:2597-2600; the contents of which are herein incorporated by reference in its entirety). A non-limiting scalable method to produce nanoparticles which can penetrate human mucus is described by Xu et al. (See e.g., J Control Release 2013, 170(2):279-86; the contents of which are herein incorporated by reference in its entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

The lipid nanoparticle engineered to penetrate mucus may include surface altering agents such as, but not limited to, mmRNA, anionic proteins (e.g., bovine serum albumin), surfactants (e.g., cationic surfactants such as for example dimethyldioctadecylammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin (34 dornase alfa, neltenexine, erdosteine) and various DNases including rhDNase. The surface altering agent may be embedded or enmeshed in the particle's surface or disposed (e.g., by coating, adsorption, covalent linkage, or other process) on the surface of the lipid nanoparticle. (see e.g., US Publication 20100215580, US Publication 20080166414 and US20130164343; each of which is herein incorporated by reference in their entirety).

In one embodiment, the mucus penetrating lipid nanoparticles may comprise at least one mmRNA described herein. The mmRNA may be encapsulated in the lipid nanoparticle and/or disposed on the surface of the particle. The mmRNA may be covalently coupled to the lipid nanoparticle. Formulations of mucus penetrating lipid nanoparticles may comprise a plurality of nanoparticles. Further, the formulations may contain particles which may interact with the mucus and alter the structural and/or adhesive properties of the surrounding mucus to decrease mucoadhesion which may increase the delivery of the mucus penetrating lipid nanoparticles to the mucosal tissue.

In another embodiment, the mucus penetrating lipid nanoparticles may be a hypotonic formulation comprising a mucosal penetration enhancing coating. The formulation may be hypotonice for the epithelium to which it is being delivered. Non-limiting examples of hypotonic formulations may be found in International Patent Publication No. WO2013110028, the contents of which are herein incorporated by reference in its entirety.

In one embodiment, in order to enhance the delivery through the mucosal barrier the formulation may comprise or be a hypotonic solution. Hypotonic solutions were found to increase the rate at which mucoinert particles such as, but not limited to, mucus-penetrating particles, were able to reach the vaginal epithelial surface (See e.g., Ensign et al. Biomaterials 2013 34(28):6922-9; the contents of which is herein incorporated by reference in its entirety).

In one embodiment, in order to reduce the mucoadhesive properties of a nanoparticle described herein, the nanoparticle may be coated with and/or associated with a triblock copolymer as described in US Patent Publication No. US20130236556 and International Patent Publication No. WO2013166385, the contents of each of which are herein incorporated by reference in its entirety. As a non-limiting example, the triblock copolymer may be a poly(ethylene glycol)-polypropylene oxide)-poly(ethylene glycol) triblock copolymer as described in US Patent Publication No. US20130236556 and International Patent Publication No. WO2013166385, the contents of each of which are herein incorporated by reference in its entirety. As another non-limiting example, the nanoparticle with reduced mucoadhesive may be prepared by the methods described by Lai et al in US Patent Publication No. US20130236556 and International Patent Publication No. WO2013166385, the contents of each of which are herein incorporated by reference in its entirety.

In one embodiment, mucus-penetrating particles (MPP) without any or with minimal use of polymeric carriers may be used to deliver and/or formulate the nucleic acid molecules, modified nucleic acid molecules and/or mmRNA described herein. As a non-limiting example, the MPP may be a nanocrystal or a particle as described in US Patent Publication No. US20130323179, the contents of which are herein incorporated by reference in its entirety.

In one embodiment, the nucleic acid molecules, modified nucleic acid molecules and/or mmRNA may be formulated in a mucoadhesive nanoparticle delivery system. As a non-limiting example, the mucoadhesive nanoparticle delivery system may be the systems and/or nanoparticles described in International Patent Publication No. WO2013188979, the contents of which are herein incorporated by reference in its entirety. The nanoparticles may comprise a plurality of amphiphilic macromolecules which may contain a hydrophobic portion, a hydrophilic portion having multiple functional moieties and a mucosal targeting moiety.

In one embodiment, the nucleic acid molecules, modified nucleic acid molecules and/or mmRNA may be formulated in lipid-based drug carriers which can penetrate through mucus linings. As a non-limiting example, the nucleic acid molecules, modified nucleic acid molecules and/or mmRNA may be formulated in mucus-penetrating liposomal nanoparticles described in International Patent Publication No. WO2013166498, the contents of which are herein incorporated by reference in its entirety. The nanoparticles may contain therapeutic agents to be delivered to a mucosal surface, one or more lipids, one or more PEG-conjugated lipids and one or more additional materials to physically and/or chemically stabilize the particles.

In one embodiment, the nucleic acid molecules, modified nucleic acid molecules and/or mmRNA may be formulated in neurophilic nanoparticles. Neurophilic nanoparticles may be useful to deliver compounds (e.g., compounds suitable for therapeutic purposes) to cells found in the peripheral nervous system and/or endothelial cells that form the blood brain barrier. The neuropilic nanoparticles may comprise at least a phospholipid, a non-ionic surfactant and a cholesterol. As a non-limiting example, the neurophilic nanoparticles are the liposomal nanoparticles described in International Patent Publication No. WO2013151650, the contents of which are herein incorporated by reference in its entirety. These neurophilic nanoparticles may be advantageous for targeting neural cells, endothelial cells of the blood vessels and epithelial cells of the choroid plexus that serve the brain.

In one embodiment, the nucleic acid molecules, modified nucleic acid molecules and/or mmRNA may be formulated in neutrophilic nanoparticles and may be administered intramuscularly.

In one embodiment, the nucleic acid molecules, modified nucleic acid molecules and/or mmRNA may be formulated in neutrophilic nanoparticles and may be administered intradermally.

In one embodiment, the nucleic acid molecules, modified nucleic acid molecule or mmRNA is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles *Hum Gene Ther.* 2008 19:125-132; all of which are incorporated herein by reference in its entirety).

In one embodiment such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. Mol Ther. 2010 18:1357-1364; Song et al., Nat Biotechnol. 2005 23:709-717; Judge et al., J Clin Invest. 2009 119:661-673; Kaufmann et al., Microvasc Res 2010 80:286-293; Santel et al., Gene Ther 2006 13:1222-1234; Santel et al., Gene Ther 2006 13:1360-1370; Gutbier et al., Pulm Pharmacol. Ther. 2010 23:334-344; Basha et al., Mol. Ther. 2011 19:2186-2200; Fenske and Cullis, Expert Opin Drug Deliv. 2008 5:25-44; Peer et al., Science. 2008 319: 627-630; Peer and Lieberman, Gene Ther. 2011 18:1127-1133; all of which are incorporated herein by reference in its entirety). One example of passive targeting of formulations to liver cells includes the DLin-DMA, DLin-KC2-DMA and DLin-MC3-DMA-based lipid nanoparticle formulations which have been shown to bind to apolipoprotein E and promote binding and uptake of these formulations into hepatocytes in vivo (Akinc et al. Mol Ther. 2010 18:1357-1364; the contents of which are herein incorporated by reference in its entirety). Formulations can also be selectively targeted through expression of different ligands on their surface as exemplified by, but not limited by, folate, transferrin, N-acetylgalactosamine (GalNAc), and antibody targeted approaches (Kolhatkar et al., Curr Drug Discov Technol. 2011 8:197-206; Musacchio and Torchilin, Front Biosci. 2011 16:1388-1412; Yu et al., Mol Membr Biol. 2010 27:286-298; Patil et al., Crit Rev Ther Drug Carrier Syst. 2008 25:1-61; Benoit et al., Biomacromolecules. 2011 12:2708-2714; Zhao et al., Expert Opin Drug Deliv. 2008 5:309-319; Akinc et al., Mol Ther. 2010 18:1357-1364; Srinivasan et al., Methods Mol Biol. 2012 820:105-116; Ben-Arie et al., Methods Mol Biol. 2012 757:497-507; Peer 2010 J Control Release. 20:63-68; Peer et al., Proc Natl Acad Sci USA. 2007 104:4095-4100; Kim et al., Methods Mol Biol. 2011 721:339-353; Subramanya et al., Mol Ther. 2010 18:2028-2037; Song et al., Nat Biotechnol. 2005 23:709-717; Peer et al., Science. 2008 319:627-630; Peer and Lieberman, Gene Ther. 2011 18:1127-1133; the contents of all of which are incorporated herein by reference in its entirety).

In one embodiment, the nucleic acid molecules, modified nucleic acid molecules or mmRNA are formulated as a solid lipid nanoparticle. A solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. In a further embodiment, the lipid nanoparticle may be a self-assembly lipid-polymer nanoparticle (see Zhang et al., ACS Nano, 2008, 2 (8), pp 1696-1702; herein incorporated by reference in its entirety). As a non-limiting example, the SLN may be the SLN described in International Patent Publication No. WO2013105101, the contents of which are herein incorporated by reference in its entirety. As another non-limiting example, the SLN may be made by the methods or processes described in International Patent Publication No. WO2013105101, the contents of which are herein incorporated by reference in its entirety.

Liposomes, lipoplexes, or lipid nanoparticles may be used to improve the efficacy of nucleic acid molecules, modified nucleic acid molecules or mmRNA directed protein production as these formulations may be able to increase cell transfection by the nucleic acid molecules, modified nucleic acid molecule or mmRNA; and/or increase the translation of encoded protein. One such example involves the use of lipid encapsulation to enable the effective systemic delivery of polyplex plasmid DNA (Heyes et al., Mol Ther. 2007 15:713-720; the contents of which are herein incorporated by reference in its entirety). The liposomes, lipoplexes, or lipid nanoparticles may also be used to increase the stability of the nucleic acid molecules, modified nucleic acid molecules or mmRNA.

In one embodiment, the nucleic acid molecules, modified nucleic acid molecules and/or the mmRNA of the present invention can be formulated for controlled release and/or targeted delivery. As used herein, "controlled release" refers to a pharmaceutical composition or compound release profile that conforms to a particular pattern of release to effect a therapeutic outcome. In one embodiment, the nucleic acid molecules, modified nucleic acids molecules or the mmRNA may be encapsulated into a delivery agent described herein and/or known in the art for controlled release and/or targeted delivery. As used herein, the term "encapsulate" means to enclose, surround or encase. As it relates to the formulation of the compounds of the invention, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention may be enclosed, surrounded or encased within the delivery agent. "Partial encapsulation" or "partially encapsulated" means that less than 10, 10, 20, 30, 40 50 or less of the pharmaceutical composition or compound of the invention may be enclosed, surrounded or encased within the delivery agent. Advantageously, encapsulation may be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the invention are encapsulated in the delivery agent.

In one embodiment, the controlled release formulation may include, but is not limited to, tri-block co-polymers. As a non-limiting example, the formulation may include two different types of tri-block co-polymers (International Pub. No. WO2012131104 and WO2012131106; the contents of each of which is herein incorporated by reference in its entirety).

In one embodiment, a controlled release formulation comprising nucleic acid molecules, modified nucleic acid molecules or mmRNA may be administered intramuscularly.

In one embodiment, a controlled release formulation comprising nucleic acid molecules, modified nucleic acid molecules or mmRNA may be administered intradermally.

In another embodiment, the nucleic acid molecules, modified nucleic acid molecules or the mmRNA may be encapsulated into a lipid nanoparticle or a rapidly eliminated lipid nanoparticle and the lipid nanoparticles or a rapidly eliminated lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, and COSEAL® (Baxter International, Inc Deerfield, Ill.).

In another embodiment, the lipid nanoparticle may be encapsulated into any polymer known in the art which may form a gel when injected into a subject. As a non-limiting example, the lipid nanoparticle may be encapsulated into a polymer matrix which may be biodegradable.

In one embodiment, the nucleic acid molecules, modified nucleic acid molecules or mmRNA formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In one embodiment, the controlled release and/or targeted delivery formulation may comprise at least one degradable polyester which may contain polycationic side chains. Degradeable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In one embodiment, the controlled release and/or targeted delivery formulation may comprise at least one PEG and/or PEG related polymer derivatives as described in U.S. Pat. No. 8,404,222, herein incorporated by reference in its entirety.

In another embodiment, the controlled release delivery formulation may be the controlled release polymer system described in US20130130348, the contents of which is herein incorporated by reference in its entirety.

In one embodiment, the nucleic acid molecules, modified nucleic acid molecules and/or the mmRNA of the present invention may be encapsulated in a therapeutic nanoparticle (e.g., a therapeutic nanoparticle from BIND Therapeutics). Therapeutic nanoparticles may be formulated by methods described herein and known in the art such as, but not limited to, International Pub Nos. WO2010005740, WO2010030763, WO2010005721, WO2010005723, WO2012054923, US Pub. Nos. US20110262491, US20100104645, US20100087337, US20100068285, US20110274759, US20100068286, US20120288541, US20130123351, US20130230567, US20130236500, US20130302433, US20130302432, US20130280339 and US20130251757, and U.S. Pat. Nos. 8,206,747, 8,293,276 8,318,208, 8,318,211, 8,623,417, 8,617,608, 8,613,954, 8,613,951, 8,609,142, 8,603,534 and 8,563,041; the contents of each of which is herein incorporated by reference in their entirety. In another embodiment, therapeutic polymer nanoparticles may be identified by the methods described in US Pub No. US20120140790, herein incorporated by reference in its entirety. As a non-limiting example, the therapeutic nanoparticle may comprise about 4 to about 25 weight percent of a therapeutic agent (e.g., modified nucleic acid molecules and/or mmRNA described herein) and about 10 to about 99 weight percent of a diblock poly(lactic) acid-poly(ethylene)glycol copolymer comprising poly(lactic) acid as described in US Patent Publication No. US20130236500 (Bind), the contents of which are herein incorporated by reference in its entirety. As another non-limiting example, the therapeutic nanoparticle may comprise about 0.2 to about 35 weight percent of a therapeutic agent (e.g., nucleic acid molecules, modified nucleic acid molecules and/or mmRNA described herein) and about 10 to about 99 weight percent of a diblock poly(lactic) acid-poly(ethylene)glycol copolymer as described in US Patent Publication No. US20130280339 (Bind) and US20130251757 and U.S. Pat. No. 8,652,528, the contents of each of which are herein incorporated by reference in their entirety.

In one embodiment, the therapeutic nanoparticle may comprise a mTOR inhibitor and one, two or three biocompatible polymers as described in U.S. Pat. No. 8,623,417 and US Patent Publication No. US20130344158, the contents of each of which are herein incorporated by reference in its entirety. As a non-limiting example, the mTOR inhibitor may be a nucleic acid molecules, modified nucleic acid molecule and/or a mmRNA described herein.

In one embodiment, the therapeutic nanoparticle may comprise an active agent or a therapeutic agent (e.g., nucleic acid molecules, modified nucleic acid molecules and/or mmRNA) and one, two or three biocompatible polymers as described in U.S. Pat. Nos. 8,617,608, 8,613,954, 8,613,951, 8,609,142 and 8,603,534, the contents of which are herein incorporated by reference in their entirety.

In one embodiment, the therapeutic nanoparticles may be prepared by the methods and processes outlined in US Patent Publication No. US20130302433, the contents of which are herein incorporated by reference in its entirety. The therapeutic nanoparticles may comprise an active agent or therapeutic agent and one, two or three biocompatiable polymers.

In one embodiment, the therapeutic nanoparticles may have a hydrodynamic diameter of about 70 to about 130 nm such as, but not limited to, the therapeutic nanoparticles described in US Patent Publication No. US20130302432, the contents of which are herein incorporated by reference in its entirety. As a non-limiting example, the therapeutic nanoparticles have about 0.2 to about 35 weight percent of a therapeutic agent and about 10 to about 99 weight percent of biocompatible polymer such as a diblock poly(lactic) acid-poly(ethylene)glycol (see e.g., US Patent Publication No. US20130302432, the contents of which are herein incorporated by reference in its entirety).

In one embodiment, the nucleic acid molecules, modified nucleic acid molecules and/or mmRNA may be delivered in therapeutic nanoparticles for parenteral administration. As a non-limiting example, the therapeutic nanoparticle may be those described in and/or those made by the methods described in U.S. Pat. No. 8,563,041, the contents of which are herein incorporated by reference in its entirety.

In one embodiment, the nucleic acid molecules, modified nucleic acid molecules and/or mmRNA formulated in therapeutic nanoparticles may be administered intramuscularly.

In one embodiment, the nucleic acid molecules, modified nucleic acid molecules and/or mmRNA formulated in therapeutic nanoparticles may be administered intradermally.

In one embodiment, the nucleic acid molecules, modified nucleic acid molecules and/or mmRNA may be delivered in therapeutic nanoparticles such as ACCURINS™ from Bind Therapeutics. ACCURINS™ are polymeric nanoparticles which have been designed to have prolonged circulation within the bloodstream and can provide for the controlled and timely release of the therapeutic payload. In one embodiment, the modified nucleic acid molecules and/or mmRNA may be targeted to specific targets such as tumors using ACCURINS™ nanoparticles. The nanoparticles may be used to target tumors tissue (e.g., size, shape and surface property optimization of the nanoparticles) and cellular targeting of tumor using targeting ligands on the surface of the nanoparticles that bind to the specific cell surface or tissue marker. In another embodiment, the modified nucleic acid molecules and/or mmRNA may be delivered across biological barriers using ACCURINS™ nanoparticles (see e.g., Oral delivery of drug-loaded nanoparticles having Fc fragments that readily bind to the neonatal Fc receptor in the intestinal epithelium described by Pridgen et al. (Sci Transl Med 5 213ra167 (2013); the contents of which are herein incorporated by reference in its entirety)).

In one embodiment, the nucleic acid molecules, modified nucleic acid molecules and/or mmRNA formulated in ACCURINS™ nanoparticles may be administered intramuscularly.

In one embodiment, the nucleic acid molecules, modified nucleic acid molecules and/or mmRNA formulated in ACCURINS™ nanoparticles may be administered intradermally.

In one embodiment, the nucleic acid molecules, modified nucleic acid molecules and/or mmRNA may be delivered in therapeutic nanoparticles having a high glass transition temperature such as, but not limited to, the nanoparticles described in US Patent Publication Nos. US20140030351 and US20110294717. As a non-limiting example, these nanoparticles may comprise an anti-cancer agent.

In one embodiment, the therapeutic nanoparticle may be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle may comprise a polymer and a therapeutic agent such as, but not limited to, the nucleic acid molecules, modified nucleic acid molecules and mmRNA of the present invention (see International Pub No. WO2010075072 and US Pub No. US20100216804, US20110217377, US20120201859, US20130243848 and US20130243827, each of which is herein incorporated by reference in their entirety). In another non-limiting example, the sustained release formulation may comprise agents which permit persistent bioavailability such as, but not limited to, crystals, macromolecular gels and/or particulate suspensions (see US Patent Publication No US20130150295, the contents of which is herein incorporated by reference in its entirety).

In one embodiment, the nucleic acid molecules, modified nucleic acid molecules and/or mmRNA formulated in sustained release nanoparticles may be administered intramuscularly.

In one embodiment, the nucleic acid molecules, modified nucleic acid molecules and/or mmRNA formulated in sustained release nanoparticles may be administered intradermally.

In one embodiment, the therapeutic nanoparticles may be formulated to be target specific. As a non-limiting example, the therapeutic nanoparticles may include a corticosteroid (see International Pub. No. WO2011084518 herein incorporated by reference in its entirety). In one embodiment, the therapeutic nanoparticles of the present invention may be formulated to be cancer specific such as, but not limited to, the cancer cell targeting nanoparticles comprising an anti-cancer agent described in U.S. Pat. Nos. 8,603,501, 8,603,500 and 8,603,499, the contents of each of which are herein incorporated by reference in their entirety. As a non-limiting example, the therapeutic nanoparticles may be formulated in nanoparticles described in International Pub No. WO2008121949, WO2010005726, WO2010005725, WO2011084521 and US Pub No. US20100069426, US20120004293 and US20100104655, each of which is herein incorporated by reference in their entirety.

In one embodiment, the nanoparticles of the present invention may comprise a polymeric matrix. As a non-limiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In one embodiment, the therapeutic nanoparticle comprises a diblock copolymer. In one embodiment, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof. In another embodiment, the diblock copolymer may comprise the diblock copolymers described in European Patent Publication No. the contents of which are herein incorporated by reference in its entirety. In yet another embodiment, the diblock copolymer may be a high-X diblock copolymer such as those described in International Patent Publication No. WO2013120052, the contents of which are herein incorporated by reference in its entirety.

As a non-limiting example the therapeutic nanoparticle comprises a PLGA-PEG block copolymer (see US Pub. No. US20120004293 and U.S. Pat. No. 8,236,330, each of which is herein incorporated by reference in their entirety). In another non-limiting example, the therapeutic nanoparticle is a stealth nanoparticle comprising a diblock copolymer of PEG and PLA or PEG and PLGA (see U.S. Pat. No. 8,246,968 and International Publication No. WO2012166923, the contents of each of which are herein incorporated by reference in their entirety). In yet another non-limiting example, the therapeutic nanoparticle is a stealth nanoparticle or a target-specific stealth nanoparticle as described in US Patent Publication No. US20130172406, the contents of which are herein incorporated by reference in its entirety.

In yet another non-limiting example, the lipid nanoparticle comprises the block copolymer PEG-PLGA-PEG (see e.g., the thermosensitive hydrogel (PEG-PLGA-PEG) was used as a TGF-beta1 gene delivery vehicle in Lee et al. Thermosensitive Hydrogel as a Tgf-β1 Gene Delivery Vehicle Enhances Diabetic Wound Healing. Pharmaceutical Research, 2003 20(12): 1995-2000; as a controlled gene delivery system in Li et al. Controlled Gene Delivery System Based on Thermosensitive Biodegradable Hydrogel. Pharmaceutical Research 2003 20(6):884-888; and Chang et al., Non-ionic amphiphilic biodegradable PEG-PLGA-PEG copolymer enhances gene delivery efficiency in rat skeletal muscle. J Controlled Release. 2007 118:245-253; each of which is herein incorporated by reference in its entirety). The nucleic acid molecules, modified nucleic acids and/or mmRNAs of the present invention may be formulated in lipid nanoparticles comprising the PEG-PLGA-PEG block copolymer.

In one embodiment, the nanoparticles (e.g., therapeutic nanoparticles) may comprise a multiblock copolymer (See e.g., U.S. Pat. Nos. 8,263,665 and 8,287,910 and US Patent Pub. No. US20130195987; the contents of each of which are herein incorporated by reference in its entirety). As a non-limiting example, the multiblock copolymer which may be used in the nanoparticles described herein may be a non-linear multiblock copolymer such as those described in US Patent Publication No. 20130272994, the contents of which are herein incorporated by reference in its entirety.

In one embodiment, the block copolymers described herein may be included in a polyion complex comprising a non-polymeric micelle and the block copolymer. (See e.g., U.S. Pub. No. 20120076836; the contents of which are herein incorporated by reference in its entirety).

In one embodiment, the block copolymers described herein may have a hydrophobic portion consisting of polylactide and a hydrophilic portion consisting of dextran such as, but not limited to, poly(D,L-lactide)-b-dextran as described in US Publication No. US20140005379, the contents of which are herein incorporated by reference in its entirety.

In one embodiment, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly (acrylic acid), poly(methacrylic acid), polycyanoacrylates and combinations thereof.

In one embodiment, the therapeutic nanoparticles may comprise at least one poly(vinyl ester) polymer. The poly (vinyl ester) polymer may be a copolymer such as a random copolymer. As a non-limiting example, the random copolymer may have a structure such as those described in International Application No. WO2013032829 or US Patent Publication Nos US20130121954, the contents of which are herein incorporated by reference in its entirety. In one aspect, the poly(vinyl ester) polymers may be conjugated to the modified nucleic acid molecules or mmRNA described herein. In another aspect, the poly(vinyl ester) polymer which may be used in the present invention may be those described in, herein incorporated by reference in its entirety.

In one embodiment, the therapeutic nanoparticle may comprise at least one diblock copolymer. The diblock copolymer may be, but it not limited to, a poly(lactic) acid-poly (ethylene)glycol copolymer (see e.g., International Publication No. WO2013044219; herein incorporated by reference in its entirety). As a non-limiting example, the therapeutic nanoparticle may be used to treat cancer (see International publication No. WO2013044219; the contents of which is herein incorporated by reference in its entirety).

In one embodiment, the therapeutic nanoparticles may comprise at least one cationic polymer described herein and/or known in the art.

In one embodiment, the therapeutic nanoparticles may comprise at least one amine-containing polymer such as, but not limited to polylysine, polyethylene imine, poly(amidoamine) dendrimers, poly(beta-amino esters) (See e.g., U.S. Pat. Nos. 8,287,849 and 8,557,231; the contents of which are herein incorporated by reference in its entirety) and combinations thereof. As a non-limiting example, the amine-containing polymer may be any of the biodegradable poly (beta-amino esters) described in U.S. Pat. No. 8,557,231, the contents of which are herein incorporated by reference in its entirety.

In another embodiment, nanoparticles may comprise an amine cationic lipid such as those described in International Patent Application No. WO2013059496, herein incorporated by reference in its entirety. In one aspect the cationic lipids may have a amino-amine or an amino-amide moiety.

In one embodiment, the therapeutic nanoparticles may comprise at least one degradable polyester which may contain polycationic side chains. Degradeable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In another embodiment, the therapeutic nanoparticle may include a conjugation of at least one targeting ligand. The targeting ligand may be any ligand known in the art such as, but not limited to, a monoclonal antibody. (Kirpotin et al, Cancer Res. 2006 66:6732-6740; herein incorporated by reference in its entirety).

In one embodiment, the therapeutic nanoparticle may be formulated in an aqueous solution which may be used to target cancer (see International Pub No. WO2011084513 and US Pub No. US20110294717, the contents of each of which is herein incorporated by reference in their entirety).

In one embodiment, the therapeutic nanoparticles described herein may be formulated using the methods described by Podobinski et al in U.S. Pat. No. 8,404,799, the contents of which is herein incorporated by reference in its entirety.

In one embodiment, the nucleic acid molecules, modified nucleic acid molecules or mmRNA may be encapsulated in, linked to and/or associated with synthetic nanocarriers. Synthetic nanocarriers include, but are not limited to, those described in International Pub. Nos. WO2010005740, WO2010030763, WO201213501, WO2012149252, WO2012149255, WO2012149259, WO2012149265, WO2012149268, WO2012149282, WO2012149301, WO2012149393, WO2012149405, WO2012149411 and WO2012149454 and US Pub. Nos. US20110262491, US20100104645, US20100087337 US20120244222 and US20130236533, and U.S. Pat. No. 8,652,487, the contents of each of which is herein incorporated by reference in their entirety. The synthetic nanocarriers may be formulated using methods known in the art and/or described herein. As a non-limiting example, the synthetic nanocarriers may be formulated by the methods described in International Pub Nos. WO2010005740, WO2010030763 and WO201213501 and US Pub. Nos. US20110262491, US20100104645, US20100087337 and US20120244222, each of which is herein incorporated by reference in their entirety. In another embodiment, the synthetic nanocarrier formulations may be lyophilized by methods described in International Pub. No. WO2011072218 and U.S. Pat. No. 8,211,473; each of which is herein incorporated by reference in their entirety. In yet another embodiment, formulations of the present invention, including, but not limited to, synthetic nanocarriers, may be lyophilized or reconstituted by the methods described in US Patent Publication No. US20130230568, the contents of which are herein incorporated by reference in its entirety.

In one embodiment, synthetic nanocarriers comprising nucleic acid molecules, modified nucleic acid molecules or mmRNA may be administered intramuscularly.

In one embodiment, synthetic nanocarriers comprising nucleic acid molecules, modified nucleic acid molecules or mmRNA may be administered intradermally.

In one embodiment, the synthetic nanocarriers may contain reactive groups to release the nucleic acid molecules, modified nucleic acid molecules and/or mmRNA described herein (see International Pub. No. WO20120952552 and US Pub No. US20120171229, the contents of each of which is herein incorporated by reference in their entirety).

In one embodiment, the synthetic nanocarriers may contain an immunostimulatory agent to enhance the immune response from delivery of the synthetic nanocarrier. As a non-limiting example, the synthetic nanocarrier may comprise a Th1 immunostimulatory agent which may enhance a Th1-based response of the immune system (see International Pub No. WO2010123569 and US Pub. No. US20110223201, the contents of each of which is herein incorporated by reference in its entirety).

In one embodiment, the synthetic nanocarrier may contain an immunomodulatory agent that may capable of stimulating an immune response in T cells or B cells such as, but not limited to, the synthetic nanocarriers described in U.S. Pat. No. 8,637,028 and US Patent Publication No. US20130236533, the contents of each of which are herein incorporated by reference in their entirety. As a non limiting example, the synthetic nanocarrier may modulate the immune system such as the synthetic nanocarriers described in U.S. Pat. No. 8,637,028 and US Patent Publication No. US20130236533, the contents of each of which are herein incorporated by reference in their entirety.

In one embodiment, the synthetic nanocarriers may be formulated for targeted release. In one embodiment, the synthetic nanocarrier is formulated to release the nucleic acid molecules, modified nucleic acid molecules and/or mmRNA at a specified pH and/or after a desired time interval. As a non-limiting example, the synthetic nanoparticle may be formulated to release the nucleic acid molecules, modified mRNA molecules and/or mmRNA after 24 hours and/or at a pH of 4.5 (see International Pub. Nos. WO2010138193 and WO2010138194 and US Pub Nos. US20110020388 and US20110027217, the contents of each of which is herein incorporated by reference in their entirety).

In one embodiment, the synthetic nanocarriers may be formulated for controlled and/or sustained release of the nucleic acid molecules, modified nucleic acid molecules and/or mmRNA described herein. As a non-limiting example, the synthetic nanocarriers for sustained release may be formulated by methods known in the art, described herein and/or as described in International Pub No. WO2010138192 and US Pub No. US20100303850, US20130243848 and US20130243827, the contents of each of which is herein incorporated by reference in their entirety.

In one embodiment, the nucleic acid molecules, modified nucleic acid molecules and/or mmRNA may be formulated for controlled and/or sustained release wherein the formulation comprise at least one polymer that is a crystalline side chain (CYSC) polymer. CYSC polymers are described in U.S. Pat. No. 8,399,007, the contents of which is herein incorporated by reference in its entirety.

In one embodiment, the synthetic nanocarrier may be formulated for use as a vaccine. In one embodiment, the synthetic nanocarrier may encapsulate at least one modified nucleic acid molecule and/or mmRNA which encodes at least one antigen. As a non-limiting example, the synthetic nanocarrier may include at least one antigen and an excipient for a vaccine dosage form (see International Pub No. WO2011150264 and US Pub No. US20110293723, each of which is herein incorporated by reference in their entirety). As another non-limiting example, a vaccine dosage form may include at least two synthetic nanocarriers with the same or different antigens and an excipient (see International Pub No. WO2011150249 and US Pub No. US20110293701, each of which is herein incorporated by reference in their entirety). The vaccine dosage form may be selected by methods described herein, known in the art and/or described in International Pub No. WO2011150258 and US Pub No. US20120027806, each of which is herein incorporated by reference in their entirety).

In one embodiment, the synthetic nanocarrier may comprise at least one nucleic acid molecules, modified nucleic acid molecule and/or mmRNA which encodes at least one adjuvant. In another embodiment, the synthetic nanocarrier may comprise at least one nucleic acid molecules, modified nucleic molecule acid and/or mmRNA and an adjuvant. As a non-limiting example, the synthetic nanocarrier comprising and adjuvant may be formulated by the methods described in International Pub No. WO2011150240 and US Pub No. US20110293700, each of which is herein incorporated by reference in its entirety.

In one embodiment, the synthetic nanocarrier may encapsulate at least one nucleic acid molecules, modified nucleic acid molecule and/or mmRNA which encodes a peptide, fragment or region from a virus. As a non-limiting example, the synthetic nanocarrier may include, but is not limited to, the nanocarriers described in International Pub No. WO2012024621, WO201202629, WO2012024632 and US Pub No. US20120064110, US20120058153 and US20120058154, each of which is herein incorporated by reference in their entirety.

In one embodiment, the nucleic acid molecules, modified nucleic acid molecules or mmRNA may be encapsulated in, linked to and/or associated with zwitterionic lipids. Non-limiting examples of zwitterionic lipids and methods of using zwitterionic lipids are described in US Patent Publication No. US20130216607, the contents of which are herein incorporated by reference in its entirety. In one aspect, the zwitterionic lipids may be used in the liposomes and lipid nanoparticles described herein.

In one embodiment, the nucleic acid molecules, modified nucleic acids and/or mmRNA may be formulated in colloid nanocarriers as described in US Patent Publication No. US20130197100, the contents of which are herein incorporated by reference in its entirety.

In one embodiment, the nanoparticle may be optimized for oral administration. The nanoparticle may comprise at least one cationic biopolymer such as, but not limited to, chitosan or a derivative thereof. As a non-limiting example, the nanoparticle may be formulated by the methods described in U.S. Pub. No. 20120282343; herein incorporated by reference in its entirety.

In some embodiments, LNPs comprise the lipid KL52 (an amino-lipid disclosed in U.S. Application Publication No. 2012/0295832 expressly incorporated herein by reference in its entirety). Activity and/or safety (as measured by examining one or more of ALT/AST, white blood cell count and cytokine induction) of LNP administration may be improved by incorporation of such lipids. LNPs comprising KL52 may be administered intravenously and/or in one or more doses. In some embodiments, administration of LNPs comprising KL52 results in equal or improved mRNA and/or protein expression as compared to LNPs comprising MC3.

In one embodiment, LNP formulations comprising KL52 and nucleic acid molecules, modified nucleic acid molecules or mmRNA may be administered intramuscularly.

In one embodiment, LNP formulations comprising KL52 and nucleic acid molecules, modified nucleic acid molecules or mmRNA may be administered intradermally.

In some embodiments, nucleic acid molecules, mRNAs, modified nucleic acid molecules or mmRNA may be delivered using smaller LNPs. Such particles may comprise a diameter from below 0.1 um up to 100 nm such as, but not limited to, less than 0.1 um, less than 1.0 um, less than 5 um, less than 10 um, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, less than 975 um, In another embodiment, nucleic acid molecules, mRNAs, modified nucleic acid molecules or mmRNA may be delivered using smaller LNPs which may comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nM, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm.

In one embodiment, nucleic acid molecules, modified nucleic acid molecules, or mmRNA may be formulated in smaller LNPs and may be administered intramuscularly.

In one embodiment, nucleic acid molecules, modified nucleic acid molecules or mmRNA may be formulated in smaller LNPs and may be administered intradermally.

In some embodiments, such LNPs are synthesized using methods comprising microfluidic mixers. Exemplary microfluidic mixers may include, but are not limited to a slit interdigitial micromixer including, but not limited to those manufactured by Microinnova (Allerheiligen bei Wildon, Austria) and/or a staggered herringbone micromixer (SHM) (Zhigaltsev, I. V. et al., Bottom-up design and synthesis of limit size lipid nanoparticle systems with aqueous and triglyceride cores using millisecond microfluidic mixing have been published (Langmuir. 2012. 28:3633-40; Belliveau, N. M. et al., Microfluidic synthesis of highly potent limit-size lipid nanoparticles for in vivo delivery of siRNA. Molecular Therapy-Nucleic Acids. 2012. 1:e37; Chen, D. et al., Rapid discovery of potent siRNA-containing lipid nanoparticles enabled by controlled microfluidic formulation. J Am Chem Soc. 2012. 134(16):6948-51; the contents of each of which is herein incorporated by reference in its entirety). In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method may also comprise a surface for fluid mixing wherein the surface changes orientations during fluid cycling. Methods of generating LNPs using SHM include those disclosed in U.S. Application Publication Nos. 2004/0262223 and 2012/0276209, the contents of each of which is herein incorporated by reference in their entirety.

In one embodiment, the nucleic acid molecules, modified nucleic acid molecules and/or mmRNA of the present invention may be formulated in lipid nanoparticles created using a micromixer such as, but not limited to, a Slit Interdigital Microstructured Mixer (SIMM-V2) or a Standard Slit Interdigital Micro Mixer (SSIMM) or Caterpillar (CPMM) or Impinging jet (IJMM) from the Institut für Mikrotechnik Mainz GmbH, Mainz Germany).

In one embodiment, the nucleic acid molecules, modified nucleic acid molecules and/or mmRNA of the present invention may be formulated in lipid nanoparticles created using microfluidic technology (see Whitesides, George M. The Origins and the Future of Microfluidics. Nature, 2006 442: 368-373; Abraham et al. Chaotic Mixer for Microchannels. Science, 2002 295: 647-651; and Valencia et al. Microfluidic Platform for Combinatorial Synthesis and Optimization of Targeted Nanoparticles for Cancer Therapy. ACS Nano 2013 (DOI/10.1021/nn403370e); the contents of each of which is herein incorporated by reference in their entirety). As a non-limiting example, controlled microfluidic formulation includes a passive method for mixing streams of steady pressure-driven flows in micro channels at a low Reynolds number (See e.g., Abraham et al. Chaotic Mixer for Microchannels. Science, 2002 295: 647-651; which is herein incorporated by reference in its entirety).

In one embodiment, the nucleic acid molecules, modified nucleic acid molecules and/or mmRNA of the present invention may be formulated in lipid nanoparticles created using a micromixer chip such as, but not limited to, those from Harvard Apparatus (Holliston, Mass.) or Dolomite Microfluidics (Royston, UK). A micromixer chip can be used for rapid mixing of two or more fluid streams with a split and recombine mechanism.

In one embodiment, the nucleic acid molecules, modified nucleic acid molecules and/or mmRNA may be formulated in nanoparticles created using a microfluidic device such as the methods for making nanoparticles described in International Patent Publication No. WO2014016439, the contents of which are herein incorporated by reference in its entirety. As a non-limiting example, the nanoparticles may be created by adding a nanoparticle precursor to the microfluidic device through one or more flow channels, generating microplasma in the microfluidic device, causing the microplasma to interact with the nanoparticle precursor to generate nanoparticles, adding a conjugate material into the microfluidic device through one or more flow channels and causing the nanoparticles to mix with the conjugate material in a continuous flow to form conjugated nanoparticles (see e.g., International Patent Publication No. WO2014016439, the contents of which are herein incorporated by reference in its entirety).

In one embodiment, the nucleic acid molecules, modified nucleic acid molecules and/or mmRNA of the invention may be formulated for delivery using the drug encapsulating microspheres described in International Patent Publication No. WO2013063468 or U.S. Pat. No. 8,440,614, each of which is herein incorporated by reference in its entirety. The microspheres may comprise a compound of the formula (I), (II), (III), (IV), (V) or (VI) as described in International patent application No. WO2013063468, herein incorporated by reference in its entirety. In another aspect, the amino acid, peptide, polypeptide, lipids (APPL) are useful in delivering the modified nucleic acid molecules and/or mmRNA of the invention to cells (see International Patent Publication No. WO2013063468, herein incorporated by reference in its entirety).

In one embodiment, the nucleic acid molecules, modified nucleic acid molecules and/or mmRNA of the invention may be formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the lipid nanoparticles may have a diameter from about 10 to 500 nm.

In one embodiment, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In one aspect, the lipid nanoparticle may be a limit size lipid nanoparticle described in International Patent Publication No. WO2013059922, herein incorporated by reference in its entirety. The limit size lipid nanoparticle may comprise a lipid bilayer surrounding an aqueous core or a hydrophobic core; where the lipid bilayer may comprise a phospholipid such as, but not limited to, diacylphosphatidylcholine, a diacylphosphatidylethanolamine, a ceramide, a sphingomyelin, a dihydrosphingomyelin, a cephalin, a cerebroside, a C8-C20 fatty acid diacylphophatidylcholine, and 1-palmitoyl-2-oleoyl phosphatidylcholine (POPC). In another aspect the limit size lipid nanoparticle may comprise a polyethylene glycol-lipid such as, but not limited to, DLPE-PEG, DMPE-PEG, DPPC-PEG and DSPE-PEG.

In one embodiment, the nucleic acid molecules, modified nucleic acids or mmRNA may be delivered, localized and/or concentrated in a specific location using the delivery methods described in International Patent Publication No. WO2013063530, the contents of which are herein incorporated by reference in its entirety. As a non-limiting example, a subject may be administered an empty polymeric particle prior to, simultaneously with or after delivering the modified nucleic acids or mmRNA to the subject. The empty polymeric particle undergoes a change in volume once in contact with the subject and becomes lodged, embedded, immobilized or entrapped at a specific location in the subject.

In one embodiment, the nucleic acid molecules, modified nucleic acid molecules and/or mmRNA may be formulated in an active substance release system (See e.g., US Patent Publication No. US20130102545, herein incorporated by reference in its entirety). The active substance release system may comprise 1) at least one nanoparticle bonded to an oligonucleotide inhibitor strand which is hybridized with a catalytically active nucleic acid and 2) a compound bonded to at least one substrate molecule bonded to a therapeutically active substance (e.g., a nucleic acid molecule, modified nucleic acid molecule or an mmRNA described herein), where the therapeutically active substance is released by the cleavage of the substrate molecule by the catalytically active nucleic acid.

In one embodiment, the nucleic acid molecules, modified nucleic acid molecules and/or mmRNA may be formulated in a nanoparticle comprising an inner core comprising a non-cellular material and an outer surface comprising a cellular membrane. The cellular membrane may be derived from a cell or a membrane derived from a virus. As a non-limiting example, the nanoparticle may be made by the methods described in International Patent Publication No. WO2013052167, herein incorporated by reference in its entirety. As another non-limiting example, the nanoparticle described in International Patent Publication No. WO2013052167, herein incorporated by reference in its entirety, may be used to deliver the nucleic acid molecules, modified nucleic acid molecules and/or mmRNA described herein.

In one embodiment, the nucleic acid molecules, modified nucleic acid molecules and/or mmRNA may be formulated in porous nanoparticle-supported lipid bilayers (protocells). Protocells are described in International Patent Publication No. WO2013056132, the contents of which are herein incorporated by reference in its entirety.

In one embodiment, the nucleic acid molecules, modified nucleic acid molecules and/or mmRNA described herein may be formulated in polymeric nanoparticles as described in or made by the methods described in U.S. Pat. Nos. 8,420,123, 8,518,963 and 8,618,240, European Patent No. EP2073848B1 and US Patent Publication No. US20130273117, the contents of each of which are herein incorporated by reference in their entirety. As a non-limiting example, the polymeric nanoparticle may have a high glass transition temperature such as the nanoparticles described in or nanoparticles made by the methods described in U.S. Pat. No. 8,518,963 and US Patent Publication Nos. US20140030351 and US20110294717, the contents of each of which are herein incorporated by reference in their entirety. As another non-limiting example, the polymer nanoparticle for oral, parenteral and topical formulations may be made by the methods described in European Patent No. EP2073848B1, the contents of which is herein incorporated by reference in its entirety. As yet another non-limiting example, the nucleic acid molecules, modified nucleic acid molecules and/or mmRNA my be formulated in a population of polymeric nanoparticles comparing a plurality of polymeric nanoparticles approximately the same size and having an amphiphilic co-polymer (e.g., PLA) as described in U.S. Pat. No. 8,618,240, the contents of which are herein incorporated by reference in its entirety.

In one embodiment, the nucleic acid molecules, modified nucleic acid molecules and/or mmRNA described herein may be formulated in lyophilized pharmaceutical compositions comprising polymeric nanoparticles such as the compositions described in U.S. Pat. Nos. 8,603,535 and 8,637,083 (BIND Therapeutics) and US Patent Publication Nos. US20130295191 and US20130295183, the contents of each of which are herein incorporated by reference in its entirety. As a non-limiting example, the lyophilized composition may include polymeric nanoparticles which may comprise a poly(lactic) acid-block-poly(ethylene)glycol copolymer or poly(lactic)-co-poly(glycolic) acid-block-poly(ethylene) glycol copolymer, and a therapeutic agent (e.g., nucleic acid molecules, modified nucleic acid molecules and/or mmRNA).

In another embodiment, the nucleic acid molecules, modified nucleic acids and/or mmRNA described herein may be formulated in nanoparticles used in imaging. The nanoparticles may be liposome nanoparticles such as those described in US Patent Publication No US20130129636, herein incorporated by reference in its entirety. As a non-limiting example, the liposome may comprise gadolinium(III)2-{4,7-bis-carboxymethyl-10-[(N,N-distearylamidomethyl-N'-amido-methyl]-1,4,7,10-tetra-azacyclododec-1-yl}-acetic acid and a neutral, fully saturated phospholipid component (see e.g., US Patent Publication No US20130129636, herein incorporated by reference in its entirety).

In one embodiment, the nanoparticles which may be used in the present invention are formed by the methods described in U.S. Patent Application No. US20130130348, herein incorporated by reference in its entirety.

The nanoparticles of the present invention may further include nutrients such as, but not limited to, those which deficiencies can lead to health hazards from anemia to neural tube defects (see e.g, the nanoparticles described in International Patent Publication No WO2013072929, herein incorporated by reference in its entirety). As a non-limiting example, the nutrient may be iron in the form of ferrous, ferric salts or elemental iron, iodine, folic acid, vitamins or micronutrients.

In one embodiment, the nucleic acid molecules, modified nucleic acids and/or mmRNA of the present invention may be formulated in a swellable nanoparticle. The swellable nanoparticle may be, but is not limited to, those described in U.S. Pat. No. 8,440,231 and US Patent Publication No. 2013032310, the contents of each of which are herein incorporated by reference in their entirety. As a non-limiting embodiment, the swellable nanoparticle may be used for delivery of the nucleic acid molecules, modified nucleic acids and/or mmRNA of the present invention to the pulmonary system (see e.g., U.S. Pat. No. 8,440,231 and US Patent Publication No. 2013032310, the contents of each of which are herein incorporated by reference in its entirety).

The nucleic acid molecules, modified nucleic acids and/or mmRNA of the present invention may be formulated in polyanhydride nanoparticles such as, but not limited to, those described in U.S. Pat. No. 8,449,916, the contents of which is herein incorporated by reference in its entirety.

The nanoparticles and microparticles of the present invention may be geometrically engineered to modulate macrophage and/or the immune response. In one aspect, the geometrically engineered particles may have varied shapes, sizes and/or surface charges in order to incorporated the nucleic acid molecules, modified nucleic acids and/or mmRNA of the present invention for targeted delivery such as, but not limited to, pulmonary delivery (see e.g., International Publication No WO2013082111, herein incorporated by reference in its entirety). Other physical features the geometrically engineering particles may have include, but are not limited to, fenestrations, angled arms, asymmetry and surface roughness, charge which can alter the interactions with cells and tissues. As a non-limiting example, nanoparticles of the present invention may be made by the methods described in International Publication No WO2013082111, herein incorporated by reference in its entirety.

In one embodiment, the nanoparticles of the present invention may be water soluble nanoparticles such as, but not limited to, those described in International Publication No. WO2013090601, the contents of which is herein incorporated by reference in its entirety. The nanoparticles may be inorganic nanoparticles which have a compact and zwitterionic ligand in order to exhibit good water solubility. The nanoparticles may also have small hydrodynamic diameters (HD), stability with respect to time, pH, and salinity and a low level of non-specific protein binding.

In one embodiment the nanoparticles of the present invention may be developed by the methods described in US Patent Publication No. US20130172406, the contents of which are herein incorporated by reference in its entirety.

In one embodiment, the nanoparticles of the present invention are stealth nanoparticles or target-specific stealth nanoparticles such as, but not limited to, those described in US Patent Publication Nos. US20130172406 (Bind), US20130251817 (Bind), US2013251816 (Bind) and US20130251766 (Bind), the contents of each of which are herein incorporated by reference in its entirety. The stealth nanoparticles may comprise a diblock copolymer and a chemotherapeutic agent. These stealth nanoparticles may be made by the methods described in US Patent Publication Nos. US20130172406, US20130251817, US2013251816 and US20130251766, the contents of each of which are herein incorporated by reference in its entirety. As a non-limiting example, the stealth nanoparticles may target cancer cells such as the nanoparticles described in US Patent Publication Nos. US20130172406, US20130251817, US2013251816 and US20130251766, the contents of each of which are herein incorporated by reference in its entirety.

In another embodiment, the stealth or target-specific stealth nanoparticles may comprise a polymeric matrix. The polymeric matrix may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates or combinations thereof.

In one embodiment, stealth nanoparticles comprising nucleic acid molecules, modified nucleic acid molecules or mmRNA may be administered intramuscularly. In one embodiment, stealth nanoparticles comprising nucleic acid molecules, modified nucleic acid molecules or mmRNa may be administered intradermally.

In one embodiment, the nanoparticle may be a nanoparticle-nucleic acid hybrid structure having a high density nucleic acid layer. As a non-limiting example, the nanoparticle-nucleic acid hybrid structure may made by the methods described in US Patent Publication No. US20130171646, the contents of which are herein incorporated by reference in its entirety. The nanoparticle may comprise a nucleic acid such as, but not limited to, modified mRNA described herein and/or known in the art.

At least one of the nanoparticles of the present invention may be embedded in the core of a nanostructure or coated with a low density porous 3-D structure or coating which is capable of carrying or associating with at least one payload within or on the surface of the nanostructure. Non-limiting examples of the nanostructures comprising at least one nanoparticle are described in International Patent Publication No. WO2013123523, the contents of which are herein incorporated by reference in its entirety.

In one embodiment, the nanoparticle may comprise self-assembling peptides described in International Publication Nos. WO2014014613 and WO2014018675, the contents of each of which are herein incorporated by reference in their entirety. As a non-limiting example, the nucleic acid molecules, modified nucleic acids and/or mmRNA may be formulated in a self-assembled peptide nanostructure as described in International Publication No. WO2014014613, the contents of which are herein incorporated by reference in its entirety. As another non-limiting example, the nucleic acid molecules, modified nucleic acids and/or mmRNA may be formulated in a self-assembled nucleic acid nanostructure as described in International Publication No. WO2014018675, the contents of which are herein incorporated by reference in its entirety.

In one embodiment, the nanoparticle described herein may be a lipid-polymer hybrid particle as described in US Patent Publication No. US20130315831, the contents of which are herein incorporated by reference in its entirety. The lipid-polymer hybrid particles may have an aqueous core, a first amphiphilic layer surrounding the aqueous core and a polymeric matrix surrounding the amphiphilic layer. As a non-limiting example, the nucleic acid molecules, modified nucleic acid molecules and/or mmRNA described herein may be formulated in a lipid-polymer hybrid particle. As another non-limiting example, the lipid-polymer hybrid nanoparticle may have heterogenous surface functional groups such as lipid-PEG-COOH, lipid-PEG-NH2 and lipid-PEG-OCH3.

In one embodiment, the nucleic acid molecules, modified nucleic acid molecules and/or mmRNA may be formulated in and/or delivered in a lipid nanoparticle as described in International Patent Publication No. WO2012170930, the contents of which are herein incorporated by reference in its entirety. The lipid nanoparticle may comprise one or more cationic lipids, one or more non-cationic lipids and one or more PEG-modified lipids. As a non-limiting example, the lipid nanoparticle comprises DLin-KC2-DMA, Cholesterol (CHOL), DOPE and DMG-PEG-2000. As another non-limiting example, the lipid nanoparticle comprises C12-200, DOPE, cholesterol (CHOL) and DMGPEG2K.

In one embodiment, the nucleic acid molecules, modified nucleic acid molecules and/or mmRNA may be formulated in and/or delivered in a lipid nanoparticle as described in US Patent Publication No. US20130338210, the contents of which are herein incorporated by reference in its entirety. As a non-limiting example, the lipid nanoparticle may comprise a neutral lipid and the cationic lipid described in paragraphs [0013]-[0049] and [0084]-[0350]. In one embodiment, a LNP formulation comprising a LNP described in US Patent Publication No. US20130338210, the contents of which are herein incorporated by reference in its entirety, and nucleic acid molecules, modified nucleic acid molecules and/or mmRNA may be delivered intramuscularly or intradermally.

In one embodiment, the nucleic acid molecules, modified nucleic acid molecules and/or mmRNA may be formulated in and/or delivered in a lipid nanoparticle comprising a plurality of cationic lipids such as, but not limited to, the lipid nanoparticles described in US Patent Publication No. US20130017223, the contents of which are herein incorporated by reference in its entirety. As a non-limiting example, the LNP formulation may comprise a first cationic lipid and a second cationic lipid. As another non-limiting example, the LNP formulation may comprise DLin-MC2-DMA and DLin-MC4-DMA. As yet another non-limiting example, the LNP formulation may comprise DLin-MC3-DMA and C12-200. In one embodiment, the LNP formulations comprising a plurality of cationic lipids (such as, but not limited to, those described in US Patent Publication No. US20130017223, the contents of which are herein incorporated by reference in its entirety) and nucleic acid molecules, modified nucleic acid molecules or mmRNA may be administered intramuscularly or intradermally.

In one embodiment, the nucleic acid molecules, modified nucleic acid molecules and/or mmRNA may be formulated in and/or delivered in a lipid nanoparticle comprising the cationic lipid DLin-MC3-DMA and the neutral lipid DOPE. The lipid nanoparticle may also comprise a PEG based lipid and a cholesterol or antioxidant. These lipid nanoparticle formulations comprising DLin-MC3-DMA and DOPE and nucleic acid molecules, modified nucleic acid molecules and/or mmRNA may be administered intramuscularly or intradermally.

In one embodiment, the lipid nanoparticle comprising DLin-MC3-DMA and DOPE may comprise a PEG lipid such as, but not limited to, pentaerythritol PEG ester tetra-succinimidyl and pentaerythritol PEG ether tetra-thiol, PEG-c-DOMG, PEG-DMG (1,2-Dimyristoyl-sn-glycerol, methoxypolyethylene Glycol), PEG-DSG (1,2-Distearoyl-sn-glycerol, methoxypolyethylene Glycol), PEG-DPG (1,2-Dipalmitoyl-sn-glycerol, methoxypolyethylene glycol), PEG-DSA (PEG coupled to 1,2-distearyloxypropyl-3-amine), PEG-DMA (PEG coupled to 1,2-dimyristyloxypropyl-3-amine, PEG-c-DNA, PEG-c-DMA, PEG-S-DSG, PEG-c-DMA, PEG-DPG, PEG-DMG 2000 and those described herein and/or known in the art.

In one embodiment, the lipid nanoparticle comprising DLin-MC3-DMA and DOPE may include 0.5% to about 3.0%, from about 1.0% to about 3.5%, from about 1.5% to about 4.0%, from about 2.0% to about 4.5%, from about 2.5% to about 5.0% and/or from about 3.0% to about 6.0% of the lipid molar ratio of a PEG lipid.

In one embodiment, the lipid nanoparticle comprising DLin-MC3-DMA and DOPE may include 25.0% cholesterol to about 50.0% cholesterol, from about 30.0% cholesterol to about 45.0% cholesterol, from about 35.0% cholesterol to about 50.0% cholesterol and/or from about 48.5% cholesterol to about 60% cholesterol. In one embodiment, formulations may comprise a percentage of cholesterol selected from the group consisting of 28.5%, 31.5%, 33.5%, 36.5%, 37.0%, 38.5%, 39.0%, 43.5% and 48.5%.

In one embodiment, the lipid nanoparticle comprising DLin-MC3-DMA and DOPE may include 25.0% antioxidant to about 50.0% antioxidant, from about 30.0% antioxidant to about 45.0% antioxidant, from about 35.0% antioxidant to about 50.0% antioxidant and/or from about 48.5% antioxidant to about 60% antioxidant. In one embodiment, formulations may comprise a percentage of antioxidant selected from the group consisting of 28.5%, 31.5%, 33.5%, 36.5%, 37.0%, 38.5%, 39.0%, 43.5% and 48.5%.

In one embodiment, the nucleic acid molecules, modified nucleic acid molecules and/or mmRNA may be formulated in and/or delivered in a nanoparticle coated with a polymer for reversible immobilization and/or controlled release of the nucleic acid molecules, modified nucleic acid molecules and/or mmRNA as described in International Patent Publication No. WO2013174409, the contents of which is herein incorporated by reference in its entirety. As a non-limiting example, the nanoparticle is coated with a biodegradable polymer as described in International Patent Publication No. WO2013174409, the contents of which is herein incorporated by reference in its entirety.

In one embodiment, the nucleic acid molecules, modified nucleic acid molecules and/or mmRNA may be formulated in and/or delivered in a hydrophobic nanoparticle. The hydrophobic nanoparticle may further comprise a liver targeting moiety such as, but not limited to, the hydrophobic nanoparticles described in US Patent Publication No. US20140017329, the contents of which are herein incorporated by reference in its entirety.

In one embodiment, the nucleic acid molecules, modified nucleic acid molecules and/or mmRNA may be formulated in and/or delivered in a milled nanoparticle. As a non-limiting example, the milled nanoparticles may be those described in or made by the methods described in U.S. Pat. No. 8,568,784, the contents of which are herein incorporated by reference in its entirety. The milled nanoparticles may comprise a biologically active agent, at least one biopolymer and a polymer or ligand coating.

In one embodiment, the nucleic acid molecules, modified nucleic acid molecules and/or mmRNA may be formulated in compositions which induce an immune response such as, but not limited to the formulations described in International Patent Publication Nos. WO2013143555 and WO2013143683, the contents of each of which are herein incorporated by reference in their entirety. As a non-limiting example, the formulations may induce an immune response after systemic administration of the nucleic acid molecules, modified nucleic acid molecules and/or mmRNA. As another non-limiting example, the formulation which may induce the immune response may include nanoparticles comprising at least one nucleic acid molecule as described in International Patent Publication Nos. WO2013143555 and WO2013143683, the contents of each of which are herein incorporated by reference in their entirety.

In one embodiment, the nucleic acid molecules, modified nucleic acid molecules and/or mmRNA may be formulated in and/or delivered in neutral nanoparticles. As a non-limiting example, the neutral nanoparticles may be those described in or made by the methods described in International Patent Publication No. WO2013149141, the contents of which are herein incorporated by reference in its entirety.

In one embodiment, the nanoparticles may be neutralized by the methods described in International Patent Publication No. WO2013149141, the contents of which are herein incorporated by reference in its entirety.

In one embodiment, the nucleic acid molecules, modified nucleic acid molecule and/or mmRNA may be formulated in and/or delivered in a nanoparticle having a nucleic acid nanostructure core and a lipid coating such as, but not limited to, the nanoparticles described in International Patent Publication No. WO2013148186, the contents of which are herein incorporated by reference in its entirety.

In one embodiment, the nucleic acid molecules, modified nucleic acid molecule and/or mmRNA may be formulated in a particle comprising a conjugate for delivering nucleic acid agents such as the particles described in US Patent Publication No. US20140037573, the contents of which are herein incorporated by reference in its entirety. As a non-limiting example, the particle comprising a plurality of hydrophobic moieties, a plurality of hydrophilic-hydrophobic polymers and nucleic acid agents.

In one embodiment, the nanoparticles which may be used to formulate and/or deliver the nucleic acid molecules, modified nucleic acids and/or mmRNA described herein may comprise a cationic lipid such as, but not limited to, the cationic lipids of formula (I) described in US Patent Publication NO. US20140045913, the contents of which are herein incorporated by reference in its entirety.

In one embodiment, the nanoparticle may be a polyethylene glycolated (PEGylated) nanoparticle such as, but not limited to, the PEGylated nanoparticles described in US Patent Publication No. US20140044791, the contents of which are herein incorporated by reference in its entirety. The PEGylated nanoparticle may comprise at least one targeting moiety coupled to the polyethylene glycol of the nanoparticle in order to target the composition to a specific cell. Non-limiting examples, of PEGylated nanoparticles and targeting moieties are described in US Patent Publication No. US20140044791, the contents of which are herein incorporated by reference in its entirety.

In one embodiment, the nanoparticle may be a mesoporous nanoparticle such as, but not limited to, those described in International Patent Publication No. WO2012142240, the contents of which are herein incorporated by reference in its entirety. The mesoporous nanoparticle may be loaded with the nucleic acid molecules, modified nucleic acid molecules and/or mmRNA and may release the load in a controlled manner for a desired period of time such as, but not limited to an extended period of time.

Polymers, Biodegradable Nanoparticles, and Core-Shell Nanoparticles

The nucleic acid molecules, modified nucleic acid molecules and mmRNA of the invention can be formulated using natural and/or synthetic polymers. Non-limiting examples of polymers which may be used for delivery include, but are not limited to, DYNAMIC POLYCONJUGATE® (Arrowhead Research Corp., Pasadena, Calif.) formulations from MIRUS® Bio (Madison, Wis.) and Roche Madison (Madison, Wis.), PHASERX™ polymer formulations such as, without limitation, SMARTT POLYMER TECHNOLOGY™ (Seattle, Wash.), DMRI/DOPE, poloxamer, VAXFECTIN® adjuvant from Vical (San Diego, Calif.), chitosan, cyclodextrin from Calando Pharmaceuticals (Pasadena, Calif.), dendrimers and poly(lactic-co-glycolic acid) (PLGA) polymers, RONDEL™ (RNAi/Oligonucleotide Nanoparticle Delivery) polymers (Arrowhead Research Corporation, Pasadena, Calif.) and pH responsive co-block polymers such as, but not limited to, PHASERX™ (Seattle, Wash.).

In one embodiment, formulations comprising natural and/or synthetic polymers and nucleic acid molecules, modified nucleic acid molecules or mmRNA may be administered intramuscularly. In one embodiment, formulations comprising natural and/or synthetic polymers and nucleic acid molecules, modified nucleic acid molecules or mmRNA may be administered intradermally.

A non-limiting example of chitosan formulation includes a core of positively charged chitosan and an outer portion of negatively charged substrate (U.S. Pub. No. 20120258176; the contents of which are herein incorporated by reference in its entirety). Chitosan includes, but is not limited to N-trimethyl chitosan, mono-N-carboxymethyl chitosan (MCC), N-palmitoyl chitosan (NPCS), EDTA-chitosan, low molecular weight chitosan, chitosan derivatives, or combinations thereof.

In one embodiment, the polymers used in the present invention have undergone processing to reduce and/or inhibit the attachment of unwanted substances such as, but not limited to, bacteria, to the surface of the polymer. The polymer may be processed by methods known and/or described in the art and/or described in International Pub. No. WO2012150467, the contents of which are herein incorporated by reference in its entirety.

A non-limiting example of PLGA formulations include, but are not limited to, PLGA injectable depots (e.g., ELIGARD® which is formed by dissolving PLGA in 66% N-methyl-2-pyrrolidone (NMP) and the remainder being aqueous solvent and leuprolide. Once injected, the PLGA and leuprolide peptide precipitates into the subcutaneous space).

Many of these polymer approaches have demonstrated efficacy in delivering oligonucleotides in vivo into the cell cytoplasm (reviewed in deFougerolles Hum Gene Ther. 2008 19:125-132; the contents of which are herein incorporated by reference in its entirety). Two polymer approaches that have yielded robust in vivo delivery of nucleic acids, in this case with small interfering RNA (siRNA), are dynamic polyconjugates and cyclodextrin-based nanoparticles (see e.g., US Patent Publication No. US20130156721, the contents of which are herein incorporated by reference in its entirety). The first of these delivery approaches uses dynamic polyconjugates and has been shown in vivo in mice to effectively deliver siRNA and silence endogenous target mRNA in hepatocytes (Rozema et al., Proc Natl Acad Sci USA. 2007 104:12982-12887; the contents of which are herein incorporated by reference in its entirety). This particular approach is a multicomponent polymer system whose key features include a membrane-active polymer to which nucleic acid, in this case siRNA, is covalently coupled via a disulfide bond and where both PEG (for charge masking) and N-acetylgalactosamine (for hepatocyte targeting) groups are linked via pH-sensitive bonds (Rozema et al., Proc Natl Acad Sci USA. 2007 104:12982-12887; the contents of which are herein incorporated by reference in its entirety). On binding to the hepatocyte and entry into the endosome, the polymer complex disassembles in the low-pH environment, with the polymer exposing its positive charge, leading to endosomal escape and cytoplasmic release of the siRNA from the polymer. Through replacement of the N-acetylgalactosamine group with a mannose group, it was shown one could alter targeting from asialoglycoprotein receptor-expressing hepatocytes to sinusoidal endothelium and Kupffer cells. Another polymer approach involves using transferrin-targeted cyclodextrin-containing polycation nanoparticles. These nanoparticles have demonstrated targeted silencing of the EWS-FLI1 gene product in transferrin receptor-expressing Ewing's sarcoma tumor cells (Hu-Lieskovan et al., Cancer Res. 2005 65: 8984-8982; herein incorporated by reference in its entirety) and siRNA formulated in these nanoparticles was well tolerated in non-human primates (Heidel et al., Proc Natl Acad Sci USA 2007 104:5715-21; herein incorporated by reference in its entirety). Both of these delivery strategies incorporate rational approaches using both targeted delivery and endosomal escape mechanisms.

The polymer formulation can permit the sustained or delayed release of nucleic acid molecules, modified nucleic acid molecules or mmRNA (e.g., following intramuscular, intradermal or subcutaneous injection). The altered release profile for the nucleic acid molecules, modified nucleic acid molecule or mmRNA can result in, for example, translation of an encoded protein over an extended period of time. The polymer formulation may also be used to increase the stability of the nucleic acid molecules, modified nucleic acid molecule or mmRNA. Biodegradable polymers have been previously used to protect nucleic acids other than mmRNA from degradation and been shown to result in sustained release of payloads in vivo (Rozema et al., Proc Natl Acad Sci USA. 2007 104:12982-12887; Sullivan et al., Expert Opin Drug Deliv. 2010 7:1433-1446; Convertine et al., Biomacromolecules. 2010 Oct. 1; Chu et al., Acc Chem Res. 2012 Jan. 13; Manganiello et al., Biomaterials. 2012 33:2301-2309; Benoit et al., Biomacromolecules. 2011 12:2708-2714; Singha et al., Nucleic Acid Ther. 2011 2:133-147; deFougerolles Hum Gene Ther. 2008 19:125-132; Schaffert and Wagner, Gene Ther. 2008 16:1131-1138; Chaturvedi et al., Expert Opin Drug Deliv. 2011 8:1455-1468; Davis, Mol Pharm. 2009 6:659-668; Davis, Nature 2010 464:1067-1070; each of which is herein incorporated by reference in its entirety).

In one embodiment, the pharmaceutical compositions may be sustained release formulations. In a further embodiment, the sustained release formulations may be for subcutaneous delivery. Sustained release formulations may include, but are not limited to, PLGA microspheres, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, and COSEAL® (Baxter International, Inc Deerfield, Ill.).

As a non-limiting example, nucleic acid molecules, modified mRNA may be formulated in PLGA microspheres by preparing the PLGA microspheres with tunable release rates (e.g., days and weeks) and encapsulating the nucleic acid molecules, modified nucleic acid molecules, modified mRNA in the PLGA microspheres while maintaining the integrity of the modified mRNA during the encapsulation process. EVAc are non-biodegradeable, biocompatible polymers which are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Duragesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C. PEG-based surgical sealants comprise two synthetic PEG components mixed in a delivery device which can be prepared in one minute, seals in 3 minutes and is reabsorbed within 30 days. GELSITE® and natural polymers are capable of in-situ gelation at the site of administration. They have been shown to interact with protein and peptide therapeutic candidates through ionic interaction to provide a stabilizing effect.

In one embodiment, PLGA microspheres comprising nucleic acid molecules, modified nucleic acid molecules or mmRNA may be administered intramuscularly. In one embodiment, PLGA microspheres comprising nucleic acid molecules, modified nucleic acid molecules or mmRNA may be administered intradermally.

Polymer formulations can also be selectively targeted through expression of different ligands as exemplified by, but not limited by, folate, transferrin, and N-acetylgalactosamine (GalNAc) (Benoit et al., Biomacromolecules. 2011 12:2708-2714; Rozema et al., Proc Natl Acad Sci USA. 2007 104:12982-12887; Davis, Mol Pharm. 2009 6:659-668; Davis, Nature 2010 464:1067-1070; each of which is herein incorporated by reference in its entirety).

The nucleic acid molecules, modified nucleic acid molecules and mmRNA of the invention may be formulated with or in a polymeric compound. The polymer may include at least one polymer such as, but not limited to, polyethenes, polyethylene glycol (PEG), poly(l-lysine)(PLL), PEG grafted to PLL, cationic lipopolymer, biodegradable cationic lipopolymer, polyethyleneimine (PEI), cross-linked branched poly(alkylene imines), a polyamine derivative, a modified poloxamer, a biodegradable polymer, elastic biodegradable polymer, biodegradable block copolymer, biodegradable random copolymer, biodegradable polyester copolymer, biodegradable polyester block copolymer, biodegradable polyester block random copolymer, multiblock copolymers, linear biodegradable copolymer, poly[α-(4-aminobutyl)-L-glycolic acid) (PAGA), biodegradable cross-linked cationic multi-block copolymers, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly (serine ester), poly(L-lactide-co-L-lysine), poly(4-hydroxy-L-proline ester), acrylic polymers, amine-containing polymers, dextran polymers, dextran polymer derivatives or combinations thereof.

As a non-limiting example, the nucleic acid molecules, modified nucleic acid molecules or mmRNA of the invention may be formulated with the polymeric compound of PEG grafted with PLL as described in U.S. Pat. No. 6,177,274; the contents of which is herein incorporated by reference in its entirety. The formulation may be used for transfecting cells in vitro or for in vivo delivery of the nucleic acid molecules, modified nucleic acid molecules and mmRNA. In another example, the nucleic acid molecules, modified nucleic acid molecules and mmRNA may be suspended in a solution or medium with a cationic polymer, in a dry pharmaceutical composition or in a solution that is capable of being dried as described in U.S. Pub. Nos. 20090042829 and 20090042825; the contents of each of which are herein incorporated by reference in their entireties.

As another non-limiting example the nucleic acid molecules, modified nucleic acid molecules or mmRNA of the invention may be formulated with a PLGA-PEG block copolymer (see US Pub. No. US20120004293 and U.S. Pat. No. 8,236,330, each of which are herein incorporated by reference in their entireties) or PLGA-PEG-PLGA block copolymers (See U.S. Pat. No. 6,004,573, herein incorporated by reference in its entirety). As a non-limiting example, the nucleic acid molecules, modified nucleic acid molecules or mmRNA of the invention may be formulated with a diblock copolymer of PEG and PLA or PEG and PLGA (see U.S. Pat. No. 8,246,968, herein incorporated by reference in its entirety).

A polyamine derivative may be used to deliver nucleic acid molecules, modified nucleic acid molecules and/or mmRNA or to treat and/or prevent a disease or to be included in an implantable or injectable device (U.S. Pub. Nos. 20100260817 (now U.S. Pat. No. 8,460,696) and 20140050775, the contents of each of which are herein incorporated by reference in its entirety). As a non-limiting example, a pharmaceutical composition may include the nucleic acid molecules, modified nucleic acid molecules and mmRNA and the polyamine derivative described in U.S. Pub. No. 20100260817 (now U.S. Pat. No. 8,460,696) (the contents of each of which are incorporated herein by reference in its entirety). As a non-limiting example the nucleic acid molecules, modified nucleic acids or mmRNA of the present invention may be delivered using a polyamine polymer such as, but not limited to, a polymer comprising a 1,3-dipolar addition polymer prepared by combining a carbohydrate diazide monomer with a dilkyne unite comprising oligoamines (U.S. Pat. No. 8,236,280; herein incorporated by reference in its entirety). As another non-limiting example, the nucleic acid molecules, modified nucleic acids and/or mmRNA of the present invention may be delivered using or formulated in compositions comprising polyamine derivatives such as those described in formulas I-VI described in US Patent Publication No. US20140050775, the contents of which are herein incorporated by reference in its entirety.

The nucleic acid molecules, modified nucleic acid molecules and/or mmRNA of the invention may be formulated with at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), polycyanoacrylates and combinations thereof. As a non-limiting example, the modified nucleic acid molecules and/or mmRNA may be formulated with at least one poly(acrylate) copolymer as described in US Patent Publication No. US20130317079, the contents of which are herein incorporated by reference in its entirety. As another non-limiting example, the nucleic acid molecules, modified nucleic acid molecules and/or mmRNA may be formulated with at least one poly(acrylate) polymer as described in International Patent Publication No. WO2013158141, the contents of which are herein incorporated by reference in its entirety.

In one embodiment, the nucleic acid molecules, modified nucleic acid molecules and/or mmRNA of the present invention may be formulated with at least one polymer and/or derivatives thereof described in International Publication Nos. WO2011115862, WO2012082574 and WO2012068187 and U.S. Pub. No. 20120283427, each of which are herein incorporated by reference in their entireties. In another embodiment, the nucleic acid molecules, modified nucleic acid molecules or mmRNA of the present invention may be formulated with a polymer of formula Z as described in WO2011115862, herein incorporated by reference in its entirety. In yet another embodiment, the nucleic acid molecules, modified nucleic acid molecules or mmRNA may be formulated with a polymer of formula Z, Z' or Z" as described in International Pub. Nos. WO2012082574 or WO2012068187, each of which are herein incorporated by reference in their entireties. The polymers formulated with the nucleic acid molecules, modified nucleic acids and/or modified mRNA of the present invention may be synthesized by the methods described in International Pub. Nos. WO2012082574 or WO2012068187, each of which are herein incorporated by reference in their entireties.

Formulations of nucleic acid molecules, modified nucleic acid molecules and/or mmRNA of the invention may include at least one amine-containing polymer such as, but not limited to polylysine, polyethylene imine, poly(amidoamine) dendrimers poly(amine-co-esters) or combinations thereof. As a non-limiting example, the poly(amine-co-esters) may be the polymers described in and/or made by the methods described in International Publication No WO2013082529, the contents of which are herein incorporated by reference in its entirety. As another non-limiting example, the poly(amido amine) polymer may be the polymers described in and/or made by the methods described in US Publication No US20130289207, the contents of which are herein incorporated by reference in its entirety.

Formulations of the nucleic acid molecules, modified nucleic acid molecules and/or mmRNA of the invention may include at least one of the cationic lipids described in International Patent Publication Nos. WO2013158127 and WO2013148541, the contents of each of which are herein incorporated by reference in its entirety. As a non-limiting example, the cationic lipid has the structure (I) as described in International Patent Publication No. WO2013158127, the contents of which are herein incorporated by reference in its entirety. As another non-limiting example, the cationic lipid has the structure formula A as described in International Patent Publication No. WO2013148541, the contents of each of which are herein incorporated by reference in its entirety.

Formulations of the nucleic acid molecules, modified nucleic acid molecules and/or mmRNA of the invention may include at least one of the diester and trimester based low molecular weight, biodegradable cationic lipids described in International Patent Publication No. WO2013158579, the contents of which are herein incorporated by reference in its entirety. As a non-limiting example, the cationic lipid has the formula A as described in International Patent Publication No. WO2013158579, the contents of which are herein incorporated by reference in its entirety.

In one embodiment, polymers described herein may be synthesized using reversible addition-fragmentation chain transfer (RAFT) polymerization. RAFT is a controlled radical polymerization that may allow synthesis of monodisperse and polymers with block or other architectures and telechelic end chemistries providing opportunities for site-specific bioconjugation (see e.g., Nelson et al. *Tunable Delivery of siRNA from a Biodegradable Scaffold to Promote Angiogenesis In Vivo*. Adv. Mater. 2013; the contents of which are herein incorporated by reference in its entirety).

For example, the nucleic acid molecules, modified nucleic acid molecules and/or mmRNA of the invention may be formulated in a pharmaceutical compound including a poly (alkylene imine), a biodegradable cationic lipopolymer, a biodegradable block copolymer, a biodegradable polymer, or a biodegradable random copolymer, a biodegradable polyester block copolymer, a biodegradable polyester polymer, a biodegradable polyester random copolymer, a linear biodegradable copolymer, PAGA, a biodegradable cross-linked cationic multi-block copolymer or combinations thereof. The biodegradable cationic lipopolymer may be made by methods known in the art and/or described in U.S. Pat. No. 6,696,038, U.S. App. Nos. 20030073619 and 20040142474 each of which is herein incorporated by reference in their entireties. The poly(alkylene imine) may be made using methods known in the art and/or as described in U.S. Pub. No. 20100004315, herein incorporated by reference in its entirety. The biodegradabale polymer, biodegradable block copolymer, the biodegradable random copolymer, biodegradable polyester block copolymer, biodegradable polyester polymer, or biodegradable polyester random copolymer may be made using methods known in the art and/or as described in U.S. Pat. Nos. 6,517,869 and 6,267,987, the contents of which are each incorporated herein by reference in their entirety. The linear biodegradable copolymer may be made using methods known in the art and/or as described in U.S. Pat. No. 6,652,886. The PAGA polymer may be made using methods known in the art and/or as described in U.S. Pat. No. 6,217,912 the contents of which is herein incorporated by reference in its entirety. The PAGA polymer may be copolymerized to form a copolymer or block copolymer with polymers such as but not limited to, poly-L-lysine, polyargine, polyornithine, histones, avidin, protamines, polylactides and poly(lactide-co-glycolides). The biodegradable cross-linked cationic multi-block copolymers may be made my methods known in the art and/or as described in U.S. Pat. Nos. 8,057,821, 8,444, 992 or U.S. Pub. No. 2012009145 each of which are herein incorporated by reference in their entireties. For example, the multi-block copolymers may be synthesized using linear polyethyleneimine (LPEI) blocks which have distinct patterns as compared to branched polyethyleneimines. Further, the composition or pharmaceutical composition may be made by the methods known in the art, described herein, or as described in U.S. Pub. No. 20100004315 or U.S. Pat. Nos. 6,267,987 and 6,217,912 each of which are herein incorporated by reference in their entireties.

The nucleic acid molecules, modified nucleic acid molecules and mmRNA of the invention may be formulated with at least one degradable polyester which may contain polycationic side chains. Degradeable polyesters include, but are not limited to, poly(serine ester), poly(L-lactide-co- L-lysine), poly(4-hydroxy-L-proline ester), and combinations thereof. In another embodiment, the degradable polyesters may include a PEG conjugation to form a PEGylated polymer.

The nucleic acid molecules, modified nucleic acid molecules and mmRNA of the invention may be formulated with at least one crosslinkable polyester. Crosslinkable polyesters include those known in the art and described in US Pub. No. 20120269761, the contents of which are herein incorporated by reference in its entirety.

The nucleic acid molecules, modified nucleic acid molecules and mmRNA of the invention may be formulated in or with at least one cyclodextrin polymer. Cyclodextrin polymers and methods of making cyclodextrin polymers include those known in the art and described in US Pub. No. 20130184453, the contents of which are herein incorporated by reference in its entirety.

In one embodiment, the nucleic acid molecules, modified nucleic acid molecules and mmRNA of the invention may be formulated in or with at least one crosslinked cation-binding polymers. Crosslinked cation-binding polymers and methods of making crosslinked cation-binding polymers include those known in the art and described in International Patent Publication No. WO2013106072, WO2013106073 and WO2013106086, the contents of each of which are herein incorporated by reference in its entirety.

In one embodiment, the nucleic acid molecules, modified nucleic acid molecules and mmRNA of the invention may be formulated in or with at least one branched polymer. Branched polymers and methods of making branched polymers include those known in the art and described in International Patent Publication No. WO2013113071, the contents of each of which are herein incorporated by reference in its entirety.

In one embodiment, the nucleic acid molecules, modified nucleic acid molecules and mmRNA of the invention may be formulated in or with at least PEGylated albumin polymer. PEGylated albumin polymer and methods of making PEGylated albumin polymer include those known in the art and described in US Patent Publication No. US20130231287, the contents of each of which are herein incorporated by reference in its entirety.

In one embodiment, the polymers described herein may be conjugated to a lipid-terminating PEG. As a non-limiting example, PLGA may be conjugated to a lipid-terminating PEG forming PLGA-DSPE-PEG. As another non-limiting example, PEG conjugates for use with the present invention are described in International Publication No. WO2008103276, herein incorporated by reference in its entirety. The polymers may be conjugated using a ligand conjugate such as, but not limited to, the conjugates described in U.S. Pat. No. 8,273,363, herein incorporated by reference in its entirety.

In one embodiment, the nucleic acid molecules, modified nucleic acid molecules and/or mmRNA disclosed herein may be mixed with the PEGs or the sodium phosphate/sodium carbonate solution prior to administration. In another embodiment, a nucleic acid molecules, modified nucleic acid molecule or mmRNA encoding a protein of interest may be mixed with the PEGs and also mixed with the sodium phosphate/sodium carbonate solution. In yet another embodiment, a nucleic acid molecules, modified nucleic acid molecule or mmRNA encoding a protein of interest may be mixed with the PEGs and a nucleic acid molecules, modified nucleic acid molecule or mmRNA encoding a second protein of interest may be mixed with the sodium phosphate/sodium carbonate solution.

In one embodiment, the nucleic acid molecules, modified nucleic acid molecules and/or mmRNA described herein may be conjugated with another compound. Non-limiting examples of conjugates are described in U.S. Pat. Nos. 7,964,578 and 7,833,992, each of which are herein incorporated by reference in their entireties. In another embodiment, nucleic acid molecules, modified nucleic acid molecules or modified RNA of the present invention may be conjugated with conjugates of formula 1-122 as described in U.S. Pat. Nos. 7,964,578 and 7,833,992, each of which are herein incorporated by reference in their entireties. The nucleic acid molecules, modified nucleic acid molecules, modified RNA described herein may be conjugated with a metal such as, but not limited to, gold. (See e.g., Giljohann et al. Journ. Amer. Chem. Soc. 2009 131(6): 2072-2073; herein incorporated by reference in its entirety). In another embodiment, the nucleic acid molecules, modified nucleic acid molecules and/or mmRNA described herein may be conjugated and/or encapsulated in gold-nanoparticles. (International Pub. No. WO201216269 and U.S. Pub. No. 20120302940 and US20130177523; the contents of each of which is herein incorporated by reference in its entirety).

As described in U.S. Pub. No. 20100004313, herein incorporated by reference in its entirety, a gene delivery composition may include a nucleotide sequence and a poloxamer. For example, the nucleic acid molecules, modified nucleic acid and mmRNA of the present invention may be used in a gene delivery composition with the poloxamer described in U.S. Pub. No. 20100004313, the contents of which is herein incorporated by reference in its entirety.

In one embodiment, the polymer formulation of the present invention may be stabilized by contacting the polymer formulation, which may include a cationic carrier, with a cationic lipopolymer which may be covalently linked to cholesterol and polyethylene glycol groups. The polymer formulation may be contacted with a cationic lipopolymer using the methods described in U.S. Pub. No. 20090042829 herein incorporated by reference in its entirety. The cationic carrier may include, but is not limited to, polyethylenimine, poly(trimethylenimine), poly(tetramethylenimine), polypropylenimine, aminoglycoside-polyamine, dideoxy-diamino-b-cyclodextrin, spermine, spermidine, poly(2-dimethylamino)ethyl methacrylate, poly(lysine), poly(histidine), poly(arginine), cationized gelatin, dendrimers, chitosan, 1,2-Dioleoyl-3-Trimethylammonium-Propane (DOTAP), N-[1-(2,3-dioleoyloxy)propyl]-N,N,N-trimethylammonium chloride (DOTMA), 1-[2-(oleoyloxy)ethyl]-2-oleyl-3-(2-hydroxyethyl)imidazolinium chloride (DOTIM), 2,3-dioleyloxy-N-[2(sperminecarboxamido)ethyl]-N,N-dimethyl-1-propanaminium trifluoroacetate (DOSPA), 3B—[N—(N',N'-Dimethylaminoethane)-carbamoyl]Cholesterol Hydrochloride (DC-Cholesterol HCl) diheptadecylamidoglycyl spermidine (DOGS), N,N-distearyl-N,N-dimethylammonium bromide (DDAB), N-(1,2-dimyristyloxyprop-3-yl)-N,N-dimethyl-N-hydroxyethyl ammonium bromide (DMRIE), N,N-dioleyl-N,N-dimethylammonium chloride DODAC) and combinations thereof. As a non-limiting example, the nucleic acid molecules, modified nucleic acid molecules and/or mmRNA may be formulated with a cationic lipopolymer such as those described in U.S. Patent Application No. 20130065942, the contents of which is herein incorporated by reference in its entirety.

The nucleic acid molecules, modified nucleic acid molecules and/or mmRNA of the invention may be formulated in a polyplex of one or more polymers (See e.g., U.S. Pat. No. 8,501,478, U.S. Pub. No. 20120237565, 20120270927, 20130149783 and 20130344117 and International Pub. No.

WO2013090861; the contents of each of which are herein incorporated by reference in its entirety). As a non-limiting example, the polyplex may be formed using the noval alpha-aminoamidine polymers described in International Publication No. WO2013090861, the contents of which are herein incorporated by reference in its entirety. As another non-limiting example, the polyplex may be formed using the click polymers described in U.S. Pat. No. 8,501,478, the contents of which is herein incorporated by reference in its entirety. As yet another non-limiting example, the polyplex may comprise a cationic polymer having formula I, I-a, I-b, II, III, III-a, III-b, IV, V, V-a, V-b, VI, VI-b, VI-a, VII as described in US Patent Publication No. US20130344117, the contents of which are herein incorporated by reference in its entirety.

In one embodiment, the polyplex comprises two or more cationic polymers. The catioinic polymer may comprise a poly(ethylene imine) (PEI) such as linear PEI. In another embodiment, the polyplex comprises p(TETA/CBA) its PEGylated analog p(TETA/CBA)-g-PEG2k and mixtures thereof (see e.g., US Patent Publication No. US20130149783, the contents of which are herein incorporated by reference in its entirety.

The nucleic acid molecules, modified nucleic acid molecules and mmRNA of the invention can also be formulated as a nanoparticle using a combination of polymers, lipids, and/or other biodegradable agents, such as, but not limited to, calcium phosphate. Components may be combined in a core-shell, hybrid, and/or layer-by-layer architecture, to allow for fine-tuning of the nanoparticle so to delivery of the nucleic acid molecules, modified nucleic acid molecule and mmRNA may be enhanced (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; each of which is herein incorporated by reference in its entirety). As a non-limiting example, the nanoparticle may comprise a plurality of polymers such as, but not limited to hydrophilic-hydrophobic polymers (e.g., PEG-PLGA), hydrophobic polymers (e.g., PEG) and/or hydrophilic polymers (International Pub. No. WO20120225129; the contents of which are herein incorporated by reference in its entirety). As another non-limiting example the nanoparticle comprising hydrophilic polymers for the nucleic acid molecules, modified nucleic acid molecules and/or mmRNA may be those described in or made by the methods described in International Patent Publication No. WO2013119936, the contents of which are herein incorporated by reference in its entirety.

In one embodiment, the biodegradable polymers which may be used in the present invention are poly(ether-anhydride) block copolymers. As a non-limiting example, the biodegradable polymers used herein may be a block copolymer as described in International Patent Publication No WO2006063249, herein incorporated by reference in its entirety, or made by the methods described in International Patent Publication No WO2006063249, the contents of which is herein incorporated by reference in its entirety.

In another embodiment, the biodegradable polymers which may be used in the present invention are alkyl and cycloalkyl terminated biodegradable lipids. As a non-limiting example, the alkyl and cycloalkyl terminated biodegradable lipids may be those described in International Publication No. WO2013086322 and/or made by the methods described in International Publication No. WO2013086322; the contents of which are herein incorporated by reference in its entirety.

In yet another embodiment, the biodegradable polymers which may be used in the present invention are cationic lipids having one or more biodegradable group located in a lipid moiety. As a non-limiting example, the biodegradable lipids may be those described in US Patent Publication No. US20130195920, the contents of which are herein incorporated by reference in its entirety.

In another embodiment, the biodegradable polymers which may be used in the present invention are described in U.S. Pat. No. 8,535,655, the contents of which are herein incorporated by reference in its entirety. The biodegradable polymer may comprise at least one bioactive moiety such as, but not limited to the nucleic acid molecules, modified nucleic acid molecules and/or mmRNA described herein. The bioactive moieties may be pendant from and/or covalently bonded to the biodegradable polymer backbone and the bioactive moieties may be released at a rate equal to or faster than the rate of the biodegradation of the polymer backbone.

In one embodiment, biodegradable polymers described herein and/or those known in the art may be used in nanoparticles to deliver the nucleic acid molecules, modified nucleic acid molecules and/or mmRNA described herein. As a non-limiting example, nanoparticles comprising biodegradable polymers which may be used to deliver nucleic acids such as the nucleic acid molecules, modified nucleic acid molecules and/or mmRNA are described in U.S. Pat. No. 8,628,801, the contents of which are herein incorporated by reference in its entirety.

Biodegradable calcium phosphate nanoparticles in combination with lipids and/or polymers have been shown to deliver nucleic acid molecules, modified nucleic acid molecules and mmRNA in vivo. In one embodiment, a lipid coated calcium phosphate nanoparticle, which may also contain a targeting ligand such as anisamide, may be used to deliver the nucleic acid molecules, modified nucleic acid molecule and mmRNA of the present invention. For example, to effectively deliver siRNA in a mouse metastatic lung model a lipid coated calcium phosphate nanoparticle was used (Li et al., J Contr Rel. 2010 142: 416-421; Li et al., J Contr Rel. 2012 158:108-114; Yang et al., Mol Ther. 2012 20:609-615; herein incorporated by reference in its entirety). This delivery system combines both a targeted nanoparticle and a component to enhance the endosomal escape, calcium phosphate, in order to improve delivery of the siRNA.

In one embodiment, calcium phosphate with a PEG-polyanion block copolymer may be used to deliver nucleic acid molecules, modified nucleic acid molecules and mmRNA (Kazikawa et al., J Contr Rel. 2004 97:345-356; Kazikawa et al., J Contr Rel. 2006 111:368-370; herein incorporated by reference in its entirety).

In one embodiment, a PEG-charge-conversional polymer (Pitella et al., Biomaterials. 2011 32:3106-3114) may be used to form a nanoparticle to deliver the modified nucleic acid molecules and mmRNA of the present invention. The PEG-charge-conversional polymer may improve upon the PEG-polyanion block copolymers by being cleaved into a polycation at acidic pH, thus enhancing endosomal escape.

In one embodiment, a polymer used in the present invention may be a pentablock polymer such as, but not limited to, the pentablock polymers described in International Patent Publication No. WO2013055331, herein incorporated by reference in its entirety. As a non-limiting example, the pentablock polymer comprises PGA-PCL-PEG-PCL-PGA, wherein PEG is polyethylene glycol, PCL is poly(E-caprolactone), PGA is poly(glycolic acid), and PLA is poly(lactic acid). As another non-limiting example, the pentablock polymer comprises PEG-PCL-PLA-PCL-PEG, wherein PEG is polyethylene glycol, PCL is poly(E-caprolactone), PGA is poly(glycolic acid), and PLA is poly(lactic acid).

In one embodiment, a polymer which may be used in the present invention comprises at least one diepoxide and at least one aminoglycoside (See e.g., International Patent Publication No. WO2013055971, herein incorporated by reference in its entirety). The diepoxide may be selected from, but is not limited to, 1,4 butanediol diglycidyl ether (1,4 B), 1,4-cyclohexanedimethanol diglycidyl ether (1,4 C), 4-vinylcyclohexene diepoxide (4VCD), ethyleneglycol diglycidyl ether (EDGE), glycerol diglycidyl ether (GDE), neopentylglycol diglycidyl ether (NPDGE), poly(ethyleneglycol) diglycidyl ether (PEGDE), poly(propyleneglycol) diglycidyl ether (PPGDE) and resorcinol diglycidyl ether (RDE). The aminoglycoside may be selected from, but is not limited to, streptomycin, neomycin, framycetin, paromomycin, ribostamycin, kanamycin, amikacin, arbekacin, bekanamycin, dibekacin, tobramycin, spectinomycin, hygromycin, gentamicin, netilmicin, sisomicin, isepamicin, verdamicin, astromicin, and apramycin. As a non-limiting example, the polymers may be made by the methods described in International Patent Publication No. WO2013055971, herein incorporated by reference in its entirety. As another non-limiting example, compositions comprising these polymer may be made by the methods described in International Patent Publication No. WO2013055971, the contents of which is herein incorporated by reference in its entirety.

In one embodiment, a polymer which may be used in the present invention may be a cross-linked polymer. As a non-limiting example, the cross-linked polymers may be used to form a particle as described in U.S. Pat. No. 8,414,927, herein incorporated by reference in its entirety. As another non-limiting example, the cross-linked polymer may be obtained by the methods described in US Patent Publication No. US20130172600, the contents of which are herein incorporated by reference in its entirety.

In another embodiment, a polymer which may be used in the present invention may be a cross-linked polymer such as those described in U.S. Pat. No. 8,461,132, herein incorporated by reference in its entirety. As a non-limiting example, the cross-linked polymer may be used in a therapeutic composition for the treatment of a body tissue. The therapeutic composition may be administered to damaged tissue using various methods known in the art and/or described herein such as injection or catheterization.

In one embodiment, a polymer which may be used in the present invention may be a di-alphatic substituted pegylated lipid such as, but not limited to, those described in International Patent Publication No. WO2013049328, the contents of which is herein incorporated by reference in its entirety.

In another embodiment, a polymer which may be used in the delivery and/or formulation of nucleic acid molecules, modified nucleic acid molecules and/or mmRNA is a pegylated polymer such as, but not limited to, those described in International Patent Publication No. WO2012099755, the contents of which are herein incorporated by reference in its entirety.

In one embodiment, a block copolymer is PEG-PLGA-PEG (see e.g., the thermosensitive hydrogel (PEG-PLGA-PEG) was used as a TGF-beta1 gene delivery vehicle in Lee et al. Thermosensitive Hydrogel as a Tgf-β1 Gene Delivery Vehicle Enhances Diabetic Wound Healing. Pharmaceutical Research, 2003 20(12): 1995-2000; as a controlled gene delivery system in Li et al. Controlled Gene Delivery System Based on Thermosensitive Biodegradable Hydrogel. Pharmaceutical Research 2003 20(6):884-888; and Chang et al., Non-ionic amphiphilic biodegradable PEG-PLGA-PEG copolymer enhances gene delivery efficiency in rat skeletal muscle. J Controlled Release. 2007 118:245-253; each of which is herein incorporated by reference in its entirety) may be used in the present invention. The present invention may be formulated with PEG-PLGA-PEG for administration such as, but not limited to, intramuscular, intradermal and subcutaneous administration.

In another embodiment, the PEG-PLGA-PEG block copolymer is used in the present invention to develop a biodegradable sustained release system. In one aspect, the modified nucleic acids of the present invention are mixed with the block copolymer prior to administration. In another aspect, the modified nucleic acids of the present invention are co-administered with the block copolymer.

In one embodiment, the polymer used in the present invention may be a multi-functional polymer derivative such as, but not limited to, a multi-functional N-maleimidyl polymer derivatives as described in U.S. Pat. No. 8,454,946, herein incorporated by reference in its entirety. In another embodiment, the polymer used in the present invention may be a multi-functional copolymer as described in US Patent Publication No. US20130236968, the contents of which are herein incorporated by reference in its entirety. As a non-limiting example, the multi-functional copolymer may have the formula (I), (II), (III), (IV), (V) or (VI) as described in US Patent Publication No. US20130236968, the contents of which are herein incorporated by reference in its entirety.

In one embodiment, the polymer which may be used in the present invention is a co-polymer having formula A-L-D (A is a linear, branched or dendritic polyamine; D is a lipid; and L is a linker comprising a water soluble polymer) as described in International Patent Publication No. WO2014025795, the contents of which are herein incorporated by reference in its entirety.

The use of core-shell nanoparticles has additionally focused on a high-throughput approach to synthesize cationic cross-linked nanogel cores and various shells (Siegwart et al., Proc Natl Acad Sci USA. 2011 108:12996-13001). The complexation, delivery, and internalization of the polymeric nanoparticles can be precisely controlled by altering the chemical composition in both the core and shell components of the nanoparticle. For example, the core-shell nanoparticles may efficiently deliver siRNA to mouse hepatocytes after they covalently attach cholesterol to the nanoparticle.

In one embodiment, a hollow lipid core comprising a middle PLGA layer and an outer neutral lipid layer containing PEG may be used to delivery of the modified nucleic acid molecules and mmRNA of the present invention. As a non-limiting example, in mice bearing a luciferase-expressing tumor, it was determined that the lipid-polymer-lipid hybrid nanoparticle significantly suppressed luciferase expression, as compared to a conventional lipoplex (Shi et al, Angew Chem Int Ed. 2011 50:7027-7031; herein incorporated by reference in its entirety).

In one embodiment, the lipid nanoparticles may comprise a core of the modified nucleic acid molecules disclosed herein and a polymer shell. The polymer shell may be any of the polymers described herein and are known in the art. In an additional embodiment, the polymer shell may be used to protect the modified nucleic acids in the core.

Core-shell nanoparticles for use with the nucleic acid molecules, modified nucleic acid molecules of the present invention are described and may be formed by the methods described in U.S. Pat. No. 8,313,777 or International Patent Publication No. WO2013124867, the contents of each of which are herein incorporated by reference in their entirety.

In one embodiment, the core-shell nanoparticles may comprise a core of the nucleic acid molecules, modified nucleic acid molecules disclosed herein and a polymer shell. The polymer shell may be any of the polymers described herein and are known in the art. In an additional embodiment, the polymer shell may be used to protect the modified nucleic acid molecules in the core.

In one embodiment, the polymer used with the formulations described herein may be a modified polymer (such as, but not limited to, a modified polyacetal) as described in International Publication No. WO2011120053, the contents of which are herein incorporated by reference in its entirety.

In one embodiment, core-shell nanoparticles comprising nucleic acid molecules, modified nucleic acid molecules or mmRNA may be administered intramuscularly. In one embodiment, core-shell nanoparticles comprising nucleic acid molecules, modified nucleic acid molecules or mmRNA may be administered intradermally.

In one embodiment, the formulation may be a polymeric carrier cargo complex comprising a polymeric carrier and at least one nucleic acid molecule, modified nucleic acid molecules or mmRNA. Non-limiting examples of polymeric carrier cargo complexes are described in International Patent Publications Nos. WO2013113326, WO2013113501, WO2013113325, WO2013113502 and WO2013113736 and European Patent Publication No. EP2623121, the contents of each of which are herein incorporated by reference in their entireties. In one aspect the polymeric carrier cargo complexes may comprise a negatively charged nucleic acid molecule such as, but not limited to, those described in International Patent Publication Nos. WO2013113325 and WO2013113502, the contents of each of which are herein incorporated by reference in its entirety.

In one embodiment, a pharmaceutical composition may comprise a nucleic acid molecules, modified nucleic acids and/or mmRNA of the invention and a polymeric carrier cargo complex. The nucleic acid molecules, modified nucleic acids and/or mmRNA may encode a protein of interest such as, but not limited to, an antigen from a pathogen associated with infectious disease, an antigen associated with allergy or allergic disease, an antigen associated with autoimmune disease or an antigen associated with cancer or tumour disease (See e.g., the antigens described in International Patent Publications Nos. WO2013113326, WO2013113501, WO2013113325, WO2013113502 and WO2013113736 and European Patent Publication No. EP2623121, the contents of each of which are herein incorporated by reference in their entireties).

Peptides and Proteins

The nucleic acid molecules, modified nucleic acid molecules and mmRNA of the invention can be formulated with peptides and/or proteins in order to increase transfection of cells by the nucleic acid molecules, modified nucleic acid molecules or mmRNA. In one embodiment, peptides such as, but not limited to, cell penetrating peptides and proteins and peptides that enable intracellular delivery may be used to deliver pharmaceutical formulations. A non-limiting example of a cell penetrating peptide which may be used with the pharmaceutical formulations of the present invention include a cell-penetrating peptide sequence attached to polycations that facilitates delivery to the intracellular space, e.g., HIV-derived TAT peptide, penetratins, transportans, or hCT derived cell-penetrating peptides (see, e.g., Caron et al., Mol. Ther. 3(3):310-8 (2001); Langel, Cell-Penetrating Peptides: Processes and Applications (CRC Press, Boca Raton Fla., 2002); El-Andaloussi et al., Curr. Pharm. Des. 11(28): 3597-611 (2003); and Deshayes et al., Cell. Mol. Life Sci. 62(16):1839-49 (2005), all of which are incorporated herein by reference). The compositions can also be formulated to include a cell penetrating agent, e.g., liposomes, which enhance delivery of the compositions to the intracellular space. Nucleic acid molecules, modified nucleic acid molecules and mmRNA of the invention may be complexed to peptides and/or proteins such as, but not limited to, peptides and/or proteins from Aileron Therapeutics (Cambridge, Mass.) and Permeon Biologics (Cambridge, Mass.) in order to enable intracellular delivery (Cronican et al., ACS Chem. Biol. 2010 5:747-752; McNaughton et al., Proc. Natl. Acad. Sci. USA 2009 106:6111-6116; Sawyer, Chem Biol Drug Des. 2009 73:3-6; Verdine and Hilinski, Methods Enzymol. 2012; 503:3-33; all of which are herein incorporated by reference in its entirety).

In one embodiment, formulations comprising peptides and nucleic acid molecules, modified nucleic acid molecules or mmRNA may be administered intramuscularly. In one embodiment, formulations comprising peptides and nucleic acid molecules, modified nucleic acid molecules or mmRNA may be administered intradermally.

In one embodiment, the cell-penetrating polypeptide may comprise a first domain and a second domain. The first domain may comprise a supercharged polypeptide. The second domain may comprise a protein-binding partner. As used herein, "protein-binding partner" includes, but are not limited to, antibodies and functional fragments thereof, scaffold proteins, or peptides. The cell-penetrating polypeptide may further comprise an intracellular binding partner for the protein-binding partner. The cell-penetrating polypeptide may be capable of being secreted from a cell where the nucleic acid molecules, modified nucleic acid molecules or mmRNA may be introduced.

Formulations of the including peptides or proteins may be used to increase cell transfection by the nucleic acid molecules, modified nucleic acid molecule or mmRNA, alter the biodistribution of the nucleic acid molecules, modified nucleic acid molecule or mmRNA (e.g., by targeting specific tissues or cell types), and/or increase the translation of encoded protein. (See e.g., International Pub. No. WO2012110636 and WO2013123298; the contents of each of which are herein incorporated by reference in its entirety).

In one embodiment, the cell penetrating peptide may be, but is not limited to, those described in US Patent Publication No US20130129726, US20130137644 and US20130164219, the contents of each of which is herein incorporated by reference in its entirety.

In one embodiment, the nucleic acid molecules, modified nucleic acid molecules and/or mmRNA may be complexed with oligopeptides as described in US Patent Publication No. US20140037660, the contents of which are herein incorporated by reference in its entirety. As a non-limiting example, the oligopeptide may be between 8 and 15 amino acids in length and have formula I as described in US Patent Publication No. US20140037660, the contents of which are herein incorporated by reference in its entirety.

Cells

The nucleic acid molecules, modified nucleic acid molecule and mmRNA of the invention can be transfected ex vivo into cells, which are subsequently transplanted into a subject. As non-limiting examples, the pharmaceutical compositions may include red blood cells to deliver nucleic acid molecules, modified RNA to liver and myeloid cells, virosomes to deliver nucleic acid molecules, modified nucleic acid molecules and mmRNA in virus-like particles (VLPs), and electroporated cells such as, but not limited to, from MAXCYTE® (Gaithersburg, Md.) and from ERY-TECH® (Lyon, France) to deliver modified RNA. Examples of use of red blood cells, viral particles and electroporated cells to deliver payloads other than nucleic acid molecules, modified nucleic acid molecules or mmRNA have been documented (Godfrin et al., Expert Opin Biol Ther. 2012 12:127-133; Fang et al., Expert Opin Biol Ther. 2012 12:385-389; Hu et al., Proc Natl Acad Sci USA. 2011 108:10980-10985; Lund et al., Pharm Res. 2010 27:400-420; Huckriede et al., J Liposome Res. 2007; 17:39-47; Cusi, Hum Vaccin. 2006 2:1-7; de Jonge et al., Gene Ther. 2006 13:400-411; all of which are herein incorporated by reference in its entirety). The nucleic acid molecules, modified nucleic acid molecules or mmRNA may be delivered in synthetic VLPs synthesized by the methods described in International Pub No. WO2011085231, WO2013116656 and US Pub No. 20110171248, the contents of each of which are herein incorporated by reference in their entireties.

Cell-based formulations of the modified nucleic acid molecules and mmRNA of the invention may be used to ensure cell transfection (e.g., in the cellular carrier), alter the biodistribution of the nucleic acid molecules, modified nucleic acid molecule or mmRNA (e.g., by targeting the cell carrier to specific tissues or cell types), and/or increase the translation of encoded protein.

In one embodiment, cells comprising nucleic acid molecules, modified nucleic acid molecules or mmRNA may be administered intramuscularly. In one embodiment, cells comprising nucleic acid molecules, modified nucleic acid molecules or mmRNA may be administered intradermally.

Introduction into Cells

A variety of methods are known in the art and suitable for introduction of nucleic acid into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion.

The technique of sonoporation, or cellular sonication, is the use of sound (e.g., ultrasonic frequencies) for modifying the permeability of the cell plasma membrane. Sonoporation methods are known to those in the art and are taught for example as it relates to bacteria in US Patent Publication 20100196983 and as it relates to other cell types in, for example, US Patent Publication 20100009424, each of which are incorporated herein by reference in their entirety. Sonorporation may be combined with microbubbles (air-filled vesicles stabilized by surface active molecules such as albumin, polymers or phospholipids) to increase transdermal penetration of drugs. While not wishing to be bound by theory, upon absorption of the ultrasound waves, the microbubbles cavitate, oscillate, break up and release localized shock waves that can disrupt the nearby cell membranes and promote penetration of drugs. The size of the microspheres may be optimized to ensure efficient transfection of the drug. As a non-limiting example, the microbubbles may be about 1 to about 6 um in diameter, e.g., about 1 um, about 2 um, about 3 um, about 4 um, about 5 um or about 6 um in diameter.

Electroporation techniques are also well known in the art and are used to deliver nucleic acids in vivo and clinically (Andre et al., Curr Gene Ther. 2010 10:267-280; Chiarella et al., Curr Gene Ther. 2010 10:281-286; Hojman, Curr Gene Ther. 2010 10:128-138; all herein incorporated by reference in their entirety). Electroporation parameters, when optimized, may produce a transfection efficiency which may be equal to the efficiency achieved by viral vectors. Electroporation devices are sold by many companies worldwide including, but not limited to BTX® Instruments (Holliston, Mass.) (e.g., the AgilePulse In Vivo System) and Inovio (Blue Bell, Pa.) (e.g., Inovio SP-5P intramuscular delivery device or the CELLECTRA® 3000 intradermal delivery device). Electroporation may be used after, before and/or during administration of the modified nucleic acid molecules and/or mmRNA described herein. As a non-limiting example, electroporation may be used after local injection. As another non-limiting example, electroporation may be used after systemic injection. In one embodiment, modified nucleic acid molecules or mmRNA may be delivered by electroporation as described in Example 8.

In one embodiment, electroporation may be used to improve the generation of T and B cell responses from administration of a therapeutic agent (e.g., nucleic acid molecules, modified nucleic acid molecules and/or mmRNA (see e.g., Cu et al. *Enhanced Delivery and Potency of Self-Amplifying mRNA Vaccines by Electroporation in Situ*. Vaccines 2013, 1, 367-383; the contents of which are herein incorporated by reference in its entirety)).

In one embodiment, electroporation may be used after nucleic acid molecules, modified nucleic acid molecules or mmRNA are administered intramuscularly. In one embodiment, electroporation may be used after nucleic acid molecules, modified nucleic acid molecules or mmRNA are administered intradermally.

Micro-Organ

The nucleic acid molecules, modified nucleic acid molecule or mmRNA may be contained in a micro-organ which can then express the encoded polypeptide of interest in a long-lasting therapeutic formulation. In one aspect, the micro-organ may comprise a vector comprising a nucleic acid sequence (e.g., the nucleic acid molecules, modified nucleic acid molecules and/or the mmRNA of the present invention) encoding a polypeptide of interest, operably linked to one or more regulatory sequences. As a non-limiting example, the long-lasting therapeutic micro-organ used with the present invention may be those described in U.S. Pat. No. 845,948, herein incorporated by reference in its entirety. As another non-limiting example, the micro-organ may be used to maintain a desired level of a polypeptide of interest for a sustained period of time (e.g., maintaining physiological hemoglobin levels as described in U.S. Pat. No. 845,948, herein incorporated by reference in its entirety).

The micro-organ may be able to produce the polypeptide of interest for at least a day, at least two days, at least three days, at least four days, at least five days, at least six days, a least 7 days, at least 8 days, at least 9 days, at least 10 days, at least 11 days, at least 12 days, at least 13 days, at least 14 days, at least 3 weeks, at least 1 month and/or at least 2 months, at least 3 months, at least 4 months, at least 5 months, at least 6 months or greater than 6 months.

In one embodiment, the micro-organ may have a diameter of at least 0.5 mm to at least 20 mm such as, but not limited to, at least 0.5 mm, at least 1 mm, at least 1.5 mm, at least 2 mm, at least 2.5 mm, at least 3 mm, at least 3.5 mm, at least 4 mm, at least 4.5 mm, at least 5 mm, at least 5.5 mm, at least 6 mm, at least 6.5 mm, at least 7 mm, at least 7.5 mm, at least 8 mm, at least 8.5 mm, at least 9 mm, at least 9.5 mm, at least 10 mm, at least 10.5 mm, at least 11 mm, at least 11.5 mm, at least 12 mm, at least 12.5 mm, at least 13 mm, at least 13.5 mm, at least 14 mm, at least 14.5 mm, at least 15 mm, at least 15.5. mm, at least 16 mm, at least 16.5 mm, at least 17 mm, at least 17.5 mm, at least 18 mm, at least 18.5 mm, at least 19 mm, at least 19.5 mm or at least 20 mm. In another embodiment, the micro-organ may have a diameter of 0.5-2.5 mm, 1-2.5 mm, 1.5-2.5 mm, 0.5-3 mm, 1-3 mm, 1.5-3 mm, 0.5-3.5 mm, 1-3.5 mm, 1.5-3.5 mm, 0.5-4 mm, 1-4 mm, 1.5-4 mm, 2-4 mm, 0.5-5 mm, 1-5 mm, 1.5-5 mm, 2-5 mm, 2.5-5 mm, 3-5 mm, 0.5-6 mm, 1-6 mm, 1.5-6 mm, 2-6 mm, 2.5-6 mm, 3-6 mm, 3.5-6 mm, 4-6 mm, 0.5-7 mm, 1-7 mm, 1.5-7 mm, 2-7 mm, 2.5-7 mm, 3-7 mm, 3.5-7 mm, 4-7 mm, 4.5-7 mm, 5-7 mm, 0.5-8 mm, 1-8 mm, 1.5-8 mm, 2-8 mm, 2.5-8 mm, 3-8 mm, 3.5-8 mm, 4-8 mm, 4.5-8 mm, 5-8 mm, 5.5-8 mm, 6-8 mm, 0.5-9 mm, 1-9 mm, 1.5-9 mm, 2-9 mm, 2.5-9 mm, 3-9 mm, 3.5-9 mm, 4-9 mm, 4.5-9 mm, 5-9 mm, 5.5-9 mm, 6-9 mm, 6.5-9 mm, 7-9 mm, 0.5-10 mm, 1-10 mm, 1.5-10 mm, 2-10 mm, 2.5-10 mm, 3-10 mm, 3.5-10 mm, 4-10 mm, 4.5-10 mm, 5-10 mm, 5.5-10 mm, 6-10 mm, 6.5-10 mm, 7-10 mm, 7.5-10 nm or 8-10 nm.

In one embodiment, the micro-organ may have a length of at least 2 mm to at least 150 mm such as, but not limited to, at least 2 mm, at least 3 mm, at least 4 mm, at least 5 mm, at least 6 mm, at least 7 mm, at least 8 mm, at least 9 mm, at least 10 mm, at least 15 mm, at least 20 mm, at least 25 mm, at least 30 mm, at least 35 mm, at least 40 mm, at least 45 mm, at least 50 mm, at least 55 mm, at least 60 mm, at least 65 mm, at least 70 mm, at least 75 mm, at least 80 mm, at least 85 mm, at least 90 mm, at least 95 mm, at least 100 mm, at least 105 mm, at least 110 mm, at least 115 mm, at least 120 mm, at least 125 mm, at least 130 mm, at least 135 mm, at least 140 mm, at least 145 mm or at least 150 mm. In another embodiment, the micro-organ may have a length of 5-100 mm, 10-100 mm, 15-100 mm, 20-100 mm, 25-10 mm, 30-100 mm, 35-100 mm, 40-100 mm, 45-100 mm, 50-100 mm, 55-100 mm, 60-100 mm, 65-100 mm, 70-100 mm, 75-100 mm, 80-100 mm, 85-100 mm, 90-100 mm, 5-90 mm, 10-90 mm, 15-90 mm, 20-90 mm, 25-10 mm, 30-90 mm, 35-90 mm, 40-90 mm, 45-90 mm, 50-90 mm, 55-90 mm, 60-90 mm, 65-90 mm, 70-90 mm, 75-90 mm, 80-90 mm, 5-80 mm, 10-80 mm, 15-80 mm, 20-80 mm, 25-10 mm, 30-80 mm, 35-80 mm, 40-80 mm, 45-80 mm, 50-80 mm, 55-80 mm, 60-80 mm, 65-80 mm, 70-80 mm, 5-70 mm, 10-70 mm, 15-70 mm, 20-70 mm, 25-10 mm, 30-70 mm, 35-70 mm, 40-70 mm, 45-70 mm, 50-70 mm, 55-70 mm, 60-70 mm, 5-60 mm, 10-60 mm, 15-60 mm, 20-60 mm, 25-10 mm, 30-60 mm, 35-60 mm, 40-60 mm, 45-60 mm, 50-60 mm, 5-50 mm, 10-50 mm, 15-50 mm, 20-50 mm, 25-10 mm, 30-50 mm, 35-50 mm, 40-50 mm, 5-40 mm, 10-40 mm, 15-40 mm, 20-40 mm, 25-10 mm, 30-40 mm, 5-30 mm, 10-30 mm, 15-30 mm, 20-30 mm, 5-20 mm, 10-20 mm or 5-10 mm.

In one embodiment, the nucleic acid molecules, modified nucleic acid molecules and/or mmRNA may be delivered to a subject using a genetically modified micro-organ such as, but not limited to, those described in US Patent Publication No. US20130251679, the contents of which are herein incorporated by reference in its entirety. As a non-limiting example, the micro-organ may be provided to a subject in order to secrete a protein encoded by the nucleic acid molecules, modified nucleic acid molecules and/or mmRNA described herein.

Hyaluronidase

The intramuscular, intradermal or subcutaneous localized injection of nucleic acid molecules, modified nucleic acid molecules or mmRNA of the invention can include hyaluronidase, which catalyzes the hydrolysis of hyaluronan. By catalyzing the hydrolysis of hyaluronan, a constituent of the interstitial barrier, hyaluronidase lowers the viscosity of hyaluronan, thereby increasing tissue permeability (Frost, Expert Opin. Drug Deliv. (2007) 4:427-440; the contents of which is herein incorporated by reference in its entirety). It is useful to speed their dispersion and systemic distribution of encoded proteins produced by transfected cells. Alternatively, the hyaluronidase can be used to increase the number of cells exposed to a nucleic acid molecule, modified nucleic acid molecule or mmRNA of the invention administered intramuscularly, intramuscularly or subcutaneously.

Nanoparticle Mimics

The nucleic acid molecules, modified nucleic acid molecules and mmRNA of the invention may be encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example the nucleic acid molecules, modified nucleic acid molecules or modified mRNA of the invention may be encapsulated in a non-viron particle which can mimic the delivery function of a virus (see International Pub. No. WO2012006376 and US Patent Publication No. US20130171241 and US20130195968, the content of each of which are herein incorporated by reference in its entirety).

Nanotubes

The nucleic acid molecules, modified nucleic acid molecules or mmRNA of the invention can be attached or otherwise bound to at least one nanotube such as, but not limited to, rosette nanotubes, rosette nanotubes having twin bases with a linker, carbon nanotubes and/or single-walled carbon nanotubes, The nucleic acid molecules, modified nucleic acid molecules or mmRNA may be bound to the nanotubes through forces such as, but not limited to, steric, ionic, covalent and/or other forces.

In one embodiment, the nanotube can release one or more nucleic acid molecules, modified nucleic acid molecule or mmRNA into cells. The size and/or the surface structure of at least one nanotube may be altered so as to govern the interaction of the nanotubes within the body and/or to attach or bind to the nucleic acid molecules, modified nucleic acid molecule or mmRNA disclosed herein. In one embodiment, the building block and/or the functional groups attached to the building block of the at least one nanotube may be altered to adjust the dimensions and/or properties of the nanotube. As a non-limiting example, the length of the nanotubes may be altered to hinder the nanotubes from passing through the holes in the walls of normal blood vessels but still small enough to pass through the larger holes in the blood vessels of tumor tissue.

In one embodiment, at least one nanotube may also be coated with delivery enhancing compounds including polymers, such as, but not limited to, polyethylene glycol. In another embodiment, at least one nanotube and/or the nucleic acid molecules, modified nucleic acid molecules, or modified mRNA may be mixed with pharmaceutically acceptable excipients and/or delivery vehicles.

In one embodiment, the nucleic acid molecules, modified nucleic acid molecules or modified mRNA are attached and/or otherwise bound to at least one rosette nanotube. The rosette nanotubes may be formed by a process known in the art and/or by the process described in International Publication No. WO2012094304, the contents of which are herein incorporated by reference in its entirety. At least one nucleic acid molecule, modified nucleic acid molecule or modified mRNA may be attached and/or otherwise bound to at least one rosette nanotube by a process as described in International Publication No. WO2012094304, herein incorporated by reference in its entirety, where rosette nanotubes or modules forming rosette nanotubes are mixed in aqueous media with at least one nucleic acid molecule, modified nucleic acid molecule or modified mRNA under conditions which may cause at least one nucleic acid molecule, modified nucleic acid molecule or modified mRNA to attach or otherwise bind to the rosette nanotubes.

In one embodiment, the nucleic acid molecule, modified nucleic acid molecule or mmRNA may be attached to and/or otherwise bound to at least one carbon nanotube. As a non-limiting example, the nucleic acid molecule, modified nucleic acid molecule or mmRNA may be bound to a linking agent and the linked agent may be bound to the carbon nanotube (See e.g., U.S. Pat. No. 8,246,995; herein incorporated by reference in its entirety). The carbon nanotube may be a single-walled nanotube (See e.g., U.S. Pat. No. 8,246,995; herein incorporated by reference in its entirety).

In one embodiment, carbon nanotubes are filled with a therapeutic agent (e.g., nucleic acid molecules, modified nucleic acid molecules and/or mmRNA) formulated in a temperature sensitive gel as described in International Patent Publication No. WO2014015334, the contents of which are herein incorporated by reference in its entirety. The release of the therapeutic agent may be triggered by inductive heating such as, but not limited to, from an alternating or pulsed magnetic field or an electrical field.

In one embodiment, nucleic acid molecules, modified nucleic acid molecules or mmRNA formulated in nanotubes may be administered intramuscularly. In one embodiment, nucleic acid molecules, modified nucleic acid molecules or mmRNA formulated in nanotubes may be administered intradermally.

Conjugates

The nucleic acid molecules, modified nucleic acids molecules and mmRNA of the invention include conjugates, such as a nucleic acid molecule, modified nucleic acid molecule or mmRNA covalently linked to a carrier or targeting group, or including two encoding regions that together produce a fusion protein (e.g., bearing a targeting group and therapeutic protein or peptide).

The conjugates of the invention include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Representative U.S. patents that teach the preparation of polynucleotide conjugates, particularly to RNA, include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; each of which is herein incorporated by reference in their entireties.

In one embodiment, the conjugate of the present invention may function as a carrier for the nucleic acid molecules, modified nucleic acid molecules and mmRNA of the present invention. The conjugate may comprise a cationic polymer such as, but not limited to, polyamine, polylysine, polyalkylenimine, and polyethylenimine which may be grafted to with poly(ethylene glycol). As a non-limiting example, the conjugate may be similar to the polymeric conjugate and the method of synthesizing the polymeric conjugate described in U.S. Pat. No. 6,586,524, the contents of which are herein incorporated by reference in its entirety.

A non-limiting example of a method for conjugation to a substrate is described in US Patent Publication No. US20130211249, the contents of which are herein incorporated by reference in its entirety. The method may be used to make a conjugated polymeric particle comprising a nucleic acid molecule, modified nucleic acid molecule and/ or mmRNA.

The conjugates can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Targeting groups may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, or an activator of p38 MAP kinase.

The targeting group can be any ligand that is capable of targeting a specific receptor. Examples include, without limitation, folate, GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein.

As a non-limiting example, the targeting group may be a glutathione receptor (GR)-binding conjugate for targeted delivery across the blood-central nervous system barrier (See e.g., US Patent Publication No. US2013021661012, the contents of which are herein incorporated by reference in its entirety.

In one embodiment, the conjugate of the present invention may be a synergistic biomolecule-polymer conjugate. The synergistic biomolecule-polymer conjugate may be long-acting continuous-release system to provide a greater therapeutic efficacy. The synergistic biomolecule-polymer conjugate may be those described in US Patent Publication No. US20130195799, the contents of which are herein incorporated by reference in its entirety.

In another embodiment, the conjugate which may be used in the present invention may be an aptamer conjugate. Non-limiting examples of apatamer conjugates are described in International Patent Publication No. WO2012040524, the contents of which are herein incorporated by reference in its entirety. The aptamer conjugates may be used to provide targeted delivery of formulations comprising nucleic acid molecules, modified nucleic acid molecules and/or mmRNA.

In one embodiment, the conjugate which may be used in the present invention may be an amine containing polymer conjugate. Non-limiting examples of amine containing polymer conjugate are described in U.S. Pat. No. 8,507,653, the contents of which are herein incorporated by reference in its entirety. The factor IX moiety polymer conjugate may be uncompress releasable linkages to release the nucleic acid molecules, modified nucleic acid molecules and/or mmRNA upon and/or after delivery to a subject.

In one embodiment, pharmaceutical compositions of the present invention may include chemical modifications such as, but not limited to, modifications similar to locked nucleic acids.

Representative U.S. patents that teach the preparation of locked nucleic acid (LNA) such as those from Santaris, include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include modified nucleic acids or mmRNA with phosphorothioate backbones and oligonucleosides with other modified backbones, and in particular —CH2-NH—CH2-, —CH2-N(CH3)-O—CH2- [known as a methylene (methylimino) or MMI backbone], —CH2-O—N(CH3)-CH2-, —CH2-N(CH3)-N(CH3)-CH2- and —N(CH3)-CH2-CH2- [wherein the native phosphodiester backbone is represented as —O—P(O)2-O—CH2-] of the above-referenced U.S. Pat. No. 5,489,677, and the amide backbones of the above-referenced U.S. Pat. No. 5,602,240. In some embodiments, the polynucleotides featured herein have morpholino backbone structures of the above-referenced U.S. Pat. No. 5,034,506.

Modifications at the 2' position may also aid in delivery. Preferably, modifications at the 2' position are not located in a polypeptide-coding sequence, i.e., not in a translatable region. Modifications at the 2' position may be located in a 5' UTR, a 3' UTR and/or a tailing region. Modifications at the 2' position can include one of the following at the 2' position: H (i.e., 2'-deoxy); F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO]mCH3, O(CH2).nOCH3, O(CH2)nNH2, O(CH2) nCH3, O(CH2)nONH2, and O(CH2)nON[(CH2)nCH3)]2, where n and m are from 1 to about 10. In other embodiments, the modified nucleic acids or mmRNA include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3,NH2, heterocycloalkyl, heterocycloalkaryl, aminoalkylamino, polyalkylamino, substituted silyl, an RNA cleaving group, a reporter group, an intercalator, a group for improving the pharmacokinetic properties, or a group for improving the pharmacodynamic properties, and other substituents having similar properties. In some embodiments, the modification includes a 2'-methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below. Other modifications include 2'-methoxy (2'-OCH3), 2'-aminopropoxy (2'-OCH2CH2CH2NH2) and 2'-fluoro (2'-F). Similar modifications may also be made at other positions, particularly the 3' position of the sugar on the 3' terminal nucleotide or in 2'-5' linked dsRNAs and the 5' position of 5' terminal nucleotide. Polynucleotides of the invention may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920 and each of which is herein incorporated by reference.

In still other embodiments, the nucleic acid molecules, modified nucleic acid molecule or mmRNA is covalently conjugated to a cell-penetrating polypeptide. The cell-penetrating peptide may also include a signal sequence. The conjugates of the invention can be designed to have increased stability; increased cell transfection; and/or altered the biodistribution (e.g., targeted to specific tissues or cell types).

In another aspect, the conjugate may be a peptide that selectively directs the nanoparticle to neurons in a tissue or organism. As a non-limiting example, the peptide used may be, but is not limited to, the peptides described in US Patent Publication No US20130129627, herein incorporated by reference in its entirety.

In yet another aspect, the conjugate may be a peptide that can assist in crossing the blood-brain barrier.

In one embodiment, the conjugate may be an aptamer-mRNA conjugate which may be used for targeted expression. As a non-limiting example, the aptamer-mRNA conjugate may include any of the aptamers and/or conjugates described in US Patent Publication No. US20130022538, the contents of which is herein incorporated by reference in its entirety. The aptamer-mRNA conjugate may include an aptamer component that can bind to a membrane associated protein on a target cell.

In one embodiment, the conjugate may be a water-soluble polymer conjugate such as the conjugates described in U.S. Pat. No. 8,636,994, the contents of which are herein incorporated by reference in its entirety. As a non-limiting example, the water-soluble polymer conjugate may comprise at least one residue of an antimicrobial agent (see e.g., the conjugates described in U.S. Pat. No. 8,636,994, the contents of which are herein incorporated by reference in its entirety).

In one embodiment, the conjugate may be a targeting amino acid chain bound to a biocompatiable polymer such as, but not limited to, the targeting amino acids and biocompatiable polymers described in International Patent Publication No. WO2014025890, the contents of which are herein incorporated by reference in its entirety. As a non-limiting example, the targeting amino acid may be any of the targeting amino acid chains described in SEQ ID NO: 1-62 of International Patent Publication No. WO2014025890, the contents of which are herein incorporated by reference in its entirety. In one embodiment, the targeting amino acid chain is smaller than 50 amino acids in length.

In one embodiment, the conjugate may be a targeted poly amino-acid subunits which contains a targeting amino acid chain conjugated to a carboxylic acid such as, but not limited to, the targeting amino acids and carboxylic acids described in US Patent Publication No. US20140045950, the contents of which are herein incorporated by reference in its entirety. In one embodiment, the targeted drug delivery vehicle comprises 5 to 50 targeted amino acid subunits. As a non-limiting example, the targeting amino acid may be any of the targeting amino acid chains described in SEQ ID NO: 1-62 of US Patent Publication No. US20140045950, the contents of which are herein incorporated by reference in its entirety.

In one embodiment, formulations comprising at least one conjugate and a nucleic acid molecule, modified nucleic acid molecule or mmRNA may be administered intramuscularly. In one embodiment, formulations comprising at least one conjugate and a nucleic acid molecule, modified nucleic acid molecule or mmRNA may be administered intradermally.

Self-Assembled Nanoparticles
Nucleic Acid Self-Assembled Nanoparticles

Self-assembled nanoparticles have a well-defined size which may be precisely controlled as the nucleic acid strands may be easily reprogrammable. For example, the optimal particle size for a cancer-targeting nanodelivery carrier is 20-100 nm as a diameter greater than 20 nm avoids renal clearance and enhances delivery to certain tumors through enhanced permeability and retention effect. Using self-assembled nucleic acid nanoparticles a single uniform population in size and shape having a precisely controlled spatial orientation and density of cancer-targeting ligands for enhanced delivery. As a non-limiting example, oligonucleotide nanoparticles were prepared using programmable self-assembly of short DNA fragments and therapeutic siRNAs. These nanoparticles are molecularly identical with controllable particle size and target ligand location and density. The DNA fragments and siRNAs self-assembled into a one-step reaction to generate DNA/siRNA tetrahedral nanoparticles for targeted in vivo delivery. (Lee et al., Nature Nanotechnology 2012 7:389-393; herein incorporated by reference in its entirety).

In one embodiment, the nucleic acid molecules, modified nucleic acid molecules or mmRNA disclosed herein may be formulated as self-assembled nanoparticles. As a non-limiting example, nucleic acids may be used to make nanoparticles which may be used in a delivery system for the nucleic acid molecules, modified nucleic acid molecules and/or mmRNA of the present invention (See e.g., International Pub. No. WO2012125987; herein incorporated by reference in its entirety).

In one embodiment, the nucleic acid self-assembled nanoparticles may comprise a core of the nucleic acid molecules, modified nucleic acid molecules or mmRNA disclosed herein and a polymer shell. The polymer shell may be any of the polymers described herein and are known in the art. In an additional embodiment, the polymer shell may be used to protect the nucleic acid molecules, modified nucleic acid molecules and mmRNA in the core.

In one embodiment, nucleic acid based self-assembled nanoparticles comprising nucleic acid molecules, modified nucleic acid molecules or mmRNA may be administered intramuscularly. In one embodiment nucleic acid based self-assembled nanoparticles comprising nucleic acid molecules, modified nucleic acid molecules or mmRNA may be administered intradermally.

Polymer-Based Self-Assembled Nanoparticles

Polymers may be used to form sheets which self-assembled into nanoparticles. These nanoparticles may be used to deliver the modified nucleic acids and mmRNA of the present invention. In one embodiment, these self-assembled nanoparticles may be microsponges formed of long polymers of RNA hairpins which form into crystalline 'pleated' sheets before self-assembling into microsponges. These microsponges are densely-packed sponge like microparticles which may function as an efficient carrier and may be able to deliver cargo to a cell. The microsponges may be from 1 um to 300 nm in diameter. The microsponges may be complexed with other agents known in the art to form larger microsponges. As a non-limiting example, the microsponge may be complexed with an agent to form an outer layer to promote cellular uptake such as polycation polyethyleneime (PEI). This complex can form a 250-nm diameter particle that can remain stable at high temperatures (150° C.) (Grabow and Jaegar, Nature Materials 2012, 11:269-269; herein incorporated by reference in its entirety). Additionally these microsponges may be able to exhibit an extraordinary degree of protection from degradation by ribonucleases.

In another embodiment, the polymer-based self-assembled nanoparticles such as, but not limited to, microsponges, may be fully programmable nanoparticles. The geometry, size and stoichiometry of the nanoparticle may be precisely controlled to create the optimal nanoparticle for delivery of cargo such as, but not limited to, nucleic acid molecules, modified nucleic acid molecules and mmRNA.

In one embodiment, the polymer based nanoparticles may comprise a core of the nucleic acid molecules, modified nucleic acid molecules and mmRNA disclosed herein and a polymer shell. The polymer shell may be any of the polymers described herein and are known in the art. In an additional embodiment, the polymer shell may be used to protect the nucleic acid molecules, modified nucleic acid molecules and mmRNA in the core.

In yet another embodiment, the polymer based nanoparticle may comprise a non-nucleic acid polymer comprising a plurality of heterogenous monomers such as those described in Interantional Publication No. WO2013009736, the contents of which are herein incorporated by reference in its entirety.

In one embodiment, the nanoparticle may be a cellulose-based nanoparticle such as, but not limited to, the nanoparticles described in International Patent Publication No. WO2014015422, the contents of which are herein incorporated by reference in its entirety. As a non-limiting example, the nanoparticle may include a acetylated carboxymethylcellulose (CMC-Ac) covalently linked to at least one poly (ethylene glycol) (PEG) and may include at least one hydrophobic drug. As another non-limiting example, the nanoparticle may include a acetylated carboxymethylcellulose (CMC-Ac) covalently linked to at least one poly (ethylene glycol) (PEG) and may include at least one hydrophobic drug comprising a taxane.

In one embodiment, polymer based self-assembled nanoparticles comprising nucleic acid molecules, modified nucleic acid molecules or mmRNA may be administered intramuscularly. In one embodiment, polymer based self-assembled nanoparticles comprising nucleic acid molecules, modified nucleic acid molecules or mmRNA may be administered intradermally.

Self-Assembled Macromolecules

The nucleic acid molecules, modified nucleic acid molecules and/or mmRNA may be formulated in amphiphilic macromolecules (AMs) for delivery. AMs comprise biocompatible amphiphilic polymers which have an alkylated sugar backbone covalently linked to poly(ethylene glycol). In aqueous solution, the AMs self-assemble to form micelles. Non-limiting examples of methods of forming AMs and AMs are described in US Patent Publication No. US20130217753, the contents of which are herein incorporated by reference in its entirety.

In one embodiment, nucleic acid molecules, modified nucleic acid molecules or mmRNA may be formulated in self-assembled macromolecules (e.g., amphiphilic macromolecules) and administered intramuscularly. In one embodiment, nucleic acid molecules, modified nucleic acid molecules or mmRNA may be formulated in self-assembled macromolecules (e.g., amphiphilic macromolecules) and administered intradermally.

Inorganic Nanoparticles

The nucleic acid molecules, modified nucleic acid molecules or mmRNAs of the present invention may be formulated in inorganic nanoparticles (U.S. Pat. No. 8,257,745, the contents of which are herein incorporated by reference in its entirety). The inorganic nanoparticles may include, but are not limited to, clay substances that are water swellable. As a non-limiting example, the inorganic nanoparticle may include synthetic smectite clays which are made from simple silicates (See e.g., U.S. Pat. Nos. 5,585,108 and 8,257,745; the contents of each of which are herein incorporated by reference in their entirety).

In one embodiment, the inorganic nanoparticles may comprise a core of the nucleic acid molecules, modified nucleic acids or mmRNA disclosed herein and a polymer shell. The polymer shell may be any of the polymers described herein and are known in the art. In an additional embodiment, the polymer shell may be used to protect the nucleic acid molecules, modified nucleic acids or mmRNA in the core.

In one embodiment, inorganic nanoparticle formulations comprising nucleic acid molecules, modified nucleic acid molecules or mmRNA may be administered intramuscularly. In one embodiment, inorganic nanoparticle formulations comprising nucleic acid molecules, modified nucleic acid molecules or mmRNA may be administered intradermally.

Semi-Conductive and Metallic Nanoparticles

The nucleic acid molecules, modified nucleic acid molecules or mmRNAs of the present invention may be formulated in water-dispersible nanoparticle comprising a semi-conductive or metallic material (U.S. Pub. No. 20120228565; herein incorporated by reference in its entirety) or formed in a magnetic nanoparticle (U.S. Pub. No. 20120265001 and 20120283503; each of which is herein incorporated by reference in its entirety). The water-dispersible nanoparticles may be hydrophobic nanoparticles or hydrophilic nanoparticles.

In one embodiment, the semi-conductive and/or metallic nanoparticles may comprise a core of the modified nucleic acids disclosed herein and a polymer shell. The polymer shell may be any of the polymers described herein and are known in the art. In an additional embodiment, the polymer shell may be used to protect the modified nucleic acids in the core.

The metallic nanoparticle which may be used in the present invention may be a pH-sensitive nanoparticle such as, but not limited to, those described in US Patent Publication No US20130138032, herein incorporated by reference in its entirety.

In one aspect, the metallic and/or metal-allow nanoparticles may be made by the methods described in US Patent Publication No US20130133483, herein incorporated by reference in its entirety.

Micelles

In one embodiment, the nucleic acid molecules, modified nucleic acid molecules and/or mmRNA may be formulated in a micelle or coated on a micelle for delivery. As a non-limiting example, the micelle may be any of the micelles described in International Patent Publication No. WO2013154774 and US Patent Publication No. US20130243867, the contents of each of which are herein incorporated by reference in its entirety. As a non-limiting example, the micelle may comprise polyethylene glycol-phosphatidyl ethanolamine (PEG-PE), a DC-cholesterol and a dioleoylphosphatidly-ethanolamine (DOPE). As another non-limiting example, the micelle may comprise at least one multiblock copolymer such as those described in International Patent Publication No. WO2013154774, the contents of which are herein incorporated by reference in its entirety.

In one embodiment, the nucleic acid molecules, modified nucleic acid molecules and/or mmRNA may be encapsulated in the polymeric micelles described in US Patent Publication No. US20130266617, the contents of which are herein incorporated by reference in its entirety.

In one embodiment, micelles comprising nucleic acid molecules, modified nucleic acid molecules or mmRNA may be administered intramuscularly. In one embodiment, micelles comprising nucleic acid molecules, modified nucleic acid molecules or mmRNA may be administered intradermally.

Surgical Sealants: Gels and Hydrogels

In one embodiment, the nucleic acid molecules, modified nucleic acid molecules or modified mRNA disclosed herein may be encapsulated into any hydrogel known in the art which may form a gel when injected into a subject. Hydrogels are a network of polymer chains that are hydrophilic, and are sometimes found as a colloidal gel in which water is the dispersion medium. Hydrogels are highly absorbent (they can contain over 99% water) natural or synthetic polymers. Hydrogels also possess a degree of flexibility very similar to natural tissue, due to their significant water content. The hydrogel described herein may used to encapsulate lipid nanoparticles which are biocompatible, biodegradable and/or porous. A hydrogel can be made in situ from solution injection or implanted.

As a non-limiting example, the hydrogel may be an aptamer-functionalized hydrogel. The aptamer-functionalized hydrogel may be programmed to release one or more modified nucleic acid molecules and/or mmRNA using nucleic acid hybridization. (Battig et al., J. Am. Chem. Society. 2012 134:12410-12413; herein incorporated by reference in its entirety).

As another non-limiting example, the hydrogel may be a shaped as an inverted opal. The opal hydrogels exhibit higher swelling ratios and the swelling kinetics is an order of magnitude faster than conventional hydrogels as well. Methods of producing opal hydrogels and description of opal hydrogels are described in International Pub. No. WO2012148684, herein incorporated by reference in its entirety.

In yet another non-limiting example, the hydrogel may be an antibacterial hydrogel. The antibacterial hydrogel may comprise a pharmaceutical acceptable salt or organic material such as, but not limited to pharmaceutical grade and/or medical grade silver salt and aloe vera gel or extract. (International Pub. No. WO2012151438, herein incorporated by reference in its entirety).

In one embodiment, the nucleic acid molecules, modified nucleic acid molecules or modified mRNA may be encapsulated in a lipid nanoparticle and then the lipid nanoparticle may be encapsulated into a hydrogel.

In one embodiment, the nucleic acid molecules, modified nucleic acid molecules or modified mRNA disclosed herein may be encapsulated into any gel known in the art. As a non-limiting example the gel may be a fluorouracil injectable gel or a fluorouracil injectable gel containing a chemical compound and/or drug known in the art. As another example, the nucleic acid molecules, modified nucleic acid molecules or modified mRNA may be encapsulated in a fluorouracil gel containing epinephrine (See e.g., Smith et al. Cancer Chemotherapy and Pharmacology, 1999 44(4):267-274; herein incorporated by reference in its entirety).

In one embodiment, the nucleic acid molecules, modified nucleic acid molecules and/or mmRNA disclosed herein may be encapsulated into a fibrin gel, fibrin hydrogel or fibrin glue. In another embodiment, the nucleic acid molecules, modified nucleic acid molecules and/or mmRNA may be formulated in a lipid nanoparticle or a rapidly eliminated lipid nanoparticle prior to being encapsulated into a fibrin gel, fibrin hydrogel or a fibrin glue. In yet another embodiment, the nucleic acid molecules, modified nucleic acid molecules and/or mmRNA may be formulated as a lipoplex prior to being encapsulated into a fibrin gel, hydrogel or a fibrin glue. Fibrin gels, hydrogels and glues comprise two components, a fibrinogen solution and a thrombin solution which is rich in calcium (See e.g., Spicer and Mikos, Journal of Controlled Release 2010. 148: 49-55; Kidd et al. Journal of Controlled Release 2012. 157:80-85; each of which is herein incorporated by reference in its entirety). The concentration of the components of the fibrin gel, hydrogel and/or glue can be altered to change the characteristics, the network mesh size, and/or the degradation characteristics of the gel, hydrogel and/or glue such as, but not limited to changing the release characteristics of the fibrin gel, hydrogel and/or glue. (See e.g., Spicer and Mikos, Journal of Controlled Release 2010. 148: 49-55; Kidd et al. Journal of Controlled Release 2012. 157:80-85; Catelas et al. Tissue Engineering 2008. 14:119-128; each of which is herein incorporated by reference in its entirety). This feature may be advantageous when used to deliver the nucleic acid molecules, modified nucleic acid molecules or modified mRNA disclosed herein. (See e.g., Kidd et al. Journal of Controlled Release 2012. 157:80-85; Catelas et al. Tissue Engineering 2008. 14:119-128; each of which is herein incorporated by reference in its entirety).

In one embodiment, the nucleic acid molecules, modified nucleic acid molecules and/or mmRNA disclosed herein may be used with hydrogels such as, but not limited to, the hydrogels described in U.S. Patent Application No. 20130071450 or 20130211249, the contents of each of which is herein incorporated by reference in its entirety.

As a non-limiting example, the hydrogels which may be used in the present invention may be made by the methods described in International Patent Publication No. WO2013124620, the contents of which is herein incorporated by reference in its entirety.

In another embodiment, the nucleic acid molecules, modified nucleic acid molecules and/or mmRNA disclosed herein may be formulated for transdermal delivery. The formulation may comprise at least one hydrogel described in U.S. Patent Application No. 20130071450, herein incorporated by reference in its entirety.

In one embodiment, the hydrogel which may be used in the present invention is described in U.S. Pat. No. 8,420,605, U.S. Pat. No. 8,415,325 and/or International Patent Publication No. WO2013091001 and WO2013124620, the contents of each of which are herein incorporated by reference in its entirety.

In one embodiment, the hydrogel which may be used in the present invention may be, but is not limited to, ATRIGEL® (QLT Inc. Vancouver, British Columbia), chitosan, aliginate, collagen or hyaluronic acid hydrogel.

In another embodiment, the hydrogel which may be used in the present invention is a crosslinked methacrylate. As a non-limiting example, the hydrogel of the present invention may be used in wound dressings.

The hydrogel which may be used in the present invention may also be complexed with agents and excipients described herein including, but not limited to PEI, PVA, poly-lysine, Poloxamer 124, Poloxamer 181, Poloxamer 182, Poloxamer 407, Poloxamer 237, Poloxamer 331 and Poloxamer 338. Complexing the hydrogel with agents and/or excipients may help improve mRNA stability and uptake in a cell, tissue and/or organism. As a non-limiting example, a hydrogel may be complexed with Poloxamer 188 to improve the stability and uptake of mRNA.

In one embodiment, the hydrogel may be formed by an injectable chitosan mixture as described in US Patent Publication No. US20130244972, the contents of which are herein incorporated by reference in its entirety. The chitosan mixture may be used to form a hydrogel to deliver the nucleic acid molecules, modified nucleic acid molecules and/or mmRNA described herein. As a non-limiting example, the chitosan mixture may be used to provide a high level of modified nucleic acid and/or mmRNA to a target site.

In one embodiment, the hydrogel may comprise a polymer covalently linked to glutathione (GSH) as described in International Patent Publication No. WO2013184915, the contents of which are herein incorporated by reference in its entirety. As a non-limiting example, the nucleic acid molecules, modified nucleic acid molecules and/or mmRNA may be delivered locally using the hydrogels and/or methods described in International Patent Publication No. WO2013184915, the contents of which are herein incorporated by reference in its entirety.

In one embodiment, the hydrogel may be formulated for sustained release of a therapeutic or biologic agent such as, but not limited to, the drug delivery compositions described in International Patent Publication No. WO2013173657, the contents of which are herein incorporated by reference in its entirety. As a non-limiting example, the drug delivery composition may include a lipophilic agent or biologic agent (e.g., a nucleic acid) and a polymer wherein there is less than 35% of the agent released within the first hour of elution. Within the first hour there may be 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% or less than 1% of the agent released.

In one embodiment, the nucleic acid molecules, modified nucleic acid molecules and/or mmRNA disclosed herein may be formulated in a surgical sealant. The surgical sealant may be, but is not limited to, fibrinogen polymer based sealants (Ethicon Inc. Cornelia, Ga.), TISSELL® (Baxter International, Inc Deerfield, Ill.) or PEG-based sealants such as, but not limited to, COSEAL® (pentaerythritol peg ester tetrasuccinimidyl/pentaerythritol peg ether tetra-thiol) (Baxter International, Inc Deerfield, Ill.) and DURASEAL™ (trilysine amine/PEG-ester) (Covidien, Waltham, Mass.).

In one embodiment, nucleic acid molecules, modified nucleic acid molecules and/or mmRNA may be formulated in COSEAL® or co-administered with or administered after a cell, tissue or organism is administered COSEAL®. COSEAL® comprises two synthetic polyethylene glycols (PEGs) (pentaerythritol PEG ester tetra-succinimidyl and pentaerythritol PEG ether tetra-thiol), a dilute hydrogen chloride solution, and a sodium phosphate/sodium carbonate solution. The PEGs are kept separate from the sodium phosphate/sodium carbonate solution in the dilute hydrogen chloride solution until administration. After administration a hydrogel is formed, which may adhere to tissue, and forms a stiff gel in seconds which is resorbed within 30 days.

In another embodiment, the nucleic acid molecules, modified nucleic acid molecules and/or mmRNA disclosed herein may be formulated in a hydrogel comprising a macromolecular matrix. The macromolecular matrix may comprise a hyaluronic acid component which may be crosslinked to a collagent component. The hydrogel used in the present invention may be, but is not limited to, the hydrogels described in International Patent Publication No. WO2013106715, the contents of which are herein incorporated by reference in its entirety.

In yet another embodiment, the nucleic acid molecules, modified nucleic acid molecules and/or mmRNA disclosed herein may be formulated in a chitosan glycerophosphate (CGP) hydrogel. The formulation may further comprise a chitosanase in an effect amount to dissolve the CGP hydrogel and release the nucleic acid molecules, modified nucleic acid molecule and/or mmRNA associated with the CGP hydrogel. As a non-limiting example, the modified nucleic acid molecules and/or mmRNA may be formulated in the controlled release delivery system comprising a CGP hydrogel described in US Patent Publication No. US20130189241, the contents of which are herein incorporated by reference in its entirety.

In one embodiment, the nucleic acid molecules, modified nucleic acid molecules and/or mmRNA disclosed herein may be formulated in a hydrogel formulated for controlled release such as, but not limited to, the porous matrix composites and formulations described in US Patent Publication No. US20130196915, the contents of which are herein incorporated by reference in its entirety.

In another embodiment, the nucleic acid molecules, modified nucleic acid molecules and/or mmRNA disclosed herein may be formulated in a hydrogel comprising heterobifunctional poly(alkylene oxides) which may have degradable linkages. Non-limiting examples of heterobifunctional poly (alkylene oxides) are described in U.S. Pat. No. 8,497,357, the contents of which are herein incorporated by reference in its entirety.

In yet another embodiment, the nucleic acid molecules, modified nucleic acid molecules and/or mmRNA may be formulated in a hydrogel which may be used as an insulin delivery system. As a non-limiting example, the hydrogel may be a glucose binding amphiphilic peptide hydrogel as described in International Patent Publication No. WO2013123491, the contents of which are herein incorporated by reference in its entirety. As another non-limiting example, the hydrogel may be a microgel such as the glucose-responsive microgels described in International Patent Publication No. WO2013123492, the contents of which are herein incorporated by reference in its entirety.

In one embodiment, the nucleic acid molecules, modified nucleic acid molecules and/or mmRNA may be formulated in a hydrogel system such as, but not limited to, a multi-compartment hydrogel. A non-limiting example of a multi-compartment hydrogel and methods of making the hydrogel is described in International Patent Publication No. WO2013124855, the contents of which are herein incorporated by reference in its entirety. The multi-compartment hydrogel may be used to repair or regenerate damaged tissue in a subject.

In another embodiment, the nucleic acid molecules, modified nucleic acid molecules and/or mmRNA may be formulated in a cucurbituril-based hydrogel. A non-limiting example of a cucurbituril-based hydrogel is described in international Patent Publication No. WO2013124654, the contents of which are herein incorporated by reference in its entirety.

In one embodiment, the nucleic acid molecules, modified nucleic acid molecules and/or mmRNA may be formulated in a biocompatible mucoadhesive thermoreversible hydrogel. A non-limiting example of a biocompatible mucoadhesive thermoreversible hydrogel is described in international Patent Publication No. WO2013153550, the contents of which are herein incorporated by reference in its entirety.

In one embodiment, the nucleic acid molecules, modified nucleic acid molecules and/or mmRNA disclosed herein may be formulated in a PEG-based surgical sealant or hydrogel.

In one embodiment, the surgical sealant or hydrogel may include at least one, at least two, at least three, at least four, at least five, at least six or more than six PEG lipids. The PEG lipids may be selected from, but are not limited to, pentaerythritol PEG ester tetra-succinimidyl and pentaerythritol PEG ether tetra-thiol, PEG-c-DOMG, PEG-DMG (1,2-Dimyristoyl-sn-glycerol, methoxypolyethylene Glycol), PEG-DSG (1,2-Distearoyl-sn-glycerol, methoxypolyethylene Glycol), PEG-DPG (1,2-Dipalmitoyl-sn-glycerol, methoxypolyethylene glycol), PEG-DSA (PEG coupled to 1,2-distearyloxypropyl-3-amine), PEG-DMA (PEG coupled to 1,2-dimyristyloxypropyl-3-amine, PEG-c-DNA, PEG-c-DMA, PEG-S-DSG, PEG-c-DMA, PEG-DPG, PEG-DMG 2000 and those described herein and/or known in the art. The concentration and/or ratio of the PEG lipids in the surgical sealant or hydrogel may be varied in order to optimize the formulation for delivery and/or administration.

The amount of buffer and/or acid used in combination with the PEG lipids of the surgical sealant or hydrogel may also be varied. In one non-limiting example, the ratio of buffer and/or acid with PEG lipids is 1:1. As a non-limiting example, the amount of buffer and/or acid used with the PEG lipids may be increased to alter the ratio of buffer/acid to PEG in order to optimize the surgical sealant or hydrogel.

As another non-limiting example, the amount of buffer and/or acid used with the PEG lipids may be decreased to alter the ratio of buffer/acid to PEG in order to optimize the surgical sealant or hydrogel.

The amount of nucleic acid molecules, modified nucleic acid and/or mmRNA loaded into the buffer, acid and/or PEG lipid may be varied. The amount of modified nucleic acid and/or mmRNA loaded into the buffer, acid and/or PEG lipid may be, but is not limited to, at least 1 uL, at least 2 uL, at least 5 uL, at least 10 uL, at least 15 uL, at least 20 uL, at least 25 uL, at least 30 uL, at least 35 uL, at least 40 uL, at least 45 ul, at least 50 uL, at least 55 uL, at least 60 uL, at least 65 uL, at least 70 uL, at least 75 uL, at least 80 uL, at least 85 uL, at least 90 uL, at least 100 uL, at least 125 uL, at least 150 uL, at least 200 uL, at least 250 uL, at least 300 uL, at least 350 uL, at least 400 uL, at least 450 uL, at least 500 uL or more than 500 uL.

In one embodiment, the nucleic acid molecules, modified nucleic acid and/or mmRNA of the present invention may be loaded in PEGs and also in the buffer or the acid. The amount of modified nucleic acid and/or mmRNA loaded in the PEG may be the same, greater or less than the amount loaded in the buffer or acid. In another embodiment, the nucleic acid molecules, modified nucleic acid and/or mmRNA may be formulated, by the methods described herein and/or known in the art, prior to loading in the PEGs, buffer or acid.

A non-limiting example of a PEG-based hydrogel which may be used in the present invention is described in U.S. Pat. No. 8,524,215, the contents of which is herein incorporated by reference in its entirety. The PEG-based hydrogel may be an absorbable hydrogel prepared from a multi-arm PEG-vinylsulfone having about 3 to about 8 arms and a multi-arm-PEG-R-sulfhydryl having about 3 to about 8 arms (See e.g., U.S. Pat. No. 8,524,215). In one embodiment, the PEG-based hydrogel may be an absorbable hydrogel. While not wishing to be bound by theory, an absorbable PEG-based hydrogel may be beneficial to reduce the permanent chronic foreign body reaction since the absorbable hydrogel can be absorbed and passed by the body.

In one embodiment, the hydrogel may be a thermosensitive hydrogel. In one aspect the thermosensitive hydrogel may be, but is not limited to, a triblock polymer such as those described herein and known in the art. As a non-limiting example, the tri-block polymer may be PEG-PLGA-PEG (see e.g., the thermosensitive hydrogel (PEG-PLGA-PEG) was used as a TGF-beta1 gene delivery vehicle in Lee et al. Thermosensitive Hydrogel as a Tgf-β1 Gene Delivery Vehicle Enhances Diabetic Wound Healing. Pharmaceutical Research, 2003 20(12): 1995-2000; as a controlled gene delivery system in Li et al. Controlled Gene Delivery System Based on Thermosensitive Biodegradable Hydrogel. Pharmaceutical Research 2003 20(6):884-888; and Chang et al., Non-ionic amphiphilic biodegradable PEG-PLGA-PEG copolymer enhances gene delivery efficiency in rat skeletal muscle. J Controlled Release. 2007 118:245-253; each of which is herein incorporated by reference in its entirety). As a non-limiting example, the thermosensitive hydrogel may be used to make nanoparticles and liposomes by the methods described in International Publication No. WO2013123407, the contents of which are herein incorporated by reference in its entirety.

In another embodiment, the hydrogel may be a biodegradable copolymer hydrogel (see e.g., the biodegradable hydrogels described by Nguyen and Lee (Injectable Biodegradable Hydrogels. Macromolecular Bioscience. 2010 10:563-579), herein incorporated by reference in its entirety). These hydrogels may exhibit a sol-gel phase transition that respond to external stimuli such as, but not limited to, temperature changes, pH alternations or both. Non-limiting examples of biodegradable copolymer hydrogels include triblock copolymers PEG-PLLA-PEG, PEG-PLA-PEG (see e.g., Chang et al., Non-ionic amphiphilic biodegradable PEG-PLGA-PEG copolymer enhances gene delivery efficiency in rat skeletal muscle. J Controlled Release. 2007 118:245-253, herein incorporated by reference in its entirety), PLGA-PEG-PLGA, PEG-PCL-PEG, PCL-PEG-PCL, polyesters such as poly[(R)-3-hydroxybutyrate](PHB), polyphosphazenes such as L-sioleucine ethyl ester (IleOEt), D,L-leucine ethyl ester (LeuOEt), L-valine ethyl ester (ValOEt), or di-, tri- and oligo-peptides, polypeptides and chitosan. Temperature and pH sensitive polymers which may be used to form the biodegradable copolymer hydrogels include, but are not limited to, sulfamethazine-, poly(β-amino ester)-, poly(amino urethane)-, and poly(amidoamine)-based polymers. Formulations of the biodegradable copolymer hydrogels and nucleic acid molecules, modified nucleic acids and/or mmRNAs may be administered using site-specific control of release behavior.

In one embodiment, the hydrogel used in the present invention may be a PEG based hydrogel such as, but not limited to, those described in International Patent Publication No WO2013082590, herein incorporated by reference in its entirety. The PEG based hydrogel may have, but is not limited to, an overall polymer weight concentration of less than or equal to 50% at the time of curing. As a non-limiting example, the PEG based hydrogel may be made by the methods described in International Patent Publication No WO2013082590, herein incorporated by reference in its entirety.

In another embodiment, the modified nucleic acid molecules and/or mmRNA may be formulated in a nanostructured gel composition. The nanostructured gel may be capable of controlled release of the encapsulated nucleic acid molecules, modified nucleic acid molecules and/or mmRNA. Non-limiting examples of nanostructed gels or self-assembled gels are described in International Patent Publication No. WO2012040623, the contents of which are herein incorporated by reference in its entirety.

In one embodiment, the concentration of the nucleic acid molecules, modified nucleic acids and/or mmRNA of the present invention in the surgical sealants, gels and/or hydrogels may be selected to provide a dosage within the range to have the desired therapeutic effect.

In one embodiment, the concentration of the nucleic acid molecules, modified nucleic acids and/or mmRNA of the present invention in the surgical sealants, gels and/or hydrogels may be at least 0.001 mg to at least 150 mg in at least 0.1 ml to at least 30 ml of the surgical sealant, gel or hydrogel. The concentration of the nucleic acid molecules, modified nucleic acids and/or mmRNA of the present invention may be at least 0.001 mg, at least 0.005 mg, at least 0.01 mg, at least 0.05 mg, at least 0.1 mg, at least 0.5 mg, at least 1 mg, at least 5 mg, at least 7 mg, at least 10 mg, at least 12, at least 15 mg, at least 17 mg, at least 20 mg, at least 22 mg, at least 25 mg, at least 27 mg, at least 30 mg, at least 32 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 105 mg, at least 110 mg, at least 115 mg, at least 120 mg, at least 125 mg, at least 130 mg, at least 135 mg, at least 140 mg, at least 145 mg or at least 150 mg in at least 0.1 ml, at least 0.2 ml, at least 0.3 ml, at least 0.4 ml, at least 0.5 ml, at least 0.6 ml, at least 0.7 ml, at least 0.8 ml, at least 0.9 ml, at least 1 ml, at least 2 ml, at least 3 ml, at least 4 ml, at least 5 ml, at least 6 ml, at least 7 ml, at least 8 ml, at least 9 ml, at least 10 ml, at least 11 ml, at least 12 ml, at least 13 ml, at least 14 ml, at least 15 ml, at least 16 ml, at least 17 ml, at least 18 ml, at least 19 ml, at least 20 ml, at least 21 ml, at least 22 ml, at least 23 ml, at least 24 ml, at least 25 ml, at least 26 ml, at least 27 ml, at least 28 ml, at least 29 ml or at least 30 ml of the surgical sealant, gel or hydrogel.

In another embodiment, concentration of the nucleic acid molecules, modified nucleic acids and/or mmRNA of the present invention in the surgical sealants, gels and/or hydrogels may be at least 0.001 mg/ml at least 0.005 mg/ml, at least 0.01 mg/ml, at least 0.05 mg/ml, at least 0.1 mg/ml, at least 0.5 mg/ml, at least 1 mg/ml, at least 5 mg/ml, at least 7 mg/ml, at least 10 mg/ml, at least 12, at least 15 mg/ml, at least 17 mg/ml, at least 20 mg/ml, at least 22 mg/ml, at least 25 mg/ml, at least 27 mg/ml, at least 30 mg/ml, at least 32 mg/ml, at least 35 mg/ml, at least 40 mg/ml, at least 45 mg/ml or at least 50 mg/ml.

Technology allowing for large subcutaneous infusion volumes which are known in the art, such as, but not limited to, HYLENEX® (Halozyme Therapeutics, San Diego, Calif.) may also be used. The dispersion and/or adsorption of the modified mRNA described herein may be increased with the use of HYLENEX® as HYLENEX® temporarily breaks down hyaluronic acid causing a temporty degradation in the subcutaneous space (for about 24 hours) just beneath the outside surface of the skin opening microscopic channels and allowing fluid or drugs to be dispersed and absorbed in the body.

In one embodiment, the hydrogel is a PEG based hydrogel which may be used for a topical application (See e.g., US Patent Publication No. US20130149318, herein incorporated by reference in its entirety).

In another embodiment, the hydrogel is an absorbable hydrogel. The absorbably hydrogel may be a PEG-based hydrogel as described in and/or made by the methods described in International Publication No. WO2012018718, herein incorporated by reference in its entirety. The absorbable hydrogels may be used to form sustained release compositions for use with the present invention (see e.g., International Pub. No. WO2012018718, herein incorporated by reference in its entirety).

In one embodiment, the hydrogel may comprise a polymer described in International Publication No. WO2013091001, herein incorporated by reference in its entirety.

In one embodiment, the hydrogel is a shear-thinning and stabilizing hydrogel as described in International Patent Publication No. WO2014028209, the contents of which are incorporated by reference in its entirety. As a non-limiting example, the hydrogel may comprise a hydrophilic polymer network such as those described in International Patent Publication No. WO2014028209, the contents of which are incorporated by reference in its entirety.

In one embodiment, the gel may be a self-assembled gel composition which includes a gelator such as, but not limited to, the self-assembled gels described in US Patent Publication No. US20130280334, the contents of which are herein incorporated by reference in its entirety. As a non-limiting example, the self-assembled gel composition may be able to encapsulate one or more agents such as the nucleic acid moleculesm, modified nucleic acid molecules and/or mmRNA described herein.

In one embodiment, formulations comprising surgical sealants and nucleic acid molecules, modified nucleic acid molecules or mmRNA may be administered intramuscularly.

In one embodiment, formulations comprising surgical sealants and nucleic acid molecules, modified nucleic acid molecules or mmRNA may be administered intradermally.

Nanolipogel

In one embodiment, the nucleic acid molecules, modified nucleic acid molecules and/or mmRNA may be formulated in and/or delivered using a nanolipogel. A nanolipogel is a delivery vehicle which may include one or more lipid layers surrounding a hydrogel core. Nanolipogel formulation may be used to release the nucleic acid molecules, modified nucleic acid molecules and/or mmRNA in a controlled fashion. Non-limiting examples of nanolipogels are described in International Patent Publication No. WO2013155487, the contents of which are herein incorporated by reference in its entirety. As a non-limiting example, nanolipogels which may be used in the treatment of inflammatory and autoimmune disease and disorders are described in International Patent Publication No. WO2013155493, the contents of which are herein incorporated by reference in its entirety.

In one embodiment, nanolipogel formulations comprising nucleic acid molecules, modified nucleic acid molecules or mmRNA may be administered intramuscularly. In one embodiment, nanolipogel formulations comprising nucleic acid molecules, modified nucleic acid molecules or mmRNA may be administered intradermally.

Suspension Formulations

In some embodiments, suspension formulations are provided comprising nucleic acid molecules, modified nucleic acid molecules or modified mRNA, water immiscible oil depots, surfactants and/or co-surfactants and/or co-solvents. Combinations of oils and surfactants may enable suspension formulation with mRNA. Delivery of nucleic acid molecules, modified nucleic acid molecules or modified mRNA in a water immiscible depot may be used to improve bioavailability through sustained release of nucleic acid molecules, modified nucleic acid molecules, mRNA or modified mRNA from the depot to the surrounding physiologic environment and prevent degradation by nucleases.

In some embodiments, suspension formulations of nucleic acid molecules, modified nucleic acid molecules, mRNA or mmRNA may be prepared using combinations of nucleic acid molecules, modified nucleic acid molecules, mRNA or mmRNA with oil-based solutions and surfactants. Such formulations may be prepared as a two-part system comprising an aqueous phase comprising nucleic acid molecules, modified nucleic acid molecules, mRNA or mmRNA and an oil-based phase comprising oil and surfactants. Exemplary oils for suspension formulations may include, but are not limited to sesame oil and Miglyol (comprising esters of saturated coconut and palmkernel oil-derived caprylic and capric fatty acids and glycerin or propylene glycol), corn oil, soybean oil, peanut oil, beeswax and/or palm seed oil. Exemplary surfactants may include, but are not limited to Cremophor, polysorbate 20, polysorbate 80, polyethylene glycol, transcutol, CAPMUL®, labrasol, isopropyl myristate, and/or Span 80. In some embodiments, suspensions may comprise co-solvents including, but not limited to ethanol, glycerol and/or propylene glycol.

Suspensions may be formed by first preparing a nucleic acid molecule, modified nucleic acid molecule, mRNA or mmRNA formulation comprising an aqueous solution of nucleic acid molecules, modified nucleic acid molecules, mRNA or mmRNA and an oil-based phase comprising one or more surfactants. Suspension formation occurs as a result of mixing the two phases (aqueous and oil-based). In some embodiments, such a suspension may be delivered to an aqueous phase to form an oil-in-water emulsion. In some embodiments, delivery of a suspension to an aqueous phase results in the formation of an oil-in-water emulsion in which the oil-based phase comprising nucleic acid molecules, modified nucleic acid molecules, mRNA or mmRNA forms droplets that may range in size from nanometer-sized droplets to micrometer-sized droplets. In some embodiments, specific combinations of oils, surfactants, cosurfactants and/or co-solvents may be utilized to suspend nucleic acid molecules, modified nucleic acid molecules, mRNA or mmRNA in the oil phase and/or to form oil-in-water emulsions upon delivery into an aqueous environment.

In some embodiments, suspensions may provide modulation of the release of nucleic acid molecules, modified nucleic acid molecules, mRNA or mmRNA into the surrounding environment. In such embodiments, nucleic acid molecule, modified nucleic acid molecule, mRNA or mmRNA release may be modulated by diffusion from a water immiscible depot followed by resolubilization into a surrounding environment (e.g. an aqueous environment).

In some embodiments, nucleic acid molecules, modified nucleic acid molecules, mRNA or mmRNA within a water immiscible depot (e.g. suspended within an oil phase) may result in altered nucleic acid molecule, modified nucleic acid molecule, mRNA or mmRNA stability (e.g. altered degradation by nucleases).

In some embodiments, nucleic acid molecules, modified nucleic acid molecules, mRNA or mmRNA may be formulated such that upon injection, an emulsion forms spontaneously (e.g. when delivered to an aqueous phase). Such particle formation may provide a high surface area to volume ratio for release of nucleic acid molecules, modified nucleic acid molecules, mRNA or mmRNA from an oil phase to an aqueous phase.

In one embodiment, the nucleic acid molecules, modified nucleic acid molecules, mRNA or mmRNA may be formulated in a nanoemulsion such as, but not limited to, the nanoemulsions described in U.S. Pat. No. 8,496,945 and International Patent Publication Nos. WO2013130535 and WO2012129483, the contents of each of which are herein incorporated by reference in its entirety. The nanoemulsions may comprise nanoparticles described herein. As a non-limiting example, the nanoparticles may comprise a liquid hydrophobic core which may be surrounded or coated with a lipid or surfactant layer. The lipid or surfactant layer may comprise at least one membrane-integrating peptide and may also comprise a targeting ligand (see e.g., U.S. Pat. No. 8,496,945, the contents of which are herein incorporated by reference in its entirety). As another non-limiting example, the nanoemulsion may be an oil-in-water emulsion comprising an aqueous phase, an oil phase, a surfactant and a phospholipid such as the nanoemulsions described in International Patent Publication No. WO2012129483, the contents of which are herein incorporated by reference in its entirety.

Cations and Anions

Formulations of nucleic acid molecules or modified nucleic acid molecules disclosed herein may include cations or anions. In one embodiment, the formulations include metal cations such as, but not limited to, Zn2+, Ca2+, Cu2+, Mg+ and combinations thereof. As a non-limiting example, formulations may include polymers and a mRNA or modified mRNA complexed with a metal cation (See e.g., U.S. Pat. Nos. 6,265,389 and 6,555,525, each of which is herein incorporated by reference in its entirety).

In some embodiments, cationic nanoparticles comprising combinations of divalent and monovalent cations may be formulated with modified mRNA or mRNA. Such nanoparticles may form spontaneously in solution over a give period (e.g. hours, days, etc). Such nanoparticles do not form in the presence of divalent cations alone or in the presence of monovalent cations alone. The delivery of nucleic acid molecules, modified nucleic acid molecules, mRNA or in cationic nanoparticles or in one or more depot comprising cationic nanoparticles may improve mRNA bioavailability by acting as a long-acting depot and/or reducing the rate of degradation by nucleases.

Molded Nanoparticles and Microparticles

The nucleic acid molecules, modified nucleic acid molecules and/or mm RNA disclosed herein may be formulated in molded nanoparticles and/or microparticles. These nanoparticles and/or microparticles may be molded into any size shape and chemistry. As an example, the nanoparticles and/or microparticles may be made using the PRINT® particle molding technology by LIQUIDA TECHNOLOGIES® (Morrisville, N.C.) (See e.g., International Pub. No. WO2007024323; herein incorporated by reference in its entirety).

In one embodiment, the molded nanoparticles may comprise a core of the nucleic acid molecules, modified nucleic acid molecules and/or mmRNA disclosed herein and a polymer shell. The polymer shell may be any of the polymers described herein and are known in the art. In an additional embodiment, the polymer shell may be used to protect the nucleic acid molecules, modified nucleic acid molecules and/or mmRNA in the core.

In one embodiment, the nucleic acid molecules, modified nucleic acids and/or mmRNA of the present invention may be formulated in microparticles. The microparticles may contain a core of the nucleic acid molecules, modified nucleic acids and/or mmRNA and a cortext of a biocompatible and/or biodegradable polymer. As a non-limiting example, the microparticles which may be used with the present invention may be those described in U.S. Pat. No. 8,460,709, U.S. Patent Publication No. US20130129830 and International Patent Publication No WO2013075068, each of which is herein incorporated by reference in its entirety. As another non-limiting example, the microparticles may be designed to extend the release of the nucleic acid molecules, modified nucleic acid and/or mmRNA of the present invention over a desired period of time (see e.g, extended release of a therapeutic protein in U.S. Patent Publication No. US20130129830, herein incorporated by reference in its entirety).

The microparticle for use with the present invention may have a diameter of at least 1 micron to at least 100 microns (e.g., at least 1 micron, at least 5 micron, at least 10 micron, at least 15 micron, at least 20 micron, at least 25 micron, at least 30 micron, at least 35 micron, at least 40 micron, at least 45 micron, at least 50 micron, at least 55 micron, at least 60 micron, at least 65 micron, at least 70 micron, at least 75 micron, at least 80 micron, at least 85 micron, at least 90 micron, at least 95 micron, at least 97 micron, at least 99 micron, and at least 100 micron).

The microparticle may be a hydrogel microparticle. In one embodiment, the hydrogel microparticle may be made using the methods described in International Patent publication No. WO2014025312, the contents of which are herein incorporated by reference in its entirety. The hydrogel microparticles may include one or more species of living cells attached thereon and/or encapsulated therein such as the hydrogel microparticles described in International Patent publication No. WO2014025312, the contents of which are herein incorporated by reference in its entirety. As a non-limiting example, the nucleic acid molecules, modified nucleic acid molecules and/or mmRNA may be formulated in or delivered using hydrogel microparticles.

In one embodiment, the molded nanoparticle formulation comprising nucleic acid molecules, modified nucleic acid molecules or mmRNA may be administered intramuscularly. In one embodiment, the molded nanoparticle formulation comprising nucleic acid molecules, modified nucleic acid molecules or mmRNA may be administered intradermally.

In one embodiment, the molded microparticle formulation comprising nucleic acid molecules, modified nucleic acid molecules or mmRNA may be administered intramuscularly. In one embodiment, the molded microparticle formulation comprising nucleic acid molecules, modified nucleic acid molecules or mmRNA may be administered intradermally.

NanoJackets and NanoLiposomes

The nucleic acid molecules, modified nucleic acid molecules and/or mmRNA disclosed herein may be formulated in NanoJackets and NanoLiposomes by Keystone Nano (State College, Pa.). NanoJackets are made of compounds that are naturally found in the body including calcium, phosphate and may also include a small amount of silicates. Nanojackets may range in size from 5 to 50 nm and may be used to deliver hydrophilic and hydrophobic compounds such as, but not limited to, nucleic acid molecules, modified nucleic acid molecules and/or mmRNA.

NanoLiposomes are made of lipids such as, but not limited to, lipids which naturally occur in the body. NanoLiposomes may range in size from 60-80 nm and may be used to deliver hydrophilic and hydrophobic compounds such as, but not limited to, nucleic acid molecules, modified nucleic acid molecules and/or mmRNA. In one aspect, the modified nucleic acids disclosed herein are formulated in a NanoLiposome such as, but not limited to, Ceramide NanoLiposomes.

In one embodiment, NanoLiposome formulations comprising nucleic acid molecules, modified nucleic acid molecules or mmRNA may be delivered intramuscularly. In one embodiment, NanoLiposome formulations comprising nucleic acid molecules, modified nucleic acid molecules or mmRNA may be delivered intradermally.

In one embodiment, NanoJacket formulations comprising nucleic acid molecules, modified nucleic acid molecules or mmRNA may be delivered intramuscularly. In one embodiment, NanoJacket formulations comprising nucleic acid molecules, modified nucleic acid molecules or mmRNA may be delivered intradermally.

Pseudovirions

In one embodiment, the nucleic acid molecules, modified nucleic acid molecules and/or mmRNA disclosed herein may be formulated in Pseudovirions (e.g., pseudo-virions). As a non-limiting example, the pseudovirions may be those developed and/or are described by Aura Biosciences (Cambridge, Mass.). In one aspect, the pseudovirion may be developed to deliver drugs to keratinocytes and basal membranes (See e.g., US Patent Publication Nos. US20130012450, US20130012566, US21030012426 and US20120207840 and International Publication No. WO2013009717, each of which is herein incorporated by reference in its entirety).

In one embodiment, the pseudovirion used for delivering the nucleic acid molecules, modified nucleic acids or mmRNA of the present invention may be derived from viruses such as, but not limited to, herpes and papillomaviruses (See e.g., US Patent Publication Nos. US Patent Publication Nos. US20130012450, US20130012566, US21030012426 and US20120207840 and International Publication No. WO2013009717, each of which is herein incorporated by reference in its entirety; and Ma et al. HPV pseudovirions as DNA delivery vehicles. Ther Deliv. 2011: 2(4): 427-430; Kines et al. The initial steps leading to papillomavirus infection occur on the basement membrane prior to cell surface binding. PNAS 2009:106(48), 20458-20463; Roberts et al. Genital transmission of HPV in a mouse model is potentiated by nonoxynol-9 and inhibited by carrageenan. Nature Medicine. 2007:13(7) 857-861; Gordon et al., Targeting the Vaginal Mucosa with Human Papillomavirus Pseudovirion Vaccines delivering SIV DNA. J Immunol. 2012 188(2) 714-723; Cuburu et al., Intravaginal immunization with HPV vectors induces tissue-resident CD8+ T cell responses. The Journal of Clinical Investigation. 2012: 122(12) 4606-4620; Hung et al., Ovarian Cancer Gene Therapy Using HPV-16 Psedudovirion Carrying the HSV-tk Gene. PLoS ONE. 2012: 7(7) e40983; Johnson et al., Role of Heparan Sulfate in Attachment to and Infection of the Murine Femal Genital Tract by Human Papillomavirus. J Virology. 2009: 83(5) 2067-2074; each of which is herein incorporated by reference in its entirety).

The pseudovirion may be a virus-like particle (VLP) prepared by the methods described in US Patent Publication No. US20120015899 and US20130177587 and International Patent Publication No. WO2010047839 WO2013116656, WO2013106525 and WO2013122262, the contents of each of which is herein incorporated by reference in its entirety. In one aspect, the VLP may be, but is not limited to, bacteriophages MS, Qβ, R17, fr, GA, Sp, MI, I, MXI, NL95, AP205, f2, PP7, and the plant viruses Turnip crinkle virus (TCV), Tomato bushy stunt virus (TBSV), Southern bean mosaic virus (SBMV) and members of the genus Bromovirus including Broad bean mottle virus, Brome mosaic virus, *Cassia* yellow blotch virus, Cowpea chlorotic mottle virus (CCMV), Melandrium yellow fleck virus, and Spring beauty latent virus. In another aspect, the VLP may be derived from the influenza virus as described in US Patent Publication No. US20130177587 or U.S. Pat. No. 8,506,967, the contents of each of which are herein incorporated by reference in its entirety. In yet another aspect, the VLP may comprise a B7-1 and/or B7-2 molecule anchored to a lipid membrane or the exterior of the particle such as described in International Patent Publication No. WO2013116656, the contents of which are herein incorporated by reference in its entirety. In one aspect, the VLP may be derived from norovirus, rotavirus recombinant VP6 protein or double layered VP2/VP6 such as the VLP described in International Patent Publication No. WO2012049366, the contents of which are herein incorporated by reference in its entirety.

The pseudovirion may be a human papilloma virus-like particle such as, but not limited to, those described in International Publication No. WO2010120266 and US Patent Publication No. US20120171290, each of which is herein incorporated by reference in its entirety and Ma et al. HPV pseudovirions as DNA delivery vehicles. Ther Deliv. 2011: 2(4): 427-430; Kines et al. The initial steps leading to papillomavirus infection occur on the basement membrane prior to cell surface binding. PNAS 2009:106(48), 20458-20463; Roberts et al. Genital transmission of HPV in a mouse model is potentiated by nonoxynol-9 and inhibited by carrageenan. Nature Medicine. 2007:13(7) 857-861; Gordon et al., Targeting the Vaginal Mucosa with Human Papillomavirus Pseudovirion Vaccines delivering SIV DNA. J Immunol. 2012 188(2) 714-723; Cuburu et al., Intravaginal immunization with HPV vectors induces tissue-resident CD8+ T cell responses. The Journal of Clinical Investigation. 2012: 122(12) 4606-4620; Hung et al., Ovarian Cancer Gene Therapy Using HPV-16 Pseudovirion Carrying the HSV-tk Gene. PLoS ONE. 2012: 7(7) e40983; Johnson et al., Role of Heparan Sulfate in Attachment to and Infection of the Murine Femal Genital Tract by Human Papillomavirus. J Virology. 2009: 83(5) 2067-2074; each of which is herein incorporated by reference in its entirety.

In one aspect, the pseudovirions may be virion derived nanoparticles such as, but not limited to, those described in US Patent Publication No. US20130116408 and US20130115247, each of which is herein incorporated by reference in their entirety. As a non-limiting example, the virion derived nanoparticles may be used to deliver nucleic acid molecules, modified nucleic acid molecules and/or mmRNA which may be used in the treatment for cancer and/or enhance the immune system's recognition of the tumor. As a non-limiting example, the virion-derived nanoparticle which may selectively deliver an agent to at least one tumor may be the papilloma-derived particles described in International Patent Publication No. WO2013119877, the contents of which are herein incorporated by reference in its entirety. The virion derived nanoparticles may be made by the methods described in US Patent Publication No. US20130116408 and US20130115247 or International Patent Publication No. WO2013119877, each of which is herein incorporated by reference in their entirety.

In one embodiment, the virus-like particle (VLP) may be a self-assembled particle. Non-limiting examples of self-assembled VLPs and methods of making the self-assembled VLPs are described in International Patent Publication No. WO2013122262, the contents of which are herein incorporated by reference in its entirety.

In one embodiment, pseudovirion formulations comprising nucleic acid molecules, modified nucleic acid molecules or mmRNA may be administered intramuscularly. In one embodiment, pseudovirion formulations comprising nucleic acid molecules, modified nucleic acid molecules or mmRNA may be administered intradermally.

Minicells

In one aspect, the nucleic acid molecules, modified nucleic acids and/or mmRNA may be formulated in bacterial minicells. As a non-limiting example, bacterial minicells may be those described in International Publication No. WO2013088250 or US Patent Publication No. US20130177499, the contents of each of which are herein incorporated by reference in its entirety. The bacterial minicells comprising therapeutic agents such as nucleic acid molecules, modified nucleic acids and/or mmRNA described herein may be used to deliver the therapeutic agents to brain tumors.

In one embodiment, formulations comprising minicells and nucleic acid molecules, modified nucleic acid molecules or mmRNA may be administered intramuscularly. In one embodiment, formulations comprising minicells and nucleic acid molecules, modified nucleic acid molecules or mmRNA may be administered intradermally.

Semi-Solid Compositions

In one embodiment, the nucleic acid molecules, modified nucleic acid molecules and/or mmRNA may be formulated with a hydrophobic matrix to form a semi-solid composition. As a non-limiting example, the semi-solid composition or paste-like composition may be made by the methods described in International Patent Publication No WO201307604, herein incorporated by reference in its entirety. The semi-solid composition may be a sustained release formulation as described in International Patent Publication No WO201307604, herein incorporated by reference in its entirety.

In another embodiment, the semi-solid composition may further have a micro-porous membrane or a biodegradable polymer formed around the composition (see e.g., International Patent Publication No WO201307604, herein incorporated by reference in its entirety).

The semi-solid composition using the nucleic acid molecules, modified nucleic acid molecules and/or mmRNA of the present invention may have the characteristics of the semi-solid mixture as described in International Patent Publication No WO201307604, herein incorporated by reference in its entirety (e.g., a modulus of elasticity of at least $10^{-4}$ N·mm$^{-2}$, and/or a viscosity of at least 100 mPa·s).

In one embodiment, semi-solid compositions comprising nucleic acid molecules, modified nucleic acid molecules or mmRNA may be administered intramuscularly. In one embodiment, semi-solid compositions comprising nucleic acid molecule, modified nucleic acid molecules or mmRNA may be administered intradermally.

Exosomes

In one embodiment, the nucleic acid molecules, modified nucleic acid molecules may be formulated in exosomes. The exosomes may be loaded with at least one modified nucleic acid molecule and delivered to cells, tissues and/or organisms. As a non-limiting example, the nucleic acid molecules, modified nucleic acid molecules may be loaded in the exosomes described in International Publication No. WO2013084000, herein incorporated by reference in its entirety.

In one embodiment, the exosome are obtained from cells that have been induced to undergo oxidative stress such as, but not limited to, the exosomes described in International Patent Publication No. WO2014028763, the contents of which are herein incorporated by reference in its entirety.

In one embodiment, nucleic acid molecules, modified nucleic acid molecules or mmRNA in exosomes may be administered intramuscularly. In one embodiment, nucleic acid molecules, modified nucleic acid molecules or mmRNA in exosomes may be administered intradermally.

Silk-Based Delivery

In one embodiment, the nucleic acid molecules, modified nucleic acid molecules may be formulated in a sustained release silk-based delivery system. The silk-based delivery system may be formed by contacting a silk fibroin solution with a therapeutic agent such as, but not limited to, the nucleic acid molecules, modified nucleic acid molecules described herein and/or known in the art. As a non-limiting example, the sustained release silk-based delivery system which may be used in the present invention and methods of making such system are described in U.S. Pat. No. 8,530,625 and US Patent Publication No. US20130177611, the contents of each of which are herein incorporated by reference in their entirety.

In one embodiment, nucleic acid molecules, modified nucleic acid molecules or mmRNA formulated in silk-based delivery systems may be administered intramuscularly. In one embodiment, nucleic acid molecules, modified nucleic acid molecules or mmRNA may be administered intradermally.

Microparticles

In one embodiment, formulations comprising nucleic acid molecules, modified nucleic acids and/or mmRNA may comprise microparticles. The microparticles may comprise a polymer described herein and/or known in the art such as, but not limited to, poly(α-hydroxy acid), a polyhydroxy butyric acid, a polycaprolactone, a polyorthoester and a polyanhydride. The microparticle may have adsorbent surfaces to adsorb biologically active molecules such as nucleic acid molecules, modified nucleic acids and/or mmRNA. As a non-limiting example microparticles for use with the present invention and methods of making microparticles are described in US Patent Publication No. US2013195923, US20130195898 and US 20130236550 and U.S. Pat. Nos. 8,309,139 and 8,206,749, the contents of each of which are herein incorporated by reference in its entirety. As a non-limiting example, the formulations comprising nucleic acid molecules, modified nucleic acids and/or mmRNA may comprise any of the microparticles described in or made by the methods described in US Patent Publication No. US20130236550, the contents of which are herein incorporated by reference in its entirety.

In another embodiment, the formulation may be a microemulsion comprising microparticles and nucleic acid molecules, modified nucleic acids or mmRNA. As a non-limiting example, microemulsions comprising microparticles are described in US Patent Publication No. US2013195923 and US20130195898 and U.S. Pat. Nos. 8,309,139 and 8,206,749, the contents of each of which are herein incorporated by reference in its entirety.

In one embodiment, formulations comprising microparticles and nucleic acid molecules, modified nucleic acid molecules or mmRNA may be administered intramuscularly. In one embodiment, formulations comprising microparticles and nucleic acid molecules, modified nucleic acid molecules or mmRNA may be administered intradermally.

Amino Acid Lipids

In one embodiment, the nucleic acid molecules, modified nucleic acid molecules and/or mmRNA may be formulated in amino acid lipids. Amino acid lipids are lipophilic compounds comprising an amino acid residue and one or more lipophilic tails. Non-limiting examples of amino acid lipids and methods of making amino acid lipids are described in U.S. Pat. No. 8,501,824 and US Patent Publication No. US20140037714, the contents of each of which are herein incorporated by reference in their entirety.

In one embodiment, the amino acid lipids have a hydrophilic portion and a lipophilic portion. The hydrophilic portion may be an amino acid residue and a lipophilic portion may comprise at least one lipophilic tail.

In one embodiment, the amino acid lipid formulations may be used to deliver the nucleic acid molecules, modified nucleic acid molecules and/or mmRNA to a subject.

In another embodiment, the amino acid lipid formulations may deliver a nucleic acid molecules, modified nucleic acid molecule or mmRNA in releasable form which comprises an amino acid lipid that binds and releases the nucleic acid molecules, modified nucleic acid molecule or mmRNA. As a non-limiting example, the release of the nucleic acid molecules, modified nucleic acid molecule or mmRNA may be provided by an acid-labile linker such as, but not limited to, those described in U.S. Pat. Nos. 7,098,032, 6,897,196, 6,426,086, 7,138,382, 5,563,250, and 5,505,931, the contents of each of which are herein incorporated by reference in its entirety.

In one embodiment, the amino acid lipid is a targeting amino acid lipid as described in International Publication No., WO2013135359, the contents of which are herein incorporated by reference in its entirety, such as but not limited to an amino acid lipid having formula I. As a non-limiting example, the targeting amino acid may target specific tissues and/or cells.

In another embodiment, the amino acid lipid is an ether-lipid having the general formula I as described in WO2013135360, the contents of which are herein incorporated by reference in its entirety.

In one embodiment, the amino acid lipid is an amino acid lipid of Formula I as described in US Patent Publication No., US20140037714, the contents of which are herein incorporated by reference in its entirety.

In one embodiment, formulations comprising amino acid lipids and nucleic acid molecules, modified nucleic acid molecules or mmRNA may be delivered intramuscularly. In one embodiment, formulations comprising amino acid lipids and nucleic acid molecules, modified nucleic acid molecules or mmRNA may be delivered intradermally.

Microvesicles

In one embodiment, nucleic acid molecules, modified nucleic acids and/or mmRNA may be formulated in microvesicles. Non-limiting examples of microvesicles include those described in US Patent Publication No. US20130209544, the contents of which are herein incorporated by reference in its entirety.

In one embodiment, the microvesicle is an ARRDC1-mediated microvesicles (ARMMs). Non-limiting examples of ARMMs and methods of making ARMMs are described in International Patent Publication No. WO2013119602, the contents of which are herein incorporated by reference in its entirety.

In one embodiment, the microvesicles which may be used to formulate nucleic acid molecules, modified nucleic acids and/or mmRNA may be made by the methods described in International Publication No. WO2013138427, the contents of which are herein incorporated by reference in its entirety. As a non-limiting example, microvesicles comprising nucleic acid molecules, modified nucleic acids and/or mmRNA may be used to treat diseases such as cancer as described in International Publication No. WO2013138427, the contents of which are herein incorporated by reference in its entirety.

In one embodiment, the microvesicles which may be used to formulate nucleic acid molecules, modified nucleic acids and/or mmRNA may be cell-derived microvesicles described in US Publication No. US20130195765, the contents of which are herein incorporated by reference in its entirety. As a non-limiting example, microvesicles comprising nucleic acid molecules, modified nucleic acids and/or mmRNA may be used to treat diseases such as cancer as described in US Publication No. US20130195765, the contents of which are herein incorporated by reference in its entirety.

In one embodiment, microvesicle formulations comprising nucleic acid molecules, modified nucleic acid molecules or mmRNA may be delivered intramuscularly. In one embodiment, microvesicle formulation comprising nucleic acid molecules, modified nucleic acid molecules or mmRNA may be delivered intradermally.

Interpolyelectrolyte Complexes

In one embodiment, the nucleic acid molecules, modified nucleic acid molecules and/or mmRNA may be formulated in an interpolyelectrolyte complex. Interpolyelectrolyte complexes are formed when charge-dynamic polymers are complexed with one or more anionic molecules. Non-limiting examples of charge-dynamic polymers and interpolyelectrolyte complexes and methods of making interpolyelectrolyte complexes are described in U.S. Pat. No. 8,524,368, the contents of which is herein incorporated by reference in its entirety.

In one embodiment, interpolyelectrolyte complex formulations of nucleic acid molecules, modified nucleic acid molecules or mmRNA may be administered intramuscularly. In one embodiment, interpolyelectrolyte complex formulation of nucleic acid molecules, modified nucleic acid molecules or mmRNA may be administered intradermally.

Cyrstalline Polymeric Systems

In one embodiment, the nucleic acid molecules, modified nucleic acid molecules and/or mmRNA may be formulated in crystalline polymeric systems. Crystalline polymeric systems are polymers with crystalline moieties and/or terminal units comprising crystalline moieties. Non-limiting examples of polymers with crystalline moieties and/or terminal units comprising crystalline moieties termed "CYC polymers," crystalline polymer systems and methods of making such polymers and systems are described in U.S. Pat. No. 8,524,259, the contents of which are herein incorporated by reference in its entirety.

In one embodiment, crystalline polymeric systems comprising nucleic acid molecules, modified nucleic acid molecules or mmRNA may be administered intramuscularly. In one embodiment, crystalline polymeric systems comprising nucleic acid molecules, modified nucleic acid molecules or mmRNA may be administered intradermally.

Polymer and Synthetic Scaffolds

In one embodiment, the nucleic acid molecules, modified nucleic acid molecules and/or mmRNA may be formulated in, delivered by or associated with polymer scaffolds. In one embodiment, the polymer scaffold may be a polyester urethane polymer scaffold (PEUR).

In one embodiment, the nucleic acid molecules, modified nucleic acid molecules and/or mmRNA may be formulated in, delivered by or associated with biodegradable, synthetic scaffolds such as, but not limited to, prefabricated ε-caprolactone and ethyl ethylene phosphate copolymer (PCLEEP) nanofibers, poly(lactic-co-glycolic acid) (PLGA) nanofibers, and porous polyester urethane (PEUR) scaffold design (see e.g., Nelson et al. Tunable Delivery of siRNA from a Biodegradable Scaffold to Promote Angiogenesis In Vivo. Adv. Mater. 2013; the contents of which are herein incorporated by reference in its entirety).

In one embodiment, polymeric or synthetic scaffolds comprising or associated with nucleic acid molecules, modified nucleic acid molecules or mmRNA may be administered intramuscularly. In one embodiment, polymeric or synthetic scaffolds comprising or associated with nucleic acid molecules, modified nucleic acid molecules or mmRNA may be administered intradermally.

Polymer Implant

In one embodiment, the nucleic acid molecules, modified nucleic acid molecules and/or mmRNA may be formulated in or delivered using polymer implants. As a non-limiting example, the polymer implant is inserted into or onto damaged human tissue and the nucleic acid molecules, modified nucleic acid molecules and/or mmRNA are released from the polymer implant. (See e.g., MariGen Omega3 from Kerecis for the treatment of damaged tissue).

In one embodiment, the nucleic acid molecules, modified nucleic acid molecules and/or mmRNA may be formulated in or delivered using delivery devices comprising polymer implants.

In one embodiment, polymer implants comprising or associated with nucleic acid molecules, modified nucleic acid molecules or mmRNA may be administered intramuscularly. In one embodiment, polymer implants comprising or associated with nucleic acid molecules, modified nucleic acid molecules or mmRNA may be administered intradermally.

Lipomers

In one embodiment, the nucleic acid molecules, modified nucleic acid molecules and/or mmRNA may be formulated in or delivered using a conjugated lipomer. As a non-limiting example, the conjugated lipomer may be a conjugated polyethyleneimine (PEI) polymer or a conjugated aza-macrocycle which contains one or more groups of the formula (iii) as described in International Patent Publication No. WO2012135025, the contents of which are herein incorporated by reference in its entirety.

In one embodiment, lipomers comprising or associated with nucleic acid molecules, modified nucleic acid molecules or mmRNA may be administered intramuscularly. In one embodiment, lipomers comprising or associated with nucleic acid molecules, modified nucleic acid molecules or mmRNA may be administered intradermally.

Poloxamer Delivery

In one embodiment, the nucleic acid molecules, modified nucleic acids and/or mmRNA may be formulated in or delivered using a pharmaceutical vehicle comprising at least one poloxamer. In one embodiment, the pharmaceutical vehicle may be suitable for the delivery of drugs to the mucosal surfaces such as, but not limited to, the pharmaceutical vehicles described in International Patent Publication No. WO2014027006, the contents of which are herein incorporated by reference in its entirety. As a non-limiting example the poloxamers used in the pharmaceutical vehicles are Poloxamer 407 and Poloxamer 188.

In one embodiment, poloxamer formulations comprising nucleic acid molecules, modified nucleic acid molecules or mmRNA may be administered intramuscularly. In one embodiment, poloxamer formulations comprising nucleic acid molecules, modified nucleic acid molecules or mmRNA may be administered intradermally.

Excipients

Pharmaceutical formulations may additionally comprise a pharmaceutically acceptable excipient, which, as used herein, includes, but are not limited to, any and all solvents, dispersion media, diluents, or other liquid vehicles, dispersion or suspension aids, surface active agents, isotonic agents, thickening or emulsifying agents, preservatives, solid binders, lubricants, flavoring agents, stabilizers, antioxidants, osmolality adjusting agents, pH adjusting agents and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

In some embodiments, a pharmaceutically acceptable excipient may be at least 95%, at least 96%, at least 97%, at least 98%, at least 99%, or 100% pure. In some embodiments, an excipient may be approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical compositions. The composition may also include excipients such as cocoa butter and suppository waxes, coloring agents, coating agents, sweetening, flavoring, and/or perfuming agents.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN®20], polyoxyethylene sorbitan [TWEEN®60], polyoxyethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g. polyoxyethylene monostearate [MYRJ®45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ®30]), poly(vinylpyrrolidone), diethylene glycol monolaurate, triethanolamine oleate, sodium oleate, potassium oleate, ethyl oleate, oleic acid, ethyl laurate, sodium lauryl sulfate, poly-oxyethylene-polyoxypropylene block copolymer (PLURONIC® F 68), copolymer of polyoxyethylene and polyoxypropylene (POLOXAMER®188), cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); amino acids (e.g. glycine); natural and synthetic gums (e.g. *acacia*, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Oxidation is a potential degradation pathway for mRNA, especially for liquid mRNA formulations. In order to prevent oxidation, antioxidants can be added to the formulation. Exemplary antioxidants include, but are not limited to, alpha tocopherol, ascorbic acid, acorbyl palmitate, benzyl alcohol, butylated hydroxyanisole, butylated hydroxytoluene, EDTA, m-cresol, methionine, monothioglycerol, potassium metabisulfite, propionic acid, propyl gallate, sodium ascorbate, sodium bisulfite, sodium metabisulfite, thioglycerol and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, isphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, DMDM Hydantoin and lodopropynyl Butylcarbamate (GLYDANT PLUS®), phenoxyethanol, methylparaben, ethylparaben, butylparaben, propylparaben, isobutylparaben (PHENONIP®), methylparaben, imidazolidinyl urea (GERMALL®115), propylene glycol, diazolidinyl urea, methylparaben, propylparaben (GERMABEN®II), methylisothiazolinone and phenoxyethanol (NEOLONE™) 5-chloro-2-methyl-4-isothiazolin-3-one and 2-methyl-4-isothiazolin-3-one (KATHON™), and/or benzyl alcohol, methylchloroisothiazolinone, methylisothiazolinone (EUXYL®).

In some embodiments, the pH of modified mRNA solutions are maintained between pH 5 and pH 8 to improve stability. Exemplary buffers to control pH may include, but are not limited to sodium phosphate, sodium citrate, sodium succinate, histidine (or histidine-HCl), sodium carbonate, and/or sodium malate. In another embodiment, the exemplary buffers listed above may be used with additional monovalent counterions (including, but not limited to potassium). Divalent cations may also be used as buffer counterions; however, these are not preferred due to complex formation and/or mRNA degradation.

Exemplary buffering agents may also include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Excipients such as cocoa butter and suppository waxes, coloring agents, coating agents, sweetening, flavoring, and/or perfuming agents can be present in the composition, according to the judgment of the formulator.

Exemplary additives include physiologically biocompatible buffers (e.g., trimethylamine hydrochloride), addition of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). In addition, antioxidants and suspending agents can be used.

Cryoprotectants for mRNA

In some embodiments, modified mRNA formulations may comprise cyroprotectants. As used herein, there term "cryoprotectant" refers to one or more agent that when combined with a given substance, helps to reduce or eliminate damage to that substance that occurs upon freezing. In some embodiments, cryoprotectants are combined with modified mRNA in order to stabilize them during freezing. Frozen storage of mRNA between −20° C. and −80° C. may be advantageous for long term (e.g. 36 months) stability of mRNA. In some embodiments, cryoprotectants are included in modified mRNA formulations to stabilize mRNA through freeze/thaw cycles and under frozen storage conditions. Cryoprotectants of the present invention may include, but are not limited to sucrose, trehalose, lactose, glycerol, dextrose, raffinose and/or mannitol. Trehalose is listed by the Food and Drug Administration as being generally regarded as safe (GRAS) and is commonly used in commercial pharmaceutical formulations.

Bulking Agents

In some embodiments, modified mRNA formulations may comprise bulking agents. As used herein, the term "bulking agent" refers to one or more agents included in formulations to impart a desired consistency to the formulation and/or stabilization of formulation components. In some embodiments, bulking agents are included in lyophilized mRNA formulations to yield a "pharmaceutically elegant" cake, stabilizing the lyophilized mRNA during long term (e.g. 36 month) storage. Bulking agents of the present invention may include, but are not limited to sucrose, trehalose, mannitol, glycine, lactose and/or raffinose. In some embodiments, combinations of cryoprotectants and bulking agents (for example, sucrose/glycine or trehalose/mannitol) may be included to both stabilize mRNA during freezing and provide a bulking agent for lyophilization.

Inactive Ingredients

In some embodiments, modified mRNA formulations may comprise at least one excipient which is an inactive ingredient. As used herein, the term "inactive ingredient" refers to one or more inactive agents included in formulations. In some embodiments, all, none or some of the inactive ingredients which may be used in the formulations of the present invention may be approved by the US Food and Drug Administration (FDA). A non-exhaustive list of inactive ingredients and the routes of administration the inactive ingredients may be formulated in are described in Table 4. In Table 4, "AN" means anesthetic, "CNBLK" means cervical nerve block, "NBLK" means nerve block, "IV" means intravenous, "IM" means intramuscular and "SC" means subcutaneous

TABLE 4

| Inactive Ingredients | |
|---|---|
| Inactive Ingredient | Route of Administration |
| Alpha-Terpineol | Topical |
| Alpha-Tocopherol | Intravenous; Topical |
| Alpha-Tocopherol Acetate, Dl- | Topical |
| Alpha-Tocopherol, Dl- | Intravenous; Topical |
| 1,2,6-Hexanetriol | Topical |
| 1,2-Dimyristoyl-Sn-Glycero-3-(Phospho-S-(1-Glycerol)) | Intravenous; Infusion (IV) |
| 1,2-Dimyristoyl-Sn-Glycero-3-Phosphocholine | Intravenous; Infusion (IV) |
| 1,2-Dioleoyl-Sn-Glycero-3-Phosphocholine | Epidural |
| 1,2-Dipalmitoyl-Sn-Glycero-3-(Phospho-Rac-(1-Glycerol)) | Epidural |
| 1,2-Distearoyl-Sn-Glycero-3-(Phospho-Rac-(1-Glycerol)) | Intravenous |
| 1,2-Distearoyl-Sn-Glycero-3-Phosphocholine | Intravenous |
| 1-O-Tolylbiguanide | Topical |
| 2-Ethyl-1,6-Hexanediol | Topical |
| Acetic Acid | Infiltration; Auricular (Otic); Extracorporeal; Intramuscular; Intravenous; Subcutaneous; Intra-articualr; Intralesional; Intramuscular; Intrasynovial; Intratracheal; Intravenous; Irrigation; Infusion (IV); Nasal; Nerve block; Ophthalmic; Photopheresis; Soft Tissue; Submucosal; Topical |
| Acetic Acid, Glacial | Intravenous; Infusion (IV); Subcutaneous |
| Acetic Anhydride | Intravenous |
| Acetone | Implantation; Topical |
| Acetone Sodium Bisulfite | Intrathecal (AN, CNBLK); Infiltration (AN); Dental; Inhalation; Nerve Block |
| Acetylated Lanolin Alcohols | Topical |
| Acetylated Monoglycerides | Intravenous |
| Acetylcysteine | Inhalation |
| Acetyltryptophan, DL- | Intravenous |
| Acrylates Copolymer | Topical; Transdermal |
| Acrylic Acid-Isooctyl Acrylate Copolymer | Transdermal |
| Acrylic Adhesive 788 | Transdermal |
| Activated Charcoal | Intramuscular; Intravenous; Irrigation; Infusion (IV) |
| Adcote 72A103 | Transdermal |
| Adhesive Tape | Topical |
| Adipic Acid | Intramuscular; Vaginal |
| Aerotex Resin 3730 | Transdermal |
| Alanine | Infusion (IV) |
| Albumin Aggregated | Intravenous |
| Albumin Colloidal | Intravenous |
| Albumin Human | Intravenous; Infusion (IV); Subcutaneous |
| Alcohol | Dental; Intramuscular; Intravenous; Subcutaneous; Inhalation; Intravascular; Infusion (IV); Ophthalmic; Rectal; Respiratory (Inhalation); Topical; Transdermal |
| Alcohol, Dehydrated | Dental; Extracorporeal; Intramuscular; Intravenous; Subcutaneous; Inhalation; Intracavitary; Intravascular; Intravesical; Nasal, Ophthalmic; Photopheresis, Rectal; Respiratory (Inhalation); Sublingual; Topical; Transdermal |
| Alcohol, Denatured | Denatal; Intravenous; Topical; Vaginal |
| Alcohol, Diluted | Intramuscular; Intravenous; Topical |
| Alfadex | Intracavitary |
| Alginic Acid | Ophthalmic |
| Alkyl Ammonium Sulfonic Acid Betaine | Topical |
| Alkyl Aryl Sodium Sulfonate | Topical |
| Allantoin | Topical; Vaginal |
| Allyl .Alpha.-Ionone | Nasal |
| Almond Oil | Topical |
| Aluminum Acetate | Auricular (Otic); Topical |
| Aluminum Chlorhydroxy Allantoinate | Topical |
| Aluminum Hydroxide | Topical |
| Aluminum Hydroxide - Sucrose, Hydrated | Topical |
| Aluminum Hydroxide Gel | Topical |
| Aluminum Hydroxide Gel F 500 | Topical |
| Aluminum Hydroxide Gel F 5000 | Topical |
| Aluminum Monostearate | Topical |
| Aluminum Oxide | Topical |
| Aluminum Polyester | Transdermal |
| Aluminum Silicate | Topical |
| Aluminum Starch Octenylsuccinate | Topical |
| Aluminum Stearate | Topical |
| Aluminum Subacetate | Rectal |

TABLE 4-continued

Inactive Ingredients

| Inactive Ingredient | Route of Administration |
| --- | --- |
| Aluminum Sulfate Anhydrous | Auricular (Otic); Topical |
| Amerchol C | Topical |
| Amerchol-Cab | Ophthalmic; Topical |
| Aminomethylpropanol | Topical |
| Ammonia | Inhalation |
| Ammonia Solution | Topical |
| Ammonia Solution, Strong | Topical |
| Ammonium Acetate | Intramuscular; Intravenous; Infusion (IV) |
| Ammonium Hydroxide | Intravenous; Ophthalmic; Subcutaneous; Topical |
| Ammonium Lauryl Sulfate | Topical |
| Ammonium Nonoxynol-4 Sulfate | Topical |
| Ammonium Salt Of C-12-C-15 Linear Primary Alcohol Ethoxylate | Topical |
| Ammonium Sulfate | Intravenous |
| Ammonyx | Topical |
| Amphoteric-2 | Topical |
| Amphoteric-9 | Topical |
| Anethole | Dental |
| Anhydrous Citric Acid | Intravenous; Infusion (IV); Rectal; Topical |
| Anhydrous Dextrose | Intramuscular; Intravenous; Subcutaneous; Infusion (IV); Nasal; Spinal |
| Anhydrous Lactose | Intramuscular; Intravenous; Intracavitary; Intravenous; Infusion (IV); Vaginal |
| Anhydrous Trisodium Citrate | Intramuscular; Intravenous; Intra-arterial; Intra-articular; Intrabursal; Infusion (IV); Nasal; Ophthalmic; Soft Tissue; Topical |
| Aniseed Oil | Rectal |
| Anoxid Sbn | Topical |
| Antifoam | Topical |
| Antipyrine | Ophthalmic |
| Apaflurane | Respiratory (Inhalation) |
| Apricot Kernel Oil Peg-6 Esters | Topical; Vaginal |
| Aquaphor | Topical |
| Arginine | Intramuscular; Intravenous; Infusion (IV) |
| Arlacel | Topical |
| Ascorbic Acid | Infiltration (AN); Caudal Block; Epidural; Intramuscular; Intravenous; Inhalation; Infusion (IV); Nerve Block; Rectal; Subctaneous; Topical |
| Ascorbyl Palmitate | Rectal; Topical |
| Aspartic Acid | Infusion (IV) |
| Balsam Peru | Rectal |
| Barium Sulfate | Intrauterine; Vaginal |
| Beeswax | Topical; Vaginal |
| Beeswax, Synthetic | Topical |
| Beheneth-10 | Topical |
| Bentonite | Topical; Transdermal; Vaginal |
| Benzalkonium Chloride | Auricular (Otic); Inhalation; Intra-Articular; Intrabursal; Intradermal; Intralesional; Intramuscular; Intraocular; Nasal; Ophthalmic; Respiratory (Inhalation); Topical |
| Benzenesulfonic Acid | Intravenous; Infusion (IV) |
| Benzethonium Chloride | Auricular (Otic); Intramuscular; Intravenous; Infusion (IV); Nasal; Ophthalmic |
| Benzododecinium Bromide | Ophthalmic |
| Benzoic Acid | Intramuscular; Intravenous; Irrigation; Infusion (IV); Rectal; Topical; Vaginal |
| Benzyl Alcohol | Infiltration (AN); Auricular (Otic); Dental; Epidural; Extracorporeal; Interstitial; Intra-Arterial; Intra-Articular; Intrabursal; Intracavitary; Intradermal; Intralesional; Intramuscular; Intraperitoneal; Intrapleural; Intrasynovial; Intrathecal; Intratracheal; Intratumor; Intravenous; Infusion(IV); Nasal; Nerve Block; Rectal; Soft Tissue; Subconjunctival; Subcutaneous; Topical; Ureteral; Vaginal |
| Benzyl Benzoate | Intramuscular |
| Benzyl Chloride | Intravenous |
| Betadex | Topical |
| Bibapcitide | Intravenous |
| Bismuth Subgallate | Rectal |
| Boric Acid | Auricular (Otic); Intravenous; Ophthalmic; Topical |
| Brocrinat | Infusion (IV) |
| Butane | Topical |
| Butyl Alcohol | Topical |

TABLE 4-continued

| Inactive Ingredients | |
| --- | --- |
| Inactive Ingredient | Route of Administration |
| Butyl Ester Of Vinyl Methyl Ether/Maleic Anhydride Copolymer (125000 Mw) | Topical |
| Butyl Stearate | Topical |
| Butylated Hydroxyanisole | Intramuscular; Infusion (IV); Nasal; Rectal; Topical; Vaginal |
| Butylated Hydroxytoluene | Intramuscular; Intravenous; Infusion (IV); Nasal; Rectal; Topical; Transdermal; Vaginal |
| Butylene Glycol | Topical; Transdermal |
| Butylparaben | Intramuscular; Rectal; Topical |
| Butyric Acid | Transdermal |
| C20-40 Pareth-24 | Topical |
| Caffeine | Nasal; Ophthalmic |
| Calcium | Intramuscular |
| Calcium Carbonate | Auricular (Otic); Respiratory (Inhalation) |
| Calcium Chloride | Infiltration (AN); Caudal Block; Epidural; Intramuscular; Intravenous; Intraocular; Intraperitoneal; Intravascular; Intravitreal; Nerve Block; Ophthalmic; Subctaneous; Topical |
| Calcium Gluceptate | Intravenous |
| Calcium Hydroxide | Intravenous; Subcutaneous; Topical |
| Calcium Lactate | Vaginal |
| Calcobutrol | Intravenous |
| Caldiamide Sodium | Intravenous |
| Caloxetate Trisodium | Intravenous |
| Calteridol Calcium | Intravenous |
| Canada Balsam | Topical |
| Caprylic/Capric Triglyceride | Topical; Transdermal |
| Caprylic/Capric/Stearic Triglyceride | Topical |
| Captan | Topical |
| Captisol | Intravenous |
| Caramel | Rectal; Topical |
| Carbomer 1342 | Ophthalmic; Topical; Transdermal |
| Carbomer 1382 | Topical |
| Carbomer 934 | Rectal; Topical; Vaginal |
| Carbomer 934p | Ophthalmic; Rectal; Topical; Vaginal |
| Carbomer 940 | Ophthalmic; Topical; Transdermal |
| Carbomer 941 | Topical |
| Carbomer 980 | Topical; Transdermal |
| Carbomer 981 | Topical |
| Carbomer Homopolymer Type B (Allyl Pentaerythritol Crosslinked) | Ophthalmic; Topical |
| Carbomer Homopolymer Type C (Allyl Pentaerythritol Crosslinked) | Topical |
| Carbon Dioxide | Infiltration (AN); Intramuscular (IM); Infusion (IV); Inhalation; Intra-arterial; Intracardiac; Intrathecal; Intravascular; Intravenous |
| Carboxy Vinyl Copolymer | Topical |
| Carboxymethylcellulose | Intra-articular; Intrabursal; Intralesional; Intramuscular; Soft tissue; Topical |
| Carboxymethylcellulose Sodium | Dental; Intra-articular; Intrabursal; Intradermal; Intramuscular; Intrasynovial; Intratracheal; Nasal; Ophthalmic; Soft tissue; Subcutaneous; Topical |
| Carboxypolymethylene | Rectal; Topical |
| Carrageenan | Dental; Topical; Transdermal |
| Carrageenan Salt | Topical |
| Castor Oil | Intramuscular; Ophthalmic; Topical |
| Cedar Leaf Oil | Topical |
| Cellulose | Topical |
| Cellulose, Microcrystalline | Intra-articular; Intramuscular; Intravenous; Intravitreal; Nasal; Vaginal |
| Cerasynt-Se | Rectal; Topical |
| Ceresin | Topical |
| Ceteareth-12 | Topical |
| Ceteareth-15 | Topical |
| Ceteareth-30 | Topical |
| Cetearyl Alcohol/Ceteareth-20 | Topical |
| Cetearyl Ethylhexanoate | Topical |
| Ceteth-10 | Topical |
| Ceteth-2 | Topical |
| Ceteth-20 | Topical; Vaginal |
| Ceteth-23 | Topical |
| Cetostearyl Alcohol | Topical; Vaginal |
| Cetrimonium Chloride | Topical |
| Cetyl Alcohol | Auricular (Otic); Ophthalmic; Rectal; Topical; Vaginal |

TABLE 4-continued

| Inactive Ingredients | |
|---|---|
| Inactive Ingredient | Route of Administration |
| Cetyl Esters Wax | Topical; Vaginal |
| Cetyl Palmitate | Topical; Vaginal |
| Cetylpyridinium Chloride | Inhalation; Iontophoresis; Transdermal |
| Chlorobutanol | Infiltration (AN); Auricular (Otic); Intramuscular (IM); Infusion (IV); Subcutaneous (SC); Inhalation; Intravenous; Nasal; Nerve Block; Ophthalmic; Topical |
| Chlorobutanol Hemihydrate | Intramuscular; Intravenous |
| Chlorobutanol, Anhydrous | Intramuscular; Intravenous; Ophthalmic |
| Chlorocresol | Topical |
| Chloroxylenol | Auricular (Otic); Topical |
| Cholesterol | Epidural; Infiltration; Intravenous; Ophthalmic; Topical; Vaginal |
| Choleth | Vaginal |
| Choleth-24 | Topical |
| Citrate | Intravenous |
| Citric Acid | Intrathecal (AN, CNBLK); Infiltration (AN); Auricular (Otic); Caudal Block; Epidural; Intramuscular (IM); Infusion (IV); Subcutaneous (SC); Infiltration; Inhalation; Intra-amniotic; Intra-arterial; Intra-articular; Intrabursal; Intracardiac; Intralesional; Iintrapleural; Intrasynovial; Intrathecal; Intravascular; Intravenous; Iontophoresis; Nasal; Nerve Block; Ophthalmic; Peridural; Soft tissue; Topical; Transdermal; Vaginal |
| Citric Acid Monohydrate | Infiltration (AN); Intramuscular (IM); Infusion (IV); Subcutaneous (SC); Intracardiac; Intraocular; Intravenous; Nasal; Nerve Block; Ophthalmic; Topical; Vaginal |
| Citric Acid, Hydrous | Intramuscular (IM); Infusion (IV); Subcutaneous (SC); Intravenous |
| Cocamide Ether Sulfate | Topical |
| Cocamine Oxide | Topical |
| Coco Betaine | Topical |
| Coco Diethanolamide | Topical |
| Coco Monoethanolamide | Topical |
| Cocoa Butter | Rectal; Topical |
| Coco-Glycerides | Topical |
| Coconut Oil | Topical |
| Coconut Oil, Hydrogenated | Rectal |
| Coconut Oil/Palm Kernel Oil Glycerides, Hydrogenated | Rectal; Vaginal |
| Cocoyl Caprylocaprate | Topical |
| *Cola Nitida* Seed Extract | Rectal |
| Collagen | Topical |
| Coloring Suspension | Topical |
| Corn Oil | Intramuscular |
| Cottonseed Oil | Intramuscular |
| Cream Base | Topical |
| Creatine | Intra-articular; Intralesional; Intramuscular |
| Creatinine | Auricular (Otic); Intramuscular (IM); Infusion (IV); Subcutaneous (SC); Intra-articular; Intrabursal; Intradermal; Intralesional; Intrasynovial; Ophthalmic; Soft tissue; Topical |
| Cresol | Subcutaneous |
| Croscarmellose Sodium | Intramuscular |
| Crospovidone | Implantation; Intra-articluar; Intramuscular; Intrauterine; Topical; Transdermal; Vagiinal |
| Cupric Sulfate | Auricular (Otic) |
| Cupric Sulfate Anhydrous | Auricular (Otic) |
| Cyclomethicone | Topical |
| Cyclomethicone/Dimethicone Copolyol | Topical |
| Cysteine | Intramuscular (IM); Subcutaneous (SC); Intravenous; Infusion (IV) |
| Cysteine Hydrochloride | Intravenous; Infusion (IV) |
| Cysteine Hydrochloride Anhydrous | Intradiscal |
| Cysteine, Dl- | Intradiscal |
| D&C Red No. 28 | Topical |
| D&C Red No. 33 | Topical |
| D&C Red No. 36 | Topical |
| D&C Red No. 39 | Topical |
| D&C Yellow No. 10 | Dental; Inhalation; Rectal; Topical |
| Dalfampridine | Intravenous |
| Daubert 1-5 Pestr (Matte) 164z | Transdermal |
| Decyl Methyl Sulfoxide | Topical |
| Dehydag Wax Sx | Topical |

TABLE 4-continued

Inactive Ingredients

| Inactive Ingredient | Route of Administration |
| --- | --- |
| Dehydroacetic Acid | Topical |
| Dehymuls E | Topical |
| Denatonium Benzoate | Topical |
| Deoxycholic Acid | Infusion (IV) |
| Dextran | Intravenous |
| Dextran 40 | Intravenous |
| Dextrin | Topical |
| Dextrose | Intramuscular (IM); Infusion (IV); Subcutaneous (SC); Interstitial; Intracavitary; Intraperitoneal; Intrapleural; Intraspinal; Intravenous; Nasal; Spinal |
| Dextrose Monohydrate | Intravenous |
| Dextrose Solution | Intravenous; Infusion (IV) |
| Diatrizoic Acid | Intra-arterial; Intra-articular; Intracardiac; Intradiscal; Intramuscular; Intrauterine; Intravascular; Intravenous; Infusion (IV); Periarticular; Subcutaneous; Ureteral; Urethral |
| Diazolidinyl Urea | Topical |
| Dichlorobenzyl Alcohol | Topical |
| Dichlorodifluoromethane | Inhalation; Intrapleural; Nasal; Rectal; Topical |
| Dichlorotetrafluoroethane | Inhalation; Nasal; Rectal; Topical |
| Diethanolamine | Infusion (IV); Ophthalmic; Topical |
| Diethyl Pyrocarbonate | Inflitration |
| Diethyl Sebacate | Topical |
| Diethylene Glycol Monoethyl Ether | Topical; Transdermal |
| Diethylhexyl Phthalate | Ophthalmic; Transdermal |
| Dihydroxyaluminum Aminoacetate | Topical |
| Diisopropanolamine | Topical |
| Diisopropyl Adipate | Topical |
| Diisopropyl Dilinoleate | Topical |
| Dimethicone 350 | Topical |
| Dimethicone Copolyol | Topical; Transermal |
| Dimethicone Mdx4-4210 | Transdermal |
| Dimethicone Medical Fluid 360 | Dental; Intravenous; Topical; Transdermal |
| Dimethyl Isosorbide | Topical |
| Dimethyl Sulfoxide | Infusion (IV); Subcutanous; Topical |
| Dimethylaminoethyl Methacrylate - Butyl Methacrylate - Methyl Methacrylate Copolymer | Transdermal |
| Dimethyldioctadecylammonium Bentonite | Rectal |
| Dimethylsiloxane/Methylvinylsiloxane Copolymer | Implantation; Intrauterine |
| Dinoseb Ammonium Salt | Topical |
| Dipalmitoylphosphatidylglycerol, Dl- | Inflitration |
| Dipropylene Glycol | Transdermal |
| Disodium Cocoamphodiacetate | Topical |
| Disodium Laureth Sulfosuccinate | Topical |
| Disodium Lauryl Sulfosuccinate | Topical |
| Disodium Sulfosalicylate | Topical |
| Disofenin | Topical |
| Divinylbenzene Styrene Copolymer | Ophthalmic |
| Dmdm Hydantoin | Topical |
| Docosanol | Topical |
| Docusate Sodium | Intramuscular; Topical |
| Duro-Tak 280-2516 | Transdermal |
| Duro-Tak 387-2516 | Transdermal |
| Duro-Tak 80-1196 | Transdermal |
| Duro-Tak 87-2070 | Transdermal |
| Duro-Tak 87-2194 | Transdermal |
| Duro-Tak 87-2287 | Percutaneous; Transdermal |
| Duro-Tak 87-2296 | Transdermal |
| Duro-Tak 87-2888 | Transdermal |
| Duro-Tak 87-2979 | Transdermal |
| Edetate Calcium Disodium | Infiltration (AN); Caudal Block; Epidural; Intramuscular (IM); Infusion (IV); Intra-articular; Intra-arterial; Intracardiac; Intradiscal; Intraperitoneal; Intrathecal; Intrauterine; Intravascular; Intravenous; Intravesical; Nerve Block; Periarticular; Rectal; Subcutaneous; Ureteral; Urethral |
| Edetate Disodium | Infiltration (AN), Auricular (Otic); Caudal Block; Epidural; Intramuscular (IM); Infusion (IV); Subcutaneous (SC); Inhalation; Intra-arterial; Intra-articular; Intrabursal; Intracardiac; Intradermal; Intradiscal; Intralesional; Intrasynovial; Intrauterine; Intravascular; Intravenous; Iontophoresis; Nasal; Nerve Block; Ophthalmic; Rectal; Respiratory |

TABLE 4-continued

Inactive Ingredients

| Inactive Ingredient | Route of Administration |
| --- | --- |
| | (Inhalation); Soft tissue; Topical; Transdermal; Ureteral; Urethral; Vaginal |
| Edetate Disodium Anhydrous | Intra-amniotic; Intramuscular; Intravenous; Infusion (IV); Ophthalmic |
| Edetate Sodium | Intramuscular (IM); Infusion (IV); Subcutaneous (SC); Inhalation; Ophthalmic; Topical |
| Edetic Acid | Auricular (Otic); Rectal; Submucosal; Topical |
| Egg Phospholipids | Intravenous; Infusion (IV) |
| Entsufon | Topical |
| Entsufon Sodium | Topical |
| Epilactose | Rectal |
| Epitetracycline Hydrochloride | Topical |
| Essence Bouquet 9200 | Topical |
| Ethanolamine Hydrochloride | Intravenous |
| Ethyl Acetate | Intramuscular; Topical; Transdermal |
| Ethyl Oleate | Transdermal |
| Ethylcelluloses | Topical; Transdermal; Vaginal |
| Ethylene Glycol | Topical |
| Ethylene Vinyl Acetate Copolymer | Implantation; Intrauerine; Ophthalmic; Periodontal; Subcutaneous; Transdermal |
| Ethylenediamine | Intravenous; Infusion (IV); Rectal; Topical |
| Ethylenediamine Dihydrochloride | Topical |
| Ethylene-Propylene Copolymer | Transdermal |
| Ethylene-Vinyl Acetate Copolymer (28% Vinyl Acetate) | Vaginal |
| Ethylene-Vinyl Acetate Copolymer (9% Vinylacetate) | Vaginal |
| Ethylhexyl Hydroxystearate | Topical |
| Ethylparaben | Topical |
| Eucalyptol | Dental |
| Exametazime | Intravenous |
| Fat, Edible | Rectal |
| Fat, Hard | Rectal |
| Fatty Acid Esters | Transdermal |
| Fatty Acid Pentaerythriol Ester | Topical |
| Fatty Acids | Topical |
| Fatty Alcohol Citrate | Topical |
| Fatty Alcohols | Vaginal |
| Fd&C Blue No. 1 | Dental; Rectal; Topical |
| Fd&C Green No. 3 | Dental; Rectal |
| Fd&C Red No. 4 | Topical |
| Fd&C Red No. 40 | Topical |
| Fd&C Yellow No. 10 (Delisted) | Topical |
| Fd&C Yellow No. 5 | Topical; Vaginal |
| Fd&C Yellow No. 6 | Inhalation; Rectal; Topical |
| Ferric Chloride | Intravenous |
| Ferric Oxide | Topical |
| Flavor 89-186 | Dental |
| Flavor 89-259 | Dental |
| Flavor Df-119 | Dental |
| Flavor Df-1530 | Dental |
| Flavor Enhancer | Dental |
| Flavor Fig 827118 | Rectal |
| Flavor Raspberry Pfc-8407 | Rectal |
| Flavor Rhodia Pharmaceutical No. Rf 451 | Topical |
| Fluorochlorohydrocarbons | Inhalation |
| Formaldehyde | Topical |
| Formaldehyde Solution | Topical |
| Fractionated Coconut Oil | Topical |
| Fragrance 3949-5 | Topical |
| Fragrance 520a | Topical |
| Fragrance 6.007 | Topical |
| Fragrance 91-122 | Topical |
| Fragrance 9128-Y | Topical |
| Fragrance 93498g | Topical |
| Fragrance Balsam Pine No. 5124 | Topical |
| Fragrance Bouquet 10328 | Topical |
| Fragrance Chemoderm 6401-B | Topical |
| Fragrance Chemoderm 6411 | Topical |
| Fragrance Cream No. 73457 | Topical |
| Fragrance Cs-28197 | Topical |
| Fragrance Felton 066m | Topical |
| Fragrance Firmenich 47373 | Topical |
| Fragrance Givaudan Ess 9090/1c | Topical |
| Fragrance H-6540 | Topical |
| Fragrance Herbal 10396 | Topical |

TABLE 4-continued

Inactive Ingredients

| Inactive Ingredient | Route of Administration |
|---|---|
| Fragrance Nj-1085 | Topical |
| Fragrance P O Fl-147 | Topical |
| Fragrance Pa 52805 | Topical |
| Fragrance Pera Derm D | Topical |
| Fragrance Rbd-9819 | Topical |
| Fragrance Shaw Mudge U-7776 | Topical |
| Fragrance Tf 044078 | Topical |
| Fragrance Ungerer Honeysuckle K 2771 | Topical |
| Fragrance Ungerer N5195 | Topical |
| Fructose | Infusion (IV); Rectal |
| Gadolinium Oxide | Intravenous |
| Galactose | Rectal |
| Gamma Cyclodextrin | Intravenous |
| Gelatin | Dental; Intramuscular (IM); Infusion (IV); Subcutaneous (SC); Intravenous; Respiratory (Inhalation); Topical; Vaginal |
| Gelatin, Crosslinked | Dental |
| Gelfoam Sponge | N/A |
| Gellan Gum (Low Acyl) | Ophthalmic |
| Gelva 737 | Transdermal |
| Gentisic Acid | Intravenous |
| Gentisic Acid Ethanolamide | Infusion (IV) |
| Gluceptate Sodium | Intravenous |
| Gluceptate Sodium Dihydrate | Intravenous |
| Gluconolactone | Intramuscular (IM); Infusion (IV); Intravesou; Topical |
| Glucuronic Acid | Intravenous |
| Glutamic Acid, Dl- | Vaginal |
| Glutathione | Intramuscular |
| Glycerin | Auricular (Otic); Dental; Intramuscular; Infusion (IV); Subcutaneous (SC); Inhalation; Intradermal; Intravenous; Iontophoresis; Nasal; Ophthalmic; Perfusion; Biliary; Rectal; Topical; Transdermal; Vaginal |
| Glycerol Ester Of Hydrogenated Rosin | Nasal |
| Glyceryl Citrate | Topical |
| Glyceryl Isostearate | Topical; Vaginal |
| Glyceryl Laurate | Transdermal |
| Glyceryl Monostearate | Topical; Vaginal |
| Glyceryl Oleate | Topical; Transdermal |
| Glyceryl Oleate/Propylene Glycol | Topical |
| Glyceryl Palmitate | Rectal; Topical |
| Glyceryl Ricinoleate | Topical |
| Glyceryl Stearate | Auricular (Otic); Dental; Ophthalmic; Rectal; Topical; Vaginal |
| Glyceryl Stearate - Laureth-23 | Topical |
| Glyceryl Stearate/Peg Stearate | Rectal |
| Glyceryl Stearate/Peg-100 Stearate | Topical |
| Glyceryl Stearate/Peg-40 Stearate | Rectal |
| Glyceryl Stearate-Stearamidoethyl Diethylamine | Topical |
| Glyceryl Trioleate | Epidural |
| Glycine | Intramuscular (IM); Infusion (IV); Subcutaneous (SC); Intravenous; Rectal; Respiratory (Inhalation) |
| Glycine Hydrochloride | Subcutaneous |
| Glycol Distearate | Topical |
| Glycol Stearate | Topical |
| Guanidine Hydrochloride | Intravenous |
| Guar Gum | Topical; Vaginal |
| Hair Conditioner (18n195-1m) | Topical |
| Heptane | Transdermal |
| Hetastarch | Intravenous |
| Hexylene Glycol | Topical |
| High Density Polyethylene | Dental; Intrauterine; Ophthalmic; Topical; Transdermal; Vaginal |
| Histidine | Intravenous; Infusion (IV); Subcutaneous |
| Human Albumin Microspheres | Intravenous |
| Hyaluronate Sodium | Intra-articular; Intramuscular; Intravitreal; Topical |
| Hydrocarbon | Rectal |
| Hydrocarbon Gel, Plasticized | Dental; Ophthalmic; Topical |
| Hydrochloric Acid | Intrathecal (AN, CNBLK); Inflitration (AN); Sympathetic (AN, NBLK); Auricular (Otic); Caudal Block; Dental; Diagnostic; Epidural; Extracorporeal; Intramuscular (IM); Infusion (IV); Subcutaneous (SC); Inflitration; Inhalationi; Interstitial; Intra-amniotic; Intra-arterial; Intra-articular; Intrabursal; |

TABLE 4-continued

Inactive Ingredients

| Inactive Ingredient | Route of Administration |
| --- | --- |
| | Intracardiac; Intracaudal; Intracavitary; Intradermal; Intralesional; Intraocular; Intraperitoneal; Intrapleural; Intraspinal; Intrasynovial; Intrathecal; Intratracheal; Intratumor; Intravascular; Intravenous; Intravesical; Intravitreal; Iontophoresis; Irrigation; Nasal; Nerve Block, Ophthalmic; Parenteral; Perfusion, Cardiac; Peridural; Perineural; Periodontal; Pectal; Respiratory (Inhalation); Retrobulbar; Soft tissue; Spinal; Subarachnoid; Subconjunctival; Subcutaneous; Topical; Transdermal; Ureteral; Urethral |
| Hydrochloric Acid, Diluted | Infiltration (AN); Intramuscular (IM); Infusion (IV); Subcutaneous (SC); Inhalation; Intra-arterial; Intravascular; Intravenous; Nerve Block; Ophthalmic; Topical |
| Hydrocortisone | Auricular (Otic) |
| Hydrogel Polymer | Vaginal |
| Hydrogen Peroxide | Topical |
| Hydrogenated Castor Oil | Topical |
| Hydrogenated Palm Oil | Rectal; Vaginal |
| Hydrogenated Palm/Palm Kernel Oil Peg-6 Esters | Topical |
| Hydrogenated Polybutene 635-690 | Transdermal |
| Hydroxide Ion | Intramuscular; Infusion (IV) |
| Hydroxyethyl Cellulose | Auricular (Otic); Ophthalmic; Topical; Transdermal |
| Hydroxyethylpiperazine Ethane Sulfonic Acid | Intravenous |
| Hydroxymethyl Cellulose | Topical |
| Hydroxyoctacosanyl Hydroxystearate | Topical |
| Hydroxypropyl Cellulose | Topical |
| Hydroxypropyl Methylcellulose 2906 | Ophthalmic |
| Hydroxypropyl-Bcyclodextrin | Intravenous; Infusion (IV) |
| Hypromellose 2208 (15000 Mpa.S) | Vaginal |
| Hypromellose 2910 (15000 Mpa.S) | Nasal; Ophthalmic |
| Hypromelloses | Irrigation; Ophthalmic; Rectal; Topical; Vaginal |
| Imidurea | Topical |
| Iodine | Intra-arterial; Intra-articular; Intracardiac; Intradiscal; Intravascular; Intravenous; Periarticular |
| Iodoxamic Acid | Intravenous |
| Iofetamine Hydrochloride | Intravenous |
| Irish Moss Extract | Topical |
| Isobutane | Topical |
| Isoceteth-20 | Topical |
| Isoleucine | Infusion (IV) |
| Isooctyl Acrylate | Topical |
| Isopropyl Alcohol | Intravenous; Topical |
| Isopropyl Isostearate | Topical |
| Isopropyl Myristate | Auricular (Otic); Topical; Transdermal; Vaginal |
| Isopropyl Myristate -3 Myristyl Alcohol | Topical |
| Isopropyl Palmitate | Topical; Transdermal |
| Isopropyl Stearate | Topical |
| Isostearic Acid | Topical |
| Isostearyl Alcohol | Topical |
| Isotonic Sodium Chloride Solution | Epidural; Intratracheal; Intravenous; Infusion (IV) |
| Jelene | Ophthalmic; Topical |
| Kaolin | Topical |
| Kathon Cg | Topical |
| Kathon Cg II | Topical |
| Lactate | Topical |
| Lactic Acid | Infiltration (AN); Auricular (Otic); Intramuscular (IM); Infusion (IV); Subcutaneous (SC); Intracardiac; Intravenous; Nerve Block; Topical; Vaginal |
| Lactic Acid, Dl- | Intramuscular (IM); Infusion (IV); Intravesou; Topical; Vaginal |
| Lactic Acid, L- | Intravenous; Subcutanous |
| Lactobionic Acid | Intravenous; Infusion (IV) |
| Lactose | Intramuscular (IM); Infusion (IV); Subcutaneous (SC); Inhalation; Intracavitary; Intravenous; Rectal; Transdermal; Vaginal |
| Lactose Monohydrate | Intramuscular (IM); Infusion (IV); Subcutaneous (SC); Intracavitary; Intravenous; Respiratory (Inhalation); Vaginal |
| Lactose, Hydrous | Intramuscular (IM); Infusion (IV); Intravenous; Vaginal |

TABLE 4-continued

Inactive Ingredients

| Inactive Ingredient | Route of Administration |
|---|---|
| Laneth | Topical |
| Lanolin | Ophthalmic; Rectal; Topical; Vaginal |
| Lanolin Alcohol - Mineral Oil | Topical |
| Lanolin Alcohols | Ophthalmic; Topical |
| Lanolin Anhydrous | Ophthalmic; Topical; Transdermal; Vaginal |
| Lanolin Cholesterols | Topical |
| Lanolin Nonionic Derivatives | Ophthalmic |
| Lanolin, Ethoxylated | Topical |
| Lanolin, Hydrogenated | Topical |
| Lauralkonium Chloride | Ophthalmic |
| Lauramine Oxide | Topical |
| Laurdimonium Hydrolyzed Animal Collagen | Topical |
| Laureth Sulfate | Topical |
| Laureth-2 | Topical |
| Laureth-23 | Topical |
| Laureth-4 | Topical |
| Laurie Diethanolamide | Topical |
| Lauric Myristic Diethanolamide | Topical |
| Lauroyl Sarcosine | Ophthalmic |
| Lauryl Lactate | Transdermal |
| Lauryl Sulfate | Topical |
| *Lavandula Angustifolia* Flowering Top | Topical |
| Lecithin | Inhalation; Intramuscular; Rectal; Topical; Transdermal; Vaginal |
| Lecithin Unbleached | Topical |
| Lecithin, Egg | Intravenous |
| Lecithin, Hydrogenated | Auricular (Otic) |
| Lecithin, Hydrogenated Soy | Inhalation; Intravenous |
| Lecithin, Soybean | Inhalation; Vaginal |
| Lemon Oil | Topical |
| Leucine | Infusion (IV) |
| Levulinic Acid | Transdermal |
| Lidofenin | Intravenous |
| Light Mineral Oil | Ophthalmic; Rectal; Topical; Vaginal; Transdermal |
| Light Mineral Oil (85 Ssu) | Topical |
| Limonene, (+/−)- | Topical |
| Lipocol Sc-15 | Topical |
| Lysine | Intramuscular (IM); Infusion (IV) |
| Lysine Acetate | Infusion (IV) |
| Lysine Monohydrate | Respiratory (Inhalation) |
| Magnesium Aluminum Silicate | Rectal; Topical; Vaginal |
| Magnesium Aluminum Silicate Hydrate | Rectal; Topical; Vaginal |
| Magnesium Chloride | Intramuscular; Intraocular; Intraperitoneal; Intravitreal; Infusion (IV); Ophthalmic; Subcutaneous |
| Magnesium Nitrate | Topical |
| Magnesium Stearate | Implantation; Intravitreal; Subcutaneous; Topical; Transmucosal; Vaginal |
| Maleic Acid | Intramuscular; Infusion (IV) |
| Mannitol | Intramuscular (IM); Infusion (IV); Subcutanous (SC); Intravenous; Ophthalmic; Parenteral; Respiratory (Inhalation); Submucosal; Topical; Transdermal |
| Maprofix | Topical |
| Mebrofenin | Intravenous |
| Medical Adhesive Modified S-15 | Transdermal |
| Medical Antiform A-F Emulsion | Topical |
| Medronate Disodium | Intravenous |
| Medronic Acid | Intravenous |
| Meglumine | Intra-arterial; Intra-articular; Intracardiac; Intradiscal; Intramuscular; Intrauterine; Intravascular; Intravenous; Infusion (IV); Periarticular; Ureteral; Urethral |
| Menthol | Detanl; Inhalation; Topical |
| Metacresol | Intramuscular (IM); Infusion (IV); Subcutanous (SC); Intradermal |
| Metaphosphoric Acid | Infusion (IV) |
| Methanesulfonic Acid | Intramuscular (IM); Infusion (IV); Subcutaneous (SC) |
| Methionine | Intramuscular; Intrathecal; Intravenous; Infusion (IV); Subcutaneous |
| Methyl Alcohol | Transdermal |
| Methyl Gluceth-10 | Topical |
| Methyl Gluceth-20 | Topical |
| Methyl Gluceth-20 Sesquistearate | Topical |
| Methyl Glucose Sesquistearate | Topical |

TABLE 4-continued

| Inactive Ingredients | |
|---|---|
| Inactive Ingredient | Route of Administration |
| Methyl Laurate | Transdermal |
| Methyl Pyrrolidone | Periodontal; Subcutaneous |
| Methyl Salicylate | Topical |
| Methyl Stearate | Topical; Vaginal |
| Methylboronic Acid | Intravenous |
| Methylcellulose (4000 Mpa.S) | Ophthalmic |
| Methylcelluloses | Intra-articular; Intralesional; Intramuscular; Intrasynovial; Nasal; Ophthalmic; Soft tissue; Topical |
| Methylchloroisothiazolinone | Topical |
| Methylene Blue | Intravenous |
| Methylisothiazolinone | Topical |
| Methylparaben | Infiltration (AN); Auricular (Otic); Caudal Block; Epidural; Intramuscular (IM); Infusion (IV); Subcutaneous (SC); Inhalation; Intra-arterial; Intra-articular; Intrabursal; Intradermal; Intralesional; Intrasynovial; Intravenous; Iontophoresis; Irrigation; Nasal; Nerve Block; Ophthalmic; Peridural; Rectal; Soft tissue; Topical; Ureteral; Urethral; Vaginal |
| Microcrystalline Wax | Topical; Vaginal |
| Mineral Oil | Auricular (Otic); Dental; Ophthalmic; Topical; Transdermal; Vaginal |
| Mono And Diglyceride | Topical |
| Monostearyl Citrate | Topical |
| Monothioglycerol | Infiltration (AN); Caudal Block; Epidural; Intramuscular (IM); Infusion (IV); Subcutanous (SC); Intravenous; Nerve Block |
| Multisterol Extract | Topical |
| Myristyl Alcohol | Topical |
| Myristyl Lactate | Topical |
| Myristyl-.Gamma.-Picolinium Chloride | Intra-articular; Intralesional; Intramuscular; Intrasynovial; Soft tissue |
| N-(Carbamoyl-Methoxy Peg-40)-1,2-Distearoyl-Cephalin Sodium | Intravenous |
| N,N-Dimethylacetamide | Intramuscular; Intravenous; Infusion (IV) |
| Niacinamide | Intramuscular; Infusion (IV); Intra-articular; Intralesional; Intrasynovial; Topical |
| Nioxime | Intravenous |
| Nitric Acid | Inhalation; Infusion (IV); Ophthalmic; Topical; Vaginal |
| Nitrogen | Infiltration (AN); Caudal Block; Dental; Epidural; Intramuscular; Infusion (IV); Subcutanous (SC); Inhalation; Intra-arterial; Intracavitary; Intramuscular (IM); Intrathecal; Intratumor; Intravascular; Intravenous; Intravesical; Irrigation; Nasal; Nerve Block; Ophthalmic; Parenteral; Submucosal; Topical; Transdermal |
| Nonoxynol Iodine | Topical |
| Nonoxynol-15 | Topical |
| Nonoxynol-9 | Ophthalmic; Topical |
| Norflurane | Inhalation; Nasal; Respiratory (Inhalation) |
| Oatmeal | Topical |
| Octadecene-1/Maleic Acid Copolymer | Topical |
| Octanoic Acid | Intravenous |
| Octisalate | Transdermal |
| Octoxynol-1 | Topical |
| Octoxynol-40 | Ophthalmic |
| Octoxynol-9 | Topical |
| Octyldodecanol | Topical; Transdermal; Vaginal |
| Octylphenol Polymethylene | Ophthalmic |
| Oleic Acid | Inhalation; Nasal; Respiratory (Inhalation); Topical; Transdermal |
| Oleth-10/Oleth-5 | Topical |
| Oleth-2 | Topical |
| Oleth-20 | Topical |
| Oleyl Alcohol | Topical; Transdermal |
| Oleyl Oleate | Topical; Transdermal |
| Olive Oil | Topical |
| Oxidronate Disodium | Intravenous |
| Oxyquinoline | Intravenous |
| Palm Kernel Oil | Rectal |
| Palmitamine Oxide | Topical |
| Parabens | Topical |
| Paraffin | Rectal; Topical |
| Paraffin, White Soft | Topical |
| Parfum Creme 45/3 | Topical |

TABLE 4-continued

| Inactive Ingredient | Route of Administration |
|---|---|
| Peanut Oil | Intramuscular; Intratracheal; Topical; Vaginal |
| Peanut Oil, Refined | Topical |
| Pectin | Dental; Topical |
| Peg 6-32 Stearate/Glycol Stearate | Topical; Vaginal |
| Peg Vegetable Oil | Intramuscular (IM); Infusion (IV); Subcutaneous (SC) |
| Peg-100 Stearate | Topical; Vaginal |
| Peg-12 Glyceryl Laurate | Topical |
| Peg-120 Glyceryl Stearate | Topical; Vaginal |
| Peg-120 Methyl Glucose Dioleate | Topical |
| Peg-15 Cocamine | Topical |
| Peg-150 Distearate | Topical |
| Peg-2 Stearate | Topical; Vaginal |
| Peg-20 Sorbitan Isostearate | Intramuscular |
| Peg-22 Methyl Ether/Dodecyl Glycol Copolymer | Topical |
| Peg-25 Propylene Glycol Stearate | Topical |
| Peg-4 Dilaurate | Topical |
| Peg-4 Laurate | Topical |
| Peg-40 Castor Oil | Intramuscular (IM); Subcutaneous (SC); Infusion (IV) |
| Peg-40 Sorbitan Diisostearate | Dental |
| Peg-45/Dodecyl Glycol Copolymer | Topical |
| Peg-5 Oleate | Topical; Vaginal |
| Peg-50 Stearate | Topical |
| Peg-54 Hydrogenated Castor Oil | Topical |
| Peg-6 Isostearate | Topical |
| Peg-60 Castor Oil | Infusion (IV) |
| Peg-60 Hydrogenated Castor Oil | Topical |
| Peg-7 Methyl Ether | Topical |
| Peg-75 Lanolin | Topical |
| Peg-8 Laurate | Topical |
| Peg-8 Stearate | Topical |
| Pegoxol 7 Stearate | Topical; Vaginal |
| Pentadecalactone | Transdermal |
| Pentaerythritol Cocoate | Topical |
| Pentasodium Pentetate | Intravenous |
| Pentetate Calcium Trisodium | Intrathecal; Intravenous; Infusion (IV) |
| Pentetic Acid | Intrathecal; Intravenous |
| Peppermint Oil | Dental; Topical |
| Perflutren | Intravenous |
| Perfume 25677 | Topical |
| Perfume Bouquet | Topical |
| Perfume E-1991 | Topical |
| Perfume Gd 5604 | Topical |
| Perfume Tana 90/42 Scba | Topical |
| Perfume W-1952-1 | Topical |
| Petrolatum | Auricular (Otic); Ophthalmic; Topical |
| Petrolatum, White | Auricular (Otic); Dental; Nasal; Ophthalmic; Rectal; Topical; Transdermal; Vaginal |
| Petroleum Distillates | Topical |
| Phenol | Intramuscular (IM); Infusion (IV); Subcutaneous (SC); Intra-articular; Intradermal; Intralesional; Intrasynovial; Intravenous; Soft tissue |
| Phenol, Liquefied | Intramuscular (IM); Infusion (IV); Subcutaneous (SC); Intravenous |
| Phenonip | Iontophoresis; Topical |
| Phenoxyethanol | Topical |
| Phenylalanine | Infusion (IV) |
| Phenylethyl Alcohol | Auricular (Otic); Nasal; Ophthalmic |
| Phenylmercuric Acetate | Ophthalmic; Topical; Vaginal |
| Phenylmercuric Nitrate | Intramuscular; Ophthalmic |
| Phosphatidyl Glycerol, Egg | Intravenous |
| Phospholipid | Infusion (IV) |
| Phospholipid, Egg | Intravenous; Infusion (IV) |
| Phospholipon 90 g | Vagianl |
| Phosphoric Acid | Intramuscular (IM); Infusion (IV); Subcutaneous (SC); Infiltration; Intra-articular; Intralesional; Intravenous; Ophthalmic; Soft tissue; Topical; Vaginal |
| Pine Needle Oil (Pinus Sylvestris) | Topical |
| Piperazine Hexahydrate | Vagianl |
| Plastibase-50 w | Dental; Topical |
| Polacrilin | Iontophoresis; Transdermal |
| Polidronium Chloride | Ophthalmic; Topical |
| Poloxamer 124 | Topical |

TABLE 4-continued

| Inactive Ingredients | |
|---|---|
| Inactive Ingredient | Route of Administration |
| Poloxamer 181 | Topical |
| Poloxamer 182 | Topical |
| Poloxamer 188 | Intravenous; Ophthalmic; Peridontal; Subcutaneous; Topical |
| Poloxamer 237 | Topical |
| Poloxamer 407 | Ophthalmic; Peridontal; Topical |
| Poly(Bis(P-Carboxyphenoxy)Propane Anhydride):Sebacic Acid | Implantation |
| Poly(Dimethylsiloxane/Methylvinylsiloxane/ Methylhydrogensiloxane) Dimethylvinyl Or Dimethylhydroxy Or Trimethyl Endblocked | Vagianl |
| Poly(Dl-Lactic-Co-Glycolic Acid), (50:50 | N/A |
| Poly(Dl-Lactic-Co-Glycolic Acid), Ethyl Ester Terminated, (50:50 | N/A |
| Polyacrylic Acid (250000 Mw) | Transdermal |
| Polybutene (1400 Mw) | Transdermal |
| Polycarbophil | Ophthalmic; Topical; Vaginal |
| Polyester | Transdermal; Vaginal |
| Polyester Polyamine Copolymer | Transdermal |
| Polyester Rayon | Transdermal |
| Polyethylene Glycol 1000 | Rectal; Respiratory (Inhalation); Topical; Vaginal |
| Polyethylene Glycol 1450 | Topical; Urethral |
| Polyethylene Glycol 1500 | Topical |
| Polyethylene Glycol 1540 | Dental; Rectal; Topical |
| Polyethylene Glycol 200 | Intramuscular; Topical |
| Polyethylene Glycol 300 | Intramuscular (IM); Infusion (IV); Intravenous; Ophthalmic; Topical |
| Polyethylene Glycol 300-1600 | Topical |
| Polyethylene Glycol 3350 | Intra-articular; Intralesional; Intramuscular; Intrasynovial; Nasal; Rectal; Soft tissue; Subcutaneous; Topical; Vaginal |
| Polyethylene Glycol 400 | Intramuscular (IM); Infusion (IV); Intravenous; Nasal; Ophthalmic; Rectal; Topical; Vaginal |
| Polyethylene Glycol 4000 | Intra-articular; Intralesional; Intramuscular; Intrasynovial; Rectal; Soft tissue; Topical; Vaginal |
| Polyethylene Glycol 540 | Topical |
| Polyethylene Glycol 600 | Intravenous; Topical |
| Polyethylene Glycol 6000 | Rectal; Topical; Vaginal |
| Polyethylene Glycol 8000 | Ophthalmic; Rectal; Topical; Vaginal |
| Polyethylene Glycol 900 | Topical |
| Polyethylene High Density Containing Ferric Oxide Black (<1%) | Intrauterine |
| Polyethylene Low Density Containing Barium Sulfate (20-24%) | Initrauterine |
| Polyethylene T | Initrauterine |
| Polyethylene Terephthalates | Transdermal |
| Polyglactin | Dental; Implantation; Intramuscular; Subcutaneous |
| Polyglyceryl-3 Oleate | Vagianl |
| Polyglyceryl-4 Oleate | Vagianl |
| Polyhydroxyethyl Methacrylate | Topical |
| Polyisobutylene | Topical; Transdermal |
| Polyisobutylene (1100000 Mw) | Topical; Transdermal |
| Polyisobutylene (35000 Mw) | Transdermal |
| Polyisobutylene 178-236 | Transdermal |
| Polyisobutylene 241-294 | Transdermal |
| Polyisobutylene 35-39 | Transdermal |
| Polyisobutylene Low Molecular Weight | Transdermal |
| Polyisobutylene Medium Molecular Weight | Transdermal |
| Polyisobutylene/Polybutene Adhesive | Transdermal |
| Polylactide | Intramuscular; Peridontal |
| Polyols | Dental |
| Polyoxyethylene - Polyoxypropylene 1800 | Ophthalmic; Topical |
| Polyoxyethylene Alcohols | Topical |
| Polyoxyethylene Fatty Acid Esters | Intramuscular (IM); Infusion (IV); Subcutaneous (SC); Topical |
| Polyoxyethylene Propylene | Topical |
| Polyoxyl 20 Cetostearyl Ether | Topical |
| Polyoxyl 35 Castor Oil | Intravesical; Infusion (IV); Ophthalmic |
| Polyoxyl 40 Hydrogenated Castor Oil | Dental; Ophthalmic; Topical |
| Polyoxyl 40 Stearate | Auricular (Otic); Dental; Ophthalmic; Topical |
| Polyoxyl 400 Stearate | Nasal; Topical |
| Polyoxyl 6 And Polyoxyl 32 Palmitostearate | Topical |
| Polyoxyl Distearate | Topical |
| Polyoxyl Glyceryl Stearate | Topical |
| Polyoxyl Lanolin | Topical |
| Polyoxyl Palmitate | Vagianl |

TABLE 4-continued

Inactive Ingredients

| Inactive Ingredient | Route of Administration |
|---|---|
| Polyoxyl Stearate | Auricular (Otic); Topical |
| Polypropylene | Intrauterine; Topical; Transdermal |
| Polypropylene Glycol | Intramuscular (IM); Infusion (IV); Ophthalmic |
| Polyquaternium-10 | Topical |
| Polyquaternium-7 (70/30 Acrylamide/Dadmac | N/A |
| Polysiloxane | Intravenous |
| Polysorbate 20 | Auricular (Otic); Intramuscular (IM); Subcutaneous (SC); Intravenous; Infusion (IV); Nasal; Ophthalmic; Topical; Vaginal |
| Polysorbate 40 | Intramuscular (IM); Infusion (IV); Topical |
| Polysorbate 60 | Ophthalmic; Rectal; Topical; Vaginal |
| Polysorbate 65 | Topical |
| Polysorbate 80 | Auricular (Otic); Intra-articular; Intrabursal; Intradermal; Intralesional; Intramuscular; Intrasynovial; Intravenous; Infusion (IV); Nasal; Ophthalmic; Rectal; Soft tissue; Subcutaneous; Topical; Vaginal |
| Polyurethane | Vagianl |
| Polyvinyl Acetate | Transdermal |
| Polyvinyl Alcohol | Auricular (Otic); Intramuscular; Intraocular; Intravitreal; Iontophoresis; Ophthalmic; Topical; Transdermal |
| Polyvinyl Chloride | Transdermal |
| Polyvinyl Chloride-Polyvinyl Acetate Copolymer | Transdermal |
| Polyvinylpyridine | Transdermal |
| Poppy Seed Oil | Intralymphatic; Intrauterine |
| Potash | Topical |
| Potassium Acetate | Ophthalmic; Rectal |
| Potassium Alum | Vagianl |
| Potassium Bicarbonate | Transmucosal |
| Potassium Bisulfite | Intravenous |
| Potassium Chloride | Infiltration (AN); Caudal Block; Epidural; Intraocular; Intravenous; Intravitreal; Infusion (IV); Nerve Block; Ophthalmic |
| Potassium Citrate | Topical |
| Potassium Hydroxide | Intravascular; Intravenous; Infusion (IV); Topical; Vaginal |
| Potassium Metabisulfite | Infiltration (AN); Auricular (Otic); Intramuscular (IM); Infusion (IV); Nerve Block; Rectal |
| Potassium Phosphate, Dibasic | Intra-articular; Intramuscular; Intravenous; Infusion (IV); Subcutaneous |
| Potassium Phosphate, Monobasic | Infiltration (AN); Auricular (Otic); Intramuscular (IM); Infusion (IV); Intra-articular; Intrauterine; Intravenous; Intravesical; Nasal; Nerve Block; Ophthalmic; Subcutaneous |
| Potassium Soap | Topical |
| Potassium Sorbate | Nasal; Ophthalmic; Topical |
| Povidone Acrylate Copolymer | Topical |
| Povidone Hydrogel | Iontophoresis; Topical |
| Povidone K17 | Subcutaneous |
| Povidone K25 | Respiratory (Inhalation) |
| Povidone K29/32 | Ophthalmic; Transdermal; Vaginal |
| Povidone K30 | Ophthalmic |
| Povidone K90 | Ophthalmic; Topical |
| Povidone K90f | Auricular (Otic) |
| Povidone/Eicosene Copolymer | Topical |
| Povidones | Auricular (Otic); Intramuscular; Intravenous; Infusion (IV); Ophthalmic; Subcutaneous; Topical; Transdermal; Vaginal |
| Ppg-12/Smdi Copolymer | Topical |
| Ppg-15 Stearyl Ether | Topical |
| Ppg-20 Methyl Glucose Ether Distearate | Topical |
| Ppg-26 Oleate | Topical |
| Product Wat | Topical |
| Proline | Infusion (IV) |
| Promulgen D | Topical; Vaginal |
| Promulgen G | Topical |
| Propane | Topical |
| Propellant A-46 | Topical |
| Propyl Gallate | Topical; Intramuscular |
| Propylene Carbonate | Topical |
| Propylene Glycol | Auricular (Otic); Dental; Extracorporeal; Intramuscular (IM); Infusion (IV); Inhalation; Intravenous; Nasal; Ophthalmic; Photopheresis; |

TABLE 4-continued

| Inactive Ingredient | Route of Administration |
|---|---|
| | Rectal; Subcutaneous; Topical; Transdermal; Vaginal |
| Propylene Glycol Diacetate | Auricular (Otic); Topical |
| Propylene Glycol Dicaprylate | Topical |
| Propylene Glycol Monolaurate | Transdermal |
| Propylene Glycol Monopalmitostearate | Topical; Vaginal |
| Propylene Glycol Palmitostearate | Topical |
| Propylene Glycol Ricinoleate | Topical |
| Propylene Glycol/Diazolidinyl Urea/Methylparaben/Propylparben | Topical |
| Propylparaben | Inflitration (AN); Auricular (Otic); Intramuscular (IM); Infusion (IV); Subcutaneous (SC); Inhalation; Intra-arterial; Intra-articular; Intrabursal; Intralesional; Intrasynovial; Intravenous; Nasal; Nerve Block; Ophthalmic; Rectal; Soft tissue; Topical; Ureteral; Urethral; Vaginal |
| Protamine Sulfate | Intramuscular (IM); Subcutaneous (SC); Intradermal |
| Protein Hydrolysate | Topical |
| Pvm/Ma Copolymer | Dental |
| Quaternium-15 | Topical |
| Quaternium-15 Cis-Form | Topical; Vaginal |
| Quaternium-52 | Topical |
| Ra-2397 | Transdermal |
| Ra-3011 | Transdermal |
| Saccharin | Inhalation; Topical |
| Saccharin Sodium | Dental; Intramuscular (IM); Infusion (IV); Inhalation; Intravenous; Rectal; Topical |
| Saccharin Sodium Anhydrous | Intramuscular (IM); Infusion (IV); Rectal |
| Safflower Oil | Topical |
| Sd Alcohol 3a | Topical |
| Sd Alcohol 40 | Topical |
| Sd Alcohol 40-2 | Topical |
| Sd Alcohol 40b | Topical |
| Sepineo P 600 | Topical |
| Serine | Infusion (IV) |
| Sesame Oil | Intramuscular (IM); Subcutaneous (SC) |
| Shea Butter | Topical |
| Silastic Brand Medical Grade Tubing | Implantation |
| Silastic Medical Adhesive, Silicone Type A | Implantation |
| Silica, Dental | Dental |
| Silicon | Topical; Transdermal |
| Silicon Dioxide | Dental; Topical; Vaginal |
| Silicon Dioxide, Colloidal | Endocervical; Rectal; Respiratory (Inhalation); Transdermal; Vaginal |
| Silicone | Intramuscular (IM); Infusion (IV); Intrauterine; Topical; Transdermal; Vaginal |
| Silicone Adhesive 4102 | Percutaneous; Transdermal |
| Silicone Adhesive 4502 | Transdermal |
| Silicone Adhesive Bio-Psa Q7-4201 | Transdermal; Topical |
| Silicone Adhesive Bio-Psa Q7-4301 | Transdermal; Topical |
| Silicone Emulsion | Topical |
| Silicone/Polyester Film Strip | Transdermal |
| Simethicone | Intramuscular (IM); Infusion (IV); Rectal; Topical |
| Simethicone Emulsion | Topical |
| Sipon Ls 20np | Topical |
| Soda Ash | Ophthalmic |
| Sodium Acetate | Auricular (Otic); Extracorporeal; Intramuscular (IM); Infusion (IV); Subcutaneous (SC); Interstitial; Intra-articular; Intracavitary; Intradermal; Intralesional; Intraocular; Intraperitoneal; Intrapleural; Intrasynovial; Intravenous; Intravitreal; Nasal; Ophthalmic; Parenteral; Phtotpheresis; Soft tissue; Submucosal; Topical |
| Sodium Acetate Anhydrous | Intramuscular (IM); Infusion (IV); Subcutaneous (SC); Intravenous; Topical |
| Sodium Alkyl Sulfate | Topical |
| Sodium Ascorbate | Intravenous |
| Sodium Benzoate | Dental; Intramuscular (IM); Infusion (IV); Intravenous; Rectal; Topical |
| Sodium Bicarbonate | Intramuscular (IM); Infusion (IV); Intraperitoneal; Intrathecal; Intratracheal; Intravenous; Intravitreal; Subcutaneous; Vaginal |
| Sodium Bisulfate | Intramuscular (IM); Infusion (IV); Subcutaneous (SC); Inhalation; Ophthalmic |
| Sodium Bisulfite | Inflitration (AN); Auricular (Otic); Intramuscular (IM); Infusion (IV); Subcutaneous (SC); Epidural; |

TABLE 4-continued

Inactive Ingredients

| Inactive Ingredient | Route of Administration |
| --- | --- |
| | Inhalation; Intra-arterial; Intra-articular; Intrabursal; Intracardiac; Intradermal; Intradiscal; Intralesional; Intraperitoneal; Intrasynovial; Iontophoresis; Irrigation; Intravenous; Nerve Block; Ophthalmic; soft tissue; Topical |
| Sodium Borate | Auricular (Otic); Ophthalmic; Topical |
| Sodium Borate Decahydrate | Ophthalmic |
| Sodium Carbonate | Infiltration (AN); Intramuscular (IM); Infusion (IV); Intra-arterial; Intraperitoneal; Intrapleural; Intratumor; Intravascular; Intravenous; Intravitreal; Nerve Block; Ophthalmic; Rectal |
| Sodium Carbonate Decahydrate | Intravenous |
| Sodium Carbonate Monohydrate | Intra-arterial; Intracardiac; Intravenous; Ophthalmic |
| Sodium Cetostearyl Sulfate | Topical |
| Sodium Chlorate | Infiltration (AN); Intramuscular; Infusion (IV); Nerve Block |
| Sodium Chloride | Infiltration; Inhalation; Intra-arterial; Intra-articular; Intrabursal; Intracardiac; Intracaudal; Intracavitary; Intradermal; Intralesional; Intramuscular; Intraocular; Intraperitoneal; Intrapleural; Intrasynovial; Intrathecal; Intratracheal; Intratumor; Intravascular; Intravenous; Intravenous bolus; Intravesical; Intravitreal; Iontophoresis; Infusion (IV); Intramuscular (IM); Subcutaneous (SC); Nasal; Nerve Block; Ophthalmic; Parenteral; Peridural; Photopheresis; Rectal; Respiratory (Inhalation); Soft tissue; Subarachnoid; Submucosal; Topical; Transermal |
| Sodium Chloride Injection | Intramuscular |
| Sodium Chloride Injection, Bacteriostatic | Intraveous |
| Sodium Cholesteryl Sulfate | Infusion (IV) |
| Sodium Citrate | Infiltration (AN); Auricular (Otic); Epidural; Intramuscular (IM); Infusion (IV); Subcutaneous (SC); Inhalation; Intra-arterial; Intra-articular; Intracardiac; Intravacitary; Intralesional; Intraocular; Iintraperitoneal; Intrapleural; Intrasynovial; Intrathecal; Intratracheal; Intrauterine; Intravasular; Intravenous; Iontophoresis; Irrigation; Nasal; Nerve Block; Ophthalmic; Rectal; Respiratory (Inhalation); Soft tissue; Topical; Transdermal; Ureteral; Vaginal |
| Sodium Cocoyl Sarcosinate | Topical |
| Sodium Desoxycholate | Infusion (IV) |
| Sodium Dithionite | Intramuscular (IM); Infusion (IV); Subcutaneous (SC); Intravenous |
| Sodium Dodecylbenzenesulfonate | Topical |
| Sodium Formaldehyde Sulfoxylate | Intramuscular (IM); Infusion (IV); Subcutaneous (SC); Topical |
| Sodium Gluconate | Intravenous; Infusion (IV) |
| Sodium Hydroxide | Intrathecal (AN, CNBLK); Inflitration (AN); Sympathetic (AN, NBLK); Auricular (Otic); Caudal Block; Dental; Epidural; Extracorporeal; Intramuscular (IM); Infusion (IV); Subcutaneous (SC); Inflitration; Inhalationi; Interstitial; Intra-amniotic; Intra-arterial; Intra-articular; Intrabursal; Intracardiac; Intracaudl; Intracavitary; Intradermal; Intradiscal; Intralesional; Intraocular; Intraperioneal; Intrapleural; Intraspinal; Intrasynovial; Intrathecal; Intratracheal; Intratumor; Intrauterine; Intravascular; Intravenous; Intravitreal; Iontophoresis; Irrigation; Nasal; Nerve Block; Ophthalmic; Parenteral; Perfusion, cardiac; Peridural; Perineural; Photopheresis; Rectal; Respiratory (Inhalation); Retrobular; Soft tissue; Spinal; Subarachnoid; Subconjunctival; Submucosal; Topical; Transdermal; Ureteral; Urethral; Vaginal |
| Sodium Hypochlorite | Infusion (IV) |
| Sodium Iodide | Intravenous; Topical |
| Sodium Lactate | Infiltration (AN); Caudal Black; Intramuscular (IM); Infusion (IV); Subcutaneous (SC); Intracardiac; Intraperitoneal; Intravenous; Nerve Block; Topical |
| Sodium Lactate, L- | Epidural; Intramuscular (IM); Infusion (IV); Subcutaneous (SC); Intracardiac; Nerve Block |
| Sodium Laureth-2 Sulfate | Topical |
| Sodium Laureth-3 Sulfate | Topical |
| Sodium Laureth-5 Sulfate | Topical |
| Sodium Lauroyl Sarcosinate | Topical |

TABLE 4-continued

Inactive Ingredients

| Inactive Ingredient | Route of Administration |
|---|---|
| Sodium Lauryl Sulfate | Dental; Respiratory (Inhalation); Topical; Vaginal |
| Sodium Lauryl Sulfoacetate | Topical |
| Sodium Metabisulfite | Intrathecal (AN, CNBLK); Infiltration (AN); Cardal Block; Dental; Epidural; Intramuscular (IM); Infusion (IV); Subcutaneous (SC); Inflitration; Inhalation; Intra-articular; Initrabursal; Intracardiac; Intramuscular; Intraperitoneal; Intravenous; Iontophoresis; Nerve Block; Ophthalmic; Peridural; Rectal; Submucosal; Topical; Vaginal |
| Sodium Nitrate | Ophthalmic |
| Sodium Phosphate | Intramuscular (IM); Infusion (IV); Intra-articular; Intrabursal; Intradermal; Intralesional; Nasal; Nerve Block; Ophthalmic; Soft tissue; Subcutanesou; Topical |
| Sodium Phosphate Dihydrate | Intramuscular (IM); Subcutaneous (SC); Ophthalmic |
| Sodium Phosphate, Dibasic | Intramuscular (IM); Infusion (IV); Intradermal; Intralesional; Intrasynovial; Intravenous; Nasal; Ophthalmic; Soft tissue; Topical; Subcutaneous (SC) |
| Sodium Phosphate, Dibasic, Anhydrous | Auricular (Otic); Intramuscular (IM); Infusion (IV); Subcutaneous (SC); Intra-articular; Intralesional; Intramuscular; Intravenous; Intravesical; Nasal; Ophthalmic; Topical; Vaginal |
| Sodium Phosphate, Dibasic, Dihydrate | Intramuscular (IM); Infusion (IV); Intravenous; Nasal; Ophthalmic; Subcutaneous; Topical |
| Sodium Phosphate, Dibasic, Dodecahydrate | Nasal |
| Sodium Phosphate, Dibasic, Heptahydrate | Infiltration (AN); Auricular (Otic); Intramuscular (IM); Infusion (IV); Subcutaneous (SC); Iintra-articular; Intrabursal; Intradermal; Intralesional; Intramuscular; Intrasynovial; Intravenous; Intravitreal; Nasal; Nerve Block; Ophthalmic; Soft tissue; Topical; Urethral |
| Sodium Phosphate, Monobasic | Intramuscular (IM); Infusion (IV); Intralesional; Intrasynovial; Iontophoresis; Ophthalmic; Soft tissue; Subcutaneous; Topical |
| Sodium Phosphate, Monobasic, Anhydrous | Auricular (Otic); Intramuscular (IM); Infusion (IV); Intrabursal; Intradermal; Intralesional; Intrasynovial; Intravascular; Intravenous; Intravesical; Nasal; Ophthalmic; Soft tissue; Subcutaneous; Topical; Vaginal |
| Sodium Phosphate, Monobasic, Dihydrate | Intravenous; Infusion (IV); Nasal; Ophthalmic; Subcutaneous; Topical |
| Sodium Phosphate, Monobasic, Monohydrate | Intramuscular (IM); Infusion (IV); Intra-articular; Intralesional; Intravascular; Intravenous; Intravitreal; Ophthalmic; Subcutaneous; Topical |
| Sodium Polyacrylate (2500000 Mw) | Topical |
| Sodium Pyrophosphate | Intravenous |
| Sodium Pyrrolidone Carboxylate | Topical |
| Sodium Starch Glycolate | Transmucosal |
| Sodium Succinate Hexahydrate | Intravenous |
| Sodium Sulfate | Intramuscular (IM); Infusion (IV); Ophthalmic |
| Sodium Sulfate Anhydrous | Inhalation; Iintramuscular; Ophthalmic |
| Sodium Sulfate Decahydrate | Ophthalmic |
| Sodium Sulfite | Auricular (Otic); Epidural; Intramuscular (IM); Infusion (IV); Inhalation; Intra-articular; Intralesional; Intravenous; Ophthalmic; Soft tissue; Subcutaneous; Topical |
| Sodium Sulfosuccinated Undecyclenic Monoalkylolamide | Topical |
| Sodium Tartrate | Intramuscual (IM); Infusion (IV); Intravenous |
| Sodium Thioglycolate | Subcutaneous |
| Sodium Thiomalate | Intramuscular (IM); Infusion (IV) |
| Sodium Thiosulfate | Intravenous; Ophthalmic; Topical |
| Sodium Thiosulfate Anhydrous | Intravenous |
| Sodium Trimetaphosphate | Intravenous |
| Sodium Xylenesulfonate | Topical |
| Somay 44 | Topical |
| Sorbic Acid | Ophthalmic; Topical; Vaginal |
| Sorbitan | Topical |
| Sorbitan Isostearate | Topical |
| Sorbitan Monolaurate | Ophthalmic; Topical |
| Sorbitan Monooleate | Rectal; Topical; Transdermal |
| Sorbitan Monopalmitate | Intramuscular; Topical |
| Sorbitan Monostearate | Topical; Vaginal |
| Sorbitan Sesquioleate | Rectal; Topical |
| Sorbitan Trioleate | Inhalation; Nasal |
| Sorbitan Tristearate | Topical |

TABLE 4-continued

Inactive Ingredients

| Inactive Ingredient | Route of Administration |
| --- | --- |
| Sorbitol | Dental; Intra-articular; Intralesional; Intramuscular; Intrasynovial; Intravenous; Infusion (IV); Nasal; Ophthalmic; Rectal; Topical; Vaginal |
| Sorbitol Solution | Intra-articular; Intralesional; Intramuscular; Intravenous; Infusion (IV); Nasal; Ophthalmic; Rectal; Topical; Vaginal |
| Soybean Flour | Topical |
| Soybean Oil | Intraveous; Infusion (IV); Topical |
| Spearmint Oil | Topical |
| Spermaceti | Topical; Vaginal |
| Squalane | Topical |
| Stabilized Oxychloro Complex | Ophthalmic |
| Stannous 2-Ethylhexanoate | Vagianl |
| Stannous Chloride | Intravenous; Infusion (IV) |
| Stannous Chloride Anhydrous | Intravenous; Infusion (IV) |
| Stannous Fluoride | Intravenous |
| Stannous Tartrate | Intravenous |
| Starch | Intramuscular; Rectal; Topical; Vaginal |
| Starch 1500, Pregelatinized | Vagianl |
| Starch, Corn | Vagianl |
| Stearalkonium Chloride | Topical |
| Stearalkonium Hectorite/Propylene Carbonate | Transdermal |
| Stearamidoethyl Diethylamine | Topical; Vaginal |
| Steareth-10 | Rectal; Topical |
| Steareth-100 | Topical |
| Steareth-2 | Topical |
| Steareth-20 | Topical |
| Steareth-21 | Topical |
| Steareth-40 | Topical; Rectal |
| Stearic Acid | Implantation; Subcutaneous; Topical; Vaginal |
| Stearic Diethanolamide | Topical |
| Stearoxytrimethylsilane | Topical |
| Steartrimonium Hydrolyzed Animal Collagen | Topical |
| Stearyl Alcohol | Topical; Vaginal |
| Sterile Water For Inhalation | Infusion (IV) |
| Styrene/Isoprene/Styrene Block Copolymer | Topical |
| Succimer | Intravenous |
| Succinic Acid | Intramuscular (IM); Infusion (IV); Intravenous |
| Sucralose | Nasa |
| Sucrose | Intramuscular; Intravenous; Infusion (IV); Rectal; Subcutaneous; Topical |
| Sucrose Distearate | Topical |
| Sucrose Polyesters | Topical |
| Sulfacetamide Sodium | Topical |
| Sulfobutylether.Beta.-Cyclodextrin | Intramuscular; Intravenous; Infusion (IV) |
| Sulfur Dioxide | Infusion (IV) |
| Sulfuric Acid | Auricular (Otic); Epidural; Intramuscular (IM); Infusion (IV); Inhalation; Intraperitoneal; Intravenous; Irrigation; Nasal; Ophthalmic; Respiratory (Inhalation); Topical |
| Sulfurous Acid | Intramuscular |
| Surfactol Qs | Topical |
| Tagatose, D- | Rectal |
| Talc | Topical |
| Tall Oil | Topical |
| Tallow Glycerides | Topical |
| Tartaric Acid | Intramuscular; Intravenous; Infusion (IV); Topical |
| Tartaric Acid, Dl- | Intramuscular (IM); Infusion (IV); Intravenous; Rectal; Vaginal |
| Tenox | Topical |
| Tenox-2 | Topical |
| Tert-Butyl Alcohol | Intravenous; Infusion (IV); Topical |
| Tert-Butyl Hydroperoxide | Topical |
| Tert-Butylhydroquinone | Vagianl |
| Tetrakis(2-Methoxyisobutylisocyanide)Copper(I) Tetrafluoroborate | Intravenous |
| Tetrapropyl Orthosilicate | Vagianl |
| Tetrofosmin | Infusion (IV) |
| Theophylline | Intravenous; Infusion (IV) |
| Thimerosal | Auricular (Otic); Intramuscular (IM); Infusion (IV); Subcutaneous (SC); Intravenous; Ophthalmic; Topical |

TABLE 4-continued

Inactive Ingredients

| Inactive Ingredient | Route of Administration |
|---|---|
| Threonine | Intravenous; Infusion (IV) |
| Thymol | Inhalation |
| Tin | Intravenous |
| Titanium Dioxide | Dental; Intrauterine; Ophthalmic; Respiratory (Inhalation); Topical; Transdermal |
| Tocopherol | Topical |
| Tocophersolan | Ophthalmic; Topical |
| Triacetin | Endocervical; Transdermal |
| Tricaprylin | Epidural; Infiltration |
| Trichloromonofluoromethane | Inhalation; Nasal; Topical |
| Trideceth-10 | Topical |
| Triethanolamine Lauryl Sulfate | Topical |
| Trifluoroacetic Acid | Infusion (IV) |
| Triglycerides, Medium Chain | Topical |
| Trihydroxystearin | Topical |
| Trilaneth-4 Phosphate | Topical |
| Trilaureth-4 Phosphate | Topical |
| Trisodium Citrate Dihydrate | Intramuscular (IM); Infusion (IV); Intravenous; Intravitreal; Nasal; Ophthalmic; Topical |
| Trisodium Hedta | Topical |
| Triton 720 | Ophthalmic |
| Triton X-200 | Topical |
| Trolamine | Rectal; Topical; Transdermal; Vaginal |
| Tromantadine | Intramuscular; Intravenous |
| Tromethamine | Intramuscular (IM); Infusion (IV); Intra-arterial; Intrathecal; Intratracheal; Intravasular; Intravenous; Ophthalmic; Rectal; Respiratory (Inhalation); Subcutaneous; Topical; Transdermal; Urethral |
| Tryptophan | Infusion (IV) |
| Tyloxapol | Ophthalmic; Topical |
| Tyrosine | Infusion (IV) |
| Undecylenic Acid | Topical |
| Union 76 Amsco-Res 6038 | Transdermal |
| Urea | Intramuscular; Vaginal |
| Valine | Infusion (IV) |
| Vegetable Oil | Topical |
| Vegetable Oil Glyceride, Hydrogenated | Rectal |
| Vegetable Oil, Hydrogenated | Rectal; Topical; Vaginal |
| Versetamide | Intravenous |
| Viscarin | Topical |
| Viscose/Cotton | Transdermal |
| Vitamin E | Topical |
| Wax, Emulsifying | Rectal; Topical |
| Wecobee Fs | Topical; Vaginal |
| White Ceresin Wax | Vagianl |
| White Wax | Rectal; Topical; Vaginal |
| Xanthan Gum | Rectal; Topical |
| Zinc | Subcutaneous |
| Zinc Acetate | Subcutaneous, Topical |
| Zinc Carbonate | Subcutaneous |
| Zinc Chloride | Intramuscular (IM); Subcutaneous (SC); Intradermal; Ophthalmic |
| Zinc Oxide | Intramuscular (IM); Subcutaneous (SC); Rectal; Respiratory (Inhalation) |

Delivery

The present disclosure encompasses the delivery of nucleic acid molecules, modified nucleic acid molecules or mmRNA for any of therapeutic, pharmaceutical, diagnostic or imaging by any appropriate route taking into consideration likely advances in the sciences of drug delivery. Delivery may be naked or formulated.

Naked Delivery

The nucleic acid molecules, modified nucleic acid molecules or mmRNA of the present invention may be delivered to a cell naked. As used herein in, "naked" refers to delivering nucleic acid molecules, modified nucleic acid molecules or mmRNA free from agents which promote transfection. For example, the nucleic acid molecules, modified nucleic acid molecules or mmRNA delivered to the cell may contain no modifications. The naked nucleic acid molecules, modified nucleic acid molecules or mmRNA may be delivered to the cell using routes of administration known in the art and described herein.

Formulated Delivery

The nucleic acid molecules, modified nucleic acid molecules or mmRNA of the present invention may be formulated, using the methods described herein. The formulations may contain nucleic acid molecules, modified nucleic acid molecules or mmRNA which may be modified and/or unmodified. The formulations may further include, but are not limited to, cell penetration agents, a pharmaceutically acceptable carrier, a delivery agent, a bioerodible or biocompatible polymer, a solvent, and a sustained-release delivery depot. The formulated nucleic acid molecules, modified nucleic acid molecules or mmRNA may be delivered to the cell using routes of administration known in the art and described herein.

The compositions may also be formulated for direct delivery to an organ or tissue in any of several ways in the art including, but not limited to, direct soaking or bathing, via a catheter, by gels, powder, ointments, creams, gels, lotions, and/or drops, by using substrates such as fabric or biodegradable materials coated or impregnated with the compositions, and the like.

Administration

The nucleic acid molecules, modified nucleic acid molecules or mmRNA of the present invention may be administered by any route which results in a therapeutically effective outcome. These include, but are not limited to, enteral (into the intestine), gastroenteral, epidural (into the dura mater), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intra-arterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), or in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intra-epidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aunts media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis and spinal. In specific embodiments, compositions may be administered in a way which allows them cross the blood-brain barrier, vascular barrier, or other epithelial barrier. As a non-limiting example, formulations of the nucleic acid molecules, modified nucleic acids and/or mmRNA described herein may be delivered by intramyocardial injection. As another non-limiting example, formulations of the nucleic acid molecules, modified nucleic acids and/or mmRNA described herein may be delivered by intramyocardial injection into the ischemic region prior to, during or after coronary artery ligation. As a non-limiting example, the nucleic acid molecules, modified nucleic acid molecules or mmRNA may be administered intramuscularly. As another non-limiting example, the nucleic acid molecules, modified nucleic acid molecules or mmRNA may be administered intravenously. As another non-limiting example, the nucleic acid molecules, modified nucleic acid molecules or mmRNA may be administered subcutaneously. As another non-limiting example, the nucleic acid molecules, modified nucleic acid molecules or mmRNA may be administered intradermally.

In one embodiment, a formulation for a route of administration may include at least one inactive ingredient. Non-limiting examples of routes of administration and inactive ingredients which may be included in formulations for the specific route of administration is shown in Table 5. In Table 5, "AN" means anesthetic, "CNBLK" means cervical nerve block, "NBLK" means nerve block, "IV" means intravenous, "IM" means intramuscular and "SC" means subcutaneous.

TABLE 5

Routes of Adminsitration and Inactive Ingredients

| Route of Administration | Inactive Ingredient |
| --- | --- |
| Intrathecal (AN, CNBLK) | Acetone Sodium Bisulfite; Citric Acid; Hydrochloric Acid; Sodium Chloride; Sodium Hydroxide; Sodium Metabisulfite |
| Infiltration (AN) | Acetic Acid; Acetone Sodium Bisulfite; Ascorbic Acid; Benzyl Alcohol; Calcium Chloride; Carbon Dioxide; Chlorobutanol; Citric Acid; Citric |

TABLE 5-continued

Routes of Adminsitration and Inactive Ingredients

| Route of Administration | Inactive Ingredient |
|---|---|
| | Acid Monohydrate; Edetate Calcium Disodium; Edetate Disodium; Hydrochloric Acid; Hydrochloric Acid, Diluted; Lactic Acid; Methylparaben; Monothioglycerol; Nitrogen; Potassium Chloride; Potassium Metabisulfite; Potassium Phosphate, Monobasic; Propylparaben; Sodium Bisulfite; Sodium Carbonate; Sodium Chlorate; Sodium Chloride; Sodium Citrate; Sodium Hydroxide; Sodium Lactate; Sodium Metabisulfite; Sodium Phosphate, Dibasic, Heptahydrate |
| Sympathetic NBLK (AN) | Hydrochloric Acid; Sodium Chloride; Sodium Hydroxide |
| Auricular (Otic) | Acetic Acid; Aluminum Acetate; Aluminum Sulfate Anhydrous; Benzalkonium Chloride; Benzethonium Chloride; Benzyl Alcohol; Boric Acid; Calcium Carbonate; Cetyl Alcohol; Chlorobutanol; Chloroxylenol; Citric Acid; Creatinine; Cupric Sulfate; Cupric Sulfate Anhydrous; Edetate Disodium; Edetic Acid; Glycerin; Glyceryl Stearate; Hydrochloric Acid; Hydrocortisone; Hydroxyethyl Cellulose; Isopropyl Myristate; Lactic Acid; Lecithin, Hydrogenated; Methylparaben; Mineral Oil; Petrolatum; Petrolatum, White; Phenylethyl Alcohol; Polyoxyl 40 Stearate; Polyoxyl Stearate; Polysorbate 20; Polysorbate 80; Polyvinyl Alcohol; Potassium Metabisulfite; Potassium Phosphate, Monobasic; Povidone K90f; Povidones; Propylene Glycol; Propylene Glycol Diacetate; Propylparaben; Sodium Acetate; Sodium Bisulfite; Sodium Borate; Sodium Chloride; Sodium Citrate; Sodium Hydroxide; Sodium Phosphate, Dibasic, Anhydrous; Sodium Phosphate, Dibasic, Heptahydrate; Sodium Phosphate, Monobasic, Anhydrous; Sodium Sulfite; Sulfuric Acid; Thimerosal |
| Caudal Block | Ascorbic Acid; Calcium Chloride; Citric Acid; Edetate Calcium Disodium; Edetate Disodium; Hydrochloric Acid; Methylparaben; Monothioglycerol; Nitrogen; Potassium Chloride; Sodium Chloride; Sodium Hydroxide; Sodium Lactate; Sodium Metabisulfite |
| Dental | Acetone Sodium Bisulfite; Alcohol; Alcohol, Dehydrated; Alcohol, Denatured; Anethole; Benzyl Alcohol; Carboxymethylcellulose Sodium; Carrageenan; D&C Yellow No. 10; Dimethicone Medical Fluid 360; Eucalyptol; Fd&C Blue No. 1; Fd&C Green No. 3; Flavor 89-186; Flavor 89-259; Flavor Df-119; Flavor Df-1530; Flavor Enhancer; Gelatin; Gelatin, Crosslinked; Glycerin; Glyceryl Stearate; High Density Polyethylene; Hydrocarbon Gel, Plasticized; Hydrochloric Acid; Menthol; Mineral Oil; Nitrogen; Pectin; Peg-40 Sorbitan Diisostearate; Peppermint Oil; Petrolatum, White; Plastibase-50w; Polyethylene Glycol 1540; Polyglactin; Polyols; Polyoxyl 40 Hydrogenated Castor Oil; Polyoxyl 40 Stearate; Propylene Glycol; Pvm/Ma Copolymer; Saccharin Sodium; Silica, Dental; Silicon Dioxide; Sodium Benzoate; Sodium Chloride; Sodium Hydroxide; Sodium Lauryl Sulfate; Sodium Metabisulfite; Sorbitol; Titanium Dioxide |
| Diagnostic | Hydrochloric Acid |
| Endocervical | Colloidal Silicon Dioxide; Triacetin |
| Epidural | 1,2-Dioleoyl-Sn-Glycero-3-Phosphocholine; 1,2-Dipalmitoyl-Sn-Glycero-3-(Phospho-Rac-(1-Glycerol)); Ascorbic Acid; Benzyl Alcohol; Calcium Chloride; Cholesterol; Citric Acid; Edetate Calcium Disodium; Edetate Disodium; Glyceryl Trioleate; Hydrochloric Acid; Isotonic Sodium Chloride Solution; Methylparaben; Monothioglycerol; Nitrogen; Potassium Chloride; Sodium Bisulfite; Sodium Chloride; Sodium Citrate; Sodium Hydroxide; Sodium Lactate, L-; Sodium Metabisulfite; Sodium Sulfite; Sulfuric Acid; Tricaprylin |
| Extracorporeal | Acetic Acid; Alcohol, Dehydrated; Benzyl Alcohol; Hydrochloric Acid; Propylene Glycol; Sodium Acetate; Sodium Chloride; Sodium Hydroxide |
| Intramuscular-Intravenous | Acetic Acid; Alcohol; Alcohol, Dehydrated; Alcohol, Diluted; Anhydrous Dextrose; Anhydrous Lactose; Anhydrous Trisodium Citrate; Arginine; Ascorbic Acid; Benzethonium Chloride; Benzoic Acid; Benzyl Alcohol; Calcium Chloride; Carbon Dioxide; Chlorobutanol; Citric Acid; Citric Acid Monohydrate; Creatinine; Dextrose; Edetate Calcium Disodium; Edetate Disodium; Edetate Sodium; Gluconolactone; Glycerin; Hydrochloric Acid; Hydrochloric Acid, Diluted; Lactic Acid; Lactic Acid, Dl-; Lactose; Lactose Monohydrate; Lactose, Hydrous; Lysine; Mannitol; Methylparaben; Monothioglycerol; Niacinamide; Nitrogen; Phenol; Phenol, Liquefied; Phosphoric Acid; Polyethylene Glycol 300; Polyethylene Glycol 400; Polypropylene Glycol; Polysorbate 40; Potassium Metabisulfite; Potassium Phosphate, Monobasic; Propylene Glycol; Propylparaben; Saccharin Sodium; Saccharin Sodium Anhydrous; Silicone; Simethicone; Sodium Acetate; Sodium Acetate Anhydrous; Sodium Benzoate; Sodium Bicarbonate; Sodium Bisulfate; Sodium Bisulfite; Sodium Carbonate; Sodium Chloride; Sodium Citrate; Sodium Formaldehyde Sulfoxylate; Sodium Hydroxide; Sodium Lactate, L-; Sodium Metabisulfite; Sodium Phosphate; Sodium Phosphate, Dibasic; Sodium Phosphate, Dibasic, Anhydrous; Sodium Phosphate, Dibasic, Dihydrate; Sodium Phosphate, Dibasic, Heptahydrate; Sodium Phosphate, Monobasic; Sodium |

TABLE 5-continued

Routes of Adminsitration and Inactive Ingredients

| Route of Administration | Inactive Ingredient |
|---|---|
| | Phosphate, Monobasic, Anhydrous; Sodium Phosphate, Monobasic, Monohydrate; Sodium Sulfate; Sodium Sulfite; Sodium Tartrate; Sodium Thiomalate; Succinic Acid; Sulfuric Acid; Tartaric Acid, Dl-; Thimerosal; Trisodium Citrate Dihydrate; Tromethamine |
| Intramuscular-Intravenous-Subcutaneous | Acetic Acid; Alcohol; Alcohol, Dehydrated; Benzyl Alcohol; Chlorobutanol; Citric Acid; Citric Acid Monohydrate; Citric Acid, Hydrous; Creatinine; Dextrose; Edetate Disodium; Edetate Sodium; Gelatin; Glycerin; Glycine; Hydrochloric Acid; Hydrochloric Acid, Diluted; Lactic Acid; Lactose; Lactose Monohydrate; Metacresol; Methanesulfonic Acid; Methylparaben; Monothioglycerol; Nitrogen; Phenol; Phosphoric Acid; Polyoxyethylene Fatty Acid Esters; Propylparaben; Sodium Acetate; Sodium Bisulfate; Sodium Bisulfite; Sodium Chloride; Sodium Citrate; Sodium Dithionite; Sodium Hydroxide; Sodium Lactate; Sodium Lactate, L-; Sodium Metabisulfite; Sodium Phosphate, Dibasic, Heptahydrate; Thimerosal |
| Intramuscular - Subcutaneous | Acetic Acid; Anhydrous Dextrose; Benzyl Alcohol; Chlorobutanol; Citric Acid; Cysteine; Edetate Disodium; Gelatin; Glycerin; Glycine; Hydrochloric Acid; Lactose Monohydrate; Mannitol; Metacresol; Methylparaben; Nitrogen; Peg Vegetable Oil; Peg-40 Castor Oil; Phenol; Phenol, Liquefied; Phosphoric Acid; Polyoxyethylene Fatty Acid Esters; Polysorbate 20; Propylparaben; Protamine Sulfate; Sesame Oil; Sodium Acetate; Sodium Acetate Anhydrous; Sodium Chloride; Sodium Citrate; Sodium Formaldehyde Sulfoxylate; Sodium Hydroxide; Sodium Phosphate Dihydrate; Sodium Phosphate, Dibasic, Heptahydrate; Sulfuric Acid; Thimerosal; Zinc Chloride; Zinc Oxide |
| Implantation | Acetone; Crospovidone; Dimethylsiloxane/Methylvinylsiloxane Copolymer; Ethylene Vinyl Acetate Copolymer; Magnesium Stearate; Poly(Bis(P-Carboxyphenoxy)Propane Anhydride): Sebacic Acid; Polyglactin; Silastic Brand Medical Grade Tubing; Silastic Medical Adhesive, Silicone Type A; Stearic Acid |
| Infiltration | Cholesterol; Citric Acid; Diethyl Pyrocarbonate; Dipalmitoylphosphatidylglycerol, Dl-; Hydrochloric Acid; Nitrogen; Phosphoric Acid; Sodium Chloride; Sodium Hydroxide; Sodium Metabisulfite; Tricaprylin |
| Inhalation | Acetone Sodium Bisulfite; Acetylcysteine; Alcohol; Alcohol, Dehydrated; Ammonia; Ascorbic Acid; Benzalkonium Chloride; Carbon Dioxide; Cetylpyridinium Chloride; Chlorobutanol; Citric Acid; D&C Yellow No. 10; Dichlorodifluoromethane; Dichlorotetrafluoroethane; Edetate Disodium; Edetate Sodium; Fd&C Yellow No. 6; Fluorochlorohydrocarbons; Glycerin; Hydrochloric Acid; Hydrochloric Acid, Diluted; Lactose; Lecithin; Lecithin, Hydrogenated Soy; Lecithin, Soybean; Menthol; Methylparaben; Nitric Acid; Nitrogen; Norflurane; Oleic Acid; Propylene Glycol; Propylparaben; Saccharin; Saccharin Sodium; Sodium Bisulfate; Sodium Bisulfite; Sodium Chloride; Sodium Citrate; Sodium Hydroxide; Sodium Metabisulfite; Sodium Sulfate Anhydrous; Sodium Sulfite; Sorbitan Trioleate; Sulfuric Acid; Thymol; Trichloromonofluoromethane |
| Interstitial | Benzyl Alcohol; Dextrose; Hydrochloric Acid; Sodium Acetate; Sodium Hydroxide |
| Intra-amniotic | Citric Acid; Edetate Disodium Anhydrous; Hydrochloric Acid; Sodium Hydroxide |
| Intra-arterial | Anhydrous Trisodium Citrate; Benzyl Alcohol; Carbon Dioxide; Citric Acid; Diatrizoic Acid; Edetate Calcium Disodium; Edetate Disodium; Hydrochloric Acid; Hydrochloric Acid, Diluted; Iodine; Meglumine; Methylparaben; Nitrogen; Propylparaben; Sodium Bisulfite; Sodium Carbonate; Sodium Carbonate Monohydrate; Sodium Chloride; Sodium Citrate; Sodium Hydroxide; Tromethamine |
| Intra-articular | Acetic Acid; Anhydrous Trisodium Citrate; Benzalkonium Chloride; Benzyl Alcohol; Carboxymethylcellulose; Carboxymethylcellulose Sodium; Cellulose, Microcrystalline; Citric Acid; Creatine; Creatinine; Crospovidone; Diatrizoic Acid; Edetate Calcium Disodium; Edetate Disodium; Hyaluronate Sodium; Hydrochloric Acid; Iodine; Meglumine; Methylcelluloses; Methylparaben; Myristyl-.Gamma.-Picolinium Chloride; Niacinamide; Phenol; Phosphoric Acid; Polyethylene Glycol 3350; Polyethylene Glycol 4000; Polysorbate 80; Potassium Phosphate, Dibasic; Potassium Phosphate, Monobasic; Propylparaben; Sodium Acetate; Sodium Bisulfite; Sodium Chloride; Sodium Citrate; Sodium Hydroxide; Sodium Metabisulfite; Sodium Phosphate; Sodium Phosphate, Dibasic, Anhydrous; Sodium Phosphate, Dibasic, Heptahydrate; Sodium Phosphate, Monobasic, Anhydrous; Sodium Phosphate, Monobasic, Monohydrate; Sodium Sulfite; Sorbitol; Sorbitol Solution |
| Intrabursal | Anhydrous Trisodium Citrate; Benzalkonium Chloride; Benzyl Alcohol; Carboxymethylcellulose; Carboxymethylcellulose Sodium; Citric Acid; Creatinine; Edetate Disodium; Hydrochloric Acid; Methylparaben; Polysorbate 80; Propylparaben; Sodium Bisulfite; Sodium Chloride; |

TABLE 5-continued

Routes of Adminsitration and Inactive Ingredients

| Route of Administration | Inactive Ingredient |
|---|---|
| | Sodium Hydroxide; Sodium Metabisulfite; Sodium Phosphate; Sodium Phosphate, Dibasic, Heptahydrate; Sodium Phosphate, Monobasic, Anhydrous |
| Intracardiac | Carbon Dioxide; Citric Acid; Citric Acid Monohydrate; Diatrizoic Acid; Edetate Calcium Disodium; Edetate Disodium; Hydrochloric Acid; Iodine; Lactic Acid; Meglumine; Sodium Bisulfite; Sodium Carbonate Monohydrate; Sodium Chloride; Sodium Citrate; Sodium Hydroxide; Sodium Lactate; Sodium Lactate, L-; Sodium Metabisulfite |
| Intracaudal | Hydrochloric Acid; Sodium Chloride; Sodium Hydroxide |
| Intracavitary | Alcohol, Dehydrated; Alfadex; Anhydrous Lactose; Benzyl Alcohol; Dextrose; Hydrochloric Acid; Lactose; Lactose Monohydrate; Nitrogen; Sodium Acetate; Sodium Chloride; Sodium Citrate; Sodium Hydroxide |
| Intradermal | Benzalkonium Chloride; Benzyl Alcohol; Carboxymethylcellulose Sodium; Creatinine; Edetate Disodium; Glycerin; Hydrochloric Acid; Metacresol; Methylparaben; Phenol; Polysorbate 80; Protamine Sulfate; Sodium Acetate; Sodium Bisulfite; Sodium Chloride; Sodium Hydroxide; Sodium Phosphate; Sodium Phosphate, Dibasic; Sodium Phosphate, Dibasic, Heptahydrate; Sodium Phosphate, Monobasic, Anhydrous; Zinc Chloride |
| Intradiscal | Cysteine Hydrochloride Anhydrous; Cysteine, Dl-; Diatrizoic Acid; Edetate Calcium Disodium; Edetate Disodium; Iodine; Meglumine; Sodium Bisulfite; Sodium Hydroxide |
| Intralesional | Acetic Acid; Benzalkonium Chloride; Benzyl Alcohol; Carboxymethylcellulose; Carboxymethylcellulose Sodium; Citric Acid; Creatine; Creatinine; Edetate Disodium; Hydrochloric Acid; Methylcelluloses; Methylparaben; Myristyl-.Gamma.-Picolinium Chloride; Niacinamide; Phenol; Phosphoric Acid; Polyethylene Glycol 3350; Polyethylene Glycol 4000; Polysorbate 80; Propylparaben; Sodium Acetate; Sodium Bisulfite; Sodium Chloride; Sodium Citrate; Sodium Hydroxide; Sodium Phosphate; Sodium Phosphate, Dibasic; Sodium Phosphate, Dibasic, Anhydrous; Sodium Phosphate, Dibasic, Heptahydrate; Sodium Phosphate, Monobasic; Sodium Phosphate, Monobasic, Anhydrous; Sodium Phosphate, Monobasic, Monohydrate; Sodium Sulfite; Sorbitol; Sorbitol Solution |
| Intralymphatic | Poppy Seed Oil |
| Intramuscular | Acetic Acid; Activated Charcoal; Adipic Acid; Alcohol; Alcohol, Dehydrated; Ammonium Acetate; Anhydrous Dextrose; Ascorbic Acid; Benzalkonium Chloride; Benzethonium Chloride; Benzoic Acid; Benzyl Alcohol; Benzyl Benzoate; Butylated Hydroxyanisole; Butylated Hydroxytoluene; Butylparaben; Calcium; Calcium Chloride; Carbon Dioxide; Carboxymethylcellulose; Carboxymethylcellulose Sodium; Castor Oil; Cellulose, Microcrystalline; Chlorobutanol; Chlorobutanol Hemihydrate; Chlorobutanol, Anhydrous; Citric Acid; Citric Acid Monohydrate; Corn Oil; Cottonseed Oil; Creatine; Creatinine; Croscarmellose Sodium; Crospovidone; Dextrose; Diatrizoic Acid; Docusate Sodium; Edetate Calcium Disodium; Edetate Disodium; Edetate Disodium Anhydrous; Edetate Sodium; Ethyl Acetate; Gelatin; Glutathione; Glycerin; Glycine; Hyaluronate Sodium; Hydrochloric Acid; Hydroxide Ion; Lactic Acid; Lactic Acid, Dl-; Lactose; Lactose Monohydrate; Lactose, Hydrous; Lecithin; Magnesium Chloride; Maleic Acid; Mannitol; Meglumine; Metacresol; Methionine; Methylcelluloses; Methylparaben; Monothioglycerol; Myristyl-.Gamma.-Picolinium Chloride; N,N-Dimethylacetamide; Niacinamide; Nitrogen; Peanut Oil; Peg-20 Sorbitan Isostearate; Phenol; Phenylmercuric Nitrate; Phosphoric Acid; Polyethylene Glycol 200; Polyethylene Glycol 300; Polyethylene Glycol 3350; Polyethylene Glycol 4000; Polyglactin; Polylactide; Polysorbate 20; Polysorbate 40; Polysorbate 80; Polyvinyl Alcohol; Potassium Phosphate, Dibasic; Potassium Phosphate, Monobasic; Povidones; Propyl Gallate; Propylene Glycol; Propylparaben; Saccharin Sodium; Saccharin Sodium Anhydrous; Sesame Oil; Sodium Acetate; Sodium Acetate Anhydrous; Sodium Benzoate; Sodium Bicarbonate; Sodium Bisulfite; Sodium Carbonate; Sodium Chlorate; Sodium Chloride; Sodium Chloride Injection; Sodium Citrate; Sodium Formaldehyde Sulfoxylate; Sodium Hydroxide; Sodium Metabisulfite; Sodium Phosphate; Sodium Phosphate, Dibasic; Sodium Phosphate, Dibasic, Anhydrous; Sodium Phosphate, Dibasic, Heptahydrate; Sodium Phosphate, Monobasic; Sodium Phosphate, Monobasic, Anhydrous; Sodium Phosphate, Monobasic, Monohydrate; Sodium Sulfate Anhydrous; Sodium Sulfite; Sodium Tartrate; Sorbitan Monopalmitate; Sorbitol; Sorbitol Solution; Starch; Sucrose; Sulfobutylether .Beta.-Cyclodextrin; Sulfuric Acid; Sulfurous Acid; Tartaric Acid; Thimerosal; Tromantadine; Tromethamine; Urea |
| Intraocular | Benzalkonium Chloride; Calcium Chloride; Citric Acid Monohydrate; Hydrochloric Acid; Magnesium Chloride; Polyvinyl Alcohol; Potassium Chloride; Sodium Acetate; Sodium Chloride; Sodium Citrate; Sodium Hydroxide |

TABLE 5-continued

Routes of Adminsitration and Inactive Ingredients

| Route of Administration | Inactive Ingredient |
| --- | --- |
| Intraperitoneal | Benzyl Alcohol; Calcium Chloride; Dextrose; Edetate Calcium Disodium; Hydrochloric Acid; Magnesium Chloride; Sodium Acetate; Sodium Bicarbonate; Sodium Bisulfite; Sodium Carbonate; Sodium Chloride; Sodium Citrate; Sodium Hydroxide; Sodium Lactate; Sodium Metabisulfite; Sulfuric Acid |
| Intrapleural | Benzyl Alcohol; Citric Acid; Dextrose; Dichlorodifluoromethane; Hydrochloric Acid; Sodium Acetate; Sodium Carbonate; Sodium Chloride; Sodium Citrate; Sodium Hydroxide |
| Intraspinal | Dextrose; Hydrochloric Acid; Sodium Hydroxide |
| Intrasynovial | Acetic Acid; Benzyl Alcohol; Carboxymethylcellulose Sodium; Citric Acid; Creatinine; Edetate Disodium; Hydrochloric Acid; Methylcelluloses; Methylparaben; Myristyl-.Gamma.-Picolinium Chloride; Niacinamide; Phenol; Polyethylene Glycol 3350; Polyethylene Glycol 4000; Polysorbate 80; Propylparaben; Sodium Acetate; Sodium Bisulfite; Sodium Chloride; Sodium Citrate; Sodium Hydroxide; Sodium Phosphate, Dibasic; Sodium Phosphate, Dibasic, Heptahydrate; Sodium Phosphate, Monobasic; Sodium Phosphate, Monobasic, Anhydrous; Sorbitol |
| Intrathecal | Benzyl Alcohol; Carbon Dioxide; Citric Acid; Edetate Calcium Disodium; Hydrochloric Acid; Methionine; Nitrogen; Pentetate Calcium Trisodium; Pentetic Acid; Sodium Bicarbonate; Sodium Chloride; Sodium Citrate; Sodium Hydroxide; Sulfuric Acid; Tromethamine |
| Intratracheal | Acetic Acid; Benzyl Alcohol; Carboxymethylcellulose Sodium; Hydrochloric Acid; Isotonic Sodium Chloride Solution; Peanut Oil; Sodium Bicarbonate; Sodium Chloride; Sodium Citrate; Sodium Hydroxide; Tromethamine |
| Intratumor | Benzyl Alcohol; Hydrochloric Acid; Nitrogen; Sodium Carbonate; Sodium Chloride; Sodium Hydroxide |
| Intrauterine | Barium Sulfate; Crospovidone; Diatrizoic Acid; Dimethylsiloxane/Methylvinylsiloxane Copolymer; Edetate Calcium Disodium; Edetate Disodium; Ethylene Vinyl Acetate Copolymer; High Density Polyethylene; Meglumine; Polyethylene High Density Containing Ferric Oxide Black (<1%); Polyethylene Low Density Containing Barium Sulfate (20-24%); Polyethylene T; Polypropylene; Poppy Seed Oil; Potassium Phosphate, Monobasic; Silicone; Sodium Citrate; Sodium Hydroxide; Titanium Dioxide |
| Intravascular | Alcohol; Alcohol, Dehydrated; Calcium Chloride; Carbon Dioxide; Citric Acid; Diatrizoic Acid; Edetate Calcium Disodium; Edetate Disodium; Hydrochloric Acid; Hydrochloric Acid, Diluted; Iodine; Meglumine; Nitrogen; Potassium Hydroxide; Sodium Carbonate; Sodium Chloride; Sodium Citrate; Sodium Hydroxide; Sodium Phosphate, Monobasic, Anhydrous; Sodium Phosphate, Monobasic, Monohydrate; Tromethamine |
| Intravenous | Alpha-Tocopherol; Alpha-Tocopherol, Dl-; 1,2-Dimyristoyl-Sn-Glycero-3-Phosphocholine; 1,2-Distearoyl-Sn-Glycero-3-(Phospho-Rac-(1-Glycerol)); 1,2-Distearoyl-Sn-Glycero-3-Phosphocholine; Acetic Acid; Acetic Acid, Glacial; Acetic Anhydride; Acetylated Monoglycerides; Acetyltryptophan, Dl-; Activated Charcoal; Albumin Aggregated; Albumin Colloidal; Albumin Human; Alcohol; Alcohol, Dehydrated; Alcohol, Denatured; Ammonium Acetate; Ammonium Hydroxide; Ammonium Sulfate; Anhydrous Citric Acid; Anhydrous Dextrose; Anhydrous Lactose; Anhydrous Trisodium Citrate; Arginine; Ascorbic Acid; Benzenesulfonic Acid; Benzethonium Chloride; Benzoic Acid; Benzyl Alcohol; Benzyl Chloride; Bibapcitide; Boric Acid; Butylated Hydroxytoluene; Calcium Chloride; Calcium Gluceptate; Calcium Hydroxide; Calcobutrol; Caldiamide Sodium; Caloxetate Trisodium; Calteridol Calcium; Captisol; Carbon Dioxide; Cellulose, Microcrystalline; Chlorobutanol; Chlorobutanol Hemihydrate; Chlorobutanol, Anhydrous; Cholesterol; Citrate; Citric Acid; Citric Acid Monohydrate; Citric Acid, Hydrous; Cysteine; Cysteine Hydrochloride; Dalfampridine; Dextran; Dextran 40; Dextrose; Dextrose Monohydrate; Dextrose Solution; Diatrizoic Acid; Dimethicone Medical Fluid 360; Edetate Calcium Disodium; Edetate Disodium; Edetate Disodium Anhydrous; Egg Phospholipids; Ethanolamine Hydrochloride; Ethylenediamine; Exametazime; Ferric Chloride; Gadolinium Oxide; Gamma Cyclodextrin; Gelatin; Gentisic Acid; Gluceptate Sodium; Gluceptate Sodium Dihydrate; Gluconolactone; Glucuronic Acid; Glycerin; Glycine; Guanidine Hydrochloride; Hetastarch; Histidine; Human Albumin Microspheres; Hydrochloric Acid; Hydrochloric Acid, Diluted; Hydroxyethylpiperazine Ethane Sulfonic Acid; Hydroxypropyl-Bcyclodextrin; Iodine; Iodoxamic Acid; Iofetamine Hydrochloride; Isopropyl Alcohol; Isotonic Sodium Chloride Solution; Lactic Acid; Lactic Acid, Dl-; Lactic Acid, L-; Lactobionic Acid; Lactose; Lactose Monohydrate; Lactose, Hydrous; Lecithin, Egg; Lecithin, Hydrogenated Soy; Lidofenin; Mannitol; Mebrofenin; Medronate Disodium; Medronic Acid; Meglumine; Methionine; Methylboronic Acid; Methylene Blue; |

TABLE 5-continued

Routes of Adminsitration and Inactive Ingredients

| Route of Administration | Inactive Ingredient |
|---|---|
| | Methylparaben; Monothioglycerol; N-(Carbamoyl-Methoxy Peg-40)-1,2-Distearoyl-Cephalin Sodium; N,N-Dimethylacetamide; Nioxime; Nitrogen; Octanoic Acid; Oxidronate Disodium; Oxyquinoline; Pentasodium Pentetate; Pentetate Calcium Trisodium; Pentetic Acid; Perflutren; Phenol; Phenol, Liquefied; Phosphatidyl Glycerol, Egg; Phospholipid, Egg; Phosphoric Acid; Poloxamer 188; Polyethylene Glycol 300; Polyethylene Glycol 400; Polyethylene Glycol 600; Polysiloxane; Polysorbate 20; Polysorbate 80; Potassium Bisulfite; Potassium Chloride; Potassium Hydroxide; Potassium Metabisulfite; Potassium Phosphate, Dibasic; Potassium Phosphate, Monobasic; Povidones; Propylene Glycol; Propylparaben; Saccharin Sodium; Sodium Acetate; Sodium Acetate Anhydrous; Sodium Ascorbate; Sodium Benzoate; Sodium Bicarbonate; Sodium Bisulfite; Sodium Carbonate; Sodium Carbonate Decahydrate; Sodium Carbonate Monohydrate; Sodium Chloride; Sodium Chloride Injection, Bacteriostatic; Sodium Citrate; Sodium Dithionite; Sodium Gluconate; Sodium Hydroxide; Sodium Iodide; Sodium Lactate; Sodium Metabisulfite; Sodium Phosphate; Sodium Phosphate, Dibasic; Sodium Phosphate, Dibasic, Anhydrous; Sodium Phosphate, Dibasic, Dihydrate; Sodium Phosphate, Dibasic, Heptahydrate; Sodium Phosphate, Monobasic, Anhydrous; Sodium Phosphate, Monobasic, Dihydrate; Sodium Phosphate, Monobasic, Monohydrate; Sodium Pyrophosphate; Sodium Succinate Hexahydrate; Sodium Sulfite; Sodium Tartrate; Sodium Thiosulfate; Sodium Thiosulfate Anhydrous; Sodium Trimetaphosphate; Sorbitol; Sorbitol Solution; Soybean Oil; Stannous Chloride; Stannous Chloride Anhydrous; Stannous Fluoride; Stannous Tartrate; Succimer; Succinic Acid; Sucrose; Sulfobutylether .Beta.-Cyclodextrin; Sulfuric Acid; Tartaric Acid; Tartaric Acid, Dl-; Tert-Butyl Alcohol; Tetrakis(2-Methoxyisobutylisocyanide)Copper(I) Tetrafluoroborate; Theophylline; Thimerosal; Threonine; Tin; Trisodium Citrate Dihydrate; Tromantadine; Tromethamine; Versetamide |
| Intravenous Bolus | Sodium Chloride |
| Intravesical | Alcohol, Dehydrated; Edetate Calcium Disodium; Hydrochloric Acid; Nitrogen; Polyoxyl 35 Castor Oil; Potassium Phosphate, Monobasic; Sodium Chloride; Sodium Hydroxide; Sodium Phosphate, Dibasic, Anhydrous; Sodium Phosphate, Monobasic, Anhydrous |
| Intravitreal | Calcium Chloride; Carboxymethylcellulose Sodium; Cellulose, Microcrystalline; Hyaluronate Sodium; Hydrochloric Acid; Magnesium Chloride; Magnesium Stearate; Polysorbate 80; Polyvinyl Alcohol; Potassium Chloride; Sodium Acetate; Sodium Bicarbonate; Sodium Carbonate; Sodium Chloride; Sodium Hydroxide; Sodium Phosphate, Dibasic, Heptahydrate; Sodium Phosphate, Monobasic, Monohydrate; Trisodium Citrate Dihydrate |
| Iontophoresis | Cetylpyridinium Chloride; Citric Acid; Edetate Disodium; Glycerin; Hydrochloric Acid; Methylparaben; Phenonip; Polacrilin; Polyvinyl Alcohol; Povidone Hydrogel; Sodium Bisulfite; Sodium Chloride; Sodium Citrate; Sodium Hydroxide; Sodium Metabisulfite; Sodium Phosphate, Monobasic |
| Irrigation | Acetic Acid; Activated Charcoal; Benzoic Acid; Hydrochloric Acid; Hypromelloses; Methylparaben; Nitrogen; Sodium Bisulfite; Sodium Citrate; Sodium Hydroxide; Sulfuric Acid |
| Intravenous - Subcutaneous | Acetic Acid; Alcohol; Benzyl Alcohol; Calcium Hydroxide; Chlorobutanol; Glycerin; Hydrochloric Acid; Lactose Monohydrate; Methylparaben; Nitrogen; Phenol; Phenol, Liquefied; Phosphoric Acid; Propylparaben; Sodium Acetate; Sodium Carbonate; Sodium Chloride; Sodium Hydroxide |
| Intravenous (Infusion) | 1,2-Dimyristoyl-Sn-Glycero-3-(Phospho-S-(1-Glycerol)); 1,2-Dimyristoyl-Sn-Glycero-3-Phosphocholine; Acetic Acid; Acetic Acid, Glacial; Activated Charcoal; Alanine; Albumin Human; Alcohol; Alcohol, Dehydrated; Ammonium Acetate; Anhydrous Citric Acid; Anhydrous Dextrose; Anhydrous Lactose; Anhydrous Trisodium Citrate; Arginine; Ascorbic Acid; Aspartic Acid; Benzenesulfonic Acid; Benzethonium Chloride; Benzoic Acid; Benzyl Alcohol; Brocrinat; Butylated Hydroxyanisole; Butylated Hydroxytoluene; Carbon Dioxide; Chlorobutanol; Citric Acid; Citric Acid Monohydrate; Citric Acid, Hydrous; Cysteine; Cysteine Hydrochloride; Deoxycholic Acid; Dextrose; Dextrose Solution; Diatrizoic Acid; Diethanolamine; Dimethyl Sulfoxide; Disodium Sulfosalicylate; Disofenin; Edetate Calcium Disodium; Edetate Disodium; Edetate Disodium Anhydrous; Edetate Sodium; Egg Phospholipids; Ethylenediamine; Fructose; Gelatin; Gentisic Acid Ethanolamide; Glycerin; Glycine; Histidine; Hydrochloric Acid; Hydrochloric Acid, Diluted; Hydroxide Ion; Hydroxypropyl-Bcyclodextrin; Isoleucine; Isotonic Sodium Chloride Solution; Lactic Acid; Lactic Acid, Dl-; Lactobionic Acid; Lactose; Lactose Monohydrate; Lactose, Hydrous; Leucine; Lysine; Lysine Acetate; Magnesium Chloride; Maleic Acid; Mannitol; Meglumine; Metacresol; |

TABLE 5-continued

Routes of Adminsitration and Inactive Ingredients

| Route of Administration | Inactive Ingredient |
|---|---|
| | Metaphosphoric Acid; Methanesulfonic Acid; Methionine; Methylparaben; Monothioglycerol; N,N-Dimethylacetamide; Nitric Acid; Nitrogen; Peg Vegetable Oil; Peg-40 Castor Oil; Peg-60 Castor Oil; Pentetate Calcium Trisodium; Phenol; Phenylalanine; Phospholipid; Phospholipid, Egg; Phosphoric Acid; Polyethylene Glycol 300; Polyethylene Glycol 400; Polyoxyl 35 Castor Oil; Polysorbate 20; Polysorbate 80; Potassium Chloride; Potassium Hydroxide; Potassium Metabisulfite; Potassium Phosphate, Dibasic; Potassium Phosphate, Monobasic; Povidones; Proline; Propylene Glycol; Propylparaben; Saccharin Sodium; Saccharin Sodium Anhydrous; Serine; Sodium Acetate; Sodium Acetate Anhydrous; Sodium Benzoate; Sodium Bicarbonate; Sodium Bisulfite; Sodium Carbonate; Sodium Chlorate; Sodium Chloride; Sodium Cholesteryl Sulfate; Sodium Citrate; Sodium Desoxycholate; Sodium Dithionite; Sodium Formaldehyde Sulfoxylate; Sodium Gluconate; Sodium Hydroxide; Sodium Hypochlorite; Sodium Lactate; Sodium Lactate, L-; Sodium Metabisulfite; Sodium Phosphate; Sodium Phosphate, Dibasic; Sodium Phosphate, Dibasic, Anhydrous; Sodium Phosphate, Dibasic, Dihydrate; Sodium Phosphate, Dibasic, Heptahydrate; Sodium Phosphate, Monobasic; Sodium Phosphate, Monobasic, Anhydrous; Sodium Phosphate, Monobasic, Dihydrate; Sodium Phosphate, Monobasic, Monohydrate; Sodium Sulfite; Sodium Tartrate; Sorbitol; Sorbitol Solution; Soybean Oil; Stannous Chloride; Stannous Chloride Anhydrous; Sterile Water For Inhalation; Sucrose; Sulfobutylether .Beta.-Cyclodextrin; Sulfur Dioxide; Sulfuric Acid; Tartaric Acid; Tartaric Acid, Dl-; Tert-Butyl Alcohol; Tetrofosmin; Theophylline; Threonine; Trifluoroacetic Acid; Trisodium Citrate Dihydrate; Tromethamine; Tryptophan; Tyrosine; Valine |
| Any Delivery Route | Alcohol; Benzyl Alcohol; Citric Acid Monohydrate; Gelfoam Sponge; Hydrochloric Acid; Methylparaben; Poly(Dl-Lactic-Co-Glycolic Acid), (50:50; Poly(Dl-Lactic-Co-Glycolic Acid), Ethyl Ester Terminated, (50:50; Polyquaternium-7 (70/30 Acrylamide/Dadmac; Propylene Glycol; Propylparaben; Sodium Chloride; Sodium Citrate; Sodium Hydroxide; Sodium Lactate; Sodium Phosphate, Monobasic, Monohydrate |
| Nasal | Acetic Acid; Alcohol, Dehydrated; Allyl .Alpha.-Ionone; Anhydrous Dextrose; Anhydrous Trisodium Citrate; Benzalkonium Chloride; Benzethonium Chloride; Benzyl Alcohol; Butylated Hydroxyanisole; Butylated Hydroxytoluene; Caffeine; Carbon Dioxide; Carboxymethylcellulose Sodium; Cellulose, Microcrystalline; Chlorobutanol; Citric Acid; Citric Acid Monohydrate; Dextrose; Dichlorodifluoromethane; Dichlorotetrafluoroethane; Edetate Disodium; Glycerin; Glycerol Ester Of Hydrogenated Rosin; Hydrochloric Acid; Hypromellose 2910 (15000 Mpa · S); Methylcelluloses; Methylparaben; Nitrogen; Norflurane; Oleic Acid; Petrolatum, White; Phenylethyl Alcohol; Polyethylene Glycol 3350; Polyethylene Glycol 400; Polyoxyl 400 Stearate; Polysorbate 20; Polysorbate 80; Potassium Phosphate, Monobasic; Potassium Sorbate; Propylene Glycol; Propylparaben; Sodium Acetate; Sodium Chloride; Sodium Citrate; Sodium Hydroxide; Sodium Phosphate; Sodium Phosphate, Dibasic; Sodium Phosphate, Dibasic, Anhydrous; Sodium Phosphate, Dibasic, Dihydrate; Sodium Phosphate, Dibasic, Dodecahydrate; Sodium Phosphate, Dibasic, Heptahydrate; Sodium Phosphate, Monobasic, Anhydrous; Sodium Phosphate, Monobasic, Dihydrate; Sorbitan Trioleate; Sorbitol; Sorbitol Solution; Sucralose; Sulfuric Acid; Trichloromonofluoromethane; Trisodium Citrate Dihydrate |
| Nerve Block | Acetic Acid; Acetone Sodium Bisulfite; Ascorbic Acid; Benzyl Alcohol; Calcium Chloride; Carbon Dioxide; Chlorobutanol; Citric Acid; Citric Acid Monohydrate; Edetate Calcium Disodium; Edetate Disodium; Hydrochloric Acid; Hydrochloric Acid, Diluted; Lactic Acid; Methylparaben; Monothioglycerol; Nitrogen; Potassium Chloride; Potassium Metabisulfite; Potassium Phosphate, Monobasic; Propylparaben; Sodium Bisulfite; Sodium Carbonate; Sodium Chlorate; Sodium Chloride; Sodium Citrate; Sodium Hydroxide; Sodium Lactate; Sodium Lactate, L-; Sodium Metabisulfite; Sodium Phosphate; Sodium Phosphate, Dibasic, Heptahydrate |
| Ophthalmic | Acetic Acid; Alcohol; Alcohol, Dehydrated; Alginic Acid; Amerchol-Cab; Ammonium Hydroxide; Anhydrous Trisodium Citrate; Antipyrine; Benzalkonium Chloride; Benzethonium Chloride; Benzododecinium Bromide; Boric Acid; Caffeine; Calcium Chloride; Carbomer 1342; Carbomer 934p; Carbomer 940; Carbomer Homopolymer Type B (Allyl Pentaerythritol Crosslinked); Carboxymethylcellulose Sodium; Castor Oil; Cetyl Alcohol; Chlorobutanol; Chlorobutanol, Anhydrous; Cholesterol; Citric Acid; Citric Acid Monohydrate; Creatinine; Diethanolamine; Diethylhexyl Phthalate **See Cder Guidance: Limiting The Use Of Certain Phthalates As Excipients In Cder-Regulated Products; Divinylbenzene Styrene Copolymer; Edetate Disodium; |

TABLE 5-continued

Routes of Adminsitration and Inactive Ingredients

| Route of Administration | Inactive Ingredient |
| --- | --- |
| | Edetate Disodium Anhydrous; Edetate Sodium; Ethylene Vinyl Acetate Copolymer; Gellan Gum (Low Acyl); Glycerin; Glyceryl Stearate; High Density Polyethylene; Hydrocarbon Gel, Plasticized; Hydrochloric Acid; Hydrochloric Acid, Diluted; Hydroxyethyl Cellulose; Hydroxypropyl Methylcellulose 2906; Hypromellose 2910 (15000 Mpa · S); Hypromelloses; Jelene; Lanolin; Lanolin Alcohols; Lanolin Anhydrous; Lanolin Nonionic Derivatives; Lauralkonium Chloride; Lauroyl Sarcosine; Light Mineral Oil; Magnesium Chloride; Mannitol; Methylcellulose (4000 Mpa · S); Methylcelluloses; Methylparaben; Mineral Oil; Nitric Acid; Nitrogen; Nonoxynol-9; Octoxynol-40; Octylphenol Polymethylene; Petrolatum; Petrolatum, White; Phenylethyl Alcohol; Phenylmercuric Acetate; Phenylmercuric Nitrate; Phosphoric Acid; Polidronium Chloride; Poloxamer 188; Poloxamer 407; Polycarbophil; Polyethylene Glycol 300; Polyethylene Glycol 400; Polyethylene Glycol 8000; Polyoxyethylene - Polyoxypropylene 1800; Polyoxyl 35 Castor Oil; Polyoxyl 40 Hydrogenated Castor Oil; Polyoxyl 40 Stearate; Polypropylene Glycol; Polysorbate 20; Polysorbate 60; Polysorbate 80; Polyvinyl Alcohol; Potassium Acetate; Potassium Chloride; Potassium Phosphate, Monobasic; Potassium Sorbate; Povidone K29/32; Povidone K30; Povidone K90; Povidones; Propylene Glycol; Propylparaben; Soda Ash; Sodium Acetate; Sodium Bisulfate; Sodium Bisulfite; Sodium Borate; Sodium Borate Decahydrate; Sodium Carbonate; Sodium Carbonate Monohydrate; Sodium Chloride; Sodium Citrate; Sodium Hydroxide; Sodium Metabisulfite; Sodium Nitrate; Sodium Phosphate; Sodium Phosphate Dihydrate; Sodium Phosphate, Dibasic; Sodium Phosphate, Dibasic, Anhydrous; Sodium Phosphate, Dibasic, Dihydrate; Sodium Phosphate, Dibasic, Heptahydrate; Sodium Phosphate, Monobasic; Sodium Phosphate, Monobasic, Anhydrous; Sodium Phosphate, Monobasic, Dihydrate; Sodium Phosphate, Monobasic, Monohydrate; Sodium Sulfate; Sodium Sulfate Anhydrous; Sodium Sulfate Decahydrate; Sodium Sulfite; Sodium Thiosulfate; Sorbic Acid; Sorbitan Monolaurate; Sorbitol; Sorbitol Solution; Stabilized Oxychloro Complex; Sulfuric Acid; Thimerosal; Titanium Dioxide; Tocophersolan; Trisodium Citrate Dihydrate; Triton 720; Tromethamine; Tyloxapol; Zinc Chloride |
| Parenteral | Hydrochloric Acid; Mannitol; Nitrogen; Sodium Acetate; Sodium Chloride; Sodium Hydroxide |
| Percutaneous | Duro-Tak 87-2287; Silicone Adhesive 4102 |
| Perfusion, Biliary | Glycerin |
| Perfusion, Cardiac | Hydrochloric Acid; Sodium Hydroxide |
| Periarticular | Diatrizoic Acid; Edetate Calcium Disodium; Iodine; Meglumine |
| Peridural | Citric Acid; Hydrochloric Acid; Methylparaben; Sodium Chloride; Sodium Hydroxide; Sodium Metabisulfite |
| Perineural | Hydrochloric Acid; Sodium Chloride; Sodium Hydroxide |
| Periodontal | Ethylene Vinyl Acetate Copolymer; Hydrochloric Acid; Methyl Pyrrolidone; Poloxamer 188; Poloxamer 407; Polylactide |
| Photopheresis | Acetic Acid; Alcohol, Dehydrated; Propylene Glycol; Sodium Acetate; Sodium Chloride; Sodium Hydroxide |
| Rectal | Alcohol; Alcohol, Dehydrated; Aluminum Subacetate; Anhydrous Citric Acid; Aniseed Oil; Ascorbic Acid; Ascorbyl Palmitate; Balsam Peru; Benzoic Acid; Benzyl Alcohol; Bismuth Subgallate; Butylated Hydroxyanisole; Butylated Hydroxytoluene; Butylparaben; Caramel; Carbomer 934; Carbomer 934p; Carboxypolymethylene; Cerasynt-Se; Cetyl Alcohol; Cocoa Butter; Coconut Oil, Hydrogenated; Coconut Oil/Palm Kernel Oil Glycerides, Hydrogenated; *Cola Nitida* Seed Extract; D&C Yellow No. 10; Dichlorodifluoromethane; Dichlorotetrafluoroethane; Dimethyldioctadecylammonium Bentonite; Edetate Calcium Disodium; Edetate Disodium; Edetic Acid; Epilactose; Ethylenediamine; Fat, Edible; Fat, Hard; Fd&C Blue No. 1; Fd&C Green No. 3; Fd&C Yellow No. 6; Flavor FIG. 827118; Flavor Raspberry Pfc-8407; Fructose; Galactose; Glycerin; Glyceryl Palmitate; Glyceryl Stearate; Glyceryl Stearate/Peg Stearate; Glyceryl Stearate/Peg-40 Stearate; Glycine; Hydrocarbon; Hydrochloric Acid; Hydrogenated Palm Oil; Hypromelloses; Lactose; Lanolin; Lecithin; Light Mineral Oil; Magnesium Aluminum Silicate; Magnesium Aluminum Silicate Hydrate; Methylparaben; Nitrogen; Palm Kernel Oil; Paraffin; Petrolatum, White; Polyethylene Glycol 1000; Polyethylene Glycol 1540; Polyethylene Glycol 3350; Polyethylene Glycol 400; Polyethylene Glycol 4000; Polyethylene Glycol 6000; Polyethylene Glycol 8000; Polysorbate 60; Polysorbate 80; Potassium Acetate; Potassium Metabisulfite; Propylene Glycol; Propylparaben; Saccharin Sodium; Saccharin Sodium Anhydrous; Silicon Dioxide, Colloidal; Simethicone; Sodium Benzoate; Sodium Carbonate; Sodium Chloride; Sodium Citrate; Sodium Hydroxide; Sodium Metabisulfite; Sorbitan Monooleate; Sorbitan Sesquioleate; Sorbitol; Sorbitol Solution; Starch; Steareth-10; Steareth-40; Sucrose; Tagatose, D-; Tartaric Acid, Dl-; Trolamine; Tromethamine; |

TABLE 5-continued

Routes of Adminsitration and Inactive Ingredients

| Route of Administration | Inactive Ingredient |
|---|---|
| | Vegetable Oil Glyceride, Hydrogenated; Vegetable Oil, Hydrogenated; Wax, Emulsifying; White Wax; Xanthan Gum; Zinc Oxide |
| Respiratory (Inhalation) | Alcohol; Alcohol, Dehydrated; Apaflurane; Benzalkonium Chloride; Calcium Carbonate; Edetate Disodium; Gelatin; Glycine; Hydrochloric Acid; Lactose Monohydrate; Lysine Monohydrate; Mannitol; Norflurane; Oleic Acid; Polyethylene Glycol 1000; Povidone K25; Silicon Dioxide, Colloidal; Sodium Chloride; Sodium Citrate; Sodium Hydroxide; Sodium Lauryl Sulfate; Sulfuric Acid; Titanium Dioxide; Tromethamine; Zinc Oxide |
| Retrobulbar | Hydrochloric Acid; Sodium Hydroxide |
| Soft Tissue | Acetic Acid; Anhydrous Trisodium Citrate; Benzyl Alcohol; Carboxymethylcellulose; Carboxymethylcellulose Sodium; Citric Acid; Creatinine; Edetate Disodium; Hydrochloric Acid; Methylcelluloses; Methylparaben; Myristyl-.Gamma.-Picolinium Chloride; Phenol; Phosphoric Acid; Polyethylene Glycol 3350; Polyethylene Glycol 4000; Polysorbate 80; Propylparaben; Sodium Acetate; Sodium Bisulfite; Sodium Chloride; Sodium Citrate; Sodium Hydroxide; Sodium Phosphate; Sodium Phosphate, Dibasic; Sodium Phosphate, Dibasic, Heptahydrate; Sodium Phosphate, Monobasic; Sodium Phosphate, Monobasic, Anhydrous; Sodium Sulfite |
| Spinal | Anhydrous Dextrose; Dextrose; Hydrochloric Acid; Sodium Hydroxide |
| Subarachnoid | Hydrochloric Acid; Sodium Chloride; Sodium Hydroxide |
| Subconjunctival | Benzyl Alcohol; Hydrochloric Acid; Sodium Hydroxide |
| Subcutaneous | Acetic Acid; Acetic Acid, Glacial; Albumin Human; Ammonium Hydroxide; Ascorbic Acid; Benzyl Alcohol; Calcium Chloride; Carboxymethylcellulose Sodium; Chlorobutanol; Cresol; Diatrizoic Acid; Dimethyl Sulfoxide; Edetate Calcium Disodium; Edetate Disodium; Ethylene Vinyl Acetate Copolymer; Glycerin; Glycine; Glycine Hydrochloride; Histidine; Hydrochloric Acid; Lactic Acid; Lactic Acid, L-; Lactose; Magnesium Chloride; Magnesium Stearate; Mannitol; Metacresol; Methanesulfonic Acid; Methionine; Methyl Pyrrolidone; Methylparaben; Nitrogen; Phenol; Phenol, Liquefied; Phosphoric Acid; Poloxamer 188; Polyethylene Glycol 3350; Polyglactin; Polysorbate 20; Polysorbate 80; Potassium Phosphate, Dibasic; Potassium Phosphate, Monobasic; Povidone K17; Povidones; Propylene Glycol; Propylparaben; Protamine Sulfate; Sodium Acetate; Sodium Acetate Anhydrous; Sodium Bicarbonate; Sodium Bisulfite; Sodium Chloride; Sodium Citrate; Sodium Hydroxide; Sodium Metabisulfite; Sodium Phosphate; Sodium Phosphate Dihydrate; Sodium Phosphate, Dibasic; Sodium Phosphate, Dibasic, Anhydrous; Sodium Phosphate, Dibasic, Dihydrate; Sodium Phosphate, Dibasic, Heptahydrate; Sodium Phosphate, Monobasic; Sodium Phosphate, Monobasic, Anhydrous; Sodium Phosphate, Monobasic, Dihydrate; Sodium Phosphate, Monobasic, Monohydrate; Sodium Sulfite; Sodium Thioglycolate; Stearic Acid; Sucrose; Thimerosal; Tromethamine; Zinc; Zinc Acetate; Zinc Carbonate; Zinc Chloride; Zinc Oxide |
| Sublingual | Alcohol, Dehydrated |
| Submucosal | Acetic Acid; Edetic Acid; Mannitol; Nitrogen; Sodium Acetate; Sodium Chloride; Sodium Hydroxide; Sodium Metabisulfite |
| Topical | .Alpha.-Terpineol; .Alpha.-Tocopherol; .Alpha.-Tocopherol Acetate, Dl-; .Alpha.-Tocopherol, Dl-; 1,2,6-Hexanetriol; 1-O-Tolylbiguanide; 2-Ethyl-1,6-Hexanediol; Acetic Acid; Acetone; Acetylated Lanolin Alcohols; Acrylates Copolymer; Adhesive Tape; Alcohol; Alcohol, Dehydrated; Alcohol, Denatured; Alcohol, Diluted; Alkyl Ammonium Sulfonic Acid Betaine; Alkyl Aryl Sodium Sulfonate; Allantoin; Almond Oil; Aluminum Acetate; Aluminum Chlorhydroxy Allantoinate; Aluminum Hydroxide; Aluminum Hydroxide - Sucrose, Hydrated; Aluminum Hydroxide Gel; Aluminum Hydroxide Gel F 500; Aluminum Hydroxide Gel F 5000; Aluminum Monostearate; Aluminum Oxide; Aluminum Silicate; Aluminum Starch Octenylsuccinate; Aluminum Stearate; Aluminum Sulfate Anhydrous; Amerchol C; Amerchol-Cab; Aminomethylpropanol; Ammonia Solution; Ammonia Solution, Strong; Ammonium Hydroxide; Ammonium Lauryl Sulfate; Ammonium Nonoxynol-4 Sulfate; Ammonium Salt Of C-12-C-15 Linear Primary Alcohol Ethoxylate; Ammonyx; Amphoteric-2; Amphoteric-9; Anhydrous Citric Acid; Anhydrous Trisodium Citrate; Anoxid Sbn; Antifoam; Apricot Kernel Oil Peg-6 Esters; Aquaphor; Arlacel; Ascorbic Acid; Ascorbyl Palmitate; Beeswax; Beeswax, Synthetic; Beheneth-10; Bentonite; Benzalkonium Chloride; Benzoic Acid; Benzyl Alcohol; Betadex; Boric Acid; Butane; Butyl Alcohol; Butyl Ester Of Vinyl Methyl Ether/Maleic Anhydride Copolymer (125000 Mw); Butyl Stearate; Butylated Hydroxyanisole; Butylated Hydroxytoluene; Butylene Glycol; Butylparaben; C20-40 Pareth-24; Calcium Chloride; Calcium Hydroxide; Canada Balsam; Caprylic/Capric Triglyceride; Caprylic/Capric/Stearic Triglyceride; Captan; Caramel; Carbomer 1342; Carbomer 1382; Carbomer 934; Carbomer 934p; Carbomer 940; |

TABLE 5-continued

Routes of Adminsitration and Inactive Ingredients

| Route of Administration | Inactive Ingredient |
| --- | --- |
| | Carbomer 941; Carbomer 980; Carbomer 981; Carbomer Homopolymer Type B (Allyl Pentaerythritol Crosslinked); Carbomer Homopolymer Type C (Allyl Pentaerythritol Crosslinked); Carboxy Vinyl Copolymer; Carboxymethylcellulose; Carboxymethylcellulose Sodium; Carboxypolymethylene; Carrageenan; Carrageenan Salt; Castor Oil; Cedar Leaf Oil; Cellulose; Cerasynt-Se; Ceresin; Ceteareth-12; Ceteareth-15; Ceteareth-30; Cetearyl Alcohol/Ceteareth-20; Cetearyl Ethylhexanoate; Ceteth-10; Ceteth-2; Ceteth-20; Ceteth-23; Cetostearyl Alcohol; Cetrimonium Chloride; Cetyl Alcohol; Cetyl Esters Wax; Cetyl Palmitate; Chlorobutanol; Chlorocresol; Chloroxylenol; Cholesterol; Choleth-24; Citric Acid; Citric Acid Monohydrate; Cocamide Ether Sulfate; Cocamine Oxide; Coco Betaine; Coco Diethanolamide; Coco Monoethanolamide; Cocoa Butter; Coco-Glycerides; Coconut Oil; Cocoyl Caprylocaprate; Collagen; Coloring Suspension; Cream Base; Creatinine; Crospovidone; Cyclomethicone; Cyclomethicone/Dimethicone Copolyol; D&C Red No. 28; D&C Red No. 33; D&C Red No. 36; D&C Red No. 39; D&C Yellow No. 10; Decyl Methyl Sulfoxide; Dehydag Wax Sx; Dehydroacetic Acid; Dehymuls E; Denatonium Benzoate; Dextrin; Diazolidinyl Urea; Dichlorobenzyl Alcohol; Dichlorodifluoromethane; Dichlorotetrafluoroethane; Diethanolamine; Diethyl Sebacate; Diethylene Glycol Monoethyl Ether; Dihydroxyaluminum Aminoacetate; Diisopropanolamine; Diisopropyl Adipate; Diisopropyl Dilinoleate; Dimethicone 350; Dimethicone Copolyol; Dimethicone Medical Fluid 360; Dimethyl Isosorbide; Dimethyl Sulfoxide; Dinoseb Ammonium Salt; Disodium Cocoamphodiacetate; Disodium Laureth Sulfosuccinate; Disodium Lauryl Sulfosuccinate; Dmdm Hydantoin; Docosanol; Docusate Sodium; Edetate Disodium; Edetate Sodium; Edetic Acid; Entsufon; Entsufon Sodium; Epitetracycline Hydrochloride; Essence Bouquet 9200; Ethyl Acetate; Ethylcelluloses; Ethylene Glycol; Ethylenediamine; Ethylenediamine Dihydrochloride; Ethylhexyl Hydroxystearate; Ethylparaben; Fatty Acid Pentaerythriol Ester; Fatty Acids; Fatty Alcohol Citrate; Fd&C Blue No. 1; Fd&C Red No. 4; Fd&C Red No. 40; Fd&C Yellow No. 10 (Delisted); Fd&C Yellow No. 5; Fd&C Yellow No. 6; Ferric Oxide; Flavor Rhodia Pharmaceutical No. Rf 451; Formaldehyde; Formaldehyde Solution; Fractionated Coconut Oil; Fragrance 3949-5; Fragrance 520a; Fragrance 6.007; Fragrance 91-122; Fragrance 9128-Y; Fragrance 93498g; Fragrance Balsam Pine No. 5124; Fragrance Bouquet 10328; Fragrance Chemoderm 6401-B; Fragrance Chemoderm 6411; Fragrance Cream No. 73457; Fragrance Cs-28197; Fragrance Felton 066m; Fragrance Firmenich 47373; Fragrance Givaudan Ess 9090/1c; Fragrance H-6540; Fragrance Herbal 10396; Fragrance Nj-1085; Fragrance P O Fl-147; Fragrance Pa 52805; Fragrance Pera Derm D; Fragrance Rbd-9819; Fragrance Shaw Mudge U-7776; Fragrance Tf 044078; Fragrance Ungerer Honeysuckle K 2771; Fragrance Ungerer N5195; Gelatin; Gluconolactone; Glycerin; Glyceryl Citrate; Glyceryl Isostearate; Glyceryl Monostearate; Glyceryl Oleate; Glyceryl Oleate/Propylene Glycol; Glyceryl Palmitate; Glyceryl Ricinoleate; Glyceryl Stearate; Glyceryl Stearate - Laureth-23; Glyceryl Stearate/Peg-100 Stearate; Glyceryl Stearate-Stearamidoethyl Diethylamine; Glycol Distearate; Glycol Stearate; Guar Gum; Hair Conditioner (18n195-1m); Hexylene Glycol; High Density Polyethylene; Hyaluronate Sodium; Hydrocarbon Gel, Plasticized; Hydrochloric Acid; Hydrochloric Acid, Diluted; Hydrogen Peroxide; Hydrogenated Castor Oil; Hydrogenated Palm/Palm Kernel Oil Peg-6 Esters; Hydroxyethyl Cellulose; Hydroxymethyl Cellulose; Hydroxyoctacosanyl Hydroxystearate; Hydroxypropyl Cellulose; Hypromelloses; Imidurea; Irish Moss Extract; Isobutane; Isoceteth-20; Isooctyl Acrylate; Isopropyl Alcohol; Isopropyl Isostearate; Isopropyl Myristate; Isopropyl Myristat - Myristyl Alcohol; Isopropyl Palmitate; Isopropyl Stearate; Isostearic Acid; Isostearyl Alcohol; Jelene; Kaolin; Kathon Cg; Kathon Cg Ii; Lactate; Lactic Acid; Lactic Acid, Dl-; Laneth; Lanolin; Lanolin Alcohol - Mineral Oil; Lanolin Alcohols; Lanolin Anhydrous; Lanolin Cholesterols; Lanolin, Ethoxylated; Lanolin, Hydrogenated; Lauramine Oxide; Laurdimonium Hydrolyzed Animal Collagen; Laureth Sulfate; Laureth-2; Laureth-23; Laureth-4; Lauric Diethanolamide; Lauric Myristic Diethanolamide; Lauryl Sulfate; *Lavandula Angustifolia* Flowering Top; Lecithin; Lecithin Unbleached; Lemon Oil; Light Mineral Oil; Light Mineral Oil (85 Ssu); Limonene, (+/−)-; Lipocol Sc-15; Magnesium Aluminum Silicate; Magnesium Aluminum Silicate Hydrate; Magnesium Nitrate; Magnesium Stearate; Mannitol; Maprofix; Medical Antiform A-F Emulsion; Menthol; Methyl Gluceth-10; Methyl Gluceth-20; Methyl Gluceth-20 Sesquistearate; Methyl Glucose Sesquistearate; Methyl Salicylate; Methyl Stearate; Methylcelluloses; Methylchloroisothiazolinone; Methylisothiazolinone; Methylparaben; Microcrystalline Wax; Mineral Oil; Mono And Diglyceride; Monostearyl |

TABLE 5-continued

Routes of Adminsitration and Inactive Ingredients

| Route of Administration | Inactive Ingredient |
|---|---|
| | Citrate; Multisterol Extract; Myristyl Alcohol; Myristyl Lactate; Niacinamide; Nitric Acid; Nitrogen; Nonoxynol Iodine; Nonoxynol-15; Nonoxynol-9; Oatmeal; Octadecene-1/Maleic Acid Copolymer; Octoxynol-1; Octoxynol-9; Octyldodecanol; Oleic Acid; Oleth-10/Oleth-5; Oleth-2; Oleth-20; Oleyl Alcohol; Oleyl Oleate; Olive Oil; Palmitamine Oxide; Parabens; Paraffin; Paraffin, White Soft; Parfum Creme 45/3; Peanut Oil; Peanut Oil, Refined; Pectin; Peg 6-32 Stearate/Glycol Stearate; Peg-100 Stearate; Peg-12 Glyceryl Laurate; Peg-120 Glyceryl Stearate; Peg-120 Methyl Glucose Dioleate; Peg-15 Cocamine; Peg-150 Distearate; Peg-2 Stearate; Peg-22 Methyl Ether/Dodecyl Glycol Copolymer; Peg-25 Propylene Glycol Stearate; Peg-4 Dilaurate; Peg-4 Laurate; Peg-45/Dodecyl Glycol Copolymer; Peg-5 Oleate; Peg-50 Stearate; Peg-54 Hydrogenated Castor Oil; Peg-6 Isostearate; Peg-60 Hydrogenated Castor Oil; Peg-7 Methyl Ether; Peg-75 Lanolin; Peg-8 Laurate; Peg-8 Stearate; Pegoxol 7 Stearate; Pentaerythritol Cocoate; Peppermint Oil; Perfume 25677; Perfume Bouquet; Perfume E-1991; Perfume Gd 5604; Perfume Tana 90/42 Scba; Perfume W-1952-1; Petrolatum; Petrolatum, White; Petroleum Distillates; Phenonip; Phenoxyethanol; Phenylmercuric Acetate; Phosphoric Acid; Pine Needle Oil (*Pinus Sylvestris*); Plastibase-50w; Polidronium Chloride; Poloxamer 124; Poloxamer 181; Poloxamer 182; Poloxamer 188; Poloxamer 237; Poloxamer 407; Polycarbophil; Polyethylene Glycol 1000; Polyethylene Glycol 1450; Polyethylene Glycol 1500; Polyethylene Glycol 1540; Polyethylene Glycol 200; Polyethylene Glycol 300; Polyethylene Glycol 300-1600; Polyethylene Glycol 3350; Polyethylene Glycol 400; Polyethylene Glycol 4000; Polyethylene Glycol 540; Polyethylene Glycol 600; Polyethylene Glycol 6000; Polyethylene Glycol 8000; Polyethylene Glycol 900; Polyhydroxyethyl Methacrylate; Polyisobutylene; Polyisobutylene (1100000 Mw); Polyoxyethylene - Polyoxypropylene 1800; Polyoxyethylene Alcohols; Polyoxyethylene Fatty Acid Esters; Polyoxyethylene Propylene; Polyoxyl 20 Cetostearyl Ether; Polyoxyl 40 Hydrogenated Castor Oil; Polyoxyl 40 Stearate; Polyoxyl 400 Stearate; Polyoxyl 6 And Polyoxyl 32 Palmitostearate; Polyoxyl Distearate; Polyoxyl Glyceryl Stearate; Polyoxyl Lanolin; Polyoxyl Stearate; Polypropylene; Polyquaternium-10; Polysorbate 20; Polysorbate 40; Polysorbate 60; Polysorbate 65; Polysorbate 80; Polyvinyl Alcohol; Potash; Potassium Citrate; Potassium Hydroxide; Potassium Soap; Potassium Sorbate; Povidone Acrylate Copolymer; Povidone Hydrogel; Povidone K90; Povidone/Eicosene Copolymer; Povidones; Ppg-12/Smdi Copolymer; Ppg-15 Stearyl Ether; Ppg-20 Methyl Glucose Ether Distearate; Ppg-26 Oleate; Product Wat; Promulgen D; Promulgen G; Propane; Propellant A-46; Propyl Gallate; Propylene Carbonate; Propylene Glycol; Propylene Glycol Diacetate; Propylene Glycol Dicaprylate; Propylene Glycol Monopalmitostearate; Propylene Glycol Palmitostearate; Propylene Glycol Ricinoleate; Propylene Glycol/Diazolidinyl Urea/Methylparaben/Propylparben; Propylparaben; Protein Hydrolysate; Quaternium-15; Quaternium-15 Cis-Form; Quaternium-52; Saccharin; Saccharin Sodium; Safflower Oil; Sd Alcohol 3a; Sd Alcohol 40; Sd Alcohol 40-2; Sd Alcohol 40b; Sepineo P 600; Shea Butter; Silicon; Silicon Dioxide; Silicone; Silicone Adhesive Bio-Psa Q7-4201; Silicone Adhesive Bio-Psa Q7-4301; Silicone Emulsion; Simethicone; Simethicone Emulsion; Sipon Ls 20np; Sodium Acetate; Sodium Acetate Anhydrous; Sodium Alkyl Sulfate; Sodium Benzoate; Sodium Bisulfite; Sodium Borate; Sodium Cetostearyl Sulfate; Sodium Chloride; Sodium Citrate; Sodium Cocoyl Sarcosinate; Sodium Dodecylbenzenesulfonate; Sodium Formaldehyde Sulfoxylate; Sodium Hydroxide; Sodium Iodide; Sodium Lactate; Sodium Laureth-2 Sulfate; Sodium Laureth-3 Sulfate; Sodium Laureth-5 Sulfate; Sodium Lauroyl Sarcosinate; Sodium Lauryl Sulfate; Sodium Lauryl Sulfoacetate; Sodium Metabisulfite; Sodium Phosphate; Sodium Phosphate, Dibasic; Sodium Phosphate, Dibasic, Anhydrous; Sodium Phosphate, Dibasic, Dihydrate; Sodium Phosphate, Dibasic, Heptahydrate; Sodium Phosphate, Monobasic; Sodium Phosphate, Monobasic, Anhydrous; Sodium Phosphate, Monobasic, Dihydrate; Sodium Phosphate, Monobasic, Monohydrate; Sodium Polyacrylate (2500000 Mw); Sodium Pyrrolidone Carboxylate; Sodium Sulfite; Sodium Sulfosuccinated Undecyclenic Monoalkylolamide; Sodium Thiosulfate; Sodium Xylenesulfonate; Somay 44; Sorbic Acid; Sorbitan; Sorbitan Isostearate; Sorbitan Monolaurate; Sorbitan Monooleate; Sorbitan Monopalmitate; Sorbitan Monostearate; Sorbitan Sesquioleate; Sorbitan Tristearate; Sorbitol; Sorbitol Solution; Soybean Flour; Soybean Oil; Spearmint Oil; Spermaceti; Squalane; Starch; Stearalkonium Chloride; Stearamidoethyl Diethylamine; Steareth-10; Steareth-100; Steareth-2; Steareth-20; Steareth-21; Steareth-40; Stearic Acid; Stearic Diethanolamide; Stearoxytrimethylsilane; Steartrimonium Hydrolyzed Animal Collagen; |

TABLE 5-continued

Routes of Adminsitration and Inactive Ingredients

| Route of Administration | Inactive Ingredient |
|---|---|
| | Stearyl Alcohol; Styrene/Isoprene/Styrene Block Copolymer; Sucrose; Sucrose Distearate; Sucrose Polyesters; Sulfacetamide Sodium; Sulfuric Acid; Surfactol Qs; Talc; Tall Oil; Tallow Glycerides; Tartaric Acid; Tenox; Tenox-2; Tert-Butyl Alcohol; Tert-Butyl Hydroperoxide; Thimerosal; Titanium Dioxide; Tocopherol; Tocophersolan; Trichloromonofluoromethane; Trideceth-10; Triethanolamine Lauryl Sulfate; Triglycerides, Medium Chain; Trihydroxystearin; Trilaneth-4 Phosphate; Trilaureth-4 Phosphate; Trisodium Citrate Dihydrate; Trisodium Hedta; Triton X-200; Trolamine; Tromethamine; Tyloxapol; Undecylenic Acid; Vegetable Oil; Vegetable Oil, Hydrogenated; Viscarin; Vitamin E; Wax, Emulsifying; Wecobee Fs; White Wax; Xanthan Gum; Zinc Acetate |
| Transdermal | Acrylates Copolymer; Acrylic Acid-Isooctyl Acrylate Copolymer; Acrylic Adhesive 788; Adcote 72a103; Aerotex Resin 3730; Alcohol; Alcohol, Dehydrated; Aluminum Polyester; Bentonite; Butylated Hydroxytoluene; Butylene Glycol; Butyric Acid; Caprylic/Capric Triglyceride; Carbomer 1342; Carbomer 940; Carbomer 980; Carrageenan; Cetylpyridinium Chloride; Citric Acid; Crospovidone; Daubert 1-5 Pestr (Matte) 164z; Diethylene Glycol Monoethyl Ether; Diethylhexyl Phthalate **See Cder Guidance: Limiting The Use Of Certain Phthalates As Excipients In Cder-Regulated Products; Dimethicone Copolyol; Dimethicone Mdx4-4210; Dimethicone Medical Fluid 360; Dimethylaminoethyl Methacrylate - Butyl Methacrylate - Methyl Methacrylate Copolymer; Dipropylene Glycol; Duro-Tak 280-2516; Duro-Tak 387-2516; Duro-Tak 80-1196; Duro-Tak 87-2070; Duro-Tak 87-2194; Duro-Tak 87-2287; Duro-Tak 87-2296; Duro-Tak 87-2888; Duro-Tak 87-2979; Edetate Disodium; Ethyl Acetate; Ethyl Oleate; Ethylcelluloses; Ethylene Vinyl Acetate Copolymer; Ethylene-Propylene Copolymer; Fatty Acid Esters; Gelva 737; Glycerin; Glyceryl Laurate; Glyceryl Oleate; Heptane; High Density Polyethylene; Hydrochloric Acid; Hydrogenated Polybutene 635-690; Hydroxyethyl Cellulose; Hydroxypropyl Cellulose; Isopropyl Myristate; Isopropyl Palmitate; Lactose; Lanolin Anhydrous; Lauryl Lactate; Lecithin; Levulinic Acid; Light Mineral Oil; Medical Adhesive Modified S-15; Methyl Alcohol; Methyl Laurate; Mineral Oil; Nitrogen; Octisalate; Octyldodecanol; Oleic Acid; Oleyl Alcohol; Oleyl Oleate; Pentadecalactone; Petrolatum, White; Polacrilin; Polyacrylic Acid (250000 Mw); Polybutene (1400 Mw); Polyester; Polyester Polyamine Copolymer; Polyester Rayon; Polyethylene Terephthalates; Polyisobutylene; Polyisobutylene (1100000 Mw); Polyisobutylene (35000 Mw); Polyisobutylene 178-236; Polyisobutylene 241-294; Polyisobutylene 35-39; Polyisobutylene Low Molecular Weight; Polyisobutylene Medium Molecular Weight; Polyisobutylene/Polybutene Adhesive; Polypropylene; Polyvinyl Acetate; Polyvinyl Alcohol; Polyvinyl Chloride; Polyvinyl Chloride-Polyvinyl Acetate Copolymer; Polyvinylpyridine; Povidone K29/32; Povidones; Propylene Glycol; Propylene Glycol Monolaurate; Ra-2397; Ra-3011; Silicon; Silicon Dioxide, Colloidal; Silicone; Silicone Adhesive 4102; Silicone Adhesive 4502; Silicone Adhesive Bio-Psa Q7-4201; Silicone Adhesive Bio-Psa Q7-4301; Silicone/Polyester Film Strip; Sodium Chloride; Sodium Citrate; Sodium Hydroxide; Sorbitan Monooleate; Stearalkonium Hectorite/Propylene Carbonate; Titanium Dioxide; Triacetin; Trolamine; Tromethamine; Union 76 Amsco-Res 6038; Viscose/Cotton |
| Transmucosal | Magnesium Stearate; Mannitol; Potassium Bicarbonate; Sodium Starch Glycolate |
| Ureteral | Benzyl Alcohol; Diatrizoic Acid; Edetate Calcium Disodium; Edetate Disodium; Hydrochloric Acid; Meglumine; Methylparaben; Propylparaben; Sodium Citrate; Sodium Hydroxide |
| Urethral | Diatrizoic Acid; Edetate Calcium Disodium; Edetate Disodium; Hydrochloric Acid; Meglumine; Methylparaben; Polyethylene Glycol 1450; Propylparaben; Sodium Hydroxide; Sodium Phosphate, Dibasic, Heptahydrate; Tromethamine |
| Vaginal | Adipic Acid; Alcohol, Denatured; Allantoin; Anhydrous Lactose; Apricot Kernel Oil Peg-6 Esters; Barium Sulfate; Beeswax; Bentonite; Benzoic Acid; Benzyl Alcohol; Butylated Hydroxyanisole; Butylated Hydroxytoluene; Calcium Lactate; Carbomer 934; Carbomer 934p; Cellulose, Microcrystalline; Ceteth-20; Cetostearyl Alcohol; Cetyl Alcohol; Cetyl Esters Wax; Cetyl Palmitate; Cholesterol; Choleth; Citric Acid; Citric Acid Monohydrate; Coconut Oil/Palm Kernel Oil Glycerides, Hydrogenated; Crospovidone; Edetate Disodium; Ethylcelluloses; Ethylene-Vinyl Acetate Copolymer (28% Vinyl Acetate); Ethylene-Vinyl Acetate Copolymer (9% Vinylacetate); Fatty Alcohols; Fd&C Yellow No. 5; Gelatin; Glutamic Acid, Dl-; Glycerin; Glyceryl Isostearate; Glyceryl Monostearate; Glyceryl Stearate; Guar Gum; High Density Polyethylene; Hydrogel Polymer; Hydrogenated Palm Oil; Hypromellose 2208 (15000 Mpa · S); Hypromelloses; Isopropyl |

TABLE 5-continued

Routes of Adminsitration and Inactive Ingredients

| Route of Administration | Inactive Ingredient |
|---|---|
| | Myristate; Lactic Acid; Lactic Acid, Dl-; Lactose; Lactose Monohydrate; Lactose, Hydrous; Lanolin; Lanolin Anhydrous; Lecithin; Lecithin, Soybean; Light Mineral Oil; Magnesium Aluminum Silicate; Magnesium Aluminum Silicate Hydrate; Magnesium Stearate; Methyl Stearate; Methylparaben; Microcrystalline Wax; Mineral Oil; Nitric Acid; Octyldodecanol; Peanut Oil; Peg 6-32 Stearate/Glycol Stearate; Peg-100 Stearate; Peg-120 Glyceryl Stearate; Peg-2 Stearate; Peg-5 Oleate; Pegoxol 7 Stearate; Petrolatum, White; Phenylmercuric Acetate; Phospholipon 90g; Phosphoric Acid; Piperazine Hexahydrate; Poly(Dimethylsiloxane/Methylvinylsiloxane/Methylhydrogensiloxane) Dimethylvinyl Or Dimethylhydroxy Or Trimethyl Endblocked; Polycarbophil; Polyester; Polyethylene Glycol 1000; Polyethylene Glycol 3350; Polyethylene Glycol 400; Polyethylene Glycol 4000; Polyethylene Glycol 6000; Polyethylene Glycol 8000; Polyglyceryl-3 Oleate; Polyglyceryl-4 Oleate; Polyoxyl Palmitate; Polysorbate 20; Polysorbate 60; Polysorbate 80; Polyurethane; Potassium Alum; Potassium Hydroxide; Povidone K29/32; Povidones; Promulgen D; Propylene Glycol; Propylene Glycol Monopalmitostearate; Propylparaben; Quaternium-15 Cis-Form; Silicon Dioxide; Silicon Dioxide, Colloidal; Silicone; Sodium Bicarbonate; Sodium Citrate; Sodium Hydroxide; Sodium Lauryl Sulfate; Sodium Metabisulfite; Sodium Phosphate, Dibasic, Anhydrous; Sodium Phosphate, Monobasic, Anhydrous; Sorbic Acid; Sorbitan Monostearate; Sorbitol; Sorbitol Solution; Spermaceti; Stannous 2-Ethylhexanoate; Starch; Starch 1500, Pregelatinized; Starch, Corn; Stearamidoethyl Diethylamine; Stearic Acid; Stearyl Alcohol; Tartaric Acid, Dl-; Tert-Butylhydroquinone; Tetrapropyl Orthosilicate; Trolamine; Urea; Vegetable Oil, Hydrogenated; Wecobee Fs; White Ceresin Wax; White Wax |

As a non-limiting example, the nucleic acid molecules, modified nucleic acid molecules or mmRNA may be formulated for intramuscular administration and may comprise at least one inactive ingredient for intramuscular administration described in Table 5. As another non-limiting example, the nucleic acid molecules, modified nucleic acid molecules or mmRNA may be formulated for intravenous administration and may comprise at least one inactive ingredient for intravenous administration described in Table 5. As another non-limiting example, the nucleic acid molecules, modified nucleic acid molecules or mmRNA may be formulated for subcutaneous administration and may comprise at least one inactive ingredient for subcutaneous administration described in Table 5. As another non-limiting example, the nucleic acid molecules, modified nucleic acid molecules or mmRNA may be formulated for intradermal administration and may comprise at least one inactive ingredient for intradermal administration described in Table 5.

Non-limiting routes of administration for the nucleic acid molecules, modified nucleic acids or mmRNA of the present invention are described below.

Parenteral and Injectable Administration

Liquid dosage forms for parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof.

A pharmaceutical composition for parenteral administration may comprise at least one inactive ingredient. Any or none of the inactive ingredients used may have been approved by the US Food and Drug Administration (FDA). A non-exhaustive list of inactive ingredients for use in pharmaceutical compositions for parenteral administration includes hydrochloric acid, mannitol, nitrogen, sodium acetate, sodium chloride and sodium hydroxide.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables. The sterile formulations may also comprise adjuvants such as local anesthetics, preservatives and buffering agents.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Rectal and Vaginal Administration

Compositions for rectal or vaginal (e.g., transvaginal) administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

As a non-limiting example, the formulations for rectal and/or vaginal administration may be prepared by mixing the drug with a suitable non-irritating excipient that is solid at ordinary temperatures but liquid at the rectal temperature and will therefore melt in the rectum and/or vagina to release the drug. Such materials include cocoa butter and polyethylene glycols.

A pharmaceutical composition for rectal administration may comprise at least one inactive ingredient. Any or none of the inactive ingredients used may have been approved by the US Food and Drug Administration (FDA). A non-exhaustive list of inactive ingredients for use in pharmaceutical compositions for rectal administration includes alcohol, alcohol, dehydrated, aluminum subacetate, anhydrous citric acid, aniseed oil, ascorbic acid, ascorbyl palmitate, balsam peru, benzoic acid, benzyl alcohol, bismuth subgallate, butylated hydroxyanisole, butylated hydroxytoluene, butylparaben, caramel, carbomer 934, carbomer 934p, carboxypolymethylene, cerasynt-se, cetyl alcohol, cocoa butter, coconut oil, hydrogenated, coconut oil/palm kernel oil glycerides, hydrogenated, cola nitida seed extract, d&c yellow no. 10, dichlorodifluoromethane, dichlorotetrafluoroethane, dimethyldioctadecylammonium bentonite, edetate calcium disodium, edetate disodium, edetic acid, epilactose, ethylenediamine, fat, edible, fat, hard, fd&c blue no. 1, fd&c green no. 3, fd&c yellow no. 6, flavor fig 827118, flavor raspberry pfc-8407, fructose, galactose, glycerin, glyceryl palmitate, glyceryl stearate, glyceryl stearate/peg stearate, glyceryl stearate/peg-40 stearate, glycine, hydrocarbon, hydrochloric acid, hydrogenated palm oil, hypromelloses, lactose, lanolin, lecithin, light mineral oil, magnesium aluminum silicate, magnesium aluminum silicate hydrate, methylparaben, nitrogen, palm kernel oil, paraffin, petrolatum, white, polyethylene glycol 1000, polyethylene glycol 1540, polyethylene glycol 3350, polyethylene glycol 400, polyethylene glycol 4000, polyethylene glycol 6000, polyethylene glycol 8000, polysorbate 60, polysorbate 80, potassium acetate, potassium metabisulfite, propylene glycol, propylparaben, saccharin sodium, saccharin sodium anhydrous, silicon dioxide, colloidal, simethicone, sodium benzoate, sodium carbonate, sodium chloride, sodium citrate, sodium hydroxide, sodium metabisulfite, sorbitan monooleate, sorbitan sesquioleate, sorbitol, sorbitol solution, starch, steareth-10, steareth-40, sucrose, tagatose, d-, tartaric acid, dl-, trolamine, tromethamine, vegetable oil glyceride, hydrogenated, vegetable oil, hydrogenated, wax, emulsifying, white wax, xanthan gum and zinc oxide.

A pharmaceutical composition for vaginal administration may comprise at least one inactive ingredient. Any or none of the inactive ingredients used may have been approved by the US Food and Drug Administration (FDA). A non-exhaustive list of inactive ingredients for use in pharmaceutical compositions for vaginal administration includes adipic acid, alcohol, denatured, allantoin, anhydrous lactose, apricot kernel oil peg-6 esters, barium sulfate, beeswax, bentonite, benzoic acid, benzyl alcohol, butylated hydroxyanisole, butylated hydroxytoluene, calcium lactate, carbomer 934, carbomer 934p, cellulose, microcrystalline, ceteth-20, cetostearyl alcohol, cetyl alcohol, cetyl esters wax, cetyl palmitate, cholesterol, choleth, citric acid, citric acid monohydrate, coconut oil/palm kernel oil glycerides, hydrogenated, crospovidone, edetate disodium, ethylcelluloses, ethylene-vinyl acetate copolymer (28% vinyl acetate), ethylene-vinyl acetate copolymer (9% vinylacetate), fatty alcohols, fd&c yellow no. 5, gelatin, glutamic acid, dl-, glycerin, glyceryl isostearate, glyceryl monostearate, glyceryl stearate, guar gum, high density polyethylene, hydrogel polymer, hydrogenated palm oil, hypromellose 2208 (15000 mpa·s), hypromelloses, isopropyl myristate, lactic acid, lactic acid, dl-, lactose, lactose monohydrate, lactose, hydrous, lanolin, lanolin anhydrous, lecithin, lecithin, soybean, light mineral oil, magnesium aluminum silicate, magnesium aluminum silicate hydrate, magnesium stearate, methyl stearate, methylparaben, microcrystalline wax, mineral oil, nitric acid, octyldodecanol, peanut oil, peg 6-32 stearate/glycol stearate, peg-100 stearate, peg-120 glyceryl stearate, peg-2 stearate, peg-5 oleate, pegoxol 7 stearate, petrolatum, white, phenylmercuric acetate, phospholipon 90 g, phosphoric acid, piperazine hexahydrate, poly(dimethylsiloxane/methylvinylsiloxane/methylhydrogensiloxane) dimethylvinyl or dimethylhydroxy or trimethyl endblocked, polycarbophil, polyester, polyethylene glycol 1000, polyethylene glycol 3350, polyethylene glycol 400, polyethylene glycol 4000, polyethylene glycol 6000, polyethylene glycol 8000, polyglyceryl-3 oleate, polyglyceryl-4 oleate, polyoxyl palmitate, polysorbate 20, polysorbate 60, polysorbate 80, polyurethane, potassium alum, potassium hydroxide, povidone k29/32, povidones, promulgen d, propylene glycol, propylene glycol monopalmitostearate, propylparaben, quaternium-15 cis-form, silicon dioxide, silicon dioxide, colloidal, silicone, sodium bicarbonate, sodium citrate, sodium hydroxide, sodium lauryl sulfate, sodium metabisulfite, sodium phosphate, dibasic, anhydrous, sodium phosphate, monobasic, anhydrous, sorbic acid, sorbitan monostearate, sorbitol, sorbitol solution, spermaceti, stannous 2-ethylhexanoate, starch, starch 1500, pregelatinized, starch, corn, stearamidoethyl diethylamine, stearic acid, stearyl alcohol, tartaric acid, dl-, tert-butylhydroquinone, tetrapropyl orthosilicate, trolamine, urea, vegetable oil, hydrogenated, wecobee fs, white ceresin wax and white wax.

Oral Administration

Liquid dosage forms for oral administration include, but are not limited to, pharmaceutically acceptable emulsions, microemulsions, solutions, suspensions, syrups, and/or elixirs. In addition to active ingredients, liquid dosage forms may comprise inert diluents and/or excipients commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

Suspensions for oral dosage may contain the active materials in a mixture with excipients suitable for the manufacture of aqueous suspensions. Such excipients may be suspending agents, as a non-limiting example the suspending agents may be sodium carboxymethylcellulose, methylcellulose, hydropropyl-methylcellulose, sodium alginate, polyvinylpyrrolidone, gum tragacanth and gum *acacia*; dispersing or wetting agents can be a naturally-occurring phosphatide, for example, lecithin, or condensation products of an alkylene oxide with fatty acids, for example polyoxyethylene stearate; or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions for oral dosage can be formulated by suspending the active ingredients in a vegetable oil, for example *arachis* oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid The oral dosage may also be in the form of oil-in-water emulsions. The oily phase can be a vegetable oil or a mineral oil or mixtures of these. Suitable emulsifying agents can be naturally-occurring gums, for example gum *acacia* or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

In one embodiment, the formulation or composition for oral administration may comprise methylsulfonylmethane (MSM) to promote delivery of a pharmaceutical ingredient across the oral mucosa. As a non-limiting example, the composition for oral delivery may include MSM such as the compositions described in International Patent Publication No. WO2014024193, the contents of which are herein incorporated by reference in its entirety.

Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and *acacia*), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. cetyl alcohol and glycerol monostearate), absorbents (e.g. kaolin and bentonite clay), and lubricants (e.g. talc, calcium stearate, magnesium stearate, solid polyethylene glycols, sodium lauryl sulfate), and mixtures thereof. In the case of capsules, tablets and pills, the dosage form may comprise buffering agents. The solid dosage forms may also dissolve once they come in contact with liquid such as, but not limited to, *salvia* and bile.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations.

Solid dosage forms may be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Dosage forms for oral delivery may also be chewable or may be suckable (e.g., lozenge form). The chewable dosages forms may be sustained release formulations such as, but not limited to, the sustained release compositions described in International Publication No WO2013082470 and US Publication No US20130142876, each of which is herein incorporated by reference in its entirety. The chewable dosage forms may comprise amphipathic lipids such as, but not limited to, those described in International Publication No WO2013082470 and US Publication No US20130142876, each of which is herein incorporated by reference in its entirety.

Topical or Transdermal Administration

As described herein, compositions containing the nucleic acid molecules, modified nucleic acid molecules or mmRNA of the invention may be formulated for administration topically and/or transdermally. The skin may be an ideal target site for delivery as it is readily accessible. Gene expression may be restricted not only to the skin, potentially avoiding nonspecific toxicity, but also to specific layers and cell types within the skin.

The site of cutaneous expression of the delivered compositions will depend on the route of nucleic acid delivery. Three routes are commonly considered to deliver nucleic acid molecules, modified nucleic acid molecules or mmRNA to the skin: (i) topical application (e.g. for local/regional treatment); (ii) intradermal injection (e.g. for local/regional treatment); and (iii) systemic delivery (e.g. for treatment of dermatologic diseases that affect both cutaneous and extracutaneous regions). Nucleic acid molecules, modified nucleic acid molecules or mmRNA can be delivered to the skin by several different approaches known in the art. Most topical delivery approaches have been shown to work for delivery of DNA, such as but not limited to, topical application of non-cationic liposome—DNA complex, cationic liposome—DNA complex, particle-mediated (gene gun), puncture-mediated gene transfections, and viral delivery approaches. After delivery of the nucleic acid, gene products have been detected in a number of different skin cell types, including, but not limited to, basal keratinocytes, sebaceous gland cells, dermal fibroblasts and dermal macrophages.

Ointments, creams and gels for topical administration, can, for example, can be formulated with an aqueous or oily base with the addition of suitable thickening and/or gelling agent and/or solvents. Non limiting examples of such bases can thus, for example, include water and/or an oil such as liquid paraffin or a vegetable oil such as *arachis* oil or castor oil, or a solvent such as polyethylene glycol. Various thickening agents and gelling agents can be used depending on the nature of the base. Non-limiting examples of such agents include soft paraffin, aluminum stearate, cetostearyl alcohol, polyethylene glycols, woolfat, beeswax, carboxypolymethylene and cellulose derivatives, and/or glyceryl monostearate and/or non-ionic emulsifying agents.

Lotions for topical administration may be formulated with an aqueous or oily base and will in general also contain one or more emulsifying agents, stabilizing agents, dispersing agents, suspending agents or thickening agents.

In one embodiment, the invention provides for a variety of dressings (e.g., wound dressings) or bandages (e.g., adhesive bandages) for conveniently and/or effectively carrying out methods of the present invention. Typically dressing or bandages may comprise sufficient amounts of pharmaceutical compositions and/or nucleic acid molecules, modified nucleic acid molecules or mmRNA described herein to allow a user to perform multiple treatments of a subject(s).

In one embodiment, the invention provides for the nucleic acid molecules, modified nucleic acid molecules or mmRNA compositions to be delivered in more than one injection.

In one embodiment, before topical and/or transdermal administration at least one area of tissue, such as skin, may be subjected to a device and/or solution which may increase permeability. In one embodiment, the tissue may be subjected to an abrasion device to increase the permeability of the skin (see U.S. Patent Publication No. 20080275468, herein incorporated by reference in its entirety). In another embodiment, the tissue may be subjected to an ultrasound enhancement device. An ultrasound enhancement device may include, but is not limited to, the devices described in U.S. Publication No. 20040236268 and U.S. Pat. Nos. 6,491,657 and 6,234,990; each of which are herein incorporated by reference in their entireties. Methods of enhancing the permeability of tissue are described in U.S. Publication Nos. 20040171980 and 20040236268 and U.S. Pat. No. 6,190,315; each of which are herein incorporated by reference in their entireties.

In one embodiment, a device may be used to increase permeability of tissue before delivering formulations of modified mRNA described herein. The permeability of skin may be measured by methods known in the art and/or described in U.S. Pat. No. 6,190,315, herein incorporated by reference in its entirety. As a non-limiting example, a modified mRNA formulation may be delivered by the drug delivery methods described in U.S. Pat. No. 6,190,315, herein incorporated by reference in its entirety.

In another non-limiting example tissue may be treated with a eutectic mixture of local anesthetics (EMLA) cream before, during and/or after the tissue may be subjected to a device which may increase permeability. Katz et al. (Anesth Analg (2004); 98:371-76; herein incorporated by reference in its entirety) showed that using the EMLA cream in combination with a low energy, an onset of superficial cutaneous analgesia was seen as fast as 5 minutes after a pretreatment with a low energy ultrasound.

In one embodiment, enhancers may be applied to the tissue before, during, and/or after the tissue has been treated to increase permeability. Enhancers include, but are not limited to, transport enhancers, physical enhancers, and cavitation enhancers. Non-limiting examples of enhancers are described in U.S. Pat. No. 6,190,315, herein incorporated by reference in its entirety.

In one embodiment, a device may be used to increase permeability of tissue before delivering formulations of modified mRNA described herein, which may further contain a substance that invokes an immune response. In another non-limiting example, a formulation containing a substance to invoke an immune response may be delivered by the methods described in U.S. Publication Nos. 20040171980 and 20040236268; each of which are herein incorporated by reference in their entireties.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required.

Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 0.1% to about 10% (w/w) active ingredient, although the concentration of active ingredient may be as high as the solubility limit of the active ingredient in the solvent. Formulations for topical administration may further comprise one or more of the additional ingredients described herein.

A pharmaceutical composition for topical administration may comprise at least one inactive ingredient. Any or none of the inactive ingredients used may have been approved by the US Food and Drug Administration (FDA). A non-exhaustive list of inactive ingredients for use in pharmaceutical compositions for topical administration includes alpha-terpineol, alpha-tocopherol, alpha-tocopherol acetate, DL-, alpha-tocopherol, DL-, 1,2,6-hexanetriol, 1-O-tolylbiguanide, 2-ethyl-1,6-hexanediol, acetic acid, acetone, acetylated lanolin alcohols, acrylates copolymer, adhesive tape, alcohol, alcohol, dehydrated, alcohol, denatured, alcohol, diluted, alkyl ammonium sulfonic acid betaine, alkyl aryl sodium sulfonate, allantoin, almond oil, aluminum acetate, aluminum chlorhydroxy allantoinate, aluminum hydroxide, aluminum hydroxide-sucrose, hydrated, aluminum hydroxide gel, aluminum hydroxide gel F 500, aluminum hydroxide gel F 5000, aluminum monostearate, aluminum oxide, aluminum silicate, aluminum starch octenylsuccinate, aluminum stearate, aluminum sulfate anhydrous, amerchol c, amerchol-cab, aminomethylpropanol, ammonia solution, ammonia solution, strong, ammonium hydroxide, ammonium lauryl sulfate, ammonium nonoxynol-4 sulfate, ammonium salt of c-12-c-15 linear primary alcohol ethoxylate, ammonyx, amphoteric-2, amphoteric-9, anhydrous citric acid, anhydrous trisodium citrate, anoxid sbn, antifoam, apricot kernel oil peg-6 esters, aquaphor, arlacel, ascorbic acid, ascorbyl palmitate, beeswax, beeswax, synthetic, beheneth-10, bentonite, benzalkonium chloride, benzoic acid, benzyl alcohol, betadex, boric acid, butane, butyl alcohol, butyl ester of vinyl methyl ether/maleic anhydride copolymer (125000 mw), butyl stearate, butylated hydroxyanisole, butylated hydroxytoluene, butylene glycol, butylparaben, c20-40 pareth-24, calcium chloride, calcium hydroxide, canada balsam, caprylic/capric triglyceride, caprylic/capric/stearic triglyceride, captan, caramel, carbomer 1342, carbomer 1382, carbomer 934, carbomer 934p, carbomer 940, carbomer 941, carbomer 980, carbomer 981, carbomer homopolymer type b (allyl pentaerythritol crosslinked), carbomer homopolymer type c (allyl pentaerythritol crosslinked), carboxy vinyl copolymer, carboxymethylcellulose, carboxymethylcellulose sodium, carboxypolymethylene, carrageenan, carrageenan salt, castor oil, cedar leaf oil, cellulose, cerasynt-se, ceresin, ceteareth-12, ceteareth-15, ceteareth-30, cetearyl alcohol/ceteareth-20, cetearyl ethylhexanoate, ceteth-10, ceteth-2, ceteth-20, ceteth-23, cetostearyl alcohol, cetrimonium chloride, cetyl alcohol, cetyl esters wax, cetyl palmitate, chlorobutanol, chlorocresol, chloroxylenol, cholesterol, choleth-24, citric acid, citric acid monohydrate, cocamide ether sulfate, cocamine oxide, coco betaine, coco diethanolamide, coco monoethanolamide, cocoa butter, coco-glycerides, coconut oil, cocoyl caprylocaprate, collagen, coloring suspension, cream base, creatinine, crospovidone, cyclomethicone, cyclomethicone/dimethicone copolyol, d&c red no. 28, d&c red no. 33, d&c red no. 36, d&c red no. 39, d&c yellow no. 10, decyl methyl sulfoxide, dehydag wax sx, dehydroacetic acid, dehymuls e, denatonium benzoate, dextrin, diazolidinyl urea, dichlorobenzyl alcohol, dichlorodifluoromethane, dichlorotetrafluoroethane, diethanolamine, diethyl sebacate, diethylene glycol monoethyl ether, dihydroxyaluminum aminoacetate, diisopropanolamine, diisopropyl adipate, diisopropyl dilinoleate, dimethicone 350, dimethicone copolyol, dimethicone medical fluid 360, dimethyl isosorbide, dimethyl sulfoxide, dinoseb ammonium salt, disodium cocoamphodiacetate, disodium laureth sulfosuccinate, disodium lauryl sulfosuccinate, dmdm hydantoin, docosanol, docusate sodium, edetate disodium, edetate sodium, edetic acid, entsufon, entsufon sodium, epitetracycline hydrochloride, essence bouquet 9200, ethyl acetate, ethylcelluloses, ethylene glycol, ethylenediamine, ethylenediamine dihydrochloride, ethylhexyl hydroxystearate, ethylparaben, fatty acid pentaerythriol ester, fatty acids, fatty alcohol citrate, fd&c blue no. 1, fd&c red no. 4, fd&c red no. 40, fd&c yellow no. 10 (delisted), fd&c yellow no. 5, fd&c yellow no. 6, ferric oxide, flavor rhodia pharmaceutical no. rf 451, formaldehyde, formaldehyde solution, fractionated coconut oil, fragrance 3949-5, fragrance 520a, fragrance 6.007, fragrance 91-122, fragrance 9128-y, fragrance 93498g, fragrance balsam pine no. 5124, fragrance bouquet 10328, fragrance chemoderm 6401-b, fragrance chemoderm 6411, fragrance cream no. 73457, fragrance cs-28197, fragrance felton 066m, fragrance firmenich 47373, fragrance givaudan ess 9090/1c, fragrance h-6540, fragrance herbal 10396, fragrance nj-1085, fragrance p o fl-147, fragrance pa 52805, fragrance pera derm d, fragrance rbd-9819, fragrance shaw mudge u-7776, fragrance tf 044078, fragrance ungerer honeysuckle k 2771, fragrance ungerer n5195, gelatin, gluconolactone, glycerin, glyceryl citrate, glyceryl isostearate, glyceryl monostearate, glyceryl oleate, glyceryl oleate/propylene glycol, glyceryl palmitate, glyceryl ricinoleate, glyceryl stearate, glyceryl stearate-laureth-23, glyceryl stearate/peg-100 stearate, glyceryl stearate-stearamidoethyl diethylamine, glycol distearate, glycol stearate, guar gum, hair conditioner (18n195-1m), hexylene glycol, high density polyethylene, hyaluronate sodium, hydrocarbon gel, plasticized, hydrochloric acid, hydrochloric acid, diluted, hydrogen peroxide, hydrogenated castor oil, hydrogenated palm/palm kernel oil peg-6 esters, hydroxyethyl cellulose, hydroxymethyl cellulose, hydroxyoctacosanyl hydroxystearate, hydroxypropyl cellulose, hypromelloses, imidurea, irish moss extract, isobutane, isoceteth-20, isooctyl acrylate, isopropyl alcohol, isopropyl isostearate, isopropyl myristate, isopropyl myristate-myristyl alcohol, isopropyl palmitate, isopropyl stearate, isostearic acid, isostearyl alcohol, jelene, kaolin, kathon cg, kathon cg ii, lactate, lactic acid, lactic acid, dl-, laneth, lanolin, lanolin alcohol-mineral oil, lanolin alcohols, lanolin anhydrous, lanolin cholesterols, lanolin, ethoxylated, lanolin, hydrogenated, lauramine oxide, laurdimonium hydrolyzed animal collagen, laureth sulfate, laureth-2, laureth-23, laureth-4, lauric diethanolamide, lauric myristic diethanolamide, lauryl sulfate, *lavandula angustifolia* flowering top, lecithin, lecithin unbleached, lemon oil, light mineral oil, light mineral oil (85 ssu), limonene, (+/−)-, lipocol sc-15, magnesium aluminum silicate, magnesium aluminum silicate hydrate, magnesium nitrate, magnesium stearate, mannitol, maprofix, medical antiform a-f emulsion, menthol, methyl gluceth-10, methyl gluceth-20, methyl gluceth-20 sesquistearate, methyl glucose sesquistearate, methyl salicylate, methyl stearate, methylcelluloses, methylchloroisothiazolinone, methylisothiazolinone, methylparaben, microcrystalline wax, mineral oil, mono and diglyceride, monostearyl citrate, multisterol extract, myristyl alcohol, myristyl lactate, niacinamide, nitric acid, nitrogen, nonoxynol iodine, nonoxynol-15, nonoxynol-9, oatmeal, octadecene-1/maleic acid copolymer, octoxynol-1, octoxynol-9, octyldodecanol, oleic acid, oleth-10/oleth-5, oleth-2, oleth-20, oleyl alcohol, oleyl oleate, olive oil, palmitamine oxide, parabens, paraffin, paraffin, white soft, parfum creme 45/3, peanut oil, peanut oil, refined, pectin, peg 6-32 stearate/glycol stearate, peg-100 stearate, peg-12 glyceryl laurate, peg-120 glyceryl stearate, peg-120 methyl glucose dioleate, peg-15 cocamine, peg-150 distearate, peg-2 stearate, peg-22 methyl ether/dodecyl glycol copolymer, peg-25 propylene glycol stearate, peg-4 dilaurate, peg-4 laurate, peg-45/dodecyl glycol copolymer, peg-5 oleate, peg-50 stearate, peg-54 hydrogenated castor oil, peg-6 isostearate, peg-60 hydrogenated castor oil, peg-7 methyl ether, peg-75 lanolin, peg-8 laurate, peg-8 stearate, pegoxol 7 stearate, pentaerythritol cocoate, peppermint oil, perfume 25677, perfume bouquet, perfume e-1991, perfume gd 5604, perfume tana 90/42 scba, perfume w-1952-1, petrolatum, petrolatum, white, petroleum distillates, phenonip, phenoxyethanol, phenylmercuric acetate, phosphoric acid, pine needle oil (*pinus sylvestris*), plastibase-50w, polidronium chloride, poloxamer 124, poloxamer 181, poloxamer 182, poloxamer 188, poloxamer 237, poloxamer 407, polycarbophil, polyethylene glycol 1000, polyethylene glycol 1450, polyethylene glycol 1500, polyethylene glycol 1540, polyethylene glycol 200, polyethylene glycol 300, polyethylene glycol 300-1600, polyethylene glycol 3350, polyethylene glycol 400, polyethylene glycol 4000, polyethylene glycol 540, polyethylene glycol 600, polyethylene glycol 6000, polyethylene glycol 8000, polyethylene glycol 900, polyhydroxyethyl methacrylate, polyisobutylene, polyisobutylene (1100000 mw), polyoxyethylene-polyoxypropylene 1800, polyoxyethylene alcohols, polyoxyethylene fatty acid esters, polyoxyethylene propylene, polyoxyl 20 cetostearyl ether, polyoxyl 40 hydrogenated castor oil, polyoxyl 40 stearate, polyoxyl 400 stearate, polyoxyl 6 and polyoxyl 32 palmitostearate, polyoxyl distearate, polyoxyl glyceryl stearate, polyoxyl lanolin, polyoxyl stearate, polypropylene, polyquaternium-10, polysorbate 20, polysorbate 40, polysorbate 60, polysorbate 65, polysorbate 80, polyvinyl alcohol, potash, potassium citrate, potassium hydroxide, potassium soap, potassium sorbate, povidone acrylate copolymer, povidone hydrogel, povidone k90, povidone/eicosene copolymer, povidones, ppg-12/smdi copolymer, ppg-15 stearyl ether, ppg-20 methyl glucose ether distearate, ppg-26 oleate, product wat, promulgen d, promulgen g, propane, propellant a-46, propyl gallate, propylene carbonate, propylene glycol, propylene glycol diacetate, propylene glycol dicaprylate, propylene glycol monopalmitostearate, propylene glycol palmitostearate, propylene glycol ricinoleate, propylene glycol/diazolidinyl urea/methylparaben/propylparben, propylparaben, protein hydrolysate, quaternium-15, quaternium-15 cis-form, quaternium-52, saccharin, saccharin sodium, safflower oil, sd alcohol 3a, sd alcohol 40, sd alcohol 40-2, sd alcohol 40b, sepineo p 600, shea butter, silicon, silicon dioxide, silicone, silicone adhesive bio-psa q7-4201, silicone adhesive bio-psa q7-4301, silicone emulsion, simethicone, simethicone emulsion, sipon is 20np, sodium acetate, sodium acetate anhydrous, sodium alkyl sulfate, sodium benzoate, sodium bisulfite, sodium borate, sodium cetostearyl sulfate, sodium chloride, sodium citrate, sodium cocoyl sarcosinate, sodium dodecylbenzenesulfonate, sodium formaldehyde sulfoxylate, sodium hydroxide, sodium iodide, sodium lactate, sodium laureth-2 sulfate, sodium laureth-3 sulfate, sodium laureth-5 sulfate, sodium lauroyl sarcosinate, sodium lauryl sulfate, sodium lauryl sulfoacetate, sodium metabisulfite, sodium phosphate, sodium phosphate, dibasic, sodium phosphate, dibasic, anhydrous, sodium phosphate, dibasic, dihydrate, sodium phosphate, dibasic, heptahydrate, sodium phosphate, monobasic, sodium phosphate, monobasic, anhydrous, sodium phosphate, monobasic, dihydrate, sodium phosphate, monobasic, monohydrate, sodium polyacrylate (2500000 mw), sodium pyrrolidone carboxylate, sodium sulfite, sodium sulfosuccinated undecyclenic monoalkylolamide, sodium thiosulfate, sodium xylenesulfonate, somay 44, sorbic acid, sorbitan, sorbitan isostearate, sorbitan monolaurate, sorbitan monooleate, sorbitan monopalmitate, sorbitan monostearate, sorbitan sesquioleate, sorbitan tristearate, sorbitol, sorbitol solution, soybean flour, soybean oil, spearmint oil, spermaceti, squalane, starch, stearalkonium chloride, stearamidoethyl diethylamine, steareth-10, steareth-100, steareth-2, steareth-20, steareth-21, steareth-40, stearic acid, stearic diethanolamide, stearoxytrimethylsilane, steartrimonium hydrolyzed animal collagen, stearyl alcohol, styrene/isoprene/styrene block copolymer, sucrose, sucrose distearate, sucrose polyesters, sulfacetamide sodium, sulfuric acid, surfactol qs, talc, tall oil, tallow glycerides, tartaric acid, tenox, tenox-2, tert-butyl alcohol, tert-butyl hydroperoxide, thimerosal, titanium dioxide, tocopherol, tocophersolan, trichloromonofluoromethane, trideceth-10, triethanolamine lauryl sulfate, triglycerides, medium chain, trihydroxystearin, trilaneth-4 phosphate, trilaureth-4 phosphate, trisodium citrate dihydrate, trisodium hedta, triton x-200, trolamine, tromethamine, tyloxapol, undecylenic acid, vegetable oil, vegetable oil, hydrogenated, viscarin, vitamin E, wax, emulsifying, wecobee fs, white wax, xanthan gum and zinc acetate.

A pharmaceutical composition for transdermal administration may comprise at least one inactive ingredient. Any or none of the inactive ingredients used may have been approved by the US Food and Drug Administration (FDA). A non-exhaustive list of inactive ingredients for use in pharmaceutical compositions for transdermal administration includes acrylates copolymer, acrylic acid-isooctyl acrylate copolymer, acrylic adhesive 788, adcote 72a103, aerotex resin 3730, alcohol, alcohol, dehydrated, aluminum polyester, bentonite, butylated hydroxytoluene, butylene glycol, butyric acid, caprylic/capric triglyceride, carbomer 1342, carbomer 940, carbomer 980, carrageenan, cetylpyridinium chloride, citric acid, crospovidone, daubert 1-5 pestr (matte) 164z, diethylene glycol monoethyl ether, diethylhexyl phthalate, dimethicone copolyol, dimethicone mdx4-4210, dimethicone medical fluid 360, dimethylaminoethyl methacrylate-butyl methacrylate-methyl methacrylate copolymer, dipropylene glycol, duro-tak 280-2516, duro-tak 387-2516, duro-tak 80-1196, duro-tak 87-2070, duro-tak 87-2194, duro-tak 87-2287, duro-tak 87-2296, duro-tak 87-2888, duro-tak 87-2979, edetate disodium, ethyl acetate, ethyl oleate, ethylcelluloses, ethylene vinyl acetate copolymer, ethylene-propylene copolymer, fatty acid esters, gelva 737, glycerin, glyceryl laurate, glyceryl oleate, heptane, high density polyethylene, hydrochloric acid, hydrogenated polybutene 635-690, hydroxyethyl cellulose, hydroxypropyl cellulose, isopropyl myristate, isopropyl palmitate, lactose, lanolin anhydrous, lauryl lactate, lecithin, levulinic acid, light mineral oil, medical adhesive modified s-15, methyl alcohol, methyl laurate, mineral oil, nitrogen, octisalate, octyldodecanol, oleic acid, oleyl alcohol, oleyl oleate, pentadecalactone, petrolatum, white, polacrilin, polyacrylic acid (250000 mw), polybutene (1400 mw), polyester, polyester polyamine copolymer, polyester rayon, polyethylene terephthalates, polyisobutylene, polyisobutylene (1100000 mw), polyisobutylene (35000 mw), polyisobutylene 178-236, polyisobutylene 241-294, polyisobutylene 35-39, polyisobutylene low molecular weight, polyisobutylene medium molecular weight, polyisobutylene/polybutene adhesive, polypropylene, polyvinyl acetate, polyvinyl alcohol, polyvinyl chloride, polyvinyl chloride-polyvinyl acetate copolymer, polyvinylpyridine, povidone k29/32, povidones, propylene glycol, propylene glycol monolaurate, ra-2397, ra-3011, silicon, silicon dioxide, colloidal, silicone, silicone adhesive 4102, silicone adhesive 4502, silicone adhesive bio-psa q7-4201, silicone adhesive bio-psa q7-4301, silicone/polyester film strip, sodium chloride, sodium citrate, sodium hydroxide, sorbitan monooleate, stearalkonium hectorite/propylene carbonate, titanium dioxide, triacetin, trolamine, tromethamine, union 76 amsco-res 6038 and viscose/cotton.

A pharmaceutical composition for intradermal administration may comprise at least one inactive ingredient. Any or none of the inactive ingredients used may have been approved by the US Food and Drug Administration (FDA). A non-exhaustive list of inactive ingredients for use in pharmaceutical compositions for intradermal administration includes benzalkonium chloride, benzyl alcohol, carboxymethylcellulose sodium, creatinine, edetate disodium, glycerin, hydrochloric acid, metacresol, methylparaben, phenol, polysorbate 80, protamine sulfate, sodium acetate, sodium bisulfite, sodium chloride, sodium hydroxide, sodium phosphate, sodium phosphate, dibasic, sodium phosphate, dibasic, heptahydrate, sodium phosphate, monobasic, anhydrous and zinc chloride.

Depot Administration

As described herein, in some embodiments, the composition is formulated in depots for extended release. Generally, a specific organ or tissue (a "target tissue") is targeted for administration.

In some aspects of the invention, the nucleic acid molecules, modified nucleic acid molecules or mmRNA are spatially retained within or proximal to a target tissue. Provided are method of providing a composition to a target tissue of a mammalian subject by contacting the target tissue (which contains one or more target cells) with the composition under conditions such that the composition, in particular the nucleic acid component(s) of the composition, is substantially retained in the target tissue, meaning that at least 10, 20, 30, 40, 50, 60, 70, 80, 85, 90, 95, 96, 97, 98, 99, 99.9, 99.99 or greater than 99.99% of the composition is retained in the target tissue. Advantageously, retention is determined by measuring the amount of the nucleic acid present in the composition that enters one or more target cells. For example, at least 1, 5, 10, 20, 30, 40, 50, 60, 70, 80, 85, 90, 95, 96, 97, 98, 99, 99.9, 99.99 or greater than 99.99% of the nucleic acids administered to the subject are present intracellularly at a period of time following administration. For example, intramuscular injection to a mammalian subject is performed using an aqueous composition containing a ribonucleic acid and a transfection reagent, and retention of the composition is determined by measuring the amount of the ribonucleic acid present in the muscle cells.

Aspects of the invention are directed to methods of providing a composition to a target tissue of a mammalian subject, by contacting the target tissue (containing one or more target cells) with the composition under conditions such that the composition is substantially retained in the target tissue. The composition contains an effective amount of a nucleic acid molecules or mmRNA such that the polypeptide of interest is produced in at least one target cell. The compositions generally contain a cell penetration agent, although "naked" nucleic acid (such as nucleic acids without a cell penetration agent or other agent) is also contemplated, and a pharmaceutically acceptable carrier.

In some circumstances, the amount of a protein produced by cells in a tissue is desirably increased. Preferably, this increase in protein production is spatially restricted to cells within the target tissue. Thus, provided are methods of increasing production of a protein of interest in a tissue of a mammalian subject. A composition is provided that contains nucleic acid molecules, modified nucleic acid molecule or mmRNA characterized in that a unit quantity of composition has been determined to produce the polypeptide of interest in a substantial percentage of cells contained within a predetermined volume of the target tissue.

In some embodiments, the composition includes a plurality of different nucleic acid molecules, modified nucleic acid molecules or mmRNA, where one or more than one of the nucleic acid molecules, modified nucleic acid molecules or mmRNA encodes a polypeptide of interest. Optionally, the composition also contains a cell penetration agent to assist in the intracellular delivery of the composition. A determination is made of the dose of the composition required to produce the polypeptide of interest in a substantial percentage of cells contained within the predetermined volume of the target tissue (generally, without inducing significant production of the polypeptide of interest in tissue adjacent to the predetermined volume, or distally to the target tissue). Subsequent to this determination, the determined dose is introduced directly into the tissue of the mammalian subject.

In one embodiment, the invention provides for the nucleic acid molecules, modified nucleic acid molecules or mmRNA to be delivered in more than one injection or by split dose injections.

In one embodiment, the invention may be retained near target tissue using a small disposable drug reservoir, patch pump or osmotic pump. Non-limiting examples of patch pumps include those manufactured and/or sold by BD®, (Franklin Lakes, N.J.), Insulet Corporation (Bedford, Mass.), SteadyMed Therapeutics (San Francisco, Calif.), Medtronic (Minneapolis, Minn.) (e.g., MiniMed), UniLife (York, Pa.), Valeritas (Bridgewater, N.J.), and SpringLeaf Therapeutics (Boston, Mass.). A non-limiting example of an osmotic pump include those manufactured by DURECT® (Cupertino, Calif.) (e.g., DUROS® and ALZET®).

Pulmonary Administration

A pharmaceutical composition may be prepared, packaged, and/or sold in a formulation suitable for pulmonary administration via the buccal cavity. Such a formulation may comprise dry particles which comprise the active ingredient and which have a diameter in the range from about 0.5 nm to about 7 nm or from about 1 nm to about 6 nm. Such compositions are suitably in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and active ingredient may constitute 0.1% to 20% (w/w) of the composition. A propellant may further comprise additional ingredients such as a liquid non-ionic and/or solid anionic surfactant and/or a solid diluent (which may have a particle size of the same order as particles comprising the active ingredient).

As a non-limiting example, the nucleic acid molecules, modified nucleic acid molecules or mmRNA described herein may be formulated for pulmonary delivery by the methods described in U.S. Pat. No. 8,257,685; herein incorporated by reference in its entirety.

In one embodiment, the nucleic acid molecules, modified nucleic acid molecules and/or mmRNA described herein may be formulated with or in a lipid carrier vehicle for pulmonary delivery as described in International Patent Publication Nos. WO2013185069 and WO2013182683, the contents of which are herein incorporated by reference in its entirety. As a non-limiting example, the nucleic acid molecules, modified nucleic acid molecules and/or mmRNA may be formulated with or in a lipid carrier vehicle for pulmonary delivery of mRNA to non-lung target cells as described in International Patent Publication No. WO2013185069, the contents of which are herein incorporated by reference in its entirety. The nucleic acid molecules, modified nucleic acid molecules and/or mmRNA may be used to treat any of the diseases or disorders listed in Table 4 of WO2013185069 and/or may encode any of the proteins recited in Tables 1, 2 and/or 3 of WO2013185069. As another non-limiting example, the nucleic acid molecules, modified nucleic acid molecules and/or mmRNA may be formulated with or in a lipid carrier vehicle for pulmonary delivery of mRNA to lung target cells as described in International Patent Publication No. WO2013182683, the contents of which are herein incorporated by reference in its entirety. The nucleic acid molecules, modified nucleic acid molecules and/or mmRNA may be used to treat a pulmonary defects such as, but not limited to, the pulmonary defects recited in International Publication No. WO2013182683 including surfactant protein B (SPB) deficiency, ATP-binding cassette sub-family A member 3 (ABCA3) deficiency, cystic fibrosis, alpha-1 antitrypsin (A1AT) deficiency, lung cancer, surfactant protein C (SPC) deficiency, alveolar proteinosis, sarcoidosis, acute and chronic bronchitis, emphysema, McLeod-Syndrom, chronic obstructive pulmonary disease (COPD), asthma bronchiale, bronchiectasis, pneumoconiosis, asbestosis, Acute Respiratory Distress Syndrome (ARDS), Infant respiratory distress syndrome (IRDS), pulmonary oedema, pulmonary eosinophilia, Loffler's pneumonia, Hamman-Rich syndrome, idiopathic pulmonary fibrosis, interstitial pulmonary diseases, primary ciliary dyskinesia, pulmonary arterial hypertension (PAH) and STAT5b deficiency, clotting defects, especially hemophilia A and B; complement defects, especially protein C deficiency, thrombotic thrombocytopenic purpura and congenital hemochromatosis, especially Hepcidin deficiency; pulmonary infectious diseases, preferably respiratory syncytial virus (RSV) infection, parainfluenza virus (PIV) infection, influenza virus infection, rhinoviruses infection, and severe acute respiratory syndrome (corona virus (SARS-CoV) infection, tuberculosis, *Pseudomonas aeruginosa* infection, *Burkholderia cepacia* infection, Methicillin-Resistant *Staphylococcus aureus* (MRSA) infection, and *Haemophilus influenzae* infection. The nucleic acid molecules, modified nucleic acid molecules and/or mmRNA may encode any of the proteins described in International Publication No. WO2013182683 such as, but not limited to, Cystic fibrosis transmembrane conductance regulator (CFTR), Surfactant Protein B (SPB), ATP-binding cassette subfamily A member 3 (ABCA3) or alpha-1 antitrypsin (A1AT), surfactant protein C (SPC), erythropoietin, Factor VIII, Factor IX, van Willebrand Factor, granulocyte macrophage colony stimulating factor, ADAMTS 13, Hepcidin, angiotensin converting enzyme II or antigens of viral and bacterial pathogens.

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

The compositions and formulations provided herein which may be used for pulmonary delivery may further comprise one or more surfactants. Suitable surfactants or surfactant components for enhancing the uptake of the compositions of the invention include synthetic and natural as well as full and truncated forms of surfactant protein A, surfactant protein B, surfactant protein C, surfactant protein D and surfactant Protein E, di-saturated phosphatidylcholine (other than dipalmitoyl), dipalmitoylphosphatidylcholine, phosphatidylcholine, phosphatidylglycerol, phosphatidylinositol, phosphatidylethanolamine, phosphatidylserine; phosphatidic acid, ubiquinones, lysophosphatidylethanolamine, lysophosphatidylcholine, palmitoyl-lysophosphatidylcholine, dehydroepiandrosterone, dolichols, sulfatidic acid, glycerol-3-phosphate, dihydroxyacetone phosphate, glycerol, glycero-3-phosphocholine, dihydroxyacetone, palmitate, cytidine diphosphate (CDP) diacylglycerol, CDP choline, choline, choline phosphate; as well as natural and artificial lamellar bodies which are the natural carrier vehicles for the components of surfactant, omega-3 fatty acids, polyenic acid, polyenoic acid, lecithin, palmitinic acid, non-ionic block copolymers of ethylene or propylene oxides, polyoxypropylene, monomeric and polymeric, polyoxyethylene, monomeric and polymeric, poly(vinyl amine) with dextran and/or alkanoyl side chains, Brij 35, Triton X-100 and synthetic surfactants ALEC, Exosurf, Survan and Atovaquone, among others. These surfactants can be used either as single or part of a multiple component surfactant in a formulation, or as covalently bound additions to the 5' and/or 3' ends of the nucleic acid component of a pharmaceutical composition herein.

Intranasal, Nasal and Buccal Administration

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

A pharmaceutical composition for inhalation (respiratory) administration may comprise at least one inactive ingredient. Any or none of the inactive ingredients used may have been approved by the US Food and Drug Administration (FDA). A non-exhaustive list of inactive ingredients for use in pharmaceutical compositions for inhalation (respiratory) administration includes acetone sodium bisulfite, acetylcysteine, alcohol, alcohol, dehydrated, ammonia, apaflurane, ascorbic acid, benzalkonium chloride, calcium carbonate, carbon dioxide, cetylpyridinium chloride, chlorobutanol, citric acid, d&c yellow no. 10, dichlorodifluoromethane, dichlorotetrafluoroethane, edetate disodium, edetate sodium, fd&c yellow no. 6, fluorochlorohydrocarbons, gelatin, glycerin, glycine, hydrochloric acid, hydrochloric acid, diluted, lactose, lactose monohydrate, lecithin, lecithin, hydrogenated soy, lecithin, soybean, lysine monohydrate, mannitol, menthol, methylparaben, nitric acid, nitrogen, norflurane, oleic acid, polyethylene glycol 1000, povidone k25, propylene glycol, propylparaben, saccharin, saccharin sodium, silicon dioxide, colloidal, sodium bisulfate, sodium bisulfite, sodium chloride, sodium citrate, sodium hydroxide, sodium lauryl sulfate, sodium metabisulfite, sodium sulfate anhydrous, sodium sulfite, sorbitan trioleate, sulfuric acid, thymol, titanium dioxide, trichloromonofluoromethane, tromethamine and zinc oxide.

A pharmaceutical composition for nasal administration may comprise at least one inactive ingredient. Any or none of the inactive ingredients used may have been approved by the US Food and Drug Administration (FDA). A non-exhaustive list of inactive ingredients for use in pharmaceutical compositions for nasal administration includes acetic acid, alcohol, dehydrated, allyl .alpha.-ionone, anhydrous dextrose, anhydrous trisodium citrate, benzalkonium chloride, benzethonium chloride, benzyl alcohol, butylated hydroxyanisole, butylated hydroxytoluene, caffeine, carbon dioxide, carboxymethylcellulose sodium, cellulose, microcrystalline, chlorobutanol, citric acid, citric acid monohydrate, dextrose, dichlorodifluoromethane, dichlorotetrafluoroethane, edetate disodium, glycerin, glycerol ester of hydrogenated rosin, hydrochloric acid, hypromellose 2910 (15000 mpa·s), methylcelluloses, methylparaben, nitrogen, norflurane, oleic acid, petrolatum, white, phenylethyl alcohol, polyethylene glycol 3350, polyethylene glycol 400, polyoxyl 400 stearate, polysorbate 20, polysorbate 80, potassium phosphate, monobasic, potassium sorbate, propylene glycol, propylparaben, sodium acetate, sodium chloride, sodium citrate, sodium hydroxide, sodium phosphate, sodium phosphate, dibasic, sodium phosphate, dibasic, anhydrous, sodium phosphate, dibasic, dihydrate, sodium phosphate, dibasic, dodecahydrate, sodium phosphate, dibasic, heptahydrate, sodium phosphate, monobasic, anhydrous, sodium phosphate, monobasic, dihydrate, sorbitan trioleate, sorbitol, sorbitol solution, sucralose, sulfuric acid, trichloromonofluoromethane and trisodium citrate dihydrate.

Ophthalmic and Auricular (Otic) Administration

A pharmaceutical composition may be prepared, packaged, and/or sold in a formulation suitable for delivery to and/or around the eye and/or delivery to the ear (e.g., auricular (otic) administration). Non-limiting examples of route of administration for delivery to and/or around the eye include retrobulbar, conjuctival, intracorneal, intraocular, intravitreal, ophthlamic and subconjuctiva. Such formulations may, for example, be in the form of eye drops or ear drops including, for example, a 0.1/1.0% (w/w) solution and/or suspension of the active ingredient in an aqueous or oily liquid excipient. Such drops may further comprise buffering agents, salts, and/or one or more other of any additional ingredients described herein. Other ophthalmically-administrable formulations which are useful include those which comprise the active ingredient in microcrystalline form and/or in a liposomal preparation. Ear drops and/or eye drops are contemplated as being within the scope of this invention. A multilayer thin film device may be prepared to contain a pharmaceutical composition for delivery to the eye and/or surrounding tissue.

A pharmaceutical composition for ophthalmic administration may comprise at least one inactive ingredient. Any or none of the inactive ingredients used may have been approved by the US Food and Drug Administration (FDA). A non-exhaustive list of inactive ingredients for use in pharmaceutical compositions for ophthalmic administration includes acetic acid, alcohol, alcohol, dehydrated, alginic acid, amerchol-cab, ammonium hydroxide, anhydrous trisodium citrate, antipyrine, benzalkonium chloride, benzethonium chloride, benzododecinium bromide, boric acid, caffeine, calcium chloride, carbomer 1342, carbomer 934p, carbomer 940, carbomer homopolymer type b (allyl pentaerythritol crosslinked), carboxymethylcellulose sodium, castor oil, cetyl alcohol, chlorobutanol, chlorobutanol, anhydrous, cholesterol, citric acid, citric acid monohydrate, creatinine, diethanolamine, diethylhexyl phthalate, divinylbenzene styrene copolymer, edetate disodium, edetate disodium anhydrous, edetate sodium, ethylene vinyl acetate copolymer, gellan gum (low acyl), glycerin, glyceryl stearate, high density polyethylene, hydrocarbon gel, plasticized, hydrochloric acid, hydrochloric acid, diluted, hydroxyethyl cellulose, hydroxypropyl methylcellulose 2906, hypromellose 2910 (15000 mpa·s), hypromelloses, jelene, lanolin, lanolin alcohols, lanolin anhydrous, lanolin nonionic derivatives, lauralkonium chloride, lauroyl sarcosine, light mineral oil, magnesium chloride, mannitol, methylcellulose (4000 mpa·s), methylcelluloses, methylparaben, mineral oil, nitric acid, nitrogen, nonoxynol-9, octoxynol-40, octylphenol polymethylene, petrolatum, petrolatum, white, phenylethyl alcohol, phenylmercuric acetate, phenylmercuric nitrate, phosphoric acid, polidronium chloride, poloxamer 188, poloxamer 407, polycarbophil, polyethylene glycol 300, polyethylene glycol 400, polyethylene glycol 8000, polyoxyethylene-polyoxypropylene 1800, polyoxyl 35 castor oil, polyoxyl 40 hydrogenated castor oil, polyoxyl 40 stearate, polypropylene glycol, polysorbate 20, polysorbate 60, polysorbate 80, polyvinyl alcohol, potassium acetate, potassium chloride, potassium phosphate, monobasic, potassium sorbate, povidone k29/32, povidone k30, povidone k90, povidones, propylene glycol, propylparaben, soda ash, sodium acetate, sodium bisulfate, sodium bisulfite, sodium borate, sodium borate decahydrate, sodium carbonate, sodium carbonate monohydrate, sodium chloride, sodium citrate, sodium hydroxide, sodium metabisulfite, sodium nitrate, sodium phosphate, sodium phosphate dihydrate, sodium phosphate, dibasic, sodium phosphate, dibasic, anhydrous, sodium phosphate, dibasic, dihydrate, sodium phosphate, dibasic, heptahydrate, sodium phosphate, monobasic, sodium phosphate, monobasic, anhydrous, sodium phosphate, monobasic, dihydrate, sodium phosphate, monobasic, monohydrate, sodium sulfate, sodium sulfate anhydrous, sodium sulfate decahydrate, sodium sulfite, sodium thiosulfate, sorbic acid, sorbitan monolaurate, sorbitol, sorbitol solution, stabilized oxychloro complex, sulfuric acid, thimerosal, titanium dioxide, tocophersolan, trisodium citrate dihydrate, triton 720, tromethamine, tyloxapol and zinc chloride.

A pharmaceutical composition for retrobulbar administration may comprise at least one inactive ingredient. Any or none of the inactive ingredients used may have been approved by the US Food and Drug Administration (FDA). A non-exhaustive list of inactive ingredients for use in pharmaceutical compositions for retrobulbar administration includes hydrochloric acid and sodium hydroxide.

A pharmaceutical composition for intraocular administration may comprise at least one inactive ingredient. Any or none of the inactive ingredients used may have been approved by the US Food and Drug Administration (FDA). A non-exhaustive list of inactive ingredients for use in pharmaceutical compositions for intraocular administration includes benzalkonium chloride, calcium chloride, citric acid monohydrate, hydrochloric acid, magnesium chloride, polyvinyl alcohol, potassium chloride, sodium acetate, sodium chloride, sodium citrate and sodium hydroxide.

A pharmaceutical composition for intravitreal administration may comprise at least one inactive ingredient. Any or none of the inactive ingredients used may have been approved by the US Food and Drug Administration (FDA). A non-exhaustive list of inactive ingredients for use in pharmaceutical compositions for intravitreal administration includes calcium chloride, carboxymethylcellulose sodium, cellulose, microcrystalline, hyaluronate sodium, hydrochloric acid, magnesium chloride, magnesium stearate, polysorbate 80, polyvinyl alcohol, potassium chloride, sodium acetate, sodium bicarbonate, sodium carbonate, sodium chloride, sodium hydroxide, sodium phosphate dibasic heptahydrate, sodium phosphate monobasic monohydrate and trisodium citrate dehydrate.

A pharmaceutical composition for subconjunctival administration may comprise at least one inactive ingredient. Any or none of the inactive ingredients used may have been approved by the US Food and Drug Administration (FDA). A non-exhaustive list of inactive ingredients for use in pharmaceutical compositions for subconjunctival administration includes benzyl alcohol, hydrochloric acid and sodium hydroxide.

A pharmaceutical composition for auricular administration may comprise at least one inactive ingredient. Any or none of the inactive ingredients used may have been approved by the US Food and Drug Administration (FDA). A non-exhaustive list of inactive ingredients for use in pharmaceutical compositions for auricular administration includes acetic acid, aluminum acetate, aluminum sulfate anhydrous, benzalkonium chloride, benzethonium chloride, benzyl alcohol, boric acid, calcium carbonate, cetyl alcohol, chlorobutanol, chloroxylenol, citric acid, creatinine, cupric sulfate, cupric sulfate anhydrous, edetate disodium, edetic acid, glycerin, glyceryl stearate, hydrochloric acid, hydrocortisone, hydroxyethyl cellulose, isopropyl myristate, lactic acid, lecithin, hydrogenated, methylparaben, mineral oil, petrolatum, petrolatum, white, phenylethyl alcohol, polyoxyl 40 stearate, polyoxyl stearate, polysorbate 20, polysorbate 80, polyvinyl alcohol, potassium metabisulfite, potassium phosphate, monobasic, povidone k90f, povidones, propylene glycol, propylene glycol diacetate, propylparaben, sodium acetate, sodium bisulfite, sodium borate, sodium chloride, sodium citrate, sodium hydroxide, sodium phosphate, dibasic, anhydrous, sodium phosphate, dibasic, heptahydrate, sodium phosphate, monobasic, anhydrous, sodium sulfite, sulfuric acid and thimerosal.

Payload Administration: Detectable Agents and Therapeutic Agents

The nucleic acid molecules, modified nucleic acid molecules or mmRNA described herein can be used in a number of different scenarios in which delivery of a substance (the "payload") to a biological target is desired, for example delivery of detectable substances for detection of the target, or delivery of a therapeutic agent. Detection methods can include, but are not limited to, both imaging in vitro and in vivo imaging methods, e.g., immunohistochemistry, bioluminescence imaging (BLI), Magnetic Resonance Imaging (MRI), positron emission tomography (PET), electron microscopy, X-ray computed tomography, Raman imaging, optical coherence tomography, absorption imaging, thermal imaging, fluorescence reflectance imaging, fluorescence microscopy, fluorescence molecular tomographic imaging, nuclear magnetic resonance imaging, X-ray imaging, ultrasound imaging, photoacoustic imaging, lab assays, or in any situation where tagging/staining/imaging is required.

The nucleic acid molecules, modified nucleic acid molecules or mmRNA can be designed to include both a linker and a payload in any useful orientation. For example, a linker having two ends is used to attach one end to the payload and the other end to the nucleobase, such as at the C-7 or C-8 positions of the deaza-adenosine or deaza-guanosine or to the N-3 or C-5 positions of cytosine or uracil. The polynucleotide of the invention can include more than one payload (e.g., a label and a transcription inhibitor), as well as a cleavable linker.

Figure 5:
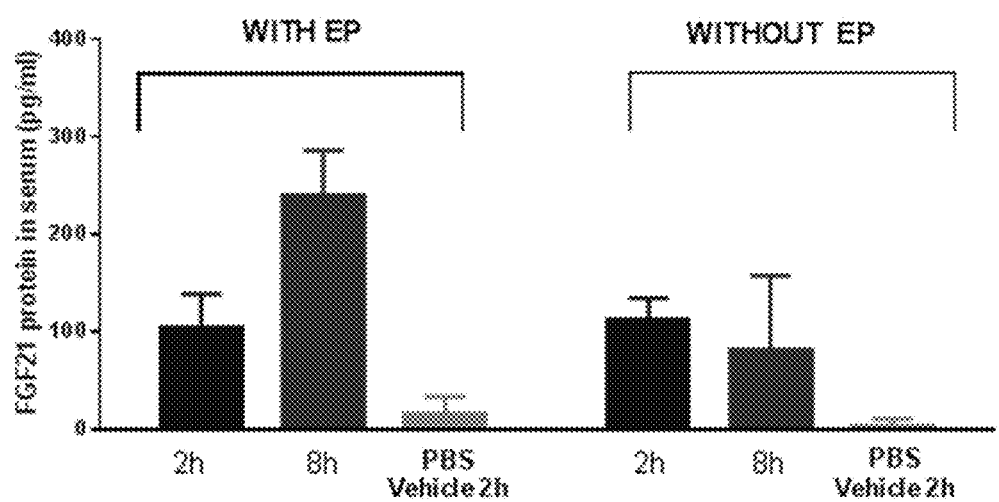
FIG. 5 is a histogram of FGF21 expression after FGF21 mRNA administration with and without electroporation.

In one embodiment, the modified nucleotide is a modified 7-deaza-adenosine triphosphate, where one end of a cleavable linker is attached to the C7 position of 7-deaza-adenine, the other end of the linker is attached to an inhibitor (e.g., to the C5 position of the nucleobase on a cytidine), and a label (e.g., Cy5) is attached to the center of the linker (see, e.g., compound 1 of A*pCp C5 Parg Capless in FIG. 5 and columns 9 and 10 of U.S. Pat. No. 7,994,304, incorporated herein by reference). Upon incorporation of the modified 7-deaza-adenosine triphosphate to an encoding region, the resulting polynucleotide having a cleavable linker attached to a label and an inhibitor (e.g., a polymerase inhibitor). Upon cleavage of the linker (e.g., with reductive conditions to reduce a linker having a cleavable disulfide moiety), the label and inhibitor are released. Additional linkers and payloads (e.g., therapeutic agents, detectable labels, and cell penetrating payloads) are described herein.

Scheme 12 below depicts an exemplary modified nucleotide wherein the nucleobase, adenine, is attached to a linker at the C-7 carbon of 7-deaza adenine. In addition, Scheme 12 depicts the modified nucleotide with the linker and payload, e.g., a detectable agent, incorporated onto the 3' end of the mRNA. Disulfide cleavage and 1,2-addition of the thiol group onto the propargyl ester releases the detectable agent. The remaining structure (depicted, for example, as pApC5Parg in Scheme 12) is the inhibitor. The rationale for the structure of the modified nucleotides is that the tethered inhibitor sterically interferes with the ability of the polymerase to incorporate a second base. Thus, it is critical that the tether be long enough to affect this function and that the inhibitor be in a stereochemical orientation that inhibits or prohibits second and follow on nucleotides into the growing polynucleotide strand.

Scheme 12
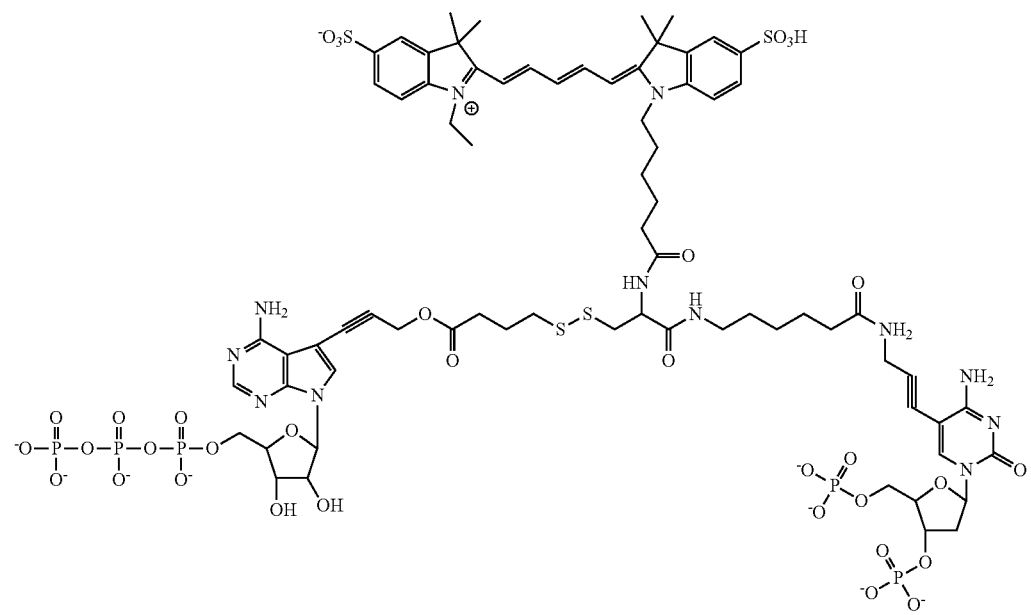
A Capless pCpC5 Parg
↓ incorporation
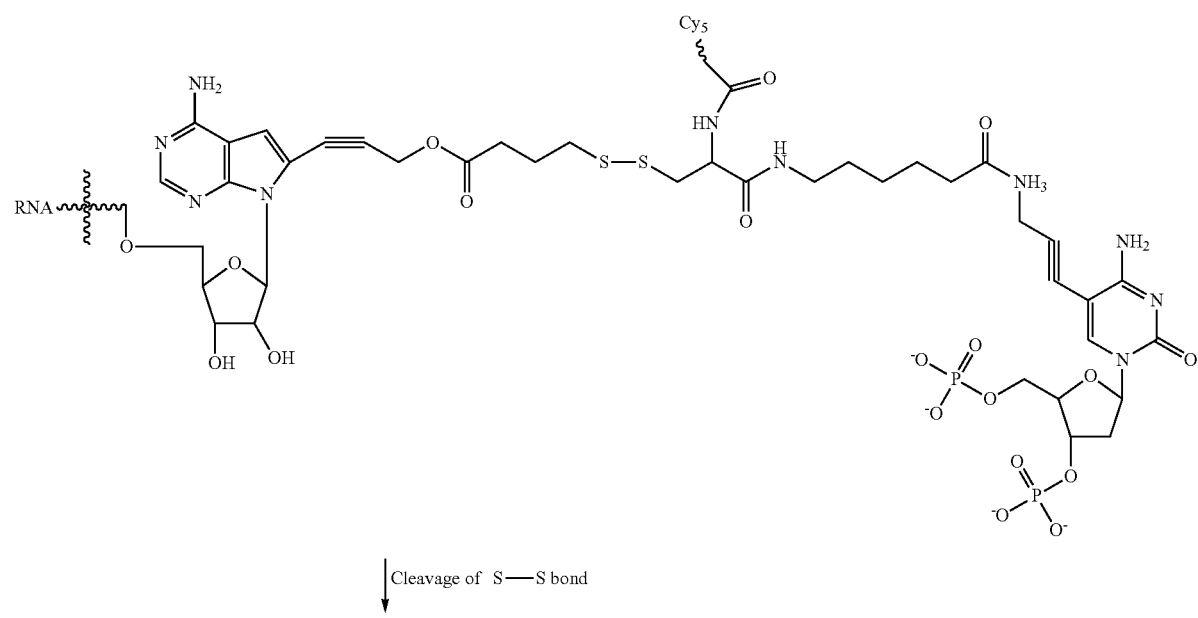
↓ Cleavage of S—S bond

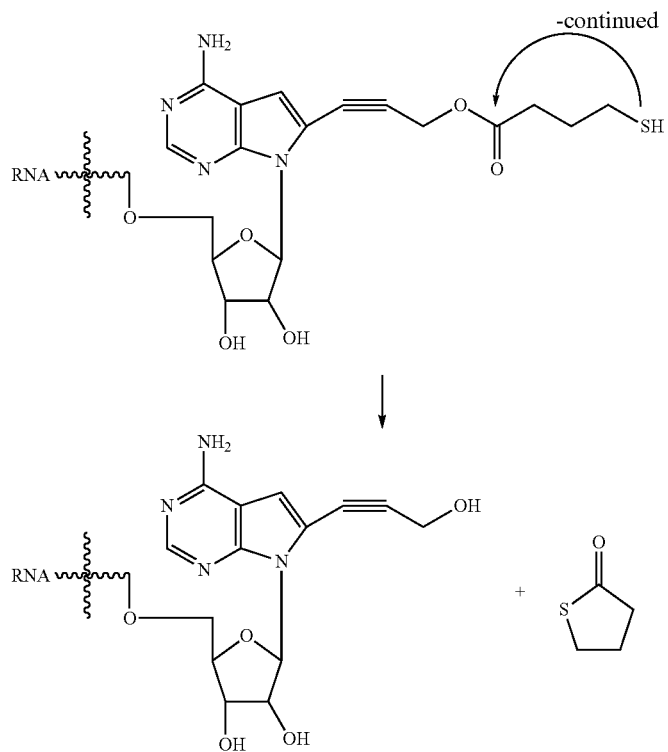

For example, the nucleic acid molecules, modified nucleic acid molecules or mmRNA described herein can be used in reprogramming induced pluripotent stem cells (iPS cells), which can directly track cells that are transfected compared to total cells in the cluster. In another example, a drug that may be attached to the nucleic acid molecules, modified nucleic acid molecules or mmRNA via a linker and may be fluorescently labeled can be used to track the drug in vivo, e.g. intracellularly. Other examples include, but are not limited to, the use of nucleic acid molecules, modified nucleic acid molecules or mmRNA in reversible drug delivery into cells.

The nucleic acid molecules, modified nucleic acid molecules or mmRNA described herein can be used in intracellular targeting of a payload, e.g., detectable or therapeutic agent, to specific organelle. Exemplary intracellular targets can include, but are not limited to, the nuclear localization for advanced mRNA processing, or a nuclear localization sequence (NLS) linked to the mRNA containing an inhibitor.

In addition, the nucleic acid molecules, modified nucleic acid molecules or mmRNA described herein can be used to deliver therapeutic agents to cells or tissues, e.g., in living animals. For example, the nucleic acid molecules, modified nucleic acids or mmRNA described herein can be used to deliver highly polar chemotherapeutics agents to kill cancer cells. The nucleic acid molecules, modified nucleic acid molecules or mmRNA attached to the therapeutic agent through a linker can facilitate member permeation allowing the therapeutic agent to travel into a cell to reach an intracellular target. As a non-limiting example, a peptide or peptide composition may be used to facilitate delivery through the stratum corneum and/or the cellular membrane of viable cells such as the skin permeating and cell entering (SPACE) peptides described in WO2012064429, the contents of which are herein incorporated by reference in its entirety. As another non-limiting example, nanoparticles designed to have enhanced entry into cancerous cells may be used to deliver the nucleic acid molecules, modified nucleic acid molecules and/or mmRNA described herein (see e.g., the nanoparticles with a first shell comprising a first shell substance, a therapeutic agent and an endocytosis-enhancing agent (different from the therapeutic agent) described in International Patent Publication No. WO2013173693, the contents of which are herein incorporated by reference in its entirety).

In one example, the linker is attached at the 2'-position of the ribose ring and/or at the 3' and/or 5' position of the modified nucleic acid molecule or mmRNA (See e.g., International Pub. No. WO2012030683, herein incorporated by reference in its entirety). The linker may be any linker disclosed herein, known in the art and/or disclosed in International Pub. No. WO2012030683, herein incorporated by reference in its entirety.

In another example, the nucleic acid molecules, modified nucleic acid molecules or mmRNA can be attached to the nucleic acid molecules, modified nucleic acid molecules or mmRNA a viral inhibitory peptide (VIP) through a cleavable linker. The cleavable linker can release the VIP and dye into the cell. In another example, the nucleic acid molecules, modified nucleic acid molecules or mmRNA can be attached through the linker to an ADP-ribosylate, which is responsible for the actions of some bacterial toxins, such as cholera toxin, diphtheria toxin, and pertussis toxin. These toxin proteins are ADP-ribosyltransferases that modify target proteins in human cells. For example, cholera toxin ADP-ribosylates G proteins modifies human cells by causing massive fluid secretion from the lining of the small intestine, which results in life-threatening diarrhea.

In some embodiments, the payload may be a therapeutic agent such as a cytotoxin, radioactive ion, chemotherapeutic, or other therapeutic agent. A cytotoxin or cytotoxic agent includes any agent that may be detrimental to cells.

Examples include, but are not limited to, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020 incorporated herein in its entirety), rachelmycin (CC-1065, see U.S. Pat. Nos. 5,475,092, 5,585,499, and 5,846,545, all of which are incorporated herein by reference), and analogs or homologs thereof. Radioactive ions include, but are not limited to iodine (e.g., iodine 125 or iodine 131), strontium 89, phosphorous, palladium, cesium, iridium, phosphate, cobalt, yttrium 90, samarium 153, and praseodymium. Other therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In some embodiments, the payload may be a detectable agent, such as various organic small molecules, inorganic compounds, nanoparticles, enzymes or enzyme substrates, fluorescent materials, luminescent materials (e.g., luminol), bioluminescent materials (e.g., luciferase, luciferin, and aequorin), chemiluminescent materials, radioactive materials (e.g., $^{18}$F, $^{67}$Ga, $^{81m}$Kr, $^{82}$Rb, $^{111}$In, $^{123}$I, $^{133}$Xe, $^{201}$Tl, $^{125}$I, $^{35}$S, $^{14}$C, $^{3}$H, or $^{99m}$Tc (e.g., as pertechnetate (technetate (VII), TcO$_4^-$)), and contrast agents (e.g., gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons). Such optically-detectable labels include for example, without limitation, 4-acetamido-4'-isothiocyanatostilbene-2,2'disulfonic acid; acridine and derivatives (e.g., acridine and acridine isothiocyanate); 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives (e.g., coumarin, 7-amino-4-methylcoumarin (AMC, Coumarin 120), and 7-amino-4-trifluoromethylcoumarin (Coumarin 151)); cyanine dyes; cyanosine; 4',6-diaminidino-2-phenylindole (DAPI); 5' 5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenyl-4'-isothiocyanate (DABITC); eosin and derivatives (e.g., eosin and eosin isothiocyanate); erythrosin and derivatives (e.g., erythrosin B and erythrosin isothiocyanate); ethidium; fluorescein and derivatives (e.g., 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, X-rhodamine-5-(and -6)-isothiocyanate (QFITC or XRITC), and fluorescamine); 2-[2-[3-[[1,3-dihydro-1,1-dimethyl-3-(3-sulfopropyl)-2H-benz[e]indol-2-ylidene]ethylidene]-2-[4-(ethoxycarbonyl)-1-piperazinyl]-1-cyclopenten-1-yl]ethenyl]-1,1-dimethyl-3-(3-sulfopropyl)-1H-benz[e]indolium hydroxide, inner salt, compound with n,n-diethylethanamine(1:1) (IR144); 5-chloro-2-[2-[3-[(5-chloro-3-ethyl-2(3H)-benzothiazol-ylidene)ethylidene]-2-(diphenylamino)-1-cyclopenten-1-yl] ethenyl]-3-ethyl benzothiazolium perchlorate (IR140); Malachite Green isothiocyanate; 4-methylumbelliferone orthocresolphthalein; nitrotyrosine; pararosaniline; Phenol Red; B-phycoerythrin; o-phthaldialdehyde; pyrene and derivatives(e.g., pyrene, pyrene butyrate, and succinimidyl 1-pyrene); butyrate quantum dots; Reactive Red 4 (Ciba-cron™ Brilliant Red 3B-A); rhodamine and derivatives (e.g., 6-carboxy-X-rhodamine (ROX), 6-carboxyrhodamine (R6G), lissamine rhodamine B sulfonyl chloride rhodarnine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'tetramethyl-6-carboxyrhodamine (TAMRA) tetramethyl rhodamine, and tetramethyl rhodamine isothiocyanate (TRITC)); riboflavin; rosolic acid; terbium chelate derivatives; Cyanine-3 (Cy3); Cyanine-5 (Cy5); cyanine-5.5 (Cy5.5), Cyanine-7 (Cy7); IRD 700; IRD 800; Alexa 647; La Jolta Blue; phthalo cyanine; and naphthalo cyanine.

In some embodiments, the detectable agent may be a non-detectable pre-cursor that becomes detectable upon activation (e.g., fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE® (VisEn Medical))). In vitro assays in which the enzyme labeled compositions can be used include, but are not limited to, enzyme linked immunosorbent assays (ELISAs), immunoprecipitation assays, immunofluorescence, enzyme immunoassays (EIA), radioimmunoassays (RIA), and Western blot analysis.

Combinations

The nucleic acid molecules or mmRNA may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that may improve their bioavailability, reduce and/or modify their metabolism, inhibit their excretion, and/or modify their distribution within the body. As a non-limiting example, the nucleic acid molecules or mmRNA may be used in combination with a pharmaceutical agent for the treatment of cancer or to control hyperproliferative cells. In U.S. Pat. No. 7,964,571, herein incorporated by reference in its entirety, a combination therapy for the treatment of solid primary or metastasized tumor is described using a pharmaceutical composition including a DNA plasmid encoding for interleukin-12 with a lipopolymer and also administering at least one anticancer agent or chemotherapeutic. Further, the nucleic acid molecules and mmRNA of the present invention that encodes anti-proliferative molecules may be in a pharmaceutical composition with a lipopolymer (see e.g., U.S. Pub. No.

20110218231, herein incorporated by reference in its entirety, claiming a pharmaceutical composition comprising a DNA plasmid encoding an anti-proliferative molecule and a lipopolymer) which may be administered with at least one chemotherapeutic or anticancer agent (See e.g., the "Combination" Section in U.S. Pat. No. 8,518,907 and International Patent Publication No. WO201218754; the contents of each of which are herein incorporated by reference in its entirety).

The nucleic acid molecules, modified nucleic acid molecules, mmRNA and pharmaceutical formulations thereof may be administered to a subject alone or used in combination with or include one or more other therapeutic agents, for example, anticancer agents. Thus, combinations of nucleic acid molecules, modified nucleic acid molecules and/or mmRNA with other anti-cancer or chemotherapeutic agents are within the scope of the invention. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The nucleic acid molecules, modified nucleic acid molecules and/or mmRNA may also be useful in combination with any therapeutic agent used in the treatment of HCC, for example, but not limitation sorafenib. Nucleic acid molecules, odified nucleic acid molecules and/or mmRNA may be particularly useful when co-administered with radiation therapy.

In certain embodiments, the nucleic acid molecules, modified nucleic acid molecules and/or mmRNA may be useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

Examples of estrogen receptor modulators that can be used in combination with the nucleic acid molecules, modified nucleic acid molecules and/or mmRNA include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

Examples of androgen receptor modulators that can be used in combination with the nucleic acid molecules, modified nucleic acid molecules and/or mmRNA include, but are not limited to, finasteride and other 5α-reductase inhibitors, nilutamide, flutamide, bicalutamide, liarozole, and abiraterone acetate.

Examples of such retinoid receptor modulators that can be used in combination with the nucleic acid molecules, modified nucleic acid molecules and/or mmRNA include, but are not limited to, bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

Examples of cytotoxic agents that can be used in combination with the nucleic acid molecules, modified nucleic acid molecules and/or mmRNA include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound that can be used in combination with the nucleic acid molecules, modified nucleic acid molecules and/or mmRNA is tirapazamine.

Examples of proteasome inhibitors that can be used in combination with the nucleic acid molecules, modified nucleic acid molecules and/or mmRNA include, but are not limited to, lactacystin and bortezomib.

Examples of microtubule inhibitors/microtubule-stabilising agents that can be used in combination with the nucleic acid molecules, modified nucleic acid molecules and/or mmRNA include, but are not limited to, paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors that can be used in combination with the nucleic acid molecules, modified nucleic acid molecules and/or mmRNA include, but are not limited to, are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13 (9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5 aB, 8aa,9b)-9-[2-[N-[2-(dimethylamino)ethyl]-N-methylamino]ethyl]-5-[4-hydrOxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H- pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, that can be used in combination with nucleic acid molecules, modified nucleic acid molecules and/or mmRNA include, but are not limited to, inhibitors described in PCT Publications WO 01/30768, WO 01/98278, WO 03/050,064, WO 03/050,122, WO 03/049,527, WO 03/049,679, WO 03/049,678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" that can be used in combination with nucleic acid molecules, modified nucleic acid molecules and/or mmRNA include, but are not limited to, TSA, oxamflatin, PXD101, MG98, valproic acid and scriptaid. Further reference to other histone deacetylase inhibitors may be found in the following manuscript; Miller, T. A. et al. J. Med. Chem. 46(24):5097-5116 (2003).

Inhibitors of kinases involved in mitotic progression that can be used in combination with nucleic acid molecules, modified nucleic acid molecules and/or mmRNA include, but are not limited to, inhibitors of aurora kinase, inhibitors of Polo-like kinases (PLK) (in particular inhibitors of PLK-1), inhibitors of bub-1 and inhibitors of bub-R1.

Antiproliferative agents that can be used in combination with nucleic acid molecules, modified nucleic acid molecules and/or mmRNA include, but are not limited to, antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl] adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo (7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents that can be used in combination with nucleic acid molecules, modified nucleic acid molecules and/or mmRNA include those therapeutic agents which have cytotoxic agents or radioisotopes attached to a cancer cell specific or target cell specific monoclonal antibody, such as, for example, Bexxar.

Examples of HMG-CoA reductase inhibitors that may be used that can be used in combination with nucleic acid molecules, modified nucleic acid molecules and/or mmRNA include, but are not limited to, lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896) and atorvastatin (LIPITOR®; see U.S. Pat. Nos. 5,273,995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry &Industry, pp. 85-89 (5 Feb. 1996) and U.S. Pat. Nos. 4,782,084 and 4,885,314.

Examples of prenyl-protein transferase inhibitors that can be used in combination with the nucleic acid molecules, modified nucleic acid molecules and/or mmRNA include, but are not limited to, can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

Examples of angiogenesis inhibitors that can be used in combination with nucleic acid molecules, modified nucleic acid molecules and/or mmRNA include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonylgumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis may also be used in combination with nucleic acid molecules, modified nucleic acid molecules and/or mmRNA and include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways that can be used in combination with nucleic acid molecules, modified nucleic acid molecules and/or mmRNA include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002).

Agents that interfere with cell cycle checkpoints that can be used in combination with the compounds of the invention include, but are not limited to, inhibitors of ATR, ATM, the Chk1 and Chk2 kinases and cdkuz and cdc kinase inhibitors and are specifically exemplified by 7-hydroxystaurosporin, flavopiridol, CYC202 (Cyclace1) and BMS-387032.

Agents that interfere with receptor tyrosine kinases (RTKs) that can be used in combination with the nucleic acid molecules, modified nucleic acid molecules and/or mmRNA include, but are not limited to, inhibitors of c-Kit, Eph, PDGF, Flt3 and CTNNB1. Further agents include inhibitors of RTKs as described by Bume-Jensen and Hunter, *Nature*, 411:355-365, 2001.

Inhibitors of cell proliferation and survival signaling pathway that can be used in combination with the nucleic acid molecules, modified nucleic acid molecules and/or mmRNA include, but are not limited to, inhibitors of EGFR (for example gefitinib and erlotinib), inhibitors of ERB-2 (for example trastuzumab), inhibitors of IGFR, inhibitors of cytokine receptors, inhibitors of CTNNB1, inhibitors of PI3K (for example LY294002), serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344), inhibitors of Raf kinase (for example BAY-43-9006), inhibitors of MEK (for example CI-1040 and PD-098059) and inhibitors of mTOR (for example Wyeth CCI-779). Such agents include small molecule inhibitor compounds and antibody antagonists.

Apoptosis inducing agents that can be used in combination with nucleic acid molecules, modified nucleic acid molecules and/or mmRNA include, but are not limited to, activators of TNF receptor family members (including the TRAIL receptors).

NSAIDs that are selective COX-2 inhibitors that can be used in combination with nucleic acid molecules, modified nucleic acid molecules and/or mmRNA include, but are not limited to, those NSAIDs disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272, and U.S. Pat. No. 5,932,598, all of which are hereby incorporated by reference.

Inhibitors of COX-2 that are particularly useful in combination with nucleic acid molecules, modified nucleic acid molecules and/or mmRNA include: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof Compounds that have been described as specific inhibitors of COX-2 and are therefore useful in the present invention include, but are not limited to: parecoxib, CELEBREX® and BEXTRA® or a pharmaceutically acceptable salt thereof.

Angiogenesis inhibitors that can be used in combination with the nucleic acid molecules, modified nucleic acid molecules and/or mmRNA include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)-phenyl]methyl]-1H-1, 2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

Tyrosine kinase inhibitors that can be used in combination with the nucleic acid molecules, modified nucleic acid molecules and/or mmRNA include, but are not limited to, N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6, 7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, imatinib (STI571), CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant compositions and methods. For example, combinations of nucleic acid molecules, modified nucleic acid molecules and/or mmRNA with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 31:909-913 (1998); *J. Biol. Chem.* 274:9116-9121 (1999); *Invest. Ophthalmol Vis. Sci.* 41:2309-2317 (2000)). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 119:709-717 (2001)). Examples of PPAR-γ agonists and PPAR-γ/α agonists that can be used in combination with nucleic acid molecules, modified nucleic acid molecules and/or mmRNA include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the nucleic acid molecules, modified nucleic acid molecules and/or mmRNA in combination with gene therapy for the treatment of cancer. For an overview of genetic strategies to treating cancer see Hall et al. (*Am J Hum Genet* 61:785-789 (1997)) and Kufe et al. (*Cancer Medicine*, 5th Ed, pp 876-889, BC Decker, Hamilton, 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 5(8):1105-13 (1998)), and interferon gamma (*J Immunol* 164:217-222 (2000)).

Nucleic acid molecules, modified nucleic acid molecules and/or mmRNA may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

Nucleic acid molecules, modified nucleic acid molecules and/or mmRNA may be employed in conjunction with anti-emetic agents to treat nausea or emesis, including acute, delayed, late-phase, and anticipatory emesis, which may result from the use of nucleic acid molecules, modified nucleic acid molecules and/or mmRNA, alone or with radiation therapy. For the prevention or treatment of emesis, nucleic acid molecules, modified nucleic acid molecules and/or mmRNA n may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the nucleic acid molecules, modified nucleic acid molecules and/or mmRNA.

Neurokinin-1 receptor antagonists of use in conjunction with nucleic acid molecules, modified nucleic acid molecules and/or mmRNA are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the nucleic acid molecules, modified nucleic acid molecules and/or mmRNA is selected from: 2-(R)-(1-(R)-(3,5-bis(trifluoromethyl)-phenyl) ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

Nucleic acid molecules, modified nucleic acid molecules and/or mmRNA may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

Nucleic acid molecules, modified nucleic acid molecules and/or mmRNA may also be administered with an agent useful in the treatment of anemia. Such an anemia treatment agent is, for example, a continuous eythropoiesis receptor activator (such as epoetin alfa).

Nucleic acid molecules, modified nucleic acid molecules and/or mmRNA may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim and PEG-filgrastim.

Nucleic acid molecules, modified nucleic acid molecules and/or mmRNA may also be administered with an immunologic-enhancing drug, such as levamisole, isoprinosine and Zadaxin.

Nucleic acid molecules, modified nucleic acid molecules and/or mmRNA may also be useful for treating or preventing breast cancer in combination with aromatase inhibitors. Examples of aromatase inhibitors include but are not limited to: anastrozole, letrozole and exemestane.

Nucleic acid molecules, modified nucleic acid molecules and/or mmRNA may also be useful for treating or preventing cancer in combination with other nucleic acid therapeutics.

Nucleic acid molecules, modified nucleic acid molecules and/or mmRNA may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

Nucleic acid molecules, modified nucleic acid molecules and/or mmRNA may also be useful for treating or preventing cancer in combination with PARP inhibitors.

Nucleic acid molecules, modified nucleic acid molecules and/or mmRNA may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); brefeldin A; busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex); cetuximab (Erbitux®); chlorambucil (Leukeran®); cisplatin (Platinol®); cladribine (Leustatin 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®); didemnin B; 17-DMAG; docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); eculizumab injection (Soliris®); Elliott's B Solution (Elliott's B Solution®); eltrombopag (Promacta®); epirubicin (Ellence®); Epoetin alfa (Epogen®); erlotinib (Tarceva®); estramustine (Emcyt®); ethinyl estradiol; etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); geldanamycin; gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); iobenguane 1123 injection (AdreView®); irinotecan (Camptosar®); ixabepilone (Ixempra®); lapatinib tablets (Tykerb®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); 8-methoxypsoralen; mitomycin C (Mutamycin®); mitotane (Lysodren®); mitoxantrone (Novantrone®); mitramycin; nandrolone phenpropionate (Durabolin-50); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrienttm®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); rapamycin; Rasburicase (Elitek®); raloxifene hydrochloride (Evista®); Rituximab (Rituxan®); romidepsin (Istodax®); romiplostim (Nplate®); sargramostim (Leukine®); Sargramostim (Prokine); sorafenib (Nexavar); streptozocin (Zanosar®); sunitinib maleate (Sutent); talc (Sclerosol); tamoxifen (Nolvadex); temozolomide (Temodar); temsirolimus (Torisel); teniposide, VM-26 (Vumon®); testolactone (Teslac®); thioguanine, 6-TG (Thioguanine®); thiopurine; thiotepa (Thioplex®); topotecan (Hycamtin®); toremifene (Fareston); Tositumomab (Bexxar); Tositumomab/I-131 tositumomab (Bexxar®); trans-retinoic acid; Trastuzumab (Herceptin®); tretinoin, ATRA (Vesanoid®); triethylenemelamine; Uracil Mustard (Uracil Mustard Capsules®); valrubicin (Valstar®); vinblastine (Velban®); vincristine (Oncovin®); vinorelbine (Navelbine®); vorinostat (Zolinza®); wortmannin; and zoledronate (Zometa®).

The combinations referred to above can conveniently be presented for use in the form of a pharmaceutical formulation and thus pharmaceutical compositions comprising a combination as defined above together with a pharmaceutically acceptable diluent or carrier represent a further aspect of the invention.

The individual compounds of such combinations can be administered either sequentially or simultaneously in separate or combined pharmaceutical formulations. In one embodiment, the individual compounds will be administered simultaneously in a combined pharmaceutical formulation.

Cell Penetrating Payloads

In some embodiments, the modified nucleotides and modified nucleosides, which are incorporated into a nucleic acid, e.g., RNA or mRNA, can also include a payload that can be a cell penetrating moiety or agent that enhances intracellular delivery of the compositions. For example, the compositions can include, but are not limited to, a cell-penetrating peptide sequence that facilitates delivery to the intracellular space, e.g., HIV-derived TAT peptide, penetratins, transportans, or hCT derived cell-penetrating peptides, see, e.g., Caron et al., (2001) Mol Ther. 3(3):310-8; Langel, Cell-Penetrating Peptides: Processes and Applications (CRC Press, Boca Raton Fla. 2002); El-Andaloussi et al., (2005) Curr Pharm Des. 11(28):3597-611; and Deshayes et al., (2005) Cell Mol Life Sci. 62(16):1839-49; all of which are incorporated herein by reference. The compositions can also be formulated to include a cell penetrating agent, e.g., liposomes, which enhance delivery of the compositions to the intracellular space.

Biological Targets

The nucleic acid molecules and modified nucleic acid molecules described herein, e.g., RNA or mRNA, can be used to deliver a payload to any biological target for which a specific ligand exists or can be generated. The ligand can bind to the biological target either covalently or non-covalently.

Examples of biological targets include, but are not limited to, biopolymers, e.g., antibodies, nucleic acids such as RNA and DNA, proteins, enzymes; examples of proteins include, but are not limited to, enzymes, receptors, and ion channels. In some embodiments the target may be a tissue- or a cell-type specific marker, e.g., a protein that is expressed specifically on a selected tissue or cell type. In some embodiments, the target may be a receptor, such as, but not limited to, plasma membrane receptors and nuclear receptors; more specific examples include, but are not limited to, G-protein-coupled receptors, cell pore proteins, transporter proteins, surface-expressed antibodies, HLA proteins, MHC proteins and growth factor receptors.

Dosing

The present invention provides methods comprising administering modified mRNAs and their encoded proteins or complexes in accordance with the invention to a subject in need thereof. Nucleic acids, proteins or complexes, or pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like. Compositions in accordance with the invention are typically formulated in dosage unit form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In certain embodiments, compositions in accordance with the present invention may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect (see e.g., the range of unit doses described in International Publication No WO2013078199, the contents of which is herein incorporated by reference in its entirety). The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

According to the present invention, administration of nucleic acid molecules, modified nucleic acid molecules mmRNA in split-dose regimens produce higher levels of proteins in mammalian subjects. As used herein, a "split dose" is the division of single unit dose or total daily dose into two or more doses, e.g., two or more administrations of the single unit dose. As used herein, a "single unit dose" is a dose of any therapeutic administered in one dose/at one time/single route/single point of contact, i.e., single administration event. As used herein, a "total daily dose" is an amount given or prescribed in 24 hr period. It may be administered as a single unit dose. In one embodiment, the nucleic acid molecules, modified nucleic acid molecules or mmRNA of the present invention are administered to a subject in split doses. The nucleic acid molecules, modified nucleic acid molecules or mmRNA may be formulated in buffer only or in a formulation described herein.

Dosage Forms

A pharmaceutical composition described herein can be formulated into a dosage form described herein, such as a topical, intranasal, intratracheal, or injectable (e.g., intravenous, intraocular, intravitreal, intramuscular, intracardiac, intraperitoneal, subcutaneous).

Liquid Dosage Forms

Liquid dosage forms for parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art including, but not limited to, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In certain embodiments for parenteral administration, compositions may be mixed with solubilizing agents such as CREMO-PHOR, alcohols, oils, modified oils, glycols, polysorbates, cyclodextrins, polymers, and/or combinations thereof.

Injectable

Injectable preparations, for example, sterile injectable aqueous or oleaginous suspensions may be formulated according to the known art and may include suitable dispersing agents, wetting agents, and/or suspending agents. Sterile injectable preparations may be sterile injectable solutions, suspensions, and/or emulsions in nontoxic parenterally acceptable diluents and/or solvents, for example, a solution in 1,3-butanediol. Among the acceptable vehicles and solvents that may be employed include, but are not limited to, water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it may be desirable to slow the absorption of the active ingredient from subcutaneous or intramuscular injection. This may be accomplished by the use of a liquid suspension of crystalline or amorphous material with poor water solubility. The rate of absorption of modified mRNA then depends upon its rate of dissolution which, in turn, may depend upon crystal size and crystalline form. Alternatively, delayed absorption of a parenterally administered modified mRNA may be accomplished by dissolving or suspending the modified mRNA in an oil vehicle. Injectable depot forms are made by forming microencapsule matrices of the modified mRNA in biodegradable polymers such as polylactide-polyglycolide. Depending upon the ratio of modified mRNA to polymer and the nature of the particular polymer employed, the rate of modified mRNA release can be controlled. Examples of other biodegradable polymers include, but are not limited to, poly(orthoesters) and poly(anhydrides). Depot injectable formulations may be prepared by entrapping the modified mRNA in liposomes or microemulsions which are compatible with body tissues.

Localized injection of naked DNA was demonstrated intramuscularly in 1990 and later was injected into several other tissues including liver, skin and brain. The uptake of the DNA was mostly localized in the area of the needle track. Different agents may be used to enhance overall gene expression. In one embodiment, the nucleic acid molecules, modified nucleic acid molecules and/or mmRNA may be administered with an agent to enhance expression. Non-limiting examples of agents include transferrin, water-immiscible solvents, nonionic polymers, surfactants, and nuclease inhibitors.

A needle-free delivery method known as jet injection may be used to deliver a drug to a tissue. The jet injection method uses a high-speed ultrafine stream of solution driven by a pressurized gas. The penetration power of this method may be adjusted by altering the gas pressure and the mechanical properties of the target tissue. As a non-limiting example, the solution may include the nucleic acid molecules, modified nucleic acid molecules and/or mmRNA described herein. The solution (approximately 3-5 ul) may be loaded into the jet injection device and administered to a tissue at a pressure of approximately 1-3 bars. Commerical liquid jet injectors include, but are not limited to, Vitaject and bioject 2000 (Bioject), Advantagect (Activa systems), Injex 30 (Injex equidyne) and Mediject VISION (Antares Pharma).

Microneedles may be used to inject the nucleic acid molecules, modified nucleic acid molecules, mmRNA and formulations thereof described herein. Microneedles are an array of microstructured projections which can be coated with a drug that can be administered to a subject to provide delivery of therapeutic agents (e.g., nucleic acid molecules, modified nucleic acid molecules and/or mmRNA) within the epidermis. Microneedles can be approximately 1 um in diameter and from about 1 um to about 100 um (e.g., about 1 um, about 2 um, about 3 um, about 4 um, about 5 um, about 6 um, about 7 um, about 8 um, about 9 um, about 10 um, about 12 um, about 14 um, about 15 um, about 16 um, about 18 um, about 20 um, about 25 um, about 30 um, about 35 um, about 40 um, about 45 um, about 50 um, about 55 um, about 60 um, about 65 um, about 70 um about 75 um, about 80 um, about 85 um, about 90 um, about 95 um, or about 100 um) in length. The material used to make microneedles may be, but is not limited to, metals, silicon, silicon dioxide, polymers, glass and other materials and the material selected may depend on the type of agent to be delivered and the tissue contacted. In one embodiment, the miconeedles may be solid and may either be straight, bend or filtered. In one embodiment, the miconeedles may be hollow and may either be straight, bend or filtered.

Pulmonary

Formulations described herein as being useful for pulmonary delivery may also be used for intranasal delivery of a pharmaceutical composition. Another formulation suitable for intranasal administration may be a coarse powder comprising the active ingredient and having an average particle from about 0.2 um to 500 μm. Such a formulation may be administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, contain about 0.1% to 20% (w/w) active ingredient, where the balance may comprise an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

General considerations in the formulation and/or manufacture of pharmaceutical agents may be found, for example, in Remington: The Science and Practice of Pharmacy 21$^{st}$ ed., Lippincott Williams & Wilkins, 2005 (incorporated herein by reference in its entirety).

Coatings or Shells

Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Multi-Dose and Repeat-Dose Administration

In some embodiments, compounds and/or compositions of the present invention may be administered in two or more doses (referred to herein as "multi-dose administration"). Such doses may comprise the same components or may comprise components not included in a previous dose. Such doses may comprise the same mass and/or volume of components or an altered mass and/or volume of components in comparison to a previous dose. In some embodiments, multi-dose administration may comprise repeat-dose administration. As used herein, the term "repeat-dose administration" refers to two or more doses administered consecutively or within a regimen of repeat doses comprising substantially the same components provided at substantially the same mass and/or volume. In some embodiments, subjects may display a repeat-dose response. As used herein, the term "repeat-dose response" refers to a response in a subject to a repeat-dose that differs from that of another dose administered within a repeat-dose administration regimen. In some embodiments, such a response may be the expression of a protein in response to a repeat-dose comprising mRNA. In such embodiments, protein expression may be elevated in comparison to another dose administered within a repeat-dose administration regimen or protein expression may be reduced in comparison to another dose administered within a repeat-dose administration regimen. Alteration of protein expression may be from about 1% to about 20%, from about 5% to about 50% from about 10% to about 60%, from about 25% to about 75%, from about 40% to about 100% and/or at least 100%. A reduction in expression of mRNA administered as part of a repeat-dose regimen, wherein the level of protein translated from the administered RNA is reduced by more than 40% in comparison to another dose within the repeat-dose regimen is referred to herein as "repeat-dose resistance".

Properties of the Pharmaceutical Compositions

The pharmaceutical compositions described herein can be characterized by one or more of the following properties:

Bioavailability

The nucleic acid molecules, modified nucleic acid molecules and mmRNA, when formulated into a composition with a delivery agent as described herein, can exhibit an increase in bioavailability as compared to a composition lacking a delivery agent as described herein. As used herein, the term "bioavailability" refers to the systemic availability of a given amount of a nucleic acid molecule or modified nucleic acid molecule administered to a mammal. Bioavailability can be assessed by measuring the area under the curve (AUC) or the maximum serum or plasma concentration ($C_{max}$) of the unchanged form of a compound following administration of the compound to a mammal. AUC is a determination of the area under the curve plotting the serum or plasma concentration of a compound along the ordinate (Y-axis) against time along the abscissa (X-axis). Generally, the AUC for a particular compound can be calculated using methods known to those of ordinary skill in the art and as described in G. S. Banker, Modern Pharmaceutics, Drugs and the Pharmaceutical Sciences, v. 72, Marcel Dekker, New York, Inc., 1996, herein incorporated by reference in its entirety.

The $C_{max}$ value is the maximum concentration of the compound achieved in the serum or plasma of a mammal following administration of the compound to the mammal. The $C_{max}$ value of a particular compound can be measured using methods known to those of ordinary skill in the art. The phrases "increasing bioavailability" or "improving the pharmacokinetics," as used herein mean that the systemic availability of a first nucleic acid molecule or modified nucleic acid molecule, measured as AUC, $C_{max}$, or $C_{min}$ in a mammal is greater, when co-administered with a delivery agent as described herein, than when such co-administration does not take place. In some embodiments, the bioavailability of the nucleic acid molecule or modified nucleic acid molecule can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

In some embodiments, liquid formulations of nucleic acid molecules or modified mRNA may have varying in vivo half-life, requiring modulation of doses to yield a therapeutic effect. To address this, in some embodiments of the present invention, nucleic acid molecule or modified mRNA formulations may be designed to improve bioavailability and/or therapeutic effect during repeat administrations. Such formulations may enable sustained release of mRNA and/or reduce mRNA degradation rates by nucleases. In some embodiments, suspension formulations are provided comprising modified mRNA, water immiscible oil depots, surfactants and/or co-surfactants and/or co-solvents. Combinations of oils and surfactants may enable suspension formulation with mRNA. Delivery of nucleic acid molecules or modified nucleic acid molecules or modified mRNA in a water immiscible depot may be used to improve bioavailability through sustained release of mRNA from the depot to the surrounding physiologic environment and/or prevent mRNA degradation by nucleases.

In some embodiments, cationic nanoparticles comprising combinations of divalent and monovalent cations may be formulated with nucleic acid molecules, modified nucleic acid molecules or modified mRNA. Such nanoparticles may form spontaneously in solution over a given period (e.g. hours, days, etc). Such nanoparticles do not form in the presence of divalent cations alone or in the presence of monovalent cations alone. The delivery of mRNA in cationic nanoparticles or in one or more depot comprising cationic nanoparticles may improve mRNA bioavailability by acting as a long-acting depot and/or reducing the rate of degradation by nucleases.

Therapeutic Window

The nucleic acid molecules, modified nucleic acid molecules and mmRNA when formulated into a composition with a delivery agent as described herein, can exhibit an increase in the therapeutic window of the administered nucleic acid molecule or modified nucleic acid molecule composition as compared to the therapeutic window of the administered nucleic acid molecule or modified nucleic acid molecule composition lacking a delivery agent as described herein. As used herein "therapeutic window" refers to the range of plasma concentrations, or the range of levels of therapeutically active substance at the site of action, with a high probability of eliciting a therapeutic effect. In some embodiments, the therapeutic window of the modified nucleic acid molecule when co-administered with a delivery agent as described herein can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Volume of Distribution

The nucleic acid molecules or modified nucleic acid molecules, when formulated into a composition with a delivery agent as described herein, can exhibit an improved volume of distribution ($V_{dist}$), e.g., reduced or targeted, relative to a modified nucleic acid molecule composition lacking a delivery agent as described herein. The volume of distribution ($V_{dist}$) relates the amount of the drug in the body to the concentration of the drug in the blood or plasma. As used herein, the term "volume of distribution" refers to the fluid volume that would be required to contain the total amount of the drug in the body at the same concentration as in the blood or plasma: $V_{dist}$ equals the amount of drug in the body/concentration of drug in blood or plasma. For example, for a 10 mg dose and a plasma concentration of 10 mg/L, the volume of distribution would be 1 liter. The volume of distribution reflects the extent to which the drug is present in the extravascular tissue. A large volume of distribution reflects the tendency of a compound to bind to the tissue components compared with plasma protein binding. In a clinical setting, $V_{dist}$ can be used to determine a loading dose to achieve a steady state concentration. In some embodiments, the volume of distribution of the nucleic acid molecule or modified nucleic acid molecule when co-administered with a delivery agent as described herein can decrease at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%.

Biological Effect

In one embodiment, the biological effect of the nucleic acid molecules, modified nucleic acid molecules or modified mRNA delivered to the animals may be categorized by analyzing the protein expression in the animals. The protein expression may be determined from analyzing a biological sample collected from a mammal administered the nucleic acid molecules, modified nucleic acid molecules or modified mRNA of the present invention. In one embodiment, the expression protein encoded by the nucleic acid molecules, modified nucleic acid molecules or modified mRNA administered to the mammal of at least 50 pg/ml may be preferred. For example, a protein expression of 50-200 pg/ml for the protein encoded by the nucleic acid molecules, modified nucleic acid molecules or modified mRNA delivered to the mammal may be seen as a therapeutically effective amount of protein in the mammal.

Detection of Nucleic Acid Molecules or Modified Nucleic Acids by Mass Spectrometry Mass spectrometry (MS) is an analytical technique that can provide structural and molecular mass/concentration information on molecules after their conversion to ions. The molecules are first ionized to acquire positive or negative charges and then they travel through the mass analyzer to arrive at different areas of the detector according to their mass/charge (m/z) ratio.

Mass spectrometry is performed using a mass spectrometer which includes an ion source for ionizing the fractionated sample and creating charged molecules for further analysis. For example ionization of the sample may be performed by electrospray ionization (ESI), atmospheric pressure chemical ionization (APCI), photoionization, electron ionization, fast atom bombardment (FAB)/liquid secondary ionization (LSIMS), matrix assisted laser desorption/ionization (MALDI), field ionization, field desorption, thermospray/plasmaspray ionization, and particle beam ionization. The skilled artisan will understand that the choice of ionization method can be determined based on the analyte to be measured, type of sample, the type of detector, the choice of positive versus negative mode, etc.

After the sample has been ionized, the positively charged or negatively charged ions thereby created may be analyzed to determine a mass-to-charge ratio (i.e., m/z). Suitable analyzers for determining mass-to-charge ratios include quadropole analyzers, ion traps analyzers, and time-of-flight analyzers. The ions may be detected using several detection modes. For example, selected ions may be detected (i.e., using a selective ion monitoring mode (SIM)), or alternatively, ions may be detected using a scanning mode, e.g., multiple reaction monitoring (MRM) or selected reaction monitoring (SRM).

Liquid chromatography-multiple reaction monitoring (LC-MS/MRM) coupled with stable isotope labeled dilution of peptide standards has been shown to be an effective method for protein verification (e.g., Keshishian et al., Mol Cell Proteomics 2009 8: 2339-2349; Kuhn et al., Clin Chem 2009 55:1108-1117; Lopez et al., Clin Chem 2010 56:281-290; each of which are herein incorporated by reference in its entirety). Unlike untargeted mass spectrometry frequently used in biomarker discovery studies, targeted MS methods are peptide sequence—based modes of MS that focus the full analytical capacity of the instrument on tens to hundreds of selected peptides in a complex mixture. By restricting detection and fragmentation to only those peptides derived from proteins of interest, sensitivity and reproducibility are improved dramatically compared to discovery-mode MS methods. This method of mass spectrometry-based multiple reaction monitoring (MRM) quantitation of proteins can dramatically impact the discovery and quantitation of biomarkers via rapid, targeted, multiplexed protein expression profiling of clinical samples.

In one embodiment, a biological sample which may contain at least one protein encoded by at least one nucleic acid molecule, modified nucleic acid molecule or modified mRNA of the present invention may be analyzed by the method of MRM-MS. The quantification of the biological sample may further include, but is not limited to, isotopically labeled peptides or proteins as internal standards.

According to the present invention, the biological sample, once obtained from the subject, may be subjected to enzyme digestion. As used herein, the term "digest" means to break apart into shorter peptides. As used herein, the phrase "treating a sample to digest proteins" means manipulating a sample in such a way as to break down proteins in a sample. These enzymes include, but are not limited to, trypsin, endoproteinase Glu-C and chymotrypsin. In one embodiment, a biological sample which may contain at least one protein encoded by at least one nucleic acid molecule, modified nucleic acid molecule or modified mRNA of the present invention may be digested using enzymes.

In one embodiment, a biological sample which may contain protein encoded by nucleic acid molecules, modified nucleic acid molecules or modified mRNA of the present invention may be analyzed for protein using electrospray ionization. Electrospray ionization (ESI) mass spectrometry (ESIMS) uses electrical energy to aid in the transfer of ions from the solution to the gaseous phase before they are analyzed by mass spectrometry. Samples may be analyzed using methods known in the art (e.g., Ho et al., Clin Biochem Rev. 2003 24(1):3-12; herein incorporated by reference in its entirety). The ionic species contained in solution may be transferred into the gas phase by dispersing a fine spray of charge droplets, evaporating the solvent and ejecting the ions from the charged droplets to generate a mist of highly charged droplets. The mist of highly charged droplets may be analyzed using at least 1, at least 2, at least 3 or at least 4 mass analyzers such as, but not limited to, a quadropole mass analyzer. Further, the mass spectrometry method may include a purification step. As a non-limiting example, the first quadrapole may be set to select a single m/z ratio so it may filter out other molecular ions having a different m/z ratio which may eliminate complicated and time-consuming sample purification procedures prior to MS analysis.

In one embodiment, a biological sample which may contain protein encoded by nucleic acid molecules, modified nucleic acid molecules or modified mRNA of the present invention may be analyzed for protein in a tandem ESIMS system (e.g., MS/MS). As non-limiting examples, the droplets may be analyzed using a product scan (or daughter scan) a precursor scan (parent scan) a neutral loss or a multiple reaction monitoring.

In one embodiment, a biological sample which may contain protein encoded by nucleic acid molecules, modified nucleic acid molecules or modified mRNA of the present invention may be analyzed using matrix-assisted laser desorption/ionization (MALDI) mass spectrometry (MALDIMS). MALDI provides for the nondestructive vaporization and ionization of both large and small molecules, such as proteins. In MALDI analysis, the analyte is first co-crystallized with a large molar excess of a matrix compound, which may also include, but is not limited to, an ultraviolet absorbing weak organic acid. Non-limiting examples of matrices used in MALDI are α-cyano-4-hydroxycinnamic acid, 3,5-dimethoxy-4-hydroxycinnamic acid and 2,5-dihydroxybenzoic acid. Laser radiation of the analyte-matrix mixture may result in the vaporization of the matrix and the analyte. The laser induced desorption provides high ion yields of the intact analyte and allows for measurement of compounds with high accuracy. Samples may be analyzed using methods known in the art (e.g., Lewis, Wei and Siuzdak, Encyclopedia of Analytical Chemistry 2000:5880-5894; herein incorporated by reference in its entirety). As non-limiting examples, mass analyzers used in the MALDI analysis may include a linear time-of-flight (TOF), a TOF reflectron or a Fourier transform mass analyzer.

In one embodiment, the analyte-matrix mixture may be formed using the dried-droplet method. A biologic sample is mixed with a matrix to create a saturated matrix solution where the matrix-to-sample ratio is approximately 5000:1. An aliquot (approximately 0.5-2.0 uL) of the saturated matrix solution is then allowed to dry to form the analyte-matrix mixture.

In one embodiment, the analyte-matrix mixture may be formed using the thin-layer method. A matrix homogeneous film is first formed and then the sample is then applied and may be absorbed by the matrix to form the analyte-matrix mixture.

In one embodiment, the analyte-matrix mixture may be formed using the thick-layer method. A matrix homogeneous film is formed with a nitro-cellulose matrix additive. Once the uniform nitro-cellulose matrix layer is obtained the sample is applied and absorbed into the matrix to form the analyte-matrix mixture.

In one embodiment, the analyte-matrix mixture may be formed using the sandwich method. A thin layer of matrix crystals is prepared as in the thin-layer method followed by the addition of droplets of aqueous trifluoroacetic acid, the sample and matrix. The sample is then absorbed into the matrix to form the analyte-matrix mixture.

Uses of Nucleic Acid Molecules and Modified Nucleic Acid Molecules

Therapeutic Agents

The nucleic acid molecules or modified nucleic acid molecules and the proteins translated from the nucleic acid molecules or modified nucleic acid molecules described herein can be used as therapeutic agents. For example, a nucleic acid molecule or modified nucleic acid molecule described herein can be administered to a subject, wherein the nucleic acid molecule or modified nucleic acid molecule is translated in vivo to produce a therapeutic peptide in the subject. Accordingly, provided herein are compositions, methods, kits, and reagents for treatment or prevention of disease or conditions in humans and other mammals. The active therapeutic agents of the present disclosure include, but are not limited to, modified nucleic acid molecules, cells containing nucleic acid molecules or modified nucleic acid molecules or polypeptides translated from the nucleic acid molecules or modified nucleic acid molecules, polypeptides translated from nucleic acid molecules or modified nucleic acid molecules, and cells contacted with cells containing modified nucleic acid molecules or polypeptides translated from the modified nucleic acid molecules.

In certain embodiments, combination therapeutics are provided which may containing one or more nucleic acid molecules or modified nucleic acid molecules containing translatable regions along with a protein that induces antibody-dependent cellular toxicity. As used herein "translatable regions" encode for a protein or proteins that may boost a subject's immunity. For example, provided herein are therapeutics containing one or more nucleic acids that encode trastuzumab and granulocyte-colony stimulating factor (G-CSF). In particular, such combination therapeutics may be useful in Her2+ breast cancer patients who develop induced resistance to trastuzumab. (See, e.g., Albrecht, Immunotherapy. 2(6):795-8 (2010); herein incorporated by reference in its entirety).

Methods of inducing translation of a recombinant polypeptide in a cell population using the modified nucleic acid molecules described herein are also provided. Such translation can be in vivo, ex vivo, in culture, or in vitro. The cell population may be contacted with an effective amount of a composition containing a nucleic acid that has at least one nucleoside modification, and a translatable region encoding the recombinant polypeptide. The population may be contacted under conditions such that the nucleic acid may be localized into one or more cells of the cell population and the recombinant polypeptide may be translated in the cell from the nucleic acid.

An effective amount of the composition may be provided based, at least in part, on the target tissue, target cell type, means of administration, physical characteristics of the nucleic acid (e.g., size, and extent of modified nucleosides), and other determinants. In general, an effective amount of the composition provides efficient protein production in the cell, preferably more efficient than a composition containing a corresponding unmodified nucleic acid molecule. Increased efficiency may be demonstrated by increased cell transfection (i.e., the percentage of cells transfected with the nucleic acid), increased protein translation from the nucleic acid, decreased nucleic acid degradation (as demonstrated, e.g., by increased duration of protein translation from a modified nucleic acid molecule), or reduced innate immune response of the host cell.

Aspects of the present disclosure are directed to methods of inducing in vivo translation of a recombinant polypeptide in a mammalian subject in need thereof. Therein, an effective amount of a composition containing a nucleic acid that has at least one nucleoside modification and a translatable region encoding the recombinant polypeptide may be administered to the subject using the delivery methods described herein. The nucleic acid may be provided in an amount and under other conditions such that the nucleic acid is localized into a cell of the subject and the recombinant polypeptide may be translated in the cell from the nucleic acid. The cell in which the nucleic acid is localized, or the tissue in which the cell is present, may be targeted with one or more than one rounds of nucleic acid administration.

Other aspects of the present disclosure relate to transplantation of cells containing nucleic acid molecules or modified nucleic acid molecules to a mammalian subject. Administration of cells to mammalian subjects is known to those of ordinary skill in the art, and include, but is not limited to, local implantation (e.g., topical or subcutaneous administration), organ delivery or systemic injection (e.g., intravenous injection or inhalation), and the formulation of cells in pharmaceutically acceptable carrier. Compositions containing nucleic acid molecules or modified nucleic acid molecules are formulated for administration intramuscularly, intra-arterially, transarterially, intraperitoneally, intravenously, intranasally, subcutaneously, endoscopically, transdermally, or intrathecally. In some embodiments, the composition may be formulated for extended release.

The subject to whom the therapeutic agent may be administered suffers from or may be at risk of developing a disease, disorder, or deleterious condition. Provided are methods of identifying, diagnosing, and classifying subjects on these bases, which may include clinical diagnosis, biomarker levels, genome-wide association studies (GWAS), and other methods known in the art.

In certain embodiments, the administered nucleic acid molecules or modified nucleic acid molecule directs production of one or more recombinant polypeptides that provide a functional activity which may be substantially absent in the cell in which the recombinant polypeptide may be translated. For example, the missing functional activity may be enzymatic, structural, or gene regulatory in nature.

In other embodiments, the administration of a nucleic acid molecule or modified nucleic acid molecule directs production of one or more recombinant polypeptides that replace a polypeptide (or multiple polypeptides) that may be substantially absent in the cell in which the recombinant polypeptide may be translated. Such absence may be due to a genetic mutation of the encoding gene or a regulatory pathway thereof. Alternatively, the recombinant polypeptide functions to antagonize the activity of an endogenous protein present in, on the surface of, or secreted from the cell. Usually, the activity of the endogenous protein may be deleterious to the subject, for example, due to the mutation of the endogenous protein resulting in altered activity or localization. Additionally, the recombinant polypeptide antagonizes, directly or indirectly, the activity of a biological moiety present in, on the surface of, or secreted from the cell. Examples of antagonized biological moieties include, but are not limited to, lipids (e.g., cholesterol), a lipoprotein (e.g., low density lipoprotein), a nucleic acid, a carbohydrate, or a small molecule toxin.

The recombinant proteins described herein may be engineered for localization within the cell, potentially within a specific compartment such as the nucleus, or are engineered for secretion from the cell or translocation to the plasma membrane of the cell.

As described herein, a useful feature of the nucleic acid molecules or modified nucleic acid molecules of the present disclosure is the capacity to reduce the innate immune response of a cell to an exogenous nucleic acid. Provided are methods for performing the titration, reduction or elimination of the immune response in a cell or a population of cells. In some embodiments, the cell may be contacted with a first composition that contains a first dose of a first exogenous nucleic acid including a translatable region and at least one nucleoside modification, and the level of the innate immune response of the cell to the first exogenous nucleic acid may be determined. Subsequently, the cell may be contacted with a second composition, which includes a second dose of the first exogenous nucleic acid, the second dose containing a lesser amount of the first exogenous nucleic acid as compared to the first dose. Alternatively, the cell may be contacted with a first dose of a second exogenous nucleic acid. The second exogenous nucleic acid may contain one or more modified nucleosides, which may be the same or different from the first exogenous nucleic acid or, alternatively, the second exogenous nucleic acid may not contain modified nucleosides. The steps of contacting the cell with the first composition and/or the second composition may be repeated one or more times. Additionally, efficiency of protein production (e.g., protein translation) in the cell may be optionally determined, and the cell may be re-transfected with the first and/or second composition repeatedly until a target protein production efficiency is achieved.

Therapeutics for Diseases and Conditions

Provided herein are methods for treating or preventing a symptom of diseases, characterized by missing or aberrant protein activity, by supplying the missing protein activity or overcoming the aberrant protein activity. Because of the rapid initiation of protein production following introduction of modified mRNA, as compared to viral DNA vectors, the compounds of the present disclosure are particularly advantageous in treating acute diseases such as sepsis, stroke, and myocardial infarction. Moreover, an accurate titration of protein may be achievable using the nucleic acid molecules, modified nucleic acid molecules or modified mRNA of the present disclosure as the nucleic acid molecules, modified nucleic acid molecules or modified mRNA may be able to alter transcription rates and thus cause changes in gene expression.

Diseases characterized by dysfunctional or aberrant protein activity include, but are not limited to, cancer and proliferative diseases, genetic diseases (e.g., cystic fibrosis), autoimmune diseases, diabetes, neurodegenerative diseases, cardiovascular diseases, and metabolic diseases. The present disclosure provides a method for treating such conditions or diseases in a subject by introducing nucleic acid or cell-based therapeutics containing the modified nucleic acid molecules provided herein, wherein the modified nucleic acid molecules encode for a protein that antagonizes or otherwise overcomes the aberrant protein activity present in the cell of the subject. Specific examples of a dysfunctional protein include, but are not limited to, the missense mutation variants of the cystic fibrosis transmembrane conductance regulator (CFTR) gene, which produce a dysfunctional protein variant of CFTR protein, which causes cystic fibrosis.

Multiple diseases may be characterized by missing (or substantially diminished such that proper protein function does not occur) protein activity. Such proteins may not be present, or they may be essentially non-functional.

Thus, provided are methods of treating cystic fibrosis in a mammalian subject by contacting a cell of the subject with a modified nucleic acid molecule having a translatable region that encodes a functional CFTR polypeptide, under conditions such that an effective amount of the CTFR polypeptide is present in the cell. Preferred target cells are epithelial cells, such as the lung, and methods of administration are determined in view of the target tissue; i.e., for lung delivery, the RNA molecules are formulated for administration by inhalation, aerosolization (e.g., intratrachael aerosolixation), nebulization or instillation. As a non-limiting example, nucleic acid molecules, modified nucleic acids and/or mmRNA may be administered to the lung by the methods and compositions described in International Patent Publication Nos. WO2013185069 and WO2013182683, the contents of each of which are herein incorporated by reference in their entirety. As another non-limiting example, the modified nucleic acids and/or mmRNA may be administered by aerosol delivery the methods and devices described in International Patent Publication No. WO2013155513, the contents of which are herein incorporated by reference in its entirety.

In another embodiment, the present disclosure provides a method for treating hyperlipidemia in a subject, by introducing into a cell population of the subject with a nucleic acid molecules, modified nucleic acid molecules or modified mRNA molecule encoding Sortilin, a protein recently characterized by genomic studies, thereby ameliorating the hyperlipidemia in a subject. The SORT1 gene encodes a trans-Golgi network (TGN) transmembrane protein called Sortilin. Genetic studies have shown that one of five individuals has a single nucleotide polymorphism, rs12740374, in the 1p13 locus of the SORT1 gene that predisposes them to having low levels of low-density lipoprotein (LDL) and very-low-density lipoprotein (VLDL). Each copy of the minor allele, present in about 30% of people, alters LDL cholesterol by 8 mg/dL, while two copies of the minor allele, present in about 5% of the population, lowers LDL cholesterol 16 mg/dL. Carriers of the minor allele have also been shown to have a 40% decreased risk of myocardial infarction. Functional in vivo studies in mice describes that overexpression of SORT1 in mouse liver tissue led to significantly lower LDL-cholesterol levels, as much as 80% lower, and that silencing SORT1 increased LDL cholesterol approximately 200% (Musunuru K et al. From noncoding variant to phenotype via SORT1 at the 1p13 cholesterol locus. *Nature* 2010; 466: 714-721; herein incorporated by reference in its entirety).

Methods of Cellular Nucleic Acid Delivery

Methods of the present disclosure enhance nucleic acid delivery into a cell population, in vivo, ex vivo, or in culture. For example, a cell culture containing a plurality of host cells (e.g., eukaryotic cells such as yeast or mammalian cells) may be contacted with a composition that contains a modified nucleic acid molecule having at least one nucleoside modification and, optionally, a translatable region. The composition may also generally contain a transfection reagent or other compound that may increases the efficiency of modified nucleic acid molecule uptake into the host cells.

The modified nucleic acid molecule may exhibit enhanced retention in the cell population, relative to a corresponding unmodified nucleic acid molecule. The retention of the modified nucleic acid molecule may greater than the retention of the unmodified nucleic acid molecule. In some embodiments, it is at least about 50%, 75%, 90%, 95%, 100%, 150%, 200% or more than 200% greater than the retention of the unmodified nucleic acid molecule. Such retention advantage may be achieved by one round of transfection with the modified nucleic acid molecule, or may be obtained following repeated rounds of transfection.

In some embodiments, the nucleic acid molecule or modified nucleic acid molecule may be delivered to a target cell population with one or more additional nucleic acids. Such delivery may be at the same time, or the nucleic acid molecule or modified nucleic acid molecule is delivered prior to delivery of the one or more additional nucleic acids. The additional one or more nucleic acids may be modified nucleic acid molecules or nucleic acid molecules. It is understood that the initial presence of the modified nucleic acid molecules may not substantially induce an innate immune response of the cell population and, moreover, that the innate immune response may not be activated by the later presence of the unmodified nucleic acid molecules. In this regard, the enhanced nucleic acid may not itself contain a translatable region, if the protein desired to be present in the target cell population is translated from the unmodified nucleic acid molecules.

Targeting Moieties

In some embodiments, nucleic acid molecules or modified nucleic acid molecules are provided to express a protein-binding partner or a receptor on the surface of the cell, which may function to target the cell to a specific tissue space or to interact with a specific moiety, either in vivo or in vitro. Suitable protein-binding partners include, but are not limited to, antibodies and functional fragments thereof, scaffold proteins, or peptides. Additionally, modified nucleic acid molecules may be employed to direct the synthesis and extracellular localization of lipids, carbohydrates, or other biological moieties.

Permanent Gene Expression Silencing

A method for epigenetically silencing gene expression in a mammalian subject, comprising a nucleic acid where the translatable region encodes a polypeptide or polypeptides capable of directing sequence-specific histone H3 methylation to initiate heterochromatin formation and reduce gene transcription around specific genes for the purpose of silencing the gene. For example, a gain-of-function mutation in the Janus Kinase 2 gene is responsible for the family of Myeloproliferative Diseases.

Expression of Ligand or Receptor on Cell Surface

In some aspects and embodiments of the aspects described herein, the nucleic acid molecules, nucleic acid molecules or modified RNA can be used to express a ligand or ligand receptor on the surface of a cell (e.g., a homing moiety). A ligand or ligand receptor moiety attached to a cell surface can permit the cell to have a desired biological interaction with a tissue or an agent in vivo. A ligand can be an antibody, an antibody fragment, an aptamer, a peptide, a vitamin, a carbohydrate, a protein or polypeptide, a receptor, e.g., cell-surface receptor, an adhesion molecule, a glycoprotein, a sugar residue, a therapeutic agent, a drug, a glycosaminoglycan, or any combination thereof. For example, a ligand can be an antibody that recognizes a cancer-cell specific antigen, rendering the cell capable of preferentially interacting with tumor cells to permit tumor-specific localization of a modified cell. A ligand can confer the ability of a cell composition to accumulate in a tissue to be treated, since a preferred ligand may be capable of interacting with a target molecule on the external face of a tissue to be treated. Ligands having limited cross-reactivity to other tissues are generally preferred.

In some cases, a ligand can act as a homing moiety which permits the cell to target to a specific tissue or interact with a specific ligand. Such homing moieties can include, but are not limited to, any member of a specific binding pair, antibodies, monoclonal antibodies, or derivatives or analogs thereof, including without limitation: Fv fragments, single chain Fv (scFv) fragments, Fab' fragments, F(ab')2 fragments, single domain antibodies, camelized antibodies and antibody fragments, humanized antibodies and antibody fragments, and multivalent versions of the foregoing; multivalent binding reagents including without limitation: monospecific or bispecific antibodies, such as disulfide stabilized Fv fragments, scFv tandems ((SCFV)2 fragments), diabodies, tribodies or tetrabodies, which typically are covalently linked or otherwise stabilized (i.e., leucine zipper or helix stabilized) scFv fragments; and other homing moieties include for example, aptamers, receptors, and fusion proteins.

In some embodiments, the homing moiety may be a surface-bound antibody, which can permit tuning of cell targeting specificity. This is especially useful since highly specific antibodies can be raised against an epitope of interest for the desired targeting site. In one embodiment, multiple antibodies are expressed on the surface of a cell, and each antibody can have a different specificity for a desired target. Such approaches can increase the avidity and specificity of homing interactions.

A skilled artisan can select any homing moiety based on the desired localization or function of the cell, for example an estrogen receptor ligand, such as tamoxifen, can target cells to estrogen-dependent breast cancer cells that have an increased number of estrogen receptors on the cell surface. Other non-limiting examples of ligand/receptor interactions include CCRI (e.g., for treatment of inflamed joint tissues or brain in rheumatoid arthritis, and/or multiple sclerosis), CCR7, CCR8 (e.g., targeting to lymph node tissue), CCR6, CCR9,CCR10 (e.g., to target to intestinal tissue), CCR4, CCR10 (e.g., for targeting to skin), CXCR4 (e.g., for general enhanced transmigration), HCELL (e.g., for treatment of inflammation and inflammatory disorders, bone marrow), Alpha4beta7 (e.g., for intestinal mucosa targeting), VLA-4NCAM-1 (e.g., targeting to endothelium). In general, any receptor involved in targeting (e.g., cancer metastasis) can be harnessed for use in the methods and compositions described herein.

Mediators of Cell Death

In one embodiment, a nucleic acid molecule or modified nucleic acid molecule composition can be used to induce apoptosis in a cell (e.g., a cancer cell) by increasing the expression of a death receptor, a death receptor ligand or a combination thereof. This method can be used to induce cell death in any desired cell and has particular usefulness in the treatment of cancer where cells escape natural apoptotic signals.

Apoptosis can be induced by multiple independent signaling pathways that converge upon a final effector mechanism consisting of multiple interactions between several "death receptors" and their ligands, which belong to the tumor necrosis factor (TNF) receptor/ligand superfamily. The best-characterized death receptors are CD95 ("Fas"), TNFRI (p55), death receptor 3 (DR3 or Apo3/TRAMO), DR4 and DR5 (apo2-TRAIL-R2). The final effector mechanism of apoptosis may be the activation of a series of proteinases designated as caspases. The activation of these caspases results in the cleavage of a series of vital cellular proteins and cell death. The molecular mechanism of death receptors/ligands-induced apoptosis is well known in the art. For example, Fas/FasL-mediated apoptosis is induced by binding of three FasL molecules which induces trimerization of Fas receptor via C-terminus death domains (DDs), which in turn recruits an adapter protein FADD (Fas-associated protein with death domain) and Caspase-8. The oligomerization of this trimolecular complex, Fas/FAIDD/caspase-8, results in proteolytic cleavage of proenzyme caspase-8 into active caspase-8 that, in turn, initiates the apoptosis process by activating other downstream caspases through proteolysis, including caspase-3. Death ligands in general are apoptotic when formed into trimers or higher order of structures. As monomers, they may serve as antiapoptotic agents by competing with the trimers for binding to the death receptors.

In one embodiment, the nucleic acid molecule or modified nucleic acid molecule composition encodes for a death receptor (e.g., Fas, TRAIL, TRAMO, TNFR, TLR etc). Cells made to express a death receptor by transfection of modified RNA become susceptible to death induced by the ligand that activates that receptor. Similarly, cells made to express a death ligand, e.g., on their surface, will induce death of cells with the receptor when the transfected cell contacts the target cell. In another embodiment, the modified RNA composition encodes for a death receptor ligand (e.g., FasL, TNF, etc). In another embodiment, the nucleic acid molecule, modified nucleic acid molecule or modified RNA composition encodes a caspase (e.g., caspase 3, caspase 8, caspase 9 etc). Where cancer cells often exhibit a failure to properly differentiate to a non-proliferative or controlled proliferative form, in another embodiment, the synthetic, modified RNA composition encodes for both a death receptor and its appropriate activating ligand. In another embodiment, the synthetic, nucleic acid molecule, modified nucleic acid molecule or modified RNA composition encodes for a differentiation factor that when expressed in the cancer cell, such as a cancer stem cell, will induce the cell to differentiate to a non-pathogenic or nonself-renewing phenotype (e.g., reduced cell growth rate, reduced cell division etc) or to induce the cell to enter a dormant cell phase (e.g., Go resting phase).

One of skill in the art will appreciate that the use of apoptosis-inducing techniques may require that the modified nucleic acid molecules are appropriately targeted to e.g., tumor cells to prevent unwanted wide-spread cell death. Thus, one can use a delivery mechanism (e.g., attached ligand or antibody, targeted liposome etc) that recognizes a cancer antigen such that the modified nucleic acid molecules are expressed only in cancer cells.

Kits and Devices

Kits

The invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments.

In one aspect, the present invention provides kits for protein production, comprising a first nucleic acid molecule, modified nucleic acid molecule or mmRNA comprising a translatable region. The kit may further comprise packaging and instructions and/or a delivery agent to form a formulation composition. The delivery agent may comprise a saline, a buffered solution, a lipidoid or any delivery agent disclosed herein.

In one embodiment, the buffer solution may include sodium chloride, calcium chloride, phosphate and/or EDTA. In another embodiment, the buffer solution may include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See e.g., U.S. Pub. No. 20120258046; herein incorporated by reference in its entirety). In a further embodiment, the buffer solutions may be precipitated or it may be lyophilized. The amount of each component may be varied to enable consistent, reproducible higher concentration saline or simple buffer formulations. The components may also be varied in order to increase the stability of nucleic acid molecules, modified nucleic acid molecules and mmRNA in the buffer solution over a period of time and/or under a variety of conditions.

In one aspect, the present invention provides kits for protein production, comprising: a nucleic acid molecule, modified nucleic acid molecule or mmRNA comprising a translatable region, provided in an amount effective to produce a desired amount of a protein encoded by the translatable region when introduced into a target cell; a second nucleic acid molecule, modified nucleic acid molecule or mmRNA comprising an inhibitory nucleic acid, provided in an amount effective to substantially inhibit the innate immune response of the cell; and packaging and instructions.

In one aspect, the present invention provides kits for protein production, comprising a nucleic acid molecule, modified nucleic acid molecule or mmRNA comprising a translatable region, wherein the nucleic acid exhibits reduced degradation by a cellular nuclease, and packaging and instructions.

In one aspect, the present invention provides kits for protein production, comprising a nucleic acid molecule, modified nucleic acid molecule or mmRNA comprising a translatable region, wherein the nucleic acid exhibits reduced degradation by a cellular nuclease, and a mammalian cell suitable for translation of the translatable region of the first nucleic acid.

Devices

The present invention provides for devices which may incorporate nucleic acid molecules, modified nucleic acid molecules or mmRNA that encode polypeptides of interest. These devices contain in a stable formulation the reagents to synthesize a nucleic acid in a formulation available to be immediately delivered to a subject in need thereof, such as a human patient. Non-limiting examples of such a polypeptide of interest include a growth factor and/or angiogenesis stimulator for wound healing, a peptide antibiotic to facilitate infection control, and an antigen to rapidly stimulate an immune response to a newly identified virus.

In some embodiments the device is self-contained, and is optionally capable of wireless remote access to obtain instructions for synthesis and/or analysis of the generated nucleic acid molecules, modified nucleic acid molecules or mmRNA. The device is capable of mobile synthesis of at least one nucleic acid molecule, modified nucleic acid molecule or mmRNA and preferably an unlimited number of different nucleic acid molecule, modified nucleic acid molecules or mmRNA. In certain embodiments, the device is capable of being transported by one or a small number of individuals. In other embodiments, the device is scaled to fit on a benchtop or desk. In other embodiments, the device is scaled to fit into a suitcase, backpack or similarly sized object.

In another embodiment, the device may be a point of care or handheld device. In further embodiments, the device is scaled to fit into a vehicle, such as a car, truck or ambulance, or a military vehicle such as a tank or personnel carrier. The information necessary to generate a nucleic acid molecule, modified nucleic acid molecule or modified mRNA encoding polypeptide of interest is present within a computer readable medium present in the device.

In one embodiment, a device may be used to assess levels of a protein which has been administered in the form of a nucleic acid molecule, modified nucleic acid or mmRNA. The device may comprise a blood, urine or other biofluidic test.

In some embodiments, the device is capable of communication (e.g., wireless communication) with a database of nucleic acid and polypeptide sequences. The device contains at least one sample block for insertion of one or more sample vessels. Such sample vessels are capable of accepting in liquid or other form any number of materials such as template DNA, nucleotides, enzymes, buffers, and other reagents. The sample vessels are also capable of being heated and cooled by contact with the sample block. The sample block is generally in communication with a device base with one or more electronic control units for the at least one sample block. The sample block preferably contains a heating module, such heating molecule capable of heating and/or cooling the sample vessels and contents thereof to temperatures between about −20 C and above +100 C. The device base is in communication with a voltage supply such as a battery or external voltage supply. The device also contains means for storing and distributing the materials for RNA synthesis.

Optionally, the sample block contains a module for separating the synthesized nucleic acids. Alternatively, the device contains a separation module operably linked to the sample block. Preferably the device contains a means for analysis of the synthesized nucleic acid. Such analysis includes sequence identity (demonstrated such as by hybridization), absence of non-desired sequences, measurement of integrity of synthesized mRNA (such has by microfluidic viscometry combined with spectrophotometry), and concentration and/or potency of nucleic acid molecules, modified nucleic acid molecules or modified RNA (such as by spectrophotometry).

In certain embodiments, the device is combined with a means for detection of pathogens present in a biological material obtained from a subject, e.g., the IBIS PLEX-ID system (Abbott, Abbott Park, Ill.) for microbial identification.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662; each of which is herein incorporated by reference in their entirety. Intradermal compositions may be administered by devices which limit the effective penetration length of a needle into the skin, such as those described in PCT publication WO 99/34850 (herein incorporated by reference in its entirety) and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537; each of which are herein incorporated by reference in their entirety. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

In some embodiments, the device may be a pump or comprise a catheter for administration of compounds or compositions of the invention across the blood brain barrier. Such devices include but are not limited to a pressurized olfactory delivery device, iontophoresis devices, multi-layered microfluidic devices, and the like. Such devices may be portable or stationary. They may be implantable or externally tethered to the body or combinations thereof.

Devices for administration may be employed to deliver the nucleic acid molecules, modified nucleic acid molecules or mmRNA of the present invention according to single, multi- or split-dosing regimens taught herein. Such devices are described below.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

According to the present invention, these multi-administration devices may be utilized to deliver the single, multi- or split doses contemplated herein.

A method for delivering therapeutic agents to a solid tissue has been described by Bahrami et al. and is taught for example in US Patent Publication 20110230839, the contents of which are incorporated herein by reference in their entirety. According to Bahrami, an array of needles is incorporated into a device which delivers a substantially equal amount of fluid at any location in said solid tissue along each needle's length.

A device for delivery of biological material across the biological tissue has been described by Kodgule et al. and is taught for example in US Patent Publication 20110172610, the contents of which are incorporated herein by reference in their entirety. According to Kodgule, multiple hollow microneedles made of one or more metals and having outer diameters from about 200 microns to about 350 microns and lengths of at least 100 microns are incorporated into the device which delivers peptides, proteins, carbohydrates, nucleic acid molecules, lipids and other pharmaceutically active ingredients or combinations thereof.

A delivery probe for delivering a therapeutic agent to a tissue has been described by Gunday et al. and is taught for example in US Patent Publication 20110270184, the contents of each of which are incorporated herein by reference in their entirety. According to Gunday, multiple needles are incorporated into the device which moves the attached capsules between an activated position and an inactivated position to force the agent out of the capsules through the needles.

A multiple-injection medical apparatus has been described by Assaf and is taught for example in US Patent Publication 20110218497, the contents of which are incorporated herein by reference in their entirety. According to Assaf, multiple needles are incorporated into the device which has a chamber connected to one or more of said needles and a means for continuously refilling the chamber with the medical fluid after each injection.

In one embodiment, the nucleic acid molecule, modified nucleic acid molecule or mmRNA is administered subcutaneously, intramuscularly or intradermally via at least 3 needles to three different, optionally adjacent, sites simultaneously, or within a 60 minutes period (e.g., administration to 4,5, 6, 7, 8, 9, or 10 sites simultaneously or within a 60 minute period). The split doses can be administered simultaneously to adjacent tissue using the devices described in U.S. Patent Publication Nos. 20110230839 and 20110218497, each of which is incorporated herein by reference in their entirety.

An at least partially implantable system for injecting a substance into a patient's body, in particular a penis erection stimulation system has been described by Forsell and is taught for example in US Patent Publication 20110196198, the contents of which are incorporated herein by reference in their entirety. According to Forsell, multiple needles are incorporated into the device which is implanted along with one or more housings adjacent the patient's left and right corpora cavernosa. A reservoir and a pump are also implanted to supply drugs through the needles.

A method for the transdermal delivery of a therapeutic effective amount of iron has been described by Berenson and is taught for example in US Patent Publication 20100130910, the contents of which are incorporated herein by reference in their entirety. According to Berenson, multiple needles may be used to create multiple micro channels in stratum corneum to enhance transdermal delivery of the ionic iron on an iontophoretic patch.

A method for delivery of biological material across the biological tissue has been described by Kodgule et al and is taught for example in US Patent Publication 20110196308, the contents of which are incorporated herein by reference in their entirety. According to Kodgule, multiple biodegradable microneedles containing a therapeutic active ingredient are incorporated in a device which delivers proteins, carbohydrates, nucleic acid molecules, lipids and other pharmaceutically active ingredients or combinations thereof.

A transdermal patch comprising a botulinum toxin composition has been described by Donovan and is taught for example in US Patent Publication 20080220020, the contents of which are incorporated herein by reference in their entirety. According to Donovan, multiple needles are incorporated into the patch which delivers botulinum toxin under stratum corneum through said needles which project through the stratum corneum of the skin without rupturing a blood vessel.

A small, disposable drug reservoir, or patch pump, which can hold approximately 0.2 to 15 mL of liquid formulations can be placed on the skin and deliver the formulation continuously subcutaneously using a small bore needed (e.g., 26 to 34 gauge). As non-limiting examples, the patch pump may be 50 mm by 76 mm by 20 mm spring loaded having a 30 to 34 gauge needle (BD™ Microinfuser, Franklin Lakes N.J.), 41 mm by 62 mm by 17 mm with a 2 mL reservoir used for drug delivery such as insulin (OMNIPOD™, Insulet Corporation Bedford, Mass.), or 43-60 mm diameter, 10 mm thick with a 0.5 to 10 mL reservoir (PATCHPUMP®, SteadyMed Therapeutics, San Francisco, Calif.). Further, the patch pump may be battery powered and/or rechargeable.

A cryoprobe for administration of an active agent to a location of cryogenic treatment has been described by Toubia and is taught for example in US Patent Publication 20080140061, the contents of which are incorporated herein by reference in their entirety. According to Toubia, multiple needles are incorporated into the probe which receives the active agent into a chamber and administers the agent to the tissue.

A method for treating or preventing inflammation or promoting healthy joints has been described by Stock et al and is taught for example in US Patent Publication 20090155186, the contents of which are incorporated herein by reference in their entirety. According to Stock, multiple needles are incorporated in a device which administers compositions containing signal transduction modulator compounds.

A multi-site injection system has been described by Kimmell et al. and is taught for example in US Patent Publication 20100256594, the contents of which are incorporated herein by reference in their entirety. According to Kimmell, multiple needles are incorporated into a device which delivers a medication into a stratum corneum through the needles.

A method for delivering interferons to the intradermal compartment has been described by Dekker et al. and is taught for example in US Patent Publication 20050181033, the contents of which are incorporated herein by reference in their entirety. According to Dekker, multiple needles having an outlet with an exposed height between 0 and 1 mm are incorporated into a device which improves pharmacokinetics and bioavailability by delivering the substance at a depth between 0.3 mm and 2 mm.

A method for delivering genes, enzymes and biological agents to tissue cells has described by Desai and is taught for example in US Patent Publication 20030073908, the contents of which are incorporated herein by reference in their entirety. According to Desai, multiple needles are incorporated into a device which is inserted into a body and delivers a medication fluid through said needles.

A method for treating cardiac arrhythmias with fibroblast cells has been described by Lee et al and is taught for example in US Patent Publication 20040005295, the contents of which are incorporated herein by reference in their entirety. According to Lee, multiple needles are incorporated into the device which delivers fibroblast cells into the local region of the tissue.

A method using a magnetically controlled pump for treating a brain tumor has been described by Shachar et al. and is taught for example in U.S. Pat. No. 7,799,012 (method) and U.S. Pat. No. 7,799,016 (device), the contents of which are incorporated herein by reference in their entirety. According Shachar, multiple needles were incorporated into the pump which pushes a medicating agent through the needles at a controlled rate.

Methods of treating functional disorders of the bladder in mammalian females have been described by Versi et al. and are taught for example in U.S. Pat. No. 8,029,496, the contents of which are incorporated herein by reference in their entirety. According to Versi, an array of micro-needles is incorporated into a device which delivers a therapeutic agent through the needles directly into the trigone of the bladder.

A micro-needle transdermal transport device has been described by Angel et al and is taught for example in U.S. Pat. No. 7,364,568, the contents of which are incorporated herein by reference in their entirety. According to Angel, multiple needles are incorporated into the device which transports a substance into a body surface through the needles which are inserted into the surface from different directions. The micro-needle transdermal transport device may be a solid micro-needle system or a hollow micro-needle system. As a non-limiting example, the solid micro-needle system may have up to a 0.5 mg capacity, with 300-1500 solid micro-needles per $cm^2$ about 150-700 µm tall coated with a drug. The micro-needles penetrate the stratum corneum and remain in the skin for short duration (e.g., 20 seconds to 15 minutes). In another example, the hollow micro-needle system has up to a 3 mL capacity to deliver liquid formulations using 15-20 microneedles per cm2 being approximately 950 µm tall. The micro-needles penetrate the skin to allow the liquid formulations to flow from the device into the skin. The hollow micro-needle system may be worn from 1 to 30 minutes depending on the formulation volume and viscosity.

A device for subcutaneous infusion has been described by Dalton et al and is taught for example in U.S. Pat. No. 7,150,726, the contents of which are incorporated herein by reference in their entirety. According to Dalton, multiple needles are incorporated into the device which delivers fluid through the needles into a subcutaneous tissue.

A device and a method for intradermal delivery of vaccines and gene therapeutic agents through microcannula have been described by Mikszta et al. and are taught for example in U.S. Pat. No. 7,473,247, the contents of which are incorporated herein by reference in their entirety. According to Mitszta, at least one hollow micro-needle is incorporated into the device which delivers the vaccines to the subject's skin to a depth of between 0.025 mm and 2 mm.

A method of delivering insulin has been described by Pettis et al and is taught for example in U.S. Pat. No. 7,722,595, the contents of which are incorporated herein by reference in their entirety. According to Pettis, two needles are incorporated into a device wherein both needles insert essentially simultaneously into the skin with the first at a depth of less than 2.5 mm to deliver insulin to intradermal compartment and the second at a depth of greater than 2.5 mm and less than 5.0 mm to deliver insulin to subcutaneous compartment.

Cutaneous injection delivery under suction has been described by Kochamba et al. and is taught for example in U.S. Pat. No. 6,896,666, the contents of which are incorporated herein by reference in their entirety. According to Kochamba, multiple needles in relative adjacency with each other are incorporated into a device which injects a fluid below the cutaneous layer.

A device for withdrawing or delivering a substance through the skin has been described by Down et al and is taught for example in U.S. Pat. No. 6,607,513, the contents of which are incorporated herein by reference in their entirety. According to Down, multiple skin penetrating members which are incorporated into the device have lengths of about 100 microns to about 2000 microns and are about 30 to 50 gauge.

A device for delivering a substance to the skin has been described by Palmer et al and is taught for example in U.S. Pat. No. 6,537,242, the contents of which are incorporated herein by reference in their entirety. According to Palmer, an array of micro-needles is incorporated into the device which uses a stretching assembly to enhance the contact of the needles with the skin and provides a more uniform delivery of the substance.

A perfusion device for localized drug delivery has been described by Zamoyski and is taught for example in U.S. Pat. No. 6,468,247, the contents of which are incorporated herein by reference in their entirety. According to Zamoyski, multiple hypodermic needles are incorporated into the device which injects the contents of the hypodermics into a tissue as said hypodermics are being retracted.

A method for enhanced transport of drugs and biological molecules across tissue by improving the interaction between micro-needles and human skin has been described by Prausnitz et al. and is taught for example in U.S. Pat. No. 6,743,211, the contents of which are incorporated herein by reference in their entirety. According to Prausnitz, multiple micro-needles are incorporated into a device which is able to present a more rigid and less deformable surface to which the micro-needles are applied.

A device for intraorgan administration of medicinal agents has been described by Ting et al and is taught for example in U.S. Pat. No. 6,077,251, the contents of which are incorporated herein by reference in their entirety. According to Ting, multiple needles having side openings for enhanced administration are incorporated into a device which by extending and retracting said needles from and into the needle chamber forces a medicinal agent from a reservoir into said needles and injects said medicinal agent into a target organ.

A multiple needle holder and a subcutaneous multiple channel infusion port has been described by Brown and is taught for example in U.S. Pat. No. 4,695,273, the contents of which are incorporated herein by reference in their entirety. According to Brown, multiple needles on the needle holder are inserted through the septum of the infusion port and communicate with isolated chambers in said infusion port.

A dual hypodermic syringe has been described by Horn and is taught for example in U.S. Pat. No. 3,552,394, the contents of which are incorporated herein by reference in their entirety. According to Horn, two needles incorporated into the device are spaced apart less than 68 mm and may be of different styles and lengths, thus enabling injections to be made to different depths.

A syringe with multiple needles and multiple fluid compartments has been described by Hershberg and is taught for example in U.S. Pat. No. 3,572,336, the contents of which are incorporated herein by reference in their entirety. According to Hershberg, multiple needles are incorporated into the syringe which has multiple fluid compartments and is capable of simultaneously administering incompatible drugs which are not able to be mixed for one injection.

A surgical instrument for intradermal injection of fluids has been described by Eliscu et al. and is taught for example in U.S. Pat. No. 2,588,623, the contents of which are incorporated herein by reference in their entirety. According to Eliscu, multiple needles are incorporated into the instrument which injects fluids intradermally with a wider disperse.

An apparatus for simultaneous delivery of a substance to multiple breast milk ducts has been described by Hung and is taught for example in EP 1818017, the contents of which are incorporated herein by reference in their entirety. According to Hung, multiple lumens are incorporated into the device which inserts though the orifices of the ductal networks and delivers a fluid to the ductal networks.

A catheter for introduction of medications to the tissue of a heart or other organs has been described by Tkebuchava and is taught for example in WO2006138109, the contents of which are incorporated herein by reference in their entirety. According to Tkebuchava, two curved needles are incorporated which enter the organ wall in a flattened trajectory.

Devices for delivering medical agents have been described by Mckay et al. and are taught for example in WO2006118804, the content of which are incorporated herein by reference in their entirety. According to Mckay, multiple needles with multiple orifices on each needle are incorporated into the devices to facilitate regional delivery to a tissue, such as the interior disc space of a spinal disc.

A method for directly delivering an immunomodulatory substance into an intradermal space within a mammalian skin has been described by Pettis and is taught for example in WO2004020014, the contents of which are incorporated herein by reference in their entirety. According to Pettis, multiple needles are incorporated into a device which delivers the substance through the needles to a depth between 0.3 mm and 2 mm.

Methods and devices for administration of substances into at least two compartments in skin for systemic absorption and improved pharmacokinetics have been described by Pettis et al. and are taught for example in WO2003094995, the contents of which are incorporated herein by reference in their entirety. According to Pettis, multiple needles having lengths between about 300 μm and about 5 mm are incorporated into a device which delivers to intradermal and subcutaneous tissue compartments simultaneously.

A drug delivery device with needles and a roller has been described by Zimmerman et al. and is taught for example in WO2012006259, the contents of which are incorporated herein by reference in their entirety. According to Zimmerman, multiple hollow needles positioned in a roller are incorporated into the device which delivers the content in a reservoir through the needles as the roller rotates.

A drug delivery device such as a stent is known in the art and is taught for example in U.S. Pub. Nos. US20060020329, US20040172127, US20100161032 and US20130129794; the contents of which are herein incorporated by reference in their entirety. Formulations of the nucleic acid molecules, modified nucleic acid molecules or mmRNA described herein may be delivered using stents. Additionally, stents used herein may be able to deliver multiple modified nucleic acid molecules and/or formulations at the same or varied rates of delivery. Non-limiting examples of manufacturers of stents include CORDIS® (Miami, Fla.) (CYPHER®), Boston Scientific Corporation (Natick, Mass.) (TAXUS®), Medtronic (Minneapolis, Minn.) (ENDEAVOUR®) and Abbott (Abbott Park, Ill.) (XIENCE V®). As a non-limiting example, the stent may have a coating which includes, but is not limited to, bioactive agents (e.g., nucleic acid molecules, modified nucleic acids and/or mmRNA). The coatings may be those described in and/or may be made by the methods described in US Patent Publication No. US20130129794, herein incorporated by reference in its entirety.

A drug delivery device for administration to solid tissue has been described by Frazier et al. and is taught for example in WO20130635030, the contents of which are incorporated herein by reference in their entirety. According to Frazier, a plurality of microdialysis probes are inserted into the solid tissue through which the drug is delivered to the solid tissue. In one aspect the drug may be a nucleic acid molecule, modified nucleic acid molecule or mmRNA described herein.

A drug delivery device for delivering an agent across a dermal barrier has been described in International Publication No. WO2013061208 and US Publication No. US20130150822, the contents of which are herein incorporated by reference in their entirety. Described in WO2013061208, the device comprises a microneedle having a plurality of nanostructures on the surface arranged in a predetermined pattern and a composition comprising an agent to flow through the microneedle. In one aspect the composition may include, but is not limited to, at least one nucleic acid molecule, modified nucleic acid molecule and/ or mmRNA described herein. As a non-limiting example, a drug delivery device is described in US20130150822 where the surface of a device has a plurality of nanostructures formed on the surface which have been arranged in a predetermined pattern. The cellular layer may be contacted with the surface of the device which in turn can increase the permeability of the layer to a drug compound or therapeutic.

Another drug delivery device for delivering a therapeutic agent transdermally has been described in WO2013082427 and WO2013082418, the contents of each of which is herein incorporated by reference in its entirety. Described in WO2013082427 and WO2013082418, the device comprises an array of microneedles with a coating comprising a therapeutic agent on or within at least a portion of the microneedles. In one aspect, the therapeutic agent may contain at least one nucleic acid molecule, modified nucleic acid molecule and/or mmRNA described herein.

A device comprising a plurality of microneedles adapted to protrude from the device is described in International Patent Publication No. WO2013101908 and US Patent Publication No. US20130165772, the contents of each of which are herein incorporated by reference in its entirety. The device may comprise a payload, such as a modified nucleic acid molecule, that can be delivered to an internal tissue of a subject or through a wall or vessel after interaction with the microneedles. As a non-limiting example, the device may be used for oral or intravenous administration. As another non-limiting example, the device can be used for implantation such as vaginal, rectal, urethral, bladder suppository or pessary.

An osmotic delivery device for delivering two or more agents has been described by Alessi et al. and is taught for example in US Patent Application No. US20130090287, herein incorporated by reference in its entirety.

A spray system for producing a matrix in situ is described by Rudolph and Uzgun and is taught for example in WO2013045455, herein incorporated by reference in its entirety. The spray system may comprise at least one lipophilic component and at least one hydrophilic component separated from each other until they are mixed at or during spraying. The combination of the two components form a film which may be used in various aspects of therapy and/or treatment such as, but not limited to, creating a film on tissue to prevent adhesions and scarring that develop after surgery. Further the spray system may include a therapeutic agent such as the nucleic acid molecule, modified nucleic acids and/or mmRNA described herein. The therapeutic agent may be in either or both components and/or administered to the subject or target area before and/or after use of the spray system.

Electroporation devices may be used to improve delivery of mRNA. Electroporation devices are sold by many companies worldwide including, but not limited to BTX® Instruments (Holliston, Mass.) (e.g., the AgilePulse In Vivo System) and Inovio (Blue Bell, Pa.) (e.g., Inovio SP-5P intramuscular delivery device or the CELLECTRA® 3000 intradermal delivery device). The electroporation devices may be used before, during and/or after administration of a compositions comprising nucleic acid molecules, modified nucleic acid molecules or mmRNA. The compositions may be administered intramuscularly, subcutaneous and/or intradermally.

A device for delivery pharmaceutical compounds to the olfactory epithelium of a subject is described in US Patent Publication No US20130142868, the contents of which are herein incorporated by reference in its entirety. A pharmaceutical aerosol suspension can contain numerous types of therapeutic pharmaceutical compounds such as RNA (e.g., the nucleic acid molecules, modified nucleic acids and/or mmRNA described herein).

A device for delivery of liquids or solids using a titania nanotube membrane is described in International Publication No. WO2013085951, herein incorporated by reference in its entirety. The device can be implanted into a subject to deliver a therapeutic agent such as RNA from a reservoir to a subject for a period of time using the nanotubes.

An aerosolization apparatus for inhalation drug delivery is described in International Publication No. WO2013090841, herein incorporated by reference in its entirety. The device comprises a housing having an outlet adapted to be inserted into a subject's mouth and one or more bypass openings. A receptacle support in the housing supports the receptacle containing a powder form of a pharmaceutical formulation which is suitable for transfection. The apparatus delivers drugs to a subject when inserted in the subject's mouth and the subject inhales. A non-limiting example of a highly dispersable formulation which may be delivered through an aerosolation apparatus is described in U.S. Pat. No. 8,501, 240, the contents of which are herein incorporated by reference in its entirety.

An implantable intraocular drug delivery apparatus and methods of using the apparatus are described in International Publication No. WO2013096626, herein incorporated by reference in its entirety. The apparatus includes an implantable scaffold and an active agent which is associated with the implantable scaffold. The scaffold and the active agent can be completely contained within the eye upon implantation.

A device having at least a portion which may be insertable or implantable in the body of a subject is described in US Patent Publication No. US20130164348, the contents of which are herein incorporated by reference in its entirety. The device includes a polymeric layer which may have a biodisintegrable polymer and a plasticizer. A high molecular weight therapeutic agent, such as a modified nucleic acid molecule, may be disposed below and/or within the polymeric layer.

Another device which may be an implantable pump and method of making such device are described in U.S. Pat. No. 8,486,278, the contents of which are herein incorporated by reference in its entirety. The implantable pump may be shaped to conform to a particular anatomical region and may be sized for any of a variety of anatomical sites in order to deliver a drug to a target location within a body.

A device for the sustained delivery of a therapeutic agent is described in US Patent Publication No. US20130211368, the contents of which are herein incorporated by reference in its entirety. The device may comprise a capsule which has a fluid impermeable wall defining a reservoir for containing a therapeutic agent for implantation into the body. The capsule may also comprise an exit port in communication with the reservoir and a nanopore membrane in communication with the exit port. The therapeutic agent may be biologically active macromolecules such as peptides, protine and polynucleic acids.

Implantable or insertable devices for controlled delivery of therapeutics are described in U.S. Pat. No. 8,535,702, the contents of which are herein incorporated by reference in its entirety. The device may comprise phase separated polymeric regions that have (a) at least one block copolymer and (b) at least one therapeutic agent. The block copolymer may have a biostable polymer block and at least one biodisintegrable polymer block. The therapeutic agent may be released in vivo upon implantation or insertion of the device. As a non-limiting example, the therapeutic agent may be the nucleic acid molecules, modified nucleic acids and/or mmRNA described herein.

Devices for administration of an active agent formulation over a predetermined interval are described in U.S. Pat. No. 8,535,701, the contents of which are herein incorporated by reference in its entirety. The device may comprise an impermeable reservoir which has been divided into a water-swellable agent chamber and an active agent formulation chamber. As a non-limiting example, the active agent formulation chamber may comprise the nucleic acid molecules, modified nucleic acids and/or mmRNA described herein and may be delivered for up to two years.

Devices for transdermal delivery are described in International Publication No. WO2013136234, the contents of which are herein incorporated by reference in its entirety. The device may comprise a patch having a therapeutic agent and a transdermal transfer enhancing agent. As a non-limiting example, the therapeutic agent may be the nucleic acid molecules, modified nucleic acids and/or mmRNA described herein.

Mucoadhesive drug delivery devices and methods of making and using such devices are described in U.S. Pat. No. 8,529,939, the contents of which are herein incorporated by reference in its entirety. The drug delivery devices may be used to adhere to mucosal tissue and thus may be used for mucosal delivery of the nucleic acid molecules, modified nucleic acid molecules and/or mmRNA described herein.

Drug delivery pumps and methods of manufacturing the pumps are described in U.S. Pat. No. 8,529,538, the contents of which are herein incorporated by reference in its entirety. The pump may comprise a first expandable diaphragm and a second flexible diaphragm. As a non-limiting example, the drug delivery pump is a minipump. The minipump may be used to deliver the nucleic acid molecules, modified nucleic acids and/or mmRNA described herein.

Drug delivery devices with inherent needle safety and a pre-filled syringe are described in International Publication No. WO2014012994 and WO2014012996, the contents of each of which are herein incorporated by reference in its entirety. The syringe is filled with a selected dosage of a therapeutic agent and after administration of the therapeutic agent, the syringe is retracted into the body of the drug delivery device for safety. As a non-limiting example, the therapeutic agent delivered with the device is the nucleic acid molecules, modified nucleic acid molecules and/or mmRNA described herein.

Methods of delivering therapeutic agents using solid biodegradable microneedles are described by O'hagan et al. in US Patent Publication No. US20130287832, the contents of which are herein incorporated by reference in its entirety. The microneedles are fabricated from the therapeutic agent (e.g., influenza vaccine) in combination with at least one solid excipient. After penetrating the skin, the microneedles dissolve in situ and release the therapeutic agent to the subject. As a non-limiting example, the therapeutic agents used in the fabrication of the microneedles are the nucleic acid molecules, modified nucleic acid molecules and/or mmRNA described herein.

A microneedle assembly for transdermal drug delivery is described by Ross et al. in U.S. Pat. No. 8,636,696, the contents of which are herein incorporated by reference in its entirety. The assembly has a first surface and a second surface where the microneedles project outwardly from the second surface of the support. The assembly may include a channel and aperture to form a junction which allows fluids (e.g., therapeutic agents or drugs) to pass.

Devices and methods for delivering agents to solid tissue is described by Gallagher et al. in International Patent Publication No. WO2014026044, the contents of which are herein incorporated by reference in its entirety. The device comprises a top block having a first plurality of holes sized to allow a needle to pass through the top block and a bottom block having a second plurality of holes sized to allow a needle to pass through the bottom block. The top and bottom blocks are in a substantially parallel arrangement. The device may also comprise a control attachment to control the depth of needle insertion into the solid tissue.

Methods and Devices Utilizing Catheters and/or Lumens

Methods and devices using catheters and lumens may be employed to administer the nucleic acid molecules, modified nucleic acid molecules or mmRNA of the present invention on a single, multi- or split dosing schedule. Such methods and devices are described below.

A catheter-based delivery of skeletal myoblasts to the myocardium of damaged hearts has been described by Jacoby et al and is taught for example in US Patent Publication 20060263338, the contents of which are incorporated herein by reference in their entirety. According to Jacoby, multiple needles are incorporated into the device at least part of which is inserted into a blood vessel and delivers the cell composition through the needles into the localized region of the subject's heart.

An apparatus for treating asthma using neurotoxin has been described by Deem et al and is taught for example in US Patent Publication 20060225742, the contents of which are incorporated herein by reference in their entirety. According to Deem, multiple needles are incorporated into the device which delivers neurotoxin through the needles into the bronchial tissue.

A method for administering multiple-component therapies has been described by Nayak and is taught for example in U.S. Pat. No. 7,699,803, the contents of which are incorporated herein by reference in their entirety. According to Nayak, multiple injection cannulas may be incorporated into a device wherein depth slots may be included for controlling the depth at which the therapeutic substance is delivered within the tissue.

A surgical device for ablating a channel and delivering at least one therapeutic agent into a desired region of the tissue has been described by McIntyre et al and is taught for example in U.S. Pat. No. 8,012,096, the contents of which are incorporated herein by reference in their entirety. According to McIntyre, multiple needles are incorporated into the device which dispenses a therapeutic agent into a region of tissue surrounding the channel and is particularly well suited for transmyocardial revascularization operations.

Methods of treating functional disorders of the bladder in mammalian females have been described by Versi et al and are taught for example in U.S. Pat. No. 8,029,496, the contents of which are incorporated herein by reference in their entirety. According to Versi, an array of micro-needles is incorporated into a device which delivers a therapeutic agent through the needles directly into the trigone of the bladder.

A device and a method for delivering fluid into a flexible biological barrier have been described by Yeshurun et al. and are taught for example in U.S. Pat. No. 7,998,119 (device) and U.S. Pat. No. 8,007,466 (method), the contents of which are incorporated herein by reference in their entirety.

According to Yeshurun, the micro-needles on the device penetrate and extend into the flexible biological barrier and fluid is injected through the bore of the hollow micro-needles.

A method for epicardially injecting a substance into an area of tissue of a heart having an epicardial surface and disposed within a torso has been described by Bonner et al and is taught for example in U.S. Pat. No. 7,628,780, the contents of which are incorporated herein by reference in their entirety. According to Bonner, the devices have elongate shafts and distal injection heads for driving needles into tissue and injecting medical agents into the tissue through the needles.

A device for sealing a puncture has been described by Nielsen et al and is taught for example in U.S. Pat. No. 7,972,358, the contents of which are incorporated herein by reference in their entirety. According to Nielsen, multiple needles are incorporated into the device which delivers a closure agent into the tissue surrounding the puncture tract.

A method for myogenesis and angiogenesis has been described by Chiu et al. and is taught for example in U.S. Pat. No. 6,551,338, the contents of which are incorporated herein by reference in their entirety. According to Chiu, 5 to 15 needles having a maximum diameter of at least 1.25 mm and a length effective to provide a puncture depth of 6 to 20 mm are incorporated into a device which inserts into proximity with a myocardium and supplies an exogeneous angiogenic or myogenic factor to said myocardium through the conduits which are in at least some of said needles.

A method for the treatment of prostate tissue has been described by Bolmsj et al. and is taught for example in U.S. Pat. No. 6,524,270, the contents of which are incorporated herein by reference in their entirety. According to Bolmsj, a device comprising a catheter which is inserted through the urethra has at least one hollow tip extendible into the surrounding prostate tissue. An astringent and analgesic medicine is administered through said tip into said prostate tissue.

A method for infusing fluids to an intraosseous site has been described by Findlay et al. and is taught for example in U.S. Pat. No. 6,761,726, the contents of which are incorporated herein by reference in their entirety. According to Findlay, multiple needles are incorporated into a device which is capable of penetrating a hard shell of material covered by a layer of soft material and delivers a fluid at a predetermined distance below said hard shell of material.

A device for injecting medications into a vessel wall has been described by Vigil et al. and is taught for example in U.S. Pat. No. 5,713,863, the contents of which are incorporated herein by reference in their entirety. According to Vigil, multiple injectors are mounted on each of the flexible tubes in the device which introduces a medication fluid through a multi-lumen catheter, into said flexible tubes and out of said injectors for infusion into the vessel wall.

A catheter for delivering therapeutic and/or diagnostic agents to the tissue surrounding a bodily passageway has been described by Faxon et al. and is taught for example in U.S. Pat. No. 5,464,395, the contents of which are incorporated herein by reference in their entirety. According to Faxon, at least one needle cannula is incorporated into the catheter which delivers the desired agents to the tissue through said needles which project outboard of the catheter.

Balloon catheters for delivering therapeutic agents have been described by Orr and are taught for example in WO2010024871, the contents of which are incorporated herein by reference in their entirety. According to Orr, multiple needles are incorporated into the devices which deliver the therapeutic agents to different depths within the tissue. In another aspect, drug-eluting balloons may be used to deliver the formulations described herein. The drug-eluting balloons may be used in target lesion applications such as, but are not limited to, in-stent restenosis, treating lesion in tortuous vessels, bifurcation lesions, femoral/popliteal lesions and below the knee lesions.

A device for delivering therapeutic agents (e.g., modified nucleic acid molecules or mmRNA) to tissue disposed about a lumin has been described by Perry et al. and is taught for example in U.S. Pat. Pub. US20100125239, the contents of which are herein incorporated by reference in their entirety. According to Perry, the catheter has a balloon which may be coated with a therapeutic agent by methods known in the art and described in Perry. When the balloon expands, the therapeutic agent will contact the surrounding tissue. The device may additionally have a heat source to change the temperature of the coating on the balloon to release the therapeutic agent to the tissue.

A device that releases a pharmaceutical agent to a target site is described by McClain and Taylor in International Patent Publication No. WO2013059509, the contents of which are herein incorporated by reference in its entirety. The device comprises a balloon which is coated at least partially with particles comprising a pharmaceutical agent which is at least partially encapsulated in a polymer layer. The device is positioned to reach the targeted site in the subject before the balloon is inflated.

Methods and Devices Utilizing Electrical Current

Methods and devices utilizing electric current may be employed to deliver the nucleic acid molecules, modified nucleic acid molecules, mmRNA of the present invention according to the single, multi- or split dosing regimens taught herein. Such methods and devices are described below.

An electro collagen induction therapy device has been described by Marquez and is taught for example in US Patent Publication 20090137945, the contents of which are incorporated herein by reference in their entirety. According to Marquez, multiple needles are incorporated into the device which repeatedly pierce the skin and draw in the skin a portion of the substance which is applied to the skin first.

An electrokinetic system has been described by Etheredge et al. and is taught for example in US Patent Publication 20070185432, the contents of which are incorporated herein by reference in their entirety. According to Etheredge, micro-needles are incorporated into a device which drives by an electrical current the medication through the needles into the targeted treatment site.

An iontophoresis device has been described by Matsumura et al. and is taught for example in U.S. Pat. No. 7,437,189, the contents of which are incorporated herein by reference in their entirety. According to Matsumura, multiple needles are incorporated into the device which is capable of delivering ionizable drug into a living body at higher speed or with higher efficiency.

Intradermal delivery of biologically active agents by needle-free injection and electroporation has been described by Hoffmann et al and is taught for example in U.S. Pat. No. 7,171,264, the contents of which are incorporated herein by reference in their entirety. According to Hoffmann, one or more needle-free injectors are incorporated into an electroporation device and the combination of needle-free injection and electroporation is sufficient to introduce the agent into cells in skin, muscle or mucosa.

A method for electropermeabilization-mediated intracellular delivery has been described by Lundkvist et al. and is taught for example in U.S. Pat. No. 6,625,486, the contents of which are incorporated herein by reference in their entirety. According to Lundkvist, a pair of needle electrodes is incorporated into a catheter. Said catheter is positioned into a body lumen followed by extending said needle electrodes to penetrate into the tissue surrounding said lumen. Then the device introduces an agent through at least one of said needle electrodes and applies electric field by said pair of needle electrodes to allow said agent pass through the cell membranes into the cells at the treatment site.

A delivery system for transdermal immunization has been described by Levin et al. and is taught for example in WO2006003659, the contents of which are incorporated herein by reference in their entirety. According to Levin, multiple electrodes are incorporated into the device which applies electrical energy between the electrodes to generate micro channels in the skin to facilitate transdermal delivery.

A method for delivering RF energy into skin has been described by Schomacker and is taught for example in WO2011163264, the contents of which are incorporated herein by reference in their entirety. According to Schomacker, multiple needles are incorporated into a device which applies vacuum to draw skin into contact with a plate so that needles insert into skin through the holes on the plate and deliver RF energy.

Definitions

At various places in the present specification, substituents of compounds of the present disclosure are disclosed in groups or in ranges. It is specifically intended that the present disclosure include each and every individual sub-combination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

About: As used herein, the term "about" means+/−10% of the recited value.

Administered in combination: As used herein, the term "administered in combination" or "combined administration" means that two or more agents (e.g., a nucleic acid molecule, modified nucleic acid or mmRNA encoding an anti-microbial polypeptide (e.g., an anti-bacterial polypeptide), e.g., an anti-microbial polypeptide described herein and an anti-microbial agent (e.g., an anti-microbial polypeptide or a small molecule anti-microbial compound described herein)) are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently close together such that a combinatorial (e.g., a synergistic) effect is achieved.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Antigens of interest or desired antigens: As used herein, the terms "antigens of interest" or "desired antigens" include those proteins and other biomolecules provided herein that are immunospecifically bound by the antibodies and fragments, mutants, variants, and alterations thereof described herein. Examples of antigens of interest include, but are not limited to, insulin, insulin-like growth factor, hGH, tPA, cytokines, such as interleukins (IL), e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosis factor (TNF), such as TNF alpha and TNF beta, TNF gamma, TRAIL; G-CSF, GM-CSF, M-CSF, MCP-1 and VEGF.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunctional: As used herein, the term "bifunctional" refers to any substance, molecule or moiety which is capable of or maintains at least two functions. The functions may effect the same outcome or a different outcome. The structure that produces the function may be the same or different. For example, bifunctional modified RNA or bifuncation RNA of the present invention may encode a cytotoxic peptide (a first function) while those nucleosides which comprise the encoding RNA are, in and of themselves, cytotoxic (second function). In this example, delivery of the bifunctional modified RNA or bifunctional RNA to a cancer cell would produce not only a peptide or protein molecule which may ameliorate or treat the cancer but would also deliver a cytotoxic payload of nucleosides to the cell should degradation, instead of translation of the RNA or modified RNA, occur.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological affect on that organism, is considered to be biologically active. In particular embodiments, the nucleic acid molecule, modified nucleic acid or mmRNA of the present invention may be considered biologically active if even a portion of the nucleic acid molecule, modified nucleic acid or mmRNA is biologically active or mimics an activity considered biologically relevant.

Chemical terms: The following provides the definition of various chemical terms from "acyl" to "thiol."

The term "acyl," as used herein, represents a hydrogen or an alkyl group (e.g., a haloalkyl group), as defined herein, that is attached to the parent molecular group through a carbonyl group, as defined herein, and is exemplified by formyl (i.e., a carboxyaldehyde group), acetyl, propionyl, butanoyl and the like. Exemplary unsubstituted acyl groups include from 1 to 7, from 1 to 11, or from 1 to 21 carbons. In some embodiments, the alkyl group is further substituted with 1, 2, 3, or 4 substituents as described herein.

The term "acylamino," as used herein, represents an acyl group, as defined herein, attached to the parent molecular group though an amino group, as defined herein (i.e., —N($R^{N1}$)—C(O)—R, where R is H or an optionally substituted $C_{1-6}$, $C_{1-10}$, or $C_{1-20}$ alkyl group and $R^{N1}$ is as defined herein). Exemplary unsubstituted acylamino groups include from 1 to 41 carbons (e.g., from 1 to 7, from 1 to 13, from 1 to 21, from 2 to 7, from 2 to 13, from 2 to 21, or from 2 to 41 carbons). In some embodiments, the alkyl group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, or aryl, and each $R^{N2}$ can be H, alkyl, or aryl.

The term "acyloxy," as used herein, represents an acyl group, as defined herein, attached to the parent molecular group though an oxygen atom (i.e., —O—C(O)—R, where R is H or an optionally substituted $C_{1-6}$, $C_{1-10}$, or $C_{1-20}$ alkyl group). Exemplary unsubstituted acyloxy groups include from 1 to 21 carbons (e.g., from 1 to 7 or from 1 to 11 carbons). In some embodiments, the alkyl group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, or aryl, and each $R^{N2}$ can be H, alkyl, or aryl.

The term "alkaryl," as used herein, represents an aryl group, as defined herein, attached to the parent molecular group through an alkylene group, as defined herein. Exemplary unsubstituted alkaryl groups are from 7 to 30 carbons (e.g., from 7 to 16 or from 7 to 20 carbons, such as $C_{1-6}$ alk-$C_{6-10}$ aryl, $C_{1-10}$ alk-$C_{6-10}$ aryl, or $C_{1-20}$ alk-$C_{6-10}$ aryl). In some embodiments, the alkylene and the aryl each can be further substituted with 1, 2, 3, or 4 substituent groups as defined herein for the respective groups. Other groups preceded by the prefix "alk-" are defined in the same manner, where "alk" refers to a $C_{1-6}$ alkylene, unless otherwise noted, and the attached chemical structure is as defined herein.

The term "alkcycloalkyl" represents a cycloalkyl group, as defined herein, attached to the parent molecular group through an alkylene group, as defined herein (e.g., an alkylene group of from 1 to 4, from 1 to 6, from 1 to 10, or form 1 to 20 carbons). In some embodiments, the alkylene and the cycloalkyl each can be further substituted with 1, 2, 3, or 4 substituent groups as defined herein for the respective group.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, 2-butenyl, and the like. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

The term "alkenyloxy" represents a chemical substituent of formula —OR, where R is a C2-20 alkenyl group (e.g., C2-6 or C2-10 alkenyl), unless otherwise specified. Exemplary alkenyloxy groups include ethenyloxy, propenyloxy, and the like. In some embodiments, the alkenyl group can be further substituted with 1, 2, 3, or 4 substituent groups as defined herein (e.g., a hydroxy group).

The term "alkheteroaryl" refers to a heteroaryl group, as defined herein, attached to the parent molecular group through an alkylene group, as defined herein. Exemplary unsubstituted alkheteroaryl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heteroaryl, $C_{1-10}$ alk-$C_{1-12}$ heteroaryl, or $C_{1-20}$ alk-$C_{1-12}$ heteroaryl). In some embodiments, the alkylene and the heteroaryl each can be further substituted with 1, 2, 3, or 4 substituent groups as defined herein for the respective group. Alkheteroaryl groups are a subset of alkheterocyclyl groups.

The term "alkheterocyclyl" represents a heterocyclyl group, as defined herein, attached to the parent molecular group through an alkylene group, as defined herein. Exemplary unsubstituted alkheterocyclyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heterocyclyl, $C_{1-10}$ alk-$C_{1-12}$ heterocyclyl, or $C_{1-20}$ alk-$C_{1-12}$ heterocyclyl). In some embodiments, the alkylene and the heterocyclyl each can be further substituted with 1, 2, 3, or 4 substituent groups as defined herein for the respective group.

The term "alkoxy" represents a chemical substituent of formula —OR, where R is a $C_{1-20}$ alkyl group (e.g., $C_{1-6}$ or $C_{1-10}$ alkyl), unless otherwise specified. Exemplary alkoxy groups include methoxy, ethoxy, propoxy (e.g., n-propoxy and isopropoxy), t-butoxy, and the like. In some embodiments, the alkyl group can be further substituted with 1, 2, 3, or 4 substituent groups as defined herein (e.g., hydroxy or alkoxy).

The term "alkoxyalkoxy" represents an alkoxy group that is substituted with an alkoxy group. Exemplary unsubstituted alkoxyalkoxy groups include between 2 to 40 carbons (e.g., from 2 to 12 or from 2 to 20 carbons, such as $C_{1-6}$ alkoxy-$C_{1-6}$ alkoxy, $C_{1-10}$ alkoxy-$C_{1-10}$ alkoxy, or $C_{1-20}$ alkoxy-$C_{1-20}$ alkoxy). In some embodiments, the each alkoxy group can be further substituted with 1, 2, 3, or 4 substituent groups as defined herein.

The term "alkoxyalkyl" represents an alkyl group that is substituted with an alkoxy group. Exemplary unsubstituted alkoxyalkyl groups include between 2 to 40 carbons (e.g., from 2 to 12 or from 2 to 20 carbons, such as $C_{1-6}$ alkoxy-$C_{1-6}$ alkyl, $C_{1-10}$ alkoxy-$C_{1-10}$ alkyl, or $C_{1-20}$ alkoxy-$C_{1-20}$ alkyl). In some embodiments, the alkyl and the alkoxy each can be further substituted with 1, 2, 3, or 4 substituent groups as defined herein for the respective group.

The term "alkoxycarbonyl," as used herein, represents an alkoxy, as defined herein, attached to the parent molecular group through a carbonyl atom (e.g., —C(O)—OR, where R is H or an optionally substituted $C_{1-6}$, $C_{1-10}$, or $C_{1-20}$ alkyl group). Exemplary unsubstituted alkoxycarbonyl include from 1 to 21 carbons (e.g., from 1 to 11 or from 1 to 7 carbons). In some embodiments, the alkoxy group is further substituted with 1, 2, 3, or 4 substituents as described herein.

The term "alkoxycarbonylalkoxy," as used herein, represents an alkoxy group, as defined herein, that is substituted with an alkoxycarbonyl group, as defined herein (e.g., —O-alkyl-C(O)—OR, where R is an optionally substituted $C_{1-6}$, $C_{1-10}$, or $C_{1-20}$ alkyl group). Exemplary unsubstituted alkoxycarbonylalkoxy include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkoxy, $C_{1-10}$ alkoxycarbonyl-$C_{1-10}$ alkoxy, or $C_{1-20}$ alkoxycarbonyl-$C_{1-20}$ alkoxy). In some embodiments, each alkoxy group is further independently substituted with 1, 2, 3, or 4 substituents, as described herein (e.g., a hydroxy group).

The term "alkoxycarbonylalkyl," as used herein, represents an alkyl group, as defined herein, that is substituted with an alkoxycarbonyl group, as defined herein (e.g., -alkyl-C(O)—OR, where R is an optionally substituted $C_{1-20}$, $C_{1-10}$, or $C_{1-6}$ alkyl group). Exemplary unsubstituted alkoxycarbonylalkyl include from 3 to 41 carbons (e.g., from 3 to 10, from 3 to 13, from 3 to 17, from 3 to 21, or from 3 to 31 carbons, such as C1-6 alkoxycarbonyl-$C_{1-6}$ alkyl, $C_{1-10}$ alkoxycarbonyl-$C_{1-10}$ alkyl, or $C_{1-20}$ alkoxycarbonyl-$C_{1-20}$ alkyl). In some embodiments, each alkyl and alkoxy group is further independently substituted with 1, 2, 3, or 4 substituents as described herein (e.g., a hydroxy group).

The term "alkyl," as used herein, is inclusive of both straight chain and branched chain saturated groups from 1 to 20 carbons (e.g., from 1 to 10 or from 1 to 6), unless otherwise specified. Alkyl groups are exemplified by methyl, ethyl, n- and iso-propyl, n-, sec-, iso- and tert-butyl, neopentyl, and the like, and may be optionally substituted with one, two, three, or, in the case of alkyl groups of two carbons or more, four substituents independently selected from the group consisting of: (1) C1-6 alkoxy; (2) $C_{1-6}$ alkylsulfinyl; (3) amino, as defined herein (e.g., unsubstituted amino (i.e., —$NH_2$) or a substituted amino (i.e., —N($R^{N1}$)$_2$, where $R^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy; (9) nitro; (10) oxo (e.g., carboxyaldehyde or acyl); (11) $C_{1-7}$ spirocyclyl; (12) thioalkoxy; (13) thiol; (14) —$CO_2R^{A'}$, where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —$(CH_2)_{s2}$($OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted C1-6 alkyl; (15) —C(O)$NR^{B'}R^{C'}$, where each of $R^{B'}$ and $R^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —$SO_2R^{D'}$, where $R^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —$SO_2NR^{E'}R^{F'}$, where each of $R^{E'}$ and $R^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —C(O)$R^{G'}$, where $R^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C1-20 alkyl, and (h) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) —$NR^{H'}C(O)R^{I'}$, wherein $R^{H'}$ is selected from the group consisting of (a1) hydrogen and (b1) $C_{1-6}$ alkyl, and $R^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) —$NR^{J'}C(O)OR^{K'}$, wherein $R^{K'}$ is selected from the group consisting of (a1) hydrogen and (b1) $C_{1-6}$ alkyl, and $R^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein. For example, the alkylene group of a $C_1$-alkaryl can be further substituted with an oxo group to afford the respective aryloyl substituent.

The term "alkylene" and the prefix "alk-," as used herein, represent a saturated divalent hydrocarbon group derived from a straight or branched chain saturated hydrocarbon by the removal of two hydrogen atoms, and is exemplified by methylene, ethylene, isopropylene, and the like. The term "$C_{x-y}$ alkylene" and the prefix "$C_{x-y}$ alk-" represent alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_{1-6}$, $C_{1-10}$, $C_{2-20}$, $C_{2-6}$, $C_{2-10}$, or $C_{2-20}$ alkylene). In some embodiments, the alkylene can be further substituted with 1, 2, 3, or 4 substituent groups as defined herein for an alkyl group.

The term "alkylsulfinyl," as used herein, represents an alkyl group attached to the parent molecular group through an —S(O)— group. Exemplary unsubstituted alkylsulfinyl groups are from 1 to 6, from 1 to 10, or from 1 to 20 carbons. In some embodiments, the alkyl group can be further substituted with 1, 2, 3, or 4 substituent groups as defined herein.

The term "alkylsulfinylalkyl," as used herein, represents an alkyl group, as defined herein, substituted by an alkylsulfinyl group. Exemplary unsubstituted alkylsulfinylalkyl groups are from 2 to 12, from 2 to 20, or from 2 to 40 carbons. In some embodiments, each alkyl group can be further substituted with 1, 2, 3, or 4 substituent groups as defined herein.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, 1-propynyl, and the like. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

The term "alkynyloxy" represents a chemical substituent of formula —OR, where R is a $C_{2-20}$ alkynyl group (e.g., $C_{2-6}$ or $C_{2-10}$ alkynyl), unless otherwise specified. Exemplary alkynyloxy groups include ethynyloxy, propynyloxy, and the like. In some embodiments, the alkynyl group can be further substituted with 1, 2, 3, or 4 substituent groups as defined herein (e.g., a hydroxy group).

The term "amidine," as used herein, represents a —C(=NH)NH$_2$ group.

The term "amino," as used herein, represents —N(R$^{N1}$)$_2$, wherein each R$^{N1}$ is, independently, H, OH, NO$_2$, N(R$^{N2}$)$_2$, SO$_2$OR$^{N2}$, SO$_2$R$^{N2}$, SOR$^{N2}$, an N-protecting group, alkyl, alkenyl, alkynyl, alkoxy, aryl, alkaryl, cycloalkyl, alkcycloalkyl, carboxyalkyl, sulfoalkyl, heterocyclyl (e.g., heteroaryl), or alkheterocyclyl (e.g., alkheteroaryl), wherein each of these recited R$^{N1}$ groups can be optionally substituted, as defined herein for each group; or two R$^{N1}$ combine to form a heterocyclyl or an N-protecting group, and wherein each R$^{N2}$ is, independently, H, alkyl, or aryl. The amino groups of the invention can be an unsubstituted amino (i.e., —NH$_2$) or a substituted amino (i.e., —N(R$^{N1}$)$_2$). In a preferred embodiment, amino is —NH$_2$ or —NHR$^{N1}$, wherein R$^{N1}$ is, independently, OH, NO$_2$, NH$_2$, NR$^{N2}$$_2$, SO$_2$OR$^{N2}$, SO$_2$R$^{N2}$, SOR$^{N2}$, alkyl, carboxyalkyl, sulfoalkyl, or aryl, and each R$^{N2}$ can be H, $C_{1-20}$ alkyl (e.g., $C_{1-6}$ alkyl), or $C_{6-10}$ aryl.

The term "amino acid," as described herein, refers to a molecule having a side chain, an amino group, and an acid group (e.g., a carboxy group of —CO$_2$H or a sulfo group of —SO$_3$H), wherein the amino acid is attached to the parent molecular group by the side chain, amino group, or acid group (e.g., the side chain). In some embodiments, the amino acid is attached to the parent molecular group by a carbonyl group, where the side chain or amino group is attached to the carbonyl group. Exemplary side chains include an optionally substituted alkyl, aryl, heterocyclyl, alkaryl, alkheterocyclyl, aminoalkyl, carbamoylalkyl, and carboxyalkyl. Exemplary amino acids include alanine, arginine, asparagine, aspartic acid, cysteine, glutamic acid, glutamine, glycine, histidine, hydroxynorvaline, isoleucine, leucine, lysine, methionine, norvaline, ornithine, phenylalanine, proline, pyrrolysine, selenocysteine, serine, taurine, threonine, tryptophan, tyrosine, and valine. Amino acid groups may be optionally substituted with one, two, three, or, in the case of amino acid groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —NH$_2$) or a substituted amino (i.e., —N(R$^{N1}$)$_2$, where R$^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy; (9) nitro; (10) oxo (e.g., carboxaldehyde or acyl); (11) $C_{1-7}$ spirocyclyl; (12) thioalkoxy; (13) thiol; (14) —CO$_2$R$^{A'}$, where R$^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (15) —C(O)NR$^{B'}$R$^{C'}$, where each of R$^{B'}$ and R$^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —SO$_2$R$^{D'}$, where R$^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —SO$_2$NR$^{E'}$R$^{F'}$, where each of R$^{E'}$ and R$^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —C(O)R$^{G'}$, where R$^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (19) —NR$^{H'}$C(O)R$^{I'}$, wherein R$^{H'}$ is selected from the group consisting of (a1) hydrogen and (b1) $C_{1-6}$ alkyl, and R$^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (20) —NR$^{J'}$C(O)OR$^{K'}$, where R$^{J'}$ is selected from the group consisting of (a1) hydrogen and (b1) $C_{1-6}$ alkyl, and R$^{K'}$ is selected from the group consisting of (a2) C1-20 alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) aminopolyethylene glycol of —$NR^{N1}(CH_2)_{s2}(CH_2CH_2O)_{s1}$ $(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted C1-6 alkyl; and (21) amidine. In some embodiments, each of these groups can be further substituted as described herein.

The term "aminoalkoxy," as used herein, represents an alkoxy group, as defined herein, substituted by an amino group, as defined herein. The alkyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy).

The term "aminoalkyl," as used herein, represents an alkyl group, as defined herein, substituted by an amino group, as defined herein. The alkyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy).

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, anthracenyl, phenanthrenyl, fluorenyl, indanyl, indenyl, and the like, and may be optionally substituted with 1, 2, 3, 4, or 5 substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) alkyl, (b) $C_{6-10}$ aryl, and (c) alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) $C_{2-20}$ alkenyl; and (27) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "arylalkoxy," as used herein, represents an alkaryl group, as defined herein, attached to the parent molecular group through an oxygen atom. Exemplary unsubstituted alkoxyalkyl groups include from 7 to 30 carbons (e.g., from 7 to 16 or from 7 to 20 carbons, such as $C_{6-10}$ aryl-$C_{1-6}$ alkoxy, $C_{6-10}$ aryl-$C_{1-10}$ alkoxy, or $C_{6-10}$ aryl-$C_{1-20}$ alkoxy). In some embodiments, the arylalkoxy group can be substituted with 1, 2, 3, or 4 substituents as defined herein The term "aryloxy" represents a chemical substituent of formula —OR', where R' is an aryl group of 6 to 18 carbons, unless otherwise specified. In some embodiments, the aryl group can be substituted with 1, 2, 3, or 4 substituents as defined herein.

The term "aryloyl," as used herein, represents an aryl group, as defined herein, that is attached to the parent molecular group through a carbonyl group. Exemplary unsubstituted aryloyl groups are of 7 to 11 carbons. In some embodiments, the aryl group can be substituted with 1, 2, 3, or 4 substituents as defined herein.

The term "azido" represents an —$N_3$ group, which can also be represented as —N=N=N.

The term "bicyclic," as used herein, refer to a structure having two rings, which may be aromatic or non-aromatic. Bicyclic structures include spirocyclyl groups, as defined herein, and two rings that share one or more bridges, where such bridges can include one atom or a chain including two, three, or more atoms. Exemplary bicyclic groups include a bicyclic carbocyclyl group, where the first and second rings are carbocyclyl groups, as defined herein; a bicyclic aryl groups, where the first and second rings are aryl groups, as defined herein; bicyclic heterocyclyl groups, where the first ring is a heterocyclyl group and the second ring is a carbocyclyl (e.g., aryl) or heterocyclyl (e.g., heteroaryl) group; and bicyclic heteroaryl groups, where the first ring is a heteroaryl group and the second ring is a carbocyclyl (e.g., aryl) or heterocyclyl (e.g., heteroaryl) group. In some embodiments, the bicyclic group can be substituted with 1, 2, 3, or 4 substituents as defined herein for cycloalkyl, heterocyclyl, and aryl groups.

The terms "carbocyclic" and "carbocyclyl," as used herein, refer to an optionally substituted C3-12 monocyclic, bicyclic, or tricyclic structure in which the rings, which may be aromatic or non-aromatic, are formed by carbon atoms. Carbocyclic structures include cycloalkyl, cycloalkenyl, and aryl groups.

The term "carbamoyl," as used herein, represents —C(O)—$N(R^{N1})_2$, where the meaning of each $R^{N1}$ is found in the definition of "amino" provided herein.

The term "carbamoylalkyl," as used herein, represents an alkyl group, as defined herein, substituted by a carbamoyl group, as defined herein. The alkyl group can be further substituted with 1, 2, 3, or 4 substituent groups as described herein.

The term "carbamyl," as used herein, refers to a carbamate group having the structure —$NR^{N1}C(=O)OR$ or —OC$(=O)N(R^{N1})_2$, where the meaning of each $R^{N1}$ is found in the definition of "amino" provided herein, and R is alkyl, cycloalkyl, alkcycloalkyl, aryl, alkaryl, heterocyclyl (e.g., heteroaryl), or alkheterocyclyl (e.g., alkheteroaryl), as defined herein.

The term "carbonyl," as used herein, represents a C(O) group, which can also be represented as C=O.

The term "carboxyaldehyde" represents an acyl group having the structure —CHO.

The term "carboxy," as used herein, means —CO$_2$H.

The term "carboxyalkoxy," as used herein, represents an alkoxy group, as defined herein, substituted by a carboxy group, as defined herein. The alkoxy group can be further substituted with 1, 2, 3, or 4 substituent groups as described herein for the alkyl group.

The term "carboxyalkyl," as used herein, represents an alkyl group, as defined herein, substituted by a carboxy group, as defined herein. The alkyl group can be further substituted with 1, 2, 3, or 4 substituent groups as described herein.

The term "cyano," as used herein, represents an —CN group.

The term "cycloalkoxy" represents a chemical substituent of formula —OR, where R is a C3-8 cycloalkyl group, as defined herein, unless otherwise specified. The cycloalkyl group can be further substituted with 1, 2, 3, or 4 substituent groups as described herein. Exemplary unsubstituted cycloalkoxy groups are from 3 to 8 carbons.

The term "cycloalkyl," as used herein represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicyclo[2.2.1]heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like. The cycloalkyl groups of this invention can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —(CH$_2$)$_q$CO$_2$R$^{A'}$, where q is an integer from zero to four, and R$^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) $C_{6-10}$ alkyl, (c) $C_{6-10}$ aryl, and (d) $C_{1-6}$ alk-$C_{6-10}$ aryl; (19) —(CH$_2$)$_q$SO$_2$R$^{D'}$, where q is an integer from zero to four and where R$^{D'}$ is selected from the group consisting of (a) $C_{6-10}$ alkyl, (b) $C_{6-10}$ aryl, and (c) $C_{1-6}$ alk-$C_{6-10}$ aryl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) $C_{6-10}$ alkyl, (c) $C_{6-10}$ aryl, and (d) $C_{1-6}$ alk-$C_{6-10}$ aryl; (21) thiol; (22) $C_{6-10}$ aryloxy; (23) C3-8 cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) oxo; (27) $C_{2-20}$ alkenyl; and (28) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "diasteromer" means stereoisomers that are not mirror images of one another and are non-superimposable.

The term "effective amount" of an agent, as used herein, is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "halo," as used herein, represents a halogen selected from bromine, chlorine, iodine, or fluorine.

The term "haloalkoxy," as used herein, represents an alkoxy group, as defined herein, substituted by a halogen group (i.e., F, Cl, Br, or I). A haloalkoxy may be substituted with one, two, three, or, in the case of alkyl groups of two carbons or more, four halogens. Haloalkoxy groups include perfluoroalkoxys (e.g., —OCF$_3$), —OCHF$_2$, —OCH$_2$F, —OCCl$_3$, —OCH$_2$CH$_2$Br, —OCH$_2$CH(CH$_2$CH$_2$Br)CH$_3$, and —OCHICH$_3$. In some embodiments, the haloalkoxy group can be further substituted with 1, 2, 3, or 4 substituent groups as described herein for alkyl groups.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens. Haloalkyl groups include perfluoroalkyls (e.g., —CF$_3$), —CHF$_2$, —CH$_2$F, —CCl$_3$, —CH$_2$CH$_2$Br, —CH$_2$CH(CH$_2$CH$_2$Br)CH$_3$, and —CHICH$_3$. In some embodiments, the haloalkyl group can be further substituted with 1, 2, 3, or 4 substituent groups as described herein for alkyl groups.

The term "heteroalkylene," as used herein, refers to an alkylene group, as defined herein, in which one or two of the constituent carbon atoms have each been replaced by nitrogen, oxygen, or sulfur. In some embodiments, the heteroalkylene group can be further substituted with 1, 2, 3, or 4 substituent groups as described herein for alkylene groups.

The term "heteroaryl," as used herein, represents that subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, benzothienyl, and the like, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl. Heterocyclic groups also include groups of the formula

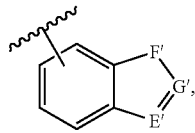

where
E' is selected from the group consisting of —N— and —CH—; F' is selected from the group consisting of —N═CH—, —NH—CH$_2$—, —NH—C(O)—, —NH—, —CH═N—, —CH$_2$—NH—, —C(O)—NH—, —CH═CH—, —CH$_2$—, —CH$_2$CH$_2$—, —CH$_2$O—, —OCH$_2$—, —O—, and —S—; and G' is selected from the group consisting of —CH— and —N—. Any of the heterocyclyl groups mentioned herein may be optionally substituted with one, two, three, four or five substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{2-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —(CH$_2$)$_q$CO$_2$R$^{A'}$, where q is an integer from zero to four, and R$^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —(CH$_2$)$_q$SO$_2$R$^{D'}$, where q is an integer from zero to four and where R$^{D'}$ is selected from the group consisting of (a) $C_{1-6}$ alkyl, (b) $C_{6-10}$ aryl, and (c) $C_{1-6}$ alk-$C_{6-10}$ aryl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) $C_{1-6}$ alkyl, (c) $C_{6-10}$ aryl, and (d) C1-6 alk-$C_{6-10}$ aryl; (21) thiol; (22) $C_{6-10}$ aryloxy; (23) $C_{3-8}$ cycloalkoxy; (24) arylalkoxy; (25) $C_{1-6}$ alk-$C_{1-12}$ heterocyclyl (e.g., $C_{1-6}$ alk-$C_{1-12}$ heteroaryl); (26) oxo; (27) ($C_{1-12}$ heterocyclyl)imino; (28) $C_{2-20}$ alkenyl; and (29) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "(heterocyclyl)imino," as used herein, represents a heterocyclyl group, as defined herein, attached to the parent molecular group through an imino group. In some embodiments, the heterocyclyl group can be substituted with 1, 2, 3, or 4 substituent groups as defined herein.

The term "(heterocyclyl)oxy," as used herein, represents a heterocyclyl group, as defined herein, attached to the parent molecular group through an oxygen atom. In some embodiments, the heterocyclyl group can be substituted with 1, 2, 3, or 4 substituent groups as defined herein.

The term "(heterocyclyl)oyl," as used herein, represents a heterocyclyl group, as defined herein, attached to the parent molecular group through a carbonyl group. In some embodiments, the heterocyclyl group can be substituted with 1, 2, 3, or 4 substituent groups as defined herein.

The term "hydrocarbon," as used herein, represents a group consisting only of carbon and hydrogen atoms.

The term "hydroxy," as used herein, represents an —OH group.

The term "hydroxyalkenyl," as used herein, represents an alkenyl group, as defined herein, substituted by one to three hydroxy groups, with the proviso that no more than one hydroxy group may be attached to a single carbon atom of the alkyl group, and is exemplified by dihydroxypropenyl, hydroxyisopentenyl, and the like.

The term "hydroxyalkyl," as used herein, represents an alkyl group, as defined herein, substituted by one to three hydroxy groups, with the proviso that no more than one hydroxy group may be attached to a single carbon atom of the alkyl group, and is exemplified by hydroxymethyl, dihydroxypropyl, and the like.

The term "isomer," as used herein, means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "N-protected amino," as used herein, refers to an amino group, as defined herein, to which is attached one or two N-protecting groups, as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups, such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —NO$_2$ group.

The term "oxo" as used herein, represents =O.

The term "perfluoroalkyl," as used herein, represents an alkyl group, as defined herein, where each hydrogen radical bound to the alkyl group has been replaced by a fluoride radical. Perfluoroalkyl groups are exemplified by trifluoromethyl, pentafluoroethyl, and the like.

The term "perfluoroalkoxy," as used herein, represents an alkoxy group, as defined herein, where each hydrogen radical bound to the alkoxy group has been replaced by a fluoride radical. Perfluoroalkoxy groups are exemplified by trifluoromethoxy, pentafluoroethoxy, and the like.

The term "spirocyclyl," as used herein, represents a $C_{2-7}$ alkylene diradical, both ends of which are bonded to the same carbon atom of the parent group to form a spirocyclic group, and also a $C_{1-6}$ heteroalkylene diradical, both ends of which are bonded to the same atom. The heteroalkylene radical forming the spirocyclyl group can containing one, two, three, or four heteroatoms independently selected from the group consisting of nitrogen, oxygen, and sulfur. In some embodiments, the spirocyclyl group includes one to seven carbons, excluding the carbon atom to which the diradical is attached. The spirocyclyl groups of the invention may be optionally substituted with 1, 2, 3, or 4 substituents provided herein as optional substituents for cycloalkyl and/or heterocyclyl groups.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

The term "sulfoalkyl," as used herein, represents an alkyl group, as defined herein, substituted by a sulfo group of —SO$_3$H. In some embodiments, the alkyl group can be further substituted with 1, 2, 3, or 4 substituent groups as described herein.

The term "sulfonyl," as used herein, represents an —S(O)$_2$— group.

The term "thioalkaryl," as used herein, represents a chemical substituent of formula —SR, where R is an alkaryl group. In some embodiments, the alkaryl group can be further substituted with 1, 2, 3, or 4 substituent groups as described herein.

The term "thioalkheterocyclyl," as used herein, represents a chemical substituent of formula —SR, where R is an alkheterocyclyl group. In some embodiments, the alkheterocyclyl group can be further substituted with 1, 2, 3, or 4 substituent groups as described herein.

The term "thioalkoxy," as used herein, represents a chemical substituent of formula —SR, where R is an alkyl group, as defined herein. In some embodiments, the alkyl group can be further substituted with 1, 2, 3, or 4 substituent groups as described herein.

The term "thiol" represents an —SH group.

Compound: As used herein, the term "compound," is meant to include all stereoisomers, geometric isomers, tautomers, and isotopes of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an oligonucleotide or polypeptide or may apply to a portion, region or feature thereof.

Controlled Release: As used herein, the term "controlled release" refers to a pharmaceutical composition or compound release profile that conforms to a particular pattern of release to effect a therapeutic outcome.

Cyclic or Cyclized: As used herein, the term "cyclic" refers to the presence of a continuous loop. Cyclic molecules need not be circular, only joined to form an unbroken chain of subunits. Cyclic molecules such as the nucleic acid molecules, modified nucleic acid molecules, mmRNA or mRNA of the present invention may be single units or multimers or comprise one or more components of a complex or higher order structure.

Cytostatic: As used herein, "cytostatic" refers to inhibiting, reducing, suppressing the growth, division, or multiplication of a cell (e.g., a mammalian cell (e.g., a human cell)), bacterium, virus, fungus, protozoan, parasite, prion, or a combination thereof.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivery: As used herein, "delivery" refers to the act or manner of delivering a compound, substance, entity, moiety, cargo or payload.

Delivery Agent: As used herein, "delivery agent" refers to any substance which facilitates, at least in part, the in vivo delivery of a modified nucleic acid or mmRNA to targeted cells.

Destabilized: As used herein, the term "destable," "destabilize," or "destabilizing region" means a region or molecule that is less stable than a starting, wild-type or native form of the same region or molecule.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the peptides or proteins disclosed herein. They may be within the amino acids, the peptides, or proteins, or located at the N- or C-termini.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Dose splitting factor (DSF)-ratio of PUD of dose split treatment divided by PUD of total daily dose or single unit dose. The value is derived from comparison of dosing regimens groups.

Encapsulate: As used herein, the term "encapsulate" means to enclose, surround or encase.

Engineered: As used herein, embodiments of the invention are "engineered" when they are designed to have a feature or property, whether structural or chemical, that varies from a starting point, wild type or native molecule.

Exosome: As used herein, "exosome" is a vesicle secreted by mammalian cells.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Feature: As used herein, a "feature" refers to a characteristic, a property, or a distinctive element.

Formulation: As used herein, a "formulation" includes at least a modified nucleic acid or mmRNA and a delivery agent.

Fragment: A "fragment," as used herein, refers to a portion. For example, fragments of proteins may comprise polypeptides obtained by digesting full-length protein isolated from cultured cells.

Functional: As used herein, a "functional" biological molecule is a biological molecule in a form in which it exhibits a property and/or activity by which it is characterized.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the invention, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the invention, two protein sequences are considered to be homologous if the proteins are at least about 50%, 60%, 70%, 80%, or 90% identical for at least one stretch of at least about 20 amino acids.

Identity: As used herein, the term "identity" refers to the overall relatedness between polymeric molecules, e.g., between oligonucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Linker: As used herein, a linker refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker may be of sufficient length as to not interfere with incorporation into a nucleic acid sequence. The linker can be used for any useful purpose, such as to form mmRNA multimers (e.g., through linkage of two or more nucleic acid molecules, modified nucleic acid molecules or mmRNA molecules) or mmRNA conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof. Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

MicroRNA (miRNA) binding site: As used herein, a microRNA (miRNA) binding site represents a nucleotide location or region of a nucleic acid transcript to which at least the "seed" region of a miRNA binds.

Modified: As used herein "modified" refers to a changed state or structure of a molecule of the invention. Molecules may be modified in many ways including chemically, structurally, and functionally. In one embodiment, the mRNA molecules of the present invention are modified by the introduction of non-natural nucleosides and/or nucleotides.

Mucus: As used herein, "mucus" refers to a natural substance that is viscous and comprises mucin glycoproteins.

Naturally occurring: As used herein, "naturally occurring" means existing in nature without artificial aid.

Non-human vertebrate: As used herein, a "non human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Paratope: As used herein, a "paratope" refers to the antigen-binding site of an antibody.

Patient: As used herein, "patient" refers to a subject who may seek or be in need of treatment, requires treatment, is receiving treatment, will receive treatment, or a subject who is under care by a trained professional for a particular disease or condition.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Pharmacologic effect: As used herein, a "pharmacologic effect" is a measurable biologic phenomenon in an organism or system which occurs after the organism or system has been contacted with or exposed to an exogenous agent. Pharmacologic effects may result in therapeutically effective outcomes such as the treatment, improvement of one or more symptoms, diagnosis, prevention, and delay of onset of disease, disorder, condition or infection. Measurement of such biologic phenomena may be quantitative, qualitative or relative to another biologic phenomenon. Quantitative measurements may be statistically significant. Qualitative measurements may be by degree or kind and may be at least 10%, 20%, 30%, 40%, 50%, 60%, 70%, 80%, 90% or more different. They may be observable as present or absent, better or worse, greater or less. Exogenous agents, when referring to pharmacologic effects are those agents which are, in whole or in part, foreign to the organism or system. For example, modifications to a wild type biomolecule, whether structural or chemical, would produce an exogenous agent. Likewise, incorporation or combination of a wild type molecule into or with a compound, molecule or substance not found naturally in the organism or system would also produce an exogenous agent. The modified mRNA of the present invention, comprise exogenous agents. Examples of pharmacologic effects include, but are not limited to, alteration in cell count such as an increase or decrease in neutrophils, reticulocytes, granulocytes, erythrocytes (red blood cells), megakaryocytes, platelets, monocytes, connective tissue macrophages, epidermal langerhans cells, osteoclasts, dendritic cells, microglial cells, neutrophils, eosinophils, basophils, mast cells, helper T cells, suppressor T cells, cytotoxic T cells, natural killer T cells, B cells, natural killer cells, or reticulocytes. Pharmacologic effects also include alterations in blood chemistry, pH, hemoglobin, hematocrit, changes in levels of enzymes such as, but not limited to, liver enzymes AST and ALT, changes in lipid profiles, electrolytes, metabolic markers, hormones or other marker or profile known to those of skill in the art.

Physicochemical: As used herein, "physicochemical" means of or relating to a physical and/or chemical property.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Prodrugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Pseudouridine: As used herein, pseudouridine refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methyl-pseudouridine ($m^1\psi$), 1-methyl-4-thio-pseudouridine ($m^1s^4\psi$) 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, N1-methyl-pseudouridine, 1-methyl-3-(3-amino-3-carboxypropyl)pseudouridine ($acp^3$ $\psi$), and 2'-O-methyl-pseudouridine ($\psi m$).

Purified: As used herein, "purify," "purified," "purification" means to make substantially pure or clear from unwanted components, material defilement, admixture or imperfection.

Sample: As used herein, the term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Signal Sequences: As used herein, the phrase "signal sequences" refers to a sequence which can direct the transport or localization of a protein.

Single unit dose: As used herein, a "single unit dose" is a dose of any therapeutic administered in one dose/at one time/single route/single point of contact, i.e., single administration event.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Split dose: As used herein, a "split dose" is the division of single unit dose or total daily dose into two or more doses.

Stable: As used herein "stable" refers to a compound that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term means within 2 seconds.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or polypeptides or other molecules of the present invention may be chemical or enzymatic.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr period. It may be administered as a single unit dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

The invention is further described in the following examples, which do not limit the scope of the invention described in the claims.

Example 1. Modified mRNA Production

Modified mRNAs (mmRNA) according to the invention may be made using standard laboratory methods and materials. The open reading frame (ORF) of the gene of interest may be flanked by a 5' untranslated region (UTR) which may contain a strong Kozak translational initiation signal and/or an alpha-globin 3' UTR which may include an oligo(dT) sequence for templated addition of a poly-A tail. The modified mRNAs may be modified to reduce the cellular innate immune response. The modifications to reduce the cellular response may include pseudouridine (ψ) and 5-methylcytidine (5meC or $m^5C$). (see, Kariko K et al. Immunity 23:165-75 (2005), Kariko K et al. Mol Ther 16:1833-40 (2008), Anderson B R et al. NAR (2010); each of which are herein incorporated by reference in their entireties).

The ORF may also include various upstream or downstream additions (such as, but not limited to, β-globin, tags, etc.) may be ordered from an optimization service such as, but limited to, DNA2.0 (Menlo Park, Calif.) and may contain multiple cloning sites which may have XbaI recognition. Upon receipt of the plasmid DNA, it may be reconstituted and transformed into chemically competent *E. coli*.

For the present invention, NEB DH5-alpha Competent *E. coli* are used. Transformations are performed according to NEB instructions using 100 ng of plasmid. The protocol is as follows:

1. Thaw a tube of NEB 5-alpha Competent *E. coli* cells on ice for 10 minutes.
2. Add 1-5 µl containing 1 pg-100 ng of plasmid DNA to the cell mixture. Carefully flick the tube 4-5 times to mix cells and DNA. Do not vortex.
3. Place the mixture on ice for 30 minutes. Do not mix.
4. Heat shock at 42° C. for exactly 30 seconds. Do not mix.
5. Place on ice for 5 minutes. Do not mix.
6. Pipette 950 µl of room temperature SOC into the mixture.
7. Place at 37° C. for 60 minutes. Shake vigorously (250 rpm) or rotate.
8. Warm selection plates to 37° C.
9. Mix the cells thoroughly by flicking the tube and inverting.

Spread 50-100 µl of each dilution onto a selection plate and incubate overnight at 37° C. Alternatively, incubate at 30° C. for 24-36 hours or 25° C. for 48 hours.

A single colony is then used to inoculate 5 ml of LB growth media using the appropriate antibiotic and then allowed to grow (250 RPM, 37° C.) for 5 hours. This is then used to inoculate a 200 ml culture medium and allowed to grow overnight under the same conditions.

To isolate the plasmid (up to 850 µg), a maxi prep is performed using the plasmid purification kit, Invitrogen PURELINK™ HiPure Maxiprep Kit (Carlsbad, Calif.), following the manufacturer's instructions.

Figure 3:
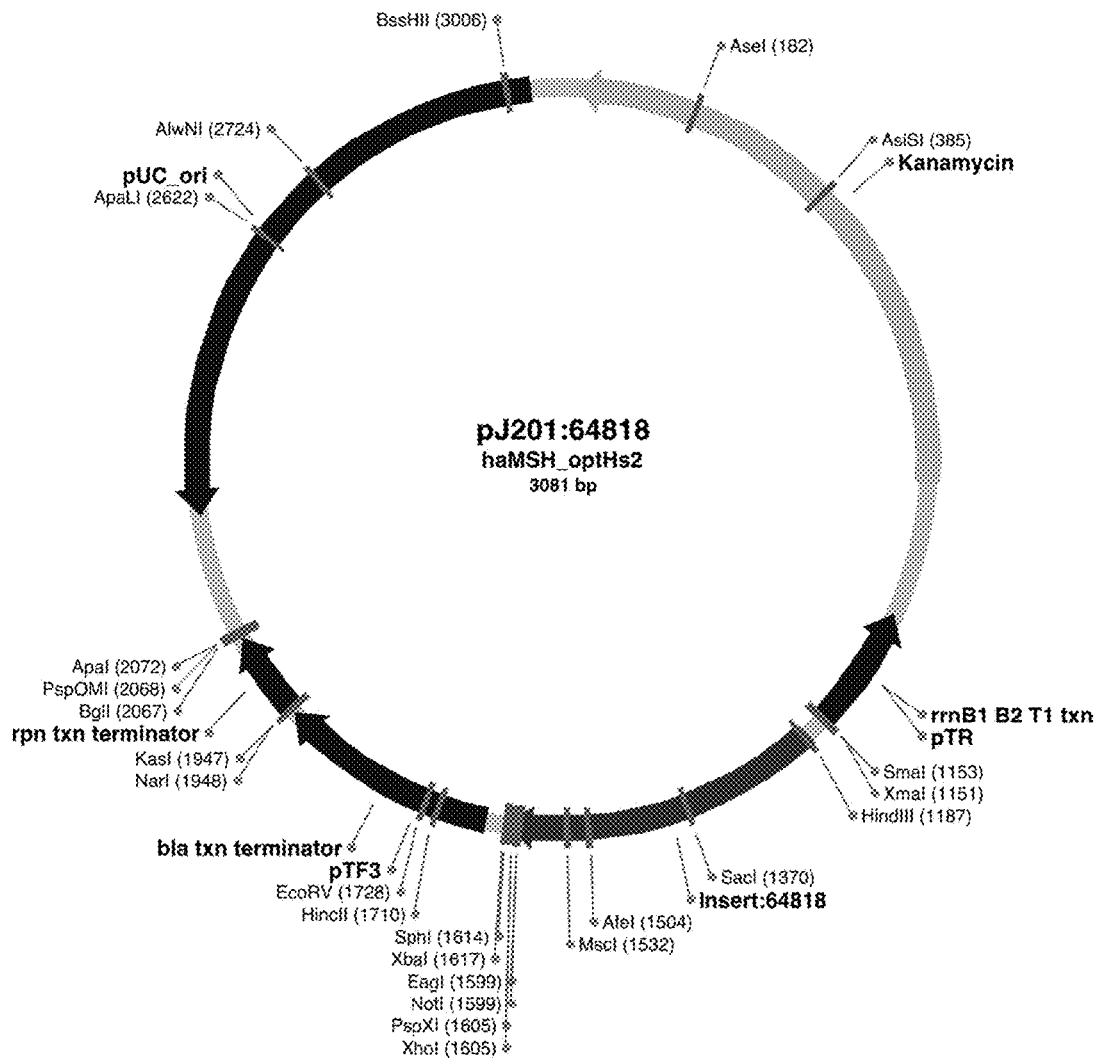
FIG. 3 is a representative plasmid useful in the IVT reactions taught herein. The plasmid contains Insert 64818, designed by the instant inventors.

In order to generate cDNA for In Vitro Transcription (IVT), the plasmid (an Example of which is shown in FIG. 3) is first linearized using a restriction enzyme such as XbaI. A typical restriction digest with XbaI will comprise the following: Plasmid 1.0 µg; 10× Buffer 1.0 µA; XbaI 1.5 µA; $dH_2O$ up to 10 µA; incubated at 37° C. for 1 hr. If performing at lab scale (<5 µg), the reaction is cleaned up using Invitrogen's PURELINK™ PCR Micro Kit (Carlsbad, Calif.) per manufacturer's instructions. Larger scale purifications may need to be done with a product that has a larger load capacity such as Invitrogen's standard PURELINK™ PCR Kit (Carlsbad, Calif.). Following the cleanup, the linearized vector is quantified using the NanoDrop and analyzed to confirm linearization using agarose gel electrophoresis.

The methods described herein to make modified mRNA may be used to produce molecules of all sizes including long molecules. Modified mRNA using the described methods has been made for different sized molecules including glucosidase, alpha; acid (GAA) (3.2 kb), cystic fibrosis transmembrane conductance regulator (CFTR) (4.7 kb), Factor VII (7.3 kb), lysosomal acid lipase (45.4 kDa), glucocerebrosidase (59.7 kDa) and iduronate 2-sulfatase (76 kDa).

As a non-limiting example, G-CSF may represent the polypeptide of interest. Sequences used in the steps outlined in Examples 1-5 are shown in Table 6. It should be noted that the start codon (ATG) has been underlined in each sequence of Table 6.

TABLE 6

G-CSF Sequences

| SEQ ID NO | Description |
|---|---|
| 1 | cDNA sequence:<br>ATGGCTGGACCTGCCACCCAGAGCCCCATGAAGCTGATGGCCCT<br>GCAGCTGCTGCTGTGGCACAGTGCACTCTGGACAGTGCAGGAAG<br>CCACCCCCCTGGGCCCTGCCAGCTCCCTGCCCCAGAGCTTCCTG<br>CTCAAGTGCTTAGAGCAAGTGAGGAAGATCCAGGGCGATGGCGC<br>AGCGCTCCAGGAGAAGCTGTGTGCCACCTACAAGCTGTGCCACC<br>CCGAGGAGCTGGTGCTGCTCGGACACTCTCTGGGCATCCCCTGG<br>GCTCCCCTGAGCAGCTGCCCCAGCCAGGCCCTGCAGCTGGCAGG<br>CTGCTTGAGCCAACTCCATAGCGGCCTTTTCCTCTACCAGGGGC<br>TCCTGCAGGCCCTGGAAGGGATCTCCCCCGAGTTGGGTCCCACC<br>TTGGACACACTGCAGCTGGACGTCGCCGACTTTGCCACCACCAT<br>CTGGCAGCAGATGGAAGAACTGGGAATGGCCCCTGCCCTGCAGC<br>CCACCCAGGGTGCCATGCCGGCCTTCGCCTCTGCTTTCCAGCGC<br>CGGGCAGGAGGGGTCCTGGTTGCCTCCCATCTGCAGAGCTTCCT<br>GGAGGTGTCGTACCGCGTTCTACGCCACCTTGCCCAGCCCTGA |
| 2 | cDNA having T7 polymerase site, AfeI and Xba restriction site:<br>TAATACGACTCACTATA<br>GGGAAATAAGAGAGAAAAGAAGAGTAAGAAGAAATATAAGAGCC<br>ACCATGGCTGGACCTGCCACCCAGAGCCCCATGAAGCTGATGGC<br>CCTGCAGCTGCTGCTGTGGCACAGTGCACTCTGGACAGTGCAGG<br>AAGCCACCCCCCTGGGCCCTGCCAGCTCCCTGCCCCAGAGCTTC<br>CTGCTCAAGTGCTTAGAGCAAGTGAGGAAGATCCAGGGCGATGG<br>CGCAGCGCTCCAGGAGAAGCTGTGTGCCACCTACAAGCTGTGCC<br>ACCCCGAGGAGCTGGTGCTGCTCGGACACTCTCTGGGCATCCCC<br>TGGGCTCCCCTGAGCAGCTGCCCCAGCCAGGCCCTGCAGCTGGC<br>AGGCTGCTTGAGCCAACTCCATAGCGGCCTTTTCCTCTACCAGG<br>GGCTCCTGCAGGCCCTGGAAGGGATCTCCCCCGAGTTGGGTCCC<br>ACCTTGGACACACTGCAGCTGGACGTCGCCGACTTTGCCACCAC<br>CATCTGGCAGCAGATGGAAGAACTGGGAATGGCCCCTGCCCTGC<br>AGCCCACCCAGGGTGCCATGCCGGCCTTCGCCTCTGCTTTCCAG<br>CGCCGGGCAGGAGGGGTCCTGGTTGCCTCCCATCTGCAGAGCTT<br>CCTGGAGGTGTCGTACCGCGTTCTACGCCACCTTGCCCAGCCCT<br>GAAGCGCTGCCTTCTGCGGGGCTTGCCTTCTGGCCATGCCCTTC<br>TTCTCTCCCTTGCACCTGTACCTCTTGGTCTTTGAATAAAGCCT<br>GAGTAGGAAGGCGGCCGCTCGAGCATGCATCTAGA |
| 3 | Optimized sequence; containing T7 polymerase site, AfeI and Xba restriction site<br>TAATACGACTCACTATA<br>GGGAAATAAGAGAGAAAAGAAGAGTAAGAAGAAATATAAGAGCC<br>ACCATGGCCGGTCCCGCGACCCAAAGCCCCATGAAACTTATGGC<br>CCTGCAGTTGCTGCTTTGGCACTCGGCCCTCTGGACAGTCCAAG<br>AAGCGACTCCTCTCGGACCTGCCTCATCGTTGCCGCAGTCATTC<br>CTTTTGAAGTGTCTGGAGCAGGTGCGAAAGATTCAGGGCGATGG<br>AGCCGCACTCCAAGAGAAGCTCTGCGCGACATACAAACTTTGCC<br>ATCCCGAGGAGCTCGTACTGCTCGGGCACAGCTTGGGGATTCCC<br>TGGGCTCCTCTCTCGTCCTGTCCGTCGCAGGCTTTGCAGTTGGC<br>AGGGTGGCCTTTCCCAGCTCCACTCCCGGTTTGTTCTTGTATCAGG<br>GACTGCTGCAAGCCCTTGAGGGAATCTCGCCAGAATTGGGCCCG<br>ACGCTGGACACGTTGCAGCTCGACGTGGCGGATTTCGCAACAAC<br>CATCTGGCAGCAGATGGAGGAACTGGGGATGGCACCCGCGCTGC<br>AGCCCACGCAGGGGGCAATGCCGGCCTTTGCGTCCGCGTTTCAG<br>CGCAGGGCGGGTGGAGTCCTCGTAGCGAGCCACCTTCAATCATT |

TABLE 6-continued

G-CSF Sequences

| SEQ ID NO | Description |
|---|---|
| | TTTGGAAGTCTCGTACCGGGTGCTGAGACATCTTGCGCAGCCGT GAAGCGCTGCCTTCTGCGGGGCTTGCCTTCTGGCCATGCCCTTC TTCTCTCCCTTGCACCTGTACCTCTTGGTCTTTGAATAAAGCCT GAGTAGGAAGGCGGCCGCTCGAGCATGCATCTAGA |
| 4 | mRNA sequence (transcribed) GGGAAAUAAGAGAGAAAAGAAGAGUAAGAAGAAAUAUAAGAGCC ACC AUGGCCGGUCCCGCGACCCAAAGCCCCAUGAAACUUAUGGCCCU GCAGUUGCUGCUUUGGCACUCGGCCCUCUGGACAGUCCAAGAAG CGACUCCUCUCGGACCUGCCUCAUCGUUGCCGCAGUCAUUCCUU UUGAAGUGUCUGGAGCAGGUGCGAAAGAUUCAGGGCGAUGGAGC CGCACUCCAAGAGAAGCUCUGCGCGACAUACAAACUUUGCCAUC CCGAGGAGCUCGUACUGCUCGGGCACAGCUUGGGGAUUCCCUGG GCUCCUCUCUCGUCCUGUCCGUCGAGGCUUUGCAGUUGGCAGG GUGCCUUUCCCAGCUCCACUCCGGUUUGUUCUUGUAUCAGGGAC UGCUGCAAGCCCUUGAGGGAAUCUCGCCAGAAUUGGGCCCGACG CUGGACACGUUGCAGCUCGACGUGGCGGAUUUCGCAACAACCAU CUGGCAGCAGAUGGAGGAACUGGGGAUGGCACCCGCGCUGCAGC CCACGCAGGGGGCAAUGCCGGCCUUUGCGUCCGCGUUUCAGCGC AGGGCGGGUGGAGUCCUCGUAGCGAGCCACCUUCAAUCAUUUUU GGAAGUCUCGUACCGGGUGCUGAGACAUCUUGCGCAGCCGUGAA GCGCUGCCUUCUGCGGGGCUUGCCUUCUGGCCAUGCCCUUCUUC UCUCCCUUGCACCUGUACCUCUUGGUCUUUGAAUAAAGCCUGAG UAGGAAG |

Example 2: PCR for cDNA Production

PCR procedures for the preparation of cDNA are performed using 2×KAPA HIFI™ HotStart ReadyMix by Kapa Biosystems (Woburn, Mass.). This system includes 2×KAPA ReadyMix 12.5 μl; Forward Primer (10 uM) 0.75 μl; Reverse Primer (10 uM) 0.75 μl; Template cDNA 100 ng; and dH₂O diluted to 25.0 μl. The reaction conditions are at 95° C. for 5 min. and 25 cycles of 98° C. for 20 sec, then 58° C. for 15 sec, then 72° C. for 45 sec, then 72° C. for 5 min. then 4° C. to termination.

The reverse primer of the instant invention incorporates a poly-T$_{120}$ for a poly-A$_{120}$ in the mRNA. Other reverse primers with longer or shorter poly(T) tracts can be used to adjust the length of the poly(A) tail in the mRNA.

The reaction is cleaned up using Invitrogen's PURELINK™ PCR Micro Kit (Carlsbad, Calif.) per manufacturer's instructions (up to 5 μg). Larger reactions will require a cleanup using a product with a larger capacity. Following the cleanup, the cDNA is quantified using the NANODROP™ spectrophotometer and analyzed by agarose gel electrophoresis to confirm the cDNA is the expected size. The cDNA is then submitted for sequencing analysis before proceeding to the in vitro transcription reaction.

Example 3. In Vitro Transcription

The in vitro transcription reaction generates mRNA containing modified nucleotides or modified RNA. The input nucleotide triphosphate (NTP) mix is made in-house using natural and un-natural NTPs.

A typical in vitro transcription reaction includes the following:

| | | |
|---|---|---|
| 1. | Template cDNA | 1.0 μg |
| 2. | 10x transcription buffer (400 mM Tris-HCl pH 8.0, 190 mM MgCl₂, 50 mM DTT, 10 mM Spermidine) | 2.0 μl |
| 3. | Custom NTPs (25 mM each) | 7.2 μl |
| 4. | RNase Inhibitor | 20U |
| 5. | T7 RNA polymerase | 3000U |
| 6. | dH₂0 | Up to 20.0 μl. and |
| 7. | Incubation at 37° C. for 3 hr-5 hrs. | |

The crude IVT mix may be stored at 4° C. overnight for cleanup the next day. 1 U of RNase-free DNase is then used to digest the original template. After 15 minutes of incubation at 37° C., the mRNA is purified using Ambion's MEGACLEAR™ Kit (Austin, Tex.) following the manufacturer's instructions. This kit can purify up to 500 μg of RNA. Following the cleanup, the RNA is quantified using the NanoDrop and analyzed by agarose gel electrophoresis to confirm the RNA is the proper size and that no degradation of the RNA has occurred.

Example 4. Enzymatic Capping of mRNA

Capping of the mRNA is performed as follows where the mixture includes: IVT RNA 60 μg-180 μg and dH₂O up to 72 μl. The mixture is incubated at 65° C. for 5 minutes to denature RNA, and then is transferred immediately to ice.

The protocol then involves the mixing of 10× Capping Buffer (0.5 M Tris-HCl (pH 8.0), 60 mM KCl, 12.5 mM MgCl₂) (10.0 μl); 20 mM GTP (5.0 μl); 20 mM S-Adenosyl Methionine (2.5 μl); RNase Inhibitor (100 U); 2'-O-Methyltransferase (400U); Vaccinia capping enzyme (Guanylyl transferase) (40 U); dH₂O (Up to 28 μl); and incubation at 37° C. for 30 minutes for 60 μg RNA or up to 2 hours for 180 μg of RNA.

The mRNA is then purified using Ambion's MEGA-CLEAR™ Kit (Austin, Tex.) following the manufacturer's instructions. Following the cleanup, the RNA is quantified using the NANODROP™ (ThermoFisher, Waltham, Mass.) and analyzed by agarose gel electrophoresis to confirm the RNA is the proper size and that no degradation of the RNA has occurred. The RNA product may also be sequenced by running a reverse-transcription-PCR to generate the cDNA for sequencing.

Example 5. PolyA Tailing Reaction

Without a poly-T in the cDNA, a poly-A tailing reaction must be performed before cleaning the final product. This is done by mixing Capped IVT RNA (100 μl); RNase Inhibitor (20 U); 10× Tailing Buffer (0.5 M Tris-HCl (pH 8.0), 2.5 M NaCl, 100 mM MgCl₂)(12.0 μl); 20 mM ATP (6.0 μl); Poly-A Polymerase (20 U); dH₂O up to 123.5 μl and incubation at 37° C. for 30 min. If the poly-A tail is already in the transcript, then the tailing reaction may be skipped and proceed directly to cleanup with Ambion's MEGA-CLEAR™ kit (Austin, Tex.) (up to 500 μg). Poly-A Polymerase is preferably a recombinant enzyme expressed in yeast.

For studies performed and described herein, the poly-A tail is encoded in the IVT template to comprise 160 nucleotides in length. However, it should be understood that the processivity or integrity of the polyA tailing reaction may not always result in exactly 160 nucleotides. Hence polyA tails of approximately 160 nucleotides, e.g, about 150-165, 155, 156, 157, 158, 159, 160, 161, 162, 163, 164 or 165 are within the scope of the invention.

Example 6. Natural 5' Caps and 5' Cap Analogues

5'-capping of modified RNA may be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5) ppp(5')A; G(5')ppp(5')G; m7G(5')ppp(5')A; m7G(5')ppp(5')G (New England BioLabs, Ipswich, Mass.). 5'-capping of modified RNA may be completed post-transcriptionally using a Vaccinia Virus Capping Enzyme to generate the "Cap 0" structure: m7G(5')ppp(5')G (New England BioLabs, Ipswich, Mass.). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes are preferably derived from a recombinant source.

When transfected into mammalian cells, the modified mRNAs have a stability of between 12-18 hours or more than 18 hours, e.g., 24, 36, 48, 60, 72 or greater than 72 hours.

Example 7. Capping

A. Protein Expression Assay

Synthetic mRNAs encoding human G-CSF (cDNA shown in SEQ ID NO: 3; mRNA sequence fully modified with 5-methylcytosine at each cytosine and pseudouridine replacement at each uridine site shown in SEQ ID NO: 4 with a polyA tail approximately 160 nucleotides in length not shown in sequence) containing the ARCA (3' O-Me-m7G(5')ppp(5')G) cap analog or the Cap1 structure can be transfected into human primary keratinocytes at equal concentrations. 6, 12, 24 and 36 hours post-transfection the amount of G-CSF secreted into the culture medium can be assayed by ELISA. Synthetic mRNAs that secrete higher levels of G-CSF into the medium would correspond to a synthetic mRNA with a higher translationally-competent Cap structure.

B. Purity Analysis Synthesis

Synthetic mRNAs encoding human G-CSF (cDNA shown in SEQ ID NO: 3; mRNA sequence fully modified with 5-methylcytosine at each cytosine and pseudouridine replacement at each uridine site shown in SEQ ID NO: 4 with a polyA tail approximately 160 nucleotides in length not shown in sequence) containing the ARCA cap analog or the Cap1 structure crude synthesis products can be compared for purity using denaturing Agarose-Urea gel electrophoresis or HPLC analysis. Synthetic mRNAs with a single, consolidated band by electrophoresis correspond to the higher purity product compared to a synthetic mRNA with multiple bands or streaking bands. Synthetic mRNAs with a single HPLC peak would also correspond to a higher purity product. The capping reaction with a higher efficiency would provide a more pure mRNA population.

C. Cytokine Analysis

Synthetic mRNAs encoding human G-CSF (cDNA shown in SEQ ID NO: 3; mRNA sequence fully modified with 5-methylcytosine at each cytosine and pseudouridine replacement at each uridine site shown in SEQ ID NO: 4 with a polyA tail approximately 160 nucleotides in length not shown in sequence) containing the ARCA cap analog or the Cap1 structure can be transfected into human primary keratinocytes at multiple concentrations. 6, 12, 24 and 36 hours post-transfection the amount of pro-inflammatory cytokines such as TNF-alpha and IFN-beta secreted into the culture medium can be assayed by ELISA. Synthetic mRNAs that secrete higher levels of pro-inflammatory cytokines into the medium would correspond to a synthetic mRNA containing an immune-activating cap structure.

D. Capping Reaction Efficiency

Synthetic mRNAs encoding human G-CSF (cDNA shown in SEQ ID NO: 3; mRNA sequence fully modified with 5-methylcytosine at each cytosine and pseudouridine replacement at each uridine site shown in SEQ ID NO: 4 with a polyA tail approximately 160 nucleotides in length not shown in sequence) containing the ARCA cap analog or the Cap1 structure can be analyzed for capping reaction efficiency by LC-MS after capped mRNA nuclease treatment. Nuclease treatment of capped mRNAs would yield a mixture of free nucleotides and the capped 5'-5-triphosphate cap structure detectable by LC-MS. The amount of capped product on the LC-MS spectra can be expressed as a percent of total mRNA from the reaction and would correspond to capping reaction efficiency. The cap structure with higher capping reaction efficiency would have a higher amount of capped product by LC-MS.

Example 8. Agarose Gel Electrophoresis of Modified RNA or RT PCR Products

Individual modified RNAs (200-400 ng in a 20 µl volume) or reverse transcribed PCR products (200-400 ng) are loaded into a well on a non-denaturing 1.2% Agarose E-Gel (Invitrogen, Carlsbad, Calif.) and run for 12-15 minutes according to the manufacturer protocol.

Example 9. Formulation of Modified mRNA Using Lipidoids

Modified mRNAs (mmRNA) are formulated for in vitro experiments by mixing the mmRNA with the lipidoid at a set ratio prior to addition to cells. In vivo formulation may require the addition of extra ingredients to facilitate circulation throughout the body. To test the ability of these lipidoids to form particles suitable for in vivo work, a standard formulation process used for siRNA-lipidoid formulations was used as a starting point. Initial mmRNA-lipidoid formulations may consist of particles composed of 42% lipidoid, 48% cholesterol and 10% PEG, with further optimization of ratios possible. After formation of the particle, mmRNA is added and allowed to integrate with the complex. The encapsulation efficiency is determined using a standard dye exclusion assays.

Materials and Methods for Examples 10-14

A. Lipid Synthesis

Six lipids, DLin-DMA, DLin-K-DMA, DLin-KC2-DMA, 98N12-5, C12-200 and DLin-MC3-DMA, were synthesized by methods outlined in the art in order to be formulated with modified RNA. DLin-DMA and precursors were synthesized as described in Heyes et. al, J. Control Release, 2005, 107, 276-287. DLin-K-DMA and DLin-KC2-DMA and precursors were synthesized as described in Semple et. al, Nature Biotechnology, 2010, 28, 172-176. 98N12-5 and precursor were synthesized as described in Akinc et. al, *Nature Biotechnology*, 2008, 26, 561-569.

C12-200 and precursors were synthesized according to the method outlined in Love et. al, PNAS, 2010, 107, 1864-1869. 2-epoxydodecane (5.10 g, 27.7 mmol, 8.2 eq) was added to a vial containing Amine 200 (0.723 g, 3.36 mmol, 1 eq) and a stirring bar. The vial was sealed and warmed to 80° C. The reaction was stirred for 4 days at 80° C. Then the mixture was purified by silica gel chromatography using a gradient from pure dichloromethane (DCM) to DCM:MeOH 98:2. The target compound was further purified by RP-HPLC to afford the desired compound.

DLin-MC3-DMA and precursors were synthesized according to procedures described in WO 2010054401 herein incorporated by reference in its entirety. A mixture of dilinoleyl methanol (1.5 g, 2.8 mmol, 1 eq), N,N-dimethylaminobutyric acid (1.5 g, 2.8 mmol, 1 eq), DIPEA (0.73 mL, 4.2 mmol, 1.5 eq) and TBTU (1.35 g, 4.2 mmol, 1.5 eq) in 10 mL of DMF was stirred for 10 h at room temperature. Then the reaction mixture was diluted in ether and washed with water. The organic layer was dried over anhydrous sodium sulfate, filtrated and concentrated under reduced pressure. The crude product was purified by silica gel chromatography using a gradient DCM to DCM:MeOH 98:2. Subsequently the target compound was subjected to an additional RP-HPLC purification which was done using a YMC—Pack C4 column to afford the target compound.

B. Formulation of Modified RNA Nanoparticles

Solutions of synthesized lipid, 1,2-distearoyl-3-phosphatidylcholine (DSPC) (Avanti Polar Lipids, Alabaster, Ala.), cholesterol (Sigma-Aldrich, Taufkirchen, Germany), and α-[3'-(1,2-dimyristoyl-3-propanoxy)-carboxamide-propyl]-w-methoxy-polyoxyethylene (PEG-c-DOMG) (NOF, Bouwelven, Belgium) were prepared at concentrations of 50 mM in ethanol and stored at −20° C. The lipids were combined to yield molar ratio of 50:10:38.5:1.5 (Lipid: DSPC: Cholesterol: PEG-c-DOMG) and diluted with ethanol to a final lipid concentration of 25 mM. Solutions of modified mRNA at a concentration of 1-2 mg/mL in water were diluted in 50 mM sodium citrate buffer at a pH of 3 to form a stock modified mRNA solution. Formulations of the lipid and modified mRNA were prepared by combining the synthesized lipid solution with the modified mRNA solution at total lipid to modified mRNA weight ratio of 10:1, 15:1, 20:1 and 30:1. The lipid ethanolic solution was rapidly injected into aqueous modified mRNA solution to afford a suspension containing 33% ethanol. The solutions were injected either manually (MI) or by the aid of a syringe pump (SP) (Harvard Pump 33 Dual Syringe Pump Harvard Apparatus Holliston, Mass.).

To remove the ethanol and to achieve the buffer exchange, the formulations were dialyzed twice against phosphate buffered saline (PBS), pH 7.4 at volumes 200-times of the primary product using a Slide-A-Lyzer cassettes (Thermo Fisher Scientific Inc. Rockford, Ill.) with a molecular weight cutoff (MWCO) of 10 kD. The first dialysis was carried at room temperature for 3 hours and then the formulations were dialyzed overnight at 4° C. The resulting nanoparticle suspension was filtered through 0.2 μm sterile filter (Sarstedt, Nümbrecht, Germany) into glass vials and sealed with a crimp closure.

C. Characterization of Formulations

A ZETASIZER NANO ZS™ particle size analyzer (Malvern Instruments Ltd, Malvern, Worcestershire, UK) was used to determine the particle size, the polydispersity index (PDI) and the zeta potential of the modified mRNA nanoparticles in 1×PBS in determining particle size and 15 mM PBS in determining zeta potential.

Ultraviolet—visible spectroscopy was used to determine the concentration of modified mRNA nanoparticle formulation. 100 μL of the diluted formulation in 1×PBS was added to 900 μL of a 4:1 (v/v) mixture of methanol and chloroform. After mixing, the absorbance spectrum of the solution was recorded between 230 nm and 330 nm on a DU 800 spectrophotometer (Beckman Coulter, Beckman Coulter, Inc., Brea, Calif.). The modified RNA concentration in the nanoparticle formulation was calculated based on the extinction coefficient of the modified RNA used in the formulation and on the difference between the absorbance at a wavelength of 260 nm and the baseline value at a wavelength of 330 nm.

QUANT-IT™ RIBOGREEN® RNA assay (Invitrogen Corporation Carlsbad, Calif.) was used to evaluate the encapsulation of modified RNA by the nanoparticle. The samples were diluted to a concentration of approximately 5 μg/mL in TE buffer (10 mM Tris-HCl, 1 mM EDTA, pH 7.5). 50 μL of the diluted samples were transferred to a polystyrene 96 well plate, then either 50 μL of TE buffer or 50 μL of a 2% Triton X-100 solution was added. The plate was incubated at a temperature of 37° C. for 15 minutes. The RIBOGREEN® reagent was diluted 1:100 in TE buffer, 100 μL of this solution was added to each well. The fluorescence intensity was measured using a fluorescence plate reader (Wallac Victor 1420 Multilablel Counter; Perkin Elmer, Waltham, Mass.) at an excitation wavelength of ~480 nm and an emission wavelength of ~520 nm. The fluorescence values of the reagent blank were subtracted from that of each of the samples and the percentage of free modified RNA was determined by dividing the fluorescence intensity of the intact sample (without addition of Triton X-100) by the fluorescence value of the disrupted sample (caused by the addition of Triton X-100).

D. In Vitro Incubation

Human embryonic kidney epithelial (HEK293) and hepatocellular carcinoma epithelial (HepG2) cells (LGC standards GmbH, Wesel, Germany) were seeded on 96-well plates (Greiner Bio-one GmbH, Frickenhausen, Germany) and plates for HEK293 cells were precoated with collagen type1. HEK293 were seeded at a density of 30,000 and HepG2 were seeded at a density of 35,000 cells per well in 100 μl cell culture medium. For HEK293 the cell culture medium was DMEM, 10% FCS, adding 2 mM L-Glutamine, 1 mM Sodiumpyruvate and 1× non-essential amino acids (Biochrom AG, Berlin, Germany) and 1.2 mg/ml Sodiumbicarbonate (Sigma-Aldrich, Munich, Germany) and for HepG2 the culture medium was MEM (Gibco Life Technologies, Darmstadt, Germany), 10% FCS adding 2 mM L-Glutamine, 1 mM Sodiumpyruvate and 1× non-essential amino acids (Biochrom AG, Berlin, Germany. Formulations containing mCherry mRNA (mRNA sequence shown in SEQ ID NO: 5; polyA tail of approximately 160 nucleotides not shown in sequence; 5'cap, Cap1); were added in quadruplicates directly after seeding the cells and incubated. The mCherry cDNA with the T7 promoter, 5'untranslated region (UTR) and 3' UTR used in in vitro transcription (IVT) is given in SEQ ID NO: 6. The mCherry mRNA was modified with 5meC at each cytosine and pseudouridine replacement at each uridine site.

Cells were harvested by transferring the culture media supernatants to a 96-well Pro-Bind U-bottom plate (Beckton Dickinson GmbH, Heidelberg, Germany). Cells were trypsinized with ½ volume Trypsin/EDTA (Biochrom AG, Berlin, Germany), pooled with respective supernatants and fixed by adding one volume PBS/2% FCS (both Biochrom AG, Berlin, Germany)/0.5% formaldehyde (Merck, Darmstadt, Germany). Samples then were submitted to a flow cytometer measurement with a 532 nm excitation laser and the 610/20 filter for PE-Texas Red in a LSRII cytometer (Beckton Dickinson GmbH, Heidelberg, Germany). The mean fluorescence intensity (MFI) of all events and the standard deviation of four independent wells are presented in for samples analyzed.

Example 10. Purification of Nanoparticle Formulations

Nanoparticle formulations of DLin-KC2-DMA and 98N12-5 in HEK293 and HepG2 were tested to determine if the mean fluorescent intensity (MFI) was dependent on the lipid to modified RNA ratio and/or purification. Three formulations of DLin-KC2-DMA and two formulations of 98N12-5 were produced using a syringe pump to the specifications described in Table 7. Purified samples were purified by SEPHADEX™ G-25 DNA grade (GE Healthcare, Sweden). Each formulation before and after purification (aP) was tested at concentration of 250 ng modified RNA per well in a 24 well plate. The percentage of cells that are positive for the marker for FL4 channel (% FL4-positive) when analyzed by the flow cytometer for each formulation and the background sample and the MFI of the marker for the FL4 channel for each formulation and the background sample are shown in Table 8. The formulations which had been purified had a slightly higher MFI than those formulations tested before purification.

TABLE 7

Formulations

| Formulation # | Lipid | Lipid/RNA wt/wt | Mean size (nm) |
|---|---|---|---|
| NPA-001-1 | DLin-KC2-DMA | 10 | 155 nm PDI: 0.08 |
| NPA-001-1 aP | DLin-KC2-DMA | 10 | 141 nm PDI: 0.14 |
| NPA-002-1 | DLin-KC2-DMA | 15 | 140 nm PDI: 0.11 |
| NPA-002-1 aP | DLin-KC2-DMA | 15 | 125 nm PDI: 0.12 |
| NPA-003-1 | DLin-KC2-DMA | 20 | 114 nm PDI: 0.08 |
| NPA-003-1 aP | DLin-KC2-DMA | 20 | 104 nm PDI: 0.06 |
| NPA-005-1 | 98N12-5 | 15 | 127 nm PDI: 0.12 |
| NPA-005-1 aP | 98N12-5 | 15 | 134 nm PDI: 0.17 |
| NPA-006-1 | 98N12 | 20 | 126 nm PDI: 0.08 |
| NPA-006-1 aP | 98N12 | 20 | 118 nm PDI: 0.13 |

TABLE 8

HEK293 and HepG2, 24-well, 250 ng Modified RNA/well

| | % FL4-positive | | FL4 MFI | |
|---|---|---|---|---|
| Formulation | HEK293 | HepG2 | HEK293 | HepG2 |
| Untreated | 0.33 | 0.40 | 0.25 | 0.30 |
| NPA-001-1 | 62.42 | 5.68 | 1.49 | 0.41 |
| NPA-001-ap | 87.32 | 9.02 | 3.23 | 0.53 |
| NPA-002-1 | 91.28 | 9.90 | 4.43 | 0.59 |
| NPA-002-ap | 92.68 | 14.02 | 5.07 | 0.90 |
| NPA-003-1 | 87.70 | 11.76 | 6.83 | 0.88 |
| NPA-003-ap | 88.88 | 15.46 | 8.73 | 1.06 |
| NPA-005-1 | 50.60 | 4.75 | 1.83 | 0.46 |
| NPA-005-ap | 38.64 | 5.16 | 1.32 | 0.46 |
| NPA-006-1 | 54.19 | 13.16 | 1.30 | 0.60 |
| NPA-006-ap | 49.97 | 13.74 | 1.27 | 0.61 |

Example 11. Concentration Response Curve

Nanoparticle formulations of 98N12-5 (NPA-005) and DLin-KC2-DMA (NPA-003) were tested at varying concentrations to determine the MFI of FL4 or mCherry (mRNA sequence shown in SEQ ID NO: 5; polyA tail of approximately 160 nucleotides not shown in sequence; 5'cap, Cap1; fully modified with 5-methylcytosine and pseudouridine) over a range of doses. The formulations tested are outlined in Table 9. To determine the optimal concentration of nanoparticle formulations of 98N12-5, varying concentrations of formulated modified RNA (100 ng, 10 ng, 1.0 ng, 0.1 ng and 0.01 ng per well) were tested in a 24-well plate of HEK293, and the results of the FL4 MFI of each dose are shown in Table 10. Likewise, to determine the optimal concentration of nanoparticle formulations of DLin-KC2-DMA, varying concentrations of formulated modified RNA (250 ng 100 ng, 10 ng, 1.0 ng, 0.1 ng and 0.01 ng per well) were tested in a 24-well plate of HEK293, and the results of the FL4 MFI of each dose are shown in Table 11. Nanoparticle formulations of DLin-KC2-DMA were also tested at varying concentrations of formulated modified RNA (250 ng, 100 ng and 30 ng per well) in a 24 well plate of HEK293, and the results of the FL4 MFI of each dose are shown in Table 12. A dose of 1 ng/well for 98N12-5 and a dose of 10 ng/well for DLin-KC2-DMA were found to resemble the FL4 MFI of the background.

To determine how close the concentrations resembled the background, we utilized a flow cytometer with optimized filter sets for detection of mCherry expression, and were able to obtain results with increased sensitivity relative to background levels. Doses of 25 ng/well, 0.25 ng/well, 0.025 ng/well and 0.0025 ng/well were analyzed for 98N12-5 (NPA-005) and DLin-KC2-DMA (NPA-003) to determine the MFI of mCherry. As shown in Table 13, the concentration of 0.025 ng/well and lesser concentrations are similar to the background MFI level of mCherry which is about 386.125.

TABLE 9

Formulations

| Formulation # | NPA-003 | NPA-005 |
|---|---|---|
| Lipid | DLin-KC2-DMA | 98N12-5 |
| Lipid/RNA wt/wt | 20 | 15 |
| Mean size | 114 nm PDI: 0.08 | 106 nm PDI: 0.12 |

TABLE 10

HEK293, NPA-005, 24-well, n = 4

| Formulation | FL4 MFI |
|---|---|
| Untreated control | 0.246 |
| NPA-005 100 ng | 2.2175 |
| NPA-005 10 ng | 0.651 |
| NPA-005 1.0 ng | 0.28425 |
| NPA-005 0.1 ng | 0.27675 |
| NPA-005 0.01 ng | 0.2865 |

TABLE 11

HEK293, NPA-003, 24-well, n = 4

| Formulation | FL4 MFI |
|---|---|
| Untreated control | 0.3225 |
| NPA-003 250 ng | 2.9575 |
| NPA-003 100 ng | 1.255 |
| NPA-003 10 ng | 0.40025 |
| NPA-003 1 ng | 0.33025 |
| NPA-003 0.1 ng | 0.34625 |
| NPA-003 0.01 ng | 0.3475 |

TABLE 12

HEK293, NPA-003, 24-well, n = 4

| Formulation | FL4 MFI |
|---|---|
| Untreated control | 0.27425 |
| NPA-003 250 ng | 5.6075 |
| NPA-003 100 ng | 3.7825 |
| NPA-003 30 ng | 1.5525 |

TABLE 13

Concentration and MFI

| | MFI mCherry | |
|---|---|---|
| Formulation | NPA-003 | NPA-005 |
| 25 ng/well | 11963.25 | 12256.75 |
| 0.25 ng/well | 1349.75 | 2572.75 |
| 0.025 ng/well | 459.50 | 534.75 |
| 0.0025 ng/well | 310.75 | 471.75 |

Example 12. Manual Injection and Syringe Pump Formulations

Two formulations of DLin-KC2-DMA and 98N12-5 were prepared by manual injection (MI) and syringe pump injection (SP) and analyzed along with a background sample to compare the MFI of mCherry (mRNA sequence shown in SEQ ID NO: 5; polyA tail of approximately 160 nucleotides not shown in sequence; 5'cap, Cap1; fully modified with 5-methylcytosine and pseudouridine) of the different formulations. Table 14 shows that the syringe pump formulations had a higher MFI as compared to the manual injection formulations of the same lipid and lipid/RNA ratio.

TABLE 14

Formulations and MFI

| Formulation # | Lipid | Lipid/RNA wt/wt | Mean size (nm) | Method of formulation | MFI |
|---|---|---|---|---|---|
| Untreated Control | N/A | N/A | N/A | N/A | 674.67 |
| NPA-002 | DLin-KC2-DMA | 15 | 140 nm PDI: 0.11 | MI | 10318.25 |
| NPA-002-2 | DLin-KC2-DMA | 15 | 105 nm PDI: 0.04 | SP | 37054.75 |
| NPA-003 | DLin-KC2-DMA | 20 | 114 nm PDI: 0.08 | MI | 22037.5 |
| NPA-003-2 | DLin-KC2-DMA | 20 | 95 nm PDI: 0.02 | SP | 37868.75 |
| NPA-005 | 98N12-5 | 15 | 127 nm PDI: 0.12 | MI | 11504.75 |
| NPA-005-2 | 98N12-5 | 15 | 106 nm PDI: 0.07 | SP | 9343.75 |
| NPA-006 | 98N12-5 | 20 | 126 nm PDI: 0.08 | MI | 11182.25 |
| NPA-006-2 | 98N12-5 | 20 | 93 nm PDI: 0.08 | SP | 5167 |

Example 13. LNP Formulations

Formulations of DLin-DMA, DLin-K-DMA, DLin-KC2-DMA, 98N12-5, C12-200 and DLin-MC3-DMA were incubated at a concentration of 60 ng/well or 62.5 ng/well in a plate of HEK293 and 62.5 ng/well in a plate of HepG2 cells for 24 hours to determine the MFI of mCherry (mRNA sequence shown in SEQ ID NO: 5; polyA tail of approximately 160 nucleotides not shown in sequence; 5'cap, Cap1; fully modified with 5-methylcytosine and pseudouridine) for each formulation. The formulations tested are outlined in Table 15 below. As shown in Table 16 for the 60 ng/well and Tables 17, 18, 19 and 20 for the 62.5 ng/well, the formulation of NPA-003 and NPA-018 have the highest mCherry MFI and the formulations of NPA-008, NPA-010 and NPA-013 are most the similar to the background sample mCherry MFI value.

TABLE 15

Formulations

| Formulation # | Lipid | Lipid/RNA wt/wt | Mean size (nm) |
|---|---|---|---|
| NPA-001 | DLin-KC2-DMA | 10 | 155 nm PDI: 0.08 |
| NPA-002 | DLin-KC2-DMA | 15 | 140 nm PDI: 0.11 |
| NPA-002-2 | DLin-KC2-DMA | 15 | 105 nm PDI: 0.04 |
| NPA-003 | DLin-KC2-DMA | 20 | 114 nm PDI: 0.08 |
| NPA-003-2 | DLin-KC2-DMA | 20 | 95 nm PDI: 0.02 |
| NPA-005 | 98N12-5 | 15 | 127 nm PDI: 0.12 |
| NPA-006 | 98N12-5 | 20 | 126 nm PDI: 0.08 |
| NPA-007 | DLin-DMA | 15 | 148 nm PDI: 0.09 |
| NPA-008 | DLin-K-DMA | 15 | 121 nm PDI: 0.08 |
| NPA-009 | C12-200 | 15 | 138 nm PDI: 0.15 |

TABLE 15-continued

Formulations

| Formulation # | Lipid | Lipid/RNA wt/wt | Mean size (nm) |
|---|---|---|---|
| NPA-010 | DLin-MC3-DMA | 15 | 126 nm PDI: 0.09 |
| NPA-012 | DLin-DMA | 20 | 86 nm PDI: 0.08 |
| NPA-013 | DLin-K-DMA | 20 | 104 nm PDI: 0.03 |
| NPA-014 | C12-200 | 20 | 101 nm PDI: 0.06 |
| NPA-015 | DLin-MC3-DMA | 20 | 109 nm PDI: 0.07 |

TABLE 16

HEK293, 96-well, 60 ng Modified RNA/well

| Formulation | MFI mCherry |
|---|---|
| Untreated | 871.81 |
| NPA-001 | 6407.25 |
| NPA-002 | 14995 |
| NPA-003 | 29499.5 |
| NPA-005 | 3762 |
| NPA-006 | 2676 |
| NPA-007 | 9905.5 |
| NPA-008 | 1648.75 |
| NPA-009 | 2348.25 |
| NPA-010 | 4426.75 |
| NPA-012 | 11466 |
| NPA-013 | 2098.25 |
| NPA-014 | 3194.25 |
| NPA-015 | 14524 |

TABLE 17

HEK293, 62.5 ng/well

| Formulation | MFI mCherry |
|---|---|
| Untreated | 871.81 |
| NPA-001 | 6407.25 |
| NPA-002 | 14995 |
| NPA-003 | 29499.5 |
| NPA-005 | 3762 |
| NPA-006 | 2676 |
| NPA-007 | 9905.5 |
| NPA-008 | 1648.75 |
| NPA-009 | 2348.25 |
| NPA-010 | 4426.75 |
| NPA-012 | 11466 |
| NPA-013 | 2098.25 |
| NPA-014 | 3194.25 |
| NPA-015 | 14524 |

TABLE 18

HEK293, 62.5 ng/well

| Formulation | MFI mCherry |
|---|---|
| Untreated | 295 |
| NPA-007 | 3504 |
| NPA-012 | 8286 |
| NPA-017 | 6128 |
| NPA-003-2 | 17528 |
| NPA-018 | 34142 |
| NPA-010 | 1095 |
| NPA-015 | 5859 |
| NPA-019 | 3229 |

TABLE 19

HepG2, 62.5 ng/well

| Formulation | MFI mCherry |
|---|---|
| Untreated | 649.94 |
| NPA-001 | 6006.25 |
| NPA-002 | 8705 |
| NPA-002-2 | 15860.25 |
| NPA-003 | 15059.25 |
| NPA-003-2 | 28881 |
| NPA-005 | 1676 |
| NPA-006 | 1473 |
| NPA-007 | 15678 |
| NPA-008 | 2976.25 |
| NPA-009 | 961.75 |
| NPA-010 | 3301.75 |
| NPA-012 | 18333.25 |
| NPA-013 | 5853 |
| NPA-014 | 2257 |
| NPA-015 | 16225.75 |

TABLE 20

HepG2, 62.5 ng/well

| Formulation | MFI mCherry |
|---|---|
| Untreated control | 656 |
| NPA-007 | 16798 |
| NPA-012 | 21993 |
| NPA-017 | 20377 |
| NPA-003-2 | 35651 |
| NPA-018 | 40154 |
| NPA-010 | 2496 |
| NPA-015 | 19741 |
| NPA-019 | 16373 |

Example 14. In Vivo Formulation Studies

Rodents (n=5) are administered intravenously, subcutaneously or intramuscularly a single dose of a formulation containing at least one modified mRNA and a lipid. The modified mRNA administered to the rodents is selected from G-CSF (mRNA sequence shown in SEQ ID NO: 4; polyA tail of approximately 160 nucleotides not shown in sequence; 5'cap, Cap1), erythropoietin (EPO) (mRNA sequence shown in SEQ ID NO: 7; polyA tail of approximately 160 nucleotides not shown in sequence; 5'cap, Cap1), Factor IX (mRNA shown in SEQ ID NO: 8; polyA tail of approximately 160 nucleotides not shown in sequence; 5'cap, Cap1) or mCherry (mRNA sequence shown in SEQ ID NO: 5; polyA tail of approximately 160 nucleotides not shown in sequence; 5'cap, Cap1). The erythropoietin cDNA with the T7 promoter, 5'untranslated region (UTR) and 3' UTR used in in vitro transcription (IVT) is given in SEQ ID NO: 9 and SEQ ID NO: 10.

Each formulation also contains a lipid which is selected from one of DLin-DMA, DLin-K-DMA, DLin-KC2-DMA, 98N12-5, C12-200, DLin-MC3-DMA, reLNP, ATUPLEX®, DACC, and DBTC. The rodents are injected with 100 ug, 10 ug or 1 ug of the formulated modified mRNA and samples are collected at specified time intervals.

Serum from the rodents administered formulations containing human G-CSF modified mRNA are measured by specific G-CSF ELISA and serum from mice administered human factor IX modified RNA is analyzed by specific factor IX ELISA or chromogenic assay. The liver and spleen from the mice administered with mCherry modified mRNA are analyzed by immunohistochemistry (IHC) or fluorescence-activated cell sorting (FACS). As a control, a group of mice are not injected with any formulation and their serum and tissue are collected analyzed by ELISA, FACS and/or IHC.

A. Time Course

The rodents are administered formulations containing at least one modified mRNA to study the time course of protein expression for the administered formulation. The rodents are bled at specified time intervals prior to and after administration of the modified mRNA formulations to determine protein expression and complete blood count. Samples are also collected from the site of administration of rodents administered modified mRNA formulations subcutaneously and intramuscularly to determine the protein expression in the tissue.

B. Dose Response

The rodents are administered formulations containing at least one modified mRNA to determine dose response of each formulation. The rodents are bled at specified time intervals prior to and after administration of the modified mRNA formulations to determine protein expression and complete blood count. The rodents are also scarified to analyze the effect of the modified mRNA formulation on the internal tissue. Samples are also collected from the site of administration of rodents administered modified mRNA formulations subcutaneously and intramuscularly to determine the protein expression in the tissue.

C. Toxicity

The rodents are administered formulations containing at least one modified mRNA to study toxicity of each formulation. The rodents are bled at specified time intervals prior to and after administration of the modified mRNA formulations to determine protein expression and complete blood count. The rodents are also sacrificed to analyze the effect of the modified mRNA formulation on the internal tissue. Samples are also collected from the site of administration of rodents administered modified mRNA formulations subcutaneously and intramuscularly to determine the protein expression in the tissue.

Example 15. PLGA Microsphere Formulations

Optimization of parameters used in the formulation of PLGA microspheres may allow for tunable release rates and high encapsulation efficiencies while maintaining the integrity of the modified RNA encapsulated in the microspheres. Parameters such as, but not limited to, particle size, recovery rates and encapsulation efficiency may be optimized to achieve the optimal formulation.

A. Synthesis of PLGA Microspheres

Polylacticglycolic acid (PLGA) microspheres were synthesized using the water/oil/water double emulsification methods known in the art using PLGA (Lactel, Cat# B6010-2, inherent viscosity 0.55-0.75, 50:50 LA:GA), polyvinylalcohol (PVA) (Sigma, Cat#348406-25G, MW 13-23 k) dichloromethane and water. Briefly, 0.1 ml of water (W1) was added to 2 ml of PLGA dissolved in dichloromethane (DCM) (O1) at concentrations ranging from 50-200 mg/ml of PLGA. The W1/O1 emulsion was homogenized (IKA Ultra-Turrax Homogenizer, T18) for 30 seconds at speed 4 (15,000 rpm). The W1/O1 emulsion was then added to 100 to 200 ml of 0.3 to 1% PVA (W2) and homogenized for 1 minute at varied speeds. Formulations were left to stir for 3 hours and then washed by centrifugation (20-25 min, 4,000 rpm, 4° C.). The supernatant was discarded and the PLGA pellets were resuspended in 5-10 ml of water, which was repeated 2×. Average particle size (represents 20-30 particles) for each formulation was determined by microscopy after washing. Table 21 shows that an increase in the PLGA concentration led to larger sized microspheres. A PLGA concentration of 200 mg/mL gave an average particle size of 14.8 µm, 100 mg/mL was 8.7 µm, and 50 mg/mL of PLGA gave an average particle size of 4.0 µm.

TABLE 21

Varied PLGA Concentration

| Sample ID | O1 Volume (mL) | PLGA Concentration (mg/mL) | W2 Volume (mL) | PVA Concentration (%) | Speed | Average Size (µm) |
|---|---|---|---|---|---|---|
| 1 | 2 | 200 | 100 | 0.3 | 5 | 14.8 |
| 2 | 2 | 100 | 100 | 0.3 | 5 | 8.7 |
| 3 | 2 | 50 | 100 | 0.3 | 5 | 4.0 |

Table 22 shows that decreasing the homogenization speed from 5 (20,000 rpm) to speed 4 (15,000 rpm) led to an increase in particle size from 14.8 µm to 29.7 µm.

TABLE 22

Varied Homogenization Speed

| Sample ID | O1 Volume (mL) | PLGA Concentration (mg/mL) | W2 Volume (mL) | PVA Concentration (%) | Speed | Average Size (µm) |
|---|---|---|---|---|---|---|
| 1 | 2 | 200 | 100 | 0.3 | 5 | 14.8 |
| 4 | 2 | 200 | 100 | 0.3 | 4 | 29.7 |

Table 23 shows that increasing the W2 volume (i.e. increasing the ratio of W2:O1 from 50:1 to 100:1), decreased average particle size slightly. Altering the PVA concentration from 0.3 to 1 wt % had little impact on PLGA microsphere size.

TABLE 23

Varied W2 Volume and Concentration

| Sample ID | O1 Volume (mL) | PLGA Concentration (mg/mL) | W2 Volume (mL) | PVA Concentration (%) | Speed | Average Size (µm) |
|---|---|---|---|---|---|---|
| 1 | 2 | 200 | 100 | 0.3 | 5 | 14.8 |
| 5 | 2 | 200 | 200 | 0.3 | 5 | 11.7 |
| 6 | 2 | 200 | 190 | 0.3 | 5 | 11.4 |
| 7 | 2 | 200 | 190 | 1.0 | 5 | 12.3 |

B. Encapsulation of Modified mRNA

Modified G-CSF mRNA (SEQ ID NO: 4; polyA tail of approximately 160 nucleotides not shown in sequence; 5'cap, Cap1; fully modified with 5-methylcytosine and pseudouridine) was dissolved in water at a concentration of 2 mg/ml (W3). Three batches of PLGA microsphere formulations were made as described above with the following parameters: 0.1 ml of W3 at 2 mg/ml, 1.6 ml of O1 at 200 mg/ml, 160 ml of W2 at 1%, and homogenized at a speed of 4 for the first emulsion (W3/O1) and homogenized at a speed of 5 for the second emulsion (W3/O1/W2). After washing by centrifugation, the formulations were frozen in liquid nitrogen and then lyophilized for 3 days. To test the encapsulation efficiency of the formulations, the lyophilized material was deformulated in DCM for 6 hours followed by an overnight extraction in water. The modified RNA concentration in the samples was then determined by OD260. Encapsulation efficiency was calculated by taking the actual amount of modified RNA and dividing by the starting amount of modified RNA. In the three batches tested, there was an encapsulation efficiency of 59.2, 49.8 and 61.3.

C. Integrity of Modified mRNA Encapsulated in PLGA Microspheres

Modified Factor IX mRNA (SEQ ID NO: 8; polyA tail of approximately 160 nucleotides not shown in sequence; 5'cap, Cap1; fully modified with 5-methylcytosine and pseudouridine) was dissolved in water at varied concentrations (W4) to vary the weight percent loading in the formulation (mg modified RNA/mg PLGA*100) and to determine encapsulation efficiency. The parameters in Table 24 were used to make four different batches of PLGA microsphere formulations with a homogenization speed of 4 for the first emulsion (W4/O1) and a homogenization speed of 5 for the second emulsion (W4/O1/W2).

TABLE 24

Factor IX PLGA Microsphere Formulation Parameters

| ID | W4 Vol (uL) | Factor IX Conc. (mg/ml) | Factor IX Amt. (ug) | O1 Vol (ml) | PLGA Conc. (mg/ml) | W2 Vol (ml) | PVA Conc (%) | Weight % (wt %) Loading |
|---|---|---|---|---|---|---|---|---|
| A | 100 | 2.0 | 200.0 | 2.0 | 200 | 200 | 1.0 | 0.05 |
| B | 100 | 4.0 | 400.0 | 2.0 | 200 | 200 | 1.0 | 0.10 |
| C | 400 | 2.0 | 800.0 | 2.0 | 200 | 200 | 1.0 | 0.20 |
| D | 400 | 4.0 | 1600.0 | 2.0 | 200 | 200 | 1.0 | 0.40 |

After lyophilization, PLGA microspheres were weighed out in 2 ml eppendorf tubes to correspond to ~10 ug of modified RNA. Lyophilization was found to not destroy the overall structure of the PLGA microspheres. To increase weight percent loading (wt %) for the PLGA microspheres, increasing amounts of modified RNA were added to the samples. PLGA microspheres were deformulated by adding 1.0 ml of DCM to each tube and then shaking the samples for 6 hours. For modified RNA extraction, 0.5 ml of water was added to each sample and the samples were shaken overnight before the concentration of modified RNA in the samples was determined by OD260. To determine the recovery of the extraction process, unformulated Factor IX modified RNA (SEQ ID NO: 8; polyA tail of approximately 160 nucleotides not shown in sequence; 5'cap, Cap1; fully modified with 5-methylcytosine and pseudouridine) (deformulation control) was spiked into DCM and was subjected to the deformulation process. Table 25 shows the loading and encapsulation efficiency for the samples. All encapsulation efficiency samples were normalized to the deformulation control.

TABLE 25

Weight Percent Loading and Encapsulation Efficiency

| ID | Theoretical modified RNA loading (wt %) | Actual modified RNA loading (wt %) | Encapsulation Efficiency (%) |
|---|---|---|---|
| A | 0.05 | 0.06 | 97.1 |
| B | 0.10 | 0.10 | 85.7 |
| C | 0.20 | 0.18 | 77.6 |
| D | 0.40 | 0.31 | 68.1 |
| Control | — | — | 100.0 |

D. Release Study of Modified mRNA Encapsulated in PLGA Microspheres

Figure 4:
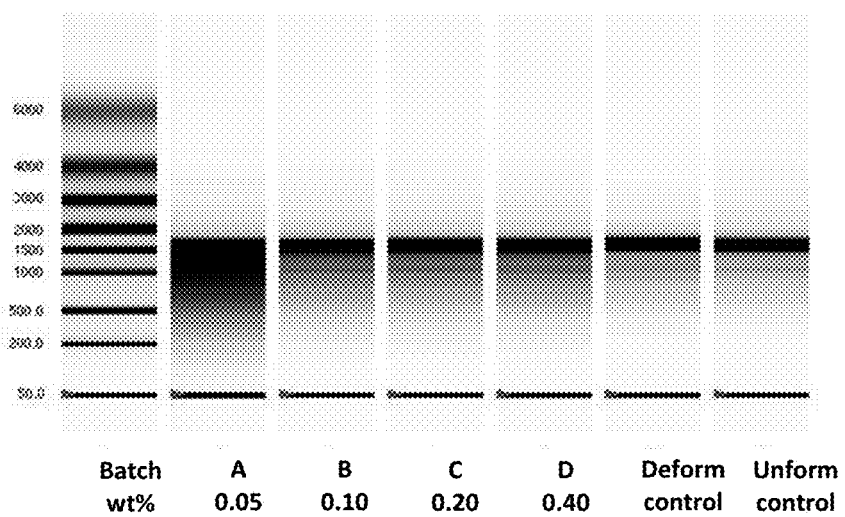
FIG. 4 is a gel profile of modified mRNA encapsulated in PLGA microspheres.

PLGA microspheres formulated with Factor IX modified RNA (SEQ ID NO: 8) were deformulated as described above and the integrity of the extracted modified RNA was determined by automated electrophoresis (Bio-Rad Experion). The extracted modified mRNA was compared against unformulated modified mRNA and the deformulation control in order to test the integrity of the encapsulated modified mRNA. As shown in FIG. 4, the majority of modRNA was intact for batch ID A, B, C and D, for the deformulated control (Deform control) and the unformulated control (Uniform control).

E. Protein Expression of Modified mRNA Encapsulated in PLGA Microspheres

PLGA microspheres formulated with Factor IX modified RNA (SEQ ID NO: 8; polyA tail of approximately 160 nucleotides not shown in sequence; 5'cap, Cap1; fully modified with 5-methylcytosine and pseudouridine) were deformulated as described above and the protein expression of the extracted modified RNA was determined by an in vitro transfection assay. HEK293 cells were reverse transfected with 250 ng of Factor IX modified RNA complexed with RNAiMAX (Invitrogen) in triplicate.

Factor IX modified RNA was diluted in nuclease-free water to a concentration of 25 ng/μl and RNAiMAX was diluted 13.3× in serum-free EMEM. Equal volumes of diluted modified RNA and diluted RNAiMAX were mixed together and were allowed to stand for 20 to 30 minutes at room temperature. Subsequently, 20 μl of the transfection mix containing 250 ng of Factor IX modified RNA was added to 80 μl of a cell suspension containing 30,000 cells. Cells were then incubated for 16h in a humidified 37° C./5% CO2 cell culture incubator before harvesting the cell culture supernatant. Factor IX protein expression in the cell supernatant was analyzed by an ELISA kit specific for Factor IX (Molecular Innovations, Novi, Mich.) and the protein expression is shown in Table 26. In all PLGA microsphere batches tested, Factor IX modified RNA remained active and expressed Factor IX protein after formulation in PLGA microspheres and subsequent deformulation.

TABLE 26

Protein Expression

| Sample | Factor IX Protein Expression (ng/ml) |
|---|---|
| Batch A | 0.83 |
| Batch B | 1.83 |
| Batch C | 1.54 |
| Batch D | 2.52 |
| Deformulated Control | 4.34 |
| Unformulated Control | 3.35 |

F. Release Study of Modified mRNA Encapsulated in PLGA Microspheres

PLGA micropsheres formulated with Factor IX modified RNA (SEQ ID NO: 8; polyA tail of approximately 160 nucleotides not shown in sequence; 5'cap, Cap1; fully modified with 5-methylcytosine and pseudouridine) were resuspended in water to a PLGA microsphere concentration of 24 mg/ml. After resuspension, 150 ul of the PLGA microsphere suspension was aliquoted into eppendorf tubes. Samples were kept incubating and shaking at 37° C. during the course of the study. Triplicate samples were pulled at 0.2, 1, 2, 8, 14, and 21 days. To determine the amount of modified RNA released from the PLGA microspheres, samples were centrifuged, the supernatant was removed, and the modified RNA concentration in the supernatant was determined by OD 260. The percent release, shown in Table 27, was calculated based on the total amount of modified RNA in each sample. After 31 days, 96% of the Factor IX modified RNA was released from the PLGA microsphere formulations.

TABLE 27

Percent Release

| Time (days) | % Release |
| --- | --- |
| 0 | 0.0 |
| 0.2 | 27.0 |
| 1 | 37.7 |
| 2 | 45.3 |
| 4 | 50.9 |
| 8 | 57.0 |
| 14 | 61.8 |
| 21 | 75.5 |
| 31 | 96.4 |

G. Particle Size Reproducibility of PLGA Microspheres

Three batches of Factor IX modified RNA (SEQ ID NO: 8 polyA tail of approximately 160 nucleotides not shown in sequence; 5'cap, Cap1; fully modified with 5-methylcytosine and pseudouridine) PLGA microspheres were made using the same conditions described for Batch D, shown in Table 24, (0.4 ml of W4 at 4 mg/ml, 2.0 ml of O1 at 200 mg/ml, 200 ml of W2 at 1%, and homogenized at a speed of 5 for the W4/O1/W2 emulsion). To improve the homogeneity of the PLGA microsphere suspension, filtration was incorporated prior to centrifugation. After stirring for 3 hours and before centrifuging, all formulated material was passed through a 100 μm nylon mesh strainer (Fisherbrand Cell Strainer, Cat #22-363-549) to remove larger aggregates. After washing and resuspension with water, 100-200 μl of a PLGA microspheres sample was used to measure particle size of the formulations by laser diffraction (Malvern Mastersizer2000). The particle size of the samples is shown in Table 28.

TABLE 28

Particle Size Summary

| ID | D10 (μm) | D50 (μm) | D90 (μm) | Volume Weighted Mean (um) | Filtration |
| --- | --- | --- | --- | --- | --- |
| Control | 19.2 | 62.5 | 722.4 | 223.1 | No |
| A | 9.8 | 31.6 | 65.5 | 35.2 | Yes |
| B | 10.5 | 32.3 | 66.9 | 36.1 | Yes |
| C | 10.8 | 35.7 | 79.8 | 41.4 | Yes |

Results of the 3 PLGA microsphere batches using filtration were compared to a PLGA microsphere batch made under the same conditions without filtration. The inclusion of a filtration step before washing reduced the mean particle size and demonstrated a consistent particle size distribution between 3 PLGA microsphere batches.

H. Serum Stability of Factor IX PLGA Microspheres

Factor IX mRNA RNA (SEQ ID NO: 8 polyA tail of approximately 160 nucleotides not shown in sequence; 5'cap, Cap1; fully modified with 5-methylcytosine and pseudouridine) in buffer (TE) or 90% serum (Se), or Factor IX mRNA in PLGA in buffer, 90% serum or 1% serum was incubated in buffer, 90% serum or 1% serum at an mRNA concentration of 50 ng/ul in a total volume of 70 ul. The samples were removed at 0, 30, 60 or 120 minutes. RNases were inactivated with proteinase K digestion for 20 minutes at 55° C. by adding 25 ul of 4× proteinase K buffer (0.4 ml 1M TRIS-HCl pH 7.5, 0.1 ml 0.5M EDTA, 0.12 ml 5M NaCl, and 0.4 ml 10% SDS) and 8 ul of proteinase K at 20 mg/ml. The Factor IX mRNA was precipitated (add 250 ul 95% ethanol for 1 hour, centrifuge for 10 min at 13 k rpm and remove supernatant, add 200 ul 70% ethanol to the pellet, centrifuge again for 5 min at 13 k rpm and remove supernatant and resuspend the pellet in 70 ul water) or extracted from PLGA microspheres (centrifuge 5 min at 13 k rpm and remove supernatant, wash pellet with 1 ml water, centrifuge 5 min at 13 k rpm and remove supernatant, add 280 ul dichloromethane to the pellet and shake for 15 minutes, add 70 ul water and then shake for 2 hours and remove the aqueous phase) before being analyzed by bioanalyzer. PLGA microspheres protect Factor IX modified mRNA from degradation in 90% and 1% serum over 2 hours. Factor IX modified mRNA completely degrades in 90% serum at the initial time point.

Example 16. Lipid Nanoparticle In Vivo Studies

G-CSF (cDNA with the T7 promoter, 5' Untranslated region (UTR) and 3'UTR used in in vitro transcription is given in SEQ ID NO: 3. mRNA sequence shown in SEQ ID NO: 4; polyA tail of approximately 160 nucleotides not shown in sequence; 5'cap, Cap 1; fully modified with 5-methylcytosine and pseudouridine) and Factor IX (cDNA with the T7 promoter, 5' UTR and 3'UTR used in in vitro transcription is given in SEQ ID NO: 11. mRNA sequence shown in SEQ ID NO: 8; polyA tail of approximately 160 nucleotides not shown in sequence; 5'cap, Cap 1; fully modified with 5-methylcytosine and pseudouridine) modified mRNA were formulated as lipid nanoparticles (LNPs) using the syringe pump method. The LNPs were formulated at a 20:1 weight ratio of total lipid to modified mRNA with a final lipid molar ratio of 50:10:38.5:1.5 (DLin-KC2-DMA: DSPC: Cholesterol: PEG-c-DOMG). Formulations, listed in Table 29, were characterized by particle size, zeta potential, and encapsulation.

TABLE 29

Formulations

| Formulation # | NPA-029-1 | NPA-030-1 |
| --- | --- | --- |
| Modified mRNA | Factor IX | G-CSF |
| Mean size | 91 nm | 106 nm |
|  | PDI: 0.04 | PDI: 0.06 |
| Zeta at pH 7.4 | 1.8 mV | 0.9 mV |
| Encaps. (RiboGr) | 92% | 100% |

LNP formulations were administered to mice (n=5) intravenously at a modified mRNA dose of 100, 10, or 1 ug. Mice were sacrificed at 8 hrs after dosing. Serum was collected by cardiac puncture from mice that were administered with G-CSF or Factor IX modified mRNA formulations. Protein expression was determined by ELISA.

There was no significant body weight loss (<5%) in the G-CSF or Factor IX dose groups. Protein expression for G-CSF or Factor IX dose groups was determined by ELISA from a standard curve. Serum samples were diluted (about 20-2500× for G-CSF and about 10-250× for Factor IX) to ensure samples were within the linear range of the standard curve. As shown in Table 30, G-CSF protein expression determined by ELISA was approximately 17, 1200, and 4700 ng/ml for the 1, 10, and 100 ug dose groups, respectively. As shown in Table 31, Factor IX protein expression determined by ELISA was approximately 36, 380, and 3000-11000 ng/ml for the 1, 10, and 100 ug dose groups, respectively.

TABLE 30

G-CSF Protein Expression

| Dose (ug) | Conc (ng/ml) | Dilution Factor | Sample Volume |
|---|---|---|---|
| 1 | 17.73 | 20x | 5 ul |
| 10 | 1204.82 | 2500x | 0.04 ul |
| 100 | 4722.20 | 2500x | 0.04 ul |

TABLE 31

Factor IX Protein Expression

| Dose (ug) | Conc (ng/ml) | Dilution Factor | Sample Volume |
|---|---|---|---|
| 1 | 36.05 | 10x | 5 ul |
| 10 | 383.04 | 10x | 5 ul |
| 100* | 3247.75 | 50x | 1 ul |
| 100* | 11177.20 | 250x | 0.2 ul |

As shown in Table 32, the LNP formulations described above have about a 10,000-100,000-fold increase in protein production compared to an administration of an intravenous (IV)-lipoplex formulation for the same dosage of modified mRNA and intramuscular (IM) or subcutaneous (SC) administration of the same dose of modified mRNA in saline. As used in Table 32, the symbol "~" means about.

TABLE 32

Protein Production

| G-CSF | Dose (ug) | Serum Concentration (pg/ml) 8-12 hours after administration |
|---|---|---|
| IM | 100 | ~20-80 |
| SC | 100 | ~10-40 |
| IV (Lipoplex) | 100 | ~30 |
| IV (LNP) | 100 | ~5,000,000 |
| IV (LNP) | 10 | ~1,000,000 |
| IV (LNP) | 1 | ~20,000 |

| Factor IX | Dose (ug) | Serum Concentration (ng/ml) 8-12 hours after administration |
|---|---|---|
| IM | 2 × 100 | ~1.6 ng/ml |
| IV (LNP) | 100 | ~3,000-10,000 ng/ml |
| IV (LNP) | 10 | ~400 ng/ml |
| IV (LNP) | 1 | ~40 ng/ml |

Materials and Methods for Examples 17-22

G-CSF (mRNA sequence shown in SEQ ID NO: 4; polyA tail of approximately 160 nucleotides not shown in sequence; 5'cap, Cap 1; fully modified with 5-methylcytosine and pseudouridine) and EPO (mRNA sequence shown in SEQ ID NO: 7; polyA tail of approximately 160 nucleotides not shown in sequence; 5'cap, Cap 1; fully modified with 5-methylcytosine and pseudouridine) modified mRNA were formulated as lipid nanoparticles (LNPs) using the syringe pump method. The LNPs were formulated at a 20:1 weight ratio of total lipid to modified mRNA with a final lipid molar ratio of 50:10:38.5:1.5 (DLin-KC2-DMA: DSPC: Cholesterol: PEG-c-DOMG). Formulations, listed in Table 33, were characterized by particle size, zeta potential, and encapsulation.

TABLE 33

Formulations

| Formulation # | NPA-030-2 | NPA-060-1 |
|---|---|---|
| Modified mRNA | G-CSF | EPO |
| Mean size | 84 nm | 85 nm |
| | PDI: 0.04 | PDI: 0.03 |
| Zeta at pH 7.4 | 0.8 mV | 1.5 mV |
| Encapsulation (RiboGreen) | 95% | 98% |

Example 17. Lipid Nanoparticle In Vivo Studies with Modified mRNA

LNP formulations, shown in Table 33 (above), were administered to rats (n=5) intravenously (IV), intramuscularly (IM) or subcutaneously (SC) at a single modified mRNA dose of 0.05 mg/kg. A control group of rats (n=4) was untreated. The rats were bled at 2 hours, 8 hours, 24 hours, 48 hours and 96 hours and after they were administered with G-CSF or EPO modified mRNA formulations to determine protein expression using ELISA. The rats administered EPO modified mRNA intravenously were also bled at 7 days.

As shown in Table 34, EPO protein expression in the rats intravenously administered modified EPO mRNA was detectable out to 5 days. G-CSF in the rats intravenously administered modified G-CSF mRNA was detectable to 7 days. Subcutaneous and intramuscular administration of EPO modified mRNA was detectable to at least 24 hours and G-CSF modified mRNA was detectable to at least 8 hours. In Table 34, "OSC" refers to values that were outside the standard curve and "NT" means not tested.

TABLE 34

G-CSF and EPO Protein Expression

| Route | Time | EPO Serum Concentration (pg/ml) | G-CSF Serum Concentration (pg/ml) |
|---|---|---|---|
| IV | 2 hours | 36,981.0 | 31,331.9 |
| IV | 8 hours | 62,053.3 | 70,532.4 |
| IV | 24 hours | 42,077.0 | 5,738.6 |
| IV | 48 hours | 5,561.5 | 233.8 |
| IV | 5 days | 0.0 | 60.4 |
| IV | 7 days | 0.0 | NT |
| IM | 2 hours | 1395.4 | 1620.4 |
| IM | 8 hours | 8974.6 | 7910.4 |
| IM | 24 hours | 4678.3 | 893.3 |
| IM | 48 hours | NT | OSC |
| IM | 5 days | NT | OSC |
| SC | 2 hours | 386.2 | 80.3 |
| SC | 8 hours | 985.6 | 164.2 |
| SC | 24 hours | 544.2 | OSC |
| SC | 48 hours | NT | OSC |
| SC | 5 days | NT | OSC |
| Untreated | All bleeds | 0 | 0 |

Example 18. Time Course In Vivo Study

LNP formulations, shown in Table 33 (above), were administered to mice (n=5) intravenously (IV) at a single modified mRNA dose of 0.5, 0.05 or 0.005 mg/kg. The mice were bled at 8 hours, 24 hours, 72 hours and 6 days after they were administered with G-CSF or EPO modified mRNA formulations to determine protein expression using ELISA.

As shown in Table 35, EPO and G-CSF protein expression in the mice administered with the modified mRNA intravenously was detectable out to 72 hours for the mice dosed with 0.005 mg/kg and 0.05 mg/kg of modified mRNA and out to 6 days for the mice administered the EPO modified mRNA. In Table 35, ">" means greater than and "ND" means not detected.

TABLE 35

Protein Expression

| Dose (mg/kg) | Time | EPO Serum Concentration (pg/ml) | G-CSF Serum Concentration (pg/ml) |
|---|---|---|---|
| 0.005 | 8 hours | 12,508.3 | 11,550.6 |
| 0.005 | 24 hours | 6,803.0 | 5,068.9 |
| 0.005 | 72 hours | ND | ND |
| 0.005 | 6 days | ND | ND |
| 0.05 | 8 hours | 92,139.9 | 462,312.5 |
| 0.05 | 24 hours | 54,389.4 | 80,903.8 |
| 0.05 | 72 hours | ND | ND |
| 0.05 | 6 days | ND | ND |
| 0.5 | 8 hours | 498,515.3 | >1,250,000 |
| 0.5 | 24 hours | 160,566.3 | 495,812.5 |
| 0.5 | 72 hours | 3,492.5 | 1,325.6 |
| 0.5 | 6 days | 21.2 | ND |

Example 19. LNP Formulations In Vivo Study in Rodents

A. LNP Formulations in Mice

LNP formulations, shown in Table 33 (above), were administered to mice (n=4) intravenously (IV) at a single modified mRNA dose 0.05 mg/kg or 0.005 mg/kg. There was also 3 control groups of mice (n=4) that were untreated. The mice were bled at 2 hours, 8 hours, 24 hours, 48 hours and 72 hours after they were administered with G-CSF or EPO modified mRNA formulations to determine the protein expression. Protein expression of G-CSF and EPO were determined using ELISA.

As shown in Table 36, EPO and G-CSF protein expression in the mice was detectable at least out to 48 hours for the mice that received a dose of 0.005 mg/kg modified RNA and 72 hours for the mice that received a dose of 0.05 mg/kg modified RNA. In Table 36, "OSC" refers to values that were outside the standard curve and "NT" means not tested.

TABLE 36

Protein Expression in Mice

| Dose (mg/kg) | Time | EPO Serum Concentration (pg/ml) | G-CSF Serum Concentration (pg/ml) |
|---|---|---|---|
| 0.005 | 2 hours | OSC | 3,447.8 |
| 0.005 | 8 hours | 1,632.8 | 11,454.0 |
| 0.005 | 24 hours | 1,141.0 | 4,960.2 |
| 0.005 | 48 hours | 137.4 | 686.4 |
| 0.005 | 72 hours | 0 | NT |
| 0.05 | 2 hours | 10,027.3 | 20,951.4 |
| 0.05 | 8 hours | 56,547.2 | 70,012.8 |
| 0.05 | 24 hours | 25,027.3 | 19,356.2 |
| 0.05 | 48 hours | 1,432.3 | 1,963.0 |
| 0.05 | 72 hours | 82.2 | 47.3 |

B. LNP Formulations in Rats

LNP formulations, shown in Table 33 (above), are administered to rats (n=4) intravenously (IV) at a single modified mRNA dose 0.05 mg/kg. There is also a control group of rats (n=4) that are untreated. The rats are bled at 2 hours, 8 hours, 24 hours, 48 hours, 72 hours, 7 days and 14 days after they were administered with G-CSF or EPO modified mRNA formulations to determine the protein expression. Protein expression of G-CSF and EPO are determined using ELISA.

Example 20. Early Time Course Study of LNPs

LNP formulations, shown in Table 33 (above), are administered to mammals intravenously (IV), intramuscularly (IM) or subcutaneously (SC) at a single modified mRNA dose of 0.5 mg/kg, 0.05 mg/kg or 0.005 mg/kg. A control group of mammals are not treated. The mammals are bled at 5 minutes, 10 minutes, 20 minutes, 30 minutes, 45 minutes, 1 hour, 1.5 hours and/or 2 hours after they are administered with the modified mRNA LNP formulations to determine protein expression using ELISA. The mammals are also bled to determine the complete blood count such as the granulocyte levels and red blood cell count.

Example 21. Non-Human Primate In Vivo Study

LNP formulations, shown in Table 33 (above), were administered to non-human primates (NHP) (cynomolgus monkey) (n=2) as a bolus intravenous injection (IV) over approximately 30 seconds using a hypodermic needle, which may be attached to a syringe/abbocath or butterfly if needed. The NHP were administered a single modified mRNA IV dose of 0.05 mg/kg of EPO or G-CSF or 0.005 mg/kg of EPO in a dose volume of 0.5 mL/kg. The NHPs were bled 5-6 days before dosing with the modified mRNA LNP formulations to determine protein expression in the serum and a baseline complete blood count. After administration with the modified mRNA formulation the NHP were bled at 8, 24, 48 and 72 hours to determined protein expression. At 24 and 72 hours after administration the complete blood count of the NHP was also determined. Protein expression of G-CSF and EPO was determined by ELISA. Urine from the NHPs was collected over the course of the entire experiment and analyzed to evaluate clinical safety. Samples were collected from the NHPs after they were administered with G-CSF or EPO modified mRNA formulations to determine protein expression using ELISA. Clinical chemistry, hematology, urinalysis and cytokines of the non-human primates were also analyzed.

As shown in Table 37, EPO protein expression in the NHPs administered 0.05 mg/kg is detectable out to 72 hours and the 0.005 mg/kg dosing of the EPO formulation is detectable out to 48 hours. In Table 37, the "<" means less than a given value. G-CSF protein expression was seen out to 24 hours after administration with the modified mRNA formulation. Preliminarily, there was an increase in granulocytes and reticulocytes levels seen in the NHP after administration with the modified mRNA formulations.

TABLE 37

Protein Expression in Non-Human Primates

| Modified mRNA | Dose (mg/kg) | Time | Female NHP Serum Concentration (pg/ml) | Male NHP Serum Concentration (pg/ml) | Average Serum Conentration (pg/ml) |
|---|---|---|---|---|---|
| G-CSF | 0.05 | Pre-bleed | 0 | 0 | 0 |
| | | 8 hours | 3289 | 1722 | 2,506 |
| | | 24 hours | 722 | 307 | 515 |
| | | 48 hours | 0 | 0 | 0 |
| | | 72 hours | 0 | 0 | 0 |
| EPO | 0.05 | Pre-bleed | 0 | 0 | 0 |
| | | 8 hours | 19,858 | 7,072 | 13,465 |
| | | 24 hours | 18,178 | 4,913 | 11,546 |
| | | 48 hours | 5,291 | 498 | 2,895 |
| | | 72 hours | 744 | 60 | 402 |
| EPO | 0.005 | Pre-bleed | 0 | 0 | 0 |
| | | 8 hours | 523 | 250 | 387 |
| | | 24 hours | 302 | 113 | 208 |
| | | 48 hours | <7.8 | <7.8 | <7.8 |
| | | 72 hours | 0 | 0 | 0 |

Example 22. Non-Human Primate In Vivo Study for G-CSF and EPO

LNP formulations, shown in Table 33 (above), were administered to non-human primates (NHP) (cynomolgus monkey) (n=2) as intravenous injection (IV). The NHP were administered a single modified mRNA IV dose of 0.5 mg/kg, 0.05 mg/kg or 0.005 mg/kg of G-CSF or EPO in a dose volume of 0.5 mL/kg. The NHPs were bled before dosing with the modified mRNA LNP formulations to determine protein expression in the serum and a baseline complete blood count. After administration with the G-CSF modified mRNA formulation the NHP were bled at 8, 24, 48 and 72 hours to determined protein expression. After administration with the EPO modified mRNA formulation the NHP were bled at 8, 24, 48, 72 hours and 7 days to determined protein expression.

Samples collected from the NHPs after they were administered with G-CSF or EPO modified mRNA formulations were analyzed by ELISA to determine protein expression. Neutrophil and reticulocyte count was also determined pre-dose, 24 hours, 3 days, 7 days, 14 days and 18 days after administration of the modified G-CSF or EPO formulation.

As shown in Table 38, G-CSF protein expression was not detected beyond 72 hours. In Table 38, "<39" refers to a value below the lower limit of detection of 39 pg/ml.

TABLE 38

G-CSF Protein Expression

| Modified mRNA | Dose (mg/kg) | Time | Female NHP Serum G-CSF Concentration (pg/ml) | Male NHP Serum G-CSF Concentration (pg/ml) |
|---|---|---|---|---|
| G-CSF | 0.5 | Pre-bleed | <39 | <39 |
| | | 8 hours | 43,525 | 43,594 |
| | | 24 hours | 11,374 | 3,628 |
| | | 48 hours | 1,100 | 833 |
| | | 72 hours | <39 | 306 |
| G-CSF | 0.05 | Pre-bleed | <39 | <39 |
| | | 8 hours | 3,289 | 1,722 |
| | | 24 hours | 722 | 307 |
| | | 48 hours | <39 | <39 |
| | | 72 hours | <39 | <39 |
| G-CSF | 0.005 | Pre-bleed | <39 | <39 |
| | | 8 hours | 559 | 700 |
| | | 24 hours | 155 | <39 |
| | | 48 hours | <39 | <39 |
| | | 72 hours | <39 | <39 |

As shown in Table 39, EPO protein expression was not detected beyond 7 days. In Table 39, "<7.8" refers to a value below the lower limit of detection of 7.8 pg/ml.

TABLE 39

EPO Protein Expression

| Modified mRNA | Dose (mg/kg) | Time | Female NHP Serum EPO Concentration (pg/ml) | Male NHP Serum EPO Concentration (pg/ml) |
|---|---|---|---|---|
| EPO | 0.5 | Pre-bleed | <7.8 | <7.8 |
| | | 8 hours | 158,771 | 119,086 |
| | | 24 hours | 133,978 | 85,825 |
| | | 48 hours | 45,250 | 64,793 |
| | | 72 hours | 15,097 | 20,407 |
| | | 7 days | <7.8 | <7.8 |
| EPO | 0.05 | Pre-bleed | <7.8 | <7.8 |
| | | 8 hours | 19,858 | 7,072 |
| | | 24 hours | 18,187 | 4,913 |
| | | 48 hours | 5,291 | 498 |
| | | 72 hours | 744 | 60 |
| | | 7 days | <7.8 | <7.8 |
| EPO | 0.005 | Pre-bleed | <7.8 | <7.8 |
| | | 8 hours | 523 | 250 |
| | | 24 hours | 302 | 113 |
| | | 48 hours | 11 | 29 |
| | | 72 hours | <7.8 | <7.8 |
| | | 7 days | <7.8 | <7.8 |

As shown in Table 40, there was an increase in neutrophils in all G-CSF groups relative to pre-dose levels.

TABLE 40

Pharmacologic Effect of G-CSF mRNA in NHP

| Dose (mg/kg) | Time | Male NHP (G-CSF) Neutrophils ($10^9$/L) | Female NHP (G-CSF) Neutrophils ($10^9$/L) | Male NHP (EPO) Neutrophils ($10^9$/L) | Female NHP (EPO) Neutrophils ($10^9$/L) |
|---|---|---|---|---|---|
| 0.5 | Pre-dose | 1.53 | 1.27 | 9.72 | 1.82 |
| | 24 hours | 14.92 | 13.96 | 7.5 | 11.85 |
| | 3 days | 9.76 | 13.7 | 11.07 | 5.22 |
| | 7 days | 2.74 | 3.81 | 11.8 | 2.85 |
| | 14/18 days | 2.58 | 1.98 | 7.16 | 2.36 |
| 0.05 | Pre-dose | 13.74 | 3.05 | 0.97 | 2.15 |
| | 24 hours | 19.92 | 29.91 | 2.51 | 2.63 |
| | 3 days | 7.49 | 10.77 | 1.73 | 4.08 |

TABLE 40-continued

Pharmacologic Effect of G-CSF mRNA in NHP

| Dose (mg/kg) | Time | Male NHP (G-CSF) Neutrophils ($10^9$/L) | Female NHP (G-CSF) Neutrophils ($10^9$/L) | Male NHP (EPO) Neutrophils ($10^9$/L) | Female NHP (EPO) Neutrophils ($10^9$/L) |
|---|---|---|---|---|---|
| | 7 days | 4.13 | 3.8 | 1.23 | 2.77 |
| | 14/18 days | 3.59 | 1.82 | 1.53 | 1.27 |
| 0.005 | Pre-dose | 1.52 | 2.54 | 5.46 | 5.96 |
| | 24 hours | 16.44 | 8.6 | 5.37 | 2.59 |
| | 3 days | 3.74 | 1.78 | 6.08 | 2.83 |
| | 7 days | 7.28 | 2.27 | 3.51 | 2.23 |
| | 14/18 days | 4.31 | 2.28 | 1.52 | 2.54 |

As shown in Table 41, there was an increase in reticulocytes in all EPO groups 3 days to 14/18 days after dosing relative to reticulocyte levels 24 hours after dosing.

TABLE 41

Pharmacologic Effect of EPO mRNA on Neutrophil Count

| Dose (mg/kg) | Time | Male NHP (G-CSF) Neutrophils ($10^{12}$/L) | Female NHP (G-CSF) Neutrophils ($10^{12}$/L) | Male NHP (EPO) Neutrophils ($10^{12}$/L) | Female NHP (EPO) Neutrophils ($10^{12}$/L) |
|---|---|---|---|---|---|
| 0.5 | Pre-dose | 0.067 | 0.055 | 0.107 | 0.06 |
| | 24 hours | 0.032 | 0.046 | 0.049 | 0.045 |
| | 3 days | 0.041 | 0.017 | 0.09 | 0.064 |
| | 7 days | 0.009 | 0.021 | 0.35 | 0.367 |
| | 14/18 days | 0.029 | 0.071 | 0.066 | 0.071 |
| 0.05 | Pre-dose | 0.055 | 0.049 | 0.054 | 0.032 |
| | 24 hours | 0.048 | 0.046 | 0.071 | 0.04 |
| | 3 days | 0.101 | 0.061 | 0.102 | 0.105 |
| | 7 days | 0.157 | 0.094 | 0.15 | 0.241 |
| | 14/18 days | 0.107 | 0.06 | 0.067 | 0.055 |
| 0.005 | Pre-dose | 0.037 | 0.06 | 0.036 | 0.052 |
| | 24 hours | 0.037 | 0.07 | 0.034 | 0.061 |
| | 3 days | 0.037 | 0.054 | 0.079 | 0.118 |
| | 7 days | 0.046 | 0.066 | 0.049 | 0.087 |
| | 14/18 days | 0.069 | 0.057 | 0.037 | 0.06 |

As shown in Tables 42-44, the administration of EPO modified RNA had an effect on other erythropoetic parameters including hemoglobin (HGB), hematocrit (HCT) and red blood cell (RBC) count.

TABLE 42

Pharmacologic Effect of EPO mRNA on Hemoglobin

| Dose (mg/kg) | Time | Male NHP (G-CSF) HGB (g/L) | Female NHP (G-CSF) HGB (g/L) | Male NHP (EPO) HGB (g/L) | Female NHP (EPO) HGB (g/L) |
|---|---|---|---|---|---|
| 0.5 | Pre-dose | 133 | 129 | 134 | 123 |
| | 24 hours | 113 | 112 | 127 | 108 |
| | 3 days | 118 | 114 | 126 | 120 |
| | 7 days | 115 | 116 | 140 | 134 |
| | 14/18 days | 98 | 113 | 146 | 133 |
| 0.05 | Pre-dose | 137 | 129 | 133 | 133 |
| | 24 hours | 122 | 117 | 123 | 116 |
| | 3 days | 126 | 115 | 116 | 120 |
| | 7 days | 126 | 116 | 126 | 121 |
| | 14/18 days | 134 | 123 | 133 | 129 |
| 0.005 | Pre-dose | 128 | 129 | 132 | 136 |
| | 24 hours | 117 | 127 | 122 | 128 |
| | 3 days | 116 | 127 | 125 | 130 |
| | 7 days | 116 | 129 | 119 | 127 |
| | 14/18 days | 118 | 129 | 128 | 129 |

TABLE 43

Pharmacologic Effect of EPO mRNA on Hematocrit

| Dose (mg/kg) | Time | Male NHP (G-CSF) HCT (L/L) | Female NHP (G-CSF) HCT (L/L) | Male NHP (EPO) HCT (L/L) | Female NHP (EPO) HCT (L/L) |
|---|---|---|---|---|---|
| 0.5 | Pre-dose | 0.46 | 0.43 | 0.44 | 0.4 |
|  | 24 hours | 0.37 | 0.38 | 0.4 | 0.36 |
|  | 3 days | 0.39 | 0.38 | 0.41 | 0.39 |
|  | 7 days | 0.39 | 0.38 | 0.45 | 0.45 |
|  | 14/18 days | 0.34 | 0.37 | 0.48 | 0.46 |
| 0.05 | Pre-dose | 0.44 | 0.44 | 0.45 | 0.43 |
|  | 24 hours | 0.39 | 0.4 | 0.43 | 0.39 |
|  | 3 days | 0.41 | 0.39 | 0.38 | 0.4 |
|  | 7 days | 0.42 | 0.4 | 0.45 | 0.41 |
|  | 14/18 days | 0.44 | 0.4 | 0.46 | 0.43 |
| 0.005 | Pre-dose | 0.42 | 0.42 | 0.48 | 0.45 |
|  | 24 hours | 0.4 | 0.42 | 0.42 | 0.43 |
|  | 3 days | 0.4 | 0.41 | 0.44 | 0.42 |
|  | 7 days | 0.39 | 0.42 | 0.41 | 0.42 |
|  | 14/18 days | 0.41 | 0.42 | 0.42 | 0.42 |

TABLE 44

Pharmacologic Effect of EPO mRNA on Red Blood Cells

| Dose (mg/kg) | Time | Male NHP (G-CSF) RBC ($10^{12}$/L) | Female NHP (G-CSF) RBC ($10^{12}$/L) | Male NHP (EPO) RBC ($10^{12}$/L) | Female NHP (EPO) RBC ($10^{12}$/L) |
|---|---|---|---|---|---|
| 0.5 | Pre-dose | 5.57 | 5.57 | 5.43 | 5.26 |
|  | 24 hours | 4.66 | 4.96 | 5.12 | 4.69 |
|  | 3 days | 4.91 | 4.97 | 5.13 | 5.15 |
|  | 7 days | 4.8 | 5.04 | 5.55 | 5.68 |
|  | 14/18 days | 4.21 | 4.92 | 5.83 | 5.72 |
| 0.05 | Pre-dose | 5.68 | 5.64 | 5.57 | 5.84 |
|  | 24 hours | 4.96 | 5.08 | 5.25 | 5.18 |
|  | 3 days | 5.13 | 5.04 | 4.81 | 5.16 |
|  | 7 days | 5.17 | 5.05 | 5.37 | 5.31 |
|  | 14/18 days | 5.43 | 5.26 | 5.57 | 5.57 |
| 0.005 | Pre-dose | 5.67 | 5.36 | 6.15 | 5.72 |
|  | 24 hours | 5.34 | 5.35 | 5.63 | 5.35 |
|  | 3 days | 5.32 | 5.24 | 5.77 | 5.42 |
|  | 7 days | 5.25 | 5.34 | 5.49 | 5.35 |
|  | 14/18 days | 5.37 | 5.34 | 5.67 | 5.36 |

As shown in Tables 45 and 46, the administration of modified RNA had an effect on serum chemistry parameters including alanine transaminase (ALT) and aspartate transaminase (AST).

TABLE 45

Pharmacologic Effect of EPO mRNA on Alanine Transaminase

| Dose (mg/kg) | Time | Male NHP (G-CSF) ALT (U/L) | Female NHP (G-CSF) ALT (U/L) | Male NHP (EPO) ALT (U/L) | Female NHP (EPO) ALT (U/L) |
|---|---|---|---|---|---|
| 0.5 | Pre-dose | 29 | 216 | 50 | 31 |
|  | 2 days | 63 | 209 | 98 | 77 |
|  | 4 days | 70 | 98 | 94 | 87 |
|  | 7 days | 41 | 149 | 60 | 59 |
|  | 14 days | 43 | 145 | 88 | 44 |
| 0.05 | Pre-dose | 58 | 53 | 56 | 160 |
|  | 2 days | 82 | 39 | 95 | 254 |
|  | 4 days | 88 | 56 | 70 | 200 |
|  | 7 days | 73 | 73 | 64 | 187 |
|  | 14 days | 50 | 31 | 29 | 216 |
| 0.005 | Pre-dose | 43 | 51 | 45 | 45 |
|  | 2 days | 39 | 32 | 62 | 48 |
|  | 4 days | 48 | 58 | 48 | 50 |
|  | 7 days | 29 | 55 | 21 | 48 |
|  | 14 days | 44 | 46 | 43 | 51 |

TABLE 46

Pharmacologic Effect of EPO mRNA on Aspartate Transaminase

| Dose (mg/kg) | Time | Male NHP (G-CSF) AST (U/L) | Female NHP (G-CSF) AST (U/L) | Male NHP (EPO) AST (U/L) | Female NHP (EPO) AST (U/L) |
|---|---|---|---|---|---|
| 0.5 | Pre-dose | 32 | 47 | 59 | 20 |
| | 2 days | 196 | 294 | 125 | 141 |
| | 4 days | 67 | 63 | 71 | 60 |
| | 7 days | 53 | 68 | 56 | 47 |
| | 14 days | 47 | 67 | 82 | 44 |
| 0.05 | Pre-dose | 99 | 33 | 74 | 58 |
| | 2 days | 95 | 34 | 61 | 80 |
| | 4 days | 69 | 42 | 48 | 94 |
| | 7 days | 62 | 52 | 53 | 78 |
| | 14 days | 59 | 20 | 32 | 47 |
| 0.005 | Pre-dose | 35 | 54 | 39 | 40 |
| | 2 days | 70 | 34 | 29 | 25 |
| | 4 days | 39 | 36 | 43 | 55 |
| | 7 days | 28 | 31 | 55 | 31 |
| | 14 days | 39 | 20 | 35 | 54 |

As shown in Table 47, the administration of modified RNA cause an increase in cytokines, interferon-alpha (IFN-alpha) after administration of modified mRNA.

TABLE 47

Pharmacologic Effect of EPO mRNA on Alanine Transaminase

| Dose (mg/kg) | Time | Male NHP (G-CSF) IFN-alpha (pg/mL) | Female NHP (G-CSF) IFN-alpha (pg/mL) | Male NHP (EPO) IFN-alpha (pg/mL) | Female NHP (EPO) IFN-alpha (pg/mL) |
|---|---|---|---|---|---|
| 0.5 | Pre-dose | 0 | 0 | 0 | 0 |
| | Day 1 + 8 hr | 503.8 | 529.2 | 16.79 | 217.5 |
| | 4 days | 0 | 0 | 0 | 0 |
| 0.05 | Pre-dose | 0 | 0 | 0 | 0 |
| | Day 1 + 8 hr | 0 | 0 | 0 | 0 |
| | 4 days | 0 | 0 | 0 | 0 |
| 0.005 | Pre-dose | 0 | 0 | 0 | 0 |
| | Day 1 + 8 hr | 0 | 0 | 0 | 0 |
| | 4 days | 0 | 0 | 0 | 0 |

Example 23. Study of Intramuscular and/or Subcutaneous Administration in Non-Human Primates Formulations containing modified EPO mRNA (SEQ ID NO: 7; polyA tail of approximately 160 nucleotides not shown in sequence; 5'cap, Cap1; fully modified with 5-methylcytosine and pseudouridine) or G-CSF mRNA (SEQ ID NO: 4; polyA tail of approximately 160 nucleotides not shown in sequence; 5'cap, Cap1; fully modified with 5-methylcytosine and pseudouridine) in saline were administered to non-human primates (Cynomolgus monkey) (NHP) intramuscularly (IM) or subcutaneously (SC). The single modified mRNA dose of 0.05 mg/kg or 0.005 mg/kg was in a dose volume of 0.5 mL/kg. The non-human primates are bled 5-6 days prior to dosing to determine serum protein concentration and a baseline complete blood count. After administration with the modified mRNA formulation the NHP are bled at 8 hours, 24 hours, 48 hours, 72 hours, 7 days and 14 days to determined protein expression. Protein expression of G-CSF and EPO is determined by ELISA. At 24 hours, 72 hours, 7 days and 14 days after administration the complete blood count of the NHP is also determined. Urine from the NHPs is collected over the course of the entire experiment and analyzed to evaluate clinical safety. Tissue near the injection site is also collected and analyzed to determine protein expression.

Example 24. Modified mRNA Trafficking

In order to determine localization and/or trafficking of the modified mRNA, studies may be performed as follows.

LNP formulations of siRNA and modified mRNA are formulated according to methods known in the art and/or described herein. The LNP formulations may include at least one modified mRNA which may encode a protein such as G-CSF, EPO, Factor VII, and/or any protein described herein. The formulations may be administered locally into muscle of mammals using intramuscular or subcutaneous injection. The dose of modified mRNA and the size of the LNP may be varied to determine the effect on trafficking in the body of the mammal and/or to assess the impact on a biologic reaction such as, but not limited to, inflammation. The mammal may be bled at different time points to determine the expression of protein encoded by the modified mRNA administered present in the serum and/or to determine the complete blood count in the mammal.

For example, modified mRNA encoding Factor VII, expressed in the liver and secreted into the serum, may be administered intramuscularly and/or subcutaneously. Coincident or prior to modified mRNA administration, siRNA is administered to knock out endogenous Factor VII. Factor VII arising from the intramuscular and/or subcutaneous injection of modified mRNA is administered is measured in the blood. Also, the levels of Factor VII is measured in the tissues near the injection site. If Factor VII is expressed in blood then there is trafficking of the modified mRNA. If Factor VII is expressed in tissue and not in the blood than there is only local expression of Factor VII.

Example 25. Formulations of Multiple Modified mRNA

LNP formulations of modified mRNA are formulated according to methods known in the art and/or described herein. The LNP formulations may include at least one modified mRNA which may encode a protein such as G-CSF, EPO, thrombopoietin and/or any protein described herein or known in the art. The at least one modified mRNA may include 1, 2, 3, 4 or 5 modified mRNA molecules. The formulations containing at least one modified mRNA may be administered intravenously, intramuscularly or subcutaneously in a single or multiple dosing regimens. Biological samples such as, but not limited to, blood and/or serum may be collected and analyzed at different time points before and/or after administration of the at least one modified mRNA formulation. An expression of a protein in a biological sample of 50-200 pg/ml after the mammal has been administered a formulation containing at least one modified mRNA encoding said protein would be considered biologically effective.

Example 26. Polyethylene Glycol Ratio Studies

A. Formulation and Characterization of PEG LNPs

Lipid nanoparticles (LNPs) were formulated using the syringe pump method. The LNPs were formulated at a 20:1 weight ratio of total lipid to modified G-CSF mRNA (SEQ ID NO: 4; polyA tail of approximately 160 nucleotides not shown in sequence; 5'cap, Cap1; fully modified with 5-methylcytosine and pseudouridine). The molar ratio ranges of the formulations are shown in Table 48.

TABLE 48

Molar Ratios

| | DLin-KC2-DMA | DSPC | Cholesterol | PEG-c-DOMG |
|---|---|---|---|---|
| Mole Percent (mol %) | 50.0 | 10.0 | 37-38.5 | 1.5-3 |

Two types of PEG lipid, 1,2-Dimyristoyl-sn-glycerol, methoxypolyethylene Glycol (PEG-DMG, NOF Cat # SUNBRIGHT® GM-020) and 1,2-Distearoyl-sn-glycerol, methoxypolyethylene Glycol (PEG-DSG, NOF Cat # SUNBRIGHT® GS-020), were tested at 1.5 or 3.0 mol %. After the formation of the LNPs and the encapsulation of the modified G-CSF mRNA, the LNP formulations were characterized by particle size, zeta potential and encapsulation percentage and the results are shown in Table 49.

TABLE 49

Characterization of LNP Formulations

| | Formulation No. | | | |
|---|---|---|---|---|
| | NPA-071-1 | NPA-072-1 | NPA-073-1 | NPA-074-1 |
| Lipid | PEG-DMG 1.5% | PEG-DMG 3% | PEG-DSA 1.5% | PEG-DSA 3% |
| Mean Size | 95 nm PDI: 0.01 | 85 nm PDI: 0.06 | 95 nm PDI: 0.08 | 75 nm PDI: 0.08 |

TABLE 49-continued

Characterization of LNP Formulations

| | Formulation No. | | | |
|---|---|---|---|---|
| | NPA-071-1 | NPA-072-1 | NPA-073-1 | NPA-074-1 |
| Zeta at pH 7.4 | −1.1 mV | −2.6 mV | 1.7 mV | 0.7 mV |
| Encapsulation (RiboGreen) | 88% | 89% | 98% | 95% |

B. In Vivo Screening of PEG LNPs

Formulations of the PEG LNPs described in Table 42 were administered to mice (n=5) intravenously at a dose of 0.5 mg/kg. Serum was collected from the mice at 2 hours, 8 hours, 24 hours, 48 hours, 72 hours and 8 days after administration of the formulation. The serum was analyzed by ELISA to determine the protein expression of G-CSF and the expression levels are shown in Table 50. LNP formulations using PEG-DMG gave substantially higher levels of protein expression than LNP formulations with PEG-DSA.

TABLE 50

Protein Expression

| Lipid | Formulation No. | Time | Protein Expression (pg/ml) |
|---|---|---|---|
| PEG-DMG, 1.5% | NPA-071-1 | 2 hours | 114,102 |
| | | 8 hours | 357,944 |
| | | 24 hours | 104,832 |
| | | 48 hours | 6,697 |
| | | 72 hours | 980 |
| | | 8 days | 0 |
| PEG-DMG, 3% | NPA-072-1 | 2 hours | 154,079 |
| | | 8 hours | 354,994 |
| | | 24 hours | 164,311 |
| | | 48 hours | 13,048 |
| | | 72 hours | 1,182 |
| | | 8 days | 13 |
| PEG-DSA, 1.5% | NPA-073-1 | 2 hours | 3,193 |
| | | 8 hours | 6,162 |
| | | 24 hours | 446 |
| | | 48 hours | 197 |
| | | 72 hours | 124 |
| | | 8 days | 5 |
| PEG-DSA, 3% | NPA-074-1 | 2 hours | 259 |
| | | 8 hours | 567 |
| | | 24 hours | 258 |
| | | 48 hours | 160 |
| | | 72 hours | 328 |
| | | 8 days | 33 |

Example 27. Cationic Lipid Formulation Studies

A. Formulation and Characterization of Cationic Lipid Nanoparticles

Lipid nanoparticles (LNPs) were formulated using the syringe pump method. The LNPs were formulated at a 20:1 weight ratio of total lipid to modified mRNA. The final lipid molar ratio ranges of cationic lipid, DSPC, cholesterol and PEG-c-DOMG are outlined in Table 51.

TABLE 51

| | Molar Ratios | | | |
|---|---|---|---|---|
| | Cationic Lipid | DSPC | Cholesterol | PEG-c-DOMG |
| Mole Percent (mol %) | 50.0 | 10.0 | 38.5 | 1.5 |

A 25 mM lipid solution in ethanol and modified RNA in 50 mM citrate at a pH of 3 were mixed to create spontaneous vesicle formation. The vesicles were stabilized in ethanol before the ethanol was removed and there was a buffer exchange by dialysis. The LNPs were then characterized by particle size, zeta potential, and encapsulation percentage. Table 52 describes the characterization of LNPs encapsulating EPO modified mRNA (SEQ ID NO: 7 polyA tail of approximately 160 nucleotides not shown in sequence; 5'cap, Cap1; fully modified with 5-methylcytosine and pseudouridine) or G-CSF modified mRNA (SEQ ID NO: 4; polyA tail of approximately 160 nucleotides not shown in sequence; 5'cap, Cap1; fully modified with 5-methylcytosine and pseudouridine) using DLin-MC3-DMA, DLin-DMA or C12-200 as the cationic lipid.

TABLE 52

Characterization of Cationic Lipid Formulations

| | Formulation No. | | | | | |
|---|---|---|---|---|---|---|
| | NPA-071-1 | NPA-072-1 | NPA-073-1 | NPA-074-1 | NPA-075-1 | NPA-076-1 |
| Lipid | DLin-MC3-DMA | DLin-MC3-DMA | DLin-DMA | DLin-DMA | C12-200 | C12-200 |
| Modified RNA | EPO | G-CSF | EPO | G-CSF | EPO | G-CSF |
| Mean Size | 89 nm PDI: 0.07 | 96 nm PDI: 0.08 | 70 nm PDI: 0.04 | 73 nm PDI: 0.06 | 97 nm PDI: 0.05 | 103 nm PDI: 0.09 |
| Zeta at pH 7.4 | −1.1 mV | −1.4 mV | −1.6 mV | −0.4 mV | 1.4 mV | 0.9 mV |
| Encapsulation (RiboGreen) | 100% | 100% | 99% | 100% | 88% | 98% |

B. In Vivo Screening of Cationic LNP Formulations

Formulations of the cationic lipid formulations described in Table 44 were administered to mice (n=5) intravenously at a dose of 0.5 mg/kg. Serum was collected from the mice at 2 hours, 24 hours, 72 hours and/or 7 days after administration of the formulation. The serum was analyzed by ELISA to determine the protein expression of EPO or G-CSF and the expression levels are shown in Table 53.

TABLE 53

Protein Expression

| Modified mRNA | Formulation No. | Time | Protein Expression (pg/ml) |
|---|---|---|---|
| EPO | NPA-071-1 | 2 hours | 304,190.0 |
| | | 24 hours | 166,811.5 |
| | | 72 hours | 1,356.1 |
| | | 7 days | 20.3 |
| EPO | NPA-073-1 | 2 hours | 73,852.0 |
| | | 24 hours | 75,559.7 |
| | | 72 hours | 130.8 |
| EPO | NPA-075-1 | 2 hours | 413,010.2 |
| | | 24 hours | 56,463.8 |
| G-CSF | NPA-072-1 | 2 hours | 62,113.1 |
| | | 24 hours | 53,206.6 |

TABLE 53-continued

Protein Expression

| Modified mRNA | Formulation No. | Time | Protein Expression (pg/ml) |
|---|---|---|---|
| G-CSF | NPA-074-1 | 24 hours | 25,059.3 |
| G-CSF | NPA-076-1 | 2 hours | 219,198.1 |
| | | 24 hours | 8,470.0 |

Toxicity was seen in the mice administered the LNPs formulations with the cationic lipid C12-200 (NPA-075-1 and NPA-076-1) and they were sacrificed at 24 hours because they showed symptoms such as scrubby fur, cowering behavior and weight loss of greater than 10%. C12-200 was expected to be more toxic but also had a high level of expression over a short period. The cationic lipid DLin-DMA (NPA-073-1 and NPA-074-1) had the lowest expression out of the three cationic lipids tested. DLin-MC3-DMA (NPA-071-1 and NPA-072-1) showed good expression up to day three and was above the background sample out to day 7 for EPO formulations.

Example 28. Method of Screening for Protein Expression

A. Electrospray Ionization

A biological sample which may contain proteins encoded by modified RNA administered to the subject is prepared and analyzed according to the manufacturer protocol for electrospray ionization (ESI) using 1, 2, 3 or 4 mass analyzers. A biologic sample may also be analyzed using a tandem ESI mass spectrometry system.

Patterns of protein fragments, or whole proteins, are compared to known controls for a given protein and identity is determined by comparison.

B. Matrix-Assisted Laser Desorption/Ionization

A biological sample which may contain proteins encoded by modified RNA administered to the subject is prepared and analyzed according to the manufacturer protocol for matrix-assisted laser desorption/ionization (MALDI).

Patterns of protein fragments, or whole proteins, are compared to known controls for a given protein and identity is determined by comparison.

C. Liquid Chromatography-Mass Spectrometry-Mass spectrometry

A biological sample, which may contain proteins encoded by modified RNA, may be treated with a trypsin enzyme to digest the proteins contained within. The resulting peptides are analyzed by liquid chromatography-mass spectrometry-mass spectrometry (LC/MS/MS). The peptides are fragmented in the mass spectrometer to yield diagnostic patterns that can be matched to protein sequence databases via computer algorithms. The digested sample may be diluted to achieve 1 ng or less starting material for a given protein. Biological samples containing a simple buffer background (e.g. water or volatile salts) are amenable to direct in-solution digest; more complex backgrounds (e.g. detergent, non-volatile salts, glycerol) require an additional clean-up step to facilitate the sample analysis.

Patterns of protein fragments, or whole proteins, are compared to known controls for a given protein and identity is determined by comparison.

Example 29. LNP In Vivo Studies mCherry mRNA (SEQ ID NO: 12; polyA tail of approximately 160 nucleotides not shown in sequence; 5'cap, Cap1; fully modified with 5-methylcytosine and pseudouridine) was formulated as a lipid nanoparticle (LNP) using the syringe pump method. The LNP was formulated at a 20:1 weight ratio of total lipid to modified mRNA with a final lipid molar ratio of 50:10:38.5:1.5 (DLin-KC2-DMA: DSPC: Cholesterol: PEG-c-DOMG). The mCherry formulation, listed in Table 54, was characterized by particle size, zeta potential, and encapsulation.

TABLE 54 mCherry Formulation

| Formulation # | NPA-003-5 |
|---|---|
| Modified mRNA | mCherry |
| Mean size | 105 nm |
| | PDI: 0.09 |
| Zeta at pH 7.4 | 1.8 mV |
| Encaps. (RiboGr) | 100% |

The LNP formulation was administered to mice (n=5) intravenously at a modified mRNA dose of 100 ug. Mice were sacrificed at 24 hrs after dosing. The liver and spleen from the mice administered with mCherry modified mRNA formulations were analyzed by immunohistochemistry (IHC), western blot, or fluorescence-activated cell sorting (FACS).

Histology of the liver showed uniform mCherry expression throughout the section, while untreated animals did not express mCherry. Western blots were also used to confirm mCherry expression in the treated animals, whereas mCherry was not detected in the untreated animals. Tubulin was used as a control marker and was detected in both treated and untreated mice, indicating that normal protein expression in hepatocytes was unaffected.

FACS and IHC were also performed on the spleens of mCherry and untreated mice. All leukocyte cell populations were negative for mCherry expression by FACS analysis. By IHC, there were also no observable differences in the spleen between mCherry treated and untreated mice.

Example 30. Syringe Pump In Vivo Studies mCherry modified mRNA is formulated as a lipid nanoparticle (LNP) using the syringe pump method. The LNP is formulated at a 20:1 weight ratio of total lipid to modified mRNA with a final lipid molar ratio of 50:10:38.5:1.5 (DLin-KC2-DMA: DSPC: Cholesterol: PEG-c-DOMG). The mCherry formulation is characterized by particle size, zeta potential, and encapsulation.

The LNP formulation is administered to mice (n=5) intravenously at a modified mRNA dose of 10 or 100 ug. Mice are sacrificed at 24 hrs after dosing. The liver and spleen from the mice administered with mCherry modified mRNA formulations are analyzed by immunohistochemistry (IHC), western blot, and/or fluorescence-activated cell sorting (FACS).

Example 31. In Vitro and In Vivo Expression

A. In Vitro Expression in Human Cells Using Lipidoid Formulations

The ratio of mmRNA to lipidoid used to test for in vitro transfection is tested empirically at different lipidoid:mmRNA ratios. Previous work using siRNA and lipidoids have utilized 2.5:1, 5:1, 10:1, and 15:1 lipidoid:siRNA wt:wt ratios. Given the longer length of mmRNA relative to siRNA, a lower wt:wt ratio of lipidoid to mmRNA may be effective. In addition, for comparison mmRNA were also formulated using RNAIMAX™ (Invitrogen, Carlsbad, Calif.) or TRANSIT-mRNA (Mirus Bio, Madison, Wis.) cationic lipid delivery vehicles. The ability of lipidoid-formulated Luciferase (IVT cDNA sequence as shown in SEQ ID NO: 13; mRNA sequence shown in SEQ ID NO: 14, polyA tail of approximately 160 nucleotides not shown in sequence, 5'cap, Cap1, fully modified with 5-methylcytosine at each cytosine and pseudouridine replacement at each uridine site), green fluorescent protein (GFP) (IVT cDNA wild-type sequence is shown in SEQ ID NO: 15; mRNA sequence shown in SEQ ID NO: 16, polyA tail of approximately 160 nucleotides not shown in sequence, 5'cap, Cap1), G-CSF (mRNA sequence shown in SEQ ID NO: 4; polyA tail of approximately 160 nucleotides not shown in sequence; 5'cap, Cap1), and EPO mRNA (mRNA sequence shown in SEQ ID NO: 7; polyA tail of approximately 160 nucleotides not shown in sequence; 5'cap, Cap1) to express the desired protein product can be confirmed by luminescence for luciferase expression, flow cytometry for GFP expression, and by ELISA for G-CSF and Erythropoietin (EPO) secretion.

B. In Vivo Expression Following Intravenous Injection

Systemic intravenous administration of the formulations are created using various different lipidoids including, but not limited to, 98N12-5, C12-200, and MD1.

Lipidoid formulations containing mmRNA are injected intravenously into animals. The expression of the modified mRNA (mmRNA)-encoded proteins are assessed in blood and/or other organs samples such as, but not limited to, the liver and spleen collected from the animal. Conducting single dose intravenous studies will also allow an assessment of the magnitude, dose responsiveness, and longevity of expression of the desired product.

In one embodiment, lipidoid based formulations of 98N12-5, C12-200, MD1 and other lipidoids, are used to deliver luciferase, green fluorescent protein (GFP), mCherry fluorescent protein, secreted alkaline phosphatase (sAP), human G-CSF, human Factor IX, or human Erythropoietin (EPO) mmRNA into the animal. After formulating mmRNA with a lipid, as described previously, animals are divided into groups to receive either a saline formulation, or a lipidoid-formulation which contains one of a different mmRNA selected from luciferase, GFP, mCherry, sAP, human G-CSF, human Factor IX, and human EPO. Prior to injection into the animal, mmRNA-containing lipidoid formulations are diluted in PBS. Animals are then administered a single dose of formulated mmRNA ranging from a dose of 10 mg/kg to doses as low as 1 ng/kg, with a preferred range to be 10 mg/kg to 100 ng/kg, where the dose of mmRNA depends on the animal body weight such as a 20 gram mouse receiving a maximum formulation of 0.2 ml (dosing is based no mmRNA per kg body weight). After the administration of the mmRNA-lipidoid formulation, serum, tissues, and/or tissue lysates are obtained and the level of the mmRNA-encoded product is determined at a single and/or a range of time intervals. The ability of lipidoid-formulated Luciferase, GFP, mCherry, sAP, G-CSF, Factor IX, and EPO mmRNA to express the desired protein product is confirmed by luminescence for the expression of Luciferase, flow cytometry for the expression of GFP and mCherry expression, by enzymatic activity for sAP, or by ELISA for the section of G-CSF, Factor IX and/or EPO.

Further studies for a multi-dose regimen are also performed to determine the maximal expression of mmRNA, to evaluate the saturability of the mmRNA-driven expression (by giving a control and active mmRNA formulation in parallel or in sequence), and to determine the feasibility of repeat drug administration (by giving mmRNA in doses separated by weeks or months and then determining whether expression level is affected by factors such as immunogenicity). An assessment of the physiological function of proteins such as G-CSF and EPO are also determined through analyzing samples from the animal tested and detecting increases in granulocyte and red blood cell counts, respectively. Activity of an expressed protein product such as Factor IX, in animals can also be assessed through analysis of Factor IX enzymatic activity (such as an activated partial thromboplastin time assay) and effect of clotting times.

C. In Vitro Expression Following Intramuscular and/or Subcutaneous Injection

The use of lipidoid formulations to deliver oligonucleotides, including mRNA, via an intramuscular route or a subcutaneous route of injection needs to be evaluated as it has not been previously reported. Intramuscular and/or subcutaneous injection of mmRNA are evaluated to determine if mmRNA-containing lipidoid formulations are capabable to produce both localized and systemic expression of a desired proteins.

Lipidoid formulations of 98N12-5, C12-200, and MD1 containing mmRNA selected from luciferase, green fluorescent protein (GFP), mCherry fluorescent protein, secreted alkaline phosphatase (sAP), human G-CSF, human factor IX, or human Erythropoietin (EPO) mmRNA are injected intramuscularly and/or subcutaneously into animals. The expression of mmRNA-encoded proteins are assessed both within the muscle or subcutaneous tissue and systemically in blood and other organs such as the liver and spleen. Single dose studies allow an assessment of the magnitude, dose responsiveness, and longevity of expression of the desired product.

Animals are divided into groups to receive either a saline formulation or a formulation containing modified mRNA. Prior to injection mmRNA-containing lipidoid formulations are diluted in PBS. Animals are administered a single intramuscular dose of formulated mmRNA ranging from 50 mg/kg to doses as low as 1 ng/kg with a preferred range to be 10 mg/kg to 100 ng/kg. A maximum dose for intramuscular administration, for a mouse, is roughly 1 mg mmRNA or as low as 0.02 ng mmRNA for an intramuscular injection into the hind limb of the mouse. For subcutaneous administration, the animals are administered a single subcutaneous dose of formulated mmRNA ranging from 400 mg/kg to doses as low as 1 ng/kg with a preferred range to be 80 mg/kg to 100 ng/kg. A maximum dose for subcutaneous administration, for a mouse, is roughly 8 mg mmRNA or as low as 0.02 ng mmRNA.

For a 20 gram mouse the volume of a single intramuscular injection is maximally 0.025 ml and a single subcutaneous injection is maximally 0.2 ml. The optimal dose of mmRNA administered is calculated from the body weight of the animal. At various points in time points following the administration of the mmRNA-lipidoid, serum, tissues, and tissue lysates is obtained and the level of the mmRNA-encoded product is determined. The ability of lipidoid-formulated luciferase, green fluorescent protein (GFP), mCherry fluorescent protein, secreted alkaline phosphatase (sAP), human G-CSF, human factor IX, or human Erythropoietin (EPO) mmRNA to express the desired protein product is confirmed by luminescence for luciferase expression, flow cytometry for GFP and mCherry expression, by enzymatic activity for sAP, and by ELISA for G-CSF, Factor IX and Erythropoietin (EPO) secretion.

Additional studies for a multi-dose regimen are also performed to determine the maximal expression using mmRNA, to evaluate the saturability of the mmRNA-driven expression (achieved by giving a control and active mmRNA formulation in parallel or in sequence), and to determine the feasibility of repeat drug administration (by giving mmRNA in doses separated by weeks or months and then determining whether expression level is affected by factors such as immunogenicity). Studies utilizing multiple subcutaneous or intramuscular injection sites at one time point, are also utilized to further increase mmRNA drug exposure and improve protein production. An assessment of the physiological function of proteins, such as GFP, mCherry, sAP, human G-CSF, human factor IX, and human EPO, are determined through analyzing samples from the tested animals and detecting a change in granulocyte and/or red blood cell counts. Activity of an expressed protein product such as Factor IX, in animals can also be assessed through analysis of Factor IX enzymatic activity (such as an activated partial thromboplastin time assay) and effect of clotting times.

Example 32. In Vivo Delivery Using Lipoplexes

A. Human EPO Modified RNA Lipoplex

A formulation containing 100 µg of modified human erythropoietin (EPO) mRNA (mRNA sequence shown in SEQ ID NO: 7; polyA tail of approximately 160 nucleotides not shown in sequence; 5'cap, Cap1) (EPO; fully modified 5-methylcytosine; N1-methylpseudouridine) was lipoplexed with 30% by volume of RNAIMAX™ (Lipoplex-h-Epo-46; Generation 2 or Gen2) in 50-70 uL delivered intramuscularly to four C57/BL6 mice. Other groups consisted of mice receiving an injection of the lipoplexed modified luciferase mRNA (Lipoplex-luc) (IVT cDNA sequence shown in SEQ ID NO: 13; mRNA sequence shown in SEQ ID NO: 14, polyA tail of approximately 160 nucleotides not shown in sequence, 5'cap, Cap1, fully modified with 5-methylcytosine at each cytosine and pseudouridine replacement at each uridine site) which served as a control containing 100 µg of modified luciferase mRNA was lipoplexed with 30% by volume of RNAiMAX™ or mice receiving an injection of the formulation buffer as negative control at a dose volume of 65 ul. 13 hours after the intramuscular injection, serum was collected from each mouse to measure the amount of human EPO protein in the mouse serum by human EPO ELISA and the results are shown in Table 55.

TABLE 55

Human EPO Production (IM Injection Route)

| Formulation | Average |
| --- | --- |
| Lipoplex-h-Epo-46 | 251.95 |
| Lipoplex-Luc | 0 |
| Formulation Buffer | 0 |

B. Human G-CSF Modified RNA Lipoplex

A formulation containing 100 µg of one of two versions of modified human G-CSF mRNA (mRNA sequence shown in SEQ ID NO: 4; polyA tail of approximately 160 nucleotides not shown in sequence; 5'cap, Cap1) (G-CSF fully modified with 5-methylcytosine and pseudouridine (G-CSF) or G-CSF fully modified with 5-methylcytosine and N1-methyl-pseudouridine (G-CSF-N1) lipoplexed with 30% by volume of RNAIMAX™ and delivered in 150 uL intramuscularly (I.M), in 150 uL subcutaneously (S.C) and in 225 uL intravenously (I.V) to C57/BL6 mice.

Three control groups were administered either 100 µg of modified luciferase mRNA (IVT cDNA sequence shown in SEQ ID NO: 13; mRNA sequence shown in SEQ ID NO: 15, polyA tail of approximately 160 nucleotides not shown in sequence, 5'cap, Cap1, fully modified with 5-methylcytosine at each cytosine and pseudouridine replacement at each uridine site) intramuscularly (Luc-unsp I.M.) or 150 µg of modified luciferase mRNA intravenously (Luc-unsp I.V.) or 150 uL of the formulation buffer intramuscularly (Buffer I.M.). 6 hours after administration of a formulation, serum was collected from each mouse to measure the amount of human G-CSF protein in the mouse serum by human G-CSF ELISA and the results are shown in Table 56.

These results demonstrate that both 5-methylcytosine/pseudouridine and 5-methylcytosine/N1-methylpseudouridine modified human G-CSF mRNA can result in specific human G-CSF protein expression in serum when delivered via I.V. or I.M. route of administration in a lipoplex formulation.

TABLE 56

Human G-CSF in Serum (I.M., I.V., S.C. Injection Route)

| Formulation | Route | G-CSF (pg/ml) |
| --- | --- | --- |
| G-CSF | I.M. | 85.6 |
| G-CSF N1 | I.M. | 40.1 |
| G-CSF | S.C. | 3.9 |
| G-CSF N1 | S.C. | 0.0 |
| G-CSF | I.V. | 31.0 |
| G-CSF N1 | I.V. | 6.1 |
| Luc-unsp | I.M. | 0.0 |
| Luc-unsp | I.V. | 0.0 |
| Buffer | I.M. | 0.0 |

C. Human G-CSF Modified RNA Lipoplex Comparison

A formulation containing 100 pg of either modified human G-CSF mRNA lipoplexed with 30% by volume of RNAIMAX™ with a 5-methylcytosine (5mc) and a pseudouridine (ψ) modification (G-CSF-Gen1-Lipoplex), modified human G-CSF mRNA with a 5mc and ψ modification in saline (G-CSF-Gen1-Saline), modified human G-CSF mRNA with a N1-5-methylcytosine (N1-5mc) and a ψ modification lipoplexed with 30% by volume of RNAIMAX™ transfection reagent (G-CSF-Gen2-Lipoplex), modified human G-CSF mRNA with a N1-5mc and ψ modification in saline (G-CSF-Gen2-Saline), modified luciferase with a 5mc and ψ modification lipoplexed with 30% by volume of RNAIMAX™ transfection reagent (Luc-Lipoplex), or modified luciferase mRNA with a 5mc and ψ modification in saline (Luc-Saline) was delivered intramuscularly (I.M.) or subcutaneously (S.C.) and a control group for each method of administration was giving a dose of 80 uL of the formulation buffer (F. Buffer) to C57/BL6 mice. 13 hours post injection serum and tissue from the site of injection were collected from each mouse and analyzed by G-CSF ELISA to compare human G-CSF protein levels. The results of the human G-CSF protein in mouse serum from the intramuscular administration and the subcutaneous administration results are shown in Table 57.

These results demonstrate that 5-methylcytosine/pseudouridine and 5-methylcytosine/N1-methylpseudouridine modified human G-CSF mRNA can result in specific human G-CSF protein expression in serum when delivered via I.M. or S.C. route of administration whether in a saline formulation or in a lipoplex formulation. As shown in Table 57, 5-methylcytosine/N1-methylpseudouridine modified human G-CSF mRNA generally demonstrates increased human G-CSF protein production relative to 5-methylcytosine/pseudouridine modified human G-CSF mRNA.

TABLE 57

Human G-CSF Protein in Mouse Serum

| | G-CSF (pg/ml) | |
| --- | --- | --- |
| Formulation | I.M. Injection Route | S.C. Injection Route |
| G-CSF-Gen1-Lipoplex | 13.988 | 42.855 |
| GCSF-Gen1-saline | 9.375 | 4.614 |
| GCSF-Gen2-lipoplex | 75.572 | 32.107 |
| GCSF-Gen2-saline | 20.190 | 45.024 |
| Luc lipoplex | 0 | 3.754 |
| Luc saline | 0.0748 | 0 |
| F. Buffer | 4.977 | 2.156 |

D. mCherry Modified RNA Lipoplex Comparison

Intramuscular and Subcutaneous Administration

A formulation containing 100 µg of either modified mCherry mRNA (mRNA sequence shown in SEQ ID NO: 5; polyA tail of approximately 160 nucleotides not shown in sequence; 5'cap, Cap1) lipoplexed with 30% by volume of RNAIMAX™ or modified mCherry mRNA in saline is delivered intramuscularly and subcutaneously to mice. A formulation buffer is also administered to a control group of mice either intramuscularly or subcutaneously. The site of injection on the mice may be collected 17 hours post injection for sectioning to determine the cell type(s) responsible for producing protein.

Intravitreal Administration

A formulation containing 10 µg of either modified mCherry mRNA lipoplexed with RNAIMAX™, modified mCherry mRNA in a formulation buffer, modified luciferase mRNA lipoplexed with RNAMAX™, modified luciferase mRNA in a formulation buffer can be administered by intravitreal injection (IVT) in rats in a dose volume of 5 µl/eye. A formulation buffer is also administered by IVT to a control group of rats in a dose volume of 5 µl/eye. Eyes from treated rats can be collected after 18 hours post injection for sectioning and lysating to determine whether mmRNA can be effectively delivered in vivo to the eye and result in protein production, and to also determine the cell type(s) responsible for producing protein in vivo.

Intranasal Administration

A formulation containing 100 µg of either modified mCherry mRNA lipoplexed with 30% by volume of RNAIMAX™, modified mCherry mRNA in saline, modified luciferase mRNA lipoplexed with 30% by volume of RNAIMAX™ or modified luciferase mRNA in saline is delivered intranasally. A formulation buffer is also administered to a control group intranasally. Lungs may be collected about 13 hours post instillation for sectioning (for those receiving mCherry mRNA) or homogenization (for those receiving luciferase mRNA). These samples will be used to determine whether mmRNA can be effectively delivered in vivo to the lungs and result in protein production, and to also determine the cell type(s) responsible for producing protein in vivo.

Example 33. In Vivo Delivery Using Varying Lipid Ratios

Modified mRNA was delivered to C57/BL6 mice to evaluate varying lipid ratios and the resulting protein expression. Formulations of 100 µg modified human EPO mRNA (mRNA sequence shown in SEQ ID NO: 7; polyA tail of approximately 160 nucleotides not shown in sequence; 5'cap, Cap1; fully modified with 5-methylcytosine and pseudouridine) lipoplexed with 10%, 30% or 50% RNAIMAX™, 100 µg modified luciferase mRNA (IVT cDNA sequence shown in SEQ ID NO: 13; mRNA sequence shown in SEQ ID NO: 14, polyA tail of approximately 160 nucleotides not shown in sequence, 5'cap, Cap1, fully modified with 5-methylcytosine at each cytosine and pseudouridine replacement at each uridine site) lipoplexed with 10%, 30% or 50% RNAIMAX™ or a formulation buffer were administered intramuscularly to mice in a single 70 µl dose. Serum was collected 13 hours post injection to undergo a human EPO ELISA to determine the human EPO protein level in each mouse. The results of the human EPO ELISA, shown in Table 58, show that modified human EPO expressed in the muscle is secreted into the serum for each of the different percentage of RNAIMAX™.

TABLE 58

Human EPO Protein in Mouse Serum (IM Injection Route)

| Formulation | EPO (pg/ml) |
|---|---|
| Epo + 10% RNAiMAX | 11.4 |
| Luc + 10% RNAiMAX | 0 |
| Epo + 30% RNAiMAX | 27.1 |
| Luc + 30% RNAiMAX | 0 |
| Epo + 50% RNAiMAX | 19.7 |
| Luc + 50% RNAiMAX | 0 |
| F. Buffer | 0 |

Example 34. Intramuscular and Subcutaneous In Vivo Delivery in Mammals

Modified human EPO mRNA (mRNA sequence shown in SEQ ID NO: 7; polyA tail of approximately 160 nucleotides not shown in sequence; 5'cap, Cap1; fully modified with 5-methylcytosine and pseudouridine) formulated in formulation buffer was delivered to either C57/BL6 mice or Sprague-Dawley rats to evaluate the dose dependency on human EPO production. Rats were intramuscularly injected with 50 µl of the modified human EPO mRNA (h-EPO), modified luciferase mRNA (Luc) (IVT cDNA sequence shown in SEQ ID NO: 13; mRNA sequence shown in SEQ ID NO: 14, polyA tail of approximately 160 nucleotides not shown in sequence, 5'cap, Cap1, fully modified with 5-methylcytosine at each cytosine and pseudouridine replacement at each uridine site) or the formulation buffer (F.Buffer) as described in the dosing chart Table 59.

Mice were intramuscularly or subcutaneously injected with 50 µl of the modified human EPO mRNA (h-EPO), modified luciferase mRNA (Luc) or the formulation buffer (F.Buffer) as described in the dosing chart Table 60. 13 hours post injection blood was collected and serum was analyzed to determine the amount human EPO for each mouse or rat. The average and geometric mean in pg/ml for the rat study are also shown in Table 59.

TABLE 59

Rat Study

| Group | Dose | Avg. pg/ml | Geometric-mean pg/ml |
|---|---|---|---|
| h-EPO | G#1 | 150 µg | 67.7 | 67.1 |
| h-EPO | G#2 | 100 µg | 79.4 | 66.9 |
| h-EPO | G#3 | 50 µg | 101.5 | 85.4 |
| h-EPO | G#4 | 10 µg | 46.3 | 31.2 |
| h-EPO | G#5 | 1 µg | 28.7 | 25.4 |
| Luc | G#6 | 100 µg | 24.5 | 22.4 |
| F. Buffer | G#7 | — | 18.7 | 18.5 |

TABLE 60

Mouse Study

| Route | Treatment | Group | Dose | Average Level in serum pg/ml |
|---|---|---|---|---|
| IM | h-EPO | 1 | 100 µg | 96.2 |
| IM | h-EPO | 2 | 50 µg | 63.5 |
| IM | h-EPO | 3 | 25 µg | 18.7 |
| IM | h-EPO | 4 | 10 µg | 25.9 |
| IM | h-EPO | 5 | 1 µg | 2.6 |
| IM | Luc | 6 | 100 µg | 0 |
| IM | F. Buffer | 7 | — | 1.0 |
| SC | h-EPO | 1 | 100 µg | 72.0 |
| SC | Luc | 2 | 100 µg | 26.7 |
| SC | F. Buffer | 3 | — | 17.4 |

Example 35. Duration of Activity after Intramuscular In Vivo Delivery

Modified human EPO mRNA (mRNA sequence shown in SEQ ID NO: 7; polyA tail of approximately 160 nucleotides not shown in sequence; 5'cap, Cap1; fully modified with 5-methylcytosine and pseudouridine) formulated in formulation buffer was delivered to Sprague-Dawley rats to determine the duration of the dose response. Rats were intramuscularly injected with 50 µl of the modified human EPO mRNA (h-EPO), modified luciferase mRNA (IVT cDNA sequence shown in SEQ ID NO: 13; mRNA sequence shown in SEQ ID NO: 14, polyA tail of approximately 160 nucleotides not shown in sequence, 5'cap, Cap1, fully modified with 5-methylcytosine at each cytosine and pseudouridine replacement at each uridine site) (Luc) or the formulation buffer (F.Buffer) as described in the dosing chart Table 61. The rats were bled 2, 6, 12, 24, 48 and 72 hours after the intramuscular injection to determine the concentration of human EPO in serum at a given time. The average and geometric mean in pg/ml for this study are also shown in Table 61.

TABLE 61

Dosing Chart

| Group | Dose | | Avg. pg/ml | Geometric-mean pg/ml |
|---|---|---|---|---|
| h-EPO | 2 hour | 100 μg | 59.6 | 58.2 |
| h-EPO | 6 hour | 100 μg | 68.6 | 55.8 |
| h-EPO | 12 hour | 100 μg | 87.4 | 84.5 |
| h-EPO | 24 hour | 100 μg | 108.6 | 95.3 |
| h-EPO | 48 hour | 100 μg | 77.9 | 77.0 |
| h-EPO | 72 hour | 100 μg | 80.1 | 75.8 |
| Luc | 24, 48 and 72 hour | 100 μg | 37.2 | 29.2 |
| F. Buffer | 24, 48 and 72 hour | — | 48.9 | 10.4 |

Example 36. Routes of Administration

Studies were performed to investigate split dosing using different routes of administration. Studies utilizing multiple subcutaneous or intramuscular injection sites at one time point were designed and performed to investigate ways to increase mmRNA drug exposure and improve protein production. In addition to detection of the expressed protein product, an assessment of the physiological function of proteins was also determined through analyzing samples from the animal tested.

Surprisingly, it has been determined that split dosing of mmRNA produces greater protein production and phenotypic responses than those produced by single unit dosing or multi-dosing schemes.

The design of a split dose experiment involved using human erythropoietin (EPO) mmRNA (mRNA sequence shown in SEQ ID NO: 7; polyA tail of approximately 160 nucleotides not shown in sequence; 5'cap, Cap1) or luciferase mmRNA (mRNA sequence shown in SEQ ID NO: 14; polyA tail of approximately 160 nucleotides not shown in sequence; 5'cap, Cap1) administered in buffer alone or formulated with 30% lipoplex (RNAIMAX™). The dosing vehicle (formulation buffer) consisted of 150 mM NaCl, 2 mM CaCl$_2$, 2 mM Natphosphate (1.4 mM monobasic sodium phosphate; 0.6 mM dibasic sodium phosphate), and 0.5 mM EDTA, pH 6.5. The pH was adjusted using sodium hydroxide and the final solution was filter sterilized. The mmRNA was modified with 5meC at each cytosine and pseudouridine replacement at each uridine site.

4 mice per group were dosed intramuscularly (I.M.), intravenously (I.V.) or subcutaneously (S.C.) by the dosing chart outlined in Table 62. Serum was collected 13 hours post injection from all mice, tissue was collected from the site of injection from the intramuscular and subcutaneous group and the spleen, liver and kidneys were collected from the intravenous group. The results from the intramuscular group and the subcutaneous group results are shown in Table 63.

TABLE 62

Dosing Chart

| Group | Treatment | Route | Dose of mmRNA | Total Dose | Dosing Vehicle |
|---|---|---|---|---|---|
| 1 | Lipoplex-human EPO mmRNA | I.M. | 4 × 100 ug + 30% Lipoplex | 4 × 70 ul | Lipoplex |
| 2 | Lipoplex-human EPO mmRNA | I.M. | 4 × 100 ug | 4 × 70 ul | Buffer |
| 3 | Lipoplex-human EPO mmRNA | S.C. | 4 × 100 ug + 30% Lipoplex | 4 × 70 ul | Lipoplex |
| 4 | Lipoplex-human EPO mmRNA | S.C. | 4 × 100 ug | 4 × 70 ul | Buffer |
| 5 | Lipoplex-human EPO mmRNA | I.V. | 200 ug + 30% Lipoplex | 140 ul | Lipoplex |
| 6 | Lipoplexed-Luciferase mmRNA | I.M. | 100 ug + 30% Lipoplex | 4 × 70 ul | Lipoplex |
| 7 | Lipoplexed-Luciferase mmRNA | I.M. | 100 ug | 4 × 70 ul | Buffer |
| 8 | Lipoplexed-Luciferase mmRNA | S.C. | 100 ug + 30% Lipoplex | 4 × 70 ul | Lipoplex |
| 9 | Lipoplexed-Luciferase mmRNA | S.C. | 100 ug | 4 × 70 ul | Buffer |
| 10 | Lipoplexed-human EPO mmRNA | I.V. | 200 ug + 30% Lipoplex | 140 ul | Lipoplex |
| 11 | Formulation Buffer | I.M. | 4x multi dosing | 4 × 70 ul | Buffer |

TABLE 63

Human EPO Protein in Mouse Serum (I.M. Injection Route)

| Formulation | I.M. Injection Route | S.C. Injection Route |
|---|---|---|
| Epo-Lipoplex | 67.115 | 2.154 |
| Luc-Lipoplex | 0 | 0 |
| Epo-Saline | 100.891 | 11.37 |
| Luc-Saline | 0 | 0 |
| Formulation Buffer | 0 | 0 |

Example 37. Rapidly Eliminated Lipid Nanoparticle (reLNP) Studies

A. Formulation of Modified RNA reLNPs

Solutions of synthesized lipid, 1,2-distearoyl-3-phosphatidylcholine (DSPC) (Avanti Polar Lipids, Alabaster, Ala.), cholesterol (Sigma-Aldrich, Taufkirchen, Germany), and α-[3'-(1,2-dimyristoyl-3-propanoxy)-carboxamide-propyl]-w-methoxy-polyoxyethylene (PEG-c-DOMG) (NOF, Bouwelven, Belgium) are prepared and stored at −20° C. The synthesized lipid is selected from DLin-DMA with an internal ester, DLin-DMA with a terminal ester, DLin-MC3-DMA-internal ester, and DLin-MC3-DMA with a terminal ester. The reLNPs are combined to yield a molar ratio of 50:10:38.5:1.5 (reLNP: DSPC: Cholesterol: PEG-c-DOMG). Formulations of the reLNPs and modified mRNA are prepared by combining the lipid solution with the modified mRNA solution at total lipid to modified mRNA weight ratio of 10:1, 15:1, 20:1 and 30:1.

B. Characterization of Formulations

A Zetasizer Nano ZS (Malvern Instruments Ltd, Malvern, Worcestershire, UK) is used to determine the particle size, the polydispersity index (PDI) and the zeta potential of the modified mRNA nanoparticles in 1×PBS in determining particle size and 15 mM PBS in determining zeta potential.

Ultraviolet-visible spectroscopy is used to determine the concentration of modified mRNA nanoparticle formulation. After mixing, the absorbance spectrum of the solution is recorded between 230 nm and 330 nm on a DU 800 spectrophotometer (Beckman Coulter, Beckman Coulter, Inc., Brea, Calif.). The modified RNA concentration in the nanoparticle formulation is calculated based on the extinction coefficient of the modified RNA used in the formulation and on the difference between the absorbance at a wavelength of 260 nm and the baseline value at a wavelength of 330 nm.

QUANT-IT™ RIBOGREEN® RNA assay (Invitrogen Corporation Carlsbad, Calif.) is used to evaluate the encapsulation of modified RNA by the nanoparticle. The samples are diluted, transferred to a polystyrene 96 well plate, then either a TE buffer or a 2% Triton X-100 solution is added. The plate is incubated and the RIBOGREEN® reagent is diluted in TE buffer, and of this solution is added to each well. The fluorescence intensity is measured using a fluorescence plate reader (Wallac Victor 1420 Multilablel Counter; Perkin Elmer, Waltham, Mass.) The fluorescence values of the reagent blank are subtracted from each of the samples and the percentage of free modified RNA is determined by dividing the fluorescence intensity of the intact sample by the fluorescence value of the disrupted sample.

C. In Vitro Incubation

Human embryonic kidney epithelial (HEK293) and hepatocellular carcinoma epithelial (HepG2) cells (LGC standards GmbH, Wesel, Germany) are seeded on 96-well plates (Greiner Bio-one GmbH, Frickenhausen, Germany) and plates for HEK293 cells are precoated with collagen type1. HEK293 are seeded at a density of about 30,000 and HepG2 are seeded at a density of about 35,000 cells per well in 100 µl cell culture medium. Formulations containing mCherry mRNA (mRNA sequence shown in SEQ ID NO: 5; polyA tail of approximately 160 nucleotides not shown in sequence; 5'cap, Cap1) are added directly after seeding the cells and incubated. The mCherry cDNA with the T7 promoter, 5'untranslated region (UTR) and 3' UTR used in in vitro transcription (IVT) is given in SEQ ID NO: 6.

Cells are harvested by transferring the culture media supernatants to a 96-well Pro-Bind U-bottom plate (Beckton Dickinson GmbH, Heidelberg, Germany). Cells are trypsinized with ½ volume Trypsin/EDTA (Biochrom AG, Berlin, Germany), pooled with respective supernatants and fixed by adding one volume PBS/2% FCS (both Biochrom AG, Berlin, Germany)/0.5% formaldehyde (Merck, Darmstadt, Germany). Samples are then submitted to a flow cytometer measurement with an excitation laser and a filter for PE-Texas Red in a LSRII cytometer (Beckton Dickinson GmbH, Heidelberg, Germany). The mean fluorescence intensity (MFI) of all events and the standard deviation of four independent wells are presented in for samples analyzed.

D. In Vivo Formulation Studies

Mice are administered intravenously a single dose of a formulation containing a modified mRNA and a reLNP. The modified mRNA administered to the mice is selected from G-CSF (mRNA sequence shown in SEQ ID NO: 4; polyA tail of approximately 160 nucleotides not shown in sequence; 5'cap, Cap1), Factor IX (mRNA shown in SEQ ID NO: 8; polyA tail of approximately 160 nucleotides not shown in sequence; 5'cap, Cap1) or mCherry (mRNA sequence shown in SEQ ID NO: 5; polyA tail of approximately 160 nucleotides not shown in sequence; 5'cap, Cap1).

The mice are injected with 100 ug, 10 ug or 1 ug of the formulated modified mRNA and are sacrificed 8 hours after they are administered the formulation. Serum from the mice administered formulations containing human G-CSF modified mRNA are measured by specific G-CSF ELISA and serum from mice administered human Factor IX modified RNA is analyzed by specific factor IX ELISA or chromogenic assay. The liver and spleen from the mice administered with mCherry modified mRNA are analyzed by immunohistochemistry (IHC) or fluorescence-activated cell sorting (FACS). As a control, a group of mice are not injected with any formulation and their serum and tissue are collected analyzed by ELISA, FACS and/or IHC.

Example 38. In Vitro Transfection of VEGF-A

Human vascular endothelial growth factor-isoform A (VEGF-A) modified mRNA (mRNA sequence shown in SEQ ID NO: 17; polyA tail of approximately 160 nucleotides not shown in sequence; 5'cap, Cap1) was transfected via reverse transfection in Human Keratinocyte cells in 24 multi-well plates. The VEGF-A cDNA with the T7 promoter, 5' untranslated region (UTR) and 3' UTR used in in vitro transcription (IVT) is given in SEQ ID NO: 18. Human Keratinocytes cells were grown in EPILIFE® medium with Supplement S7 from Invitrogen (Carlsbad, Calif.) until they reached a confluence of 50-70%. The cells were transfected with 0, 46.875, 93.75, 187.5, 375, 750, and 1500 ng of modified mRNA (mmRNA) encoding VEGF-A which had been complexed with RNAIMAX™ transfection reagent from Invitrogen (Carlsbad, Calif.). The RNA:RNAIMAX™ complex was formed by first incubating the RNA with Supplement-free EPILIFE® media in a 5× volumetric dilution for 10 minutes at room temperature. In a second vial, RNAIMAX™ transfection reagent was incubated with Supplement-free EPILIFE® Media in a 10× volumetric dilution for 10 minutes at room temperature. The RNA vial was then mixed with the RNAIMAX™ transfection reagent vial and incubated for 20-30 minutes at room temperature before being added to the cells in a drop-wise fashion.

The fully optimized mRNA encoding VEGF-A (mRNA sequence shown in SEQ ID NO: 17; polyA tail of approximately 160 nucleotides not shown in sequence; 5'cap, Cap1) transfected with the Human Keratinocyte cells included modifications during translation such as natural nucleoside triphosphates (NTP), pseudouridine at each uridine site and 5-methylcytosine at each cytosine site (pseudo-U/5mC), and N1-methyl-pseudouridine at each uridine site and 5-methylcytosine at each cytosine site (N1-methyl-Pseudo-U/5mC). Cells were transfected with the mmRNA encoding VEGF-A and secreted VEGF-A concentration (pg/ml) in the culture medium was measured at 6, 12, 24, and 48 hours post-transfection for each of the concentrations using an ELISA kit from Invitrogen (Carlsbad, Calif.) following the manufacturers recommended instructions. These data, shown in Table 64, show that modified mRNA encoding VEGF-A is capable of being translated in Human Keratinocyte cells and that VEGF-A is transported out of the cells and released into the extracellular environment.

TABLE 64

VEGF-A Dosing and Protein Secretion

| Dose (ng) | 6 hours (pg/ml) | 12 hours (pg/ml) | 24 hours (pg/ml) | 48 hours (pg/ml) |
|---|---|---|---|---|
| VEGF-A Dose Containing Natural NTPs | | | | |
| 46.875 | 10.37 | 18.07 | 33.90 | 67.02 |
| 93.75 | 9.79 | 20.54 | 41.95 | 65.75 |
| 187.5 | 14.07 | 24.56 | 45.25 | 64.39 |
| 375 | 19.16 | 37.53 | 53.61 | 88.28 |
| 750 | 21.51 | 38.90 | 51.44 | 61.79 |
| 1500 | 36.11 | 61.90 | 76.70 | 86.54 |
| VEGF-A Dose Containing Pseudo-U/5mC | | | | |
| 46.875 | 10.13 | 16.67 | 33.99 | 72.88 |
| 93.75 | 11.00 | 20.00 | 46.47 | 145.61 |
| 187.5 | 16.04 | 34.07 | 83.00 | 120.77 |
| 375 | 69.15 | 188.10 | 448.50 | 392.44 |
| 750 | 133.95 | 304.30 | 524.02 | 526.58 |
| 1500 | 198.96 | 345.65 | 426.97 | 505.41 |
| VEGF-A Dose Containing N1-methyl-Pseudo-U/5mC | | | | |
| 46.875 | 0.03 | 6.02 | 27.65 | 100.42 |
| 93.75 | 12.37 | 46.38 | 121.23 | 167.56 |
| 187.5 | 104.55 | 365.71 | 1025.41 | 1056.91 |
| 375 | 605.89 | 1201.23 | 1653.63 | 1889.23 |
| 750 | 445.41 | 1036.45 | 1522.86 | 1954.81 |
| 1500 | 261.61 | 714.68 | 1053.12 | 1513.39 |

Example 39. In Vivo Studies of Factor IX

Human Factor IX mmRNA (Gen1; fully modified 5-methycytosine and pseudouridine) formulated in formulation buffer was delivered to mice via intramuscular injection. The results demonstrate that Factor IX protein was elevated in serum as measured 13 hours after administration.

In this study, mice (N=5 for Factor IX, N=3 for Luciferase or Buffer controls) were intramuscularly injected with 50 µl of the Factor IX mmRNA (mRNA sequence shown in SEQ ID NO: 8; polyA tail of approximately 160 nucleotides not shown in sequence; 5'cap, Cap1), Luciferase (cDNA sequence for IVT shown in SEQ ID NO: 13; mRNA sequence shown in SEQ ID NO: 14, polyA tail of approximately 160 nucleotides not shown in sequence, 5'cap, Cap1, fully modified with 5-methylcytosine at each cytosine and pseudouridine replacement at each uridine site) or the formulation buffer (F.Buffer) at 2×100 ug/mouse. The mice were bled at 13 hours after the intramuscular injection to determine the concentration of human the polypeptide in serum in pg/mL. The results revealed that administration of Factor IX mmRNA resulted in levels of 1600 pg/mL at 13 hours as compared to less than 100 pg/mL of Factor IX for either Luciferase or buffer control administration.

Example 40. Multi-Site Administration: Intramuscular and Subcutaneous

Human G-CSF modified mRNA (mRNA sequence shown in SEQ ID NO: 4; polyA tail of approximately 160 nucleotides not shown in sequence; 5'cap, Cap1) modified as either Gen1 or Gen2 (5-methylcytosine (5 mc) and a pseudouridine (ψ) modification, G-CSF-Gen1; or N1-5-methylcytosine (N1-5 mc) and a ψ modification, G-CSF-Gen2) and formulated in formulation buffer were delivered to mice via intramuscular (IM) or subcutaneous (SC) injection. Injection of four doses or 2×50 ug (two sites) daily for three days (24 hrs interval) was performed. The fourth dose was administered 6 hrs before blood collection and CBC analysis. Controls included Luciferase (cDNA sequence for IVT shown in SEQ ID NO: 13; mRNA sequence shown in SEQ ID NO: 14, polyA tail of approximately 160 nucleotides not shown in sequence, 5'cap, Cap1, fully modified with 5-methylcytosine at each cytosine and pseudouridine replacement at each uridine site) or the formulation buffer (F.Buffer). The mice were bled at 72 hours after the first mRNA injection (6 hours after the last mRNA dose) to determine the effect of mRNA-encoded human G-CSF on the neutrophil count. The dosing regimen is shown in Table 65 as are the resulting neutrophil counts (thousands/uL). In Table 65, an asterisks (*) indicate statistical significance at $p<0.05$.

For intramuscular administration, the data reveal a four fold increase in neutrophil count above control at day 3 for the Gen1 G-CSF mRNA and a two fold increase for the Gen2 G-CSF mmRNA. For subcutaneous administration, the data reveal a two fold increase in neutrophil count above control at day 3 for the Gen2 G-CSF mRNA.

These data demonstrate that both 5-methylcytidine/pseudouridine and 5-methylcytidine/N1-methylpseudouridine-modified mRNA can be biologically active, as evidenced by specific increases in blood neutrophil counts.

TABLE 65

Dosing Regimen

| Gr. | Treatment | Route | N = | Dose (µg/mouse) | Dose Vol. (µl/mouse) | Dosing Vehicle | Neutrophil Thous/uL |
|---|---|---|---|---|---|---|---|
| 1 | G-CSF (Gen1) | I.M | 5 | 2 × 50 ug (four doses) | 50 | F. buffer | 840* |
| 2 | G-CSF (Gen1) | S.C | 5 | 2 × 50 ug (four doses) | 50 | F. buffer | 430 |
| 3 | G-CSF (Gen2) | I.M | 5 | 2 × 50 ug (four doses) | 50 | F. buffer | 746* |
| 4 | G-CSF (Gen2) | S.C | 5 | 2 × 50 ug (four doses) | 50 | F. buffer | 683 |
| 5 | Luc (Gen1) | I.M. | 5 | 2 × 50 ug (four doses) | 50 | F. buffer | 201 |
| 6 | Luc (Gen1) | S.C. | 5 | 2 × 50 ug (four doses) | 50 | F. buffer | 307 |
| 7 | Luc (Gen2) | I.M | 5 | 2 × 50 ug (four doses) | 50 | F. buffer | 336 |
| 8 | Luc (Gen2) | S.C | 5 | 2 × 50 ug (four doses) | 50 | F. buffer | 357 |
| 9 | F. Buffer | I.M | 4 | 0 (four doses) | 50 | F. buffer | 245 |
| 10 | F. Buffer | S.C. | 4 | 0 (four doses) | 50 | F. buffer | 509 |
| 11 | Untreated | — | 4 | | | — | 312 |

Example 41. Intravenous Administration

Human G-CSF modified mRNA (mRNA sequence shown in SEQ ID NO: 4; polyA tail of approximately 160 nucleotides not shown in sequence; 5'cap, Cap1) modified with 5-methylcytosine (5 mc) and a pseudouridine (ψ) modification (Gen1); or having no modifications and formulated in 10% lipoplex (RNAiMax) were delivered to mice at a dose of 50 ug RNA and in a volume of 100 ul via intravenous (IV) injection at days 0, 2 and 4. Neutrophils were measured at days 1, 5 and 8. Controls included non-specific mammalian RNA or the formulation buffer alone (F.Buffer). The mice were bled at days 1, 5 and 8 to determine the effect of mRNA-encoded human G-CSF to increase neutrophil count. The dosing regimen is shown in Table 66 as are the resulting neutrophil counts (thousands/uL; K/uL).

For intravenous administration, the data reveal a four to five fold increase in neutrophil count above control at day 5 with G-CSF modified mRNA but not with unmodified G-CSF mRNA or non-specific controls. Blood count returned to baseline four days after the final injection. No other changes in leukocyte populations were observed.

In Table 66, an asterisk (*) indicates statistical significance at $p<0.001$ compared to buffer.

These data demonstrate that lipoplex-formulated 5-methylcytidine/pseudouridine-modified mRNA can be biologically active, when delivered through an I.V. route of administration as evidenced by specific increases in blood neutrophil counts. No other cell subsets were significantly altered. Unmodified G-CSF mRNA similarly administered showed no pharmacologic effect on neutrophil counts.

TABLE 66

Dosing Regimen

| Gr. | Treatment | N= | Dose Vol. (μl/mouse) | Dosing Vehicle | Neutrophil K/uL |
|---|---|---|---|---|---|
| 1 | G-CSF (Gen1) Day 1 | 5 | 100 | 10% lipoplex | 2.91 |
| 2 | G-CSF (Gen1) Day 5 | 5 | 100 | 10% lipoplex | 5.32* |
| 3 | G-CSF (Gen1) Day 8 | 5 | 100 | 10% lipoplex | 2.06 |
| 4 | G-CSF (no modification) Day 1 | 5 | 100 | 10% lipoplex | 1.88 |
| 5 | G-CSF (no modification) Day 5 | 5 | 100 | 10% lipoplex | 1.95 |
| 6 | G-CSF (no modification) Day 8 | 5 | 100 | 10% lipoplex | 2.09 |
| 7 | RNA control Day 1 | 5 | 100 | 10% lipoplex | 2.90 |
| 8 | RNA control Day 5 | 5 | 100 | 10% lipoplex | 1.68 |
| 9 | RNA control Day 8 | 4 | 100 | 10% lipoplex | 1.72 |
| 10 | F. Buffer Day 1 | 4 | 100 | 10% lipoplex | 2.51 |
| 11 | F. Buffer Day 5 | 4 | 100 | 10% lipoplex | 1.31 |
| 12 | F. Buffer Day 8 | 4 | 100 | 10% lipoplex | 1.92 |

Example 42. Saline Formulation: Intramuscular Administration

A. Protein Expression

Human G-CSF modified mRNA (mRNA sequence shown in SEQ ID NO: 4; polyA tail of approximately 160 nucleotides not shown in sequence; 5'cap, Cap1) and human EPO mmRNA (mRNA sequence shown in SEQ ID NO: 7; polyA tail of approximately 160 nucleotides not shown in sequence; 5'cap, Cap1); G-CSF modified mRNA (modified with 5-methylcytosine (5 mc) and pseudouridine (ψ)) and EPO modified mRNA (modified with N1-5-methylcytosine (N1-5 mc) and ψ modification), were formulated in formulation buffer (150 mM sodium chloride, 2 mM calcium chloride, 2 mM phosphate, 0.5 mM EDTA at a pH of 6.5) and delivered to mice via intramuscular (IM) injection at a dose of 100 ug.

Controls included Luciferase (cDNA sequence for IVT, SEQ ID NO: 13; mRNA sequence shown in SEQ ID NO: 14; polyA tail of approximately 160 nucleotides not shown in sequence, 5'cap, Cap1, fully modified with 5-methylcytosine at each cytosine and pseudouridine replacement at each uridine site) or the formulation buffer (F.Buffer). The mice were bled at 13 hours after the injection to determine the concentration of the human polypeptide in serum in pg/mL (G-CSF groups measured human G-CSF in mouse serum and EPO groups measured human EPO in mouse serum). The data are shown in Table 67.

TABLE 67

Dosing Regimen

| Group | Treatment | N= | Dose Vol. (μl/mouse) | Dosing Vehicle | Average Protein Product Pg/mL, serum |
|---|---|---|---|---|---|
| G-CSF | G-CSF | 5 | 50 | Saline | 19.8 |
| G-CSF | Luciferase | 5 | 50 | Saline | 0.5 |
| G-CSF | F. buffer | 5 | 50 | F. buffer | 0.5 |
| EPO | EPO | 5 | 50 | Saline | 191.5 |
| EPO | Luciferase | 5 | 50 | Saline | 15.0 |
| EPO | F. buffer | | | F. buffer | 4.8 |

B. Dose Response

Human EPO modified mRNA (mRNA sequence shown in SEQ ID NO: 7; polyA tail of approximately 160 nucleotides not shown in sequence; 5'cap, Cap1; fully modified with 5-methylcytosine and pseudouridine) were formulated in formulation buffer and delivered to mice via intramuscular (IM) injection.

Controls included Luciferase (mRNA sequence shown in SEQ ID NO: 14, polyA tail of approximately 160 nucleotides not shown in sequence, 5'cap, Cap1, fully modified with 5-methylcytosine and pseudouridine) or the formulation buffer (F.Buffer). The mice were bled at 13 hours after the injection to determine the concentration of the human polypeptide in serum in pg/mL.

The dose and expression are shown in Table 68.

TABLE 68

Dosing Regimen and Expression

| Treatment | Dose Vol. (μl/mouse) | Average Protein Product pg/mL, serum |
|---|---|---|
| EPO | 100 | 96.2 |
| EPO | 50 | 63.5 |
| EPO | 25 | 18.7 |
| EPO | 10 | 25.9 |
| EPO | 1 | 2.6 |
| Luciferase | 100 | 0.0 |
| F. buffer | 100 | 1.0 |

Example 43. Multi-Dose/Multi-Administration

Studies utilizing multiple intramuscular injection sites at one time point were designed and performed.

The design of a single multi-dose experiment involved using human erythropoietin (EPO) mmRNA (mRNA sequence shown in SEQ ID NO: 7; polyA tail of approximately 160 nucleotides not shown in sequence; 5'cap, Cap1) or G-CSF (mRNA sequence shown in SEQ ID NO: 4; polyA tail of approximately 160 nucleotides not shown in sequence; 5'cap, Cap1) administered in formulation buffer. The dosing vehicle (F. buffer) was used as a control. The EPO and G-CSF mmRNA were modified with 5-methylcytosine at each cytosine and pseudouridine replacement at each uridine site.

Animals (n=5), Sprague-Dawley rats, were injected IM (intramuscular) for the single unit dose of 100 ug (delivered to one thigh). For multi-dosing 6 doses of 100 ug (delivered to two thighs) were used for both EPO and G-CSF mmRNA. Control dosing involved use of buffer at a single dose. Human EPO blood levels were evaluated 13 hrs post injection.

Human EPO protein was measured in rat serum 13h post I.M. Five groups of rats were treated and evaluated. The results are shown in Table 69.

TABLE 69

Multi-dose study

| Group | Treatment | Dose of mmRNA | Total Dose | Avg. pg/mL human EPO |
|---|---|---|---|---|
| 1 | Human EPO mmRNA | 1 x 100 ug | 100 ug | 143 |
| 2 | Human EPO mmRNA | 6 x 100 ug | 600 ug | 256 |
| 3 | G-CSF mmRNA | 1 x 100 ug | 100 ug | 43 |
| 4 | G-CSF mmRNA | 6 x 100 ug | 600 ug | 58 |
| 5 | Buffer Alone | — | — | 20 |

Example 44. Signal Sequence Exchange Study

Several variants of mmRNAs encoding human Granulocyte colony stimulating factor (G-CSF) (mRNA sequence shown in SEQ ID NO: 4; polyA tail of approximately 160 nucleotides not shown in sequence; 5'cap, Cap1) were synthesized using modified nucleotides pseudouridine and 5-methylcytosine (pseudo-U/5mC). These variants included the G-CSF constructs encoding either the wild-type N terminal secretory signal peptide sequence (MAGPATQSP-MKLMALQLLLWHSALWTVQEA; SEQ ID NO: 19), no secretory signal peptide sequence, or secretory signal peptide sequences taken from other mRNAs. These included sequences where the wild type GCSF signal peptide sequence was replaced with the signal peptide sequence of either: human α-1-anti trypsin (AAT) (MMPSSVSWGILL-LAGLCCLVPVSLA; SEQ ID NO: 20), human Factor IX (FIX) (MQRVNMIMAESPSLITICLLGYLLSAECTV-FLDHENANKILNRPKR; SEQ ID NO: 21), human Prolactin (Prolac) (MKGSLLLLLVSNLLLCQSVAP; SEQ ID NO: 22), or human Albumin (Alb) (MKWVTFISLLFLF-SSAYSRGVFRR; SEQ ID NO: 23).

250 ng of modified mRNA encoding each G-CSF variant was transfected into HEK293A (293A in the table), mouse myoblast (MM in the table) (C2C12, CRL-1772, ATCC) and rat myoblast (RM in the table) (L6 line, CRL-1458, ATCC) cell lines in a 24 well plate using 1 ul of Lipofectamine 2000 (Life Technologies), each well containing 300,000 cells. The supernatants were harvested after 24 hrs and the secreted G-CSF protein was analyzed by ELISA using the Human G-CSF ELISA kit (Life Technologies). The data shown in Table 70 reveal that cells transfected with G-CSF mmRNA encoding the Albumin signal peptide secrete at least 12 fold more G-CSF protein than its wild type counterpart.

TABLE 70

Signal Peptide Exchange

| Signal peptides | 293A (pg/ml) | MM (pg/ml) | RM (pg/ml) |
|---|---|---|---|
| G-CSF Natural | 9650 | 3450 | 6050 |
| α-1-anti trypsin | 9950 | 5000 | 8475 |
| Factor IX | 11675 | 6175 | 11675 |
| Prolactin | 7875 | 1525 | 9800 |

TABLE 70-continued

Signal Peptide Exchange

| Signal peptides | 293A (pg/ml) | MM (pg/ml) | RM (pg/ml) |
|---|---|---|---|
| Albumin | 122050 | 81050 | 173300 |
| No Signal peptide | 0 | 0 | 0 |

Example 45. Cytokine Study: PBMC

PBMC isolation and Culture: 50 mL of human blood from two donors was received from Research Blood Components (lots KP30928 and KP30931) in sodium heparin tubes. For each donor, the blood was pooled and diluted to 70 mL with DPBS (SAFC Bioscience 59331C, lot 071M8408) and split evenly between two 50 mL conical tubes. 10 mL of Ficoll Paque (GE Healthcare 17-5442-03, lot 10074400) was gently dispensed below the blood layer. The tubes were centrifuged at 2000 rpm for 30 minutes with low acceleration and braking. The tubes were removed and the buffy coat PBMC layers were gently transferred to a fresh 50 mL conical and washed with DPBS. The tubes were centrifuged at 1450 rpm for 10 minutes.

The supernatant was aspirated and the PBMC pellets were resuspended and washed in 50 mL of DPBS. The tubes were centrifuged at 1250 rpm for 10 minutes. This wash step was repeated, and the PBMC pellets were resuspended in 19 mL of Optimem I (Gibco 11058, lot 1072088) and counted. The cell suspensions were adjusted to a concentration of 3.0× $10^{\wedge}6$ cells/mL live cells.

These cells were then plated on five 96 well tissue culture treated round bottom plates (Costar 3799) per donor at 50 uL per well. Within 30 minutes, transfection mixtures were added to each well at a volume of 50 uL per well. After 4 hours post transfection, the media was supplemented with 10 uL of Fetal Bovine Serum (Gibco 10082, lot 1012368)

Transfection Preparation: mmRNA encoding human G-CSF (mRNA sequence shown in SEQ ID NO: 4; polyA tail of approximately 160 nucleotides not shown in sequence; 5'cap, Cap1) (containing either (1) natural NTPs, (2) 100% substitution with 5-methyl cytidine and pseudouridine, or (3) 100% substitution with 5-methyl cytidine and N1-methyl pseudouridine; mmRNA encoding luciferase (IVT cDNA sequence shown in SEQ ID NO: 13; mRNA sequence shown in SEQ ID NO: 14, polyA tail of approximately 160 nucleotides not shown in sequence, 5'cap, Cap1, fully modified with 5-methylcytosine at each cytosine and pseudouridine replacement at each uridine site) (containing either (1) natural NTPs or (2) 100% substitution with 5-methyl cytidine and pseudouridine) and TLR agonist R848 (Invivogen tlrl-r848) were diluted to 38.4 ng/uL in a final volume of 2500 uL Optimem I.

Separately, 432 uL of Lipofectamine 2000 (Invitrogen 11668-027, lot 1070962) was diluted with 13.1 mL Optimem I. In a 96 well plate nine aliquots of 135 uL of each mmRNA, positive control (R-848) or negative control (Optimem I) was added to 135 uL of the diluted Lipofectamine 2000. The plate containing the material to be transfected was incubated for 20 minutes. The transfection mixtures were then transferred to each of the human PBMC plates at 50 uL per well. The plates were then incubated at 37 C. At 2, 4, 8, 20, and 44 hours each plate was removed from the incubator, and the supernatants were frozen.

After the last plate was removed, the supernatants were assayed using a human G-CSF ELISA kit (Invitrogen KHC2032) and human IFN-alpha ELISA kit (Thermo Scientific 41105-2). Each condition was done in duplicate.

Results: The ability of unmodified and modified mRNA (mmRNAs) to produce the encoded protein was assessed (G-CSF production) over time as was the ability of the mRNA to trigger innate immune recognition as measured by interferon-alpha production. Use of in vitro PBMC cultures is an accepted way to measure the immunostimulatory potential of oligonucleotides (Robbins et al., Oligonucleotides 2009 19:89-102).

Results were interpolated against the standard curve of each ELISA plate using a four parameter logistic curve fit. Shown in Tables 71 and 72 are the average from 2 separate PBMC donors of the G-CSF and IFN-alpha production over time as measured by specific ELISA.

In the G-CSF ELISA, background signal from the Lipofectamine 2000 untreated condition was subtracted at each timepoint. The data demonstrated specific production of human G-CSF protein by human peripheral blood mononuclear is seen with G-CSF mRNA containing natural NTPs, 100% substitution with 5-methyl cytidine and pseudouridine, or 100% substitution with 5-methyl cytidine and N1-methyl pseudouridine. Production of G-CSF was significantly increased through the use of modified mRNA relative to unmodified mRNA, with the 5-methyl cytidine and N1-methyl pseudouridine containing G-CSF mmRNA showing the highest level of G-CSF production. With regards to innate immune recognition, unmodified mRNA resulted in substantial IFN-alpha production, while the modified mRNA largely prevented interferon-alpha production. G-CSF mRNA fully modified with 5-methyl cytidine and N1-methylpseudouridine did not significantly increase cytokines whereas G-CSF mRNA fully modified with 5-methyl cytidine and pseudouridine induced IFN-alpha, TNF-alpha and IP10. Many other cytokines were not affected by either modification.

TABLE 71

G-CSF Signal
G-CSF signal - 2 Donor Average

| pg/mL | 2 Hr | 4 Hr | 8 Hr | 20 Hr | 44 Hr |
|---|---|---|---|---|---|
| G-CSF (5mC/pseudouridine) | 120.3 | 136.8 | 421.0 | 346.1 | 431.8 |
| G-CSF (5mC/N1-methyl pseudouridine) | 256.3 | 273.7 | 919.3 | 1603.3 | 1843.3 |
| GCSF(Natural-no modification) | 63.5 | 92.6 | 129.6 | 258.3 | 242.4 |
| Luciferase (5mC/pseudouridine) | 4.5 | 153.7 | 33.0 | 186.5 | 58.0 |

TABLE 72

IFN-alpha signal
IFN-alpha signal - 2 donor average

| pg/mL | 2 Hr | 4 Hr | 8 Hr | 20 Hr | 44 Hr |
|---|---|---|---|---|---|
| G-CSF (5mC/pseudouridine) | 21.1 | 2.9 | 3.7 | 22.7 | 4.3 |
| G-CSF (5mC/N1-methyl pseudouridine) | 0.5 | 0.4 | 3.0 | 2.3 | 2.1 |
| G-CSF(Natural) | 0.0 | 2.1 | 23.3 | 74.9 | 119.7 |
| Luciferase (5mC/pseudouridine) | 0.4 | 0.4 | 4.7 | 1.0 | 2.4 |
| R-848 | 39.1 | 151.3 | 278.4 | 362.2 | 208.1 |
| Lpf. 2000 control | 0.8 | 17.2 | 16.5 | 0.7 | 3.1 |

Example 46. Chemical Modification Ranges of Modified mRNA

Modified nucleotides such as, but not limited to, the chemical modifications 5-methylcytosine and pseudouridine have been shown to lower the innate immune response and increase expression of RNA in mammalian cells. Surprisingly, and not previously known, the effects manifested by the chemical modifications can be titrated when the amount of chemical modification is less than 100%. Previously, it was believed that full modification was necessary and sufficient to elicit the beneficial effects of the chemical modifications and that less than 100% modification of an mRNA had little effect. However, it has now been shown that the benefits of chemical modification can be derived using less than complete modification and that the effects are target, concentration and modification dependent.

A. Modified RNA Transfected in PBMC 960 ng of G-CSF mRNA modified with 5-methylcytosine (5mC) and pseudouridine (pseudoU) or unmodified G-CSF mRNA was transfected with 0.8 uL of Lipofectamine 2000 into peripheral blood mononuclear cells (PBMC) from three normal blood donors (D1, D2, D3). The G-CSF mRNA (SEQ ID NO: 4; polyA tail of approximately 160 nucleotides not shown in sequence; 5'cap, Cap1) was completely modified with 5mC and pseudoU (100% modification), not modified with 5mC and pseudoU (0% modification) or was partially modified with 5mC and pseudoU so the mRNA would contain 50% modification, 25% modification, 10% modification, %5 modification, 1% modification or 0.1% modification. A control sample of Luciferase (mRNA sequence shown in SEQ ID NO: 14; polyA tail of approximately 160 nucleotides not shown in sequence; 5'cap, Cap1; fully modified 5 meC and pseudoU) was also analyzed for G-CSF expression. For TNF-alpha and IFN-alpha control samples of Lipofectamine2000, LPS, R-848, Luciferase (mRNA sequence shown in SEQ ID NO: 14; polyA tail of approximately 160 nucleotides not shown in sequence; 5'cap, Cap1; fully modified 5 mC and pseudo), and P(I)P(C) were also analyzed. The supernatant was harvested and run by ELISA 22 hours after transfection to determine the protein expression. The expression of G-CSF is shown in Table 73 and the expression of IFN-alpha and TNF-alpha is shown in Table 74. The expression of IFN-alpha and TNF-alpha may be a secondary effect from the transfection of the G-CSF mRNA. Tables and shows that the amount of chemical modification of G-CSF, IFN-alpha and TNF-alpha is titratable when the mRNA is not fully modified and the titratable trend is not the same for each target.

TABLE 73

G-CSF Expression

| | G-CSF Expression (pg/ml) | | |
|---|---|---|---|
| | D1 | D2 | D3 |
| 100% modification | 270.3 | 151.6 | 162.2 |
| 50% modification | 45.6 | 19.8 | 26.3 |
| 25% modification | 23.6 | 10.8 | 8.9 |
| 10% modification | 39.4 | 12.9 | 12.9 |
| 5% modification | 70.9 | 26.8 | 26.3 |
| 1% modification | 70.3 | 26.9 | 66.9 |
| 0.1% modification | 67.5 | 25.2 | 28.7 |
| Luciferase | 14.5 | 3.1 | 10.0 |

TABLE 74

IFN-alpha and TNF-alpha Expression

| | IFN-alpha Expression (pg/ml) | | | TNF-alpha Expression (pg/ml) | | |
|---|---|---|---|---|---|---|
| | D1 | D2 | D3 | D1 | D2 | D3 |
| 100% modification | 76.8 | 6.8 | 15.1 | 5.6 | 1.4 | 21.4 |
| 50% modification | 22.0 | 5.5 | 257.3 | 4.7 | 1.7 | 12.1 |
| 25% modification | 64.1 | 14.9 | 549.7 | 3.9 | 0.7 | 10.1 |
| 10% modification | 150.2 | 18.8 | 787.8 | 6.6 | 0.9 | 13.4 |
| 5% modification | 143.9 | 41.3 | 1009.6 | 2.5 | 1.8 | 12.0 |
| 1% modification | 189.1 | 40.5 | 375.2 | 9.1 | 1.2 | 25.7 |
| 0.1% modification | 261.2 | 37.8 | 392.8 | 9.0 | 2. | 13.7 |
| 0% modification | 230.3 | 45.1 | 558.3 | 10.9 | 1.4 | 10.9 |
| LF 200 | 0 | 0 | 1.5 | 45.8 | 2.8 | 53.6 |
| LPS | 0 | 0 | 1.0 | 114.5 | 70.0 | 227.0 |
| R-848 | 39.5 | 11.9 | 183.5 | 389.3 | 256.6 | 410.6 |
| Luciferase | 9.1 | 0 | 3.9 | 4.5 | 2.7 | 13.6 |
| P(I)P(C) | 1498.1 | 216.8 | 238.8 | 61.2 | 4.4 | 69.1 |

B. Modified RNA Transfected in HEK293

Human embryonic kidney epithelial (HEK293) cells were seeded on 96-well plates at a density of 30,000 cells per well in 100 ul cell culture medium. 250 ng of modified G-CSF mRNA (SEQ ID NO: 4; polyA tail of approximately 160 nucleotides not shown in sequence; 5'cap, Cap1) formulated with RNAiMAX™ (Invitrogen, Carlsbad, Calif.) was added to a well. The G-CSF was completely modified with 5mC and pseudoU (100% modification), not modified with 5mC and pseudoU (0% modification) or was partially modified with 5mC and pseudoU so the mRNA would contain 75% modification, 50% modification or 25% modification. Control samples (AK 5/2, mCherry (SEQ ID NO: 5; polyA tail of approximately 160 nucleotides not shown in sequence; 5'cap, Cap1; fully modified 5 mC and pseudoU) and untreated) were also analyzed. The half-life of G-CSF mRNA fully modified with 5-methylcytosine and pseudouridine is approximately 8-10 hours. The supernatants were harvested after 16 hours and the secreted G-CSF protein was analyzed by ELISA. Table 75 shows that the amount of chemical modification of G-CSF is titratable when the mRNA is not fully modified.

TABLE 75

G-CSF Expression

| | G-CSF Expression (ng/ml) |
|---|---|
| 100% modification | 118.4 |
| 75% modification | 101.9 |
| 50% modification | 105.7 |
| 25% modification | 231.1 |
| 0% modification | 270.9 |
| AK 5/2 | 166.8 |
| mCherry | 0 |
| Untreated | 0 |

Example 47. In Vivo Delivery of Modified mRNA (mmRNA)

Modified RNA was delivered to C57/BL6 mice intramuscularly, subcutaneously, or intravenously to evaluate the bio-distribution of modified RNA using luciferase. A formulation buffer used with all delivery methods contained 150 mM sodium chloride, 2 mM calcium chloride, 2 mM Na+-phosphate which included 1.4 mM monobasic sodium phosphate and 0.6 mM of dibasic sodium phosphate, and 0.5 mM ethylenediaminetetraacetic acid (EDTA) was adjusted using sodium hydroxide to reach a final pH of 6.5 before being filtered and sterilized. A 1× concentration was used as the delivery buffer. To create the lipoplexed solution delivered to the mice, in one vial 50 µg of RNA was equilibrated for 10 minutes at room temperature in the delivery buffer and in a second vial 10 µl RNAiMAX™ was equilibrated for 10 minutes at room temperature in the delivery buffer. After equilibrium, the vials were combined and delivery buffer was added to reach a final volume of 100 µl which was then incubated for 20 minutes at room temperature. Luciferin was administered by intraperitoneal injection (IP) at 150 mg/kg to each mouse prior to imaging during the plateau phase of the luciferin exposure curve which was between 15 and 30 minutes. To create luciferin, 1 g of D-luciferin potassium or sodium salt was dissolved in 66.6 ml of distilled phosphate buffer solution (DPBS), not containing Mg2+ or Ca2+, to make a 15 mg/ml solution. The solution was gently mixed and passed through a 0.2 µm syringe filter, before being purged with nitrogen, aliquoted and frozen at −80° C. while being protected from light as much as possible. The solution was thawed using a waterbath if luciferin was not dissolved, gently mixed and kept on ice on the day of dosing.

Whole body images were taken of each mouse 2, 8 and 24 hours after dosing. Tissue images and serum was collected from each mouse 24 hours after dosing. Mice administered doses intravenously had their liver, spleen, kidneys, lungs, heart, peri-renal adipose tissue and *thymus* imaged. Mice administered doses intramuscularly or subcutaneously had their liver, spleen, kidneys, lungs, peri-renal adipose tissue, and muscle at the injection site. From the whole body images the bioluminescence was measured in photon per second for each route of administration and dosing regimen.

A. Intramuscular Administration

Mice were intramuscularly (I.M.) administered either modified luciferase mRNA fully modified with 5-methylcytosine and pseudouridine (Naked-Luc), lipoplexed modified luciferase mRNA fully modified with 5-methylcytosine and pseudouridine (Lipoplex-luc) (IVT cDNA sequence shown in SEQ ID NO: 13; mRNA sequence shown in SEQ ID NO: 14, polyA tail of approximately 160 nucleotides not shown in sequence, 5'cap, Cap1, fully modified with 5-methylcytosine at each cytosine and pseudouridine replacement at each uridine site), lipoplexed modified granulocyte colony-stimulating factor (G-CSF) mRNA (mRNA sequence shown in SEQ ID NO: 4; polyA tail of approximately 160 nucleotides not shown in sequence; 5'cap, Cap1; fully modified with 5-methylcytosine and pseudouridine) (Lipoplex-Cytokine) or the formation buffer at a single dose of 50 µg of modified RNA in an injection volume of 50 µl for each formulation in the right hind limb and a single dose of 5 µg of modified RNA in an injection volume of 50 µl in the left hind limb. The bioluminescence average for the luciferase expression signals for each group at 2, 8 and 24 hours after dosing are shown in Table 76. The bioluminescence showed a positive signal at the injection site of the 5 µg and 50 µg modified RNA formulations containing and not containing lipoplex.

TABLE 76

In vivo Biophotoic Imaging (I.M. Injection Route)

| Formulation | Dose (ug) | Bioluminescence (photon/sec) | | |
|---|---|---|---|---|
| | | 2 hours | 8 hours | 24 hours |
| Naked-Luc | 5 | 224,000 | 683,000 | 927,000 |
| Lipolplex-Luc | 5 | 579,000 | 639,000 | 186,000 |
| Lipoplex-G-CSF | 5 | 64,600 | 85,600 | 75,100 |
| Formulation Buffer | 5 | 102,000 | 86,000 | 90,700 |
| Naked-Luc | 50 | 446,000 | 766,000 | 509,000 |
| Lipolplex-Luc | 50 | 374,000 | 501,000 | 332,000 |
| Lipoplex-G-CSF | 50 | 49,400 | 74,800 | 74,200 |
| Formulation Buffer | 50 | 59,300 | 69,200 | 63,600 |

B. Subcutaneous Administration

Mice were subcutaneously (S.C.) administered either modified luciferase mRNA (Naked-Luc), lipoplexed modified luciferase mRNA (Lipoplex-luc), lipoplexed modified G-CSF mRNA (Lipoplex-G-CSF) or the formation buffer at a single dose of 50 µg of modified mRNA in an injection volume of 100 µl for each formulation. The bioluminescence average for the luciferase expression signals for each group at 2, 8 and 24 hours after dosing are shown in Table 77. The bioluminescence showed a positive signal at the injection site of the 50 µg modified mRNA formulations containing and not containing lipoplex.

TABLE 77

In vivo Biophotoic Imaging (S.C. Injection Route)

| Formulation | Bioluminescence (photon/sec) | | |
|---|---|---|---|
| | 2 hours | 8 hours | 24 hours |
| Naked-Luc | 3,700,000 | 8,060,000 | 2,080,000 |
| Lipolplex-Luc | 3,960,000 | 1,700,000 | 1,290,000 |
| Lipoplex-G-CSF | 123,000 | 121,000 | 117,000 |
| Formulation Buffer | 116,000 | 127,000 | 123,000 |

C. Intravenous Administration

Mice were intravenously (I.V.) administered either modified luciferase mRNA (Naked-Luc), lipoplexed modified luciferase mRNA (Lipoplex-luc), lipoplexed modified G-CSF mRNA (Lipoplex-G-CSF) or the formation buffer at a single dose of 50 µg of modified mRNA in an injection volume of 100 µl for each formulation. The bioluminescence average for the luciferase expression signal in the spleen from each group at 2 hours after dosing is shown in Table 78. The bioluminescence showed a positive signal in the spleen of the 50 µg modified mRNA formulations containing lipoplex.

TABLE 78

In vivo Biophotoic Imaging (I.V. Injection Route)

| Formulation | Bioluminescence (photon/sec) of the Spleen |
|---|---|
| Naked-Luc | 58,400 |
| Lipolplex-Luc | 65,000 |
| Lipoplex-G-CSF | 57,100 |
| Formulation Buffer | 58,300 |

Example 48. Split Dose Studies

Studies utilizing multiple subcutaneous or intramuscular injection sites at one time point were designed and performed to investigate ways to increase mmRNA drug exposure and improve protein production. In addition to detection of the expressed protein product, an assessment of the physiological function of proteins was also determined through analyzing samples from the animal tested.

Surprisingly, it has been determined that split dosing of mmRNA produces greater protein production and phenotypic responses than those produced by single unit dosing or multi-dosing schemes.

The design of a single unit dose, multi-dose and split dose experiment involved using human erythropoietin (EPO) modified mRNA (mRNA shown in SEQ ID NO: 7; polyA tail of approximately 160 nucleotides not shown in sequence; 5'cap, Cap1) administered in buffer alone. The dosing vehicle (F. buffer) consisted of 150 mM NaCl, 2 mM $CaCl_2$, 2 mM $Na^+$-phosphate (1.4 mM monobasic sodium phosphate; 0.6 mM dibasic sodium phosphate), and 0.5 mM EDTA, pH 6.5. The pH was adjusted using sodium hydroxide and the final solution was filter sterilized. The mmRNA was modified with 5meC at each cytosine and pseudouridine replacement at each uridine site.

Animals (n=5) were injected IM (intramuscular) for the single unit dose of 100 ug. For multi-dosing, two schedules were used, 3 doses of 100 ug and 6 doses of 100 ug. For the split dosing scheme, two schedules were used, 3 doses at 33.3 ug and 6 doses of 16.5 ug mmRNA. Control dosing involved use of buffer only at 6 doses. Control mmRNA involved the use of luciferase mmRNA (IVT cDNA sequence shown in SEQ ID NO: 13; mRNA sequence shown in SEQ ID NO: 14; polyA tail of approximately 160 nucleotides not shown in sequence; 5'cap, Cap1; fully modified 5meC at each cytosine and pseudouridine replacement at each uridine site) dosed 6 times at 100 ug. Blood and muscle tissue were evaluated 13 hrs post injection.

Human EPO protein was measured in mouse serum 13 h post I.M. single, multi- or split dosing of the EPO mmRNA in buffer. Seven groups of mice (n=5 mice per group) were treated and evaluated. The results are shown in Table 79.

TABLE 79

Split dose study

| Group | Treatment | Dose of mmRNA | Total Dose | Avg. pmol/mL human EPO | Polypeptide per unit drug (pmol/ug) | Dose Splitting Factor |
|---|---|---|---|---|---|---|
| 1 | Human EPO mmRNA | 1 × 100 ug | 100 ug | 14.3 | 0.14 | 1 |
| 2 | Human EPO mmRNA | 3 × 100 ug | 300 ug | 82.5 | 0.28 | 2 |
| 3 | Human EPO mmRNA | 6 × 100 ug | 600 ug | 273.0 | 0.46 | 3.3 |
| 4 | Human EPO mmRNA | 3 × 33.3 ug | 100 ug | 104.7 | 1.1 | 7.9 |
| 5 | Human EPO mmRNA | 6 × 16.5 ug | 100 ug | 127.9 | 1.3 | 9.3 |
| 6 | Luciferase mmRNA | 6 × 100 ug | 600 ug | 0 | — | — |
| 7 | Buffer Alone | — | — | 0 | — | — |

The splitting factor is defined as the product per unit drug divided by the single dose product per unit drug (PUD). For example for treatment group 2 the value 0.28 or product (EPO) per unit drug (mmRNA) is divided by the single dose product per unit drug of 0.14. The result is 2. Likewise, for treatment group 4, the value 1.1 or product (EPO) per unit drug (mmRNA) is divided by the single dose product per unit drug of 0.14. The result is 7.9. Consequently, the dose splitting factor (DSF) may be used as an indicator of the efficacy of a split dose regimen. For any single administration of a total daily dose, the DSF should be equal to 1. Therefore any DSF greater than this value in a split dose regimen is an indication of increased efficacy.

To determine the dose response trends, impact of injection site and impact of injection timing, studies are performed. In these studies, varied doses of 1 μg, 5 ug, 10 ug, 25 ug, 50 ug, and values in between are used to determine dose response outcomes. Split dosing for a 100 ug total dose includes three or six doses of 1.6 ug, 4.2 ug, 8.3 ug, 16.6 ug, or values and total doses equal to administration of the total dose selected.

Injection sites are chosen from the limbs or any body surface presenting enough area suitable for injection. This may also include a selection of injection depth to target the dermis (Intradermal), epidermis (Epidermal), subcutaneous tissue (SC) or muscle (IM). Injection angle will vary based on targeted delivery site with injections targeting the intradermal site to be 10-15 degree angles from the plane of the surface of the skin, between 20-45 degrees from the plane of the surface of the skin for subcutaneous injections and angles of between 60-90 degrees for injections substantially into the muscle.

Example 49. Quantification in Exosomes

The quantity and localization of the mmRNA of the present invention can be determined by measuring the amounts (initial, timecourse, or residual basis) in isolated exosomes. In this study, since the mmRNA are typically codon-optimized and distinct in sequence from endogenous mRNA, the levels of mmRNA are quantitated as compared to endogenous levels of native or wild type mRNA by using the methods of Gibbings, PCT/IB2009/005878, the contents of which are incorporated herein by reference in their entirety.

In these studies, the method is performed by first isolating exosomes or vesicles preferably from a bodily fluid of a patient previously treated with a modified mmRNA of the invention, then measuring, in said exosomes, the modified mmRNA levels by one of mRNA microarray, qRT-PCR, or other means for measuring RNA in the art including by suitable antibody or immunohistochemical methods.

Example 50. Modified mRNA Transfection

A. Reverse Transfection

For experiments performed in a 24-well collagen-coated tissue culture plate, Keratinocytes are seeded at a cell density of $1 \times 10^5$. For experiments performed in a 96-well collagen-coated tissue culture plate, Keratinocytes are seeded at a cell density of $0.5 \times 10^5$. For each modified mRNA (mmRNA) to be transfected, modified mRNA: RNAIMAX™ is prepared as described and mixed with the cells in the multi-well plate within a period of time, e.g., 6 hours, of cell seeding before cells had adhered to the tissue culture plate.

B. Forward Transfection

In a 24-well collagen-coated tissue culture plate, Keratinocytes are seeded at a cell density of $0.7 \times 10^5$. For experiments performed in a 96-well collagen-coated tissue culture plate, Keratinocytes are seeded at a cell density of $0.3 \times 10^5$. Keratinocytes are grown to a confluency of >70% for over 24 hours. For each modified mRNA (mmRNA) to be transfected, modified mRNA: RNAIMAX™ is prepared as described and transfected onto the cells in the multi-well plate over 24 hours after cell seeding and adherence to the tissue culture plate.

C. Modified mRNA Translation Screen: G-CSF ELISA

Keratinocytes are grown in EPILIFE medium with Supplement S7 from Invitrogen (Carlsbad, Calif.) at a confluence of >70%. One set of keratinocytes were reverse transfected with 300 ng of the chemically modified mRNA (mmRNA) complexed with RNAIMAX™ transfection reagent from Invitrogen. Another set of keratinocytes are forward transfected with 300 ng modified mRNA complexed with RNAIMAX™ transfection reagent from Invitrogen. The modified mRNA: RNAIMAX™ transfection reagent complex is formed by first incubating the RNA with Supplement-free EPILIFE® media in a 5× volumetric dilution for 10 minutes at room temperature.

In a second vial, RNAIMAX™ transfection reagent was incubated with Supplement-free EPILIFE® Media in 10× volumetric dilution for 10 minutes at room temperature. The RNA vial was then mixed with the RNAIMAX™ transfection reagent vial and incubated for 20-30 minutes at room temperature before being added to the cells in a drop-wise fashion. Secreted human Granulocyte-Colony Stimulating Factor (G-CSF) concentration in the culture medium is measured at 18 hours post-transfection for each of the chemically modified mRNA in triplicate.

Secretion of Human G-CSF from transfected human keratinocytes is quantified using an ELISA kit from Invitrogen or R&D Systems (Minneapolis, Minn.) following the manufacturers recommended instructions.

D. Modified mRNA Dose and Duration: G-CSF ELISA

Keratinocytes are grown in EPILIFE® medium with Supplement S7 from Invitrogen at a confluence of >70%. Keratinocytes are reverse transfected with either 0 ng, 46.875 ng, 93.75 ng, 187.5 ng, 375 ng, 750 ng, or 1500 ng modified mRNA complexed with the RNAIMAX™ from Invitrogen (Carlsbad, Calif.). The modified mRNA: RNAIMAX™ complex is formed as described. Secreted human G-CSF concentration in the culture medium is measured at 0, 6, 12, 24, and 48 hours post-transfection for each concentration of each modified mRNA in triplicate. Secretion of human G-CSF from transfected human keratinocytes is quantified using an ELISA kit from Invitrogen or R&D Systems following the manufacturers recommended instructions.

Example 51. Detection of a Cellular Innate Immune Response to Modified mRNA Using an ELISA Assay An enzyme-linked immunosorbent assay (ELISA) for Human Tumor Necrosis Factor-α (TNF-α), Human Interferon-β (IFN-β) and Human Granulocyte-Colony Stimulating Factor (G-CSF) secreted from in vitro-transfected Human Keratinocyte cells is tested for the detection of a cellular innate immune response. Keratinocytes are grown in EPILIFE® medium with Human Keratinocyte Growth Supplement in the absence of hydrocortisone from Invitrogen (Carlsbad, Calif.) at a confluence of >70%. Secreted TNF-α keratinocytes are reverse transfected with 0 ng, 93.75 ng, 187.5 ng, 375 ng, 750 ng, 1500 ng or 3000 ng of the chemically modified mRNA (mmRNA) complexed with RNAIMAX™ from Invitrogen as described in triplicate. Secreted TNF-α in the culture medium is measured 24 hours post-transfection for each of the chemically modified mRNA using an ELISA kit from Invitrogen according to the manufacturer protocols.

Secreted IFN-β in the same culture medium is measured 24 hours post-transfection for each of the chemically modified mRNA using an ELISA kit from Invitrogen according to the manufacturer protocols. Secreted human G-CSF concentration in the same culture medium is measured at 24 hours post-transfection for each of the chemically modified mRNA. Secretion of human G-CSF from transfected human keratinocytes is quantified using an ELISA kit from Invitrogen or R&D Systems (Minneapolis, Minn.) following the manufacturers recommended instructions. These data indicate which modified mRNA (mmRNA) are capable eliciting a reduced cellular innate immune response in comparison to natural and other chemically modified polynucleotides or reference compounds by measuring exemplary type 1 cytokines TNF-α and IFN-β.

Example 52. Human Granulocyte—Colony Stimulating Factor (G-CSF) Modified mRNA-Induced Cell Proliferation Assay Human keratinocytes are grown in EPILIFE® medium with Supplement S7 from Invitrogen at a confluence of >70% in a 24-well collagen-coated TRANSWELL® (Coming, Lowell, Mass.) co-culture tissue culture plate. Keratinocytes are reverse transfected with 750 ng of the indicated chemically modified mRNA (mmRNA) complexed with RNAIMAX from Invitrogen as described in triplicate. The modified mRNA:RNAIMAX complex is formed as described. Keratinocyte media is exchanged 6-8 hours post-transfection. 42-hours post-transfection, the 24-well TRANSWELL® plate insert with a 0.4 µm-pore semi-permeable polyester membrane is placed into the human GCSF modified mRNA-transfected keratinocyte containing culture plate Human myeloblast cells, Kasumi-1 cells or KG-1 ($0.2 \times 10^5$ cells), are seeded into the insert well and cell proliferation is quantified 42 hours post-co-culture initiation using the CyQuant Direct Cell Proliferation Assay (Invitrogen, Carlsbad, Calif.) in a 100-120 µl volume in a 96-well plate. Modified mRNA-encoding human G-CSF-induced myeloblast cell proliferation is expressed as a percent cell proliferation normalized to untransfected keratinocyte/myeloblast co-culture control wells. Secreted human G-CSF concentration in both the keratinocyte and myeloblast insert co-culture wells is measured at 42 hours post-co-culture initiation for each modified mRNA in duplicate. Secretion of human G-CSF is quantified using an ELISA kit from Invitrogen following the manufacturer recommended instructions.

Transfected human G-CSF modified mRNA in human keratinocyte feeder cells and untransfected human myeloblast cells are detected by RT-PCR. Total RNA from sample cells is extracted and lysed using RNEASY® kit (Qiagen, Valencia, Calif.) according to the manufacturer instructions. Extracted total RNA is submitted to RT-PCR for specific amplification of modified mRNA-G-CSF using PROTOSCRIPT® M-MuLV Taq RT-PCR kit (New England BioLabs, Ipswich, Mass.) according to the manufacturer instructions with human G-CSF-specific primers. RT-PCR products are visualized by 1.2% agarose gel electrophoresis.

Example 53. Buffer Formulation Studies

G-CSF modified mRNA (SEQ ID NO: 4; polyA tail of approximately 160 nucleotides not shown in sequence; 5'cap, Cap1; fully modified with N1-pseudouridine and 5-methylcytosine) or Factor IX modified mRNA (SEQ ID NO: 8; polyA tail of approximately 160 nucleotides not shown in sequence; 5'cap, Cap1; fully modified with N1-pseudouridine and 5-methylcytosine) in a buffer solution is administered intramuscularly to rats in an injection volume of 50 µl (n=5) at a modified mRNA dose of 200 ug per rat as described in Table 80. The modified mRNA is lyophilized in water for 1-2 days. It is then reconstituted in the buffers listed below to a target concentration of 6 mg/ml. Concentration is determined by OD 260. Samples are diluted to 4 mg/ml in the appropriate buffer before dosing.

To precipitate the modified mRNA, 3M sodium acetate, pH 5.5 and pure ethanol are added at $\frac{1}{10}^{th}$ the total volume and 4 times the total volume of modified mRNA, respectively. The material is placed at −80C for a minimum of 1 hour. The material is then centrifuged for 30 minutes at 4000 rpm, 4C. The supernatant is removed and the pellet is centrifuged and washed 3× with 75% ethanol. Finally, the pellet is reconstituted with buffer to a target concentration of 6 mg/ml. Concentration is determined by OD 260. Samples are diluted to 4 mg/ml in the appropriate buffer before dosing. All samples are prepared by lyophilization unless noted below.

TABLE 80

Buffer Dosing Groups

| Group | Treatment | Buffer | Dose (ug/rat) |
| --- | --- | --- | --- |
| 1 | G-CSF | 0.9% Saline | 200 |
|   | Factor IX | 0.9% Saline | 200 |
| 2 | G-CSF | 0.9% Saline + 2 mM Calcium | 200 |
|   | Factor IX | 0.9% Saline + 2 mM Calcium | 200 |
| 3 | G-CSF | Lactated Ringer's | 200 |
|   | Factor IX | Lactated Ringer's | 200 |
| 4 | G-CSF | 5% Sucrose | 200 |
|   | Factor IX | 5% Sucrose | 200 |
| 5 | G-CSF | 5% Sucrose + 2 mM Calcium | 200 |
|   | Factor IX | 5% Sucrose + 2 mM Calcium | 200 |
| 6 | G-CSF | 5% Mannitol | 200 |
|   | Factor IX | 5% Mannitol | 200 |
| 7 | G-CSF | 5% Mannitol + 2 mM Calcium | 200 |
|   | Factor IX | 5% Mannitol + 2 mM Calcium | 200 |
| 8 | G-CSF | 0.9% saline (precipitation) | 200 |
|   | Factor IX | 0.9% saline (precipitation) | 200 |

Serum samples are collected from the rats at various time intervals and analyzed for G-CSF or Factor IX protein expression using G-CSF or Factor IX ELISA.

Example 54. Multi-Dose Study

Sprague-Dawley rats (n=8; 4 female, 4 male) are injected intravenously eight times (twice a week) over 28 days. The rats are injected with 0.5 mg/kg, 0.05 mg/kg, 0.005 mg/kg or 0.0005 mg/kg of human G-CSF modified mRNA of luciferase modified mRNA formulated in a lipid nanoparticle, 0.5 mg/kg of human G-CSF modified mRNA in saline, 0.2 mg/kg of the human G-CSF protein Neupogen or non-translatable human G-CSF modified mRNA formulated in a lipid nanoparticle. Serum is collected during pre-determined time intervals to evaluate G-CSF protein expression (8, 24 and 72 hours after the first dose of the week), complete blood count and white blood count (24 and 72 hours after the first dose of the week) and clinical chemistry (24 and 72 hours after the first dose of the week). The rats are sacrificed at day 29, 4 days after the final dosing, to determine the complete blood count, white blood count, clinical chemistry, protein expression and to evaluate the effect on the major organs by histopathology and necropsy. Further, an antibody assay is performed on the rats on day 29.

Example 55. Luciferase LNP In Vivo Study

Luciferase modified mRNA (SEQ ID NO: 14; polyA tail of approximately 160 nucleotides not shown in sequence, 5' cap, Cap1; fully modified with 5-methylcytosine and pseudouridine) was formulated as a lipid nanoparticle (LNP) using the syringe pump method. The LNP was formulated at a 20:1 weight ratio of total lipid to modified mRNA with a final lipid molar ratio of 50:10:38.5:1.5 (DLin-KC2-DMA: DSPC: Cholesterol: PEG-DMG). As shown in Table 81, the luciferase LNP formulation was characterized by particle size, zeta potential, and encapsulation.

TABLE 81

Luciferase Formulation

| Formulation | NPA-098-1 |
|---|---|
| Modified mRNA | Luciferase |
| Mean size | 135 nm |
|  | PDI: 0.08 |
| Zeta at pH 7.4 | −0.6 mV |
| Encaps. (RiboGr) | 91% |

As outlined in Table 82, the luciferase LNP formulation was administered to Balb-C mice (n=3) intramuscularly, intravenously and subcutaneously and a luciferase modified RNA formulated in PBS was administered to mice intravenously.

TABLE 82

Luciferase Formulations

| Formulation | Vehicle | Route | Concentration (mg/ml) | Injection Volume (ul) | Amount of modified RNA (ug) | Dose (mg/kg) |
|---|---|---|---|---|---|---|
| Luc-LNP | PBS | IV | 0.20 | 50 | 10 | 0.50 |
| Luc-LNP | PBS | IM | 0.20 | 50 | 10 | 0.50 |
| Luc-LNP | PBS | SC | 0.20 | 50 | 10 | 0.50 |
| Luc-PBS | PBS | IV | 0.20 | 50 | 10 | 0.50 |

The mice administered the luciferase LNP formulation intravenously and intramuscularly were imaged at 2, 8, 24, 48, 120 and 192 hours and the mice administered the luciferase LNP formulation subcutaneously were imaged at 2, 8, 24, 48 and 120 hours to determine the luciferase expression as shown in Table 83. In Table 83, "NT" means not tested. Twenty minutes prior to imaging, mice were injected intraperitoneally with a D-luciferin solution at 150 mg/kg. Animals were then anesthetized and images were acquired with an IVIS Lumina II imaging system (Perkin Elmer). Bioluminescence was measured as total flux (photons/second) of the entire mouse.

TABLE 83

Luciferase Expression

| | | Average Expression (photon/second) | | | | | |
|---|---|---|---|---|---|---|---|
| Formulation | Route of Administration | 2 hours | 8 hours | 24 hours | 48 hours | 120 hours | 192 hours |
| Luc-LNP | IV | 1.62E+08 | 3.00E+09 | 7.77E+08 | 4.98E+08 | 1.89E+08 | 6.08E+07 |
| Luc-LNP | IM | 4.85E+07 | 4.92E+08 | 9.02E+07 | 3.17E+07 | 1.22E+07 | 2.38E+06 |
| Luc-LNP | SC | 1.85E+07 | 9.79E+08 | 3.09E+08 | 4.94E+07 | 1.98E+06 | NT |
| Luc-PBS | IV | 3.61E+05 | 5.64E+05 | 3.19E+05 | NT | NT | NT |

One mouse administered the LNP formulation intravenously was sacrificed at 8 hours to determine the luciferase expression in the liver and spleen. Also, one mouse administered the LNP formulation intramuscular was sacrificed at 8 hours to determine the luciferase expression of the muscle around the injection site and in the liver and spleen. As shown in Table 84, expression was seen in the both the liver and spleen after intravenous and intramuscular administration and in the muscle around the intramuscular injection site.

TABLE 84

Luciferase Expression in Tissue

| | Expression (photon/second) |
|---|---|
| Luciferase LNP: IV Administration | |
| Liver | 7.984E+08 |
| Spleen | 3.951E+08 |
| Luciferase LNP: IM Administration | |
| Muscle around the injection site | 3.688E+07 |
| Liver | 1.507E+08 |
| Spleen | 1.096E+07 |

Example 56. In Vitro PBMC Studies: Percent Modification 480 ng of G-CSF mRNA modified with 5-methylcytosine (5mC) and pseudouridine (pseudoU) or unmodified G-CSF mRNA was transfected with 0.4 uL of Lipofectamine 2000 into peripheral blood mononuclear cells (PBMC) from three normal blood donors (D1, D2, and D3). The G-CSF mRNA (SEQ ID NO: 4; polyA tail of approximately 160 nucleotides not shown in sequence; 5'cap, Cap1) was completely modified with 5mC and pseudoU (100% modification), not modified with 5mC and pseudoU (0% modification) or was partially modified with 5mC and pseudoU so the mRNA would contain 75% modification, 50% modification or 25% modification. A control sample of Luciferase (mRNA sequence shown in SEQ ID NO: 14; polyA tail of approximately 160 nucleotides not shown in sequence; 5'cap, Cap1; fully modified 5 meC and pseudoU) was also analyzed for G-CSF expression. For TNF-alpha and IFN-alpha control samples of Lipofectamine2000, LPS, R-848, Luciferase (mRNA sequence shown in SEQ ID NO: 14; polyA tail of approximately 160 nucleotides not shown in sequence; 5'cap, Cap1; fully modified 5mC and pseudo), and P(I)P(C) were also analyzed. The supernatant was harvested and run by ELISA 22 hours after transfection to determine the protein expression. The expression of G-CSF is shown in Table 85 and the expression of IFN-alpha and TNF-alpha is shown in Table 86. The expression of IFN-alpha and TNF-alpha may be a secondary effect from the transfection of the G-CSF mRNA. Tables 85 and 86 show that the amount of chemical modification of G-CSF, interferon alpha (IFN-alpha) and tumor necrosis factor-alpha (TNF-alpha) is titratable when the mRNA is not fully modified and the titratable trend is not the same for each target.

As mentioned above, using PBMC as an in vitro assay system it is possible to establish a correlation between translation (in this case G-CSF protein production) and cytokine production (in this case exemplified by IFN-alpha protein production). Better protein production is correlated with lower induction of innate immune activation pathway, and the percentage modification of a chemistry can be judged favorably based on this ratio (Table 87). As calculated from Tables 85 and 86 and shown in Table 87, full modification with 5-methylcytidine and pseudouridine shows a much better ratio of protein cytokine production than without any modification (natural G-CSF mRNA) (100-fold for IFN-alpha and 27-fold for TNF-alpha). Partial modification shows a linear relationship with increasingly less modification resulting in a lower protein cytokine ratio.

TABLE 85

G-CSF Expression

| | G-CSF Expression (pg/ml) | | |
| --- | --- | --- | --- |
| | D1 | D2 | D3 |
| 100% modification | 1968.9 | 2595.6 | 2835.7 |
| 75% modification | 566.7 | 631.4 | 659.5 |
| 50% modification | 188.9 | 187.2 | 191.9 |
| 25% modification | 139.3 | 126.9 | 102.0 |
| 0% modification | 194.8 | 182.0 | 183.3 |
| Luciferase | 90.2 | 0.0 | 22.1 |

TABLE 86

IFN-alpha and TNF-alpha Expression

| | IFN-alpha Expression (pg/ml) | | | TNF-alpha Expression (pg/ml) | | |
| --- | --- | --- | --- | --- | --- | --- |
| | D1 | D2 | D3 | D1 | D2 | D3 |
| 100% modification | 336.5 | 78.0 | 46.4 | 115.0 | 15.0 | 11.1 |
| 75% modification | 339.6 | 107.6 | 160.9 | 107.4 | 21.7 | 11.8 |
| 50% modification | 478.9 | 261.1 | 389.7 | 49.6 | 24.1 | 10.4 |
| 25% modification | 564.3 | 400.4 | 670.7 | 85.6 | 26.6 | 19.8 |
| 0% modification | 1421.6 | 810.5 | 1260.5 | 154.6 | 96.8 | 45.9 |
| LPS | 0.0 | 0.6 | 0.0 | 0.0 | 12.6 | 4.3 |
| R-848 | 0.5 | 3.0 | 14.1 | 655.2 | 989.9 | 420.4 |
| P(I)P(C) | 130.8 | 297.1 | 585.2 | 765.8 | 2362.7 | 1874.4 |
| Lipid only | 1952.2 | 866.6 | 855.8 | 248.5 | 82.0 | 60.7 |

TABLE 87

PC Ratio and Effect of Percentage of Modification

| % Modification | Average G-CSF (pg/ml) | Average IFN-a (pg/ml) | Average TNF-a (pg/ml) | G-CSF/IFN-alpha (PC ratio) | G-CSF/TNF-alpha (PC ratio) |
| --- | --- | --- | --- | --- | --- |
| 100 | 2466 | 153 | 47 | 16 | 52 |
| 75 | 619 | 202 | 47 | 3.1 | 13 |
| 50 | 189 | 376 | 28 | 0.5 | 6.8 |
| 25 | 122 | 545 | 44 | 0.2 | 2.8 |
| 0 | 186 | 1164 | 99 | 0.16 | 1.9 |

Example 57. Modified RNA Transfected in PBMC 500 ng of G-CSF mRNA modified with 5-methylcytosine (5mC) and pseudouridine (pseudoU) or unmodified G-CSF mRNA was transfected with 0.4 uL of Lipofectamine 2000 into peripheral blood mononuclear cells (PBMC) from three normal blood donors (D1, D2, and D3). The G-CSF mRNA (SEQ ID NO: 4; polyA tail of approximately 160 nucleotides not shown in sequence; 5'cap, Cap1) was completely modified with 5mC and pseudoU (100% modification), not modified with 5mC and pseudoU (0% modification) or was partially modified with 5mC and pseudoU so the mRNA would contain 50% modification, 25% modification, 10% modification, %5 modification, 1% modification or 0.1% modification. A control sample of mCherry (mRNA sequence shown in SEQ ID NO: 5; polyA tail of approximately 160 nucleotides not shown in sequence; 5'cap, Cap1; fully modified 5meC and pseudouridine) and G-CSF fully modified with 5-methylcytosine and pseudouridine (Control G-CSF) was also analyzed for G-CSF expression. For tumor necrosis factor-alpha (TNF-alpha) and interferon-alpha (IFN-alpha) control samples of Lipofectamine2000, LPS, R-848, Luciferase (mRNA sequence shown in SEQ ID NO: 14; polyA tail of approximately 160 nucleotides not shown in sequence; 5'cap, Cap1; fully modified 5mC and pseudo), and P(I)P(C) were also analyzed. The supernatant was harvested 6 hours and 18 hours after transfection and run by ELISA to determine the protein expression. The expression of G-CSF, IFN-alpha, and TNF-alpha for Donor 1 is shown in Table 88, Donor 2 is shown in Table 89 and Donor 3 is shown in Table 90.

Full 100% modification with 5-methylcytidine and pseudouridine resulted in the most protein translation (G-CSF) and the least amount of cytokine produced across all three human PBMC donors. Decreasing amounts of modification results in more cytokine production (IFN-alpha and TNF-alpha), thus further highlighting the importance of fully modification to reduce cytokines and to improve protein translation (as evidenced here by G-CSF production).

TABLE 88

Donor 1

| | G-CSF (pg/mL) | | IFN-alpha (pg/mL) | | TNF-alpha (pg/mL) | |
| --- | --- | --- | --- | --- | --- | --- |
| | 6 hours | 18 hours | 6 hours | 18 hours | 6 hours | 18 hours |
| 100% Mod | 1815 | 2224 | 1 | 13 | 0 | 0 |
| 75% Mod | 591 | 614 | 0 | 89 | 0 | 0 |
| 50% Mod | 172 | 147 | 0 | 193 | 0 | 0 |
| 25% Mod | 111 | 92 | 2 | 219 | 0 | 0 |
| 10% Mod | 138 | 138 | 7 | 536 | 18 | 0 |

TABLE 88-continued

Donor 1

| | G-CSF (pg/mL) | | IFN-alpha (pg/mL) | | TNF-alpha (pg/mL) | |
|---|---|---|---|---|---|---|
| | 6 hours | 18 hours | 6 hours | 18 hours | 6 hours | 18 hours |
| 1% Mod | 199 | 214 | 9 | 660 | 18 | 3 |
| 0.1% Mod | 222 | 208 | 10 | 597 | 0 | 6 |
| 0% Mod | 273 | 299 | 10 | 501 | 10 | 0 |
| Control G-CSF | 957 | 1274 | 3 | 123 | 18633 | 1620 |
| mCherry | 0 | 0 | 0 | 10 | 0 | 0 |
| Untreated | N/A | N/A | 0 | 0 | 1 | 1 |

TABLE 89

Donor 2

| | G-CSF (pg/mL) | | IFN-alpha (pg/mL) | | TNF-alpha (pg/mL) | |
|---|---|---|---|---|---|---|
| | 6 hours | 18 hours | 6 hours | 18 hours | 6 hours | 18 hours |
| 100% Mod | 2184 | 2432 | 0 | 7 | 0 | 11 |
| 75% Mod | 935 | 958 | 3 | 130 | 0 | 0 |
| 50% Mod | 192 | 253 | 2 | 625 | 7 | 23 |
| 25% Mod | 153 | 158 | 7 | 464 | 6 | 6 |
| 10% Mod | 203 | 223 | 25 | 700 | 22 | 39 |
| 1% Mod | 288 | 275 | 27 | 962 | 51 | 66 |
| 0.1% Mod | 318 | 288 | 33 | 635 | 28 | 5 |
| 0% Mod | 389 | 413 | 26 | 748 | 1 | 253 |
| Control G-CSF | 1461 | 1634 | 1 | 59 | 481 | 814 |
| mCherry | 0 | 7 | 0 | 1 | 0 | 0 |
| Untreated | N/A | N/A | 1 | 0 | 0 | 0 |

TABLE 90

Donor 3

| | G-CSF (pg/mL) | | IFN-alpha (pg/mL) | | TNF-alpha (pg/mL) | |
|---|---|---|---|---|---|---|
| | 6 hours | 18 hours | 6 hours | 18 hours | 6 hours | 18 hours |
| 100% Mod | 6086 | 7549 | 7 | 658 | 11 | 11 |
| 75% Mod | 2479 | 2378 | 23 | 752 | 4 | 35 |
| 50% Mod | 667 | 774 | 24 | 896 | 22 | 18 |
| 25% Mod | 480 | 541 | 57 | 1557 | 43 | 115 |
| 10% Mod | 838 | 956 | 159 | 2755 | 144 | 123 |
| 1% Mod | 1108 | 1197 | 235 | 3415 | 88 | 270 |
| 0.1% Mod | 1338 | 1177 | 191 | 2873 | 37 | 363 |
| 0% Mod | 1463 | 1666 | 215 | 3793 | 74 | 429 |
| Control G-CSF | 3272 | 3603 | 16 | 1557 | 731 | 9066 |

TABLE 90-continued

Donor 3

| | G-CSF (pg/mL) | | IFN-alpha (pg/mL) | | TNF-alpha (pg/mL) | |
|---|---|---|---|---|---|---|
| | 6 hours | 18 hours | 6 hours | 18 hours | 6 hours | 18 hours |
| mCherry | 0 | 0 | 2 | 645 | 0 | 0 |
| Untreated | N/A | N/A | 1 | 1 | 0 | 8 |

Example 58. Innate Immune Response Study in BJ Fibroblasts

A. Single Transfection

Human primary foreskin fibroblasts (BJ fibroblasts) were obtained from American Type Culture Collection (ATCC) (catalog # CRL-2522) and grown in Eagle's Minimum Essential Medium (ATCC, catalog #30-2003) supplemented with 10% fetal bovine serum at 37° C., under 5% $CO_2$. BJ fibroblasts were seeded on a 24-well plate at a density of 300,000 cells per well in 0.5 ml of culture medium. 250 ng of modified G-CSF mRNA (mRNA sequence shown in SEQ ID NO: 4; polyA tail of approximately 140 nucleotides not shown in sequence; 5'cap, Cap1) fully modified with 5-methylcytosine and pseudouridine (Gen1) or fully modified with 5-methylcytosine and N1-methylpseudouridine (Gen2) having Cap0, Cap1 or no cap was transfected using Lipofectamine 2000 (Invitrogen, catalog #11668-019), following manufacturer's protocol. Control samples of poly I:C (PIC), Lipofectamine 2000 (Lipo), natural luciferase mRNA (mRNA sequence shown in SEQ ID NO: 14; polyA tail of approximately 160 nucleotides not shown in sequence; 5'cap, Cap1) and natural G-CSF mRNA were also transfected. The cells were harvested after 18 hours, the total RNA was isolated and DNASE® treated using the RNeasy micro kit (catalog #74004) following the manufacturer's protocol. 100 ng of total RNA was used for cDNA synthesis using High Capacity cDNA Reverse Transcription kit (catalog #4368814) following the manufacturer's protocol. The cDNA was then analyzed for the expression of innate immune response genes by quantitative real time PCR using SybrGreen in a Biorad CFX 384 instrument following manufacturer's protocol. Table 91 shows the expression level of innate immune response transcripts relative to house-keeping gene HPRT (hypoxanthine phosphoribosytransferase) and is expressed as fold-induction relative to HPRT. In the table, the panel of standard metrics includes: RIG-I is retinoic acid inducible gene 1, IL6 is interleukin-6, OAS-1 is oligoadenylate synthetase 1, IFNb is interferon-beta, AIM2 is absent in melanoma-2, IFIT-1 is interferon-induced protein with tetratricopeptide repeats 1, PKR is protein kinase R, TNFa is tumor necrosis factor alpha and IFNa is interferon alpha.

TABLE 91

Innate Immune Response Transcript Levels

| Formulation | RIG-I | IL6 | OAS-1 | IFNb | AIM2 | IFIT-1 | PKR | TNFa | IFNa |
|---|---|---|---|---|---|---|---|---|---|
| Natural Luciferase | 71.5 | 20.6 | 20.778 | 11.404 | 0.251 | 151.218 | 16.001 | 0.526 | 0.067 |
| Natural G-CSF | 73.3 | 47.1 | 19.359 | 13.615 | 0.264 | 142.011 | 11.667 | 1.185 | 0.153 |
| PIC | 30.0 | 2.8 | 8.628 | 1.523 | 0.100 | 71.914 | 10.326 | 0.264 | 0.063 |
| G-CSF Gen1-UC | 0.81 | 0.22 | 0.080 | 0.009 | 0.008 | 2.220 | 1.592 | 0.090 | 0.027 |
| G-CSF Gen1-Cap0 | 0.54 | 0.26 | 0.042 | 0.005 | 0.008 | 1.314 | 1.568 | 0.088 | 0.038 |
| G-CSF Gen1-Cap1 | 0.58 | 0.30 | 0.035 | 0.007 | 0.006 | 1.510 | 1.371 | 0.090 | 0.040 |
| G-CSF Gen2-UC | 0.21 | 0.20 | 0.002 | 0.007 | 0.007 | 0.603 | 0.969 | 0.129 | 0.005 |
| G-CSF Gen2-Cap0 | 0.23 | 0.21 | 0.002 | 0.0014 | 0.007 | 0.648 | 1.547 | 0.121 | 0.035 |

TABLE 91-continued

Innate Immune Response Transcript Levels

| Formulation | RIG-I | IL6 | OAS-1 | IFNb | AIM2 | IFIT-1 | PKR | TNFa | IFNa |
|---|---|---|---|---|---|---|---|---|---|
| G-CSF Gen2-Cap1 | 0.27 | 0.26 | 0.011 | 0.004 | 0.005 | 0.678 | 1.557 | 0.099 | 0.037 |
| Lipo | 0.27 | 0.53 | 0.001 | 0 | 0.007 | 0.954 | 1.536 | 0.158 | 0.064 |

B. Repeat Transfection

Human primary foreskin fibroblasts (BJ fibroblasts) were obtained from American Type Culture Collection (ATCC) (catalog # CRL-2522) and grown in Eagle's Minimum Essential Medium (ATCC, catalog #30-2003) supplemented with 10% fetal bovine serum at 37° C., under 5% $CO_2$. BJ fibroblasts were seeded on a 24-well plate at a density of 300,000 cells per well in 0.5 ml of culture medium. 250 ng of modified G-CSF mRNA (mRNA sequence shown in SEQ ID NO: 4; polyA tail of approximately 140 nucleotides not shown in sequence; 5'cap, Cap1) unmodified, fully modified with 5-methylcytosine and pseudouridine (Gen1) or fully modified with 5-methylcytosine and N1-methylpseudouridine (Gen2) was transfected daily for 5 days following manufacturer's protocol. Control samples of Lipofectamine 2000 (L2000) and mCherry mRNA (mRNA sequence shown in SEQ ID NO: 5; polyA tail of approximately 160 nucleotides not shown in sequence; 5'cap, Cap1; fully modified with 5-methylcytidine and pseudouridine) were also transfected daily for 5 days. The results are shown in Table 92.

Unmodified mRNA showed a cytokine response in interferon-beta (IFN-beta) and interleukin-6 (IL-6) after one day. mRNA modified with at least pseudouridine showed a cytokine response after 2-3 days whereas mRNA modified with 5-methylcytosine and N1-methylpseudouridine showed a reduced response after 3-5 days.

TABLE 92

Cytokine Response

| Formulation | Transfection | IFN-beta (pg/ml) | IL-6 (pg/ml) |
|---|---|---|---|
| G-CSF unmodified | 6 hours | 0 | 3596 |
|  | Day 1 | 1363 | 15207 |
|  | Day 2 | 238 | 12415 |
|  | Day 3 | 225 | 5017 |
|  | Day 4 | 363 | 4267 |
|  | Day 5 | 225 | 3094 |
| G-CSF Gen 1 | 6 hours | 0 | 3396 |
|  | Day 1 | 38 | 3870 |
|  | Day 2 | 1125 | 16341 |
|  | Day 3 | 100 | 25983 |
|  | Day 4 | 75 | 18922 |
|  | Day 5 | 213 | 15928 |
| G-CSF Gen 2 | 6 hours | 0 | 3337 |
|  | Day 1 | 0 | 3733 |
|  | Day 2 | 150 | 974 |
|  | Day 3 | 213 | 4972 |
|  | Day 4 | 1400 | 4122 |
|  | Day 5 | 350 | 2906 |
| mCherry | 6 hours | 0 | 3278 |
|  | Day 1 | 238 | 3893 |
|  | Day 2 | 113 | 1833 |
|  | Day 3 | 413 | 25539 |
|  | Day 4 | 413 | 29233 |
|  | Day 5 | 213 | 20178 |
| L2000 | 6 hours | 0 | 3270 |
|  | Day 1 | 13 | 3933 |
|  | Day 2 | 388 | 567 |
|  | Day 3 | 338 | 1517 |
|  | Day 4 | 475 | 1594 |
|  | Day 5 | 263 | 1561 |

Example 59. In Vivo Detection of Innate Immune Response Study

Female BALB/C mice (n=5) were injected intramuscularly with G-CSF mRNA (GCSF mRNA unmod) (mRNA sequence shown in SEQ ID NO: 4; polyA tail of approximately 160 nucleotides not shown in sequence;) with a 5'cap of Cap1, G-CSF mRNA fully modified with 5-methylcytosine and pseudouridine (GCSF mRNA 5 mc/pU), G-CSF mRNA fully modified with 5-methylcytosine and N1-methylpseudouridine with (GCSF mRNA 5 mc/N1pU) or without a 5' cap (GCSF mRNA 5 mc/N1 pU no cap) or a control of either R848 or 5% sucrose as described in Table 93. Blood is collected at 8 hours after dosing and using ELISA the protein levels of G-CSF and interferon-alpha (IFN-alpha) is determined by ELISA and are shown in Table 93.

As shown in Table 93, unmodified, 5 mc/pU, and 5 mc/N1pU modified G-CSF mRNA resulted in human G-CSF expression in mouse serum. The uncapped 5mC/N1pU modified G-CSF mRNA showed no human G-CSF expression in serum, highlighting the importance of having a 5' cap structure for protein translation.

As expected, no human G-CSF protein was expressed in the R848, 5% sucrose only, and untreated groups. Importantly, significant differences were seen in cytokine production as measured by mouse IFN-alpha in the serum. As expected, unmodified G-CSF mRNA demonstrated a robust cytokine response in vivo (greater than the R848 positive control). The 5 mc/pU modified G-CSF mRNA did show a low but detectable cytokine response in vivo, while the 5 mc/N1pU modified mRNA showed no detectable IFN-alpha in the serum (and same as vehicle or untreated animals).

Also, the response of 5 mc/N1pU modified mRNA was the same regardless of whether it was capped or not. These in vivo results reinforce the conclusion that 1) that unmodified mRNA produce a robust innate immune response, 2) that this is reduced, but not abolished, through 100% incorporation of 5 mc/pU modification, and 3) that incorporation of 5 mc/N1pU modifications results in no detectable cytokine response.

Lastly, given that these injections are in 5% sucrose (which has no effect by itself), these result should accurately reflect the immunostimulatory potential of these modifications.

From the data it is evident that N1pU modified molecules produce more protein while concomitantly having little or no effect on IFN-alpha expression. It is also evident that capping is required for protein production for this chemical modification. The Protein: Cytokine Ratio of 748 as compared to the PC Ratio for the unmodified mRNA (PC=9) means that this chemical modification is far superior as related to the effects or biological implications associated with IFN-alpha.

TABLE 93

Human G-CSF and Mouse IFN-alpha in serum

| Formulation | Route | Dose (ug/mouse) | Dose (ul) | G-CSF protein (pg/ml) | IFN-alpha expression (pg/ml) | PC Ratio |
|---|---|---|---|---|---|---|
| GCSF mRNA unmod | I.M. | 200 | 50 | 605.6 | 67.01 | 9 |
| GCSF mRNA 5mc/pU | I.M. | 200 | 50 | 356.5 | 8.87 | 40 |
| GCSF mRNA5mc/N1pU | I.M. | 200 | 50 | 748.1 | 0 | 748 |
| GCSF mRNA5mc/N1pU no cap | I.M. | 200 | 50 | 6.5 | 0 | 6.5 |
| R848 | I.M. | 75 | 50 | 3.4 | 40.97 | .08 |
| 5% sucrose | I.M. | — | 50 | 0 | 1.49 | 0 |
| Untreated | I.M. | — | — | 0 | 0 | 0 |

Example 60: In Vivo Delivery of Modified RNA

Protein production of modified mRNA was evaluated by delivering modified G-CSF mRNA or modified Factor IX mRNA to female Sprague Dawley rats (n=6). Rats were injected with 400 ug in 100 ul of G-CSF mRNA (mRNA sequence shown in SEQ ID NO: 4; polyA tail of approximately 160 nucleotides not shown in sequence; 5'cap, Cap1) fully modified with 5-methylcytosine and pseudouridine (G-CSF Gen1), G-CSF mRNA fully modified with 5-methylcytosine and N1-methylpseudouridine (G-CSF Gen2) or Factor IX mRNA (mRNA sequence shown in SEQ ID NO: 8; polyA tail of approximately 160 nucleotides not shown in sequence; 5'cap, Cap1) fully modified with 5-methylcytosine and pseudouridine (Factor IX Gen1) reconstituted from the lyophilized form in 5% sucrose. Blood was collected 8 hours after injection and the G-CSF protein level in serum was measured by ELISA. Table 94 shows the G-CSF protein levels in serum after 8 hours.

These results demonstrate that both G-CSF Gen 1 and G-CSF Gen 2 modified mRNA can produce human G-CSF protein in a rat following a single intramuscular injection, and that human G-CSF protein production is improved when using Gen 2 chemistry over Gen 1 chemistry.

TABLE 94

G-CSF Protein in Rat Serum (I.M. Injection Route)

| Formulation | G-CSF protein (pg/ml) |
|---|---|
| G-CSF Gen1 | 19.37 |
| G-CSF Gen2 | 64.72 |
| Factor IX Gen 1 | 2.25 |

Example 61. Stability of Modified RNA

Stability experiments were conducted to obtain a better understanding of storage conditions to retain the integrity of modified RNA. Unmodified G-CSF mRNA (mRNA sequence shown in SEQ ID NO: 4; polyA tail of approximately 160 nucleotides not shown in sequence; 5'cap, Cap1), G-CSF mRNA (mRNA sequence shown in SEQ ID NO: 4; polyA tail of approximately 160 nucleotides not shown in sequence; 5'cap, Cap1) fully modified with 5-methylcytosine and pseudouridine and G-CSF mRNA fully modified with 5-methylcytosine and pseudouridine lipoplexed with 0.75% by volume of RNAIMAX™ was stored at 50° C., 40° C., 37° C., 25° C., 4° C. or −20° C. After the mRNA had been stored for 0 hours, 2 hours, 6 hours, 24 hours, 48 hours, 5 days and 14 days, the mRNA was analyzed by gel electrophoresis using a Bio-Rad EXPERION™ system. The modified, unmodified and lipoplexed G-CSF mRNA was also stored in RNASTABLE® (Biomatrica, Inc. San Diego, Calif.) at 40° C. or water at −80° C. or 40° C. for 35 days before being analyzed by gel electrophoresis.

All mRNA samples without stabilizer were stable after 2 weeks after storage at 4° C. or −20° C. Modified G-CSF mRNA, with or without lipoplex, was more stable than unmodified G-CSF when stored at 25° C. (stable out to 5 days versus 48 hours), 37° C. (stable out to 24 hours versus 6 hours) and 50° C. (stable out to 6 hours versus 2 hours). Unmodified G-CSF mRNA, modified G-CSF mRNA with or without lipoplex tolerated 12 freeze/thaw cycles.

mRNA samples stored in stabilizer at 40° C. showed similar stability to the mRNA samples stored in water at −80° C. after 35 days whereas the mRNA stored in water at 40° C. showed heavy degradation after 18 days.

mRNA samples stored at 4° C., 25° C. and 37° C. were stored in 1×TE buffer or the formulation buffer (150 mM sodium chloride, 2 mM calcium chloride, 2 mM phosphate, 0.5 mM EDTA at a pH of 6.5). The mRNA stored at 4° C. was stable to at least 60 days in both the TE and formulation buffer. At 25° C. the mRNA in formulation buffer was stable out to 14 days and the TE buffer was stable out to at least 6 days. Storage of mRNA in the formulation buffer at 37° C. was stable to 6 days compared to the TE buffer which was stable only until 4 days.

Example 62. Effects of Chemical Modifications on Expression of Formulated mRNA Luciferase mRNA (SEQ ID NO: 14; polyA tail of approximately 140 nucleotides not shown in sequence; 5'cap, Cap1) fully modified with 5-methylcytosine and 2'Fluorouridine is formulated in saline or DLin-MC3-DMA and administered intravenously, intramuscularly or subcutaneously to rodents at a dose of 0.5 mg/kg, 0.05 mg/kg, 0.005 mg/kg and/or 0.0005 mg/kg. Luciferase mRNA (SEQ ID NO: 14; polyA tail of approximately 160 nucleotides not shown in sequence; 5'cap, Cap1) fully modified with 5-methylcytosine and pseudouridine is formulated in DLin-MC3-DMA and administered intramuscularly or subcutaneously to rodents at a dose of 0.5 mg/kg, 0.05 mg/kg, 0.005 mg/kg and/or 0.0005 mg/kg. The DLin-MC3-DMA formulations are analyzed prior to administration to determine the mean size and zeta potential. The rodents are imaged at 2 hours, 8 hours, 24 hours, 72 hours, 96 hours, 144 hours and 168 hours after dosing and the bioluminescence is measured in photon per second for each route of administration and formulation.

Example 63. Expression of PLGA Formulated mRNA

A. Synthesis and Characterization of Luciferase PLGA Microspheres

Luciferase mRNA (mRNA sequence shown in SEQ ID NO: 14; polyA tail of approximately 140 nucleotides not shown in sequence; 5'cap, Cap1) fully modified with 5-methylcytosine and N1-methyl pseudouridine, modified with 25% of uridine replaced with 2-thiouridine and 25% of cytosine replaced with 5-methylcytosine, fully modified with N1-methyl pseudouridine, or fully modified with pseudouridine was reconstituted in 1×TE buffer and then formulated in PLGA microspheres. PLGA microspheres were synthesized using the water/oil/water double emulsification methods known in the art using PLGA-ester cap (Lactel, Cat# B6010-2, inherent viscosity 0.55-0.75, 50:50 LA:GA), polyvinylalcohol (PVA) (Sigma, Cat#348406-25G, MW 13-23 k) dichloromethane and water. Briefly, 0.4 ml of mRNA in TE buffer at 4 mg/ml (W1) was added to 2 ml of PLGA dissolved in dichloromethane (DCM) (O1) at a concentration of 200 mg/ml of PLGA. The W1/O1 emulsion was homogenized (IKA Ultra-Turrax Homogenizer, T18) for 30 seconds at speed 5 (~19,000 rpm). The W1/O1 emulsion was then added to 250 ml 1% PVA (W2) and homogenized for 1 minute at speed 5 (~19,000 rpm). Formulations were left to stir for 3 hours, then passed through a 100 μm nylon mesh strainer (Fisherbrand Cell Strainer, Cat #22-363-549) to remove larger aggregates, and finally washed by centrifugation (10 min, 9,250 rpm, 4° C.). The supernatant was discarded and the PLGA pellets were resuspended in 5-10 ml of water, which was repeated 2×. After washing and resuspension with water, 100-200 μl of a PLGA microspheres sample was used to measure particle size of the formulations by laser diffraction (Malvern Mastersizer2000). The washed formulations were frozen in liquid nitrogen and then lyophilized for 2-3 days.

After lyophilization, ~10 mg of PLGA MS were weighed out in 2 ml eppendorf tubes and deformulated by adding 1 ml of DCM and letting the samples shake for 2-6 hrs. The mRNA was extracted from the deformulated PLGA microspheres by adding 0.5 ml of water and shaking the sample overnight. Unformulated luciferase mRNA in TE buffer (unmodulated control) was spiked into DCM and went through the deformulation process (deformulation control) to be used as controls in the transfection assay. The encapsulation efficiency, weight percent loading and particle size are shown in Table 95. Encapsulation efficiency was calculated as mg of mRNA from deformulation of PLGA microspheres divided by the initial amount of mRNA added to the formulation. Weight percent loading in the formulation was calculated as mg of mRNA from deformulation of PLGA microspheres divided by the initial amount of PLGA added to the formulation.

TABLE 95

| PLGA Characteristics | | | | | |
|---|---|---|---|---|---|
| Chemical Modifications | Sample ID | Encapsulation Efficiency (%) | Theoretical mRNA Loading (wt %) | Actual mRNA Loading (wt %) | Particle Size (D50, um) |
| Fully modified with 5-methylcytosine and N1-methyl pseudouridine | 43-66A | 45.8 | 0.4 | 0.18 | 33.4 |
| | 43-66B | 29.6 | | 0.12 | 27.7 |
| | 43-66C | 25.5 | | 0.10 | 27.1 |
| 25% of uridine replaced with 2-thiouridine and 25% of cytosine replaced with 5-methylcytosine | 43-67A | 34.6 | 0.4 | 0.14 | 29.9 |
| | 43-67B | 22.8 | | 0.09 | 30.2 |
| | 43-67C | 23.9 | | 0.10 | 25.1 |
| Fully modified with N1-methyl pseudouridine | 43-69A | 55.8 | 0.4 | 0.22 | 40.5 |
| | 43-69B | 31.2 | | 0.12 | 41.1 |
| | 43-69C | 24.9 | | 0.10 | 46.1 |
| Fully modified with pseudouridine | 43-68-1 | 49.3 | 0.4 | 0.20 | 34.8 |
| | 43-68-2 | 37.4 | | 0.15 | 35.9 |
| | 43-68-3 | 45.0 | | 0.18 | 36.5 |

B. Protein Expression of Modified mRNA Encapsulated in PLGA Microspheres

The day before transfection, 20,000 HeLa cells (ATCC no. CCL-2; Manassas, Va.) were harvested by treatment with Trypsin-EDTA solution (LifeTechnologies, Grand Island, N.Y.) and seeded in a total volume of 100 ul EMEM medium (supplemented with 10% FCS and 1× Glutamax) per well in a 96-well cell culture plate (Corning, Manassas, Va.). The cells were grown at 37° C. in a 5% CO2 atmosphere overnight. The next day, 83 ng of the deformulated luciferase mRNA PLGA microsphere samples, deformulated luciferase mRNA control (Deform control), or unformulated luciferase mRNA control (Unfomul control) was diluted in a 10 ul final volume of OPTI-MEM (LifeTechnologies, Grand Island, N.Y.). Lipofectamine 2000 (LifeTechnologies, Grand Island, N.Y.) was used as a transfection reagent and 0.2 ul was diluted in a 10 ul final volume of OPTI-MEM. After 5 min of incubation at room temperature, both solutions were combined and incubated an additional 15 min at room temperature. Then 20 ul of the combined solution was added to 100 ul of cell culture medium containing the HeLa cells. The plates were then incubated as described before.

After a 18 to 22 hour incubation, cells expressing luciferase were lysed with 100 ul Passive Lysis Buffer (Promega, Madison, Wis.) according to manufacturer instructions. Aliquots of the lysates were transferred to white opaque polystyrene 96-well plates (Corning, Manassas, Va.) and combined with 100 ul complete luciferase assay solution (Promega, Madison, Wis.). The background signal of the plates without reagent was about 200 relative light units per well. The plate reader was a BioTek Synergy H1 (BioTek, Winooski, Vt.).

Cells were harvested and the bioluminescence (in relative light units, RLU) for each sample is shown in Table 96. Transfection of these samples confirmed that the varied chemistries of luciferase mRNA is still able to express luciferase protein after PLGA microsphere formulation.

TABLE 96

| Chemical Modifications | | |
|---|---|---|
| Chemical Modifications | Sample ID | Biolum. (RLU) |
| Fully modified with 5-methylcytosine and N1-methyl pseudouridine | Deform contol | 164266.5 |
| | Unformul control | 113714 |
| | 43-66A | 25174 |
| | 43-66B | 25359 |
| | 43-66C | 20060 |
| 25% of uridine replaced with 2-thiouridine and 25% of cytosine replaced with 5-methylcytosine | Deform contol | 90816.5 |
| | Unformul control | 129806 |
| | 43-67A | 38329.5 |
| | 43-67B | 8471.5 |
| | 43-67C | 10991.5 |
| Fully modified with N1-methyl pseudouridine | Deform contol | 928093.5 |
| | Unformul control | 1512273.5 |
| | 43-69A | 1240299.5 |
| | 43-69B | 748667.5 |
| | 43-69C | 1193314 |
| Fully modified with pseudouridine | Deform contol | 154168 |
| | Unformul control | 151581 |
| | 43-68-1 | 120974.5 |
| | 43-68-2 | 107669 |
| | 43-68-3 | 97226 |

Example 64. In Vitro Studies of Factor IX

A. Serum-Free Media

Human Factor IX mRNA (mRNA sequence shown in SEQ ID NO: 8; polyA tail of approximately 160 nucleotides not shown in sequence; 5'cap, Cap1; fully modified with 5-methylcytosine and pseudouridine) was transfected in serum-free media. The cell culture supernatant was collected and subjected to trypsin digestion before undergoing 2-dimensional HPLC separation of the peptides. Matrix-assisted laser desorption/ionization was used to detect the peptides. 8 peptides were detected and 7 of the detected peptides are unique to Factor IX. These results indicate that the mRNA transfected in the serum-free media was able to express full-length Factor IX protein.

B. Human Embryonic Kidney (HEK) 293A Cells 250 ng of codon optimized Human Factor IX mRNA (mRNA sequence shown in SEQ ID NO: 8; fully modified with 5-methylcytosine and pseudouridine; polyA tail of approximately 160 nucleotides not shown in sequence; 5'cap, Cap1) was transfected into HEK 293A cells (150,000 cells/well) using Lipofectamine 2000 in DMEM in presence of 10% FBS. The transfection complexes were removed 3 hours after transfection. Cells were harvested at 3, 6, 9, 12, 24, 48 and 72 hours after transfection. Total RNA was isolated and used for cDNA synthesis. The cDNA was subjected to analysis by quantitative Real-Time PCR using codon optimized Factor IX specific primer set. Human hypoxanthine phosphoribosyltransfersase 1 (HPRT) level was used for normalization. The data is plotted as a percent of detectable mRNA considering the mRNA level as 100% at the 3 hour time point. The half-life of Factor IX modified mRNA fully modified with 5-methylcytosine and pseudouridine in human embryonic kidney 293 (HEK293) cells is about 8-10 hours.

Example 65. Saline Formulation: Subcutaneous Administration

Human G-CSF modified mRNA (mRNA sequence shown in SEQ ID NO: 4; polyA tail of approximately 160 nucleotides not shown in sequence; 5'cap, Cap1; fully modified with 5-methylcytosine and pseudouridine) and human EPO modified mRNA (mRNA sequence shown in SEQ ID NO: 7; polyA tail of approximately 160 nucleotides not shown in sequence; 5'cap, Cap1; fully modified with 5-methylcytosine and pseudouridine), were formulated in saline and delivered to mice via intramuscular (IM) injection at a dose of 100 ug.

Controls included Luciferase (mRNA sequence shown in SEQ ID NO: 14; polyA tail of approximately 160 nucleotides not shown in sequence; 5'cap, Cap1; fully modified with 5-methylcytosine and pseudouridine)) or the formulation buffer (F.Buffer). The mice were bled at 13 hours after the injection to determine the concentration of the human polypeptide in serum in pg/mL. (G-CSF groups measured human G-CSF in mouse serum and EPO groups measured human EPO in mouse serum). The data are shown in Table 97.

mRNA degrades rapidly in serum in the absence of formulation suggesting the best method to deliver mRNA to last longer in the system is by formulating the mRNA. As shown in Table 97, mRNA can be delivered subcutaneously using only a buffer formulation.

TABLE 97

| Dosing Regimen | | | | |
|---|---|---|---|---|
| Group | Treatment | Dose Vol. (µl/mouse) | Dosing Vehicle | Average Protein Product pg/mL, serum |
| G-CSF | G-CSF | 100 | F. buffer | 45 |
| G-CSF | Luciferase | 100 | F. buffer | 0 |
| G-CSF | F. buffer | 100 | F. buffer | 2.2 |
| EPO | EPO | 100 | F. buffer | 72.03 |
| EPO | Luciferase | 100 | F. buffer | 26.7 |
| EPO | F. buffer | 100 | F. buffer | 13.05 |

Example 66. Stability of Nanoparticle of Formulations

Formulations of DLin-KC2-DMA, Teta-5-Lap, DLin-DMA, DLin-K-DMA, C12-200, DLin-MC3-DMA at a lipid:mRNA ratio of 20:1 were evaluated for particle size, polydispersity index and encapsulation efficiency for stability at room temperature. Most nanoparticles are stable at room temperature for at least one month as shown in Tables 98 and 99.

TABLE 98

| Particle Size and Polydispersity Index | | | | | |
|---|---|---|---|---|---|
| Formulation # | Lipid | 0 hours | 24 hours | 48 hours | 30 days |
| NPA-003-4 | DLin-KC2-DMA | 112 nm PDI: 0.05 | 110 nm PDI: 0.06 | 103 nm PDI: 0.09 | 104 nm PDI: 0.08 |
| NPA-006-2 | Teta-5-Lap | 95 nm PDI: 0.09 | 95 nm PDI: 012 | 95 nm PDI: 0.10 | 100 nm PDI: 0.11 |
| NPA-012-1 | DLin-DMA | 90 nm PDI: 0.09 | 87 nm PDI: 0.07 | 89 nm PDI: 0.08 | 82 nm PDI: 0.08 |
| NPA-013-1 | DLin-K-DMA | 92 nm PDI: 0.07 | 91 nm PDI: 0.06 | 96 nm PDI: 0.05 | 91 nm PDI: 0.06 |
| NPA-014-1 | C12-200 | 99 nm PDI: 0.06 | 98 nm PDI: 0.09 | 99 nm PDI: 0.07 | 94 nm PDI: 0.07 |
| NPA-015-1 | DLin-MC3-DMA | 106 nm PDI: 0.07 | 100 nm PDI: 0.06 | 100 nm PDI: 0.05 | 99 nm PDI: 0.05 |

TABLE 99

Encapsulation Efficiency

| Formulation | | Time | | | |
|---|---|---|---|---|---|
| # | Lipid | 0 hours | 24 hours | 48 hours | 30 days |
| NPA-003-4 | DLin-KC2-DMA | 100% | 98% | 100% | 100% |
| NPA-006-2 | Teta-5-Lap | 99% | 100% | 100% | 100% |
| NPA-012-1 | DLin-DMA | 100% | 100% | 100% | 100% |
| NPA-013-1 | DLin-K-DMA | 83% | 85% | 96% | 100% |
| NPA-014-1 | C12-200 | 88% | 93% | 90% | 96% |
| NPA-015-1 | DLin-MC3-DMA | 100% | 99% | 100% | 100% |

Example 67. Intravitreal Delivery mCherry modified mRNA (mRNA sequence shown in SEQ ID NO: 5; polyA tail of approximately 160 nucleotides not shown in sequence; 5'cap, Cap1; fully modified with 5-methylcytosine and pseudouridine) and luciferase modified mRNA (mRNA sequence shown in SEQ ID NO: 14; polyA tail of approximately 160 nucleotides not shown in sequence; 5'cap, Cap1; fully modified with 5-methylcytosine and pseudouridine) formulated in saline was delivered intravitreally in rats as described in Table 100. The sample was compared against a control of saline only delivered intravitreally.

TABLE 100

Dosing Chart

| Group No. | Dose Level (µg modified RNA/eye) | Dose volume (µL/eye) | Treatment Right Eye (OD) | Treatment Left Eye (OS) |
|---|---|---|---|---|
| Control | 0 | 5 | Delivery buffer only | Delivery buffer only |
| Modified RNA in delivery buffer | 10 | 5 | mCherry | Luciferase |

The formulation will be administered to the left or right eye of each animal on day 1 while the animal is anesthetized. On the day prior to administration gentamicin ophthalmic ointment or solution was applied to both eyes twice. The gentamicin ophthalmic ointment or solution was also applied immediately following the injection and on the day following the injection. Prior to dosing, mydriatic drops (1% tropicamide and/or 2.5% phenylephrine) are applied to each eye.

18 hours post dosing the eyes receiving the dose of mCherry and delivery buffer are enucleated and each eye was separately placed in a tube containing 10 mL 4% paraformaldehyde at room temperature for overnight tissue fixation. The following day, eyes will be separately transferred to tubes containing 10 mL of 30% sucurose and stored at 21° C. until they were processed and sectioned. The slides prepared from different sections were evaluated under F-microscopy. Positive expression was seen in the slides prepared with the eyes administered mCherry modified mRNA and the control showed no expression.

Example 68. In Vivo Cytokine Expression Study

Mice were injected intramuscularly with 200 ug of G-CSF modified mRNA (mRNA sequence shown in SEQ ID NO: 4; polyA tail of approximately 160 nucleotides not shown in sequence) which was unmodified with a 5'cap, Cap1 (unmodified), fully modified with 5-methylcytosine and pseudouridine and a 5'cap, Cap1 (Gen1) or fully modified with 5-methylcytosine and N1-methylpseudouridine and a 5'cap, Cap1 (Gen2 cap) or no cap (Gen2 uncapped). Controls of R-848, 5% sucrose and untreated mice were also analyzed. After 8 hours serum was collected from the mice and analyzed for interferon-alpha (IFN-alpha) expression. The results are shown in Table 101.

TABLE 101

IFN-alpha Expression

| Formulation | IFN-alpha (pg/ml) |
|---|---|
| G-CSF unmodified | 67.012 |
| G-CSF Gen1 | 8.867 |
| G-CSF Gen2 cap | 0 |
| G-CSF Gen2 uncapped | 0 |
| R-848 | 40.971 |
| 5% sucrose | 1.493 |
| Untreated | 0 |

Example 69. In Vitro Expression of VEGF Modified mRNA

HEK293 cells were transfected with modified mRNA (mmRNA) VEGF-A (mRNA sequence shown in SEQ ID NO: 17; polyA tail of approximately 160 nucleotides not shown in sequence; 5'cap, Cap1; fully modified with 5-methylcytosine and pseudouridine) which had been complexed with Lipofectamine2000 from Invitrogen (Carlsbad, Calif.) at the concentration shown in Table 102. The protein expression was detected by ELISA and the protein (pg/ml) is shown in Table 102.

TABLE 102

Protein Expression

| | Amount Transfected | | | | | | | |
|---|---|---|---|---|---|---|---|---|
| | 10 ng | 2.5 ng | 625 pg | 156 pg | 39 pg | 10 pg | 2 pg | 610 fg |
| Protein (pg/ml) | 10495 | 10038 | 2321.23 | 189.6 | 0 | 0 | 0 | 0 |

Example 70. In Vitro Screening in HeLa Cells of GFP

The day before transfection, 20,000 HeLa cells (ATCC no. CCL-2; Manassas, Va.) were harvested by treatment with Trypsin-EDTA solution (LifeTechnologies, Grand Island, N.Y.) and seeded in a total volume of 100 ul EMEM medium (supplemented with 10% FCS and 1× Glutamax) per well in a 96-well cell culture plate (Corning, Manassas, Va.). The cells were grown at 37° C. in 5% $CO_2$ atmosphere overnight. Next day, 37.5 ng or 75 ng of Green Fluorescent protein (GFP) modified RNA (mRNA sequence shown in SEQ ID NO: 16; polyA tail of approximately 160 nucleotides not shown in sequence; 5'cap, Cap1) with the chemical modification described in Table 103, were diluted in 10 ul final volume of OPTI-MEM (LifeTechnologies, Grand Island, N.Y.). Lipofectamine 2000 (LifeTechnologies, Grand Island, N.Y.) was used as transfection reagent and 0.2 ul were diluted in 10 ul final volume of OPTI-MEM. After 5 minutes of incubation at room temperature, both solutions were combined and incubated an additional 15 minute at room temperature. Then the 20 ul combined solution was added to the 100 ul cell culture medium containing the HeLa cells and incubated at room temperature.

After a 18 to 22 hour incubation cells expressing luciferase were lysed with 100 ul of Passive Lysis Buffer (Promega, Madison, Wis.) according to manufacturer instructions. Aliquots of the lysates were transferred to white opaque polystyrene 96-well plates (Corning, Manassas, Va.) and combined with 100 ul complete luciferase assay solution (Promega, Madison, Wis.). The median fluorescence intensity (MFI) was determined for each chemistry and is shown in Table 103.

These results demonstrate that GFP fully modified with N1-methylpseudouridine and 5-methylcytosine produces more protein in HeLa cells compared to the other chemistry. Additionally the higher dose of GFP administered to the cells resulted in the highest MFI value.

TABLE 103

| Mean Fluorescence Intensity | | |
|---|---|---|
| Chemistry | 37.5 ng MFI | 75 ng MFI |
| No modifications | 97400 | 89500 |
| 5-methylcytosine/pseudouridine | 324000 | 715000 |
| 5-methylcytosine/N1-methylpseudouridine | 643000 | 1990000 |

Example 71. Toxicity Studies

A. Study Design

Sprague-Dawley rats (n=8, 4 male, 4 female) were administered by injection modified luciferase mRNA (mRNA sequence shown in SEQ ID NO: 14; polyA tail of approximately 160 nucleotides not shown in sequence; 5'cap, Cap1; fully modified with 5-methylcytosine and pseudouridine) as outlined in the dosing chart in Table 104. A control group were administered the formulation buffer (F. Buffer). After 7 days the rats were sacrificed.

TABLE 104

| Dosing Chart | | | |
|---|---|---|---|
| Formulation | mRNA Dose (ug) | Dose Volume (mL) | Dose Concentration (mg/mL) |
| Luciferase | 100 | 0.1 | 0 |
| Luciferase | 300 | 0.1 | 1.0 |

TABLE 104-continued

| Dosing Chart | | | |
|---|---|---|---|
| Formulation | mRNA Dose (ug) | Dose Volume (mL) | Dose Concentration (mg/mL) |
| Luciferase | 1000 | 0.1 | 3.0 |
| Luciferase | 3x1000 | 0.3 (each dose was 0.1) | 10 |
| F. Buffer | 0 | | 10 |

B. Weight Gain and Food Consumption

The rats were weighed before the administration of mRNA and 7 days after administration. Table 105 shows the mean weight gain and weight gain percent per group tested separated by gender. All animals continued to gain weight and behave normally. Each group analyzed consumed about the same amount of food over the course of the study.

TABLE 105

| Weight Gain | | |
|---|---|---|
| Group | Mean weight Gain (g) | Weight Gain (%) |
| 100 ug | 16.875 | 6.5 |
| 300 ug | 22.125 | 8.3 |
| 1000 ug | 19 | 6.95 |
| 3 x 1000 ug | 20.375 | 7.7 |
| F. Buffer | 18.75 | 6.8 |

C. Electrolytes

After 7 days the rats were sacrificed and samples were taken to determine electrolytes. The calcium, bicarbonate, potassium, phosphorus, chloride and sodium levels in each group were analyzed. The results are shown in Table 106. There was no change in electrolytes seen in the rats after 7 days.

TABLE 106

| Electrolytes | | | | | | |
|---|---|---|---|---|---|---|
| Group | Calcium (mg/dL) | Bicarbonate (mEg/L) | Potassium (mEg/L) | Phosphorus (mg/dL) | Chloride (mEg/L) | Sodium (mEg/L) |
| 100 ug | 9.8 | 19.9 | 4.7 | 8.3 | 101.0 | 139.6 |
| 300 ug | 9.8 | 23.3 | 4.4 | 8.2 | 100.5 | 139.6 |
| 1000 ug | 10.6 | 22.5 | 5.2 | 9.1 | 101.0 | 138.8 |
| 3 x 1000 ug | 10.2 | 22.6 | 4.6 | 8.11 | 100.4 | 138.8 |
| F. Buffer | 9.6 | 20.1 | 5.4 | 9.2 | 99.5 | 139.9 |

D. Hematology

After 7 days the rats were sacrificed and samples were taken to determine hematology levels. The red blood cell (RBC), hematocrit (HGT), mean corpuscular volume (MCV), hemoglobin (HGB), mean corpuscular hemoglobin (MCH) and mean corpuscular hemoglobin concentration (MCHC) was determined for each group. The results are shown in Table 107. There was no change in blood count or blood clotting factors 7 days after administration.

TABLE 107

Hematology

| Group | RBC (Million/uL) | HCT (%) | MCV (fL) | HGB (g/dL) | MCH (pg) | MCHC (g/dL) |
|---|---|---|---|---|---|---|
| 100 ug | 7.5 | 44.1 | 58.7 | 14.7 | 19.5 | 3.4 |
| 300 ug | 7.3 | 43.5 | 59.6 | 14.5 | 19.8 | 33.3 |
| 1000 ug | 7.2 | 42.5 | 58.8 | 14.2 | 19.55 | 33.3 |
| 3 × 1000 ug | 7.2 | 43.5 | 60.6 | 14.4 | 20.0 | 33.1 |
| F. Buffer | 8.0 | 46.6 | 58.0 | 15.5 | 19.3 | 33.4 |

E. White Blood Cells

After 7 days the rats were sacrificed and samples were taken to determine white blood cell count. Neutrophils (percent segmented neutrophils), monocytes, basophils, lymphocytes, eosinophil and white blood cell (WBC) was determined for each group. The results are shown in Table 108. In Table 108, "NT" means not tested. 7 days after administration there was no increase in white blood cells which suggests there was no inflammation.

TABLE 108

White Blood Cell

| Group | Neutrophil (NEU-SEG %) | Monocytes (MON %) | Basophils (BASO %) | Lymphocytes (LYM %) | Eosinophils (EOS %) | WBC (Thous./uL) |
|---|---|---|---|---|---|---|
| 100 ug | 10.6 | 2.0 | 0.4 | 85.9 | 1.3 | 14 |
| 300 ug | 12.0 | 2.8 | 0.4 | 83.6 | 1.0 | 10.2 |
| 1000 ug | 12.8 | 2.3 | NT | 83.0 | 1.5 | 10.7 |
| 3 × 1000 ug | 11.6 | 2.0 | 0.1 | 85.5 | 0.9 | 10.9 |
| F. Buffer | 16.6 | 2.3 | 0.9 | 79.6 | 0.9 | 13.0 |

F. Serum Chemistry

After 7 days the rats were sacrificed and samples were taken to determine serum chemistry. The alkaline phosphatase (ALP), aspartate transaminase (AST), alanine transaminase (ALT) and creatine phosphokinase (CPK) was determined for each group. The results are shown in Table 109.

TABLE 109

Serum Chemistry

| Group | ALP (IU/L) | AST (IU/L) | ALT (IU/L) | CPK (IU/L) |
|---|---|---|---|---|
| 100 ug | 144.4 | 198.3 | 60.8 | 488.1 |
| 300 ug | 169.5 | 200.3 | 49.3 | 968.3 |
| 1000 ug | 150.5 | 189.8 | 51.5 | 744 |
| 3 × 1000 ug | 152.0 | 14.3 | 45.9 | 481.1 |
| F. Buffer | 183 | 170.4 | 62.8 | 589.8 |

G. Liver Proteins

After 7 days the rats were sacrificed and samples were taken to determine liver protein levels. The level of albumin, globulin and total protein was determined for each group. The results are shown in Table 110. There was no change seen in liver enzyme or liver protein production 7 days after administration with the modified mRNA.

TABLE 110

Hematology

| Group | Albumin (g/dL) | Globulin (g/dL) | Total Protein (g/dL) |
|---|---|---|---|
| 100 ug | 3.3 | 2.5 | 5.8 |
| 300 ug | 3.2 | 2.4 | 5.6 |
| 1000 ug | 3.2 | 2.7 | 5.9 |
| 3 × 1000 ug | 3.4 | 2.6 | 6.0 |
| F. Buffer | 3.6 | 2.6 | 6.2 |

H. Conclusions

From the analysis of the rats 7 days after administration with the modified mRNA, administration of high doses of mRNA do not result in adverse effects. Doses as high as 30 times the effective dose appear to be safe from this analysis. Histopathology showed only minimal inflammation at the site of injection and the site of injection showed only changes consistent with injection and nothing to suggest dose related issues. Additionally there was no chance in muscle enzymes to suggest there was muscle damage.

Example 72. Storage Conditions for Modified RNA

A. Organics

To evaluate the ability of mRNA to withstand an organic environment, luciferase mRNA (mRNA sequence shown in SEQ ID NO: 14; polyA tail of approximately 160 nucleotides not shown in sequence; 5'cap, Cap1; fully modified with 5-methylcytosine and pseudouridine) was stored at room temperature in solutions of ethanol, methanol or dichloromethane at a concentration of 1 mg/ml. Samples were collected at 1 hour, 6 hours and 1 day. The sample was diluted with water to 200 ng/ul and incubated overnight at room temperature in a fume hood to evaporate off the organic solvent. Control samples were completed in parallel with mRNA in water (Water control, organic). The mRNA was stable at room temperature for 1 day in each of the three solutions as determined by running samples on a bioanalyzer.

B. Aqueous Solvent

Luciferase mRNA (mRNA sequence shown in SEQ ID NO: 14; polyA tail of approximately 160 nucleotides not shown in sequence; 5'cap, Cap1; fully modified with pseudouridine and 5-methylcytosine) was added to 3 different buffers and water to evaluate the effect of aqueous solvents on mRNA stability. mRNA was added to citrate buffer (pH3, 100 mM citric acid), phosphate buffered saline (PBS) buffer (pH 7.4, 6.7 mM phosphate and 154 mM sodium chloride), TE buffer (pH 8, 10 mM Tris-hydrochloric acid and 1 mM ethylenediaminetetraacetic acid) or water (pH 5.5, water for injection (WFI)) at 1 mg/ml. Samples were collected at 1 hour, 6 hours and 1 day and diluted with water to a concentration of 200 ng/ul. Control samples were completed in parallel with mRNA in water (Water control, aqueous). The incubation of mRNA in the PBS buffer, TE buffer and water did not affect the mRNA integrity after 1 day. Samples incubated in citrate were not detectable by bioanalyzer.

In additional studies to evaluate the citrate buffer, citrate buffer at a pH of 2, 3 and 4 each having 10 mM citrate and 1 mg/ml of luciferase mRNA (mRNA sequence shown in SEQ ID NO: 14; polyA tail of approximately 160 nucleotides not shown in sequence; 5'cap, Cap1; fully modified with pseudouridine and 5-methylcytosine) were evaluated. At a pH of 2 precipitation was visually detected and mRNA was not detected by bioanalyzer below a pH of 4. When compared against phosphate buffer, mRNA was not detected in samples with low pH and precipitation was visible in phosphate buffer samples having a pH of 2.

C. pH

In order to study the effects of pH on the stability of mRNA, luciferase mRNA (mRNA sequence shown in SEQ ID NO: 14; polyA tail of approximately 160 nucleotides not shown in sequence; 5'cap, Cap1; fully modified with pseudouridine and 5-methylcytosine) was stored at room temperature in aqueous buffers having a pH of 5.8, 6.5 or 7.2. Samples were collected at 1 hour, 1 day and 1 week after the mRNA was added to the pH sample. After collection the samples were incubated at 1 mg/ml concentration and then diluted to 200 ng/ul with water before freezing and characterizing by bioanalyzer. The mRNA was stable after 1 week of storage at room temperature in the pH range of 5.8-7.2 evaluated.

D. Freeze/thaw and Lyophilization

To evaluate the effect of freeze/thaw cycles on mRNA stability, luciferase mRNA (mRNA sequence shown in SEQ ID NO: 14; polyA tail of approximately 160 nucleotides not shown in sequence; 5'cap, Cap1; fully modified with 5-methylcytosine and pseudouridine) in formulation buffer was subjected to numerous freeze/thaw cycles. mRNA was found to be stable for at least 18 cycles.

In addition, luciferase mRNA (mRNA SEQ ID NO: 14; polyA tail of approximately 160 nucleotides not shown in sequence; 5'cap, Cap1; fully modified with 5-methylcytosine and pseudouridine) was subjected to 3 rounds of lyophilization to test the stability of the mRNA. mRNA was added to water and samples were collected after each of the 3 rounds of lyophilization. The dried mRNA was diluted with water to reach a concentration of 1 mg/ml. The samples were stored frozen until bioanalyzer characterization at 200 ng/ul. Control samples were completed in parallel with mRNA and water formulations and followed the same freezing and thawing cycles. The mRNA was found to be stable after 3 cycles of lyophilization when analyzed by bioanalyzer characterization at 200 ng/ul.

E. Centrifugation

To evaluate the effects of centrifugation on mRNA integrity, luciferase mRNA (mRNA sequence shown in SEQ ID NO: 14; polyA tail of approximately 160 nucleotides not shown in sequence; 5'cap, Cap1; 5-methylcytosine and pseudouridine) in water at 1 mg/ml was exposed to 10 cycles of 10 k RPM (13.3 k×g) for 10 minutes at 4° C. mRNA and water samples were stored at 4° C. as a control during centrifugation. After 10 cycles of centrifugation the mRNA was still stable when analyzed by bioanalyzer characterization at 200 ng/ul.

F. In Vitro Transfection After Storage

The day before transfection, 20,000 HeLa cells (ATCC no. CCL-2; Manassas, Va.) were harvested by treatment with Trypsin-EDTA solution (LifeTechnologies, Grand Island, N.Y.) and seeded in a total volume of 100 ul EMEM medium (supplemented with 10% FCS and 1× Glutamax) per well in a 96-well cell culture plate (Corning, Manassas, Va.). The cells were grown at 37° C. in a 5% CO2 atmosphere overnight. The next day, 250 ng of luciferase mRNA from the formulations of the lyophilized, centrifuged, organic and aqueous solvent samples were diluted in a 10 ul final volume of OPTI-MEM (LifeTechnologies, Grand Island, N.Y.). Lipofectamine 2000 (LifeTechnologies, Grand Island, N.Y.) was used as a transfection reagent and 0.2 ul was diluted in a 10 ul final volume of OPTI-MEM. After 5 min of incubation at room temperature, both solutions were combined and incubated an additional 15 min at room temperature. Then 20 ul of the combined solution was added to 100 ul of cell culture medium containing the HeLa cells. The plates were then incubated as described before.

After 18 h to 22 h incubation, cells expressing luciferase were lysed with 100 ul Passive Lysis Buffer (Promega, Madison, Wis.) according to manufacturer instructions. Aliquots of the lysates were transferred to white opaque polystyrene 96-well plates (Corning, Manassas, Va.) and combined with 100 ul complete luciferase assay solution (Promega, Madison, Wis.). The background signal of the plates without reagent was about 200 relative light units per well. The plate reader was a BioTek Synergy H1 (BioTek, Winooski, Vt.).

Controls of mock transfection (transfection reagent alone), luciferase mRNA control in water, and untreated were also evaluated. Cells were harvested and the bioluminescence average (in relative light units, RLU) for each signal is shown in Table 111. Transfection of these samples confirmed that lyophilization, centrifugation, organic solvents and aqueous solvents except citrate buffer did not impact the activity of luciferase mRNA. Citrate buffer showed a reduced activity after transfection.

TABLE 111

| Bioluminescence | |
|---|---|
| Sample | Bioluminescence (RLU) |
| 1 lyophilization | 2832350 |
| 1 lyophilization control | 3453250 |
| 2 lyophilizations | 2480000 |
| 2 lyophilizations control | 3716130 |
| 3 lyophilizations | 1893960 |
| 3 lyophilizations control | 3009020 |
| Centrifugation, 10 cycles | 3697590 |
| Centrifugation control | 5472920 |
| Ethanol, 1 day | 4214780 |
| Methanol, 1 day | 2834520 |
| Dichloromethane, 1 day | 3017890 |
| Water control, organic, 1 day | 2641450 |
| Citrate buffer, 1 hour | 280160 |
| PBS buffer, 1 hour | 2762050 |
| TE buffer, 1 hour | 3141250 |
| Water control, aqueous, 1 hour | 3394000 |
| Citrate buffer, 1 day | 269790 |
| PBS buffer, 1 day | 4084330 |
| TE buffer, 1 day | 5344400 |
| Water control, aqueous, 1 day | 3579270 |
| Untreated | 5580 |
| Mock Transfection | 7560 |
| Luciferase mRNA control | 4950090 |

Example 73. Homogenization

Different luciferase mRNA solutions (as described in Table 112 where "X" refers to the solution containing that component) (mRNA sequence shown in SEQ ID NO: 14; polyA tail of approximately 160 nucleotides not shown in sequence; 5'cap, Cap1; fully modified with 5-methylcytosine and pseudouridine) were evaluated to test the percent yield of the different solutions, the integrity of the mRNA by bioanalyzer, and the protein expression of the mRNA by in vitro transfection. The mRNA solutions were prepared in water, 1×TE buffer at 4 mg/ml as indicated in Table 112, and added to either dichloromethane (DCM) or DCM containing 200 mg/ml of poly(lactic-co-glycolic acid) (PLGA) (Lactel, Cat# B6010-2, inherent viscosity 0.55-0.75, 50:50 LA:GA) to achieve a final mRNA concentration of 0.8 mg/ml. The solutions requiring homogenization were homogenized for 30 seconds at speed 5 (approximately 19,000 rpm) (IKA Ultra-Turrax Homogenizer, T18). The mRNA samples in water, dicloromethane and poly(lactic-co-glycolic acid) (PLGA) were not recoverable (NR). All samples, except the NR samples, maintained integrity of the mRNA as determined by bioanalyzer (Bio-rad Experion).

The day before transfection, 20,000 HeLa cells (ATCC no. CCL-2; Manassas, Va.) were harvested by treatment with Trypsin-EDTA solution (LifeTechnologies, Grand Island, N.Y.) and seeded in a total volume of 100 ul EMEM medium (supplemented with 10% FCS and 1× Glutamax) per well in a 96-well cell culture plate (Corning, Manassas, Va.). The cells were grown at 37° C. in a 5% CO2 atmosphere overnight. The next day, 250 ng of luciferase mRNA from the recoverable samples was diluted in a 10 ul final volume of OPTI-MEM (LifeTechnologies, Grand Island, N.Y.). Lipofectamine 2000 (LifeTechnologies, Grand Island, N.Y.) was used as a transfection reagent and 0.2 ul was diluted in a 10 ul final volume of OPTI-MEM. After 5 minutes of incubation at room temperature, both solutions were combined and incubated an additional 15 minutes at room temperature. Then 20 ul of the combined solution was added to 100 ul of cell culture medium containing the HeLa cells. The plates were then incubated as described before. Controls luciferase mRNA (luciferase mRNA formulated in saline) (Control) and untreated cells (Untreat.) were also evaluated. Cells were harvested and the bioluminescence average (in photons/second) (biolum. (p/s)) for each signal is also shown in Table 112. The recoverable samples all showed activity of luciferase mRNA when analyzed.

After 18 to 22 hour incubation, cells expressing luciferase were lysed with 100 ul Passive Lysis Buffer (Promega, Madison, Wis.) according to manufacturer instructions. Aliquots of the lysates were transferred to white opaque polystyrene 96-well plates (Corning, Manassas, Va.) and combined with 100 ul complete luciferase assay solution (Promega, Madison, Wis.). The background signal of the plates without reagent was about 200 relative light units per well. The plate reader was a BioTek Synergy H1 (BioTek, Winooski, Vt.).

Cells were harvested and the bioluminescence average (in relative light units, RLU) (biolum. (RLU)) for each signal is also shown in Table 110. The recoverable samples all showed activity of luciferase mRNA when analyzed.

TABLE 112

Solutions

| Solution No. | Water | 1x TE Buffer | DCM | DCM/PLGA | Homogenizer | Yield (%) | Biolum. (RLU) |
|---|---|---|---|---|---|---|---|
| 1 | X | | | | | 96 | 5423780 |
| 2 | | X | | | X | 95 | 4911950 |
| 3 | X | | | | X | 92 | 2367230 |
| 4 | | X | | | X | 90 | 4349410 |
| 5 | X | | X | | X | 66 | 4145340 |
| 6 | | X | X | | X | 71 | 3834440 |
| 7 | X | | | X | X | NR | n/a |
| 8 | | X | | X | X | 24 | 3182080 |
| 9 | X | | | X | | NR | n/a |
| 10 | | X | | X | | 79 | 3276800 |
| 11 | X | | X | | | 79 | 5563550 |
| 12 | | X | X | | | 79 | 4919100 |
| Control | | | | | | | 2158060 |
| Untreat. | | | | | | | 3530 |

Example 74. TE Buffer and Water Evaluation

Luciferase mRNA (mRNA sequence shown in SEQ ID NO: 14; polyA tail of approximately 160 nucleotides not shown in sequence; 5'cap, Cap1; fully modified with 5-methylcytosine and pseudouridine) was reconstituted in water or TE buffer as outlined in Table 113 and then formulated in PLGA microspheres. PLGA microspheres were synthesized using the water/oil/water double emulsification methods known in the art using PLGA (Lactel, Cat# B6010-2, inherent viscosity 0.55-0.75, 50:50 LA:GA), polyvinylalcohol (PVA) (Sigma, Cat#348406-25G, MW 13-23 k) dichloromethane and water. Briefly, 0.2 to 0.6 ml of mRNA in water or TE buffer at a concentration of 2 to 6 mg/ml (W1) was added to 2 ml of PLGA dissolved in dichloromethane (DCM) (O1) at a concentration of 100 mg/ml of PLGA. The W1/O1 emulsion was homogenized (IKA Ultra-Turrax Homogenizer, T18) for 30 seconds at speed 5 (~19,000 rpm). The W1/O1 emulsion was then added to 250 ml 1% PVA (W2) and homogenized for 1 minute at speed 5 (~19,000 rpm). Formulations were left to stir for 3 hours, then passed through a 100 µm nylon mesh strainer (Fisherbrand Cell Strainer, Cat #22-363-549) to remove larger aggregates, and finally washed by centrifugation (10 min, 9,250 rpm, 4° C.). The supernatant was discarded and the PLGA pellets were resuspended in 5-10 ml of water, which was repeated 2×. The washed formulations were frozen in liquid nitrogen and then lyophilized for 2-3 days. After lyophilization, ~10 mg of PLGA MS were weighed out in 2 ml eppendorf tubes and deformulated by adding 1 ml of DCM and letting the samples shake for 2-6 hrs. mRNA was extracted from the deformulated PLGA micropsheres by adding 0.5 ml of water and shaking the sample overnight. Unformulated luciferase mRNA in water or TE buffer (deformulation controls) was spiked into DCM and went through the deformulation process to be used as controls in the transfection assay.

The day before transfection, 20,000 HeLa cells (ATCC no. CCL-2; Manassas, Va.) were harvested by treatment with Trypsin-EDTA solution (LifeTechnologies, Grand Island, N.Y.) and seeded in a total volume of 100 ul EMEM medium (supplemented with 10% FCS and 1× Glutamax) per well in a 96-well cell culture plate (Corning, Manassas, Va.). The cells were grown at 37° C. in a 5% CO2 atmosphere overnight. The next day, 100 ng of the deformulated luciferase mRNA samples was diluted in a 10 ul final volume of OPTI-MEM (LifeTechnologies, Grand Island, N.Y.). Lipofectamine 2000 (LifeTechnologies, Grand Island, N.Y.) was used as a transfection reagent and 0.2 ul was diluted in a 10 ul final volume of OPTI-MEM. After 5 minutes of incubation at room temperature, both solutions were combined and incubated an additional 15 minutes at room temperature. Then 20 ul of the combined solution was added to 100 ul of cell culture medium containing the HeLa cells. The plates were then incubated as described before.

After 18 to 22 hour incubation, cells expressing luciferase were lysed with 100 ul Passive Lysis Buffer (Promega, Madison, Wis.) according to manufacturer instructions. Aliquots of the lysates were transferred to white opaque polystyrene 96-well plates (Corning, Manassas, Va.) and combined with 100 ul complete luciferase assay solution (Promega, Madison, Wis.). The background signal of the plates without reagent was about 200 relative light units per well. The plate reader was a BioTek Synergy H1 (BioTek, Winooski, Vt.). To determine the activity of the luciferase mRNA from each formulation, the relative light units (RLU) for each formulation was divided by the RLU of the appropriate mRNA deformulation control (mRNA in water or TE buffer). Table 113 shows the activity of the luciferase mRNA. The activity of the luciferase mRNA in the PLGA microsphere formulations (Form.) was substantially improved by formulating in TE buffer versus water.

TABLE 113

| | | Formulations | | | | | |
|---|---|---|---|---|---|---|---|
| Form. | mRNA conc. (mg/ml) | W1 Solvent volume (ul) | Total mRNA (ug) | Theoretical mRNA Loading (wt %) | Actual mRNA Loading (wt %) | W1 Solvent | Activity (% of de-formulation control) |
| PLGA A | 4 | 400 | 1600 | 0.80 | 0.14 | Water | 12.5% |
| PLGA B | 4 | 200 | 800 | 0.40 | 0.13 | Water | 1.3% |
| PLGA C | 4 | 600 | 2400 | 1.20 | 0.13 | Water | 12.1% |
| PLGA D | 2 | 400 | 800 | 0.40 | 0.07 | Water | 1.3% |
| PLGA E | 6 | 400 | 2400 | 1.20 | 0.18 | TE Buffer | 38.9% |
| PLGA F | 4 | 400 | 1600 | 0.80 | 0.16 | TE Buffer | 39.7% |
| PLGA G | 4 | 400 | 1600 | 0.80 | 0.10 | TE Buffer | 26.6% |

Example 75. Chemical Modifications on mRNA

The day before transfection, 20,000 HeLa cells (ATCC no. CCL-2; Manassas, Va.) were harvested by treatment with Trypsin-EDTA solution (Life Technologies, Grand Island, N.Y.) and seeded in a total volume of 100 ul EMEM medium (supplemented with 10% FCS and 1× Glutamax) per well in a 96-well cell culture plate (Corning, Manassas, Va.). The cells were grown at 37° C. in 5% CO2 atmosphere overnight. The next day, 83 ng of Luciferase modified RNA (mRNA sequence shown SEQ ID NO: 14; polyA tail of approximately 140 nucleotides not shown in sequence; 5'cap, Cap1) with the chemical modification described in Table 114, were diluted in 10 ul final volume of OPTI-MEM (LifeTechnologies, Grand Island, N.Y.). Lipofectamine 2000 (LifeTechnologies, Grand Island, N.Y.) was used as transfection reagent and 0.2 ul were diluted in 10 ul final volume of OPTI-MEM. After 5 minutes of incubation at room temperature, both solutions were combined and incubated an additional 15 minute at room temperature. Then the 20 ul combined solution was added to the 100 ul cell culture medium containing the HeLa cells and incubated at room temperature.

After 18 to 22 hours of incubation cells expressing luciferase were lysed with 100 ul of Passive Lysis Buffer (Promega, Madison, Wis.) according to manufacturer instructions. Aliquots of the lysates were transferred to white opaque polystyrene 96-well plates (Corning, Manassas, Va.) and combined with 100 ul complete luciferase assay solution (Promega, Madison, Wis.). The lysate volumes were adjusted or diluted until no more than 2 mio relative light units (RLU) per well were detected for the strongest signal producing samples and the RLUs for each chemistry tested are shown in Table 114. The plate reader was a BioTek Synergy H1 (BioTek, Winooski, Vt.). The background signal of the plates without reagent was about 200 relative light units per well.

TABLE 114

| Chemical Modifications | |
|---|---|
| Sample | RLU |
| Untreated | 336 |
| Unmodified Luciferase | 33980 |
| 5-methylcytosine and pseudouridine | 1601234 |
| 5-methylcytosine and N1-methylpseudouridine | 421189 |
| 25% cytosines replaced with 5-methylcytosine and 25% of uridines replaced with 2-thiouridine | 222114 |

TABLE 114-continued

| Chemical Modifications | |
|---|---|
| Sample | RLU |
| N1-methylpseudouridine | 3068261 |
| Pseudouridine | 140234 |
| N4-Acetylcytidine | 1073251 |
| 5-methoxyuridine | 219657 |
| 5-Bromouridine | 6787 |
| N4-Acetylcytidine and N1-methylpseudouridine | 976219 |
| 5-methylcytosine and 5-methoxyuridine | 66621 |
| 5-methylcytosine and 2'fluorouridine | 11333 |

Example 76. Intramuscular and Subcutaneous Administration of Modified mRNA

Luciferase modified mRNA (mRNA sequence shown in SEQ ID NO: 14; polyA tail of approximately 140 nucleotides not shown in sequence; 5'cap, Cap1) fully modified with 5-methylcytosine and pseudouridine (5 mC/pU), fully modified with 5-methylcytosine and N1-methylpseudouridine (5 mC/N1mpU), fully modified with pseudouridine (pU), fully modified with N1-methylpseudouridine (N1mpU) or modified where 25% of the cytosines replaced with 5-methylcytosine and 25% of the uridines replaced with 2-thiouridine (5mC/s2U) formulated in PBS (pH 7.4) was administered to Balb-C mice intramuscularly or subcutaneously at a dose of 2.5 mg/kg. The mice were imaged at 2 hours, 8 hours, 24 hours, 48 hours, 72 hours, 96 hours, 120 hours and 144 hours for intramuscular delivery and 2 hours, 8 hours, 24 hours, 48 hours, 72 hours, 96 hours and 120 hours for subcutaneous delivery. Twenty minutes prior to imaging, mice were injected intraperitoneally with a D-luciferin solution at 150 mg/kg. Animals were then anesthetized and images were acquired with an IVIS Lumina II imaging system (Perkin Elmer). Bioluminescence was measured as total flux (photons/second) of the entire mouse. The average total flux (photons/second) for intramuscular administration is shown in Table 115 and the average total flux (photons/second) for subcutaneous administration is shown in Table 116. The background signal was 3.79E+05 (p/s). The peak expression for intramuscular administration was seen between 24 and 48 hours for all chemistry and expression was still detected at 144 hours. For subcutaneous delivery the peak expression was seen at 2-8 hours and expression was detected at 72 hours.

TABLE 115

Intramuscular Administration

| | 5mC/pU Flux (p/s) | 5mC/N1mpU Flux (p/s) | 5mC/s2U Flux (p/s) | pU Flux (p/s) | N1mpU Flux (p/s) |
|---|---|---|---|---|---|
| 2 hours | 1.98E+07 | 4.65E+06 | 4.68E+06 | 2.33E+06 | 3.66E+07 |
| 8 hours | 1.42E+07 | 3.64E+06 | 3.78E+06 | 8.07E+06 | 7.21E+07 |
| 24 hours | 2.92E+07 | 1.22E+07 | 3.35E+07 | 1.01E+07 | 1.75E+08 |
| 48 hours | 2.64E+07 | 1.01E+07 | 5.06E+07 | 7.46E+06 | 3.42E+08 |
| 72 hours | 2.18E+07 | 8.59E+06 | 3.42E+07 | 4.08E+06 | 5.83E+07 |
| 96 hours | 2.75E+07 | 2.70E+06 | 2.38E+07 | 4.35E+06 | 7.15E+07 |
| 120 hours | 2.19E+07 | 1.60E+06 | 1.54E+07 | 1.25E+06 | 3.87E+07 |
| 144 hours | 9.17E+06 | 2.19E+06 | 1.14E+07 | 1.86E+06 | 5.04E+07 |

TABLE 116

Subcutaneous Administration

| | 5mC/pU Flux (p/s) | 5mC/N1mpU Flux (p/s) | 5mC/s2U Flux (p/s) | pU Flux (p/s) | N1mpU Flux (p/s) |
|---|---|---|---|---|---|
| 2 hours | 5.26E+06 | 4.54E+06 | 9.34E+06 | 2.43E+06 | 2.80E+07 |
| 8 hours | 2.32E+06 | 8.75E+05 | 8.15E+06 | 2.12E+06 | 3.09E+07 |
| 24 hours | 2.67E+06 | 5.49E+06 | 3.80E+06 | 2.24E+06 | 1.48E+07 |
| 48 hours | 1.22E+06 | 1.77E+06 | 3.07E+06 | 1.58E+06 | 1.24E+07 |
| 72 hours | 1.12E+06 | 8.00E+05 | 8.53E+05 | 4.80E+05 | 2.29E+06 |
| 96 hours | 5.16E+05 | 5.33E+05 | 4.30E+05 | 4.30E+05 | 6.62E+05 |
| 120 hours | 3.80E+05 | 4.09E+05 | 3.21E+05 | 6.82E+05 | 5.05E+05 |

Example 77. Osmotic Pump Study

Prior to implantation, an osmotic pump (ALZET® Osmotic Pump 2001D, DURECT Corp. Cupertino, Calif.) is loaded with the 0.2 ml of 1×PBS (pH 7.4) (PBS loaded pump) or 0.2 ml of luciferase modified mRNA (mRNA sequence shown in SEQ ID NO: 14; polyA tail of approximately 140 nucleotides not shown in sequence; 5'cap, Cap1; fully modified with 5-methylcytosine and N1-methylpseudouridine) at 1 mg/ml in 1×PBS (pH 7.4) (Luciferase loaded pump) and incubated overnight in 1×PBS (pH 7.4) at 37° C.

Balb-C mice (n=3) are implanted subcutaneously with either the PBS loaded pump or the luciferase loaded pump and imaged at 2 hours, 8 hours and 24 hours. As a control a PBS loaded pump is implanted subcutaneously and the mice are injected subcutaneously with luciferase modified mRNA in 1×PBS (PBS loaded pump; SC Luciferase) or an osmotic pump is not implanted and the mice are injected subcutaneously with luciferase modified mRNA in 1×PBS (SC Luciferase). The luciferase formulations are outlined in Table 117

TABLE 117

Luciferase Formulations

| Group | Vehicle | Conc (mg/ml) | Inj. Vol. (ul) | Amt (ug) | Dose (mg/kg) |
|---|---|---|---|---|---|
| PBS loaded pump; SC Luciferase | PBS | 1.00 | 50 | 50 | 2.5 |
| Luciferase loaded pump | PBS | 1.00 | — | 200 | 10.0 |
| PBS loaded pump | PBS | — | — | — | — |
| SC Luciferase | PBS | 1.00 | 50 | 50 | 2.5 |

Example 78. External Osmotic Pump Study

An external osmotic pump (ALZET® Osmotic Pump 2001D, DURECT Corp. Cupertino, Calif.) is loaded with the 0.2 ml of 1×PBS (pH 7.4) (PBS loaded pump) or 0.2 ml of luciferase modified mRNA (mRNA sequence shown in SEQ ID NO: 14; polyA tail of approximately 140 nucleotides not shown in sequence; 5'cap, Cap1; fully modified with 5-methylcytosine and N1-methylpseudouridine) at 1 mg/ml in 1×PBS (pH 7.4) (luciferase loaded pump) and incubated overnight in 1×PBS (pH 7.4) at 37° C.

Using a catheter connected to the external PBS loaded pump or the luciferase loaded pump Balb-C mice (n=3) are administered the formulation. The mice are imaged at 2 hours, 8 hours and 24 hours. As a control an external PBS loaded pump is used and the mice are injected subcutaneously with luciferase modified mRNA in 1×PBS (PBS loaded pump; SC Luciferase) or the external pump is not used and the mice are only injected subcutaneously with luciferase modified mRNA in 1×PBS (SC Luciferase). Twenty minutes prior to imaging, mice are injected intraperitoneally with a D-luciferin solution at 150 mg/kg. Animals are then anesthetized and images are acquired with an IVIS Lumina II imaging system (Perkin Elmer). Bioluminescence is measured as total flux (photons/second) of the entire mouse. The luciferase formulations are outlined in Table 118 and the average total flux (photons/second).

TABLE 118

Luciferase Formulations

| Group | Vehicle | Conc (mg/ml) | Inj. Vol. (ul) | Amt (ug) | Dose (mg/kg) |
|---|---|---|---|---|---|
| PBS loaded pump; SC Luciferase | PBS | 1.00 | 50 | 50 | 2.5 |

TABLE 118-continued

Luciferase Formulations

| Group | Vehicle | Conc (mg/ml) | Inj. Vol. (ul) | Amt (ug) | Dose (mg/kg) |
|---|---|---|---|---|---|
| Luciferase loaded pump | PBS | 1.00 | — | 200 | 10.0 |
| PBS loaded pump | PBS | — | — | — | — |
| SC Luciferase | PBS | 1.00 | 50 | 50 | 2.5 |

Example 79. Fibrin Sealant Study

Fibrin sealant, such as Tisseel (Baxter Healthcare Corp., Deerfield, Ill.), is composed of fibrinogen and thrombin in a dual-barreled syringe. Upon mixing, fibrinogen is converted to fibrin to form a fibrin clot in about 10 to 30 seconds. This clot can mimic the natural clotting mechanism of the body. Additionally a fibrin hydrogel is a three dimensional structure that can potentially be used in sustained release delivery. Currently, fibrin sealant is approved for application in hemostasis and sealing to replace conventional surgical techniques such as suture, ligature and cautery.

The thrombin and fibrinogen components were loaded separately into a dual barreled syringe. Balb-C mice (n=3) were injected subcutaneously with 50 ul of fibrinogen, 50 ul of thrombin and they were also injected at the same site with modified luciferase mRNA (mRNA sequence shown in SEQ ID NO: 14; polyA tail of approximately 140 nucleotides not shown in sequence; 5'cap, Cap1; fully modified with 5-methylcytosine and N1-methylpseudouridine) (Tisseel+Luciferase), 50 ul of fibrinogen and 50 ul thrombin (Tisseel) or modified luciferase mRNA (Luciferase). The injection of fibrinogen and thrombin was done simultaneously using the dual-barreled syringe. The subcutaneous injection of luciferase was done 15 minutes after the fibrinogen/thrombin injection to allow the fibrin hydrogel to polymerize (Tisseel+Luciferase group). A control group of untreated mice were also evaluated. The mice were imaged at 5 hours and 24 hours. Twenty minutes prior to imaging, mice were injected intraperitoneally with a D-luciferin solution at 150 mg/kg. Animals were then anesthetized and images were acquired with an IVIS Lumina II imaging system (Perkin Elmer). Bioluminescence was measured as total flux (photons/second) of the entire mouse. The luciferase formulations are outlined in Table 119 and the average total flux (photons/second) is shown in Table 120. The fibrin sealant was found to not interfere with imaging and the injection of luciferase and Tisseel showed expression of luciferase.

TABLE 119

Luciferase Formulations

| Group | Vehicle | Conc (mg/ml) | Inj. Vol. (ul) | Amt (ug) | Dose (mg/kg) |
|---|---|---|---|---|---|
| Tisseel + Luciferase | PBS | 1.00 | 50 | 50 | 2.5 |
| Tisseel | — | — | — | — | — |
| Luciferase | PBS | 1.00 | 50 | 50 | 2.5 |
| Untreated | — | — | — | — | — |

TABLE 120

Total Flux

| Group | 5 Hours Flux (p/s) | 24 Hours Flux (p/s) |
|---|---|---|
| Tisseel + Luciferase | 4.59E+05 | 3.39E+05 |
| Tisseel | 1.99E+06 | 1.06E+06 |
| Luciferase | 9.94E+05 | 7.44E+05 |
| Untreated | 3.90E+05 | 3.79E+05 |

Example 80. Fibrin Containing mRNA Sealant Study

A. Modified mRNA and Calcium Chloride

Prior to reconstitution, luciferase mRNA (mRNA sequence shown in SEQ ID NO: 14; polyA tail of approximately 140 nucleotides not shown in sequence; 5'cap, Cap1) fully modified with 5-methylcytosine and N1-methylpseudouridine or fully modified with N1-methylpseudouridine is added to calcium chloride. The calcium chloride is then used to reconstitute thrombin. Fibrinogen is reconstituted with fibrinolysis inhibitor solution per the manufacturer's instructions. The reconstituted thrombin containing modified mRNA and fibrinogen is loaded into a dual barreled syringe. Mice are injected subcutaneously with 50 ul of fibrinogen and 50 ul of thrombin containing modified mRNA or they were injected with 50 ul of PBS containing an equivalent dose of modified luciferase mRNA. A control group of untreated mice is also evaluated. The mice are imaged at predetermined intervals to determine the average total flux (photons/second).

B. Lipid Nanoparticle Formulated Modified mRNA and Calcium Chloride

Prior to reconstitution, luciferase mRNA (mRNA sequence shown in SEQ ID NO: 14; polyA tail of approximately 140 nucleotides not shown in sequence; 5'cap, Cap1) fully modified with 5-methylcytosine and N1-methylpseudouridine or fully modified with N1-methylpseudouridine is formulated in a lipid nanoparticle is added to calcium chloride. The calcium chloride is then used to reconstitute thrombin. Fibrinogen is reconstituted with fibrinolysis inhibitor solution per the manufacturer's instructions. The reconstituted thrombin containing modified mRNA and fibrinogen is loaded into a dual barreled syringe. Mice are injected subcutaneously with 50 ul of fibrinogen and 50 ul of thrombin containing modified mRNA or they were injected with 50 ul of PBS containing an equivalent dose of modified luciferase mRNA. A control group of untreated mice is also evaluated. The mice are imaged at predetermined intervals to determine the average total flux (photons/second).

C. Modified mRNA and Fibrinogen

Prior to reconstitution, luciferase mRNA (mRNA sequence shown in SEQ ID NO: 14; polyA tail of approximately 140 nucleotides not shown in sequence; 5'cap, Cap1) fully modified with 5-methylcytosine and N1-methylpseudouridine or fully modified with N1-methylpseudouridine is added to the fibrinolysis inhibitor solution. The fibrinolysis inhibitor solution is then used to reconstitute fibrinogen. Thrombin is reconstituted with the calcium chloride solution per the manufacturer's instructions. The reconstituted fibrinogen containing modified mRNA and thrombin is loaded into a dual barreled syringe. Mice are injected subcutaneously with 50 ul of thrombin and 50 ul of fibrinogen containing modified mRNA or they were injected with 50 ul of PBS containing an equivalent dose of modified luciferase mRNA. A control group of untreated mice is also evaluated. The mice are imaged at predetermined intervals to determine the average total flux (photons/second).

D. Lipid Nanoparticle Formulated Modified mRNA and Fibrinogen

Prior to reconstitution, luciferase mRNA (mRNA sequence shown in SEQ ID NO: 14; polyA tail of approximately 140 nucleotides not shown in sequence; 5'cap, Cap1) fully modified with 5-methylcytosine and N1-methylpseudouridine or fully modified with N1-methylpseudouridine is formulated in a lipid nanoparticle is added to the fibrinolysis inhibitor solution. The fibrinolysis inhibitor solution is then used to reconstitute fibrinogen. Thrombin is reconstituted with the calcium chloride solution per the manufacturer's instructions. The reconstituted fibrinogen containing modified mRNA and thrombin is loaded into a dual barreled syringe. Mice are injected subcutaneously with 50 ul of thrombin and 50 ul of fibrinogen containing modified mRNA or they were injected with 50 ul of PBS containing an equivalent dose of modified luciferase mRNA. A control group of untreated mice is also evaluated. The mice are imaged at predetermined intervals to determine the average total flux (photons/second).

E. Modified mRNA and Thrombin

Prior to reconstitution, luciferase mRNA (mRNA sequence shown in SEQ ID NO: 14; polyA tail of approximately 140 nucleotides not shown in sequence; 5'cap, Cap1) fully modified with 5-methylcytosine and N1-methylpseudouridine or fully modified with N1-methylpseudouridine is added to the reconstituted thrombin after it is reconstituted with the calcium chloride per the manufacturer's instructions. The fibrinolysis inhibitor solution is then used to reconstitute fibrinogen per the manufacturer's instructions. The reconstituted fibrinogen and thrombin containing modified mRNA is loaded into a dual barreled syringe. Mice are injected subcutaneously with 50 ul of thrombin containing modified mRNA and 50 ul of fibrinogen or they were injected with 50 ul of PBS containing an equivalent dose of modified luciferase mRNA. A control group of untreated mice is also evaluated. The mice are imaged at predetermined intervals to determine the average total flux (photons/second).

F. Lipid Nanoparticle Formulated Modified mRNA and Thrombin

Prior to reconstitution, luciferase mRNA (mRNA sequence shown in SEQ ID NO: 14; polyA tail of approximately 140 nucleotides not shown in sequence; 5'cap, Cap1) fully modified with 5-methylcytosine and N1-methylpseudouridine or fully modified with N1-methylpseudouridine is formulated in a lipid nanoparticle is added to the reconstituted thrombin after it is reconstituted with the calcium chloride per the manufactuer's instructions. The fibrinolysis inhibitor solution is then used to reconstitute fibrinogen per the manufacturer's instructions. The reconstituted fibrinogen and thrombin containing modified mRNA is loaded into a dual barreled syringe. Mice are injected subcutaneously with 50 ul of thrombin containing modified mRNA and 50 ul of fibrinogen or they were injected with 50 ul of PBS containing an equivalent dose of modified luciferase mRNA. A control group of untreated mice is also evaluated. The mice are imaged at predetermined intervals to determine the average total flux (photons/second).

Example 81. Cationic Lipid Formulation of 5-Methylcytosine and N1-Methylpseudouridine Modified mRNA Luciferase mRNA (SEQ ID NO: 14; polyA tail of approximately 140 nucleotides not shown in sequence; 5'cap, Cap1) fully modified with 5-methylcytosine and N1-methylpseudouridine was formulated in the cationic lipids described in Table 121. The formulations were administered intravenously (I.V.), intramuscularly (I.M.) or subcutaneously (S.C.) to Balb-C mice at a dose of 0.05 mg/kg.

TABLE 121

Cationic Lipid Formulations

| Formulation | NPA-126-1 | NPA-127-1 | NPA-128-1 | NPA-129-1 | 111612-B |
|---|---|---|---|---|---|
| Lipid | DLin-MC3-DMA | DLin-KC2-DMA | C12-200 | DLinDMA | DODMA |
| Lipid/mRNA ratio (wt/wt) | 20:1 | 20:1 | 20:1 | 20:1 | 20:1 |
| Mean Size | 122 nm PDI: 0.13 | 114 nm PDI: 0.10 | 153 nm PDI: 0.17 | 137 nm PDI: 0.09 | 223.2 nm PDI: 0.142 |
| Zeta at pH 7.4 | −1.4 mV | −0.5 mV | −1.4 mV | 2.0 mV | −3.09 mV |
| Encaps. (RiboGr) | 95% | 77% | 69% | 80% | 64% | er's instructions. The fibrinolysis inhibitor solution is then used to reconstitute fibrinogen per the manufacturer's instructions. The reconstituted fibrinogen and thrombin containing modified mRNA is loaded into a dual barreled syringe. Mice are injected subcutaneously with 50 ul of thrombin containing modified mRNA and 50 ul of fibrinogen or they were injected with 50 ul of PBS containing an equivalent dose of modified luciferase mRNA. A control group of untreated mice is also evaluated. The mice are imaged at predetermined intervals to determine the average total flux (photons/second).

Twenty minutes prior to imaging, mice were injected intraperitoneally with a D-luciferin solution at 150 mg/kg. Animals were then anesthetized and images were acquired with an IVIS Lumina II imaging system (Perkin Elmer). Bioluminescence was measured as total flux (photons/second) of the entire mouse. The mice were imaged at 2 hours, 8 hours and 24 hours after dosing and the average total flux (photons/second) was measured for each route of administration and cationic lipid formulation. The background flux was about 4.17E+05 p/s. The results of the imaging are shown in Table 122. In Table 122, "NT" means not tested.

TABLE 122

| Route | Time Point | DLin-MC3-DMA Flux (p/s) | DLin-KC2-DMA Flux (p/s) | C12-200 Flux (p/s) | DLinDMA Flux (p/s) | DODMA Flux (p/s) |
|---|---|---|---|---|---|---|
| I.V. | 2 hrs | 1.92E+08 | 2.91E+08 | 1.08E+08 | 2.53E+07 | 8.40E+06 |
| I.V. | 8 hrs | 1.47E+08 | 2.13E+08 | 3.72E+07 | 3.82E+07 | 5.62E+06 |
| I.V. | 24 hrs | 1.32E+07 | 2.41E+07 | 5.35E+06 | 4.20E+06 | 8.97E+05 |
| I.M. | 2 hrs | 8.29E+06 | 2.37E+07 | 1.80E+07 | 1.51E+06 | NT |
| I.M. | 8 hrs | 5.83E+07 | 2.12E+08 | 2.60E+07 | 1.99E+07 | NT |
| I.M. | 24 hrs | 4.30E+06 | 2.64E+07 | 3.01E+06 | 9.46E+05 | NT |
| S.C. | 2 hrs | 1.90E+07 | 5.16E+07 | 8.91E+06 | 4.66E+06 | 9.61E+06 |
| S.C. | 8 hrs | 7.74E+07 | 2.00E+08 | 4.58E+07 | 9.67E+07 | 1.90E+07 |
| S.C. | 24 hrs | 7.49E+07 | 2.47E+07 | 6.96E+06 | 6.50E+06 | 1.28E+06 |

Example 82. Lipid Nanoparticle Intravenous Study

Luciferase mRNA (SEQ ID NO: 14; polyA tail of approximately 160 nucleotides not shown in sequence; 5'cap, Cap1; fully modified with 5-methylcytosine and pseudouridine) was formulated in a lipid nanoparticle containing 50% DLin-MC3-DMA OR DLin-KC2-DMA as described in Table 123, 38.5% cholesterol, 10% DSPC and 1.5% PEG. The formulation was administered intravenously (I.V.) to Balb-C mice at a dose of 0.5 mg/kg, 0.05 mg/kg, 0.005 mg/kg or 0.0005 mg/kg. Twenty minutes prior to imaging, mice were injected intraperitoneally with a D-luciferin solution at 150 mg/kg. Animals were then anesthetized and images were acquired with an IVIS Lumina II imaging system (Perkin Elmer). Bioluminescence was measured as total flux (photons/second) of the entire mouse.

TABLE 123

| Formulations | | |
|---|---|---|
| Formulation | NPA-098-1 | NPA-100-1 |
| Lipid | DLin-KC2-DMA | DLin-MC3-DMA |
| Lipid/mRNA ratio (wt/wt) | 20:1 | 20:1 |
| Mean Size | 135 nm PDI: 0.08 | 152 nm PDI: 0.08 |
| Zeta at pH 7.4 | −0.6 mV | −1.2 mV |
| Encaps. (RiboGr) | 91% | 94% |

For DLin-KC2-DMA the mice were imaged at 2 hours, 8 hours, 24 hours, 72 hours, 96 hours and 168 hours after dosing and the average total flux (photons/second) was measured for each route of administration and cationic lipid formulation. The background flux was about 3.66E+05 p/s. The results of the imaging are shown in Table 124. Organs were imaged at 8 hours and the average total flux (photons/second) was measured for the liver, spleen, lung and kidney. A control for each organ was also analyzed. The results are shown in Table 125. The peak signal for all dose levels was at 8 hours after administration. Also, distribution to the various organs (liver, spleen, lung, and kidney) may be able to be controlled by increasing or decreasing the LNP dose.

TABLE 124

| Flux | | | | |
|---|---|---|---|---|
| Time Point | 0.5 mg/kg Flux (p/s) | 0.05 mg/kg Flux (p/s) | 0.005 mg/kg Flux (p/s) | 0.0005 mg/kg Flux (p/s) |
| 2 hrs | 3.54E+08 | 1.75E+07 | 2.30E+06 | 4.09E+05 |
| 8 hrs | 1.67E+09 | 1.71E+08 | 9.81E+06 | 7.84E+05 |

TABLE 124-continued

| Flux | | | | |
|---|---|---|---|---|
| Time Point | 0.5 mg/kg Flux (p/s) | 0.05 mg/kg Flux (p/s) | 0.005 mg/kg Flux (p/s) | 0.0005 mg/kg Flux (p/s) |
| 24 hrs | 2.05E+08 | 2.67E+07 | 2.49E+06 | 5.51E+05 |
| 72 hrs | 8.17E+07 | 1.43E+07 | 1.01E+06 | 3.75E+05 |
| 96 hrs | 4.10E+07 | 9.15E+06 | 9.58E+05 | 4.29E+05 |
| 168 hrs | 3.42E+07 | 9.15E+06 | 1.47E+06 | 5.29E+05 |

TABLE 125

| Organ Flux | | | | |
|---|---|---|---|---|
| | Liver Flux (p/s) | Spleen Flux (p/s) | Lung Flux (p/s) | Kidney Flux (p/s) |
| 0.5 mg/kg | 1.42E+08 | 4.86E+07 | 1.90E+05 | 3.20E+05 |
| 0.05 mg/kg | 7.45E+06 | 4.62E+05 | 6.86E+04 | 9.11E+04 |
| 0.005 mg/kg | 3.32E+05 | 2.97E+04 | 1.42E+04 | 1.15E+04 |
| 0.0005 mg/kg | 2.34E+04 | 1.08E+04 | 1.87E+04 | 9.78E+03 |
| Untreated | 1.88E+04 | 1.02E+04 | 1.41E+04 | 9.20E+03 |

For DLin-MC3-DMA the mice were imaged at 2 hours, 8 hours, 24 hours, 48 hours, 72 hours and 144 hours after dosing and the average total flux (photons/second) was measured for each route of administration and cationic lipid formulation. The background flux was about 4.51E+05 p/s. The results of the imaging are shown in Table 126. Organs were imaged at 8 hours and the average total flux (photons/second) was measured for the liver, spleen, lung and kidney. A control for each organ was also analyzed. The results are shown in Table 127. The peak signal for all dose levels was at 8 hours after administration. Also, distribution to the various organs (liver, spleen, lung, and kidney) may be able to be controlled by increasing or decreasing the LNP dose.

TABLE 126

| Flux | | | | |
|---|---|---|---|---|
| Time Point | 0.5 mg/kg Flux (p/s) | 0.05 mg/kg Flux (p/s) | 0.005 mg/kg Flux (p/s) | 0.0005 mg/kg Flux (p/s) |
| 2 hrs | 1.23E+08 | 7.76E+06 | 7.66E+05 | 4.88E+05 |
| 8 hrs | 1.05E+09 | 6.79E+07 | 2.75E+06 | 5.61E+05 |
| 24 hrs | 4.44E+07 | 1.00E+07 | 1.06E+06 | 5.71E+05 |
| 48 hrs | 2.12E+07 | 4.27E+06 | 7.42E+05 | 4.84E+05 |
| 72 hrs | 1.34E+07 | 5.84E+06 | 6.90E+05 | 4.38E+05 |
| 144 hrs | 4.26E+06 | 2.25E+06 | 4.58E+05 | 3.99E+05 |

TABLE 127

| | Liver Flux (p/s) | Spleen Flux (p/s) | Lung Flux (p/s) | Kidney Flux (p/s) |
|---|---|---|---|---|
| | Organ Flux | | | |
| 0.5 mg/kg | 1.19E+08 | 9.66E+07 | 1.19E+06 | 1.85E+05 |
| 0.05 mg/kg | 1.10E+07 | 1.79E+06 | 7.23E+04 | 5.82E+04 |
| 0.005 mg/kg | 3.58E+05 | 6.04E+04 | 1.33E+04 | 1.33E+04 |
| 0.0005 mg/kg | 2.25E+04 | 1.88E+04 | 2.05E+04 | 1.65E+04 |
| Untreated | 1.91E+04 | 1.66E+04 | 2.63E+04 | 2.14E+04 |

Example 83. Lipid Nanoparticle Subcutaneous Study

Luciferase mRNA (SEQ ID NO: 14; polyA tail of approximately 160 nucleotides not shown in sequence; 5'cap, Cap1; fully modified with 5-methylcytosine and pseudouridine) was formulated in a lipid nanoparticle containing 50% DLin-KC2-DMA as described in Table 128, 385% cholesterol, 10% DSPC and 1.5% PEG. The formulation was administered subcutaneously (S.C.) to Balb-C mice at a dose of 0.5 mg/kg, 0.05 mg/kg or 0.005 mg/kg.

TABLE 128

| DLin-KC2-DMA Formulation | |
|---|---|
| Formulation | NPA-098-1 |
| Lipid | DLin-KC2-DMA |
| Lipid/mRNA ratio (wt/wt) | 20:1 |
| Mean Size | 135 nm |
| | PDI: 0.08 |
| Zeta at pH 7.4 | −0.6 mV |
| Encaps. (RiboGr) | 91% |

Twenty minutes prior to imaging, mice were injected intraperitoneally with a D-luciferin solution at 150 mg/kg. Animals were then anesthetized and images were acquired with an IVIS Lumina II imaging system (Perkin Elmer). Bioluminescence was measured as total flux (photons/second) of the entire mouse. The mice were imaged at 2 hours, 8 hours, 24 hours, 48 hours, 72 hours and 144 hours after dosing and the average total flux (photons/second) was measured for each route of administration and cationic lipid formulation. The lower limit of detection was about 3E+05 p/s. The results of the imaging are shown in Table 129. Organs were imaged at 8 hours and the average total flux (photons/second) was measured for the liver, spleen, lung and kidney. A control for each organ was also analyzed. The results are shown in Table 130. The peak signal for all dose levels was at 8 hours after administration. Also, distribution to the various organs (liver, spleen, lung, and kidney) may be able to be controlled by increasing or decreasing the LNP dose. At high doses, the LNP formulations migrates outside of the subcutaneous injection site, as high levels of luciferase expression are detected in the liver, spleen, lung, and kidney.

TABLE 129

| | Flux | | |
|---|---|---|---|
| Time Point | 0.5 mg/kg Flux (p/s) | 0.05 mg/kg Flux (p/s) | 0.005 mg/kg Flux (p/s) |
| 2 hrs | 3.18E+07 | 7.46E+06 | 8.94E+05 |
| 8 hrs | 5.15E+08 | 2.18E+08 | 1.34E+07 |
| 24 hrs | 1.56E+08 | 5.30E+07 | 7.16E+06 |
| 48 hrs | 5.22E+07 | 8.75E+06 | 9.06E+05 |
| 72 hrs | 8.87E+06 | 1.50E+06 | 2.98E+05 |
| 144 hrs | 4.55E+05 | 3.51E+05 | 2.87E+05 |

TABLE 130

| | Liver Flux (p/s) | Spleen Flux (p/s) | Lung Flux (p/s) | Kidney Flux (p/s) |
|---|---|---|---|---|
| | Organ Flux | | | |
| 0.5 mg/kg | 1.01E+07 | 7.43E+05 | 9.75E+04 | 1.75E+05 |
| 0.05 mg/kg | 1.61E+05 | 3.94E+04 | 4.04E+04 | 3.29E+04 |
| 0.005 mg/kg | 2.84E+04 | 2.94E+04 | 2.42E+04 | 9.79E+04 |
| Untreated | 1.88E+04 | 1.02E+04 | 1.41E+04 | 9.20E+03 |

Example 84. Catioinic Lipid Nanoparticle Subcutaneous Study

Luciferase mRNA (SEQ ID NO: 14; polyA tail of approximately 160 nucleotides not shown in sequence; 5'cap, Cap1; fully modified with 5-methylcytosine and pseudouridine) is formulated in a lipid nanoparticle containing 50% DLin-MC3-DMA, 38.5% cholesterol, 10% DSPC and 1.5% PEG. The formulation is administered subcutaneously (S.C.) to Balb-C mice at a dose of 0.5 mg/kg, 0.05 mg/kg or 0.005 mg/kg.

The mice are imaged at 2 hours, 8 hours, 24 hours, 48 hours, 72 hours and 144 hours after dosing and the average total flux (photons/second) was measured for each route of administration and cationic lipid formulation. Organs are imaged at 8 hours and the average total flux (photons/second) is measured for the liver, spleen, lung and kidney. A control for each organ is also analyzed.

Example 85. Lipoplex Study

Lipoplexed luciferase mRNA (SEQ ID NO: 14; polyA tail of approximately 140 nucleotides not shown in sequence; 5'cap, Cap1) fully modified with 5-methylcytosine and pseudouridine (5 mC/pU), fully modified with 5-methylcytosine and N1-methylpseudouridine (5 mC/N1mpU) or modified where 25% of the cytosines replaced with 5-methylcytosine and 25% of the uridines replaced with 2-thiouridine (5 mC/s2U). The formulation was administered intravenously (I.V.), intramuscularly (I.M.) or subcutaneously (S.C.) to Balb-C mice at a dose of 0.10 mg/kg.

Twenty minutes prior to imaging, mice were injected intraperitoneally with a D-luciferin solution at 150 mg/kg. Animals were then anesthetized and images were acquired with an IVIS Lumina II imaging system (Perkin Elmer). Bioluminescence was measured as total flux (photons/second) of the entire mouse. The mice were imaged at 8 hours, 24 hours and 48 hours after dosing and the average total flux (photons/second) was measured for each route of administration and chemical modification. The background signal was about 3.91E+05 p/s. The results of the imaging are shown in Table 131. Organs were imaged at 6 hours and the average total flux (photons/second) was measured for the liver, spleen, lung and kidney. A control for each organ was also analyzed. The results are shown in Table 132.

TABLE 131

| | | Flux | | |
|---|---|---|---|---|
| Route | Time Point | 5mC/pU Flux (p/s) | 5mC/N1mpU Flux (p/s) | 5mC/s2U Flux (p/s) |
| I.V. | 8 hrs | 5.76E+06 | 1.78E+06 | 1.88E+06 |
| I.V. | 24 hrs | 1.02E+06 | 7.13E+05 | 5.28E+05 |
| I.V. | 48 hrs | 4.53E+05 | 3.76E+05 | 4.14E+05 |
| I.M. | 8 hrs | 1.90E+06 | 2.53E+06 | 1.29E+06 |

TABLE 131-continued

| | | Flux | | |
|---|---|---|---|---|
| Route | Time Point | 5mC/pU Flux (p/s) | 5mC/N1mpU Flux (p/s) | 5mC/s2U Flux (p/s) |
| I.M. | 24 hrs | 9.33E+05 | 7.84E+05 | 6.48E+05 |
| I.M. | 48 hrs | 8.51E+05 | 6.59E+05 | 5.49E+05 |
| S.C. | 8 hrs | 2.85E+06 | 6.48E+06 | 1.14E+06 |
| S.C. | 24 hrs | 6.66E+05 | 7.15E+06 | 3.93E+05 |
| S.C. | 48 hrs | 3.24E+05 | 3.20E+06 | 5.45E+05 |

TABLE 132

| | | Organ Flux | | | | |
|---|---|---|---|---|---|---|
| Route | Chemistry | Liver Flux (p/s) | Spleen Flux (p/s) | Lung Flux (p/s) | Kidney Flux (p/s) | Inj. Site Flux (p/s) |
| I.V. | 5mC/pU | 5.26E+05 | 2.04E+07 | 4.28E+06 | 1.77E+04 | n/a |
| I.V. | 5mC/N1mpU | 1.48E+05 | 5.00E+06 | 1.93E+06 | 1.77E+04 | n/a |
| I.V. | 5mC/s2U | 2.14E+04 | 3.29E+06 | 5.48E+05 | 2.16E+04 | n/a |
| I.M. | 5mC/pU | 2.46E+04 | 1.38E+04 | 1.50E+04 | 1.44E+04 | 1.15E+06 |
| I.M. | 5mC/N1mpU | 1.72E+04 | 1.76E+04 | 1.99E+04 | 1.56E+04 | 1.20E+06 |
| I.M. | 5mC/s2U | 1.28E+04 | 1.36E+04 | 1.33E+04 | 1.07E+04 | 7.60E+05 |
| S.C. | 5mC/pU | 1.55E+04 | 1.67E+04 | 1.45E+04 | 1.69E+04 | 4.46E+04 |
| S.C. | 5mC/N1mpU | 1.20E+04 | 1.46E+04 | 1.38E+04 | 1.14E+04 | 8.29E+04 |
| S.C. | 5mC/s2U | 1.22E+04 | 1.31E+04 | 1.45E+04 | 1.08E+04 | 5.62E+04 |
| | Untreated | 2.59E+04 | 1.34E+04 | 1.26E+04 | 1.22E+04 | n/a |

Example 86. Cationic Lipid Formulation of Modified mRNA

Luciferase mRNA (SEQ ID NO: 14; polyA tail of approximately 140 nucleotides not shown in sequence; 5'cap, Cap1) modified where 25% of the cytosines replaced with 5-methylcytosine and 25% of the uridines replaced with 2-thiouridine (5 mC/s2U) was formulated in the cationic lipids described in Table 133. The formulations were administered intravenously (I.V.), intramuscularly (I.M.) or subcutaneously (S.C.) to Balb-C mice at a dose of 0.05 mg/kg.

TABLE 133

| | Cationic Lipid Formulations | | | | |
|---|---|---|---|---|---|
| Formulation | NPA-130-1 | NPA-131-1 | NPA-132-1 | NPA-133-1 | 111612-C |
| Lipid | DLin-MC3-DMA | DLin-KC2-DMA | C12-200 | DLinDMA | DODMA |
| Lipid/mRNA ratio (wt/wt) | 20:1 | 20:1 | 20:1 | 20:1 | 20:1 |
| Mean Size | 120 nm PDI: 0.10 | 105 nm PDI: 0.11 | 122 nm PDI: 0.13 | 105 nm PDI: 0.14 | 221.3 nm PDI: 0.063 |
| Zeta at pH 7.4 | 0.2 mV | −0.6 mV | −0.5 mV | −0.3 mV | −3.10 mV |
| Encaps. (RiboGr) | 100% | 100% | 93% | 93% | 60% |

Twenty minutes prior to imaging, mice were injected intraperitoneally with a D-luciferin solution at 150 mg/kg. Animals were then anesthetized and images were acquired with an IVIS Lumina II imaging system (Perkin Elmer). Bioluminescence was measured as total flux (photons/second) of the entire mouse. The mice were imaged at 2 hours, 8 hours and 24 hours after dosing and the average total flux (photons/second) was measured for each route of administration and cationic lipid formulation. The background flux was about 3.31E+05 p/s. The results of the imaging are shown in Table 134. In Table 134, "NT" means not tested. Untreated mice showed an average flux of 3.14E+05 at 2 hours, 3.33E+05 at 8 hours and 3.46E+05 at 24 hours. Peak expression was seen for all three routes tested at 8 hours. DLin-KC2-DMA has better expression than DLin-MC3-DMA and DODMA showed expression for all routes evaluated. For intramuscular administration the majority of expression was seen at the site of injection but expression was also detected in the liver and small amounts were detected in the spleen.

TABLE 134

| | | Flux | | | | |
|---|---|---|---|---|---|---|
| Route | Time Point | DLin-MC3-DMA Flux (p/s) | DLin-KC2-DMA Flux (p/s) | C12-200 Flux (p/s) | DLinDMA Flux (p/s) | DODMA Flux (p/s) |
| I.V. | 2 hrs | 9.88E+06 | 6.98E+07 | 9.18E+06 | 3.98E+06 | 5.79E+06 |
| I.V. | 8 hrs | 1.21E+07 | 1.23E+08 | 1.02E+07 | 5.98E+06 | 6.14E+06 |
| I.V. | 24 hrs | 2.02E+06 | 1.05E+07 | 1.25E+06 | 1.35E+06 | 5.72E+05 |
| I.M. | 2 hrs | 6.72E+05 | 3.66E+06 | 3.25E+06 | 7.34E+05 | 4.42E+05 |
| I.M. | 8 hrs | 7.78E+06 | 2.85E+07 | 4.29E+06 | 2.22E+06 | 1.38E+05 |
| I.M. | 24 hrs | 4.22E+05 | 8.79E+05 | 5.95E+05 | 8.48E+05 | 4.80E+05 |
| S.C. | 2 hrs | 2.37E+06 | 4.77E+06 | 4.44E+06 | 1.07E+06 | 1.05E+06 |
| S.C. | 8 hrs | 3.65E+07 | 1.17E+08 | 3.71E+06 | 9.33E+06 | 2.57E+06 |
| S.C. | 24 hrs | 4.47E+06 | 1.28E+07 | 6.39E+05 | 8.89E+05 | 4.27E+05 |

Example 87. Formulation of 5-Methylcytosine and N1-Methylpseudouridine Modified mRNA Luciferase mRNA (SEQ ID NO: 14; polyA tail of approximately 140 nucleotides not shown in sequence; 5'cap, Cap1) fully modified with 5-methylcytosine and N1-methylpseudouridine was formulated in PBS (pH of 7.4). The formulations were administered intramuscularly (I.M.) or subcutaneously (S.C.) to Balb-C mice at a dose of 2.5 mg/kg.

Twenty minutes prior to imaging, mice were injected intraperitoneally with a D-luciferin solution at 150 mg/kg. Animals were then anesthetized and images were acquired with an IVIS Lumina II imaging system (Perkin Elmer). Bioluminescence was measured as total flux (photons/second) of the entire mouse. The mice were imaged at 5 minutes, 30 minutes, 60 minutes and 120 minutes after dosing and the average total flux (photons/second) was measured for each route of administration and cationic lipid formulation. The background flux was about 3.78E+05 p/s. The results of the imaging are shown in Table 135. Expression of luciferase was already seen at 30 minutes with both routes of delivery. Peak expression from subcutaneous administration appears between 30 to 60 minutes. Intramuscular expression was still increasing at 120 minutes.

TABLE 135

| | Flux | |
|---|---|---|
| Route | Time Point | PBS (pH 7.4) Flux (p/s) |
| I.M. | 5 min | 4.38E+05 |
| I.M. | 30 min | 1.09E+06 |
| I.M. | 60 min | 1.18E+06 |
| I.M. | 120 min | 2.86E+06 |
| S.C. | 5 min | 4.19E+05 |
| S.C. | 30 min | 6.38E+06 |
| S.C. | 60 min | 5.61E+06 |
| S.C. | 120 min | 2.66E+06 |

Example 88. Intramuscular and Subcutaneous Administration of Chemically Modified mRNA Luciferase modified mRNA (mRNA sequence shown in SEQ ID NO: 14; polyA tail of approximately 140 nucleotides not shown in sequence; 5'cap, Cap1) fully modified with N4-acetylcytidine, fully modified with 5-methoxyuridine, fully modified with N4-acetylcytidine and N1-methylpseudouridine or fully modified 5-methylcytosine and 5-methoxyuridine formulated in PBS (pH 7.4) was administered to Balb-C mice intramuscularly or subcutaneously at a dose of 2.5 mg/kg. Twenty minutes prior to imaging, mice were injected intraperitoneally with a D-luciferin solution at 150 mg/kg. Animals were then anesthetized and images were acquired with an IVIS Lumina II imaging system (Perkin Elmer). Bioluminescence was measured as total flux (photons/second) of the entire mouse. The mice were imaged at 2 hours, 8 hours and 24 hours. The average total flux (photons/second) for intramuscular administration is shown in Table 136 and the average total flux (photons/second) for subcutaneous administration is shown in Table 137. The background signal was 3.84E+05 (p/s). The peak expression for intramuscular administration was seen between 24 and 48 hours for all chemistry and expression was still detected at 120 hours. For subcutaneous delivery the peak expression was seen at 2-8 hours and expression was detected at 72 hours.

TABLE 136

| | Intramuscular Administration | | |
|---|---|---|---|
| | 2 hours Flux (p/s) | 8 hours Flux (p/s) | 24 hours Flux (p/s) |
| N4-acetylcytidine | 1.32E+07 | 2.15E+07 | 4.01E+07 |
| 5-methoxyuridine | 4.93E+06 | 1.80E+07 | 4.53E+07 |

TABLE 136-continued

Intramuscular Administration

| | 2 hours Flux (p/s) | 8 hours Flux (p/s) | 24 hours Flux (p/s) |
|---|---|---|---|
| N4-acetylcytidine/ N1-methylpseudouridine | 2.02E+07 | 1.93E+07 | 1.63E+08 |
| 5-methylcytosine/5-methoxyuridine | 6.79E+06 | 4.55E+07 | 3.44E+07 |

TABLE 137

Subcutaneous Administration

| | 2 hours Flux (p/s) | 8 hours Flux (p/s) | 24 hours Flux (p/s) |
|---|---|---|---|
| N4-acetylcytidine | 3.07E+07 | 1.23E+07 | 1.28E+07 |
| 5-methoxyuridine | 7.10E+06 | 9.38E+06 | 1.32E+07 |
| N4-acetylcytidine/ N1-methylpseudouridine | 7.12E+06 | 3.07E+06 | 1.03E+07 |
| 5-methylcytosine/5-methoxyuridine | 7.15E+06 | 1.25E+07 | 1.11E+07 |

Example 89. In Vivo Study

Luciferase modified mRNA containing at least one chemical modification is formulated as a lipid nanoparticle (LNP) using the syringe pump method and characterized by particle size, zeta potential, and encapsulation.

As outlined in Table 138, the luciferase LNP formulation is administered to Balb-C mice intramuscularly (I.M.), intravenously (I.V.) and subcutaneously (S.C.). As a control luciferase modified RNA formulated in PBS is administered intravenously to mice.

TABLE 138

Luciferase Formulations

| Formulation | Vehicle | Route | Concentration (mg/ml) | Injection Volume (ul) | Amount of modified RNA (ug) | Dose (mg/kg) |
|---|---|---|---|---|---|---|
| Luc-LNP | PBS | S.C. | 0.2000 | 50 | 10 | 0.5000 |
| Luc-LNP | PBS | S.C. | 0.0200 | 50 | 1 | 0.0500 |
| Luc-LNP | PBS | S.C. | 0.0020 | 50 | 0.1 | 0.0050 |
| Luc-LNP | PBS | S.C. | 0.0002 | 50 | 0.01 | 0.0005 |
| Luc-LNP | PBS | I.V. | 0.2000 | 50 | 10 | 0.5000 |
| Luc-LNP | PBS | I.V. | 0.0200 | 50 | 1 | 0.0500 |
| Luc-LNP | PBS | I.V. | 0.0020 | 50 | 0.1 | 0.0050 |
| Luc-LNP | PBS | I.V. | 0.0002 | 50 | 0.01 | 0.0005 |
| Luc-LNP | PBS | I.M. | 0.2000 | 50 | 10 | 0.5000 |
| Luc-LNP | PBS | I.M. | 0.0200 | 50 | 1 | 0.0500 |
| Luc-LNP | PBS | I.M. | 0.0020 | 50 | 0.1 | 0.0050 |
| Luc-LNP | PBS | I.M. | 0.0002 | 50 | 0.01 | 0.0005 |
| Luc-PBS | PBS | I.V. | 0.20 | 50 | 10 | 0.50 |

The mice are imaged at 2, 8, 24, 48, 120 and 192 hours to determine the bioluminescence (measured as total flux (photons/second) of the entire mouse). At 8 hours or 192 hours the liver, spleen, kidney and injection site for subcutaneous and intramuscular administration are imaged to determine the bioluminescence.

Example 90. Cationic Lipid Formulation Studies of Chemically Modified mRNA

Luciferase mRNA (SEQ ID NO: 14; polyA tail of approximately 140 nucleotides not shown in sequence; 5'cap, Cap1) fully modified with 5-methylcytosine and pseudouridine (5 mC/pU), pseudouridine (pU) or N1-methylpseudouridine (N1mpU) was formulated in the cationic lipids described in Table 139. The formulations were administered intravenously (I.V.), intramuscularly (I.M.) or subcutaneously (S.C.) to Balb-C mice at a dose of 0.05 mg/kg.

TABLE 139

Cationic Lipid Formulations

| Formulation | NPA-137-1 | NPA-134-1 | NPA-135-1 | NPA-136-1 | 111612-A |
|---|---|---|---|---|---|
| Lipid | DLin-MC3-DMA | DLin-MC3-DMA | DLin-KC2-DMA | C12-200 | DODMA |
| Lipid/mRNA ratio (wt/wt) | 20:1 | 20:1 | 20:1 | 20:1 | 20:1 |
| Mean Size | 111 nm PDI: 0.15 | 104 nm PDI: 0.13 | 95 nm PDI: 0.11 | 143 nm PDI: 0.12 | 223.2 nm PDI: 0.142 |
| Zeta at pH 7.4 | −4.1 mV | −1.9 mV | −1.0 mV | 0.2 mV | −3.09 mV |
| Encaps. (RiboGr) | 97% | 100% | 100% | 78% | 64% |
| Chemistry | pU | N1mpU | N1mpU | N1mpU | 5mC/pU |

Twenty minutes prior to imaging, mice were injected intraperitoneally with a D-luciferin solution at 150 mg/kg. Animals were then anesthetized and images were acquired with an IVIS Lumina II imaging system (Perkin Elmer). Bioluminescence was measured as total flux (photons/second) of the entire mouse. The mice were imaged at 2 hours, 8 hours and 24 hours after dosing and the average total flux (photons/second) was measured for each route of administration and cationic lipid formulation. The background flux was about 4.11E+05 p/s. The results of the imaging are shown in Table 140. Peak expression was seen for all three routes tested at 8 hours.

TABLE 140

| | | Flux | | | | |
|---|---|---|---|---|---|---|
| Route | Time Point | DLin-MC3-DMA (pU) Flux (p/s) | DLin-MC3-DMA (N1mpU) Flux (p/s) | DLin-KC2-DMA (N1mpU) Flux (p/s) | C12-200 (N1mpU) Flux (p/s) | DODMA (5mC/pU) Flux (p/s) |
| I.V. | 2 hrs | 3.21E+08 | 1.24E+09 | 1.01E+09 | 9.00E+08 | 3.90E+07 |
| I.V. | 8 hrs | 1.60E+09 | 3.22E+09 | 2.38E+09 | 1.11E+09 | 1.17E+07 |
| I.V. | 24 hrs | 1.41E+08 | 3.68E+08 | 3.93E+08 | 8.06E+07 | 1.11E+07 |
| I.M. | 2 hrs | 2.09E+07 | 3.29E+07 | 8.32E+07 | 9.43E+07 | 4.66E+06 |
| I.M. | 8 hrs | 2.16E+08 | 6.14E+08 | 1.00E+09 | 8.77E+07 | 7.05E+06 |
| I.M. | 24 hrs | 1.23E+07 | 1.40E+08 | 5.09E+08 | 1.36E+07 | 1.14E+06 |
| S.C. | 2 hrs | 2.32E+07 | 3.60E+07 | 2.14E+08 | 1.01E+08 | 3.11E+07 |
| S.C. | 8 hrs | 5.55E+08 | 9.80E+08 | 4.93E+09 | 1.01E+09 | 8.04E+07 |
| S.C. | 24 hrs | 1.81E+08 | 2.74E+08 | 2.12E+09 | 4.74E+07 | 1.34E+07 |

Example 91. Studies of Chemical Modified mRNA

Luciferase mRNA (SEQ ID NO: 14; polyA tail of approximately 140 nucleotides not shown in sequence; 5'cap, Cap1) fully modified with N4-acetylcytidine (N4-acetyl), fully modified with 5-methoxyuridine (5meth), fully modified with N4-acetylcytidine and N1-methylpseudouridine (N4-acetyl/N1mpU) or fully modified with 5-methylcytosine and 5-methoxyuridine (5 mC/5-meth) was formulated in DLin-MC3-DMA as described in Table 141. The formulations were administered intravenously (I.V.), intramuscularly (I.M.) or subcutaneously (S.C.) to Balb-C mice at a dose of 0.05 mg/kg.

TABLE 141

| | Cationic Lipid Formulations | | | |
|---|---|---|---|---|
| Formulation | NPA-141-1 | NPA-142-1 | NPA-143-1 | NPA-144-1 |
| Lipid | DLin-MC3-DMA | DLin-MC3-DMA | DLin-MC3-DMA | DLin-MC3-DMA |
| Lipid/mRNA ratio (wt/wt) | 20:1 | 20:1 | 20:1 | 20:1 |
| Mean Size | 138 nm PDI: 0.16 | 116 nm PDI: 0.15 | 144 nm PDI: 0.15 | 131 nm PDI: 0.15 |
| Zeta at pH 7.4 | −2.8 mV | −2.8 mV | −4.3 mV | −5.0 mV |
| Encaps. (RiboGr) | 97% | 100% | 75% | 72% |
| Chemistry | N4-acetyl | 5meth | N4-acetyl/N1mpU | 5mC/5-meth |

Twenty minutes prior to imaging, mice were injected intraperitoneally with a D-luciferin solution at 150 mg/kg. Animals were then anesthetized and images were acquired with an IVIS Lumina II imaging system (Perkin Elmer). Bioluminescence was measured as total flux (photons/second) of the entire mouse. The mice were imaged at 2 hours, 6 hours and 24 hours after dosing and the average total flux (photons/second) was measured for each route of administration and cationic lipid formulation. The background flux was about 2.70E+05 p/s. The results of the imaging are shown in Table 142.

TABLE 142

| | | Flux | | | |
|---|---|---|---|---|---|
| Route | Time Point | N4-acetyl Flux (p/s) | 5meth Flux (p/s) | N4-acetyl/N1mpU Flux (p/s) | 5mC/5-meth Flux (p/s) |
| I.V. | 2 hrs | 9.17E+07 | 3.19E+06 | 4.21E+07 | 1.88E+06 |
| I.V. | 6 hrs | 7.70E+08 | 9.28E+06 | 2.34E+08 | 7.75E+06 |
| I.V. | 24 hrs | 6.84E+07 | 1.04E+06 | 3.55E+07 | 3.21E+06 |
| I.M. | 2 hrs | 8.59E+06 | 7.86E+05 | 5.30E+06 | 5.11E+05 |
| I.M. | 6 hrs | 1.27E+08 | 8.88E+06 | 3.82E+07 | 3.17E+06 |
| I.M. | 24 hrs | 4.46E+07 | 1.38E+06 | 2.00E+07 | 1.39E+06 |
| S.C. | 2 hrs | 1.83E+07 | 9.67E+05 | 4.45E+06 | 1.01E+06 |
| S.C. | 6 hrs | 2.89E+08 | 1.78E+07 | 8.91E+07 | 1.29E+07 |
| S.C. | 24 hrs | 6.09E+07 | 6.40E+06 | 2.08E+08 | 6.63E+06 |

Example 92. PLGA Microspheres

A. Synthesis of PLGA Microspheres

Polylacticglycolic acid (PLGA) microspheres were synthesized using the water/oil/water double emulsification methods known in the art using PLGA-ester cap (Lactel, Cat# B6010-2, inherent viscosity 0.55-0.75, 50:50 LA:GA) or PLGA-acid cap (Lactel, Cat#B6013-2, inherent viscosity 0.55-0.75, 50:50 LA:GA), polyvinylalcohol (PVA) (Sigma, Cat#348406-25G, MW 13-23 k) dichloromethane and water. Briefly, 0.4 ml of mRNA in water (W1) at 4 mg/ml was added to 2 ml of PLGA dissolved in dichloromethane (DCM) (O1) at concentrations ranging from 50-200 mg/ml of PLGA. The W1/O1 emulsion was homogenized (IKA Ultra-Turrax Homogenizer, T18) for 30 seconds at speed 4 (~15,000 rpm). The W1/O1 emulsion was then added to 250 ml of 1% PVA (W2) and homogenized for 1 minute at speed 5 (~19,000 rpm). Formulations were left to stir for 3 hours, then passed through a 100 μm nylon mesh strainer (Fisherbrand Cell Strainer, Cat #22-363-549) to remove larger aggregates, and finally washed by centrifugation (10 min, 9,250 rpm, 4° C.). The supernatant was discarded and the PLGA pellets were resuspended in 5-10 ml of water, which was repeated 2×. The washed formulations were frozen in liquid nitrogen and then lyophilized for 2-3 days.

B. Decreasing Homogenization Speed or PLGA Concentration

PLGA luciferase microspheres (luciferase mRNA shown in SEQ ID NO: 14; polyA tail of approximately 160 nucleotides not shown in sequence; 5'cap, Cap1; fully modified with 5-methylcysotine and pseudouridine) were made using the conditions described above with ester-capped PLGA. After washing and resuspension with water, 100-200 μl of a PLGA microspheres sample was used to measure particle size of the formulations by laser diffraction (Malvern Mastersizer2000). The particle size of the microspheres made by decreasing homogenization speed during the addition of the first emulsion to the second emulsion with a PLGA concentration of 200 mg/ml is shown in Table 143 and the particle size of the microspheres made by decreasing PLGA concentration in dichloromethane (DCM) is shown in Table 144 with a homogenization speed of 5 during the addition of the first emulsion to the second emulsion.

TABLE 143

Decreasing Homogenization Speed

| Addition Homogenizer Speed | D50 Average Size (μm) |
|---|---|
| 2 | 41.5 |
| 3 | 35.9 |
| 4 | 32.5 |
| 5 | 26.5 |
| 6 | 25.0 |

TABLE 144

Decreasing PLGA Concentration in DCM

| PLGA Concentration (mg/mL) | D50 Average Size (μm) |
|---|---|
| 200 | 27.7 |
| 100 | 14.2 |
| 50 | 8.7 |

PLGA with an inherent viscosity of 0.55-0.75 either acid or ester-capped was used to make microspheres shown in Table 145. The particle size of the microspheres and the release kinetics were also determined and are shown in Table 145.

TABLE 145

Decreasing PLGA Concentration in DCM

| Sample | PLGA conc. mg/ml | End-group | Addition Homogenizer Speed | Theoretical mRNA Loading (wt %) | Actual mRNA Loading (wt %) | Encap. Eff. % | D50 Average Size (μm) |
|---|---|---|---|---|---|---|---|
| A | 200 | Ester | 3 | 0.4 | 0.14 | 45 | 38.7 |
| B | 200 | Acid | 3 | 0.4 | 0.06 | 18 | 31.3 |
| C | 200 | Ester | 5 | 0.4 | 0.13 | 41 | 32.2 |
| D | 200 | Acid | 5 | 0.4 | 0.07 | 22 | 28.0 |
| E | 100 | Ester | 5 | 0.8 | 0.15 | 23 | 17.1 |
| F | 100 | Acid | 5 | 0.8 | 0.10 | 18 | 15.9 |

C. Release Study of Modified mRNA Encapsulated in PLGA Microspheres

PLGA microspheres formulated with Luciferase modified RNA (SEQ ID NO: 14; polyA tail of approximately 160 nucleotides not shown in sequence; 5'cap, Cap1; fully modified with 5-methylcytosine and pseudouridine) were deformulated and the integrity of the extracted modified RNA was determined by automated electrophoresis (Bio-Rad Experion). After lyophilization, ~10 mg of PLGA MS were weighed out in 2 ml eppendorf tubes and deformulated by adding 1 ml of DCM and letting the samples shake for 2-6 hrs. mRNA was extracted from the deformulated PLGA microspheres by adding 0.5 ml of water and shaking the sample overnight. Unformulated luciferase mRNA in water (Deform control) was spiked into DCM and went through the deformulation process to be used as a control. The extracted modified mRNA was compared against unformulated modified mRNA and the deformulation control in order to test the integrity of the encapsulated modified mRNA. The majority of modified RNA was intact for batch ID A, B, C, D, E, as compared to the deformulated control (Deform control) and the unformulated control (Uniform control).

D. Release Study of Modified mRNA Encapsulated in PLGA Microspheres

PLGA micropsheres formulated with Luciferase modified RNA (SEQ ID NO: 14; polyA tail of approximately 160 nucleotides not shown in sequence; 5'cap, Cap1; fully modified with 5-methylcytosine and pseudouridine) were resuspended in TE buffer to a PLGA microsphere concentration of 80 mg/ml in duplicate or triplicate. After resuspension, samples were kept incubating and shaking at 37° C. during the course of the study. For each time point (0.04, 0.25, 1.2, 4, and 7 days), the tubes were centrifuged, the supernatant was removed and the pellet was resuspended in 0.25 ml of fresh TE buffer. To determine the amount of modified RNA released from the PLGA microspheres, the modified RNA concentration in the supernatant was determined by OD 260. The percent release, shown in Table 146, was calculated based on the total amount of modified RNA in each sample. The release rate of mRNA formulations can be tailored by altering the particle size, the PLGA concentration, and the acid versus ester-end cap.

TABLE 146

Percent Release

| Time (days) | Batch A % Release | Batch B % Release | Batch C % Release | Batch D % Release | Batch E % Release | Batch F % Release |
|---|---|---|---|---|---|---|
| 0.04 | 7.1 | 13.6 | 9.5 | 9.5 | 21.2 | 21.7 |
| 0.25 | 18.0 | 23.3 | 17.5 | 24.0 | 31.3 | 37.7 |

TABLE 146-continued

Percent Release

| Time (days) | Batch A % Release | Batch B % Release | Batch C % Release | Batch D % Release | Batch E % Release | Batch F % Release |
|---|---|---|---|---|---|---|
| 1.2 | 26.3 | 29.1 | 22.8 | 31.6 | 41.0 | 46.5 |
| 4 | 33.5 | 37.1 | 29.0 | 40.4 | 48.8 | 60.7 |
| 7 | 37.6 | 41.5 | 32.4 | 45.2 | 55.0 | 68.3 |

E. Luciferase PLGA Microspheres In Vivo Study

PLGA microspheres containing luciferase mRNA (SEQ ID NO: 14; polyA tail of approximately 140 nucleotides not shown in sequence; 5'cap, Cap1) fully modified with 5-methylcytosine and N1-methylpseudouridine or fully modified with N1-methylpseudouridine are formulated as described in Table 147 and injected subcutaneously into mice. Twenty minutes prior to imaging, mice are injected intraperitoneally with a D-luciferin solution at 150 mg/kg. Animals are then anesthetized and images were acquired with an IVIS Lumina II imaging system (Perkin Elmer). Bioluminescence was measured as total flux (photons/second) of the entire mouse.

TABLE 147

| | | | | Formulation |
|---|---|---|---|---|
| Group | n | Dose (ug) | Volume (ul) | Vehicle |
| 1 | 6 | 50 | 200 | 0.5% CMC, 5% Mannitol, 0.1% Polysorbate 80 |
| 2 | 6 | 50 | 200 | 5% Sucrose |
| 3 | 3 | 5 | 200 | 5% Sucrose |

Example 93. Buffer Formulations

Modified mRNA may be formulated in water based buffers. Buffers which are similar to biological systems are traditionally isotonic. Such buffers and buffer solutions may be prepared according to the following guidelines. Example components are given in Table 148.

In some embodiments, calcium ions may be added to a buffer solution for formulations.

TABLE 148

| Buffers | |
|---|---|
| Buffer | Components |
| Tris buffered saline | Tris and sodium chloride |
| Phosphate buffered saline | sodium chloride, sodium phosphate, and, in some formulations, potassium chloride and potassium phosphate |
| Ringer's lactate (for one liter) | 130 mEq of sodium ion = 130 mmol/L<br>109 mEq of chloride ion = 109 mmol/L<br>28 mEq of lactate = 28 mmol/L<br>4 mEq of potassium ion = 4 mmol/L<br>3 mEq of calcium ion = 1.5 mmol/L |

Example 94. Lipid Nanoparticle Containing a Plurality of Modified mRNAs

EPO mRNA (SEQ ID NO: 7; polyA tail of approximately 140 nucleotides not shown in sequence; 5'cap, Cap1; fully modified with 5-methylcytosine and N1-methylpseudouridine), G-CSF mRNA (SEQ ID NO: 4; polyA tail of approximately 140 nucleotides not shown in sequence; 5'cap, Cap1; fully modified with 5-methylcytosine and N1-methylpseudouridine) and Factor IX mRNA (SEQ ID NO: 8; polyA tail of approximately 140 nucleotides not shown in sequence; 5'cap, Cap1; fully modified with 5-methylcytosine and N1-methylpseudouridine), is formulated in DLin-MC3-DMA as described in Table 149. The formulations are administered intravenously (I.V.), intramuscularly (I.M.) or subcutaneously (S.C.) to Balb-C mice at a dose of 0.05 mg/kg. Control LNP formulations containing only one mRNA are also administered at an equivalent dose.

TABLE 149

| DLin-MC3-DMA Formulation | |
|---|---|
| Formulation | NPA-157-1 |
| Lipid | DLin-MC3-DMA |
| Lipid/mRNA ratio (wt/wt) | 20:1 |
| Mean Size | 89 nm<br>PDI: 0.08 |
| Zeta at pH 7.4 | 1.1 mV |
| Encaps. (RiboGr) | 97% |

Serum is collected from the mice at 8 hours, 24 hours, 72 hours and/or 7 days after administration of the formulation. The serum is analyzed by ELISA to determine the protein expression of EPO, G-CSF, and Factor IX.

Example 95. Cationic Lipid Formulation Studies of 5-Methylcytosine and N1-Methylpseudouridine Modified mRNA EPO mRNA (SEQ ID NO: 7; polyA tail of approximately 140 nucleotides not shown in sequence; 5'cap, Cap1; fully modified with 5-methylcytosine and N1-methylpseudouridine) or G-CSF mRNA (SEQ ID NO: 4; polyA tail of approximately 140 nucleotides not shown in sequence; 5'cap, Cap1; fully modified with 5-methylcytosine and N1-methylpseudouridine) is formulated in DLin-MC3-DMA and DLin-KC2-DMA as described in Table 150. The formulations are administered intravenously (I.V), intramuscularly (I.M.) or subcutaneously (S.C.) to Balb-C mice at a dose of 0.05 mg/kg.

TABLE 150

| DLin-MC3-DMA and DLin-KC2-DMA Formulations | | | | |
|---|---|---|---|---|
| Formulation | NPA-147-1 | NPA-148-1 | NPA-150-1 | NPA-151-1 |
| mRNA | EPO | EPO | G-CSF | G-CSF |
| Lipid | DLin-MC3-DMA | DLin-KC2-DMA | DLin-MC3-DMA | DLin-KC2-DMA |
| Lipid/mRNA ratio (wt/wt) | 20:1 | 20:1 | 20:1 | 20:1 |
| Mean Size | 117 nm<br>PDI: 0.14 | 82 nm<br>PDI: 0.08 | 119 nm<br>PDI: 0.13 | 88 nm<br>PDI: 0.08 |
| Zeta at pH 7.4 | −1.7 mV | 0.6 mV | 3.6 mV | 2.2 mV |
| Encaps. (RiboGr) | 100% | 96% | 100% | 100% |

Serum is collected from the mice at 8 hours, 24 hours, 72 hours and/or 7 days after administration of the formulation. The serum is analyzed by ELISA to determine the protein expression of EPO and G-CSF.

Example 96. Directed SAR of Pseudouridine and N1-Methyl PseudoUridine

With the recent focus on the pyrimidine nucleoside pseudouridine, a series of structure-activity studies were designed to investigate mRNA containing modifications to pseudouridine or N1-methyl-pseudourdine.

The study was designed to explore the effect of chain length, increased lipophilicity, presence of ring structures, and alteration of hydrophobic or hydrophilic interactions when modifications were made at the N1 position, C6 position, the 2-position, the 4-position and on the phosphate backbone. Stability is also investigated.

To this end, modifications involving alkylation, cycloalkylation, alkyl-cycloalkylation, arylation, alkyl-arylation, alkylation moieties with amino groups, alkylation moieties with carboxylic acid groups, and alkylation moieties containing amino acid charged moieties are investigated. The degree of alkylation is generally $C_1$-$C_6$. Examples of the chemistry modifications include those listed in Table 151 and Table 152.

TABLE 151

Pseudouridine and N1-methyl Pseudo Uridine SAR

| Chemistry Modification | Compound # | Naturally occuring |
|---|---|---|
| N1-Modifications | | |
| N1-Ethyl-pseudo-UTP | 1 | N |
| N1-Propyl-pseudo-UTP | 2 | N |
| N1-iso-propyl-pseudo-UTP | 3 | N |
| N1-(2,2,2-Trifluoroethyl)-pseudo-UTP | 4 | N |
| N1-Cyclopropyl-pseudo-UTP | 5 | N |
| N1-Cyclopropylmethyl-pseudo-UTP | 6 | N |
| N1-Phenyl-pseudo-UTP | 7 | N |
| N1-Benzyl-pseudo-UTP | 8 | N |
| N1-Aminomethyl-pseudo-UTP | 9 | N |
| Pseudo-UTP-N1-2-ethanoic acid | 10 | N |
| N1-(3-Amino-3-carboxypropyl)pseudo-UTP | 11 | N |
| N1-Methyl-3-(3-amino-3-carboxypropyl)pseudo-UTP | 12 | Y |
| C-6 Modifications | | |
| 6-Methyl-pseudo-UTP | 13 | N |
| 6-Trifluoromethyl-pseudo-UTP | 14 | N |
| 6-Methoxy-pseudo-UTP | 15 | N |
| 6-Phenyl-pseudo-UTP | 16 | N |
| 6-Iodo-pseudo-UTP | 17 | N |
| 6-Bromo-pseudo-UTP | 18 | N |
| 6-Chloro-pseudo-UTP | 19 | N |
| 6-Fluoro-pseudo-UTP | 20 | N |
| 2- or 4-position Modifications | | |
| 4-Thio-pseudo-UTP | 21 | N |
| 2-Thio-pseudo-UTP | 22 | N |
| Phosphate backbone Modifications | | |
| Alpha-thio-pseudo-UTP | 23 | N |
| N1-Me-alpha-thio-pseudo-UTP | 24 | N |

TABLE 152

Pseudouridine and N1-methyl Pseudo Uridine SAR

| Chemistry Modification | Compound # | Naturally occuring |
|---|---|---|
| N1-Methyl-pseudo-UTP | 1 | Y |
| N1-Butyl-pseudo-UTP | 2 | N |
| N1-tert-Butyl-pseudo-UTP | 3 | N |
| N1-Pentyl-pseudo-UTP | 4 | N |
| N1-Hexyl-pseudo-UTP | 5 | N |
| N1-Trifluoromethyl-pseudo-UTP | 6 | Y |
| N1-Cyclobutyl-pseudo-UTP | 7 | N |
| N1-Cyclopentyl-pseudo-UTP | 8 | N |
| N1-Cyclohexyl-pseudo-UTP | 9 | N |
| N1-Cycloheptyl-pseudo-UTP | 10 | N |
| N1-Cyclooctyl-pseudo-UTP | 11 | N |
| N1-Cyclobutylmethyl-pseudo-UTP | 12 | N |
| N1-Cyclopentylmethyl-pseudo-UTP | 13 | N |
| N1-Cyclohexylmethyl-pseudo-UTP | 14 | N |
| N1-Cycloheptylmethyl-pseudo-UTP | 15 | N |
| N1-Cyclooctylmethyl-pseudo-UTP | 16 | N |
| N1-p-tolyl-pseudo-UTP | 17 | N |
| N1-(2,4,6-Trimethyl-phenyl)pseudo-UTP | 18 | N |
| N1-(4-Methoxy-phenyl)pseudo-UTP | 19 | N |
| N1-(4-Amino-phenyl)pseudo-UTP | 20 | N |
| N1(4-Nitro-phenyl)pseudo-UTP | 21 | N |

TABLE 152-continued

Pseudouridine and N1-methyl Pseudo Uridine SAR

| Chemistry Modification | Compound # | Naturally occuring |
|---|---|---|
| Pseudo-UTP-N1-p-benzoic acid | 22 | N |
| N1-(4-Methyl-benzyl)pseudo-UTP | 24 | N |
| N1-(2,4,6-Trimethyl-benzyl)pseudo-UTP | 23 | N |
| N1-(4-Methoxy-benzyl)pseudo-UTP | 25 | N |
| N1-(4-Amino-benzyl)pseudo-UTP | 26 | N |
| N1-(4-Nitro-benzyl)pseudo-UTP | 27 | N |
| Pseudo-UTP-N1-methyl-p-benzoic acid | 28 | N |
| N1-(2-Amino-ethyl)pseudo-UTP | 29 | N |
| N1-(3-Amino-propyl)pseudo-UTP | 30 | N |
| N1-(4-Amino-butyl)pseudo-UTP | 31 | N |
| N1-(5-Amino-pentyl)pseudo-UTP | 32 | N |
| N1-(6-Amino-hexyl)pseudo-UTP | 33 | N |
| Pseudo-UTP-N1-3-propionic acid | 34 | N |
| Pseudo-UTP-N1-4-butanoic acid | 35 | N |
| Pseudo-UTP-N1-5-pentanoic acid | 36 | N |
| Pseudo-UTP-N1-6-hexanoic acid | 37 | N |
| Pseudo-UTP-N1-7-heptanoic acid | 38 | N |
| N1-(2-Amino-2-carboxyethyl)pseudo-UTP | 39 | N |
| N1-(4-Amino-4-carboxybutyl)pseudo-UTP | 40 | N |
| N3-Alkyl-pseudo-UTP | 41 | N |
| 6-Ethyl-pseudo-UTP | 42 | N |
| 6-Propyl-pseudo-UTP | 43 | N |
| 6-iso-Propyl-pseudo-UTP | 44 | N |
| 6-Butyl-pseudo-UTP | 45 | N |
| 6-tert-Butyl-pseudo-UTP | 46 | N |
| 6-(2,2,2-Trifluoroethyl)-pseudo-UTP | 47 | N |
| 6-Ethoxy-pseudo-UTP | 48 | N |
| 6-Trifluoromethoxy-pseudo-UTP | 49 | N |
| 6-Phenyl-pseudo-UTP | 50 | N |
| 6-(Substituted-Phenyl)-pseudo-UTP | 51 | N |
| 6-Cyano-pseudo-UTP | 52 | N |
| 6-Azido-pseudo-UTP | 53 | N |
| 6-Amino-pseudo-UTP | 54 | N |
| 6-Ethylcarboxylate-pseudo-UTP | 54b | N |
| 6-Hydroxy-pseudo-UTP | 55 | N |
| 6-Methylamino-pseudo-UTP | 55b | N |
| 6-Dimethylamino-pseudo-UTP | 57 | N |
| 6-Hydroxyamino-pseudo-UTP | 59 | N |
| 6-Formyl-pseudo-UTP | 60 | N |
| 6-(4-Morpholino)-pseudo-UTP | 61 | N |
| 6-(4-Thiomorpholino)-pseudo-UTP | 62 | N |
| N1-Me-4-thio-pseudo-UTP | 63 | N |
| N1-Me-2-thio-pseudo-UTP | 64 | N |
| 1,6-Dimethyl-pseudo-UTP | 65 | N |
| 1-Methyl-6-trifluoromethyl-pseudo-UTP | 66 | N |
| 1-Methyl-6-ethyl-pseudo-UTP | 67 | N |
| 1-Methyl-6-propyl-pseudo-UTP | 68 | N |
| 1-Methyl-6-iso-propyl-pseudo-UTP | 69 | N |
| 1-Methyl-6-butyl-pseudo-UTP | 70 | N |
| 1-Methyl-6-tert-butyl-pseudo-UTP | 71 | N |
| 1-Methyl-6-(2,2,2-Trifluoroethyl)pseudo-UTP | 72 | N |
| 1-Methyl-6-iodo-pseudo-UTP | 73 | N |
| 1-Methyl-6-bromo-pseudo-UTP | 74 | N |
| 1-Methyl-6-chloro-pseudo-UTP | 75 | N |
| 1-Methyl-6-fluoro-pseudo-UTP | 76 | N |
| 1-Methyl-6-methoxy-pseudo-UTP | 77 | N |
| 1-Methyl-6-ethoxy-pseudo-UTP | 78 | N |
| 1-Methyl-6-trifluoromethoxy-pseudo-UTP | 79 | N |
| 1-Methyl-6-phenyl-pseudo-UTP | 80 | N |
| 1-Methyl-6-(substituted phenyl)pseudo-UTP | 81 | N |
| 1-Methyl-6-cyano-pseudo-UTP | 82 | N |
| 1-Methyl-6-azido-pseudo-UTP | 83 | N |
| 1-Methyl-6-amino-pseudo-UTP | 84 | N |
| 1-Methyl-6-ethylcarboxylate-pseudo-UTP | 85 | N |
| 1-Methyl-6-hydroxy-pseudo-UTP | 86 | N |
| 1-Methyl-6-methylamino-pseudo-UTP | 87 | N |
| 1-Methyl-6-dimethylamino-pseudo-UTP | 88 | N |
| 1-Methyl-6-hydroxyamino-pseudo-UTP | 89 | N |
| 1-Methyl-6-formyl-pseudo-UTP | 90 | N |
| 1-Methyl-6-(4-morpholino)-pseudo-UTP | 91 | N |
| 1-Methyl-6-(4-thiomorpholino)-pseudo-UTP | 92 | N |
| 1-Alkyl-6-vinyl-pseudo-UTP | 93 | N |
| 1-Alkyl-6-allyl-pseudo-UTP | 94 | N |
| 1-Alkyl-6-homoallyl-pseudo-UTP | 95 | N |
| 1-Alkyl-6-ethynyl-pseudo-UTP | 96 | N |

TABLE 152-continued

Pseudouridine and N1-methyl Pseudo Uridine SAR

| Chemistry Modification | Compound # | Naturally occuring |
|---|---|---|
| 1-Alkyl-6-(2-propynyl)-pseudo-UTP | 97 | N |
| 1-Alkyl-6-(1-propynyl)-pseudo-UTP | 98 | N |

Example 97. Incorporation of Naturally and Non-Naturally Occurring Nucleosides

Naturally and non-naturally occurring nucleosides are incorporated into mRNA encoding a polypeptide of interest. Examples of these are given in Tables 153 and 154. Certain commercially available nucleoside triphosphates (NTPs) are investigated in the polynucleotides of the invention. A selection of these are given in Table 154. The resultant mRNA are then examined for their ability to produce protein, induce cytokines, and/or produce a therapeutic outcome.

TABLE 153

Naturally and non-naturally occurring nucleosides

| Chemistry Modification | Compound # | Naturally occuring |
|---|---|---|
| N4-Methyl-Cytosine | 1 | Y |
| N4,N4-Dimethyl-2'-OMe-Cytosine | 2 | Y |
| 5-Oxyacetic acid-methyl ester-Uridine | 3 | Y |
| N3-Methyl-pseudo-Uridine | 4 | Y |
| 5-Hydroxymethyl-Cytosine | 5 | Y |
| 5-Trifluoromethyl-Cytosine | 6 | N |
| 5-Trifluoromethyl-Uridine | 7 | N |
| 5-Methyl-amino-methyl-Uridine | 8 | Y |
| 5-Carboxy-methyl-amino-methyl-Uridine | 9 | Y |
| 5-Carboxymethylaminomethyl-2'-OMe-Uridine | 10 | Y |
| 5-Carboxymethylaminomethyl-2-thio-Uridine | 11 | Y |
| 5-Methylaminomethyl-2-thio-Uridine | 12 | Y |
| 5-Methoxy-carbonyl-methyl-Uridine | 13 | Y |
| 5-Methoxy-carbonyl-methyl-2'-OMe-Uridine | 14 | Y |
| 5-Oxyacetic acid-Uridine | 15 | Y |
| 3-(3-Amino-3-carboxypropyl)-Uridine | 16 | Y |
| 5-(carboxyhydroxymethyl)uridine methyl ester | 17 | Y |
| 5-(carboxyhydroxymethyl)uridine | 18 | Y |

TABLE 154

Non-naturally occurring nucleoside triphosphates

| Chemistry Modification | Compound # | Naturally occuring |
|---|---|---|
| N1-Me-GTP | 1 | N |
| 2'-OMe-2-Amino-ATP | 2 | N |
| 2'-OMe-pseudo-UTP | 3 | Y |
| 2'-OMe-6-Me-UTP | 4 | N |
| 2'-Azido-2'-deoxy-ATP | 5 | N |
| 2'-Azido-2'-deoxy-GTP | 6 | N |
| 2'-Azido-2'-deoxy-UTP | 7 | N |
| 2'-Azido-2'-deoxy-CTP | 8 | N |
| 2'-Amino-2'-deoxy-ATP | 9 | N |
| 2'-Amino-2'-deoxy-GTP | 10 | N |
| 2'-Amino-2'-deoxy-UTP | 11 | N |
| 2'-Amino-2'-deoxy-CTP | 12 | N |
| 2-Amino-ATP | 13 | N |
| 8-Aza-ATP | 14 | N |
| Xanthosine-5'-TP | 15 | N |
| 5-Bromo-CTP | 16 | N |
| 2'-F-5-Methyl-2'-deoxy-UTP | 17 | N |

TABLE 154-continued

Non-naturally occurring nucleoside triphosphates

| Chemistry Modification | Compound # | Naturally occuring |
|---|---|---|
| 5-Aminoallyl-CTP | 18 | N |
| 2-Amino-riboside-TP | 19 | N |

Example 98. Incorporation of Modifications to the Nucleobase and Carbohydrate (Sugar)

Naturally and non-naturally occurring nucleosides are incorporated into mRNA encoding a polypeptide of interest. Commercially available nucleosides and NTPs having modifications to both the nucleobase and carbohydrate (sugar) are examined for their ability to be incorporated into mRNA and to produce protein, induce cytokines, and/or produce a therapeutic outcome. Examples of these nucleosides are given in Tables 155 and 156.

TABLE 155

Combination modifications

| Chemistry Modification | Compound # |
|---|---|
| 5-iodo-2'-fluoro-deoxyuridine | 1 |
| 5-iodo-cytidine | 6 |
| 2'-bromo-deoxyuridine | 7 |
| 8-bromo-adenosine | 8 |
| 8-bromo-guanosine | 9 |
| 2,2'-anhydro-cytidine hydrochloride | 10 |
| 2,2'-anhydro-uridine | 11 |
| 2'-Azido-deoxyuridine | 12 |
| 2-amino-adenosine | 13 |
| N4-Benzoyl-cytidine | 14 |
| N4-Amino-cytidine | 15 |
| 2'-O-Methyl-N4-Acetyl-cytidine | 16 |
| 2'Fluoro-N4-Acetyl-cytidine | 17 |
| 2'Fluor-N4-Bz-cytidine | 18 |
| 2'O-methyl-N4-Bz-cytidine | 19 |
| 2'O-methyl-N6-Bz-deoxyadenosine | 20 |
| 2'Fluoro-N6-Bz-deoxyadenosine | 21 |
| N2-isobutyl-guanosine | 22 |
| 2'Fluro-N2-isobutyl-guanosine | 23 |
| 2'O-methyl-N2-isobutyl-guanosine | 24 |

TABLE 156

Naturally occuring combinations

| Name | Compound # | Naturally occurring |
|---|---|---|
| 5-Methoxycarbonylmethyl-2-thiouridine TP | 1 | Y |
| 5-Methylaminomethyl-2-thiouridine TP | 2 | Y |
| 5-Crbamoylmethyluridine TP | 3 | Y |
| 5-Carbamoylmethyl-2'-O-methyluridine TP | 4 | Y |
| 1-Methyl-3-(3-amino-3-carboxypropyl) pseudouridine TP | 5 | Y |
| 5-Methylaminomethyl-2-selenouridine TP | 6 | Y |
| 5-Carboxymethyluridine TP | 7 | Y |
| 5-Methyldihydrouridine TP | 8 | Y |
| lysidine TP | 9 | Y |
| 5-Taurinomethyluridine TP | 10 | Y |
| 5-Taurinomethyl-2-thiouridine TP | 11 | Y |
| 5-(iso-Pentenylaminomethyl)uridine TP | 12 | Y |
| 5-(iso-Pentenylaminomethyl)-2-thiouridine TP | 13 | Y |
| 5-(iso-Pentenylaminomethyl)-2'-O-methyluridine TP | 14 | Y |
| N4-Acetyl-2'-O-methylcytidine TP | 15 | Y |
| N4,2'-O-Dimethylcytidine TP | 16 | Y |
| 5-Formyl-2'-O-methylcytidine TP | 17 | Y |

TABLE 156-continued

Naturally occuring combinations

| Name | Compound # | Naturally occurring |
|---|---|---|
| 2'-O-Methylpseudouridine TP | 18 | Y |
| 2-Thio-2'-O-methyluridine TP | 19 | Y |
| 3,2'-O-Dimethyluridine TP | 20 | Y |

In the tables "UTP" stands for uridine triphosphate, "GTP" stands for guanosine triphosphate, "ATP" stands for adenosine triphosphate, "CTP" stands for cytosine triphosphate, "TP" stands for triphosphate and "Bz" stands for benzyl.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

Example 99. LNP Formulation and Optimization to Reduce Repeat-Dose Resistance Experiments are carried out in order to optimize lipid nanoparticle (LNP) compositions for use in multi-dosing mRNA delivery. The goal is to develop LNP formulations that allow for consistent protein expression without repeat-dose resistance during repeat-dose administration (characterized by a greater than 40% reduction in protein expression) while not triggering an immune response.

LNP parameters that are manipulated include: 1. the molar percentage (Mol %) of polyethyleneglycol (PEG) lipid; 2. PEG lipid anchor chain length (14 carbons to 18 carbons); 3. the Mol % of cationic lipid; and 4. the ratio of total lipid:mRNA (10:1 to 50:1). To test each formulation, mRNAs encoding luciferase as well as a secreted target (e.g., EPO or factor IX) are used.

Examples of LNP formulations are presented in Tables 157-160. In these tables, DSPC is disteroylphosphatidyl choline, DMG is 1,2-Dimyristoyl-sn-glycerol, DSG is 1,2-Distearoyl-sn-glycerol, DPG is 1,2-Dipalmitoyl-sn-glycerol and PEG2K is a PEG chain with a molecular weight of 2,000. In Table 158, "X" represents DMG, DPG or DSG.

TABLE 157

20:1 lipid:mRNA LNP formulations with modified PEG:lipid ratios

| # | Cationic (Mol %) | DSPC (Mol %) | Cholesterol (Mol %) | PEG2K-DMG (Mol %) |
|---|---|---|---|---|
| 1 | 50 | 10 | 38.5 | 1.5 |
| 2 | 50 | 10 | 39 | 1 |
| 3 | 50 | 10 | 37 | 3 |
| 4 | 50 | 10 | 35 | 5 |

TABLE 158

20:1 lipid:mRNA LNP formulations with modified PEG lipid anchor chain length

| # | Cationic (Mol %) | DSPC (Mol %) | Cholesterol (Mol %) | PEG2K-X (Mol %) |
|---|---|---|---|---|
| 1 | 50 | 10 | 38.5 | 1.5 |
| 5 | 50 | 10 | 38.5 | 1.5 |
| 6 | 50 | 10 | 38.5 | 1.5 |

TABLE 159

20:1 lipid:mRNA LNP formulations with modified cationic lipid levels

| # | Cationic (Mol %) | DSPC (Mol %) | Cholesterol (Mol %) | PEG2K-DMG (Mol %) |
|---|---|---|---|---|
| 1 | 50 | 10 | 38.5 | 1.5 |
| 7 | 40 | 10 | 48.5 | 1.5 |
| 8 | 45 | 10 | 43.5 | 1.5 |
| 9 | 55 | 10 | 33.5 | 1.5 |
| 10 | 55 | 7 | 36.5 | 1.5 |
| 11 | 60 | 7 | 31.5 | 1.5 |
| 12 | 60 | 10 | 28.5 | 1.5 |

TABLE 160

LNP formulations with modified lipid:mRNA ratios

| # | Cationic (Mol %) | DSPC (Mol %) | Cholesterol (Mol %) | PEG2K-DMG (Mol %) | Lipid:mRNA ratio |
|---|---|---|---|---|---|
| 1 | 50 | 10 | 38.5 | 1.5 | 20:1 |
| 2 | 50 | 10 | 38.5 | 1.5 | 10:1 |
| 3 | 50 | 10 | 38.5 | 1.5 | 15:1 |
| 4 | 50 | 10 | 38.5 | 1.5 | 30:1 |

Example 100. Factor IX Expression with Repeat Dosing

A. Lipid Nanoparticle Formulation

EPO mRNA (SEQ ID NO: 7; polyA tail of approximately 140 nucleotides not shown in sequence; 5'cap, Cap1; fully modified with 5-methylcytosine and 1-methylpseudouridine), G-CSF mRNA (SEQ ID NO: 4; polyA tail of approximately 140 nucleotides not shown in sequence; 5'cap, Cap1; fully modified with 5-methylcytosine and 1-methylpseudouridine) and Factor IX mRNA (SEQ ID NO: 8; polyA tail of approximately 140 nucleotides not shown in sequence; 5'cap, Cap1; fully modified with 5-methylcytosine and 1-methylpseudouridine), were formulated in DLin-KC2-DMA as described in Table 161.

TABLE 161

| DLin-KC2-DMA Formulation | |
| --- | --- |
| Formulation | NPA-157-1 |
| Lipid | DLin-KC2-DMA |
| Lipid/mRNA ratio (wt/wt) | 20:1 |
| Mean Size | 89 nm PDI: 0.08 |
| Zeta at pH 7.4 | 1.1 mV |
| Encaps. (RiboGr) | 97% |

B. Two Doses, One Week Apart

Experiments were carried out to evaluate the expression of factor IX following weekly intravenous (IV) repeat-dose administration in normal rats. Factor IX (FIX) modified mRNA (SEQ ID NO: 8; polyA tail of approximately 140 nucleotides not shown in sequence; 5'cap, Cap1; fully modified with 5-methylcytosine and 1-methylpseudouridine) was administered alone (FIX only), or in combination (FIX/GCSF/EPO) with G-CSF modified mRNA (SEQ ID NO: 4; polyA tail of approximately 140 nucleotides not shown in sequence; 5'cap, Cap1; fully modified with 5-methylcytosine and 1-methylpseudouridine) and EPO modified mRNAs (SEQ ID NO: 7; polyA tail of approximately 140 nucleotides not shown in sequence; 5'cap, Cap1; fully modified with 5-methylcytosine and 1-methylpseudouridine) formulated in a lipid nanoparticle as described in Table 161. The formulations were administered according to Table 162, using an mRNA dose of 0.005 mg/kg for FIX-only test articles and an mRNA dose of 0.005 mg/kg for each mRNA included in the combination (FIX/GCSF/EPO) test article (0.015 mg/kg total mRNA). Phosphate buffered saline (PBS) was used as a negative control. Male Harlan Sprague Dawley rats (about 0.36 kg/each) were fitted with jugular vein catheters for test article administration. Rats received an initial administration of test article (or negative control), followed by a second repeat-dose, 1 week after the initial administration.

TABLE 162

| | FIX administration parameters | | | | | | |
| --- | --- | --- | --- | --- | --- | --- | --- |
| Group | Test article | Cationic lipid | Vehicle | n | mRNA dose/rat (mg) | Injection volume (ml) | Total volume needed (ml)/group |
| A | FIX only | KC2 | LNP(KC2) | 5 | 0.0018 | 0.15 | 0.75 |
| B | FIX/GCSF/EPO | KC2 | LNP(KC2) | 5 | 0.0054 | 0.15 | 0.75 |
| C | Control | none | PBS | 5 | N/A | 0.15 | 0.75 |

Blood samples were taken at 2.0 hours, 8.0 hours, 24.0 hours and 72.0 hours after the initial administration and at 2.0 hours, 8.0 hours and 48.0 hours after the administration of the repeat-dose. Levels of FIX were determined in each blood sample by enzyme-linked immunosorbent assay (ELISA) (Molecular Innovations, Novi, Mich.).

FIX levels in Groups A and B were detected following the first dose at 8.0 hours with increasing levels detected after 24.0 hours (see Table 163). In samples collected after the repeat-dose was administered, comparable FIX levels were detected at 8.0 hours, suggesting that no repeat-dose resistance occurred with repeat dosing. FIX levels in the 48.0 hour sample declined, presumably due to normal protein degradation.

TABLE 163

| | | FIX serum ELISA results | | | | | |
| --- | --- | --- | --- | --- | --- | --- | --- |
| | | Average FIX detected (ng/ml) after dose 1 | | | Average FIX detected (ng/ml) after dose 2 | | |
| Group | Test article | 2.0 hrs | 8.0 hrs | 24.0 hrs | 2.0 hrs | 8.0 hrs | 48.0 hrs |
| A | FIX only | 0.3 | 0.8 | 1.7 | 0.4 | 0.3 | 0.4 |
| B | FIX/GCSF/EPO | 0.1 | 0.7 | 2.0 | 0.3 | 1.5 | 0.4 |
| C | Control | 0.0 | 0.0 | 0.0 | 0.2 | 0.3 | 0.0 |

B. Two Doses, Three Days Apart

Experiments were carried out to evaluate the expression of FIX mRNA following two repeat-doses (via IV) in normal rats, administered three days apart. FIX modified mRNAs (SEQ ID NO: 8; polyA tail of approximately 140 nucleotides not shown in sequence; 5'cap, Cap1; fully modified with 5-methylcytosine and 1-methylpseudouridine) alone (FIX only) or in combination (FIX/GCSF/EPO) with G-CSF modified mRNA (SEQ ID NO: 4; polyA tail of approximately 140 nucleotides not shown in sequence; 5'cap, Cap1; fully modified with 5-methylcytosine and 1-methylpseudouridine) and EPO modified mRNAs (SEQ ID NO: 7; polyA tail of approximately 140 nucleotides not shown in sequence; 5'cap, Cap1; fully modified with 5-methylcytosine and 1-methylpseudouridine) formulated in a lipid nanoparticle as described in Table 161. The formulations were administered according to Table 164, using an mRNA dose of either 0.025 mg/kg or 0.005 mg/kg for FIX-only test articles and using an mRNA dose of 0.075 mg/kg or 0.015 mg/kg for FIX/G-CSF/EPO test articles (formulated for dosing at 0.025 and 0.005 mg/kg for each of the three mRNAs). Phosphate buffered saline (PBS) was used as a negative control. Male Harlan Sprague Dawley rats (about 0.36 kg/each) were fitted with jugular vein catheters for test article administration. Rats received an initial administration of the test article (or negative control), followed by a repeat-dose administered 3 days after the initial administration.

TABLE 164

FIX administration parameters

| Group | Test article | Cationic lipid | Vehicle | n | mRNA dose/rat (mg) | Injection volume (ml) | Total volume needed (ml)/group |
|---|---|---|---|---|---|---|---|
| A | FIX only | KC2 | LNP(KC2) | 5 | 0.0075 | 0.15 | 0.75 |
| B | FIX only | KC2 | LNP(KC2) | 5 | 0.0015 | 0.15 | 0.75 |
| C | FIX/GCSF/EPO | KC2 | LNP(KC2) | 5 | 0.0225 | 0.15 | 0.75 |
| D | FIX/GCSF/EPO | KC2 | LNP(KC2) | 5 | 0.0045 | 0.15 | 0.75 |
| E | Control | none | PBS | 5 | N/A | 0.15 | 0.75 |

Blood samples were taken at 2.0 hours, 8.0 hours, 24.0 hours and 72.0 hours after the initial administration and at 2.0 hours, 8.0 hours and 24.0 hours after the repeat-dose administration. Levels of FIX were determined in each blood sample by ELISA (Molecular Innovations, Novi, Mich.).

Delivery of FIX mRNA (at the 0.025 mg/kg dose) formulated in a KC2 lipid nanoparticles produced a time-dependent increase in human FIX in rat serum with peak levels (7 ng/ml) observed within 8.0 hours (see Table 165). Human FIX concentrations were maintained at this level for 24.0 hours post-dose and fell to background levels by 72.0 hours.

The serum levels of FIX following a repeat-dose of FIX mRNA three days later did not display repeat-dose resistance with FIX expression following a similar time course to that seen following the first dose. Surprisingly, levels of FIX in rat sera were about two-fold higher when FIX was administered in combination with human G-CSF and human EPO in KC2 nanoparticles. Serum concentration of human FIX reached a peak of about 12 ng/ml within 8.0 hours post-dosing. Levels were maintained for 24.0 hours and then declined to baseline by 72.0 hours. Similar elevations in human FIX in rat sera were seen following a repeat-dose of the FIX/G-CSF/EPO mRNA combination. The higher degree of expression of FIX protein with the combination formulation correlates with increased levels of cationic lipid present in the combination formulations.

TABLE 165

FIX serum ELISA results

| Group | Test article | Average FIX detected (ng/ml) after dose 1 | | | Average FIX detected (ng/ml) after dose 2 | |
|---|---|---|---|---|---|---|
| | | 8.0 hrs | 24.0 hrs | 72.0 hrs | 8.0 hrs | 24.0 hrs |
| A | FIX | 7.0 ± 3.0 | 6.0 ± 1.5 | 0.1 ± 0.1 | 3.5 ± 1.5 | 7.0 ± 4.0 |
| B | FIX | 0.5 ± 0.1 | 0.5 ± 0.1 | 0.1 ± 0.1 | 0.0 ± 0.0 | 0.5 ± 0.5 |
| C | FIX/GCSF/EPO | 13.0 ± 2.5 | 11.3 ± 2.0 | 0.1 ± 0.1 | 12.5 ± 2.5 | 13.5 ± 3.5 |

TABLE 165-continued

FIX serum ELISA results

| Group | Test article | Average FIX detected (ng/ml) after dose 1 | | | Average FIX detected (ng/ml) after dose 2 | |
|---|---|---|---|---|---|---|
| | | 8.0 hrs | 24.0 hrs | 72.0 hrs | 8.0 hrs | 24.0 hrs |
| D | FIX/GCSF/EPO | 1.0 ± 0.2 | 1.0 ± 0.2 | 0.0 ± 0.0 | 1.0 ± 0.5 | 1.3 ± 0.2 |
| E | Control | 0.0 ± 0.0 | 0.0 ± 0.0 | 0.0 ± 0.0 | 0.0 ± 0.0 | 0.1 ± 0.1 |

Example 101. Sesame Oil-Based Formulations with Modified mRNA

A mRNA suspension formulation was prepared using GCSF mRNA (SEQ ID NO: 4; polyA tail of approximately 140 nucleotides not shown in sequence; 5'cap, Cap1; fully modified with 5-methylcytosine and 1-methylpseudouridine) in an oil-phase consisting of sesame oil, polyethylene glycol 400 and propylene glycol monolaurate (also referred to as Capmul®). GCSF mRNA was lyophilized and reconstituted using water for injection to yield an aqueous mRNA solution at 5.8 mg/ml. An oil phase was prepared by combining 400 µl of sesame oil (Spectrum Labs, Houston, Tex.), 200 µl of polyethylene glycol 400 (Sigma Aldrich, St. Louis, Mo.) and 200 µl of propylene glycol monolaurate (Pfaltz and Bauer, Waterbury, Conn.).

An mRNA suspension formed upon addition of 94.8 µl of mRNA solution (0.55 mg) to the oil phase. The mixture was vortexed to yield a uniform suspension of mRNA solution as assessed by visual appearance. To simulate delivery of the suspension formulation to a physiological fluid, 20 µl of the mRNA and sesame oil-based suspension was added to 1 ml of phosphate buffered saline (PBS), pH 7.4 (prepared from a 10× solution consisting of 55 mM sodium phosphate dibasic, 12 mM potassium phosphate monobasic and 1.54 M NaCl, Teknova, Hollister, Calif.). After adding the oil phase to PBS, an oil-in-water emulsion formed after vortexing. Particle size of the mRNA emulsion was measured using dynamic light scattering (Malvern Zetasier Model Nano-SZ90, Malvern, Worcestershire, UK). The average particle size was 316 nm.

Example 102. Luciferase-Based Monitoring of Sesame Oil mRNA Emulsion Administration In vivo administration of mRNA in a sesame oil emulsion is demonstrated using luciferase mRNA. To prepare the mRNA suspension, 98 µl of mRNA at a concentration of 4.83 mg/ml is added to 352 µl of the oil phase comprising a 2:1:1 volume ratio of sesame oil:polyethylene glycol 400:propylene glycol monolaurate. The resulting combination yields a 1 mg/ml mRNA suspension. The suspension is administered to mice at a dose of 2.5 mg/kg via an intramuscular injection. Luciferase expression is monitored following administration.

Example 103. Cationic Nanoparticle Formation

Nanoparticles were produced in the presence of monovalent and divalent cations, sodium and calcium. These nanoparticles did not form immediately, but rather formed in the period comprising hours to days.

Example 104. Hydrogel Preparation Comprising PEG-Based Sealants

At least two PEG-based lipids are mixed vigorously with a dilute hydrogen chloride solution and then transferred to a storage tube. A basic buffer solution is transferred to a different storage tube. mRNA is added to the PEG-based solution or the buffer solution prior to the contacting of the two solutions. Analysis of the protein expression, release rate and/or effect of varying the concentration of the PEG lipids, ratio of solutions or the amount of mRNA used are evaluated.

In follow-up studies, the concentration of PEG-based lipids, the ratio of PEG-based lipids, the ratio of the buffer and the acid and the amount of mRNA that is loaded in the solutions may be varied in order to determine the optimal conditions for delivery of the mRNA.

Example 105. Release Rate from PEG-Based Hydrogel

To determine the release rate of luciferase mRNA ((mRNA sequence shown in SEQ ID NO: 14; polyA tail of approximately 140 nucleotides not shown in sequence; 5'cap, Cap1) fully modified with 5-methylcytosine and 1-methylpseudouridine was evaluated in COSEAL® (Baxter, Deerfield, Ill.). The polymers pentaerythritol PEG ether tetra-succinimidyl glutarate and pentaerythritol PEG ether tetra-thiol were mixed vigorously with a dilute hydrogen chloride solution to form a PEG solution. 90 uL of the PEG solution in dilute hydrochloric acid was added to a 24 well plate with 1.2% Agarose gel and either 20 uL of a control of 1×PBS, 20 uL of luciferase mRNA in 1×PBS at a concentration of 9 mg/mL (Luc-PBS) or 20 uL of LNP formulated luciferase mRNA (Luc-LNP) at 0.5 mg/mL in 1×PBS was added to the PEG-based lipid solution. The molar ranges of the LNP formulation are shown in Table 166.

TABLE 166

| | Molar ratio | | | | |
|---|---|---|---|---|---|
| | DODMA | DSPC | Cholesterol | DMG-PEG | Fluorescent Lipid Rhodamine-DOPE |
| Percent Mole (mol %) | 50 | 10 | 38.4 | 1.5 | 0.1 |

After the formation of the LNPs and the encapsulation of the modified luciferase mRNA (at a 20:1 lipid:mRNA w/w ratio), the LNP formulation was characterized by particle size and encapsulation efficiency (%) and the results are shown in Table 167.

TABLE 167

Characterization of LNP Formulations

| Lipid Ratio | Mean size (nm) | Encapsulation (%) |
|---|---|---|
| 20:1 | 196.6<br>PDI: 0.174 | 54 |

90 uL of a sodium carbonate/sodium phosphate buffer was added to the plate and mixed with a pipette. 2 ml of 1×PBS was added to the plate and the plate was placed in a 37° C. incubator on an orbital shaker at the lowest speed. At 0 hours, 2 hours, 6 hours, 24 hours, 48 hours, 72 hours and 144 hours 200 uL of PBS was removed and replaced from the plate. The release of the luciferase mRNA formulated in the buffer was evaluated by RiboGreen assay and the release of the luciferase mRNA formulated in the LNP was evaluated by fluorescence.

As shown in Table 168, about 29% of the mRNA in the buffer was released at the 24 hour time point whereas at 24 hours about 11% of the mRNA formulated in LNPs was released from the hydrogel. The amount of mRNA released is shown in Table 169.

TABLE 168 mRNA Release Profile-Cumulative Release

| Time point | Cumulative Release (%) | |
|---|---|---|
| (hours) | Luc-PBS | Luc-LNP |
| 0 | 0.07 | 1.18 |
| 2 | 0.20 | 1.29 |
| 6 | 0.57 | 1.25 |
| 24 | 29.09 | 11.02 |
| 48 | 66.78 | 71.06 |
| 72 | 76.08 | 89.90 |
| 144 | 100.53 | 102.88 |

TABLE 169 mRNA Release Profile-Released mRNA

| Time point | Released mRNA (ug) | |
|---|---|---|
| (hours) | Luc-PBS | Luc-LNP |
| 0 | 0.13 | 0.12 |
| 2 | 0.37 | 0.13 |
| 6 | 1.03 | 0.13 |
| 24 | 52.36 | 1.10 |
| 48 | 120.21 | 7.11 |
| 72 | 136.95 | 8.99 |
| 144 | 180.94 | 10.28 |

Example 106. Micromixer Formed Lipid Nanoparticle

Lipid nanoparticles (LNPs) were formulated using a micromixer mixing junction at a flow rate of 0.5 ml/min. LNPs were formulated at a 10:1, 20:1, 27:1 or 50:1 weight ratio of total lipid to modified G-CSF mRNA (SEQ ID NO: 4; polyA tail of approximately 140 nucleotides not shown in sequence; 5'cap, Cap1; fully modified with 1-methylpseudourine and 5-methylcytosine). The molar ranges of the LNP formulation are shown in Table 170.

TABLE 170

| Molar Ratios | | | | |
|---|---|---|---|---|
| | DODMA | DSPC | Cholesterol | PEG-DMG |
| Mole Percent (mol %) | 50.0 | 10.0 | 38.5 | 1.5 |

After the formation of the LNPs and the encapsulation of the modified G-CSF mRNA, the LNP formulations were characterized by particle size, zeta potential and encapsulation efficiency (%) and the results are shown in Table 171.

TABLE 171

Characterization of LNP Formulations

| Lipid Ratio | Mean size (nm) | Zeta at pH 7.4 (mV) | Encapsulation (%) |
|---|---|---|---|
| 10:1 | 186.5<br>PDI: 0.34 | −8.12 | 68.2 |
|  | 159.4<br>PDI: 0.21 | −10 | 80.2 |
| 20:1 | 117<br>PDI: 0.40 | −7.91 | 90.1 |
|  | 120.8<br>PDI: 0.24 | −6.25 | 89.6 |
| 27:1 | 106.6<br>PDI: 0.08 | −16.7 | 94.6 |
|  | 71.9<br>PDI: 0.15 | −10.8 | 94.1 |
| 50:1 | 86.6<br>PDI: 0.18 | −6.65 | 96.8 |
|  | 86.7<br>PDI: 0.18 | −4.27 | 92.1 |

The micromixer was found to reduce the size an average of 25% compared to standard "T" junction mixing and was also found to increase encapsulation efficiency. Increasing the mRNA:lipid ratio was found to decrease particle size and increase encapsulation efficiency.

Example 107. Micromixer Formed Lipid Nanoparticle with Increased PEG Percentage

Lipid nanoparticles (LNPs) were formulated using a micromixer mixing junction at a flow rate of 0.5 ml/min. LNPs were formulated at a 10:1, 20:1, 27:1 or 50:1 weight ratio of total lipid to modified G-CSF mRNA (SEQ ID NO: 4; polyA tail of approximately 140 nucleotides not shown in sequence; 5'Cap, Cap1; fully modified with 1-methylpseudourine and 5-methylcytosine). The molar ranges of the LNP formulation are shown in Table 172.

TABLE 172

| Molar Ratios | | | | |
|---|---|---|---|---|
| | DODMA | DSPC | Cholesterol | PEG-DMG |
| Mole Percent (mol %) | 15.0 | 20.0 | 55.0 | 10 |

After the formation of the LNPs and the encapsulation of the modified G-CSF mRNA, the LNP formulations were characterized by particle size, zeta potential and encapsulation efficiency (%) and the results are shown in Table 173.

TABLE 173

| Lipid Ratio | Mean size (nm) | Zeta at pH 7.4 (mV) | Encapsulation (%) |
|---|---|---|---|
| Characterization of LNP Formulations | | | |
| 10:1 | 84.5 PDI: 0.25 | -2.2 | 11.1 |
|  | 61.2 PDI: 0.22 | -2.0 | 21.6 |
| 20:1 | 97.6 PDI: 0.22 | -2.7 | 51.7 |
|  | 64.9 PDI: 0.32 | 1.8 | 65.3 |
| 27:1 | 73.0 PDI: 0.20 | -2.4 | 52.1 |
|  | 72.6 PDI: 0.12 | 3.6 | 56.6 |
| 50:1 | 56.8 PDI: 0.21 | 3.6 | 86.9 |
|  | 57.5 PDI: 0.23 | -2.6 | 82.4 |

The micromixer was found to reduce the size an average of 25% compared to standard "T" junction mixing and was also found to increase encapsulation efficiency. Increasing the mRNA:lipid ratio was found to decrease particle size and increase encapsulation efficiency.

Example 108. Effect of Electroporation on Modified mRNA Delivery

Luciferase modified mRNA (mRNA sequence shown in SEQ ID NO: 14; polyA tail of approximately 140 nucleotides not shown in sequence; 5'cap, Cap1) fully modified with 5-methylcytosine and 1-methylpseudouridine (5 mC/1 mpU), formulated in PBS (pH 7.4) or a control of PBS alone was delivered to Balb-C mice (n=3) intramuscularly at a dose of 2.5 mg/kg of luciferase mRNA as outlined in Table 174.

TABLE 174

Dosing Regimen

| Group | Vehicle | Electroporation | Conc (mg/ml) | Inj Vol. (ul) | Amg (ug) | Dose (mg/kg) |
|---|---|---|---|---|---|---|
| 1: Luciferase mRNA | PBS | No | 1.0 | 50 | 50 | 2.5 |
| 2: Luciferase mRNA | PBS | Yes | 1.0 | 50 | 50 | 2.5 |
| 3: Vehicle only | PBS | No | — | — | — | — |

The mice of Group 2 were treated with electroporation (EP) using the AGILEPULSE™ instrument (Harvard Apparatus/BTX®, Holliston, Mass.) immediately after administration of luciferase. The electroporation treatment is summarized in Table 175.

TABLE 175

Electroporation Treatment

| Stage | 1 | 2 | 3 |
|---|---|---|---|
| Amplitude (V) | 450 | 450 | 110 |
| Pulse Duration (ms) | 0.05 | 0.05 | 10 |
| Pause Interval (ms) | 0.2 | 50 | 20 |
| Pulse Number (#) | 1 | 1 | 8 |

All of the mice were imaged at 3 hours, 24 hours, 48 hours, 72 hours, 168 hours, 240 hours, 336 hours and 480 hours after administration. Twenty minutes prior to imaging, the mice were injected intraperitoneally with a D-luciferin solution at 150 mg/kg. Animals were then anesthetized and images were acquired with an IVIS Lumina II imaging system (Perkin Elmer). Bioluminescence was measured as total flux (photons/second) of the entire mouse. The average total flux (photons/second) for intramuscular administration is shown in Table 176.

TABLE 176

Expression Over Time

| | Group 1 (Luciferase – EP) Total Flux (photons/s) | Group 2 (Luciferase + EP) Total Flux (photons/s) | Group 3 (Vehicle) Total Flux (photons/s) |
|---|---|---|---|
| 3 Hours | 2.57E+07 | 1.25E+07 | 8.82E+04 |
| 24 Hours | 3.81E+07 | 8.27E+07 | 6.73E+04 |
| 48 Hours | 1.24E+07 | 7.06E+07 | 7.17E+04 |
| 72 Hours | 5.69E+06 | 6.50E+07 | 8.22E+04 |
| 168 Hours | 1.48E+06 | 1.81E+07 | 9.93E+04 |
| 240 Hours | 6.50E+05 | 1.44E+07 | 6.32E+04 |
| 360 Hours | 1.86E+05 | 3.98E+06 | 7.98E+04 |
| 480 Hours | 6.65E+04 | 1.47E+06 | 7.51E+04 |

Luciferase expression was observed at greater than an order of magnitude above background levels out to 480 hours (nearly 3 weeks) in the group treated with electroporation, but not in the group without the electroporation treatment.

Example 109. Modified mRNA Dose Response Study with Electroporation

Luciferase modified mRNA (mRNA sequence shown in SEQ ID NO: 14; polyA tail of approximately 140 nucleotides not shown in sequence; 5'cap, Cap1) fully modified with 5-methylcytosine and 1-methylpseudouridine (5 mC/1 mpU), formulated in PBS (pH 7.4) or a control of PBS alone was delivered to Balb-C mice (n=6 for luciferase, n=3 for control) intramuscularly at a dose of luciferase mRNA as outlined in Table 177.

TABLE 177

Dosing Regimen

| Group | Vehicle | Electroporation | Conc (mg/ml) | Inj Vol. (ul) | Amg (ug) | Dose (mg/kg) |
|---|---|---|---|---|---|---|
| 1: Luciferase mRNA | PBS | No | 1.00 | 50 | 50 | 2.5 |
| 2: Luciferase mRNA | PBS | Yes | 1.00 | 50 | 50 | 2.5 |
| 3: Luciferase mRNA | PBS | No | 0.10 | 50 | 5 | 0.25 |
| 4: Luciferase mRNA | PBS | Yes | 0.10 | 50 | 5 | 0.25 |
| 5: Luciferase mRNA | PBS | No | 0.01 | 50 | 0.5 | 0.025 |
| 6: Luciferase mRNA | PBS | Yes | 0.01 | 50 | 0.5 | 0.025 |
| 7: Vehicle only | PBS | No | — | — | — | — |

The mice of Group 2, Group 4 and Group 6 are treated with electroporation (EP) using the AGILEPULSE™ electroporation instrument (Harvard Apparatus/BTX®, Holliston, Mass.) immediately after the administration of luciferase.

All of the mice are imaged at pre-determined intervals after administration. Twenty minutes prior to imaging, the mice are injected intraperitoneally with a D-luciferin solution at 150 mg/kg. Animals are then anesthetized and images were acquired with an IVIS Lumina II imaging system (Perkin Elmer). Bioluminescence is measured as total flux (photons/second) of the entire mouse.

Example 110. Modified mRNA Dose Response Study with Electroporation

EPO modified mRNA (mRNA sequence shown in SEQ ID NO: 7; polyA tail of approximately 140 nucleotides not shown in sequence; 5'cap, Cap1) fully modified with 5-methylcytosine and 1-methylpseudouridine (5 mC/1 mpU), formulated in PBS (pH 7.4) or a control of PBS alone was delivered to Balb-C mice (n=5 for EPO, n=3 for control) intramuscularly at a dose of EPO mRNA as outlined in Table 178.

TABLE 178

Dosing Regimen

| Group | Vehicle | Electroporation | Conc (mg/ml) | Inj Vol. (ul) | Amg (ug) | Dose (mg/kg) |
|---|---|---|---|---|---|---|
| 1: EPO mRNA | PBS | No | 2.00 | 50 | 100 | 5.0 |
| 2: EPO mRNA | PBS | Yes | 2.00 | 50 | 100 | 5.0 |
| 3: Vehicle only | PBS | No | — | — | — | — |

The mice of Group 2, Group 4 and Group 6 are treated with electroporation (EP) using the AGILEPULSE™ instrument (Harvard Apparatus/BTX®, Holliston, Mass.) immediately after administration of EPO. Serum is collected at 8 hours, 24 hours, 72 hours and 100 hours after administration of EPO. Muscle at the site of injection is collected at the end of the study. The serum and muscle are evaluated by ELISA for the expression of EPO.

Example 111. Microphysiological Systems

The polynucleotides, primary constructs and/or mmRNA are formulated using one of the methods described herein such as in buffer, lipid nanoparticles and PLGA. These formulations are then administered to or contacted with microphysiological systems created from organ chips as described in International Publication Nos. WO2013086502, WO2013086486 and WO2013086505, the contents of each of which are herein incorporated by reference in its entirety.

Example 112. Modified mRNA Electroporation Dose Response Study

Luciferase modified (mRNA sequence shown in SEQ ID NO: 14; polyA tail of approximately 140 nucleotides not shown in sequence; 5'cap, Cap1) fully modified with 5-methylcytosine and 1-methylpseudouridine, formulated in PBS (pH 7.4) or a control of PBS alone was delivered to Balb-C mice intramuscularly at a dose of 2.5 mg/kg, 0.25 mg/kg or 0.0.25 mg/kg luciferase mRNA with or without electroporation.

The mice undergoing electroporation were subjected to electroporation (EP) using the AGILEPULSE™ instrument (Harvard Apparatus/BTX®, Holliston, Mass.), as outlined in Table 179, immediately after the administration of luciferase or the control.

TABLE 179

| Electroporation Stages | | | |
|---|---|---|---|
| Stage | 1 | 2 | 3 |
| Amplitude (V) | 450 | 450 | 110 |
| Pulse Duration (ms) | 0.05 | 0.05 | 10 |
| Pause Interval (ms) | 0.2 | 50 | 20 |
| Pulse Number (#) | 1 | 1 | 8 |

All of the mice are imaged at 3 hours, 24 hours, 48 hours, 168 hours, 336 hours and 504 hours post-administration of luciferase modified mRNA. Twenty minutes prior to imaging, the mice are injected intraperitoneally with a D-luciferin solution at 150 mg/kg. Animals are then anesthetized and images were acquired with an IVIS Lumina II imaging system (Perkin Elmer). Bioluminescence is measured as total flux (photons/second) of the entire mouse. The results are shown in Table 180. The mice subjected to electroporation showed increase protein expression as compared to the mice not subjected to electroporation after luciferase modified mRNA administration.

TABLE 180

| Treatment | | Expression (Total Flux [p/s]) | | | | | |
|---|---|---|---|---|---|---|---|
| Dose | EP | 3 hr | 24 hr | 48 hr | 168 hr | 336 hr | 504 hr |
| 2.5 mg/kg | No | 2.77E+06 | 9.81E+06 | 9.39E+06 | 9.26E+05 | 3.18E+05 | 1.28E+05 |
| 2.5 mg/kg | Yes | 1.68E+07 | 1.93E+07 | 2.00E+07 | 5.29E+06 | 9.23E+05 | 3.87E+05 |
| 0.25 mg/kg | No | 7.58E+04 | 2.46E+05 | 7.90E+05 | 4.07E+05 | 1.15E+05 | 9.14E+04 |
| 0.25 mg/kg | Yes | 1.11E+06 | 5.13E+06 | 2.15E+07 | 1.39E+06 | 3.08E+05 | 1.32E+05 |
| 0.025 mg/kg | No | 1.21E+05 | 5.52E+04 | 1.45E+05 | 9.40E+04 | 8.22E+04 | 9.04E+04 |
| 0.025 mg/kg | Yes | 7.81E+04 | 6.48E+05 | 6.19E+05 | 9.58E+04 | 8.34E+04 | 1.09E+05 |
| Untreated | N/A | 7.37E+04 | 5.40E+04 | 7.42E+04 | 7.34E+04 | 8.11E+04 | 1.13E+05 |

Example 113. FGF21 Modified mRNA Electroporation Dose Response Study

Fibroblast Growth Factor 21 (FGF21) modified mRNA (mRNA sequence shown in SEQ ID NO: 24; polyA tail of approximately 140 nucleotides not shown in sequence; 5'cap, Cap1) fully modified with 5-methylcytosine and 1-methylpseudouridine, formulated in PBS (pH 7.4) or a control of PBS alone was delivered to Balb-C mice intramuscularly at a dose of 5 mg/kg FGF21 mRNA with or without electroporation.

The mice undergoing electroporation were subjected to electroporation (EP) using the AGILEPULSE™ instrument (Harvard Apparatus/BTX®, Holliston, Mass.), as outlined in Table 181, immediately after the administration of FGF21 mRNA or the control.

TABLE 181

| Electroporation Stages | | | |
|---|---|---|---|
| Stage | 1 | 2 | 3 |
| Amplitude (V) | 450 | 450 | 110 |
| Pulse Duration (ms) | 0.05 | 0.05 | 10 |
| Pause Interval (ms) | 0.2 | 50 | 20 |
| Pulse Number (#) | 1 | 1 | 8 |

Serum was collected from the mice at 2 hours and 8 hours. The results are shown in Table 182 and in FIG. 5.

TABLE 182

| FGF21 Protein Expression | | |
|---|---|---|
| | Serum Expression (pg/ml) 2 hours | Serum Expression (pg/ml) 8 hours |
| With EP | 102.8 | 239.4 |
| Without EP | 111.8 | 102.6 |

The mice subjected to electroporation showed increase protein production as compared to the mice not subjected to electroporation after FGF21 modified mRNA administration. There was no detectable protein expression from the control group.

Example 114. Mouse EPO Modified mRNA Electroporation Multi-Dose Study

Mouse erythropoietin (EPO) modified mRNA comprising a miR-142-3p sequence mRNA (mRNA sequence shown in SEQ ID NO: 25; polyA tail of approximately 140 nucleotides not shown in sequence; 5'cap, Cap1) fully modified with 5-methylcytosine and 1-methylpseudouridine (EPO miR-142-3p) or without a miR-142-3p sequence (mRNA sequence shown in SEQ ID NO: 26; polyA tail of approximately 140 nucleotides not shown in sequence; 5'cap, Cap1) fully modified with 5-methylcytosine and 1-methylpseudouridine (EPO), was formulated in PBS (pH 7.4) or a control of 5% isotonic mannitol was delivered to C57BL/6 intramuscularly at four times a dose of 0.2 mg/kg EPO miR-142-3p mRNA or 0.2 mg/kg EPO mRNA for each administration.

The mice were subjected to electroporation (EP) using the AGILEPULSE™ instrument (Harvard Apparatus/BTX®, Holliston, Mass.), as outlined in Table 183, immediately after the administration of each dose of EPO miR-142-3p mRNA, EPO mRNA or the control.

TABLE 183

| Electroporation Stages | | | |
|---|---|---|---|
| Stage | 1 | 2 | 3 |
| Amplitude (V) | 450 | 450 | 110 |
| Pulse Duration (ms) | 0.05 | 0.05 | 10 |
| Pause Interval (ms) | 0.2 | 50 | 20 |
| Pulse Number (#) | 1 | 1 | 8 |

Serum was collected from the mice at 24 hours post the first, second, third and fourth doses. The results are shown in Table 184.

TABLE 184

| | Expression | | | |
|---|---|---|---|---|
| | First Dose EPO (pg/ml) | Second Dose EPO (pg/ml) | Third Dose EPO (pg/ml) | Fourth Dose EPO (pg/ml) |
| EPO | 151.9 | 357.8 | 898.5 | 258.1 |
| EPO miR-142-3p | 257.4 | 518.4 | 789.5 | 242.9 |
| Control | 34.6 | 72.4 | 43.3 | 37.4 |

Consistent levels of EPO were shown after each dose of EPO miR-142-3p mRNA and EPO mRNA.

Example 115. Human EPO Modified mRNA Electroporation Multi-Dose Study

Human erythropoietin (EPO) modified mRNA comprising a miR-142-3p sequence mRNA (mRNA sequence shown in SEQ ID NO: 27; polyA tail of approximately 140 nucleotides not shown in sequence; 5'cap, Cap1) fully modified with 5-methylcytosine and 1-methylpseudouridine (EPO miR-142-3p) or without a miR-142-3p sequence mRNA (mRNA sequence shown in SEQ ID NO: 28; polyA tail of approximately 140 nucleotides not shown in sequence; 5'cap, Cap1) fully modified with 5-methylcytosine and 1-methylpseudouridine (EPO), was formulated in PBS (pH 7.4) or a control of 5% isotonic mannitol was delivered to C57BL/6 intramuscularly at four times a dose of 0.2 mg/kg EPO miR-142-3p mRNA or 0.2 mg/kg EPO mRNA for each administration.

The mice were subjected to electroporation (EP) using the AGILEPULSE™ instrument (Harvard Apparatus/BTX®, Holliston, Mass.), as outlined in Table 185, immediately after the administration of each dose of EPO miR-142-3p mRNA, EPO mRNA or the control.

TABLE 185

| Electroporation Stages | | | |
|---|---|---|---|
| Stage | 1 | 2 | 3 |
| Amplitude (V) | 450 | 450 | 110 |
| Pulse Duration (ms) | 0.05 | 0.05 | 10 |
| Pause Interval (ms) | 0.2 | 50 | 20 |
| Pulse Number (#) | 1 | 1 | 8 |

Serum was collected from the mice at 24 hours post the first, second, third and fourth doses. The results (EPO pg/ml) are shown in Table 185.

TABLE 185

| | Expression | | | |
|---|---|---|---|---|
| | First Dose EPO (pg/ml) | Second Dose EPO (pg/ml) | Third Dose EPO (pg/ml) | Fourth Dose EPO (pg/ml) |
| EPO | 9.5 | 27.9 | 284.5 | 139.9 |
| EPO miR-142-3p | 6.8 | 24.4 | 57.2 | 53.8 |
| Control | 0 | 0 | 0 | 0 |

Consistent levels of EPO were shown after each dose of EPO miR-142-3p mRNA and EPO mRNA.

Example 116. Mouse EPO Modified mRNA Mannitol Multi-Dose Study

Mouse erythropoietin (EPO) modified mRNA comprising a miR-142-3p sequence mRNA (mRNA sequence shown in SEQ ID NO: 25; polyA tail of approximately 140 nucleotides not shown in sequence; 5'cap, Cap1) fully modified with 5-methylcytosine and 1-methylpseudouridine (EPO miR-142-3p) or without a miR-142-3p sequence (mRNA sequence shown in SEQ ID NO: 26; polyA tail of approximately 140 nucleotides not shown in sequence; 5'cap, Cap1) fully modified with 5-methylcytosine and 1-methylpseudouridine (EPO) was formulated in 5% isotonic Mannitol or a control of 5% isotonic Mannitol was delivered to C57BL/6 intramuscularly at eight times a dose of 2.5 mg/kg EPO miR-142-3p mRNA or 2.5 mg/kg EPO mRNA for each administration.

Serum was collected from the mice at 24 hours post the second, fourth, sixth and eighth doses. The results (EPO pg/ml) are shown in Table 186.

TABLE 186

| | Expression | | | |
|---|---|---|---|---|
| | Second Dose EPO (pg/ml) | Fourth Dose EPO (pg/ml) | Sixth Dose EPO (pg/ml) | Eighth Dose EPO (pg/ml) |
| EPO | 334.7 | 483.4 | 328.9 | 239.3 |
| EPO miR-142-3p | 496.3 | 512.7 | 366.4 | 359.6 |
| Control | 57.7 | 80.0 | 102.6 | 36.4 |

Consistent levels of EPO were shown after each dose of EPO miR-142-3p mRNA and EPO mRNA.

Example 115. Human EPO Modified mRNA Mannitol Multi-Dose Study

Human erythropoietin (EPO) modified mRNA comprising a miR-142-3p sequence mRNA (mRNA sequence shown in SEQ ID NO: 27; polyA tail of approximately 140 nucleotides not shown in sequence; 5'cap, Cap1) fully modified with 5-methylcytosine and 1-methylpseudouridine (EPO miR-142-3p) or without a miR-142-3p sequence mRNA (mRNA sequence shown in SEQ ID NO: 28; polyA tail of approximately 140 nucleotides not shown in sequence; 5'cap, Cap1) fully modified with 5-methylcytosine and 1-methylpseudouridine (EPO), was formulated in Mannitol or a control of Mannitol was delivered to C57BL/6 intramuscularly at eight times a dose of 2.5 mg/kg EPO miR-142-3p mRNA or 2.5 mg/kg EPO mRNA for each administration.

Serum was collected from the mice 24 hours post the second, fourth, sixth and eighth doses. The results (EPO pg/ml) are shown in Table 187.

TABLE 187

| | Expression | | | |
|---|---|---|---|---|
| | Second Dose EPO (pg/ml) | Fourth Dose EPO (pg/ml) | Sixth Dose EPO (pg/ml) | Eighth Dose EPO (pg/ml) |
| EPO | 43.5 | 44.3 | 46.3 | 7.9 |
| EPO miR-142-3p | 42.7 | 40.3 | 43.2 | 11.8 |
| Control | 0 | 0 | 0 | 0 |

Consistent levels of EPO were shown after each dose of EPO miR-142-3p mRNA and EPO mRNA.

Example 116. Formulation and Route of Administration Study

Luciferase modified (mRNA sequence shown in SEQ ID NO: 14; polyA tail of approximately 140 nucleotides not shown in sequence; 5'cap, Cap1) fully modified with 5-methylcytosine and 1-methylpseudouridine, was formulated in as outlined in Table 188 was administered to Balb-C mice (n=3) as outlined in Table 188. In Table 188, "IM" means intramuscular administration and "SC" means subcutaneous administration.

TABLE 188

| | Dosing Regimen | | | | | |
|---|---|---|---|---|---|---|
| Group | Vehicle | Route | Conc (mg/ml) | Inj Vol (ul) | Amt (ug) | Dose (mg/kg) |
| 1 | 8.5% Sucrose (control) | IM | 0.20 | 50 | 10.0 | 0.5 |
| 2 | 8.5% Sucrose (control) | SC | 0.20 | 250 | 50.0 | 2.5 |
| 3 | KC2 LNP (control) | IM | 0.20 | 50 | 10.0 | 0.5 |
| 4 | KC2 LNP (control) | SC | 0.20 | 250 | 50.0 | 2.5 |
| 5 | 10 mM citrate pH = 7, 130 mM NaCl | IM | 0.20 | 50 | 10.0 | 0.5 |
| 6 | 10 mM citrate pH = 7, 130 mM NaCl | SC | 0.20 | 250 | 50.0 | 2.5 |
| 7 | 3% P407, 10 mM citrate, 130 mM NaCl | IM | 0.20 | 50 | 10.0 | 0.5 |
| 8 | 3% P407, 10 mM citrate, 130 mM NaCl | SC | 0.20 | 250 | 50.0 | 2.5 |

TABLE 188-continued

Dosing Regimen

| Group | Vehicle | Route | Conc (mg/ml) | Inj Vol (ul) | Amt (ug) | Dose (mg/kg) |
|---|---|---|---|---|---|---|
| 9 | 20% P407, 10 mM citrate, 65 mM NaCl (* gels in vivo) | IM | 0.20 | 50 | 10.0 | 0.5 |
| 10 | 20% P407, 10 mM citrate, 65 mM NaCl (* gels in vivo) | SC | 0.20 | 250 | 50.0 | 2.5 |
| 11 | 10% P188, 10 mM citrate, 65 mM NaCl | IM | 0.20 | 50 | 10.0 | 0.5 |
| 12 | 10% P188, 10 mM citrate, 65 mM NaCl | SC | 0.20 | 250 | 50.0 | 2.5 |
| 13 | Invivofectamine, 1 X PBS | IM | 0.20 | 50 | 10.0 | 0.5 |
| 14 | Invivofectamine, 1 X PBS | SC | 0.20 | 250 | 50.0 | 2.5 |
| 15 | jet PEI | IM | 0.20 | 50 | 10.0 | 0.5 |
| 16 | jet PEI | SC | 0.20 | 250 | 50.0 | 2.5 |
| 17 | PBS | IM | — | 50 | — | — |
| 18 | PBS | SC | — | 250 | — | — |

The final lipid molar ratio ranges of DLin-KC2-DMA, DSPC, cholesterol and PEG2K-DMG (PEG2000-dimyristoyl glycerol) for the KC2 LNP are outlined in Table 189. The weight ratio of total lipid to mRNA was 20:1 mol/mol.

TABLE 189

Molar Ratios

| | DLin-KC2-DMA | DSPC | Cholesterol | PEG2K-DMG |
|---|---|---|---|---|
| Mole Percent (mol %) | 50.0 | 10.0 | 38.5 | 1.5 |

All of the mice are imaged at 3 hours, 8 hours, 24 hours and 48 hours post-administration of luciferase modified mRNA. Twenty minutes prior to imaging, the mice are injected intraperitoneally with a D-luciferin solution at 150 mg/kg. Animals are then anesthetized and images were acquired with an IVIS Lumina II imaging system (Perkin Elmer). Bioluminescence is measured as total flux (photons/second) of the entire mouse. The results for intramuscular administration of 0.5 mg/kg modified mRNA are shown in Table 190.

TABLE 190

Expression After 0.5 mg/kg mRNA Intramuscular Administration

| | 3 Hours Flux (p/s) | 8 Hours Flux (p/s) | 24 Hours Flux (p/s) | 48 Hours Flux (p/s) |
|---|---|---|---|---|
| 8.5% sucrose | 1.42E+05 | 4.98E+05 | 1.05E+06 | 8.35E+05 |
| LNP | 8.14E+07 | 1.94E+08 | 6.81E+07 | 1.45E+07 |
| 10 mM citrate | 3.33E+05 | 4.66E+05 | 1.04E+06 | 5.10E+05 |
| 3% P407 | 1.32E+06 | 5.03E+05 | 3.36E+05 | 9.52E+05 |
| 20% P407 | 2.32E+05 | 1.93E+05 | 1.93E+05 | — |
| 10% P188 | 6.01E+05 | 2.50E+05 | 4.58E+05 | 7.02E+05 |
| Invivofectamine | 3.18E+06 | 4.22E+06 | 1.72E+06 | 2.04E+06 |
| jet PEI | 2.44E+05 | 2.03E+05 | 2.02E+05 | — |
| PBS | 2.02E+05 | 1.51E+05 | 1.30E+05 | — |

The results for subcutaneous administration of 2.5 mg/kg of modified mRNA are shown in Table 191.

TABLE 191

Expression After 2.5 mg/kg mRNA Subcutaneous Administration

| | 3 Hours Flux (p/s) | 8 Hours Flux (p/s) | 24 Hours Flux (p/s) | 48 Hours Flux (p/s) |
|---|---|---|---|---|
| 8.5% sucrose | 4.99E+05 | 6.32E+05 | 1.36E+06 | 2.64E+05 |
| LNP | 3.17E+08 | 3.29E+08 | 2.96E+08 | 2.82E+08 |
| 10 mM citrate | 7.82E+05 | 6.80E+05 | 5.97E+05 | 3.97E+05 |
| 3% P407 | 6.78E+05 | 5.67E+05 | 3.15E+05 | 3.01E+05 |
| 20% P407 | 2.32E+05 | 2.99E+05 | 2.48E+05 | — |
| 10% P188 | 4.28E+05 | 2.88E+05 | 2.44E+05 | — |
| Invivofectamine | 6.64E+07 | 3.39E+07 | 2.19E+07 | 8.77E+06 |
| jet PEI | 3.92E+05 | 2.42E+05 | 2.29E+05 | — |
| PBS | 2.67E+05 | 2.22E+05 | 2.22E+05 | — |

For intramuscular and subcutaneous delivery the lipid formulations produced the greatest protein expression.

Example 117. Repeat Dose Luciferase LNP Study

Luciferase modified mRNA (mRNA sequence shown in SEQ ID NO: 14; polyA tail of approximately 140 nucleotides not shown in sequence; 5'cap, Cap1) fully modified with 1-methylpseudouridine, was formulated in a lipid nanoparticle with DLin-KC2-DMA (KC2 LNP) or phosphate buffered saline (PBS) was administered to Balb-C mice (n=3) as outlined in Tables 192 (live imaging) and 193 (tissue imaging). In Tables 192 and 193, "IM" means intramuscular administration, "IM-1" means the groups were administered a single dose. "IM-2" means the groups were administered with 2 doses, administered 24 hours apart, "IV" means intravenous administration, "IV-1" means the groups were administered a single dose tail vein injection and "IV-2" means the groups were administered with 2 doses, administered 7 days apart. 2 groups of untreated Balb-C mice (n=3) were also evaluated. Groups 1, 3 and 7 were injected in the right leg and administration was repeated but into the left leg with 24 hours between injections. Groups 2, 4, and 9 were administered the mRNA in the right leg followed by repeat administration in the right leg with 24 hours between injections for Group 2 and 7 days between injections for Groups 4 and 9.

TABLE 192

Dosing Regimen - Live Imaging

| Group | Vehicle | Route | Conc (mg/ml) | Inj Vol (ul) | Amt (ug) | Dose (mg/kg) |
|---|---|---|---|---|---|---|
| 1 | KC2 LNP | IM-2 | 0.020 | 50 | 1.00 | 0.050 |
| 2 | KC2 LNP | IM-2 | 0.020 | 50 | 1.00 | 0.050 |
| 3 | Luc G5 in 1x PBS | IM-2 | 1.000 | 50 | 50 | 2.50 |
| 4 | KC2 LNP | IV-2 | 0.002 | 50 | 0.10 | 0.005 |
| 5 | Untreated | — | — | — | — | — |

TABLE 193

Dosing Regimen - Tissue Imaging

| Group | Vehicle | Route | Conc (mg/ml) | Inj Vol (ul) | Amt (ug) | Dose (mg/kg) |
|---|---|---|---|---|---|---|
| 6 | KC2 LNP | IM-1 | 0.020 | 50 | 1.00 | 0.050 |
| 7 | KC2 LNP | IM-2 | 0.020 | 50 | 1.00 | 0.050 |
| 8 | KC2 LNP | IV-1 | 0.002 | 50 | 0.10 | 0.005 |
| 9 | KC2 LNP | IV-2 | 0.002 | 50 | 0.10 | 0.005 |
| 10 | Untreated | — | — | — | — | — |

The final lipid molar ratio ranges of DLin-KC2-DMA, DSPC, cholesterol and PEG-DMG for the KC2 LNP are outlined in Table 194. The weight ratio of total lipid to mRNA was 20:1, the mean size was 95 nm (PDI: 0.11), the zeta at pH 7.4 was −1.0 mV and the encapsulation (RiboGreen) was essentially 100%.

TABLE 194

Molar Ratios

| | DLin-KC2-DMA | DSPC | Cholesterol | PEG-DMG |
|---|---|---|---|---|
| Mole Percent (mol %) | 50.0 | 10.0 | 38.5 | 1.5 |

Live imaging mice were imaged at 8 hours post-administration of each dose of luciferase modified mRNA and tissue imaging mice imaged 8 post-administration of the final dose of luciferase modified mRNA. Twenty minutes prior to imaging, the mice were injected intraperitoneally with a D-luciferin solution at 150 mg/kg. Animals were then anesthetized and images were acquired with an IVIS Lumina II imaging system (Perkin Elmer). For the tissue imaging mice (Groups 6-9), the mice were dissected twenty minutes after the D-luciferin injection and organs and tissue were subsequently imaged (muscle around injection site, liver and spleen for Groups 6 and 7 and were subsequently imaged the liver and spleen for Groups 8 and 9). Bioluminescence was measured as total flux (photons/second) of the mid-section and the entire mouse (IV administration), the injection site (IM administration), or the entire organ (tissue imaging).

The results of the weekly repeat intravenous administration of luciferase mRNA formulated in the KC2 LNP are shown in Table 195.

TABLE 195

KC2 LNP IV Administration

| Image Group | Expression (Avg flux p/s) 8 Hour Post-Dose 1 | Expression (Avg flux p/s) 8 Hour Post-Dose 2 |
|---|---|---|
| IV, KC2 LNP Mid-section | 2.81E+08 | 3.26E+06 |
| IV, KC2 LNP Whole | 2.91E+08 | 5.22E+06 |
| Untreated | 1.74E+05 | 1.74E+05 |

The tissue quantification of the liver and spleen for the once weekly intravenous administration is shown in Table 196.

TABLE 196

Expression in Liver and Spleen

| | Post-Dose 1 (Flux p/s) | Post-Dose 2 (Flux p/s) | Untreated (Flux p/s) |
|---|---|---|---|
| Liver | 29673333 | 641167 | 22160 |
| Spleen | 353400 | 91920 | 18890 |

The results of the daily intramuscular repeat dose in the right limb of luciferase mRNA formulated in the KC2 LNP are shown in Table 197 and the results of the daily intramuscular repeat dose in right and left limb of luciferase mRNA formulated in the KC2 LNP are shown in Table 198. As shown in Table 197 and Table 198, the expression is reduced after the second dose.

TABLE 197

IM Repeat Administration in Right Limb

| Image Group | Expression (Avg flux p/s) 8 Hour Post-Dose 1 | Expression (Avg flux p/s) 8 Hour Post-Dose 2 |
|---|---|---|
| IM Repeat Right Limb | 5.82E+08 | 1.08E+08 |
| Untreated | 1.46E+05 | 1.05E+05 |

TABLE 198

IM Repeat Administration in Right and Left Limb

| Image Group | Expression (Avg flux p/s) Hour Post-Dose 1 | | Expression (Avg flux p/s) 8 Hour Post-Dose 2 | |
|---|---|---|---|---|
| | Left (undosed) | Right (dosed) | Left (dosed) | Right (undosed) |
| IM Repeat | 8.12E+06 | 8.11E+08 | 1.21E+08 | 2.34E+08 |
| Untreated | 9.93E+04 | 1.46E+05 | 1.11E+05 | 1.05E+05 |

The results of the organ imaging after the intramuscular administration of luciferase mRNA in the right and left limb are shown in Table 199. The greatest expression was seen in the muscle (post dose 1: 94.7%, post dose 2: 89.74%) followed by the liver (post dose 1: 5.15%, post dose 2: 9.82%) and the spleen (post dose 1: 0.15%, post dose 2: 0.44%).

TABLE 199

| Organ Imaging | | | |
|---|---|---|---|
| | Muscle (Flux p/s) | Liver (Flux p/s) | Spleen (Flux p/s) |
| Post-dose 1 | 3.76E+08 | 2.05E+07 | 5.87E+05 |
| Pose-dose 2 | 5.52E+07 | 6.04E+06 | 2.68E+05 |
| Untreated | 4.04E+04 | 2.22E+04 | 1.89E+04 |

The results of the daily intramuscular repeat dose in the right limb and left limb of luciferase mRNA formulated in PBS is shown in Table 200.

TABLE 200

| Expression After IM Injection | | | |
|---|---|---|---|
| | | Limb and Dose | Expression (Flux (p/s)) |
| Dose 1 | Undosed | Left- Luciferase | 2.28E+05 |
| | | Left- Untreated | 9.93E+04 |
| | Dosed | Right - Luciferase | 6.71E+06 |
| | | Right - Untreated | 1.46E+05 |
| Dose 2 | Dosed | Left- Luciferase | 1.16E+07 |
| | | Left- Untreated | 1.11E+05 |
| | Undosed | Right - Luciferase | 2.44E+07 |
| | | Right - Untreated | 1.05E+05 |

Example 118. DODMA Lipid Nanoparticle Subcutaneous Study

Luciferase mRNA (mRNA sequence shown in SEQ ID NO: 14; polyA tail of approximately 140 nucleotides not shown in sequence; 5'cap, Cap1) fully modified with 5-methylcytosine and pseudouridine was formulated in a lipid nanoparticle at a 20:1 weight ratio of total lipid to modified mRNA with a final lipid molar ratio of 50:10:38.5:1.5 (DODMA: DSPC: Cholesterol: PEG-DMG). The formulation was administered subcutaneously (S.C.) to Balb-C mice at a dose of 0.5 mg/kg, 0.05 mg/kg, 0.005 mg/kg or 0.0005 mg/kg.

Twenty minutes prior to imaging, mice were injected intraperitoneally with a D-luciferin solution at 150 mg/kg. Animals were then anesthetized and images were acquired with an IVIS Lumina II imaging system (Perkin Elmer). Bioluminescence was measured as total flux (photons/second) of the entire mouse. The mice were imaged at 2 hours, 8 hours, 24 hours, 48 hours, 72 hours and 144 hours after dosing and the average total flux (photons/second) was measured for each route of administration and cationic lipid formulation. The lower limit of detection was about 4.9E+05. The results of the imaging are shown in Table 201. The peak signal for all dose levels was at 8 hours after administration with expression still detected at 72 hours after dosing at the 0.5 mg/kg dosing level.

Organs were imaged at 8 hours and the average total flux (photons/second) was measured for the liver, spleen, lung and kidney. A control for each organ was also analyzed. The results are shown in Table 202. The majority of expression for the subcutaneous administration was localized to the injection site but at the highest doses was seen in the liver and spleen. Levels of Luciferase based on luminescence at 8 hours were at background levels in the lung and kidney at all doses. 0.5 mg/kg levels of mRNA were required to generate luminescence from Luciferase in the organs at 8 hours after subcutaneous administration.

TABLE 201

| In Vivo Expression | | | | |
|---|---|---|---|---|
| Time Point | 0.5 mg/kg Flux (p/s) | 0.05 mg/kg Flux (p/s) | 0.005 mg/kg Flux (p/s) | 0.0005 mg/kg Flux (p/s) |
| 2 hrs | 7.30E+07 | 1.56E+07 | 3.44E+06 | 5.64E+05 |
| 8 hrs | 1.40E+08 | 2.43E+07 | 4.84E+06 | 7.55E+05 |
| 24 hrs | 4.57E+07 | 4.12E+06 | 2.41E+06 | 9.70E+05 |
| 48 hrs | 1.51E+07 | 1.49E+06 | 7.43E+05 | 6.72E+05 |
| 72 hrs | 4.15E+06 | 8.80E+05 | 6.27E+05 | 6.19E+05 |
| 144 hrs | 8.01E+05 | 5.28E+05 | 5.11E+05 | 5.35E+05 |

TABLE 202

| Organ Expression | | | | |
|---|---|---|---|---|
| | Liver Flux (p/s) | Spleen Flux (p/s) | Lung Flux (p/s) | Kidney Flux (p/s) |
| 0.5 mg/kg | 6.89E+05 | 1.63E+06 | 2.31E+04 | 1.43E−04 |
| 0.05 mg/kg | 4.32E+04 | 4.63E+04 | 1.70E+04 | 1.31E+04 |
| 0.005 mg/kg | 2.93E+04 | 2.09E+04 | 1.73E+04 | 1.65E+04 |
| 0.0005 mg/kg | 2.24E+04 | 1.72E+04 | 1.59E+04 | 1.06E+04 |
| Untreated | 2.50E+04 | 1.85E+04 | 1.68E+04 | 1.57E+04 |

Example 119. Repeat Dose Luciferase LNP Intramuscular and Intravenous Study

Luciferase modified mRNA (mRNA sequence shown in SEQ ID NO: 14; polyA tail of approximately 140 nucleotides not shown in sequence; 5'Cap, Cap1) fully modified with 1-methylpseudouridine, is formulated in a lipid nanoparticle with DLin-KC2-DMA (KC2 LNP) or Phosphate Buffered Saline (PBS) is administered to Balb-C mice (n=3) as outlined in Tables 203 (live imaging) and 204 (tissue imaging). In Tables 203 and 204, "IM" means intramuscular administration, "IM-1" means the groups are administered a single dose. "IM-3" means the groups are administered with 2 doses, administered 7 days apart, "IV" means intravenous administration, "IV-1" means the groups are administered a single dose tail vein injection and "IV-3" means the groups are administered with 2 doses, administered 24 hours apart. 2 groups of untreated Balb-C mice (n=3) are also evaluated. Groups 1, 3 and 7 are injected in the right leg and administration is repeated but into the left leg with 7 days between injections. Groups 2, 4, and 9 are administered the mRNA in the right leg followed by repeat administration in the right leg with 7 days between injections for Group 2 and 24 hours between injections for Groups 4 and 9.

TABLE 203

| Dosing Regimen - Live Imaging | | | | | | |
|---|---|---|---|---|---|---|
| Group | Vehicle | Route | Conc (mg/ml) | Inj Vol (ul) | Amt (ug) | Dose (mg/kg) |
| 1 | KC2 LNP | IM-3 | 0.020 | 50 | 1.00 | 0.050 |
| 2 | KC2 LNP | IM-3 | 0.020 | 50 | 1.00 | 0.050 |
| 3 | Luc G5 in 1x PBS | IM-3 | 1.000 | 50 | 50 | 2.50 |
| 4 | KC2 LNP | IV-3 | 0.002 | 50 | 0.10 | 0.005 |
| 5 | Untreated | — | — | — | — | — |

TABLE 204

Dosing Regimen - Tissue Imaging

| Group | Vehicle | Route | Conc (mg/ml) | Inj Vol (ul) | Amt (ug) | Dose (mg/kg) |
|---|---|---|---|---|---|---|
| 6 | KC2 LNP | IM-1 | 0.020 | 50 | 1.00 | 0.050 |
| 7 | KC2 LNP | IM-3 | 0.020 | 50 | 1.00 | 0.050 |
| 8 | KC2 LNP | IV-1 | 0.002 | 50 | 0.10 | 0.005 |
| 9 | KC2 LNP | IV-3 | 0.002 | 50 | 0.10 | 0.005 |
| 10 | Untreated | — | — | — | — | — |

The lipid nanoparticle is formulated at a 20:1 weight ratio of total lipid to modified mRNA with a final lipid molar ratio of 50:10:38.5:1.5 (DLin-KC2-DMA: DSPC: Cholesterol: PEG-DMG).

Live imaging mice are imaged at 8 hours post-administration of each dose of luciferase modified mRNA and tissue imaging mice imaged 8 post-administration of the final dose of luciferase modified mRNA. Twenty minutes prior to imaging, the mice are injected intraperitoneally with a D-luciferin solution at 150 mg/kg. Animals are then anesthetized and images were acquired with an IVIS Lumina II imaging system (Perkin Elmer). For the tissue imaging mice (Groups 6-9), the mice are dissected twenty minutes after the D-luciferin injection and organs and tissue were subsequently imaged (muscle around injection site, liver and spleen for Groups 6 and 7 and are subsequently imaged the liver and spleen for Groups 8 and 9). Bioluminescence is measured as total flux (photons/second) of the mid-section and the entire mouse (IV administration), the injection site (IM administration), or the entire organ (tissue imaging).

Example 120. LNP Component Evaluation Study

Luciferase modified mRNA (SEQ ID NO: 20; polyA tail of approximately 140 nucleotides not shown in sequence, 5' cap 1; fully modified with 1-methylpseudouridine and 5-methylcytidine) was formulated in a lipid nanoparticle (LNP) comprising DODMA, Cholesterol, PEG-DMG, and DSPC (DODMA-DSPC) or DODMA, Cholesterol, PEG-DMG, and DOPE (DODMA-DOPE) or DLin-MC3-DMA, Cholesterol, PEG-lipid DMG, and DSPC (MC3-DSPC) or DLin-MC3-DMA, Cholesterol, PEG-DMG, and DOPE (MC3-DOPE) or the control DLin-KC2-DMA, Cholesterol, PEG-DMG, and DSPC (KC2 control) as described in Table 205 or in the PBS vehicle only. The LNP was formulated by nanoprecipitation at an N:P ratio of 5:1 and weight ratio of 21:1 total lipid to modified mRNA, with a final lipid molar ratio as described in Table 205. As shown in Table 206, the luciferase LNP formulations were characterized by particle size, zeta potential and encapsulation. The drug concentration was determined by ribogreen assay from a standard curve.

TABLE 205

LNP formulations

| Formulation | Cationic Lipid Mole percent (mol %) | Helper Lipid Mole percent (mol %) | Structural Mole percent (mol %) | PEG lipid Mole percent (mol %) |
|---|---|---|---|---|
| DODMA-DSPC system | DODMA 40 | DSPC 10 | Cholesterol 48.5 | PEG-DMG 1.5 |
| DODMA-DOPE system | DODMA 40 | DOPE 10 | Cholesterol 48.5 | PEG-DMG 1.5 |
| MC3-DSPC system | DLin-MC3-DMA 40 | DSPC 10 | Cholesterol 48.5 | PEG-DMG 1.5 |
| MC3-DOPE system | DLin-MC3-DMA 40 | DOPE 10 | Cholesterol 48.5 | PEG-DMG 1.5 |
| KC2 LNP control | DLin-KC2-DMA 50 | DSPC 10 | Cholesterol 38.5 | PEG-DMG 1.5 |

TABLE 206

Luciferase Formulation Characterizations

| Formulation | Lipid:mRNA Ratio | Mean size (nm) | Zeta at pH 7.4 (mV) | Encapsulation (%) (Ribogreen) | Drug Concentration (mg/mL) |
|---|---|---|---|---|---|
| DODMA-DSPC system | 21:1 | 104 | −1.7 | 85.9 | 0.02 |
| DODMA-DOPE system | 21:1 | 96.2 | 0.9 | 83.8 | 0.02 |
| MC3-DSPC system | 21:1 | 183 | 2.6 | 94.8 | 0.02 |
| MC3-DOPE system | 21:1 | 115 | −1.3 | 53.5 | 0.02 |
| KC2 LNP control | 20:1 | 81.6 | 1.2 | 100 | 0.15 |

The luciferase LNP formulations were administered to Balb-C mice (n=3) intramuscularly at a dose of 0.1 mg/kg and a control of luciferase modified RNA formulated in PBS was administered to mice intramuscularly at a dose of 0.1 mg/kg. The mice were imaged at 24 hours post dose and results are shown in Table 207. Animals were then anesthetized and images were acquired with an IVIS Lumina II imaging system (Perkin Elmer). Bioluminescence was measured as total flux (photons/second) of the entire mouse.

TABLE 207

Luciferase Expression

| Formulation system | Average Expression (photon/second) 24 hours | Fold Expression, DOPE/DSPC systems | Fold Expression over KC2 LNP |
|---|---|---|---|
| DODMA-DSPC | 9.84E+05 | — | 0.28 |
| DODMA-DOPE | 2.25E+06 | 2.3 | 0.64 |
| MC3-DSPC | 6.93E+06 | — | 2.0 |
| MC3-DOPE | 1.49E+07 | 2.2 | 4.2 |
| KC2 control | 3.53E+06 | — | 1 |
| PBS control | 8.23E+04 | — | — |

The mice administered MC3 formulations showed an increase in luciferase expression as compared to the KC2 control LNP formulation (2 fold increase for MC3-DSPC LNP system and 4.2 fold increase for MC3-DOPE system). The LNP formulations containing DOPE showed increased expression as compared to the LNP formulations containing DSPC (2.3-fold increase for DODMA-DOPE and 2.2 fold increase for MC3-DOPE). The expression increases in DOPE-containing formulations are not explained by LNP average size, which is larger than the average size of KC2 LNP control for all MC3 and DODMA LNP systems (DOPE and DSPC).

Other Embodiments

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

What is claimed is:

1. A method of administering an mRNA to a subject, the method comprising:
(a) injecting the subject with the mRNA, and
(b) delivering electric pulses at or near the site of injection in three stages, wherein
(i) the first stage is a single pulse at an amplitude of approximately 450V for a pulse duration of approximately 0.05 ms and a pause interval of approximately 0.2 ms;
(ii) the second stage is a single pulse at an amplitude of approximately 450V for a pulse duration of approximately 0.05 ms and a pause interval of approximately 50 ms; and
(iii) the third stage is a pulse repeated eight times at an amplitude of approximately 11 OV for a pulse duration of approximately 10 ms and a pause interval of approximately 20 ms,
wherein the method results in an increase in the duration of protein expression at the site of injection from the mRNA in a cell or tissue of the subject compared to protein expression at the site of injection in the subject with the mRNA without electroporation.

2. The method of claim 1, wherein the injection is selected from the group consisting of intramuscular injection and intradermal injection.

3. The method of claim 2, wherein the injection is intramuscular injection.

4. The method of claim 1, wherein the mRNA comprises at least one chemical modification.

5. The method of claim 4, wherein the at least one chemical modification is selected from the group consisting of pseudouridine, 1-methylpseudouridine and 5-methylcytosine.

6. The method of claim 1, wherein the mRNA is administered at a dose selected from the group consisting of 0.025 mg/kg, 0.25 mg/kg, 2.5 mg/kg and 5 mg/kg.

* * * * *

SEQUENCE LISTING

```
<160> NUMBER OF SEQ ID NOS: 28

<210> SEQ ID NO 1
<211> LENGTH: 615
<212> TYPE: DNA
<213> ORGANISM: Homo sapiens

<400> SEQUENCE: 1
atggctggac ctgccaccca gagccccatg aagctgatgg ccctgcagct gctgctgtgg      60
cacagtgcac tctggacagt gcaggaagcc acccccctgg gccctgccag ctccctgccc     120
cagagcttcc tgctcaagtg cttagagcaa gtgaggaaga tccagggcga tggcgcagcg     180
ctccaggaga agctgtgtgc cacctacaag ctgtgccacc ccgaggagct ggtgctgctc     240
ggacactctc tgggcatccc ctgggctccc ctgagcagct gccccagcca ggccctgcag     300
ctggcaggct gcttgagcca actccatagc ggccttttcc tctaccaggg gctcctgcag     360
gccctggaag ggatctcccc cgagttgggt cccaccttgg acacactgca gctggacgtc     420
gccgactttg ccaccaccat ctggcagcag atggaagaac tgggaatggc ccctgccctg     480
cagcccaccc agggtgccat gccggccttc gcctctgctt tccagcgccg ggcaggaggg     540
gtcctggttg cctcccatct gcagagcttc ctggaggtgt cgtaccgcgt tctacgccac     600
cttgcccagc cctga                                                     615

<210> SEQ ID NO 2
<211> LENGTH: 800
<212> TYPE: DNA
<213> ORGANISM: Artificial Sequence
<220> FEATURE:
<223> OTHER INFORMATION: Description of Artificial Sequence: Synthetic      transcript sequence

<400> SEQUENCE: 2
taatacgact cactataggg aaataagaga gaaagaaga gtaagaagaa atataagagc       60
caccatggct ggacctgcca cccagagccc catgaagctg atggccctgc agctgctgct     120
gtggcacagt gcactctgga cagtgcagga agccaccccc ctgggccctg ccagctccct    180
```

```
gccccagagc ttcctgctca agtgcttaga gcaagtgagg aagatccagg gcgatggcgc    240
agcgctccag gagaagctgt gtgccaccta caagctgtgc caccccgagg agctggtgct    300
gctcggacac tctctgggca tcccctgggc tcccctgagc agctgcccca gccaggccct    360
gcagctggca ggctgcttga gccaactcca tagcggcctt ttcctctacc aggggctcct    420
gcaggccctg aagggatct ccccgagtt gggtcccacc ttggacacac tgcagctgga    480
cgtcgccgac tttgccacca ccatctggca gcagatggaa gaactgggaa tggcccctgc    540
cctgcagccc acccagggtg ccatgccggc cttcgcctct gctttccagc gccgggcagg    600
aggggtcctg gttgcctccc atctgcagag cttcctggag gtgtcgtacc gcgttctacg    660
ccaccttgcc cagccctgaa gcgctgcctt ctgcggggct tgccttctgg ccatgccctt    720
cttctctccc ttgcacctgt acctcttggt ctttgaataa agcctgagta ggaaggcggc    780
cgctcgagca tgcatctaga                                               800

<210> SEQ ID NO 3
<211> LENGTH: 800
<212> TYPE: DNA
<213> ORGANISM: Artificial Sequence
<220> FEATURE:
<223> OTHER INFORMATION: Description of Artificial Sequence: Synthetic     transcript sequence

<400> SEQUENCE: 3
taatacgact cactataggg aaataagaga gaaagaaga gtaagaagaa atataagagc    60
caccatggcc ggtcccgcga cccaaagccc catgaaactt atggccctgc agttgctgct    120
ttggcactcg gccctctgga cagtccaaga agcgactcct ctcggacctg cctcatcgtt    180
gccgcagtca ttccttttga agtgtctgga gcaggtgcga aagattcagg gcgatggagc    240
cgcactccaa gagaagctct gcgcgacata caaactttgc catcccgagg agctcgtact    300
gctcgggcac agcttgggga ttccctgggc tcctctctcg tcctgtccgt cgcaggcttt    360
gcagttggca gggtgccttt cccagctcca ctccggtttg ttcttgtatc agggactgct    420
gcaagccctt gagggaatct cgccagaatt gggcccgacg ctggacacgt tgcagctcga    480
cgtggcggat ttcgcaacaa ccatctgca gcagatggag gaactgggga tggcacccgc    540
gctgcagccc acgcaggggg caatgccggc ctttgcgtcc gcgtttcagc gcagggcggg    600
tggagtcctc gtagcgagcc accttcaatc attttggaa gtctcgtacc gggtgctgag    660
acatcttgcg cagccgtgaa gcgctgcctt ctgcggggct tgccttctgg ccatgccctt    720
cttctctccc ttgcacctgt acctcttggt ctttgaataa agcctgagta ggaaggcggc    780
cgctcgagca tgcatctaga                                               800

<210> SEQ ID NO 4
<211> LENGTH: 758
<212> TYPE: RNA
<213> ORGANISM: Artificial Sequence
<220> FEATURE:
<223> OTHER INFORMATION: Description of Artificial Sequence: Synthetic     transcript sequence

<400> SEQUENCE: 4
gggaaauaag agagaaaaga agaguaagaa gaaauauaag agccaccaug gccggucccg    60
cgacccaaag ccccaugaaa cuuauggccc ugcaguugcu gcuuuggcac ucggcccucu    120 ggacaguccaa agaagcgacu ccucucggac cugccucauc guugccgcag ucauuccuuu    180
ugaagugucu ggagcaggug cgaaagauuc agggcgaugg agccgcacuc caagagaagc    240
```

| | |
|---|---|
| ucugcgcgac auacaaacuu ugccaucccg aggagcucgu acugcucggg cacagcuugg | 300 |
| ggauucccug ggcuccucuc ucguccuguc cgucgcaggc uuugcaguug cagggugcc | 360 |
| uuucccagcu ccacuccggu uuguucuugu aucagggacu gcugcaagcc cuugagggaa | 420 |
| ucucgccaga auugggcccg acgcuggaca cguugcagcu cgacguggcg gauuucgcaa | 480 |
| caaccaucug gcagcagaug gaggaacugg ggauggcacc cgcgcugcag cccacgcagg | 540 |
| gggcaaugcc ggccuuugcg uccgcguuuc agcgcagggc ggguggaguc cucguagcga | 600 |
| gccaccuuca aucauuuuug gaagucucgu accggguqcu gagacaucuu gcgcagccgu | 660 |
| gaagcgcugc cuucgcgggg gcuugccuuc uggccaugcc cuucuucucu cccuugcacc | 720 |
| uguaccucuu ggucuuugaa uaaagccuga guaggaag | 758 |

<210> SEQ ID NO 5
<211> LENGTH: 854
<212> TYPE: RNA
<213> ORGANISM: Artificial Sequence
<220> FEATURE:
<223> OTHER INFORMATION: Description of Artificial Sequence: Synthetic transcript sequence

<400> SEQUENCE: 5

| | |
|---|---|
| gggaauaag agagaaaaga agaguaagaa gaaauauaag agccaccaug guauccaagg | 60 |
| gggaggagga caacauggcg aucaucaagg aguucaugcg auucaaggug cacauggaag | 120 |
| guucggucaa cggacacgaa uuugaaaucg aaggagaggg ugaaggaagg cccuaugaag | 180 |
| ggacacagac cgcgaaacuc aaggucacga aggggggacc acuccuuuc gccugggaca | 240 |
| uucuuucgcc ccaguuuaug uacgggucca agcauaugu gaagcauccc gccgauauuc | 300 |
| cugacuaucu gaaacucagc uuucccgagg gauucaagug ggagcgdguc augaacuuug | 360 |
| aggacggggg uguagucacc guaacccaag acucaagccu ccaagacggc gaguucaucu | 420 |
| acaaggucaa acugcggggg acuaacuuuc cgucggaugg gccggugaug cagaagaaaa | 480 |
| cgauqggaug ggaagcguca ucggagagga uguacccaga agauggugca uugaagqggg | 540 |
| agaucaagca gagacugaag uugaaagaug ggqgacauua ugauqccgag gugaaaacga | 600 |
| cauacaaagc gaaaaagccg gugcagcuuc ccggagcgua uaaugugaau ucaaguugg | 660 |
| auauuacuuc acacaaugag gacuacacaa uugucgaaca guacgaacgc gcugagggua | 720 |
| gacacucgac gggaggcaug gacgaguugu acaaaugaua agcugccuuc ucgcgggcuu | 780 |
| gccuucuggc caugcccuuc uucucucccu ugcaccugua ccucuugguc uuugaauaaa | 840 |
| gccugaguag gaag | 854 |

<210> SEQ ID NO 6
<211> LENGTH: 896
<212> TYPE: DNA
<213> ORGANISM: Artificial Sequence
<220> FEATURE:
<223> OTHER INFORMATION: Description of Artificial Sequence: Synthetic transcript sequence

<400> SEQUENCE: 6

| | |
|---|---|
| taatacgact cactataggg aaataagaga gaaaagaaga gtaagaagaa atataagagc | 60 |
| caccatggta tccaaggggg aggaggacaa catggcgatc atcaaggagt tcatgcgatt | 120 |
| caaggtgcac atggaaggtt cggtcaacgg acacgaattt gaaatcgaag gagagggtga | 180 |
| aggaaggccc tatgaaggga cacagaccgc gaaactcaag gtcacgaaag ggggaccact | 240 |
| tccttttcgcc tggacattc tttcgcccca gtttatgtac gggtccaaag catatgtgaa | 300 |
| gcatcccgcc gatattcctg actatctgaa actcagcttt cccgagggat tcaagtggga | 360 |

```
gcgggtcatg aactttgagg acggggtgt  agtcaccgta acccaagact caagcctcca    420
agacggcgag ttcatctaca aggtcaaact gcggggact  aactttccgt cggatgggcc    480
ggtgatgcag aagaaaacga tgggatggga agcgtcatcg agaggatgt  acccagaaga    540 tggtgcattg aaggggggaga tcaagcagag actgaagttg aaagatgggg gacattatga   600
tgccgaggtg aaaacgacat acaaagcgaa aaagccggtg cagcttcccg gagcgtataa    660
tgtgaatatc aagttggata ttacttcaca caatgaggac tacacaattg tcgaacagta    720
cgaacgcgct gagggtagac actcgacggg aggcatggac gagttgtaca aatgataagc    780
tgccttctgc ggggcttgcc ttctggccat gcccttcttc tctcccttgc acctgtacct    840
cttggtcttt gaataaagcc tgagtaggaa ggcggccgct cgagcatgca tctaga        896

<210> SEQ ID NO 7
<211> LENGTH: 725
<212> TYPE: RNA
<213> ORGANISM: Artificial Sequence
<220> FEATURE:
<223> OTHER INFORMATION: Description of Artificial Sequence: Synthetic     transcript sequence

<400> SEQUENCE: 7
gggaaauaag agagaaaaga agaguaagaa gaaauauaag agccaccaug ggagugcacg     60
agugucccgc ugguugugg  uugcugcugu cgcucuugag ccuccacug  ggacugccug    120 ugcuggggc  accacccaga uugaucgcg  acucacgggu acuugagagg uaccuucuug    180
aagccaaaga agccgaaaac aucacaaccg gaucgccga  gcacugcucc cucaaugaga    240
acauuacugu accggauaca aaggucaauu ucuaugcaug aagagaaug  gaaguaggac    300 agcaggccgu cgaagugugg caggggcucg cgcuuuugc  ggaggcgug  uugcggguc     360 aggcccuccu cgucaacuca ucacagccgu gggagcccu  ccaacuucau gucgauaaag    420 cgguguggg  gcuccgcagc uugacgacgu ugcuucgggc ucuggcgca  caaaggagg     480 cuauuucgcc gccugacgcg gccuccgcgg caccccuccg aacgaucacc gcggacacgu    540
uuaggaagcu uuuuagagug uacagcaauu uccuccgcgg aaagcugaaa uuguauacug    600
gugaagcgug uaggacaggg gaucgcugau aagcugccuu cugcggggcu ugccuucugg    660 ccaugccuu  cuucucuccc uugcaccugu acccucuuggu cuuugaauaa agccugagua   720
ggaag                                                                725

<210> SEQ ID NO 8
<211> LENGTH: 1536
<212> TYPE: RNA
<213> ORGANISM: Artificial Sequence
<220> FEATURE:
<223> OTHER INFORMATION: Description of Artificial Sequence: Synthetic     transcript sequence

<400> SEQUENCE: 8
gggaaauaag agagaaaaga agaguaagaa gaaauauaag agccaccaau gcagcgcguc     60
aacaugauua uggccgaauc gccgggacuc aucacaaucu gccucuuggg uuaucucuug    120
ucggcagaau guaccguguu cuuggaucac gaaaacgcga acaaaauucu uaaucgcccg    180
aagcgguaua acucccggga acuugaggag uuugugcagg gcaaucuuga acgagagugc    240
auggaggaga aaugcucccu ugaggaggcg agggaagugu uugaaaacac agagcgaaca    300
acggaguuuu ggaagcaaua cguagaugggg gaccagugug agucgaaucc gugccucaau    360
ggggaaucau guaaagauga caucaauagc uaugaaugcu ggugcccguu uggguuugaa    420
```

| | |
|---|---|
| gggaagaacu gugagcugga ugugacgugc aacaucaaaa acggacgcug ugagcaguuu | 480 |
| uguaagaacu cggcugacaa uaagguagua ugcucgugca cagagggaua ccggcuggcg | 540 |
| gagaaccaaa aaucgugcga gcccgcaguc ccguucccuu gugggagggu gagcguguca | 600 |
| cagacuagca aguugacgag agcggagacu guauuccccg acguggacua cgucaacagc | 660 |
| accgaagccg aaacaauccu cgauaacauc acgcagagca cucaguccuu caaugacuuu | 720 |
| acgagggucg uagguggga ggacgcgaaa cccggucagu uccccuggca gguguauug | 780 |
| aacggaaaag ucgaugccuu uuguggaggu uccauguca acgagaagug gauugucaca | 840 |
| gcggcacacu gcguagaaac aggagugaaa aucacggu ag uggcgggaga gcauaacauu | 900 |
| gaagagacag agcacacgga acaaaagcga aaugucauca gaaucauucc acaccauaac | 960 |
| uauaacgcgg caaucaauaa guacaaucac gacaucgcac uuuuggagcu ugacgaaccu | 1020 |
| uuggugcuua auucguacgu cacccccuauu uguauugccg acaaagagua acaaacauc | 1080 |
| uucuugaaau ucggcuccgg guacguaucg ggcuggggca gaguguucca uaaggguaga | 1140 |
| uccgcacugg uguugcaaua ccucaggug cccucgugg aucgagccac uugucugcgg | 1200 |
| uccaccaaau ucacaaucua caacaauaug uucugugcgg gauuccauga aggugggaga | 1260 |
| gauagcugcc aggagacuc aggggguccc cacgugacgg aagucgaggg gacgucauuu | 1320 |
| cugacgggaa uuaucucaug gggagaggaa ugugcgauga aggggaaaua uggcaucuac | 1380 |
| acuaaagugu cacgguaugu caauuggauc aaggaaaaga cgaaacucac gugaucagcc | 1440 |
| agcgcugccu ucugcggggc uugccuucug gccaugcccu ucuucucucc cuugcaccug | 1500 |
| uaccucuugg ucuuugaaua aagccugagu aggaag | 1536 |

<210> SEQ ID NO 9
<211> LENGTH: 767
<212> TYPE: DNA
<213> ORGANISM: Artificial Sequence
<220> FEATURE:
<223> OTHER INFORMATION: Description of Artificial Sequence: Synthetic transcript sequence

<400> SEQUENCE: 9

| | |
|---|---|
| taatacgact cactataggg aaataagaga gaaaagaaga gtaagaagaa atataagagc | 60 |
| caccatggga gtgcacgagt gtcccgcgtg gttgtggttg ctgctgtcgc tcttgagcct | 120 |
| cccactggga ctgcctgtgc tgggggcacc acccagattg atctgcgact cacgggtact | 180 |
| tgagaggtac cttcttgaag ccaaagaagc cgaaaacatc acaaccggat gcgccgagca | 240 |
| ctgctccctc aatgagaaca ttactgtacc ggatacaaag gtcaatttct atgcatggaa | 300 |
| gagaatggaa gtaggacagc aggccgtcga agtgtggcag gggctcgcgc ttttgtcgga | 360 |
| ggcggtgttg cggggtcagg ccctcctcgt caactcatca cagccgtggg agccccctcca | 420 |
| acttcatgtc gataaagcgg tgtcggggct ccgcagcttg acgacgttgc ttcgggctct | 480 |
| gggcgcacaa aaggaggcta tttcgccgcc tgacgcggcc tccgcggcac ccctccgaac | 540 |
| gatcaccgcg gacacgttta ggaagctttt tagagtgtac agcaatttcc tccgcggaaa | 600 |
| gctgaaattg tatactggtg aagcgtgtag gacaggggat cgctgataag ctgccttctg | 660 |
| cggggcttgc cttctggcca tgcccttctt ctctcccttg cacctgtacc tcttggtctt | 720 |
| tgaataaagc ctgagtagga aggcggccgc tcgagcatgc atctaga | 767 |

<210> SEQ ID NO 10
<211> LENGTH: 750
<212> TYPE: DNA
<213> ORGANISM: Artificial Sequence

```
<220> FEATURE:
<223> OTHER INFORMATION: Description of Artificial Sequence: Synthetic     transcript sequence

<400> SEQUENCE: 10
taatacgact cactataggg aaataagaga gaaaagaaga gtaagaagaa atataagagc      60
caccatggga gtgcacgagt gtcccgcgtg gttgtggttg ctgctgtcgc tcttgagcct     120
cccactggga ctgcctgtgc tgggggcacc acccagattg atctgcgact cacgggtact     180
tgagaggtac cttcttgaag ccaaagaagc cgaaaacatc acaaccggat gcgccgagca     240
ctgctccctc aatgagaaca ttactgtacc ggatacaaag gtcaatttct atgcatggaa     300
gagaatggaa gtaggacagc aggccgtcga agtgtggcag gggctcgcgc ttttgtcgga     360
ggcggtgttg cggggtcagg ccctcctcgt caactcatca cagccgtggg agcccctcca     420
acttcatgtc gataaagcgg tgtcgggggct ccgcagcttg acgacgttgc ttcgggctct     480
gggcgcacaa aaggaggcta tttcgccgcc tgacgcggcc tccgcggcac ccctccgaac     540
gatcaccgcg gacacgttta ggaagctttt tagagtgtac agcaatttcc tccgcggaaa     600
gctgaaattg tatactggtg aagcgtgtag gacagggat cgctgataag ctgccttctg      660
cggggcttgc cttctggcca tgcccttctt ctctcccttg cacctgtacc tcttggtctt     720
tgaataaagc ctgagtagga aggcggccgc                                      750

<210> SEQ ID NO 11
<211> LENGTH: 1578
<212> TYPE: DNA
<213> ORGANISM: Artificial Sequence
<220> FEATURE:
<223> OTHER INFORMATION: Description of Artificial Sequence: Synthetic     transcript sequence

<400> SEQUENCE: 11
taatacgact cactataggg aaataagaga gaaaagaaga gtaagaagaa atataagagc      60
caccaatgca gcgcgtcaac atgattatgg ccgaatcgcc gggactcatc acaatctgcc     120
tcttgggtta tctcttgtcg gcagaatgta ccgtgttctt ggatcacgaa aacgcgaaca     180
aaattcttaa tcgcccgaag cggtataact ccgggaaact tgaggagttt gtgcagggca     240
atcttgaacg agagtgcatg gaggagaaat gctcctttga ggaggcgagg gaagtgtttg     300
aaaacacaga gcgaacaacg gagttttgga agcaatacgt agatggggac cagtgtgagt     360
cgaatccgtg cctcaatggg ggatcatgta agatgacat caatagctat gaatgctggt      420
gcccgtttgg gtttgaaggg aagaactgtg agctggatgt gacgtgcaac atcaaaaacg     480
gacgctgtga gcagttttgt aagaactcgg ctgacaataa ggtagtatgc tcgtgcacag     540
agggataccg gctggcggag aaccaaaaat cgtgcgagcc cgcagtcccg ttcccttgtg     600
ggagggtgag cgtgtcacag actagcaagt tgacgagagc ggagactgta ttccccgacg     660
tggactacgt caacagcacc gaagccgaaa caatcctcga taacatcacg cagagcactc     720
agtccttcaa tgactttacg agggtcgtag gtggtgagga cgcgaaaccc ggtcagttcc     780
cctggcaggt ggtattgaac ggaaaagtcg atgccttttg tggaggttcc attgtcaacg     840
agaagtggat tgtcacagcg gcacactgcg tagaaacagg agtgaaaatc acggtagtgg     900
cgggagagca taacattgaa gagacagagc acacggaaca aaagcgaaat gtcatcagaa     960
tcattccaca ccataactat aacgcggcaa tcaataagta caatcacgac atcgcacttt    1020
tggagcttga cgaacctttg gtgcttaatt cgtacgtcac ccctatttgt attgccgaca    1080
aagagtatac aaacatcttc ttgaaattcg gctccgggta cgtatcgggc tggggcagag    1140
```

| | |
|---|---|
| tgttccataa gggtagatcc gcactggtgt tgcaatacct cagggtgccc ctcgtggatc | 1200 |
| gagccacttg tctgcggtcc accaaattca caatctacaa caatatgttc tgtgcgggat | 1260 |
| tccatgaagg tgggagagat agctgccagg gagactcagg gggtccccac gtgacggaag | 1320 |
| tcgaggggac gtcatttctg acgggaatta tctcatgggg agaggaatgt gcgatgaagg | 1380 |
| ggaaatatgg catctacact aaagtgtcac ggtatgtcaa ttggatcaag gaaaagacga | 1440 |
| aactcacgtg atcagccagc gctgccttct gcggggcttg ccttctggcc atgcccttct | 1500 |
| tctctcccctt gcacctgtac ctcttggtct ttgaataaag cctgagtagg aaggcggccg | 1560 |
| ctcgagcatg catctaga | 1578 |

<210> SEQ ID NO 12
<211> LENGTH: 848
<212> TYPE: RNA
<213> ORGANISM: Artificial Sequence
<220> FEATURE:
<223> OTHER INFORMATION: Description of Artificial Sequence: Synthetic transcript sequence

<400> SEQUENCE: 12

| | |
|---|---|
| aaauaagaga gaaaagaaga guaagaagaa auauaagagc caccaugguug agcaagggcg | 60 |
| aggaggauaa cauggccauc aucaaggagu ucaugcgcuu caaggugcac auggagggcu | 120 |
| ccgugaacgg ccacgaguuc gagaucgagg gcgagggcga gggccgcccc uacgagggca | 180 |
| cccagaccgc caagcugaag gugaccaagg gugggccccu gcccuucgcc ugggacaucc | 240 |
| uguccccuca guucauguac ggcuccaagg ccuacgugaa gcaccccgcc gacauccccg | 300 |
| acuacuugaa gcuguccuuc cccgagggcu ucaagugggca gcgcgugaug aacuucgagg | 360 |
| acggcggcgu ggugaccgug acccaggacu ccucccugca ggacggcgag uucaucuaca | 420 |
| aggugaagcu gcgcggcacc aacuucccccu ccgacgggccc cguaaugcag aagaagacca | 480 |
| ugggcuggga ggccuccucc gagcggaugu accccgagga cggcgcccug aagggcgaga | 540 |
| ucaagcagag gcugaagcug aaggacggcg gccacuacga cgcugagguc aagaccaccu | 600 |
| acaaggccaa gaagcccgug cagcugcccg gcgccuacaa cgucaacauc aaguuggaca | 660 |
| ucacccuccca caacgaggac uacaccaucg uggaacagua cgaacgcgcc gagggccgcc | 720 |
| acuccaccgg cggcauggac gagcuguaca agugagcugc cuucugcggg gcuugccuuc | 780 |
| uggccaugcc cuucuucucu cccuugcacc uguaccucuu ggucuuugaa uaaagccuga | 840 |
| guaggaag | 848 |

<210> SEQ ID NO 13
<211> LENGTH: 1838
<212> TYPE: DNA
<213> ORGANISM: Artificial Sequence
<220> FEATURE:
<223> OTHER INFORMATION: Description of Artificial Sequence: Synthetic transcript sequence

<400> SEQUENCE: 13

| | |
|---|---|
| taatacgact cactataggg aaataagaga gaaaagaaga gtaagaagaa atataagagc | 60 |
| caccatggaa gatgcgaaga acatcaagaa gggacctgcc ccgttttacc ctttggagga | 120 |
| cggtacagca ggagaacagc tccacaaggc gatgaaacgc tacgccctgg tccccggaac | 180 |
| gattgcgttt accgatgcac atattgaggt agacatcaca tacgcagaat acttcgaaat | 240 |
| gtcggtgagg ctggcggaag cgatgaagag atatggtctt aacactaatc accgcatcgt | 300 |
| ggtgtgttcg gagaactcat tgcagttttt catgccggtc cttggagcac ttttcatcgg | 360 |
| ggtcgcagtc gcgccagcga acgacatcta caatgagcgg gaactcttga atagcatggg | 420 |

```
aatctcccag ccgacggtcg tgtttgtctc caaaaagggg ctgcagaaaa tcctcaacgt     480
gcagaagaag ctccccatta ttcaaaagat catcattatg gatagcaaga cagattacca    540
agggttccag tcgatgtata cctttgtgac atcgcatttg ccgccagggt ttaacgagta    600
tgacttcgtc cccgagtcat ttgacagaga taaaaccatc gcgctgatta tgaattcctc    660
gggtagcacc ggtttgccaa agggggtggc gttgccccac cgcactgctt gtgtgcggtt    720
ctcgcacgct agggatccta tctttggtaa tcagatcatt cccgacacag caatcctgtc    780
cgtggtacct tttcatcacg gttttggcat gttcacgact ctcggctatt tgatttgcgg    840
tttcagggtc gtacttatgt atcggttcga ggaagaactg tttttgagat ccttgcaaga    900
ttacaagatc cagtcggccc tccttgtgcc aacgcttttc tcattctttg cgaaatcgac    960
acttattgat aagtatgacc tttccaatct gcatgagatt gcctcagggg gagcgccgct   1020
tagcaaggaa gtcggggagg cagtggccaa gcgcttccac cttcccggaa ttcggcaggg   1080
atacgggctc acggagacaa catccgcgat ccttatcacg cccgagggtg acgataagcc   1140
gggagccgtc ggaaaagtgg tccccttctt tgaagccaag gtcgtagacc tcgacacggg   1200
aaaaaccctc ggagtgaacc agaggggcga gctctgcgtg agagggccga tgatcatgtc   1260
aggttacgtg aataaccctg aagcgacgaa tgcgctgatc gacaaggatg ggtggttgca   1320
ttcgggagac attgcctatt gggatgagga tgagcacttc tttatcgtag atcgacttaa   1380
gagcttgatc aaatacaaag gctatcaggt agcgcctgcc gagctcgagt caatcctgct   1440
ccagcacccc aacattttcg acgccggagt ggccggttg cccgatgacg acgcgggtga    1500
gctgccagcg gccgtggtag tcctcgaaca tgggaaaaca atgaccgaaa aggagatcgt   1560
ggactacgta gcatcacaag tgacgactgc gaagaaactg aggggagggg tagtctttgt   1620
ggacgaggtc ccgaaaggct tgactgggaa gcttgacgct cgcaaaatcc gggaaatcct   1680
gattaaggca agaaaggcg ggaaaatcgc tgtctgataa gctgccttct gcggggcttg    1740
ccttctggcc atgcccttct tctctccctt gcacctgtac ctcttggtct ttgaataaag   1800
cctgagtagg aaggcggccg ctcgagcatg catctaga                           1838
```

<210> SEQ ID NO 14
<211> LENGTH: 1796
<212> TYPE: RNA
<213> ORGANISM: Artificial Sequence
<220> FEATURE:
<223> OTHER INFORMATION: Description of Artificial Sequence: Synthetic transcript sequence

<400> SEQUENCE: 14

```
gggaauaag agagaaaga agaguaagaa gaaauauaag agccaccaug gaagaugcga     60
agaacaucaa gaagggaccu gccccguuuu acccuuugga ggacgguaca gcaggagaac   120
agcuccacaa ggcgaugaaa cgcuacgccc ugguccccgg aacgauugcg uuuaccgaug   180
cacauauuga gguagacauc acauacgcag aauacuucga aaugucggug aggcuggcgg   240
aagcgaugaa gagauauggu cuuaacacua aucaccgcau cguggugugu ucggagaacu   300
cauugcaguu uucaugccg guccuuggag cacuuuucau cggggucgca gucgcgccag   360
cgaacgacau cuacaaugag cgggaacucu ugaauagcau gggaaucucc cagccgacgg   420
ucguguuugu cuccaaaaag gggcugcaga aaauccucaa cgugcagaag aagcuccccca   480 uuauucaaaa gaucaucauu auggauagca agacagauua ccaagggguuc cagucgaugu   540 auaccuuugu gacaucgcau uugccgccag ggguuaacga guaugacuuc gucccccgagu   600
```

```
cauuugacag agauaaaacc aucgcgcuga uuaugaauuc cucgggu agc accgguuugc     660 caaaggggu ggcguugccc caccgcacug cuuguguguc guucucgcac gcuagggauc      720
cuaucuuugg uaaucagauc auucccgaca cagcaauccu guccgguggua ccuuuucauc    780 acgguuuugg cauguucacg acucucggcu auuugauuug cgguuucagg gucguacuua    840
uguaucgguu cgaggaagaa cuguuuuuga gauccuugca agauuacaag auccagucgg    900
cccuccuugu gccaacgcuu uucucauucu uugcgaaauc gacacuuauu gauaaguaug    960
accuuuccaa ucugcaugag auugccucag ggggagcgcc gcuuagcaag gaagucgggg    1020 aggcagugc caagcgcuuc caccuucccg gaauucggca gggauacggg cucacggaga     1080
caacauccgc gauccuuauc acgcccgagg gugacgauaa gccgggagcc gucggaaaag    1140 uggucccuu cuuugaagcc aaggucuag accucgacac gggaaaaacc cucggaguga     1200
accagagggg cgagcucugc gugagagggc cgaugaucau gucagguuac gugaauaacc    1260
cugaagcgac gaaugcgcug aucgacaagg auggggugguu gcauucggga gacauugccu   1320
auugggauga ggaugagcac uucuuuaucg uagaucgacu uaagagcuug aucaaauaca    1380
aaggcuauca gguagcgccu gccgagcucg agucaauccu gcuccagcac cccaacauuu    1440
ucgacgccgg aguggccggg uugcccgaug acgacgcggg ugagcugcca gcggccgugg    1500
uaguccucga acaugggaaa acaaugaccg aaaaggagau cguggacuac guagcaucac    1560
aagugacgac ugcgaagaaa cugaggggag ggguagucuu uggaucgag gucccgaaag    1620 gcuugacugg gaagcuugac gcucgcaaaa uccgggaaau ccugauuaag gcaaagaaag    1680
gcgggaaaau cgcugucuga uaagcugccu ucucgcgggc uugccuucug gccaugcccu    1740
ucuucucucc cuugcaccug uaccucuugg ucuuugaaua aagccugagu aggaag        1796
```

<210> SEQ ID NO 15
<211> LENGTH: 902
<212> TYPE: DNA
<213> ORGANISM: Artificial Sequence
<220> FEATURE:
<223> OTHER INFORMATION: Description of Artificial Sequence: Synthetic       transcript sequence

<400> SEQUENCE: 15

```
taatacgact cactataggg aaataagaga gaaagaagaa gtaagaagaa atataagagc     60
caccatggtg agcaagggcg aggagctgtt caccggggtg gtgcccatcc tggtcgagct    120
ggacggcgac gtaaacggcc acaagttcag cgtgtccggc gagggcgagg gcgatgccac    180
ctacggcaag ctgaccctga agttcatctg caccaccggc aagctgcccg tgccctggcc    240 cacccctcgtg accaccctga cctacggcgt gcagtgcttc agccgctacc ccgaccacat    300
gaagcagcac gacttcttca gtccgccat gcccgaaggc tacgtccagg agcgcaccat    360
cttcttcaag gacgacggca actacaagac ccgcgccgag gtgaagttcg agggcgacac    420
cctggtgaac cgcatcgagc tgaagggcat cgacttcaag gaggacggca acatcctggg    480
gcacaagctg gagtacaact acaacagcca caacgtctat atcatggccg acaagcagaa    540
gaacggcatc aaggtgaact tcaagatccg ccacaacatc gaggacggca gcgtgcagct    600
cgccgaccac taccagcaga acaccccat cggcgacggc cccgtgctgc tgcccgacaa    660
ccactacctg agcacccagt ccgccctgag caaagacccc aacgagaagc gcgatcacat    720
ggtcctgctg gagttcgtga ccgccgccgg gatcactctc ggcatggacg agctgtacaa    780
gtaagctgcc ttctgcgggg cttgccttct ggccatgccc ttcttctctc ccttgcacct    840
gtacctcttg gtctttgaat aaagcctgag taggaaggcg gccgctcgag catgcatcta    900
```

| | 902 | ga

<210> SEQ ID NO 16
<211> LENGTH: 863
<212> TYPE: RNA
<213> ORGANISM: Artificial Sequence
<220> FEATURE:
<223> OTHER INFORMATION: Description of Artificial Sequence: Synthetic transcript sequence

<400> SEQUENCE: 16

| | | | | | |
|---|---|---|---|---|---|
| gggaaauaag | agagaaaaga | agaguaagaa | gaaauauaag | agccaccaug | guguccaagg | 60 |
| gugaggaauu | guuuaccggg | guggugccua | uucucgucga | acuugacggg | gaugugaaug | 120 |
| gacacaaguu | uucgguaucc | ggagaaggag | agggugacgc | cacauacgga | aagcuuacac | 180 |
| ucaaauucau | cuguacgacg | gggaaacugc | ccguacccug | gccuacgcuc | guaaccacgc | 240 |
| ugacuuaugg | agugcagugc | uuuagcagau | accccgacca | uaugaagcag | cacgacuucu | 300 |
| ucaagucggc | gaugcccgag | ggguacgugc | aagagaggac | cauuuucuuc | aaagacgaug | 360 |
| gcaauuacaa | aacacgcgca | gaagucaagu | uugagggcga | uacucugguc | aaucggaucg | 420 |
| aauugaaggg | aaucgauuuc | aaagaagaug | gaaacauccu | uggccauaag | cucgaguaca | 480 |
| acuauaacuc | gcauaauguc | uauaucaugg | cugacaagca | gaaaaacggu | aucaaaguca | 540 |
| acuuuaagau | ccgacacaau | auugaggacg | guucggugca | gcuugcggac | cacuaucaac | 600 |
| agaauacgcc | gauuggggau | gguccggucc | uuuugccgga | uaaccauuau | cucucaaccc | 660 |
| agucagcccu | gagcaaagau | ccaaacgaga | gagggaccca | cauggucuug | cucgaauucg | 720 |
| ugacagcggc | agggaucacu | cugggaaugg | acgaguugua | caagugauaa | gcugccuucu | 780 |
| gcggggcuug | ccuucggcc | augcccuucu | ucucucccuu | gcaccuguac | cucuuggucu | 840 |
| uugaauaaag | ccugaguagg | aag | | | | 863 |

<210> SEQ ID NO 17
<211> LENGTH: 716
<212> TYPE: RNA
<213> ORGANISM: Artificial Sequence
<220> FEATURE:
<223> OTHER INFORMATION: Descrption of Artificial Sequence: Synthetic transcript sequence

<400> SEQUENCE: 17

| | | | | | |
|---|---|---|---|---|---|
| gggaaauaag | agagaaaaga | agaguaagaa | gaaauauaag | agccaccaug | aacuuucucu | 60 |
| ugucaugggu | gcacuggagc | cuugcgcugc | ugcuguaucu | ucaucacgcu | aaguggagcc | 120 |
| aggccgcacc | cauggcggag | ggguggcggac | agaaucacca | cgaaguaguc | aaauucaugg | 180 |
| acguguacca | gaggucguau | ugccauccga | uugaaacucu | gugggauauc | uuucaagaau | 240 |
| accccgauga | aaucgaguac | auuuucaaac | cgucgugugu | cccucucaug | agggucgggg | 300 |
| gaugcugcaa | ugaugaaggg | uuggaguguu | ccccacggga | ggagucgaau | aucacaaugc | 360 |
| aaaucaugcg | caucaaacca | caucaggguc | agcauauugg | agagaugucc | uuucuccagc | 420 |
| acaacaaaug | ugaguguaga | ccgaagaagg | accgagcccg | acaggaaaac | ccaugcggac | 480 |
| cgugcuccga | gcggcgcaaa | cacuuguucu | acaagacccc | ccagacaugc | aagugcucau | 540 |
| guaagaauac | cgauucgcgg | guaaggcga | gacagcugga | auugaacgag | cgcacgugua | 600 |
| ggugcgacaa | gccuagacgg | ugagcugccu | ucugcggggc | uugccuucug | gccaugcccu | 660 |
| ucuucucucc | cuugcaccug | uaccucuugg | ucuuugaaua | aagccugagu | aggaag | 716 |

<210> SEQ ID NO 18

```
<211> LENGTH: 758
<212> TYPE: DNA
<213> ORGANISM: Artificial Sequence
<220> FEATURE:
<223> OTHER INFORMATION: Description of Artificial Sequence: Synthetic     transcript sequence

<400> SEQUENCE: 18
taatacgact cactataggg aaataagaga gaaagaaga gtaagaagaa atataagagc      60
caccatgaac tttctcttgt catgggtgca ctggagcctt gcgctgctgc tgtatcttca    120
tcacgctaag tggagccagg ccgcacccat ggcggagggt ggcggacaga atcaccacga    180
agtagtcaaa ttcatggacg tgtaccagag gtcgtattgc catccgattg aaactcttgt    240
ggatatcttt caagaatacc ccgatgaaat cgagtacatt ttcaaaccgt cgtgtgtccc    300
tctcatgagg tgcgggggat gctgcaatga tgaagggttg gagtgtgtcc ccacggagga    360
gtcgaatatc acaatgcaaa tcatgcgcat caaaccacat cagggtcagc atattggaga    420
gatgtccttt ctccagcaca acaaatgtga gtgtagaccg aagaaggacc gagcccgaca    480
ggaaaaccca tgcggaccgt gctccgagcg gcgcaaacac ttgttcgtac aagaccccca    540
gacatgcaag tgctcatgta agaataccga ttcgcggtgt aaggcgagac agctggaatt    600
gaacgagcgc acgtgtaggt gcgacaagcc tagacggtga gctgccttct gcggggcttg    660
ccttctggcc atgcccttct tctctcccctt gcacctgtac ctcttggtct ttgaataaag    720
cctgagtagg aaggcggccg ctcgagcatg catctaga                            758

<210> SEQ ID NO 19
<211> LENGTH: 30
<212> TYPE: PRT
<213> ORGANISM: Homo sapiens

<400> SEQUENCE: 19

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala
            20                  25                  30

<210> SEQ ID NO 20
<211> LENGTH: 25
<212> TYPE: PRT
<213> ORGANISM: Homo sapiens

<400> SEQUENCE: 20

Met Met Pro Ser Ser Val Ser Trp Gly Ile Leu Leu Leu Ala Gly Leu
1               5                   10                  15

Cys Cys Leu Val Pro Val Ser Leu Ala
            20                  25

<210> SEQ ID NO 21
<211> LENGTH: 46
<212> TYPE: PRT
<213> ORGANISM: Homo sapiens

<400> SEQUENCE: 21

Met Gln Arg Val Asn Met Ile Met Ala Glu Ser Pro Ser Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg
        35                  40                  45
```

<210> SEQ ID NO 22
<211> LENGTH: 21
<212> TYPE: PRT
<213> ORGANISM: Homo sapiens

<400> SEQUENCE: 22

Met Lys Gly Ser Leu Leu Leu Leu Val Ser Asn Leu Leu Leu Cys
1               5                   10                  15

Gln Ser Val Ala Pro
            20

<210> SEQ ID NO 23
<211> LENGTH: 24
<212> TYPE: PRT
<213> ORGANISM: Homo sapiens

<400> SEQUENCE: 23

Met Lys Trp Val Thr Phe Ile Ser Leu Leu Phe Leu Phe Ser Ser Ala
1               5                   10                  15

Tyr Ser Arg Gly Val Phe Arg Arg
            20

<210> SEQ ID NO 24
<211> LENGTH: 793
<212> TYPE: RNA
<213> ORGANISM: Artificial Sequence
<220> FEATURE:
<223> OTHER INFORMATION: Description of Artificial Sequence: Synthetic     transcript sequence

<400> SEQUENCE: 24
gggaaauaag agagaaaaga agaguaagaa gaaauauaag agccaccaug gacucggacg        60
agaccggguu cgagcacuca ggacugugg uuucugugcu ggcuggucuu cugcugggag        120
ccugccaggc acaccccauc ccugacucca guccucuccu gcaaucgggg ggccaagucc       180
ggcagcggua ccucuacaca gaugaugccc agcagacaga agcccaccug gagaucaggg       240
aggaugggac ggugggggc gcugcugacc agagccccga aagucuccug cagcugaaag        300
ccuugaagcc gggaguuauu caaaucuugg gagucaagac auccagguuc cugugccagc       360
ggccagaugg ggcccuguau ggaucgcucc acuuugaccc ugaggccugc agcuuccggg       420
agcugcuucu ugaggacgga uacaauguuu accaguccga agcccacggc ucccgcugc        480 accugccagg gaacaaguc ccacaccggg acccugcacc ccgaggacca gcucgcuucc       540
ugccacuacc aggccugccc ccgcacccc cggagccacc cggaauccug gcccccagc        600 ccccgauguu gggcuccucg gacccucuga gcaugguggg accuuccag ggccgaagcc       660 ccagcuacgc uuccugauaa uaggcuggag ccucggugc caugcuucuu gcccuuggg        720 ccucccccca gccccuccuc cccuuccugc acccguaccc ccguggucuu ugaauaaagu       780 cugaguggc ggc                                                          793

<210> SEQ ID NO 25
<211> LENGTH: 761
<212> TYPE: RNA
<213> ORGANISM: Artificial Sequence
<220> FEATURE:
<223> OTHER INFORMATION: Description of Artificial Sequence: Synthetic     transcript sequence

<400> SEQUENCE: 25
gggaaauaag agagaaaaga agaguaagaa gaaauauaag agccaccaug ggggugcccg        60
aacgucccac ccugcugcuu uuacucuccu ugcuacugau uccucuggc cucccaguccc       120

```
ucugugcucc cccacgccuc aucugcgaca gucgaguucu ggagagguac aucuuagagg    180
ccaaggaggc agaaaauguc acgaugggu ugcagaagg ucccagacug agugaaaaua     240
```
(line 240 second group should read: acgauggguu — preserving as shown)

```
ucugugcucc cccacgccuc aucugcgaca gucgaguucu ggagagguac aucuuagagg    180
ccaaggaggc agaaaauguc acgaugggu ugcagaagg ucccagacug agugaaaaua     240
uuacagcccc agauaccaaa gucaacuucu augcuuggaa agaauggag guggaagaac    300
aggccauaga aguuuggcaa ggccuguccc ugcucucaga agccauccug caggcccagg    360
cccugcuagc caauuccucc cagccaccag agacccuuca gcuucauaua gacaaagcca   420
ucaggugucu acguagccuc acuucacugc uucggguacu gggagcucag aaggaauuga   480
ugucgccucc agauaccacc ccaccugcuc cacuccgaac acucacagug gauacuuucu   540
gcaagcucuu ccggucuac gccaacuucc uccgggggaa acugaagcug uacacgggag    600
aggucugcag gagaggggac aggugauaau aggagccucg guggccaugc uucuugcccc   660
uugggccucc ccccagcccc uccuccccuu ccugcacccg uaccccccuc auaaaguagg   720
aaacacuaca guggucuuug aauaaagucu gagugggcgg c                      761
```

<210> SEQ ID NO 26
<211> LENGTH: 742
<212> TYPE: RNA
<213> ORGANISM: Artificial Sequence
<220> FEATURE:
<223> OTHER INFORMATION: Description of Artificial Sequence: Synthetic transcript sequence

<400> SEQUENCE: 26

```
gggaaauaag agagaaaaga agaguaagaa gaaauauaag agccaccaug ggggugcccg    60
aacgucccac ccugcugcuu uuacucuccu ugcuacugau uccucugggc cucccagucc   120
ucugugcucc cccacgccuc aucugcgaca gucgaguucu ggagagguac aucuuagagg   180
ccaaggaggc agaaaauguc acgauggguu ugcagaagg ucccagacug agugaaaaua    240
uuacagcccc agauaccaaa gucaacuucu augcuuggaa agaauggag guggaagaac    300
aggccauaga aguuuggcaa ggccuguccc ugcucucaga agccauccug caggcccagg   360
cccugcuagc caauuccucc cagccaccag agacccuuca gcuucauaua gacaaagcca   420
ucaggugucu acguagccuc acuucacugc uucggguacu gggagcucag aaggaauuga   480
ugucgccucc agauaccacc ccaccugcuc cacuccgaac acucacagug gauacuuucu   540
gcaagcucuu ccggucuac gccaacuucc uccgggggaa acugaagcug uacacgggag    600
aggucugcag gagaggggac aggugauaau aggcuggagc cucgguggcc augcuucuug   660
ccccuugggc cucccccag ccccuccucc ccuuccugca cccguacccc cguggucuuu    720
gaauaaaguc ugagugggcg gc                                            742
```

<210> SEQ ID NO 27
<211> LENGTH: 768
<212> TYPE: RNA
<213> ORGANISM: Artificial Sequence
<220> FEATURE:
<223> OTHER INFORMATION: Description of Artificial Sequence: Synthetic transcript sequence

<400> SEQUENCE: 27

```
gggaaauaag agagaaaaga agaguaagaa gaaauauaag agccaccaug ggagugcacg    60
aguccccgc gguugugg uugcugcugu cgcucuugag ccucccacug ggacugccug       120
ugcuggggc accacccaga uugaucgcg acucacgggu acuugagagg uaccuucuug     180
aagccaaaga agccgaaaac aucacaaccg gaugcgccga gcacugcucc cucaaugaga   240
acauuacugu accggauaca aaggucaauu ucuaugcaug gaagagaaug gaaguaggac   300
```

```
agcaggccgu cgaagugugg caggggcucg cgcuuuuguc ggaggcggug uugcgggguc    360
aggcccuccu cgucaacuca ucacagccgu gggagcccu ccaacuucau gucgauaaag     420
cggugucggg gcuccgcagc uugacgacgu ugcuucgggc ucgggcgca caaaaggagg    480 cuauuucgcc gccugacgcg gccuccgcgg caccccuccg aacgaucacc gcggacacgu    540
uuaggaagcu uuuuagagug uacagcaauu uccuccgcgg aaagcugaaa uuguauacug    600
gugaagcgug uaggacaggg gaucgcugau aauaggcugg agccucggug gccaugcuuc    660 uugcccuug ggccucccc cagccccucc uccccuuccu gcacccguac ccccuccaua     720
aaguaggaaa cacuacagug gucuuugaau aaagucugag ugggcggc                 768
```

`<210> SEQ ID NO 28`
`<211> LENGTH: 745`
`<212> TYPE: RNA`
`<213> ORGANISM: Artificial Sequence`
`<220> FEATURE:`
`<223> OTHER INFORMATION: Description of Artificial Sequence: Synthetic     transcript sequence`

`<400> SEQUENCE: 28`

```
gggaaauaag agagaaaaga agaguaagaa gaaauauaag agccaccaug ggagugcacg    60
agugucccgc gugguugugg uugcugcugu cgcucuugag ccucccacug ggacugccug    120 ugcuggggc accacccaga uugaucugcg acucacgggu acuugagagg uaccuucuug    180
aagccaaaga agccgaaaac aucacaaccg gaugcgccga gcacugcucc cucaaugaga    240
acauuacugu accggauaca aaggucaauu ucuaugcaug gaagagaaug gaaguaggac    300
agcaggccgu cgaagugugg caggggcucg cgcuuuuguc ggaggcggug uugcgggguc    360
aggcccuccu cgucaacuca ucacagccgu gggagcccu ccaacuucau gucgauaaag     420
cggugucggg gcuccgcagc uugacgacgu ugcuucgggc ucgggcgca caaaaggagg    480 cuauuucgcc gccugacgcg gccuccgcgg caccccuccg aacgaucacc gcggacacgu    540
uuaggaagcu uuuuagagug uacagcaauu uccuccgcgg aaagcugaaa uuguauacug    600
gugaagcgug uaggacaggg gaucgcugau aauaggcugg agccucggug gccaugcuuc    660 uugcccuug ggccucccc cagccccucc uccccuuccu gcacccguac cccgugguc      720 uuugaauaaa gucugagugg gcggc                                          745
```